United States Patent
DeGrado et al.

(10) Patent No.: US 10,131,658 B2
(45) Date of Patent: Nov. 20, 2018

(54) ANTI-ALPHAVBETA1 INTEGRIN COMPOUNDS AND METHODS

(71) Applicant: The Regents of the University of California, Oakland, CA (US)

(72) Inventors: William F. DeGrado, San Francisco, CA (US); Dean Sheppard, Oakland, CA (US); Hyunil Jo, Lafayette, CA (US); Nilgun Isik Reed, San Francisco, CA (US); Youzhi Tang, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/083,836

(22) Filed: Mar. 29, 2016

(65) Prior Publication Data

US 2016/0376266 A1    Dec. 29, 2016

Related U.S. Application Data

(63) Continuation of application No. PCT/US2014/058491, filed on Sep. 30, 2014.

(60) Provisional application No. 61/884,853, filed on Sep. 30, 2013.

(51) Int. Cl.

| | |
|---|---|
| *C07D 471/04* | (2006.01) |
| *C07D 401/12* | (2006.01) |
| *A47B 47/00* | (2006.01) |
| *A47B 96/14* | (2006.01) |
| *A47B 46/00* | (2006.01) |
| *H05K 7/14* | (2006.01) |
| *A61M 31/00* | (2006.01) |
| *C07D 207/48* | (2006.01) |
| *C07D 211/96* | (2006.01) |
| *C07D 277/06* | (2006.01) |
| *C07D 403/12* | (2006.01) |
| *C07D 409/12* | (2006.01) |
| *C07D 413/12* | (2006.01) |
| *C07D 417/12* | (2006.01) |

(52) U.S. Cl.
CPC ........... *C07D 471/04* (2013.01); *A47B 46/00* (2013.01); *A47B 47/0083* (2013.01); *A47B 96/1416* (2013.01); *A61M 31/002* (2013.01); *A61M 31/007* (2013.01); *C07D 207/48* (2013.01); *C07D 211/96* (2013.01); *C07D 277/06* (2013.01); *C07D 401/12* (2013.01); *C07D 403/12* (2013.01); *C07D 409/12* (2013.01); *C07D 413/12* (2013.01); *C07D 417/12* (2013.01); *H05K 7/1488* (2013.01); *Y10T 29/49826* (2015.01)

(58) Field of Classification Search
CPC .................. C07D 471/04; C07D 401/12
See application file for complete search history.

(56) References Cited

U.S. PATENT DOCUMENTS

| | | | |
|---|---|---|---|
| 4,676,980 A | 6/1987 | Segal et al. | |
| 4,816,567 A | 3/1989 | Cabilly et al. | |
| 4,946,778 A | 8/1990 | Ladner et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 6,492,421 B1 * | 12/2002 | Thorsett | C07K 5/06165 514/217.08 |
| 6,583,139 B1 * | 6/2003 | Thorsett | A61K 31/401 514/227.5 |
| 6,586,602 B2 * | 7/2003 | Thorsett | C07K 5/06139 544/59 |
| 7,288,526 B2 * | 10/2007 | Thorsett | C07K 5/06026 514/1.7 |
| 8,309,735 B2 | 11/2012 | Zischinsky et al. | |
| 2008/0045521 A1 | 2/2008 | Arnould et al. | |
| 2008/0255183 A1 | 10/2008 | Arnould et al. | |
| 2009/0104116 A1 | 4/2009 | Zischinsky et al. | |
| 2014/0038910 A1 | 2/2014 | Ruminski et al. | |
| 2016/0264566 A1 | 9/2016 | DeGrado et al. | |

FOREIGN PATENT DOCUMENTS

| | | |
|---|---|---|
| WO | WO-91/00360 A1 | 1/1991 |
| WO | WO-93/08829 A1 | 5/1993 |
| WO | WO-98/53814 A1 | 12/1998 |
| WO | WO-2001/042225 A2 | 6/2001 |
| WO | WO-2001/042225 A3 | 6/2001 |
| WO | WO-2001/042225 A8 | 6/2001 |
| WO | WO-01/54690 A1 | 8/2001 |
| WO | WO-2002/016329 A1 | 2/2002 |
| WO | WO-2003/008380 A1 | 1/2003 |
| WO | WO-03/089410 A1 | 10/2003 |
| WO | WO-2004/066931 A2 | 8/2004 |
| WO | WO-2004/066931 A3 | 8/2004 |

(Continued)

OTHER PUBLICATIONS

Takayanagi et al (2003): STN International, HCAPLUS database (Columbus, Ohio), Accession No. 2003: 76750.*

Thorsett et al (2003): STN International, HCAPLUS database (Columbus, Ohio), Accession No. 2003: 485719.*

Thorsett et al (2002): STN International, HCAPLUS database (Columbus, Ohio), Accession No. 2002: 942792.*

Choi, S. et al. (Nov. 1, 2007, e-published Oct. 4, 2007). "Small molecule inhibitors of integrin $\alpha_2\beta_1$," *J Med Chem* 50(22):5457-5462.

Cole, S.P.C. et al. (1985). "The EBV-Hybridoma Technique and Its Application to Human Lung Cancer," *Monoclonal Antibodies and Cancer Therapy* pp. 77-96.

(Continued)

*Primary Examiner* — Golam M Shameem

(74) *Attorney, Agent, or Firm* — Mintz Levin Cohn Ferris Glovsky and Popeo, P.C.; Kenneth E. Jenkins; Joohee Lee

(57) ABSTRACT

Provided herein, inter alia, are methods and compositions for inhibiting $\alpha v \beta 1$ integrin and for treating fibrosis.

18 Claims, 11 Drawing Sheets

(56) References Cited

FOREIGN PATENT DOCUMENTS

| WO | WO-2005/000244 A2 | 1/2005 |
|---|---|---|
| WO | WO-2005/000244 A3 | 1/2005 |
| WO | WO-2005/070921 A1 | 8/2005 |
| WO | WO-2007/060408 A2 | 5/2007 |
| WO | WO-2007/060408 A3 | 5/2007 |
| WO | WO-2007/088041 A1 | 8/2007 |
| WO | WO-2007/131764 A2 | 11/2007 |
| WO | WO-2007/131764 A3 | 11/2007 |
| WO | WO-2007/141473 A1 | 12/2007 |
| WO | WO-2008/062859 A1 | 5/2008 |
| WO | WO-2008/125811 A1 | 10/2008 |
| WO | WO-2009/055487 A1 | 4/2009 |
| WO | WO-2015/048819 A1 | 4/2015 |
| WO | WO-2016/145258 A1 | 9/2016 |

OTHER PUBLICATIONS

Corbett, J.W. et al. (1997). Solid-Phase Synthesis of a Selective $\alpha_v\beta_3$ Integrin Antagonist Library, *Bioorganic & Miedicinal Chemisty Letters* 7(11):1371-1376.

De Corte, B.L. et al. (Oct. 18, 2004). "Piperidine-containing beta-arylpropionic acids as potent antagonists of $\alpha_v\beta_3/\alpha_v\beta_5$ integrins," *Bioorg Med Chem Lett* 14(20):5227-5232.

Delouvrié, B. et al. (Jun. 15, 2012 e-published Apr. 21, 2012). "Structure-activity relationship of a series of non peptidic RGD integrin antagonists targeting $\alpha 5\beta 1$: part 1," *Bioorg Med Chem Lett* 22(12):4111-41116.

Delouvrié, B. et al. (Jun. 2012, e-published Apr. 21, 2012). "Structure-activity relationship of a series of non peptidic RGD integrin antagonists targeting $\alpha 5\beta 1$: part 2," *Bioorg Med Chem Lett* 22(12):4117-4121.

Fishwild, D.M. et al. (Jul. 1996). "High-avidity human IgGκ monoclonal antibodies from a novel strain of minilocus transgenic mice," *Nat Biotechnol* 14(7):845-851.

Ghosh, A.K. et al. (Jan. 1, 2012). "Fibrosis: Is It a Coactivator Disease?" *Frontiers in Bioscience E4*, 1556-1570.

Hagmann, W.K. et al. (Oct. 22, 2001). "The discovery of sulfonylated dipeptides as potent VLA-4 antagonists," *Bioorg Med Chem Lett* 11(20):2709-2713.

Heckmann, D. et al. (2007). "Probing integrin selectivity: rational design of highly active and selective ligands for the $\alpha 5\beta 1$ and $\alpha v\beta 3$ integrin receptor," *Angew Chem Int Ed Engl* 46(19):3571-3574.

Heckmann, D. et al. (Jun. 16, 2008). "Rational design of highly active and selective ligands for the $\alpha 5\beta 1$ integrin receptor," *Chembiochem* 9(9):1397-1407.

Heckmann, D. et al. (2009). "Breaking the dogma of the metal-coordinating carboxylate group in integrin ligands: introducing hydroxamic acids to the MIDAS to tune potency and selectivity," *Angew Chem Int Ed Engl* 48(24):4436-4440.

Henderson, N.C. et al. (Dec. 2013, e-published Nov. 10, 2013). "Targeting of $\alpha v$ integrin identifies a core molecular pathway that regulates fibrosis in several organs," *Nat Med* 19(12):1617-1624.

Hynes, R.O. et al. (Sep. 20, 2002). "Integrins: bidirectional, allosteric signaling machines," *Cell* 110(6):673-687.

International Search Report dated Jan. 16, 2015, for PCT Application No. PCT/US2014/058491, filed on Sep. 30, 2014, 4 pages.

International Search Report dated Jun. 3, 2016, for PCT Application No. PCT/US2016/021879, filed on Mar. 10, 2016 4 pages.

Jones. P.T. et al. (May 29-Jun. 4, 1986). "Replacing the complementarity-determining regions in a human antibody with those from a mouse," *Nature* 321(6069):522-525.

Klingberg, F. et al. (Jan. 2013). "The myofibroblast matrix: implications for tissue repair and fibrosis," *J Pathol* 229(2):298-309.

Kohler, G. et al. (Aug. 7, 1975). "Continuous cultures of fused cells secreting antibody of predefined specificity," *Nature* 256(5517):495-497.

Kozbor, D. et al. (Mar. 1983). "The production of monoclonal antibodies from human lymphocytes," *Immunol Today* 4(3):72-79.

Lonberg, N. et al. (Apr. 28, 1994). "Antigen-specific human antibodies from mice comprising four distinct genetic modifications," *Nature* 368(6474):856-859.

MacDonald, E.M. et al. (Nov. 2012). "TGFβ signaling: its role in fibrosis formation and myopathies," *Curr Opin Rheumatol* 24(6):628-634.

Margadant, C. et al. (Feb. 2010, e-published Jan. 15, 2010). "Integrin-TGF-β crosstalk in fibrosis, cancer and wound healing," *EMBO Rep* 11(2):97-105.

Marks, J.D. et al. (Jul. 1992). "By-passing immunization: building high affinity human antibodies by chain shuffling," *Biotechnology* 10(7):779-783.

McCafferty, J. et al. (Dec. 6, 1990). "Phage antibodies: filamentous phage displaying antibody variable domains," *Nature* 348(6301):552-554.

Miller, M.W. et al. (Jan. 20, 2009, e-published Jan. 13, 2009). "Small-molecule inhibitors of integrin alpha2beta1 that prevent pathological thrombus formation via an allosteric mechanism," *Proc Natl Acad Sci USA* 106(3):719-724.

Morrison, S.L. (Apr. 28, 1994). "Immunology. Success in specification," *Nature* 368(6474):812-813.

Mousa, S.A. et al. (Feb. 1, 1996). "Oral antiplatelet, antithrombotic efficacy of DMP 728, a novel platelet GPIIb/IIIa antagonist," *Circulation* 93(3):537-543.

Neuberger, M. (Jul. 1996). "Generating high-avidity human Mabs in mice," *Nat Biotechnol* 14(7):826.

O'Neil, K.T. et al. (Dec. 1992). "Identification of novel peptide antagonists for GPIIb/IIIa from a conformationally constrained phage peptide library," *Proteins* 14(4):509-515.

Pepinsky, R.B. et al. (Jun. 4, 2002). "Comparative assessment of the ligand and metal ion binding properties of integrins $\alpha 9\beta 1$ and $\alpha 4\beta 1$," *Biochemistry* 41(22):7125-7141.

Perdih, A. et al. (2010). "Small molecule antagonists of integrin receptors," *Curr Med Chem* 17(22):2371-2392.

Presta, L. (1992). "Antibody engineering," *Curr Opin Struc Biol* 2(4):593-596.

Presta, L. (Aug. 2003). "Antibody engineering for therapeutics," *Curr Opin Struc Biol* 13(4):519-525.

Ray, A.M. et al. (Sep. 2014, e-published May 5, 2014). "Single cell tracking assay reveals an opposite effect of selective small non-peptidic $\alpha 5\beta 1$ or $\alpha v\beta 3/\beta 5$ integrin antagonists in U87MG glioma cells," *Biochim Biophys Acta* 1840(9):2978-2987.

Riechmann, L. et al. (Mar. 24, 1988). "Reshaping human antibodies for therapy," *Nature* 332(6162):323-327.

Rockwell, A.L. et al. (Apr. 5, 1999). "Rapid synthesis of RGD mimetics with isoxazoline scaffolds on solid phase: identification of alphavbeta3 antagonists lead compounds," *Bioorg Med Chem Lett* 9(7):937-942.

Ruoslahti, E. et al. (1996). "RGD and other recognition sequences for integrins," *Annu Rev Cell Dev Biol* 12:697-715.

Saku, O. et al. (Feb. 1, 2008, e-published Dec. 14, 2007). "Synthetic study of VLA-4/VCAM-1 inhibitors: synthesis and structure-activity relationship of piperazinylphenylalanine derivatives," *Bioorg Med Chem Lett* 18(3):1053-1057.

Suresh. M.R. et al. (1986). "Bispecific monoclonal antibodies from hybrid hybridomas," *Methods Enzymol* 121:210-228.

Traunecker, A. et al. (Dec. 1991). "Bispecific single chain molecules (Janusins) target cytotoxic lymphocytes on HIV infected cells," *EMBO J* 10(12):3655-3659.

Verhoeyen, M. et al. (Mar. 25, 1988). "Reshaping human antibodies: grafting an antilysozyme activity," *Science* 239(4847):1534-1536.

Wipff, P.J. et al. (Dec. 17, 2007). "Myofibroblast contraction activates latent TGF-beta1 from the extracellular matrix," *J Cell Biol* 179(6):1311-1323.

Written Opinion dated Jan. 16, 2015, for PCT Application No. PCT/US2014/058491, filed on Sep. 30, 2014, 4 pages.

Written Opinion dated Jun. 3, 2016, for PCT Application No. PCT/US2016/021879, filed on Mar. 10, 2016 16 pages.

Xue, C-B. et al. (Apr. 1997). "Design, synthesis, and in vitro activities of benzamide-core glycoprotein IIb/IIIa antagonists: 2,3-diaminopropionic acid derivatives as surrogates of aspartic acid," *Bioorg Med Chem* 5(4):693-705.

(56) References Cited

OTHER PUBLICATIONS

Xue, C-B. et al. (Dec. 15, 1998). "Synthesis and antiplatelet effects of an isoxazole series of glycoprotein IIb/IIIa antagonists," *Bioorg Med Chem Lett* 8(24):3499-3504.

Yin, H. et al. (Jul. 1, 2006, e-published May 5, 2006). "Arylamide derivatives as allosteric inhibitors of the integrin $\alpha_2\beta_1$/type I collagen interaction," *Bioorg Med Chem Lett* 16(13):3380-3382.

Zischinsky, G. et al. (Jan. 1, 2010, e-published Nov. 14, 2009). "SAR of N-phenyl piperidine based oral integrin $\alpha 5\beta 1$ antagonists," *Bioorg Med Chem Lett* 20(1):65-68.

Zischinsky, G. et al. (Jan. 1, 2010, e-published Oct. 28, 2009). "Discovery of orally available integrin alpha5beta1 antagonists," *Bioorg Med Chem Lett* 20(1):380-382.

Australian Examination Report dated Dec. 19, 2017, for Australian Application No. 2014324426, 7 pages.

\* cited by examiner

αvβ1 integrin inhibitor c8 (n=4)

FIG. 1E

| Integrin | c8 IC$_{50}$ (nmol/L) |
|---|---|
| ● α5β1 | >100,000 |
| ■ α8β1 | >100,000 |
| ▲ αvβ1 | 0.089±0.02 |
| ▼ αvβ3 | >100,000 |
| ◆ αvβ5 | >100,000 |
| ● αvβ6 | >100,000 |
| ■ αvβ8 | >100,000 |

ANTI-ALPHAVBETA1 INTEGRIN COMPOUNDS AND METHODS

CROSS-REFERENCES TO RELATED APPLICATIONS

This application is a continuation of International Application No. PCT/US2014/058491, filed Sep. 30, 2014, which claims the benefit of U.S. Provisional Application No. 61/884,583, filed Sep. 30, 2013.

STATEMENT AS TO RIGHTS TO INVENTIONS MADE UNDER FEDERALLY SPONSORED RESEARCH AND DEVELOPMENT

This invention was made with government support under grant numbers P01 HL108794 and R37 HL053949 awarded by the National Institutes of Health. The government has certain rights in this invention.

BACKGROUND OF THE INVENTION

Fibrosis is a pathologic process, characterized by overproduction of extracellular matrix (ECM) as a response to tissue injury. Nearly 45% of all deaths in the developed world can be attributed to some type of chronic fibroproliferative disease. Despite their high prevalence, current therapeutic options for fibrotic diseases are quite limited to elimination of triggering stimuli and organ transplantation. No effective agent exists that can directly halt the disease progression at the cellular level, which represents a major unmet medical need. Pharmacological modulation of the $\alpha v\beta 1$ integrin by small molecules presents one route to test the role of the $\alpha v\beta 1$ integrin in tissue fibrosis. Most integrins contain either an $\alpha v$ chain or $\beta 1$ chain, and targeting either subunit by itself provides little specificity. Accordingly, there is a need in the art for potent, selective $\alpha v\beta 1$ integrin inhibitors. Provided herein are solutions to these and other problems in the art.

BRIEF SUMMARY OF THE INVENTION

Herein are provided, inter alia, methods for treating fibrosis using an $\alpha v\beta 1$ inhibitor and compositions of $\alpha v\beta 1$ inhibitors.

In a first aspect is a compound having the formula:

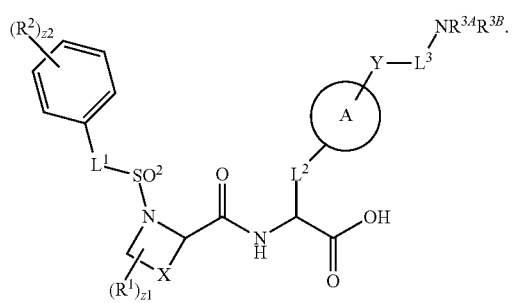

(I)

Ring A is cycloalkyl, heterocycloalkyl, aryl, or heteroaryl. $L^1$ and $L^2$ are independently a bond or substituted or unsubstituted $C_1$-$C_{10}$ alkylene. $L^3$ is a bond, substituted or unsubstituted $C_1$-$C_{10}$ alkylene, substituted or unsubstituted 2 to 10 membered heteroalkylene, substituted or unsubstituted cycloalkylene, substituted or unsubstituted heterocycloalkylene, or substituted or unsubstituted alkylarylene. X is a bond, —C—, —C—C—, —C=C—, —C—C—C—, —C=C—C—, —C—C=C—, —O—C—, —C—O—, —C—O—C, —S—C—, —C—S—, —C—S—C—. Y is a bond, —C(O)N($R^4$)—, —O—, —C(O)O—, —S—, —N($SO_2$—$R^4$)—, —N(C(O)$R^4$)—, —N(C(O)O$R^4$)—, —(N$R^4$)C(O)—, —N($R^4$)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^1$ is independently halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$OSO_3H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety. $R^2$ is independently halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$OSO_3H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety, or wherein if z2 an integer of 2 to 5, two $R^2$ substituents attached to adjacent ring carbons are optionally joined to form a substituted or unsubstituted aryl or substituted or unsubstituted heteroaryl. $R^{3A}$ and $R^{3B}$ are independently hydrogen, —C(NH)$NH_2$, —C(NH)$R^{3D}$, —C(N$R^{3C}$)$NH_2$, —C(N$R^{3C}$)$R^{3D}$, —C(NCN)$NH_2$, NH, $NH_2$, —C(NH)NH$R^{3D}$, —C(N$R^{3C}$)NH$R^{3D}$, —C(NCN)NH$R^{3D}$, substituted or unsubstituted cycloalkyl, substituted or unsubstituted heterocycloalkyl, substituted or unsubstituted aryl, substituted or unsubstituted heteroaryl, or $R^{3A}$ and $R^{3B}$ are optionally joined to form a substituted or unsubstituted heterocycloalkyl or substituted or unsubstituted heteroaryl. $R^{3C}$ and $R^{3D}$ are independently hydrogen, halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^4$ is independently hydrogen or unsubstituted $C_1$-$C_5$ alkyl. z1 is an integer from 1 to 9. z2 is an integer from 1 to 5.

In another aspect is a pharmaceutical composition including a compound as described herein, including embodiments thereof, and a pharmaceutically acceptable excipient.

Further provided herein are methods for treating fibrosis. In one aspect is a method for treating fibrosis by administering to a subject in need thereof a therapeutically effective amount of an $\alpha v\beta 1$-inhibitor. The $\alpha v\beta 1$-inhibitor is an $\alpha v\beta 1$-inhibitor antibody, an $\alpha v\beta 1$-inhibitor RGD peptide, or an $\alpha v\beta 1$-inhibitor compound, and the $\alpha v\beta 1$-inhibitor compound has the formula:

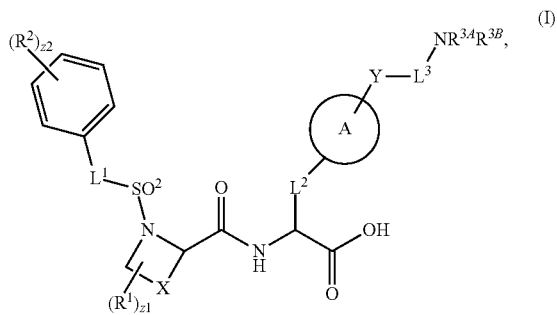

Ring A is cycloalkyl, heterocycloalkyl, aryl, or heteroaryl. $L^1$ and $L^2$ are independently a bond or substituted or unsubstituted $C_1$-$C_{10}$ alkylene. $L^3$ is a bond, substituted or unsubstituted $C_1$-$C_{10}$ alkylene, substituted or unsubstituted 2 to 10 membered heteroalkylene, substituted or unsubstituted cycloalkylene, or substituted or unsubstituted heterocycloalkylene, or substituted or unsubstituted alkylarylene. X is a bond, —C—, —C—C—, —C═C—, —C—C—C—, —C═C—C—, —C—C═C—, —O—C—, —C—O—, —C—O—C, —S—C—, —C—S—, —C—S—C—. Y is a bond, —C(O)N($R^4$)—, —O—, —C(O)O—, —S—, —N(SO$_2$—$R^4$)—, —N(C(O)$R^4$)—, —N(C(O)O$R^4$)—, —(N$R^4$)C(O)—, —N($R^4$)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^1$ is independently halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_2$CH$_3$— SO$_3$H, —OSO$_3$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety. $R^2$ is independently halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —OSO$_3$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety, or wherein if z2 an integer of 2 to 5, two $R^2$ substituents attached to adjacent ring carbons are optionally joined to form a substituted or unsubstituted aryl or substituted or unsubstituted heteroaryl. $R^{3A}$ and $R^{3B}$ are independently hydrogen, —C(NH)NH$_2$, —C(NH)$R^{3D}$, —C(N$R^{3C}$)NH$_2$, —C(N$R^{3C}$)$R^{3D}$, —C(NCN)NH$_2$, NH, NH$_2$, —C(NH)NH$R^{3D}$, —C(N$R^{3C}$)NH$R^{3D}$, —C(NCN)NH$R^{3D}$, substituted or unsubstituted cycloalkyl, substituted or unsubstituted heterocycloalkyl, substituted or unsubstituted aryl, substituted or unsubstituted heteroaryl, or $R^{3A}$ and $R^{3B}$ are optionally joined to form a substituted or unsubstituted heterocycloalkyl or substituted or unsubstituted heteroaryl. $R^{3C}$ and $R^{3D}$ are independently hydrogen, halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^4$ is independently hydrogen or unsubstituted $C_1$-$C_5$ alkyl. z1 is an integer from 1 to 9. z2 is an integer from 1 to 5.

In another aspect is a method of detecting αvβ1 expression in a cell. The method includes contacting a cell with an αvβ1-specific moiety and allowing the αvβ1-specific moiety to bind to the cell. The αvβ1-specific moiety is detected, thereby detecting αvβ1 expression in a cell.

In another aspect is a method for determining whether a test compound inhibits αvβ1 integrin binding. The method includes combining an αvβ1 integrin-expressing cell and a test compound in a reaction vessel covalently attached to an αvβ1 ligand. The method includes determining whether the αvβ1 integrin-expressing cell binds to the ligand in the presence of the test compound, thereby determining whether the test compound inhibits αvβ1 integrin binding.

In another aspect is a method of inhibiting TGFβ activation. The method includes contacting a cell expressing αvβ1 integrin with an αvβ1-inhibitor and allowing the compound to bind to αvβ1 in the presence of latent TGFβ. The method includes comparing a level of activated TGFβ to a control to thereby identify a level of TGFβ activation and identify inhibition of TGFβ activation.

BRIEF DESCRIPTION OF THE DRAWINGS

FIGS. 1A-1E. FIG. 1A: design principle of αvβ1 integrin inhibitor from combination of positively charged guanidine moiety in αvβ3 integrin inhibitor (blue shading) and sulfonamidoproline moiety in α2β1 integrin inhibitor. (shading) FIG. 1B: structures of αvβ1 integrin specific inhibitor c8. FIG. 1C: docking model of αvβ1 integrin inhibitor c6 bound to αvβ1 integrin where α and β subunits are respectively shaded. The model predicted that a linker length of n=3 or 4 would have highest affinity. FIG. 1D: dose dependent cell adhesion assay of c8 against all αv and related integrins. Data are expressed in mean±S.E.M. FIG. 1E: Curve-fitted IC$_{50}$ (±S.E.M) of c8 against RGD binding integrins in cell-adhesion assay.

FIG. 2A: Co-immunoprecipitation (IP) and western blot reveals expression of αvβ1 heterodimers in human and murine fibroblasts from the liver and lung. nhLu fb control (normal human lung fibroblasts from an uninjured control subject); IPF fb (lung fibroblasts isolated from a patient with idiopathic pulmonary fibrosis (IPF)); mLu fb (mouse lung fibroblasts); mLi fb (mouse hepatic stellate cells (liver fibroblasts); WI38 (diploid human lung fibroblast cell line); CHO WT (wild type chinese hamster ovary cells, which lack expression of β1); CHO αv (CHO cells with forced expression of αvβ1); hAT2 (human alveolar type II cells, which lack expression of β1); hPAEC (human pulmonary artery endothelial cells, which lack expression of β1). FIG. 2B: Wild type CHO cells (lacking αvβ1) adhere poorly, while CHO cells with forced expression of αvβ1 (CHO αv) and WI38 cells strongly adhere, to TGFβ1LAP. FIG. 2C: WI38 cell adhesion to 0.3 ug/ml TGFβ1LAP is inhibited by c8. FIG. 2D: c8 treatment reduced activation of TGFβ by cells expressing αvβ1. Fibroblasts (as indicated) were co-cultured with TGFβ reporter (PAIL-luciferase) cell line in the presence of a range of c8.

FIG. 3A: effects of c8 or c16 on murine fibrosis model. (liver). c8 or c16 (inactive control compound) delivered by Alzet pump beginning 3 weeks after intraperitoneal administration with oil (sham) or CCl$_4$ to induce liver fibrosis, treatment with c8 significantly reduced liver fibrosis, as determined by FIG. 3B Picrosirius red staining (collagen deposition) of liver tissue after olive oil (top panels) or $CCl_4$ treatment (bottom panels), FIG. 3C Digital image analysis quantification of collagen staining, and Hydroxyproline analysis. FIG. 3D effects of c8 or c16 on murine fibrosis model. (lung), c8 or c16 was continuously delivered to mice using Alzet pumps beginning 14 days after intra-tracheal instillation of bleomycin (Bleo) to induce pulmonary fibrosis, or water ($H_2O$; sham), treatment with C8 significantly reduced lung fibrosis, as determined by FIG. 3E Picrosirius red staining (collagen deposition) of lung tissue after olive oil (upper panels) or $CCl_4$ treatment (lower panels).

FIG. 4A: Representative liver (top panels) and lung (bottom panels) sections from mice treated with c16 or c8 after induced fibrotic injury stained for fibroblasts (PDGFR β) and phosphorylated Smad3 (pSmad3). FIG. 4B: Quantification of pSmad3 nuclear intensity within individual PDGFRβ+ cells documents a significant reduction in fibroblasts-specific pSmad3 in fibrotic mice treated with c8. P values from Student's t tests. Scale bar: 100 µm. Data are mean±S.E.M.

DETAILED DESCRIPTION OF THE INVENTION

Figure 1A:
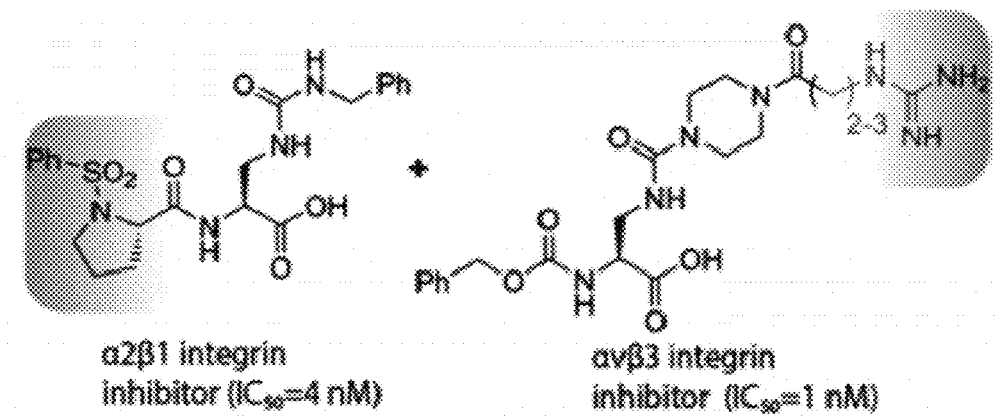
Figure 1B:
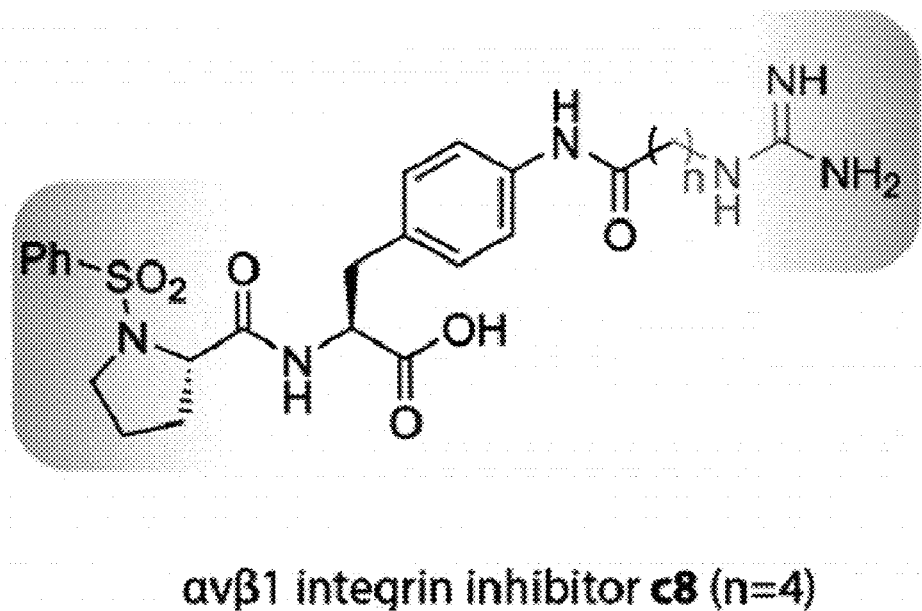
Figure 1C:
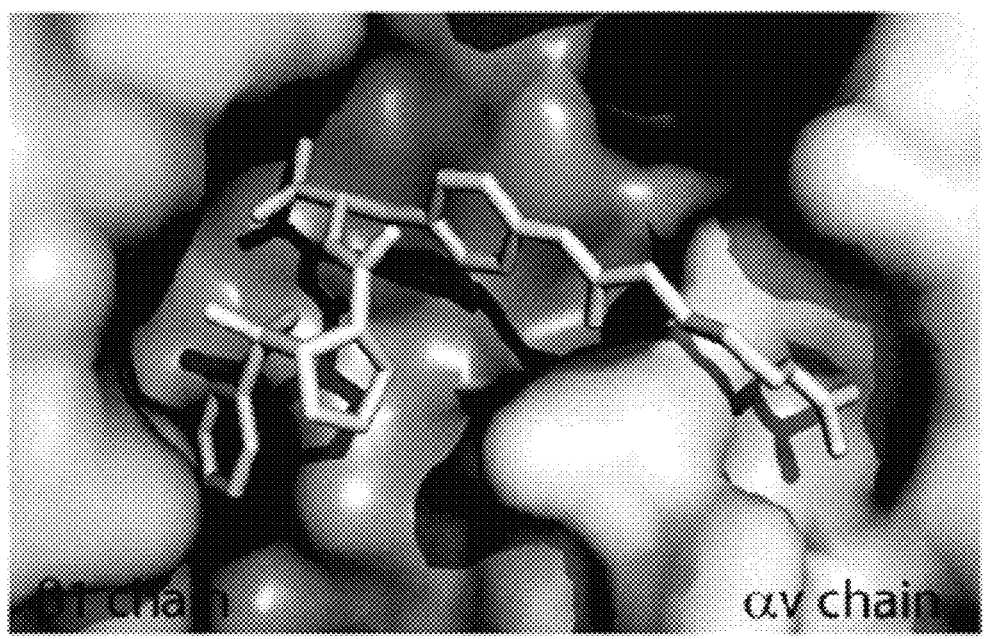
Figure 1D:
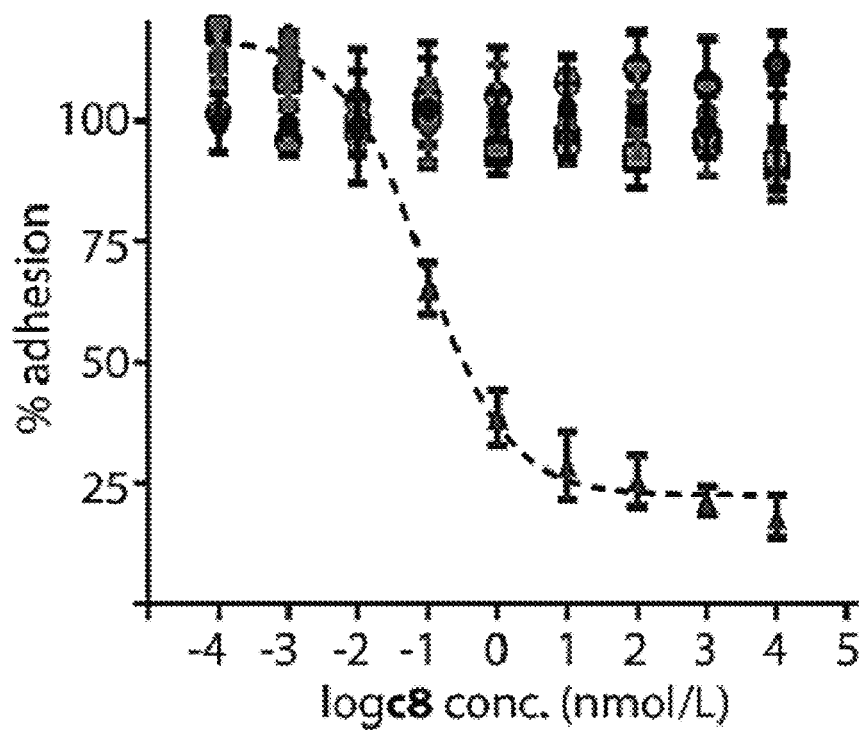
Figure 2A:
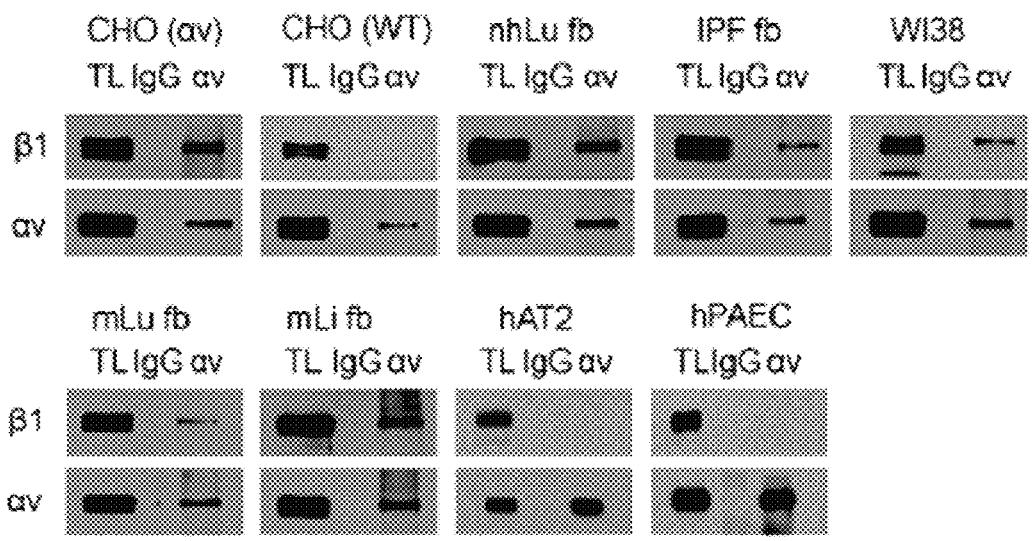
FIGS. 2A-2D. c8 inhibits αvβ1-mediated TGFβ activation.
Figure 2B:
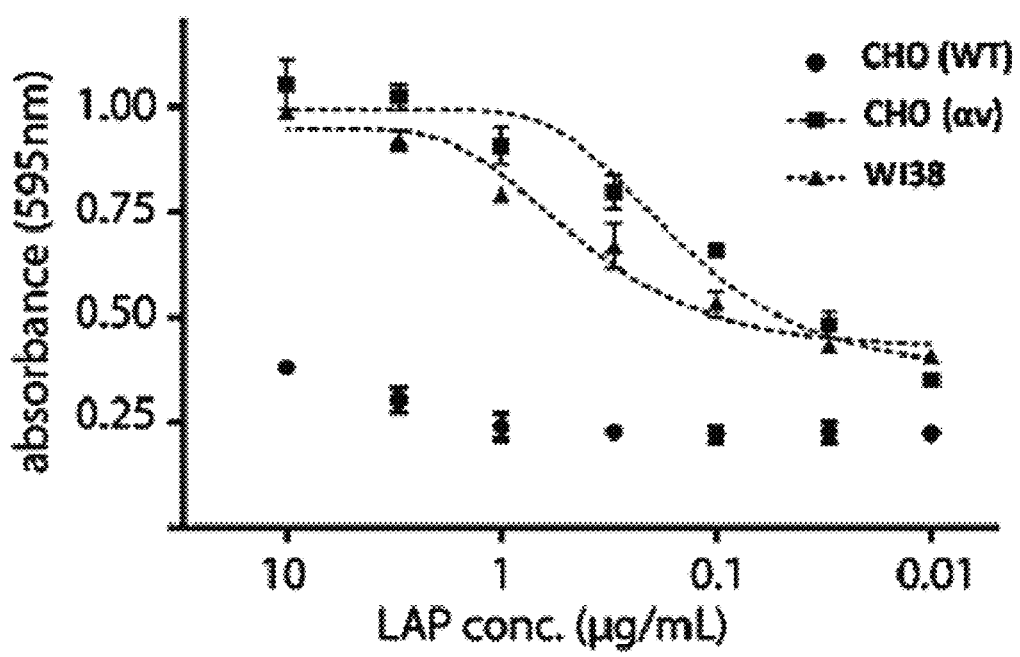
Figure 2C:
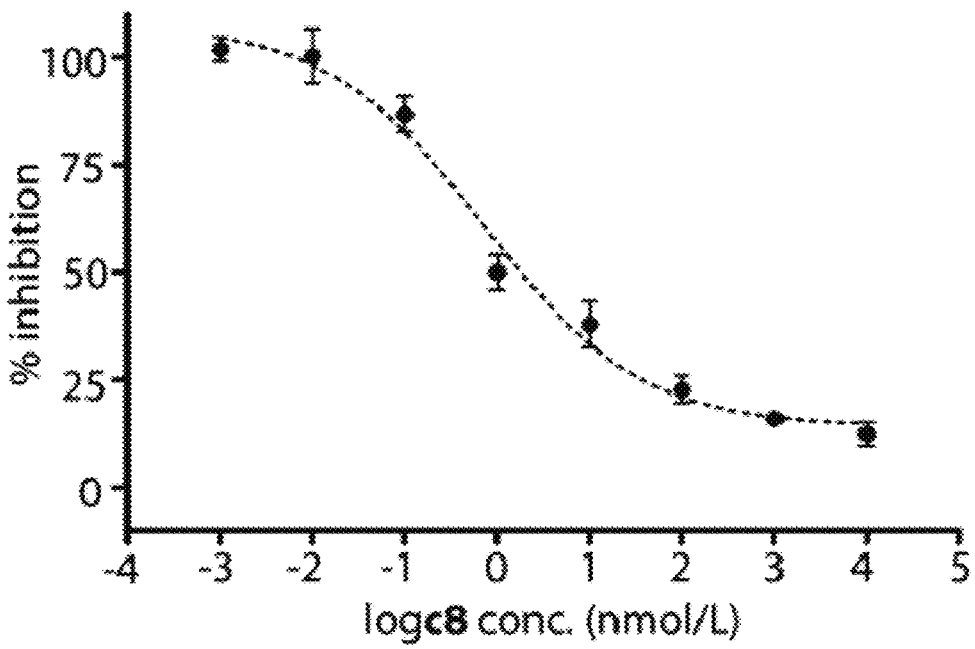
Figure 2D:
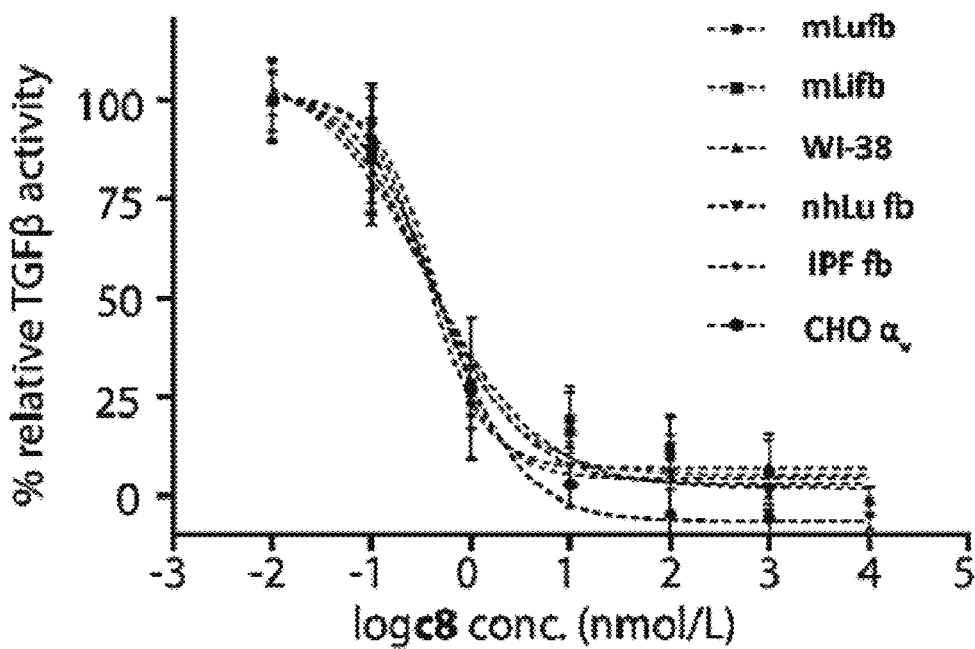
Figure 3A:
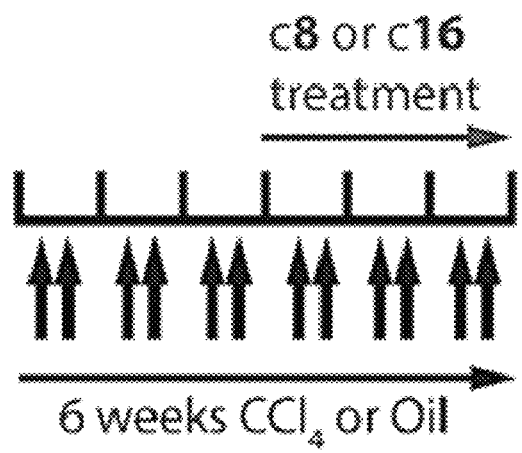
FIGS. 3A-3E.
Figure 3B:
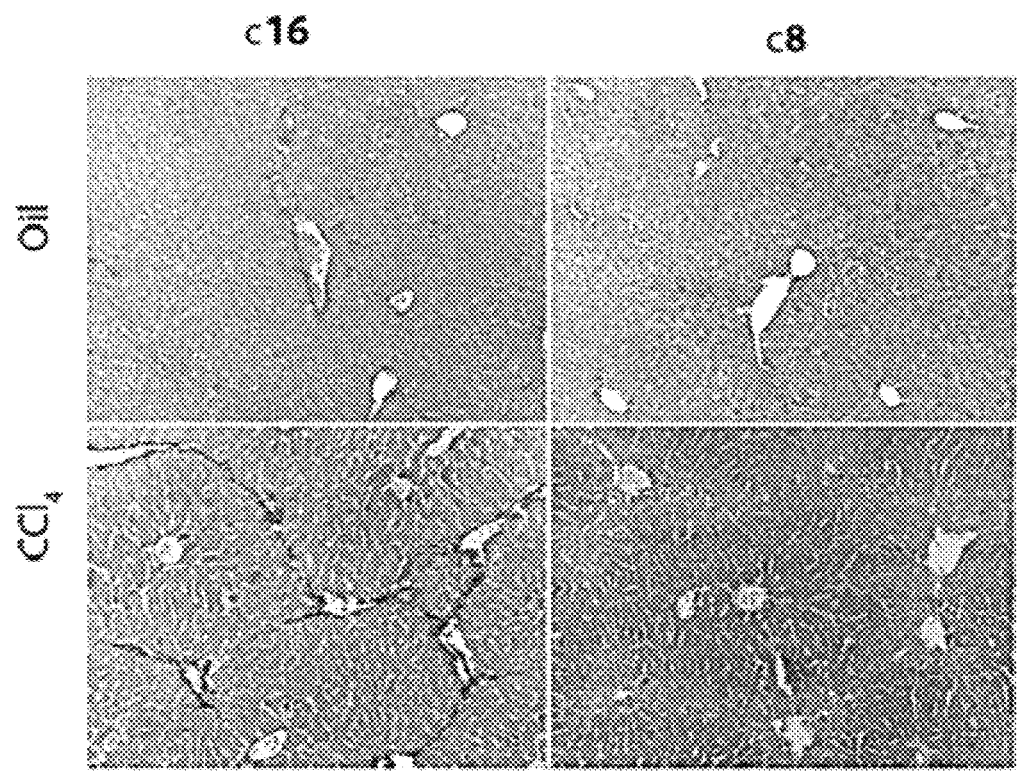
Figure 3C:
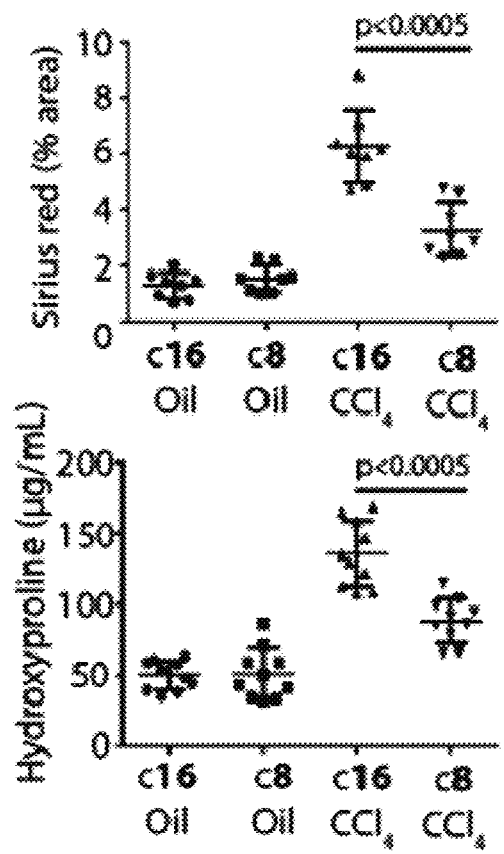
Figure 3D:
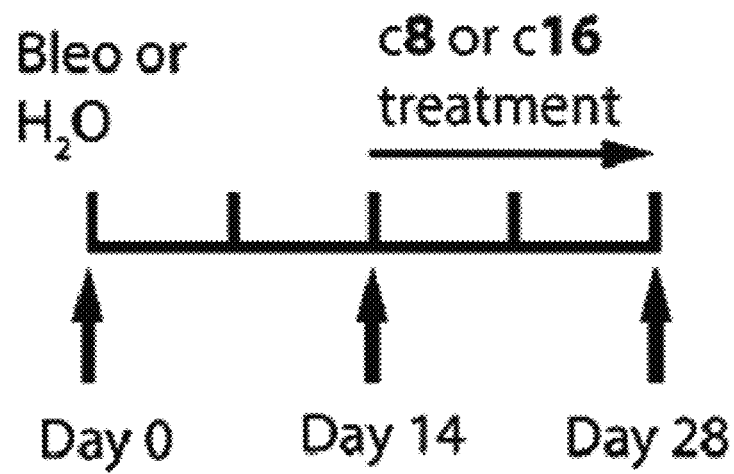
Figure 3E:
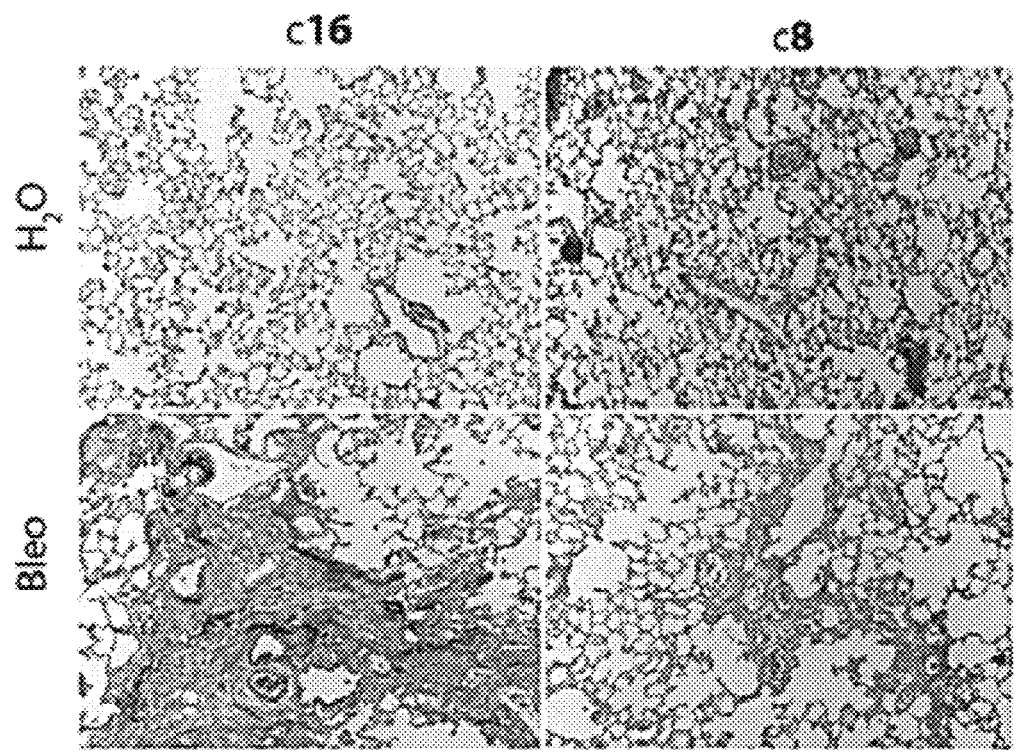
Figure 4A:
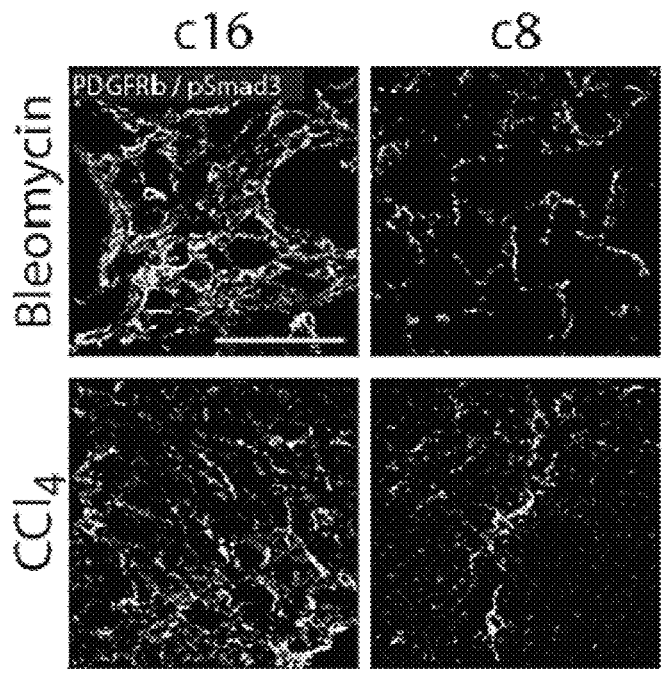
FIGS. 4A-4B.
Figure 4B:
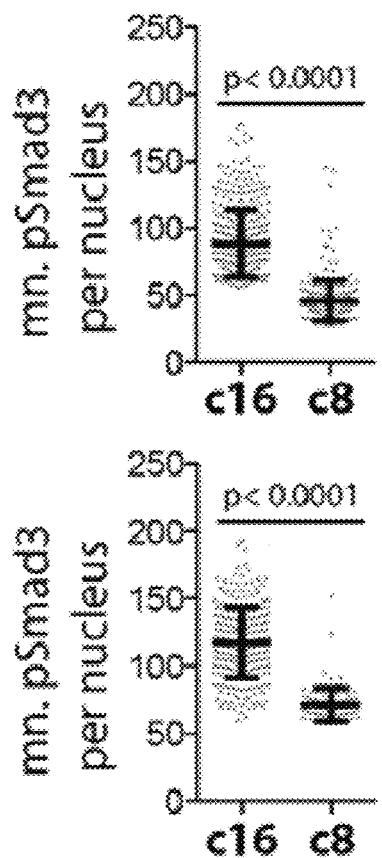
Figure 5:
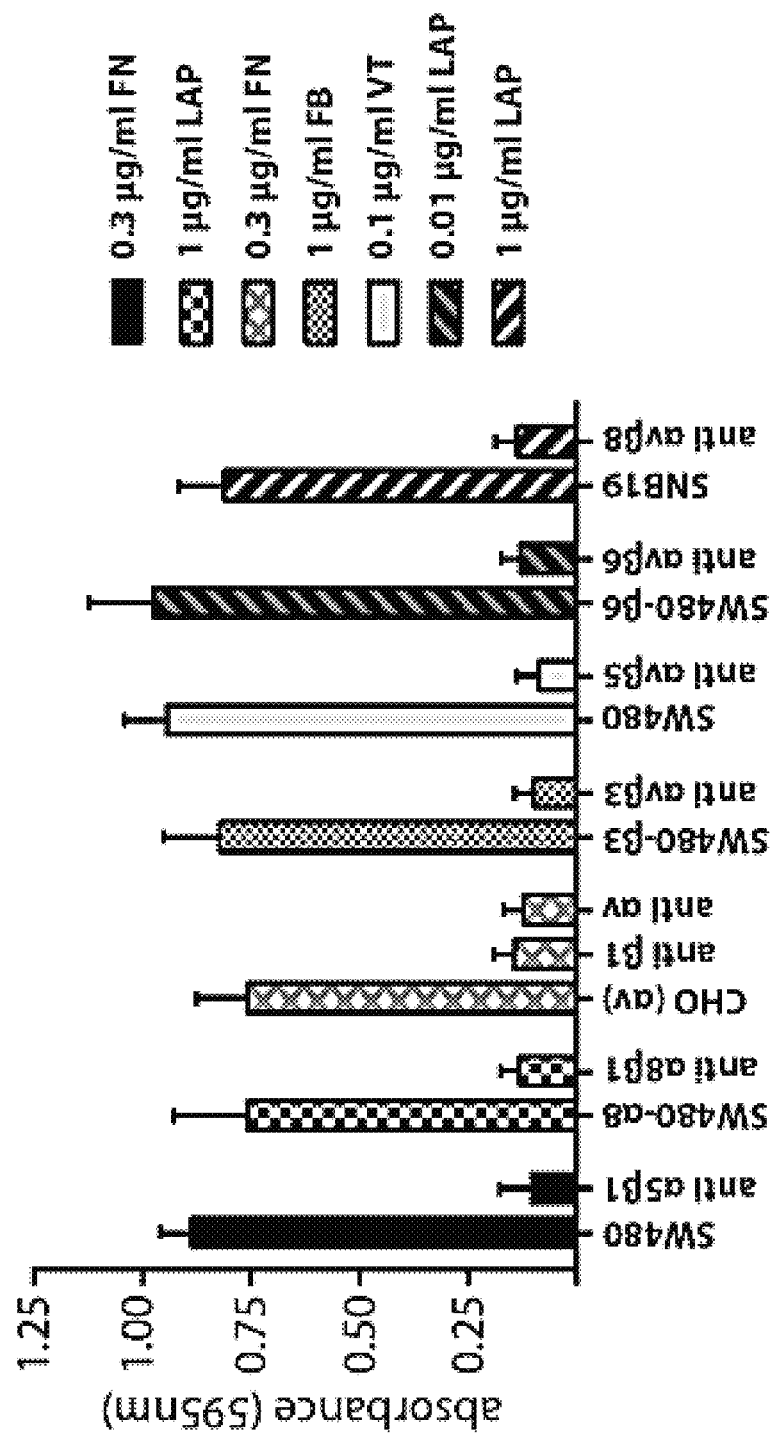
FIG. 5. Integrin specific antibodies inhibited cell adhesion assays using a panel of cell lines which express specific integrin (second column), comparing to without antibody (first column).
Figure 6:
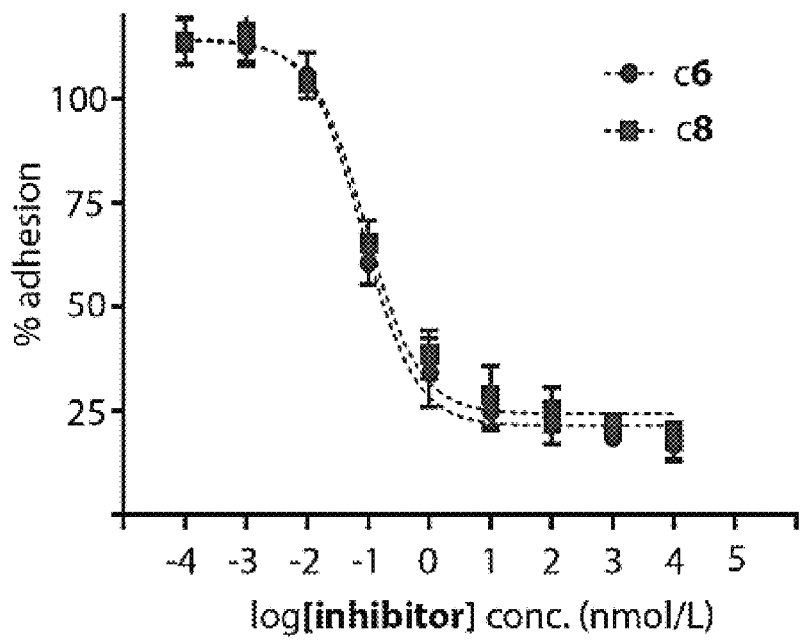
FIG. 6. c6 and c8 inhibited αvβ1-mediated cell adhesion to fibronectin.
Figure 7:
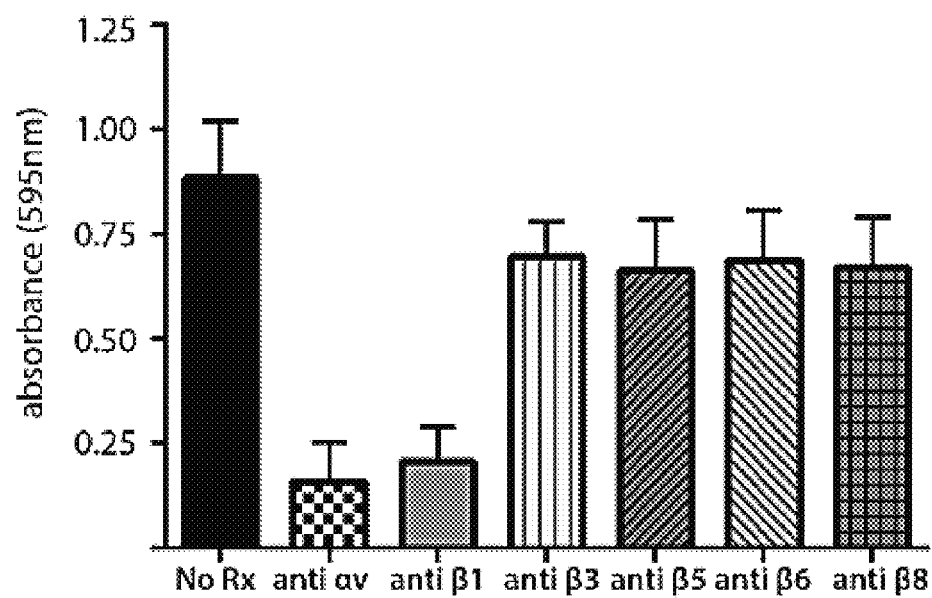
FIG. 7. Adhesion to LAP inhibited by antibodies to either β1 or αv, but not with antibodies to αvβ3, αvβ5, αvβ6 or αvβ8.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH₂O— is equivalent to —OCH₂—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl) methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH₂CH₂CH₂CH₂—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, B, As, and Si may be placed at any interior position of the heteroalkyl group or at the position at which the alkyl group is attached to the remainder of the molecule. Heteroalkyl is an uncyclized chain. Examples include, but are not limited to: —CH₂—CH₂—O—CH₃, —CH₂—CH₂—NH—CH₃, —CH₂—CH₂—N(CH₃)—CH₃, —CH₂—S—CH₂—CH₃, —CH₂—CH₂, —S(O)—CH₃, —CH₂—CH₂—S(O)₂—CH₃, —CH=CH—O—CH₃, —Si(CH₃)₃, —CH₂—CH=N—OCH₃, —CH=CH—N(CH₃)—CH₃, —O—CH₃, —O—CH₂—CH₃, and —CN. Up to two or three heteroatoms may be consecutive, such as, for example, —CH₂—NH—OCH₃ and —CH₂—O—Si(CH₃)₃.

Similarly, the term "heteroalkylene," by itself or as part of another substituent, means, unless otherwise stated, a divalent radical derived from heteroalkyl, as exemplified, but not limited by, —CH₂—CH₂—S—CH₂—CH₂— and —CH₂—S—CH₂—CH₂—NH—CH₂—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)₂R'— represents both —C(O)₂R'— and —R'C(O)₂—. As described above, heteroalkyl groups, as used herein, include those groups that are attached to the remainder of the molecule through a heteroatom, such as —C(O)R', —C(O)NR', —NR'R", —OR', —SR', and/or —SO₂R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heteroalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, unless otherwise stated, mean, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "〜〜" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

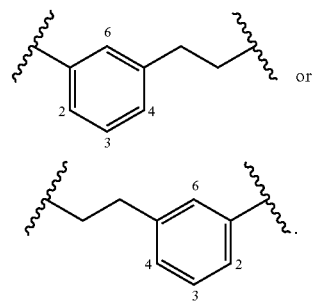

An alkylarylene moiety may be substituted (e.g. with a substituent group) on the alkylene moiety or the arylene linker (e.g. at carbons 2, 3, 4, or 6) with halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$OSO_3H$, —$SO_2NH_2$, —$NHNH_2$, —$ONH_2$, —NHC(O)$NHNH_2$, substituted or unsubstituted $C_1$-$C_5$ alkyl or substituted or unsubstituted 2 to 5 membered heteroalkyl). In embodiments, the alkylarylene is unsubstituted.

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R, —C(O)R', —$CO_2$R', —CONR'R", —OC(O)NR'R", —NR"C(O)R', —NR'—C(O)NR"R", —NR"C(O)$_2$R', —NR—C(NR'R"R''')=NR''', —NR—C(NR'R")=NR''', —S(O)R', —S(O)₂R', —S(O)₂NR'R", —NRSO₂R', —NR'NR"R''', —ONR'R", —NR'C(O)NR"NR'''R'''', —CN, —NO₂, —NR'SO₂R", —NR'C(O)R", —NR'C(O)—OR", —NR'OR", in a number ranging from zero to (2m'+1), where m' is the total number of carbon atoms in such radical. R, R', R", R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R', and R''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF₃ and —CH₂CF₃) and acyl (e.g., —C(O)CH₃, —C(O)CF₃, —C(O)CH₂OCH₃, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —CO₂R', —CONR'R", —OC(O)NR'R", —NR"C(O)R', —NR'—C(O)NR"R''', —NR"C(O)₂R', —NR—C(NR'R"R''')=NR'''', —NR—C(NR'R")=NR''', —S(O)R', —S(O)₂R', —S(O)₂NR'R", —NRSO₂R', —NR'NR"R''', —ONR'R", —NR'C(O)NR"NR'''R'''', —CN, —NO₂, —R', —N₃, —CH(Ph)₂, fluoro(C₁-C₄)alkoxy, and fluoro(C₁-C₄)alkyl, —NR'SO₂R", —NR'C(O)R", —NR'C(O)—OR", —NR'OR", in a number ranging from zero to the total number of open valences on the aromatic ring system; and where R', R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R''', and R'''' groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH₂)$_r$—B—, wherein A and B are independently —CRR'—, —O—, —NR—, —S—, —S(O)—, —S(O)₂—, —S(O)₂NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where s and d are independently integers of from 0 to 3, and X is —O—, —NR'—, —S—, —S(O)—, —S(O)₂—, or —S(O)₂NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) —OH, —NH₂, —SH, —CN, —CF₃, —NO₂, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:
  (i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, and heteroaryl, substituted with at least one substituent selected from:
    (a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and
    (b) alkyl, heteroalkyl, cycloalkyl, heterocycloalkyl, aryl, or heteroaryl, substituted with at least one substituent selected from: oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_3$-C$_8$ aryl, and each substituted or unsubstituted heteroaryl is a substituted or unsubstituted C$_3$-C$_8$ heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_3$-C$_7$ aryl, and each substituted or unsubstituted heteroaryl is a substituted or unsubstituted C$_3$-C$_7$ heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, and/or each substituted or unsubstituted heterocycloalkyl is a substituted or unsubstituted 3 to 8 membered heterocycloalkyl. In some embodiments of the compounds herein, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_8$ cycloalkylene, each substituted or unsubstituted heterocycloalkylene is a substituted or unsubstituted 3 to 8 membered heterocycloalkylene, each substituted or unsubstituted arylene is a substituted or unsubstituted C$_3$-C$_8$ arylene, and/or each substituted or unsubstituted heteroaryl is a substituted or unsubstituted C$_3$-C$_8$ heteroarylene.

In some embodiments, each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_3$-C$_7$ aryl, and/or each substituted or unsubstituted heteroaryl is a substituted or unsubstituted C$_3$-C$_7$ heteroaryl. In some embodiments, each substituted or unsubstituted alkylene is a substituted or unsubstituted C$_1$-C$_8$ alkylene, each substituted or unsubstituted heteroalkylene is a substituted or unsubstituted 2 to 8 membered heteroalkylene, each substituted or unsubstituted cycloalkylene is a substituted or unsubstituted C$_3$-C$_7$ cycloalkylene, each substituted or unsubstituted heterocycloalkylene is a substituted or unsubstituted 3 to 7 membered heterocycloalkylene, each substituted or unsubstituted arylene is a substituted or unsubstituted C$_3$-C$_7$ arylene, and/or each substituted or unsubstituted heteroarylene is a substituted or unsubstituted C$_3$-C$_7$ heteroarylene.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those that are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}$H), iodine-125 ($^{125}$I), or carbon-14 ($^{14}$C). All isotopic variations of the compounds of the present invention, whether radioactive or not, are encompassed within the scope of the present invention.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

A "detectable moiety" as used herein refers to a moiety that can be covalently or noncovalently attached to a compound or biomolecule that can be detected for instance, using techniques known in the art. In embodiments, the detectable moiety is covalently attached. The detectable moiety may provide for imaging of the attached compound or biomolecule. The detectable moiety may indicate the contacting between two compounds. Exemplary detectable moieties are fluorophores, antibodies, reactive dies, radiolabeled moieties, magnetic contrast agents, and quantum dots. Exemplary fluorophores include fluorescein, rhodamine, GFP, coumarin, FITC, Alexa fluor, Cy3, Cy5, BODIPY, and cyanine dyes. Exemplary radionuclides include Fluorine-18, Gallium-68, and Copper-64. Exemplary magnetic contrast agents include gadolinium, iron oxide and iron platinum, and manganese.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

A "test compound" as used herein refers to an experimental compound used in a screening process to identify activity, non-activity, or other modulation of a particularized biological target or pathway.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

An "$\alpha v \beta 1$-inhibitor" as used herein refers to a composition (e.g. a compound, nucleic acid, polynucleotide, peptide, protein, or antibody) capable of reducing the activity of $\alpha v \beta 1$ integrin when compared to a control compound (e.g. known to have no reduction in $\alpha v \beta 1$ integrin activity) or the absence of the $\alpha v \beta 1$-inhibitor compound. An "$\alpha v \beta 1$-inhibitor compound" refers to a compound (e.g. compounds described herein) that reduce the activity of $\alpha v \beta 1$ integrin when compared to a control, such as absence of the compound or a compound with known inactivity. An "$\alpha v \beta 1$-inhibitor-antibody" refers to an antibody that reduces the activity of $\alpha v \beta 1$ integrin when compared to a control (e.g. the absence of the antibody). An "$\alpha v \beta 1$-inhibitor-RGD peptide" refers to a RGD-peptide that reduces the activity of $\alpha v \beta 1$ integrin when compared to a control (e.g. the absence of the peptide).

An "$\alpha v \beta 1$-specific moiety", "specific," "specifically", "specificity", or the like of a composition (e.g. a compound, nucleic acid, polynucleotide, peptide, protein, or antibody) refers to the composition's ability to discriminate between particular molecular targets to a significantly greater extent than other proteins in the cell (e.g. a compound having specificity towards $\alpha v \beta 1$ integrin binds to $\alpha v \beta 1$ integrin whereas the same compound displays little-to-no binding to other integrins such as $\alpha 5 \beta 1$, $\alpha 8 \beta 1$, $\alpha v \beta 3$, $\alpha v \beta 5$, or $\alpha v \beta 6$). An "$\alpha v \beta 1$-specific compound". An "$\alpha v \beta 1$-specific compound" refers to a compound (e.g. compounds described herein) having specificity towards $\alpha v \beta 1$ integrin. An "$\alpha v \beta 1$-specific antibody" refers to an antibody having specificity towards $\alpha v \beta 1$ integrin. An "$\alpha v \beta 1$-specific RGD peptide" refers to a RGD peptide having specificity towards $\alpha v \beta 1$ integrin.

The terms "$\alpha v \beta 1$-selective," "selective," or "selectivity" or the like of a compound refers to the composition's (e.g. a compound, nucleic acid, polynucleotide, peptide, protein, or antibody) ability to cause a particular action in a particular molecular target (e.g. a compound having selectivity toward $\alpha v \beta 1$ integrin would inhibit only $\alpha v \beta 1$). An "$\alpha v \beta 1$-selective compound" refers to a compound (e.g. compounds described herein) having selectivity towards $\alpha v \beta 1$ integrin. An "$\alpha v \beta 1$-selective antibody" refers to an antibody having selectivity towards $\alpha v \beta 1$ integrin. An "$\alpha v \beta 1$-selective RGD peptide" refers to a RGD peptide having selectivity towards $\alpha v \beta 1$ integrin.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A polypeptide, or a cell is "recombinant" when it is artificial or engineered, or derived from or contains an artificial or engineered protein or nucleic acid (e.g. non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

"RGD peptide" as used herein refers to a tripeptide comprising Arg., Gly., and Asp. RGD peptides typically act as recognition sequences for integrins and in some embodiments, promote cellular adhesion via integrin binding. RGD peptides as used herein refers to naturally occurring RGD sequences, RGD mimetics (e.g. substitutions of R, G, or D with non-proteinogenic amino acids), RGD peptides covalently bound to a targeting-moiety (e.g. a molecule for targeting the peptide to a specific integrin or specific location in a cell or organism), and cyclized RGD peptides of embodiments described herein. Exemplary RGD peptides include Arg-Gly-Asp, Asp-Gly-Arg, cyclo-Gly-Arg-Gly-Asp-Ser-Pro, and KGD peptides include Cys-Asn-Thr-Leu-Lys-Gly-Asp-Cys and Asn-Thr-Leu-Lys-Gly-Asp, and those found in Ann. Rev. Cell & Dev. Biol., 1996, November, Vol. 12: 697-715 and Proteins, 1992 December; 14(4):509-15.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$—$C_H1$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

For preparation of suitable antibodies of the invention and for use according to the invention, e.g., recombinant, monoclonal, or polyclonal antibodies, many techniques known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332: 323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As defined herein, the term "activation", "activate", "activating" and the like in reference to a protein refers to conversion of a protein into a biologically active derivative from an initial inactive or deactivated state. The terms reference activation, or activating, sensitizing, or up-regulating signal transduction or enzymatic activity or the amount of a protein decreased in a disease.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition refers means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation).

Integrins are transmembrane proteins that mediate interactions between adhesion molecules on adjacent cells and/or the extracellular matrix (ECM). Integrins have diverse roles in several biological processes including, for example, cell migration during development and wound healing, cell differentiation, and apoptosis. Integrins typically exist as heterodimers consisting of a subunits (about 120-170 kDa in size) and β subunits (about 90-100 kDa in size).

The terms "αvβ1" and "αvβ1 integrin" refer to an integrin comprised of αv subunit and a β1 subunit and is used according to its common, ordinary meaning. "αvβ1" refers to proteins of the same or similar names, homologs, isoforms, and functional fragments thereof, so long as such fragments retain αvβ1 integrin activity. The term includes any recombinant or naturally-occurring form of αvβ1, or an αvβ1 preprotein, or variants thereof that maintain αvβ1 activity (e.g. within at least 30%, 40%, 50%, 60%, 70%, 80%, 90%, 95%, or 100% activity compared to wildtype αvβ1). In embodiments, αvβ1 has the amino acid sequence set forth in for example GI: 4504763.

Fibronectin is used according to its common, ordinary meaning and refers to proteins of the same or similar names, homologs, isoforms, and functional fragments thereof, so long as such fragments retain fibronectin activity. Fibronectin refers to glycoprotein dimers capable of binding integrins and mediating interactions between adhesion molecules in the ECM. The term includes any recombinant or naturally-occurring form of fibronectin, or a fibronectin preprotein, or variants thereof that maintain fibronectin activity (e.g. within at least 30%, 40%, 50%, 60%, 70%, 80%, 90%, 95%, or 100% activity compared to wildtype fibronectin).

"TGF-β," "TGFβ" or "transforming growth factor β" is used according to its common and ordinary meaning. TGFβ refers to proteins of the same or similar names, homologs, isoforms, and functional fragments thereof known to have TGFβ activity.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The terms "disease" or "condition" refer to a state of being or health status of a patient or subject capable of being treated with the compounds or methods provided herein. The disease may be fibrosis, such as for example, pulmonary fibrosis, liver fibrosis, skin fibrosis, cardiac fibrosis, or kidney fibrosis.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, Pharmaceutical Dosage Forms (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal) compatible with the preparation. Parenteral administration includes, e.g., intravenous, intramuscular, intraarteriole, intradermal, subcutaneous, intraperitoneal, intraventricular, and intracranial. Other modes of delivery include, but are not limited to, the use of liposomal formulations, intravenous infusion, transdermal patches, etc.

"Co-administer" it is meant that a composition described herein is administered at the same time, just prior to, or just after the administration of one or more additional therapies. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered transdermally, by a topical route, or formulated as applicator sticks, solutions, suspensions, emulsions, gels, creams, ointments, pastes, jellies, paints, powders, and aerosols.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

As used herein "Fibrosis" refers to any disease or condition characterized by the formation of excess fibrous connective tissue. The formation of excess fibrous connective tissue may be in response to a reparative or reactive process. Fibrosis may be pulmonary fibrosis, liver fibrosis, myelofibrosis, skin fibrosis (e.g. nephrogenic systemic fibrosis and keloid fibrosis), mediastinal fibrosis, cardiac fibrosis, kidney fibrosis, stromal fibrosis, epidural fibrosis, or idiopathic fibrosis.

I. Compounds

Provided herein are compounds having the formula:

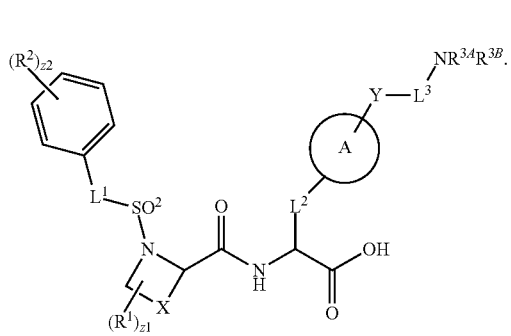

Ring A is cycloalkyl, heterocycloalkyl, aryl, or heteroaryl. $L^1$ and $L^2$ are independently a bond or substituted or unsubstituted $C_1$-$C_{10}$ alkylene. $L^3$ is a bond, substituted or unsubstituted $C_1$-$C_{10}$ alkylene, substituted or unsubstituted 2 to 10 membered heteroalkylene, substituted or unsubstituted cycloalkylene, substituted or unsubstituted heterocycloalkylene, or substituted or unsubstituted alkylarylene. X is a bond, —C—, —C—C—, —C=C—, —C—C—C—, —C=C—C—, —C—C=C—, —O—C—, —C—O—, —C—O—C—, —S—C—, —C—S—, —C—S—C—. Y is a bond, —C(O)N($R^4$)—, —O—, —C(O)O—, —S—, —N($SO_2$—$R^4$)—, —N(C(O)$R^4$)—, —N(C(O)O$R^4$)—, —(N$R^4$)C(O)—, —N($R^4$)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^1$ is independently halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$OSO_3H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety. $R^2$ is independently halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$OSO_3H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety, or wherein if z2 an integer of 2 to 5, two $R^2$ substituents attached to adjacent ring carbons are optionally joined to form a substituted or unsubstituted aryl or substituted or unsubstituted heteroaryl. $R^{3A}$ and $R^{3B}$ are independently hydrogen, —C(NH)$NH_2$, —C(NH)$R^{3D}$, —C(N$R^{3C}$)$NH_2$, —C(N$R^{3C}$)$R^{3D}$, —C(NCN)$NH_2$, NH, $NH_2$, —C(NH)$NHR^{3D}$, —C(N$R^{3C}$)$NHR^{3D}$, —C(NCN)$NHR^{3D}$, substituted or unsubstituted cycloalkyl, substituted or unsubstituted heterocycloalkyl, substituted or unsubstituted aryl, substituted or unsubstituted heteroaryl, or $R^{3A}$ and $R^{3B}$ are optionally joined to form a substituted or unsubstituted heterocycloalkyl or substituted or unsubstituted heteroaryl. $R^{3C}$ and $R^{3D}$ are independently hydrogen, halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^4$ is independently hydrogen or unsubstituted $C_1$-$C_5$ alkyl. z1 is an integer from 1 to 9. z2 is an integer from 1 to 5. Where the compound includes more than one of a given R substituent, each of the R substituents are optionally different. For example, where the compound includes more than one $R^1$ substituent, each $R^1$ is optionally different. Likewise, where the compound includes more than one $R^2$ substituent, each $R^2$ is optionally different.

In another aspect is a compound having the formula:

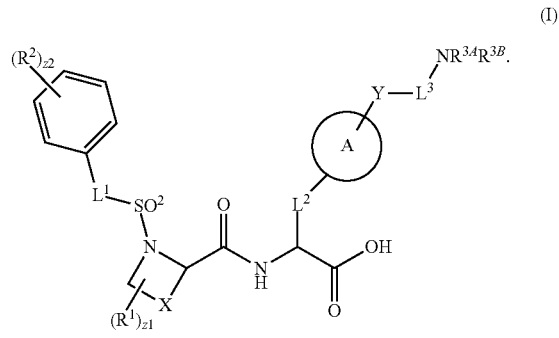

Ring A is cycloalkyl, heterocycloalkyl, aryl, or heteroaryl. $L^1$ and $L^2$ are independently a bond or substituted or unsubstituted $C_1$-$C_{10}$ alkylene. $L^3$ is a bond, substituted or unsubstituted $C_1$-$C_{10}$ alkylene, substituted or unsubstituted 2 to 10 membered heteroalkylene, or substituted or unsubstituted alkylarylene. X is a bond, —C—, —C—C—, —C=C—, —C—C—C—, —C=C—C—, —C—C=C—, —O—C—, —C—O—, —C—O—C—, —S—C—, —C—S—, —C—S—C—. Y is a bond, —C(O)N($R^4$)—, —O—, —C(O)O—, —S—, —N($SO_2$—$R^4$)—, —N(C(O)$R^4$)—, —N(C(O)O$R^4$)—, —(N$R^4$)C(O)—, —N($R^4$)—, substituted or unsubstituted heterocycloalkylene, substituted or unsubstituted arylene, or substituted or unsubstituted heteroarylene. $R^1$ and $R^2$ are independently halogen, oxo, —$N_3$, —$CF_3$, —$CCl_3$, —$CBr_3$, —$CI_3$, —CN, —CHO, —OH, —COOH, —$CONH_2$, —$NO_2$, —SH, —$SO_2$, —$SO_2Cl$, —$SO_2CH_3$—$SO_3H$, —$OSO_3H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety. $R^{3A}$ and $R^{3B}$ are independently hydrogen, —C(NH)$NH_2$, —C(NCN)$NH_2$, substituted or unsubstituted cycloalkyl, substituted or unsubstituted heterocycloalkyl, substituted or unsubstituted aryl or substituted or unsubstituted heteroaryl or $R^{3A}$ and $R^{3B}$ are optionally joined to form substituted or unsubstituted heterocycloalkyl or substituted or unsubstituted heteroaryl. $R^4$ is independently hydrogen or unsubstituted $C_1$-$C_5$ alkyl. The symbol z1 is an integer from 1 to 9. The symbol z2 is an integer from 1 to 5. Where the compound includes more than one of a given R substituent, each of the R substituents are optionally different. For example, where the compound includes more than one $R^1$ substituent, each R¹ is optionally different. Likewise, where the compound includes more than one R² substituent, each R² is optionally different.

Ring A may be aryl. Ring A may be 5 or 6 membered aryl. Ring A may be phenyl. Ring A may be a 4 to 6 membered heterocycloalkyl. Ring A may be a 5 or 6 membered heterocycloalkyl. Ring A may be 5 membered heterocycloalkyl. Ring A may be a heterocycloalkyl such as, for example, pyrrolidine, imidazolidine, oxazolidine, thiazolidine, dioxolane, dithiolane, piperidine, morpholine, dioxane, or dithiane, aziridinyl, azetidinyl, substituted or unsubstituted azepinyl, oxiranyl, oxetanyl, tetrahydrofuranyl, or tetrahydropyranyl. Ring A may be a 6 membered heterocycloalkyl. Ring A may be heteroaryl. Ring A may be 5 or 6 membered heteroaryl. Ring a may be a heteroaryl such as, for example, pyridine, pyrrole, furan, thiophene, imidazole, pyrazole, oxazole, thiazole, pyran, thiopyrane, pyrazine, pyriminde, pyridazine, oxazine, thiazine, doxine, dithiine, azete, oxete, thiete, azirine, oxirene or thirene. Ring A may be pyridinyl.

$L^1$ may be a bond or substituted or unsubstituted $C_1$-$C_{10}$ alkylene. $L^1$ may be a bond or $R^5$-substituted or unsubstituted $C_1$-$C_{10}$ alkylene. $L^1$ may be a bond or substituted or unsubstituted $C_1$-$C_8$ alkylene. $L^1$ may be a bond or $R^5$-substituted or unsubstituted $C_1$-$C_8$ alkylene. $L^1$ may be a bond or substituted or unsubstituted $C_1$-$C_5$ alkylene. $L^1$ may be a bond or $R^5$-substituted $C_1$-$C_5$ alkylene. $L^1$ may be a bond or substituted or unsubstituted $C_1$-$C_3$ alkylene. $L^1$ may be a bond or $R^5$-substituted $C_1$-$C_3$ alkylene. $L^1$ may be a bond. $L^1$ may be unsubstituted methylene or unsubstituted ethylene. $L^1$ may be a unsubstituted methylene.

$L^2$ may be a bond or substituted or unsubstituted $C_1$-$C_{10}$ alkylene. $L^2$ may be a bond or $R^{5A}$-substituted or unsubstituted $C_1$-$C_{10}$ alkylene. $L^2$ may be a bond or substituted or unsubstituted $C_1$-$C_8$ alkylene. $L^2$ may be a bond or $R^{5A}$-substituted $C_1$-$C_8$ alkylene. $L^2$ may be a bond or substituted or unsubstituted $C_1$-$C_5$ alkylene. $L^2$ may be a bond or $R^{5A}$-substituted $C_1$-$C_5$ alkylene. $L^2$ may be a bond or substituted or unsubstituted $C_1$-$C_3$ alkylene. $L^2$ may be a bond or $R^{5A}$-substituted $C_1$-$C_3$ alkylene. $L^2$ may be a bond. $L^2$ may be $R^{5A}$-substituted or unsubstituted methylene or $R^{5A}$-substituted or unsubstituted ethylene. $L^2$ may be unsubstituted methylene or unsubstituted ethylene. $L^2$ may be unsubstituted methylene. $L^2$ may be $R^{5A}$-substituted methylene where $R^{5A}$ is independently hydrogen, halogen or methyl.

$R^5$ and $R^{5A}$ are independently hydrogen, halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$, —$SO_3H$, —$SO_4H$, —$SO_2NH_2$, —$NHNH_2$, —$ONH_2$, —$NHC(O)NHNH_2$, unsubstituted alkyl, unsubstituted heteroalkyl, unsubstituted cycloalkyl, unsubstituted heterocycloalkyl, unsubstituted aryl, or unsubstituted heteroaryl.

$L^3$ may be a bond or substituted or unsubstituted alkylene. $L^3$ may be substituted or unsubstituted $C_1$-$C_{10}$ alkylene. $L^3$ may be substituted $C_1$-$C_{10}$ alkylene. $L^3$ may be unsubstituted $C_1$-$C_{10}$ alkylene. $L^3$ may be $R^6$-substituted or unsubstituted $C_1$-$C_{10}$ alkylene. $L^3$ may be $R^6$-substituted alkylene. $L^3$ may be a bond or substituted or unsubstituted $C_1$-$C_8$ alkylene. $L^3$ may be substituted or unsubstituted $C_1$-$C_8$ alkylene. $L^3$ may be substituted $C_1$-$C_8$ alkylene. $L^3$ may be unsubstituted $C_1$-$C_8$ alkylene. $L^3$ may be $R^6$-substituted or unsubstituted $C_1$-$C_8$ alkylene. $L^3$ may be $R^6$-substituted $C_1$-$C_8$ alkylene. $L^3$ may be a bond or substituted or unsubstituted $C_1$-$C_5$ alkylene. $L^3$ may be substituted or unsubstituted $C_1$-$C_5$ alkylene. $L^3$ may be substituted $C_1$-$C_5$ alkylene. $L^3$ may be unsubstituted $C_1$-$C_5$ alkylene. $L^3$ may be $R^6$-substituted or unsubstituted $C_1$-$C_5$ alkylene. $L^3$ may be $R^6$-substituted $C_1$-$C_5$ alkylene. $L^3$ may be a bond or substituted or unsubstituted $C_1$-$C_3$ alkylene. $L^3$ may be substituted or unsubstituted $C_1$-$C_3$ alkylene. $L^3$ may be substituted $C_1$-$C_3$ alkylene. $L^3$ may be unsubstituted $C_1$-$C_3$ alkylene. $L^3$ may be $R^6$-substituted or unsubstituted $C_1$-$C_3$ alkylene. $L^3$ may be $R^6$-substituted $C_1$-$C_3$ alkylene. $L^3$ may be $R^6$-substituted $C_1$-$C_3$ alkylene, where $R^6$ is —NHC(O)$R^{6A}$ and $R^{6A}$ is as described herein. $L^3$ may be $R^6$-substituted $C_1$-$C_3$ alkylene, where $R^6$ is —NHC(O)$R^{6A}$ and $R^{6A}$ is —C(NCN)$R^{6C}$, —C(NH)$R^{6C}$, $R^{3C}$-substituted or unsubstituted alkyl, or $R^{6C}$-substituted or unsubstituted heteroalkyl.

$L^3$ may be substituted or unsubstituted 2 to 10 membered heteroalkylene. $L^3$ may be substituted 2 to 10 membered heteroalkylene. $L^3$ may be unsubstituted 2 to 10 membered heteroalkylene. $L^3$ may be $R^6$-substituted or unsubstituted 2 to 10 membered heteroalkylene. $L^3$ may be $R^6$-substituted 2 to 10 membered heteroalkylene. $L^3$ may be substituted or unsubstituted 2 to 8 membered heteroalkylene. $L^3$ may be substituted 2 to 8 membered heteroalkylene. $L^3$ may be unsubstituted 2 to 8 membered heteroalkylene. $L^3$ may be $R^6$-substituted or unsubstituted 2 to 8 membered heteroalkylene. $L^3$ may be $R^6$-substituted 2 to 8 membered heteroalkylene. $L^3$ may be substituted or unsubstituted 2 to 6 membered heteroalkylene. $L^3$ may be substituted 2 to 6 membered heteroalkylene. $L^3$ may be unsubstituted 2 to 6 membered heteroalkylene. $L^3$ may be $R^6$-substituted or unsubstituted 2 to 6 membered heteroalkylene. $L^3$ may be $R^6$-substituted 2 to 6 membered heteroalkylene.

$L^3$ may be substituted or unsubstituted $C_3$-$C_6$ cycloalkylene. $L^3$ may be substituted $C_3$-$C_6$ cycloalkylene. $L^3$ may be unsubstituted $C_3$-$C_6$ cycloalkylene. $L^3$ may be $R^6$-substituted or unsubstituted $C_3$-$C_6$ cycloalkylene. $L^3$ may be $R^6$-substituted $C_3$-$C_6$ cycloalkylene. $L^3$ may be substituted or unsubstituted $C_3$ cycloalkylene. $L^3$ may be $R^6$-substituted or unsubstituted $C_3$ cycloalkylene. $L^3$ may be unsubstituted $C_3$ cycloalkylene. $L^3$ may be substituted or unsubstituted $C_4$ cycloalkylene. $L^3$ may be $R^6$-substituted or unsubstituted $C_4$ cycloalkylene. $L^3$ may be unsubstituted $C_4$ cycloalkylene. $L^3$ may be substituted or unsubstituted $C_5$ cycloalkylene. $L^3$ may be $R^6$-substituted or unsubstituted $C_5$ cycloalkylene. $L^3$ may be unsubstituted $C_5$ cycloalkylene. $L^3$ may be substituted or unsubstituted $C_6$ cycloalkylene. $L^3$ may be $R^6$-substituted or unsubstituted $C_6$ cycloalkylene. $L^3$ may be unsubstituted $C_6$ cycloalkylene.

$L^3$ may be substituted or unsubstituted alkylarylene (e.g. substituted or unsubstituted on the alkylene moiety or the arylene linker). $L^3$ may be unsubstituted alkylarylene. $L^3$ may be $R^6$-substituted or unsubstituted alkylarylene (e.g. $R^6$-substituted or unsubstituted on the alkylene moiety or the arylene linker). $L^3$ may be $R^6$-substituted alkylarylene. $L^3$ may be unsubstituted oxoalkylene or unsubstituted oxoheteroalkylene.

$R^6$ is hydrogen, halogen, oxo, —$N_3$, —$CF_3$, —$CCl_3$, —$CBr_3$, —$CI_3$, —CN, —COR$^{6A}$, —OR$^{6A}$, —NR$^{6A}$R$^{6B}$, COOR$^{6A}$, —CONR$^{6A}$R$^{6B}$, —NHC(O)R$^{6A}$, —NO$_2$, —SR$^{6A}$, —SO$_2$, —SO$_n$$_6$R$^{6A}$, —NHNR$^{6A}$R$^{6B}$, —ONR$^{6A}$R$^{6B}$, NHC(O)NHNR$^{6A}$R$^{6B}$, $R^{6A}$— substituted or unsubstituted alkyl, $R^{6A}$-substituted or unsubstituted heteroalkyl, $R^{6A}$-substituted or unsubstituted cycloalkyl, $R^{6A}$-substituted or unsubstituted heterocycloalkyl, $R^{6A}$-substituted or unsubstituted aryl, or $R^{6A}$-substituted or unsubstituted heteroaryl. The symbol n6 is 2, 3, or 4.

$R^6$ may be hydrogen, halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$— $SO_3H$, —$SO_4H$, —$SO_2NH_2$, —$NHNH_2$, —$ONH_2$, —NHC (O)NHNH$_2$, unsubstituted alkyl, unsubstituted heteroalkyl, unsubstituted cycloalkyl, unsubstituted heterocycloalkyl, unsubstituted aryl, or unsubstituted heteroaryl.

R$^{6A}$ is hydrogen, halogen, oxo, —N$_3$, —CF$_3$, —CCl$_3$, —CBr$_3$, —CI$_3$, —CN, —COR$^{6C}$, —OR$^{6C}$, —NHR$^{6C}$, —COOR$^{6C}$, —CONHR$^{6C}$, —NO$_2$, —SR$^{6C}$, —SO$_2$, —SO$_2$R$^{6C}$, —NHNHR$^{6C}$, —ONHR$^{6C}$, —NHC(O)NHNHR$^{6C}$, —C(NCN)R$^{6C}$, —C(NH)R$^{6C}$, R$^{6C}$-substituted or unsubstituted alkyl, R$^{6C}$-substituted or unsubstituted heteroalkyl, R$^{6C}$-substituted or unsubstituted cycloalkyl, R$^{6C}$-substituted or unsubstituted heterocycloalkyl, R$^{6C}$-substituted or unsubstituted aryl, R$^{6C}$-substituted or unsubstituted heteroaryl, or a detectable moiety.

R$^{6A}$ may be hydrogen, halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, —C(NCN)R$^{6C}$, —C(NH)R$^{6C}$, R$^{6C}$-substituted or unsubstituted alkyl, R$^{6C}$-substituted or unsubstituted heteroalkyl, R$^{6C}$-substituted or unsubstituted cycloalkyl, R$^{6C}$-substituted or unsubstituted heterocycloalkyl, R$^{6C}$-substituted or unsubstituted aryl, R$^{6C}$-substituted or unsubstituted heteroaryl, or a detectable moiety.

R$^{6C}$ is hydrogen, halogen, oxo, —N$_3$, —CF$_3$, —CCl$_3$, —CBr$_3$, —CI$_3$, —CN, —COR$^{6D}$, —OR$^{6D}$, —NR$^{6D}$R$^{6E}$, —COOR$^{6D}$, —CONR$^{6D}$R$^{6E}$, —NHC(O)R$^{6D}$, —NO$_2$, —SR$^{6D}$, —SO$_{n6}$R$^{6D}$, —NHNR$^{6D}$R$^{6E}$, —ONR$^{6D}$R$^{6E}$, —NHC(O)NHNR$^{6D}$R$^{6E}$, —C(NCN)R$^{6D}$, —C(NH)R$^{6D}$, R$^{6F}$-substituted or unsubstituted alkyl, R$^{6F}$-substituted or unsubstituted heteroalkyl, R$^{6F}$-substituted or unsubstituted cycloalkyl, R$^{6F}$-substituted or unsubstituted heterocycloalkyl, R$^{6F}$-substituted or unsubstituted aryl, or R$^{6F}$-substituted or unsubstituted heteroaryl. The symbol n6 is 2, 3, or 4.

R$^{6C}$ may be hydrogen, halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, unsubstituted alkyl, unsubstituted heteroalkyl, unsubstituted cycloalkyl, unsubstituted heterocycloalkyl, unsubstituted aryl, or unsubstituted heteroaryl.

R$^{6F}$ is hydrogen, halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety. R$^{6F}$ may be unsubstituted alkyl, unsubstituted heteroalkyl, unsubstituted cycloalkyl, unsubstituted heterocycloalkyl, unsubstituted aryl, unsubstituted heteroaryl, or a detectable moiety.

R$^{6F}$ may be hydrogen, halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, R$^{6G}$-substituted or unsubstituted alkyl, R$^{6G}$-substituted or unsubstituted heteroalkyl, R$^{6G}$-substituted or unsubstituted cycloalkyl, R$^{6G}$-substituted or unsubstituted heterocycloalkyl, R$^{6G}$-substituted or unsubstituted aryl, R$^{6G}$-substituted or unsubstituted heteroaryl, or a detectable moiety.

R$^{6B}$, R$^{6D}$, R$^{6E}$, and R$^{6G}$ are independently hydrogen, halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, unsubstituted alkyl, unsubstituted heteroalkyl, unsubstituted cycloalkyl, unsubstituted heterocycloalkyl, unsubstituted aryl, unsubstituted heteroaryl, or a detectable moiety.

X may be —C—C—, —C=C—, —O—C—, —C—O—, —C—O—C—, —C—S—, —S—C, or —C—S—C—. X may be a C$_5$ or C$_6$ heterocycloalkyl. A person having ordinary skill in the art will immediately recognize that the compound of Formula I requires each "—C—" within X to be independently substituted with hydrogen or R$^1$ (e.g. —C(R$^1$)H— or —C(R$^1$)$_2$— or —CH$_2$—) to fill the carbon valency, wherein each R$^1$ is optionally different in keeping with Formula I. Further, one skilled in the art would understand that heteroatoms (e.g. S) within the compound of formula (I) may also be substituted with Win keeping with the normal rules of chemical valency (e.g. —C—S(R$^1$)$_t$— or —S(R$^1$)$_t$—C— or —C—S(R$^1$)$_t$—C—, where the symbol t is an integer of 2, 3, or 4; and where t may be 2). XR$^1$ is as described herein, including embodiments thereof. X may be —C—C—. X may be —C—S— (e.g. a thiazolidinyl). X may be —C—O— (e.g. a oxazolidinyl). X may be —C=C—. X may be —C—O—C—. X may be —C—S—C—. In embodiments, when X is —C—C—, the symbol z1 is 6 or 7. In embodiments, when X is —C—C—, the symbol z1 is 6. In embodiments, when X is —C—C—, the symbol z1 is 7. In embodiments, when X is —C—S—, the symbol z1 is 4 or 5. In embodiments, when X is —C—S—, the symbol z1 is 4. In embodiments, when X is —C—S—, the symbol z1 is 5. In embodiments, when X is —C—O—, the symbol z1 is 4 or 5. In embodiments, when X is —C—S—, the symbol z1 is 4. In embodiments, when X is —C—O—, the symbol z1 is 5. The symbol z2 may be 5.

R$^1$ may independently be hydrogen, halogen, oxo, —CF$_3$, —CCl$_3$, —CBr$_3$, —CI$_3$, —CN, —OH, or —NH$_2$. R$^1$ may independently be independently hydrogen, halogen, oxo, N$_3$, —CF$_3$, —CCl$_3$, —CBr$_3$, —CI$_3$, —CN, —OH, —NH$_2$, —COOH, —CONH$_2$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$. R$^1$ may independently be hydrogen.

R$^1$ may be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^1$ may be R$^7$-substituted or unsubstituted alkyl, R$^7$-substituted or unsubstituted heteroalkyl, R$^7$-substituted or unsubstituted cycloalkyl, R$^7$-substituted or unsubstituted heterocycloalkyl, R$^7$-substituted or unsubstituted aryl, or R$^7$-substituted or unsubstituted heteroaryl.

R$^1$ may independently be substituted or unsubstituted C$_1$-C$_{10}$ alkyl. R$^1$ may independently be substituted C$_1$-C$_{10}$ alkyl. R$^1$ may independently be unsubstituted C$_1$-C$_{10}$ alkyl. R$^1$ may independently be R$^7$-substituted or unsubstituted C$_1$-C$_{10}$ alkyl. R$^1$ may independently be R$^7$-substituted C$_1$-C$_{10}$ alkyl. R$^1$ may independently be substituted or unsubstituted C$_1$-C$_8$ alkyl. R$^1$ may independently be substituted C$_1$-C$_8$ alkyl. R$^1$ may independently be unsubstituted C$_1$-C$_8$ alkyl. R$^1$ may independently be R$^7$-substituted or unsubstituted C$_1$-C$_8$ alkyl. R$^1$ may independently be R$^7$-substituted C$_1$-C$_8$ alkyl. R$^1$ may independently be substituted or unsubstituted C$_1$-C$_5$ alkyl. R$^1$ may independently be substituted C$_1$-C$_5$ alkyl. R$^1$ may independently be unsubstituted C$_1$-C$_5$ alkyl. R$^1$ may independently be R$^7$-substituted or unsubstituted C$_1$-C$_5$ alkyl. R$^1$ may independently be R$^7$-substituted C$_1$-C$_5$ alkyl. R$^1$ may independently be substituted or unsubstituted $C_1$-$C_3$ alkyl. $R^1$ may independently be substituted $C_1$-$C_3$ alkyl. $R^1$ may independently be unsubstituted $C_1$-$C_3$ alkyl. $R^1$ may independently be $R^7$-substituted or unsubstituted $C_1$-$C_3$ alkyl. $R^1$ may independently be $R^7$-substituted $C_1$-$C_3$ alkyl.

$R^1$ may independently be substituted or unsubstituted 2 to 10 membered heteroalkyl. $R^1$ may independently be substituted 2 to 10 membered heteroalkyl. $R^1$ may independently be unsubstituted 2 to 10 membered heteroalkyl. $R^1$ may independently be $R^7$-substituted or unsubstituted 2 to 10 membered heteroalkyl. $R^1$ may independently be $R^7$-substituted 2 to 10 membered heteroalkyl. $R^1$ may independently be substituted or unsubstituted 2 to 8 membered heteroalkyl. $R^1$ may independently be substituted 2 to 8 membered heteroalkyl. $R^1$ may independently be unsubstituted 2 to 8 membered heteroalkyl. $R^1$ may independently be $R^7$-substituted or unsubstituted 2 to 8 membered heteroalkyl. $R^1$ may independently be $R^7$-substituted 2 to 8 membered heteroalkyl. $R^1$ may independently be substituted or unsubstituted 2 to 6 membered heteroalkyl. $R^1$ may independently be substituted 2 to 6 membered heteroalkyl. $R^1$ may independently be unsubstituted 2 to 6 membered heteroalkyl. $R^1$ may independently be $R^7$-substituted or unsubstituted 2 to 6 membered heteroalkyl. $R^1$ may independently be $R^7$-substituted 2 to 6 membered heteroalkyl.

$R^1$ may independently be substituted or unsubstituted $C_3$-$C_8$ cycloalkyl. $R^1$ may independently be unsubstituted $C_3$-$C_8$ cycloalkyl. $R^1$ may independently be substituted $C_3$-$C_8$ cycloalkyl. $R^1$ may independently be $R^7$-substituted or unsubstituted $C_3$-$C_8$ cycloalkyl. $R^1$ may independently be $R^7$-substituted $C_3$-$C_8$ cycloalkyl. $R^1$ may independently be substituted or unsubstituted $C_3$-$C_6$ cycloalkyl. $R^1$ may independently be substituted $C_3$-$C_6$ cycloalkyl. $R^1$ may independently be unsubstituted $C_3$-$C_6$ cycloalkyl. $R^1$ may independently be $R^7$-substituted or unsubstituted $C_3$-$C_6$ cycloalkyl. $R^1$ may independently be $R^7$-substituted $C_3$-$C_6$ cycloalkyl. $R^1$ may independently be substituted or unsubstituted $C_4$-$C_6$ cycloalkyl. $R^1$ may independently be substituted $C_4$-$C_6$ cycloalkyl. $R^1$ may independently be unsubstituted $C_4$-$C_6$ cycloalkyl. $R^1$ may independently be $R^7$-substituted or unsubstituted $C_4$-$C_6$ cycloalkyl. $R^1$ may independently be $R^7$-substituted $C_4$-$C_6$ cycloalkyl. $R^1$ may independently be substituted or unsubstituted $C_5$ cycloalkyl. $R^1$ may independently be substituted $C_4$ cycloalkyl. $R^1$ may independently be unsubstituted $C_4$ cycloalkyl. $R^1$ may independently be $R^7$-substituted or unsubstituted $C_4$ cycloalkyl. $R^1$ may independently be $R^7$-substituted $C_4$ cycloalkyl. $R^1$ may independently be substituted or unsubstituted $C_5$ cycloalkyl. $R^1$ may independently be substituted $C_5$ cycloalkyl. $R^1$ may independently be unsubstituted $C_5$ cycloalkyl. $R^1$ may independently be $R^7$-substituted or unsubstituted $C_5$ cycloalkyl. $R^1$ may independently be $R^7$-substituted $C_5$ cycloalkyl. $R^1$ may independently be substituted or unsubstituted $C_6$ cycloalkyl. $R^1$ may independently be substituted $C_6$ cycloalkyl. $R^1$ may independently be unsubstituted $C_6$ cycloalkyl. $R^1$ may independently be $R^7$-substituted or unsubstituted $C_6$ cycloalkyl. $R^1$ may independently be $R^7$-substituted $C_6$ cycloalkyl.

$R^1$ may independently be substituted or unsubstituted 3 to 8 membered heterocycloalkyl. $R^1$ may independently be unsubstituted 3 to 8 membered heterocycloalkyl. $R^1$ may independently be substituted 3 to 8 membered heterocycloalkyl. $R^1$ may independently be $R^7$-substituted or unsubstituted 3 to 8 membered heterocycloalkyl. $R^1$ may independently be $R^7$-substituted 3 to 8 membered heterocycloalkyl. $R^1$ may independently be substituted or unsubstituted 3 to 6 membered heterocycloalkyl. $R^1$ may independently be substituted 3 to 6 membered heterocycloalkyl. $R^1$ may independently be unsubstituted 3 to 6 membered heterocycloalkyl. $R^1$ may independently be $R^7$-substituted or unsubstituted 3 to 6 membered heterocycloalkyl. $R^1$ may independently be $R^7$-substituted 3 to 6 membered heterocycloalkyl. $R^1$ may independently be substituted or unsubstituted 4 to 6 membered heterocycloalkyl. $R^1$ may independently be substituted 4 to 6 membered heterocycloalkyl. $R^1$ may independently be unsubstituted 4 to 6 membered heterocycloalkyl. $R^1$ may independently be $R^7$-substituted or unsubstituted 4 to 6 membered heterocycloalkyl. $R^1$ may independently be $R^7$-substituted 4 to 6 membered heterocycloalkyl. $R^1$ may independently be substituted or unsubstituted 4 membered heterocycloalkyl. $R^1$ may independently be substituted 4 membered heterocycloalkyl. $R^1$ may independently be unsubstituted 4 membered heterocycloalkyl. $R^1$ may independently be $R^7$-substituted or unsubstituted 4 membered heterocycloalkyl. $R^1$ may independently be $R^7$-substituted 4 membered heterocycloalkyl. $R^1$ may independently be substituted or unsubstituted 5 membered heterocycloalkyl. $R^1$ may independently be substituted 5 membered heterocycloalkyl. $R^1$ may independently be unsubstituted 5 membered heterocycloalkyl. $R^1$ may independently be $R^7$-substituted or unsubstituted 5 membered heterocycloalkyl. $R^1$ may independently be $R^7$-substituted 5 membered heterocycloalkyl. $R^1$ may independently be substituted or unsubstituted 6 membered heterocycloalkyl. $R^1$ may independently be substituted 6 membered heterocycloalkyl. $R^1$ may independently be unsubstituted 6 membered heterocycloalkyl. $R^1$ may independently be $R^7$-substituted or unsubstituted 6 membered heterocycloalkyl. $R^1$ may independently be $R^7$-substituted 6 membered heterocycloalkyl.

$R^1$ may independently be substituted or unsubstituted $C_5$-$C_8$ aryl. $R^1$ may independently be substituted $C_5$-$C_8$ aryl. $R^1$ may independently be unsubstituted $C_5$-$C_8$ aryl. $R^1$ may independently be $R^7$-substituted or unsubstituted $C_5$-$C_8$ aryl. $R^1$ may independently be $R^7$-substituted $C_5$-$C_8$ aryl. $R^1$ may independently be substituted or unsubstituted $C_5$-$C_6$ aryl. $R^1$ may independently be substituted $C_5$-$C_6$ aryl. $R^1$ may independently be unsubstituted $C_5$-$C_6$ aryl. $R^1$ may independently be $R^7$-substituted or unsubstituted $C_5$-$C_6$ aryl. $R^1$ may independently be $R^7$-substituted $C_5$-$C_6$ aryl. $R^1$ may independently be substituted or unsubstituted $C_5$ aryl. $R^1$ may independently be substituted $C_5$ aryl. $R^1$ may independently be unsubstituted $C_5$ aryl. $R^1$ may independently be $R^7$-substituted or unsubstituted $C_5$ aryl. $R^1$ may independently be $R^7$-substituted $C_5$ aryl. $R^1$ may independently be substituted or unsubstituted $C_6$ aryl. $R^1$ may independently be substituted $C_6$ aryl. $R^1$ may independently be unsubstituted $C_6$ aryl. $R^1$ may independently be $R^7$-substituted or unsubstituted $C_6$ aryl. $R^1$ may independently be $R^7$-substituted $C_6$ aryl.

$R^1$ may independently be substituted or unsubstituted 5-8 membered heteroaryl. $R^1$ may independently be substituted 5-8 membered heteroaryl. $R^1$ may independently be unsubstituted 5-8 membered heteroaryl. $R^1$ may independently be $R^7$-substituted or unsubstituted 5-8 membered heteroaryl. $R^1$ may independently be $R^7$-substituted 5-8 membered heteroaryl. $R^1$ may independently be substituted or unsubstituted 5-6 membered heteroaryl. $R^1$ may independently be substituted 5-6 membered heteroaryl. $R^1$ may independently be unsubstituted 5-6 membered heteroaryl. $R^1$ may independently be $R^7$-substituted or unsubstituted 5-6 membered heteroaryl. $R^1$ may independently be $R^7$-substituted 5-6 membered heteroaryl. $R^1$ may independently be substituted or unsubstituted 5 membered heteroaryl. $R^1$ may independently be substituted 5 membered heteroaryl. $R^1$ may independently be unsubstituted 5 membered heteroaryl. $R^1$ may independently be $R^7$-substituted or unsubstituted 5 membered heteroaryl. $R^1$ may independently be $R^7$-substituted 5 membered heteroaryl. $R^1$ may independently be substituted or unsubstituted 6 membered heteroaryl. $R^1$ may independently be substituted 6 membered heteroaryl. $R^1$ may independently be unsubstituted 6 membered heteroaryl. $R^1$ may independently be $R^7$-substituted or unsubstituted 6 membered heteroaryl. $R^1$ may independently be $R^7$-substituted 6 membered heteroaryl.

$R^7$ is hydrogen, halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$— $SO_2NH_2$, —$NHNH_2$, —$ONH_2$, —$NHC(O)NHNH_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^1$ may independently be hydrogen, oxo, substituted or unsubstituted $C_1$-$C_5$ alkyl, or a detectable moiety. $R^1$ may independently be a detectable moiety.

$R^2$ may independently be hydrogen, halogen, —$CF_3$, —$CCl_3$, —$CBr_3$, —$CI_3$, —$NH_2$, —$NO_2$, —$SO_2CH_3$. $R^2$ may independently be independently hydrogen, halogen, oxo, $N_3$, —$CF_3$, —$CCl_3$, —$CBr_3$, —$CI_3$, —CN, —OH, —$NH_2$, —COOH, —$CONH_2$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —$NHC(O)$—OH, —NHOH, —$OCHF_2$.

$R^2$ may independently be substituted or unsubstituted $C_1$-$C_{10}$ alkyl. $R^2$ may independently be substituted $C_1$-$C_{10}$ alkyl. $R^2$ may independently be unsubstituted $C_1$-$C_{10}$ alkyl. $R^2$ may independently be $R^8$-substituted or unsubstituted $C_1$-$C_{10}$ alkyl. $R^2$ may independently be $R^8$-substituted $C_1$-$C_{10}$ alkyl. $R^2$ may independently be substituted or unsubstituted $C_1$-$C_8$ alkyl. $R^2$ may independently be substituted $C_1$-$C_8$ alkyl. $R^2$ may independently be unsubstituted $C_1$-$C_8$ alkyl. $R^2$ may independently be $R^8$-substituted or unsubstituted $C_1$-$C_8$ alkyl. $R^2$ may independently be $R^8$-substituted $C_1$-$C_8$ alkyl. $R^2$ may independently be substituted or unsubstituted $C_1$-$C_5$ alkyl. $R^2$ may independently be substituted $C_1$-$C_5$ alkyl. $R^2$ may independently be unsubstituted $C_1$-$C_5$ alkyl. $R^2$ may independently be $R^8$-substituted or unsubstituted $C_1$-$C_5$ alkyl. $R^2$ may independently be $R^8$-substituted $C_1$-$C_5$ alkyl. $R^2$ may independently be substituted or unsubstituted $C_1$-$C_3$ alkyl. $R^2$ may independently be substituted $C_1$-$C_3$ alkyl. $R^2$ may independently be unsubstituted $C_1$-$C_3$ alkyl. $R^2$ may independently be $R^8$-substituted or unsubstituted $C_1$-$C_3$ alkyl. $R^2$ may independently be $R^8$-substituted $C_1$-$C_3$ alkyl.

$R^2$ may independently be substituted or unsubstituted 2 to 10 membered heteroalkyl. $R^2$ may independently be substituted 2 to 10 membered heteroalkyl. $R^2$ may independently be unsubstituted 2 to 10 membered heteroalkyl. $R^2$ may independently be $R^8$-substituted or unsubstituted 2 to 10 membered heteroalkyl. $R^2$ may independently be $R^8$-substituted 2 to 10 membered heteroalkyl. $R^2$ may independently be substituted or unsubstituted 2 to 8 membered heteroalkyl. $R^2$ may independently be substituted 2 to 8 membered heteroalkyl. $R^2$ may independently be unsubstituted 2 to 8 membered heteroalkyl. $R^2$ may independently be $R^8$-substituted or unsubstituted 2 to 8 membered heteroalkyl. $R^2$ may independently be $R^8$-substituted 2 to 8 membered heteroalkyl. $R^2$ may independently be substituted or unsubstituted 2 to 6 membered heteroalkyl. $R^2$ may independently be substituted 2 to 6 membered heteroalkyl. $R^2$ may independently be unsubstituted 2 to 6 membered heteroalkyl. $R^2$ may independently be $R^8$-substituted or unsubstituted 2 to 6 membered heteroalkyl. $R^2$ may independently be $R^8$-substituted 2 to 6 membered heteroalkyl.

$R^2$ may independently be substituted or unsubstituted $C_3$-$C_8$ cycloalkyl. $R^2$ may independently be substituted $C_3$-$C_8$ cycloalkyl. $R^2$ may independently be unsubstituted $C_3$-$C_8$ cycloalkyl. $R^2$ may independently be $R^8$-substituted or unsubstituted $C_3$-$C_8$ cycloalkyl. $R^2$ may independently be $R^8$-substituted $C_3$-$C_8$ cycloalkyl. $R^2$ may independently be substituted or unsubstituted $C_3$-$C_6$ cycloalkyl. $R^2$ may independently be substituted $C_3$-$C_6$ cycloalkyl. $R^2$ may independently be unsubstituted $C_3$-$C_6$ cycloalkyl. $R^2$ may independently be $R^8$-substituted or unsubstituted $C_3$-$C_6$ cycloalkyl. $R^2$ may independently be $R^8$-substituted $C_3$-$C_6$ cycloalkyl. $R^2$ may independently be substituted or unsubstituted $C_4$-$C_6$ cycloalkyl. $R^2$ may independently be substituted $C_4$-$C_6$ cycloalkyl. $R^2$ may independently be unsubstituted $C_4$-$C_6$ cycloalkyl. $R^2$ may independently be $R^8$-substituted or unsubstituted $C_4$-$C_6$ cycloalkyl. $R^2$ may independently be $R^8$-substituted $C_4$-$C_6$ cycloalkyl. $R^2$ may independently be substituted or unsubstituted $C_5$ cycloalkyl. $R^2$ may independently be substituted $C_4$ cycloalkyl. $R^2$ may independently be unsubstituted $C_4$ cycloalkyl. $R^2$ may independently be $R^8$-substituted or unsubstituted $C_4$ cycloalkyl. $R^2$ may independently be $R^8$-substituted $C_4$ cycloalkyl. $R^2$ may independently be substituted or unsubstituted $C_5$ cycloalkyl. $R^2$ may independently be substituted $C_5$ cycloalkyl. $R^2$ may independently be unsubstituted $C_5$ cycloalkyl. $R^2$ may independently be $R^8$-substituted or unsubstituted $C_5$ cycloalkyl. $R^2$ may independently be $R^8$-substituted $C_5$ cycloalkyl. $R^2$ may independently be substituted or unsubstituted $C_6$ cycloalkyl. $R^2$ may independently be substituted $C_6$ cycloalkyl. $R^2$ may independently be unsubstituted $C_6$ cycloalkyl. $R^2$ may independently be $R^8$-substituted or unsubstituted $C_6$ cycloalkyl. $R^2$ may independently be $R^8$-substituted $C_6$ cycloalkyl.

$R^2$ may independently be substituted or unsubstituted 3 to 8 membered heterocycloalkyl. $R^2$ may independently be unsubstituted 3 to 8 membered heterocycloalkyl. $R^2$ may independently be substituted 3 to 8 membered heterocycloalkyl. $R^2$ may independently be $R^8$-substituted or unsubstituted 3 to 8 membered heterocycloalkyl. $R^2$ may independently be $R^8$-substituted 3 to 8 membered heterocycloalkyl. $R^2$ may independently be substituted or unsubstituted 3 to 6 membered heterocycloalkyl. $R^2$ may independently be substituted 3 to 6 membered heterocycloalkyl. $R^2$ may independently be unsubstituted 3 to 6 membered heterocycloalkyl. $R^2$ may independently be $R^8$-substituted or unsubstituted 3 to 6 membered heterocycloalkyl. $R^2$ may independently be $R^8$-substituted 3 to 6 membered heterocycloalkyl. $R^2$ may independently be substituted or unsubstituted 4 to 6 membered heterocycloalkyl. $R^2$ may independently be substituted 4 to 6 membered heterocycloalkyl. $R^2$ may independently be unsubstituted 4 to 6 membered heterocycloalkyl. $R^2$ may independently be $R^8$-substituted or unsubstituted 4 to 6 membered heterocycloalkyl. $R^2$ may independently be $R^8$-substituted 4 to 6 membered heterocycloalkyl. $R^2$ may independently be substituted or unsubstituted 4 membered heterocycloalkyl. $R^2$ may independently be substituted 4 membered heterocycloalkyl. $R^2$ may independently be unsubstituted 4 membered heterocycloalkyl. $R^2$ may independently be $R^8$-substituted or unsubstituted 4 membered heterocycloalkyl. $R^2$ may independently be $R^8$-substituted 4 membered heterocycloalkyl. $R^2$ may independently be substituted or unsubstituted 5 membered heterocycloalkyl. $R^2$ may independently be substituted 5 membered heterocycloalkyl. $R^2$ may independently be unsubstituted 5 membered heterocycloalkyl. $R^2$ may independently be $R^8$-substituted or unsubstituted 5 membered heterocycloalkyl. $R^2$ may independently be $R^8$-substituted 5 membered heterocycloalkyl. $R^2$ may independently be substituted or unsubstituted 6 membered heterocycloalkyl. $R^2$ may independently be substituted 6 membered heterocycloalkyl. $R^2$ may independently be unsubstituted 6 membered heterocycloalkyl. $R^2$ may independently be $R^8$-substituted or unsubstituted 6 membered heterocycloalkyl. $R^2$ may independently be $R^8$-substituted 6 membered heterocycloalkyl.

$R^2$ may independently be substituted or unsubstituted $C_5$-$C_8$ aryl. $R^2$ may independently be substituted $C_5$-$C_8$ aryl. $R^2$ may independently be unsubstituted $C_5$-$C_8$ aryl. $R^2$ may independently be $R^8$-substituted or unsubstituted $C_5$-$C_8$ aryl. $R^2$ may independently be $R^8$-substituted $C_5$-$C_8$ aryl. $R^2$ may independently be substituted or unsubstituted $C_5$-$C_6$ aryl. $R^2$ may independently be substituted $C_5$-$C_6$ aryl. $R^2$ may independently be unsubstituted $C_5$-$C_6$ aryl. $R^2$ may independently be $R^8$-substituted or unsubstituted $C_5$-$C_6$ aryl. $R^2$ may independently be $R^8$-substituted $C_5$-$C_6$ aryl. $R^2$ may independently be substituted or unsubstituted $C_5$ aryl. $R^2$ may independently be substituted $C_5$ aryl. $R^2$ may independently be unsubstituted $C_5$ aryl. $R^2$ may independently be $R^8$-substituted or unsubstituted $C_5$ aryl. $R^2$ may independently be $R^8$-substituted $C_5$ aryl. $R^2$ may independently be substituted or unsubstituted $C_6$ aryl. $R^2$ may independently be substituted $C_6$ aryl. $R^2$ may independently be unsubstituted $C_6$ aryl. $R^2$ may independently be $R^8$-substituted or unsubstituted $C_6$ aryl. $R^2$ may independently be $R^8$-substituted $C_6$ aryl.

$R^2$ may independently be substituted or unsubstituted 5-8 membered heteroaryl. $R^2$ may independently be substituted 5-8 membered heteroaryl. $R^2$ may independently be unsubstituted 5-8 membered heteroaryl. $R^2$ may independently be $R^8$-substituted or unsubstituted 5-8 membered heteroaryl. $R^2$ may independently be $R^8$-substituted 5-8 membered heteroaryl. $R^2$ may independently be substituted or unsubstituted 5-6 membered heteroaryl. $R^2$ may independently be substituted 5-6 membered heteroaryl. $R^2$ may independently be unsubstituted 5-6 membered heteroaryl. $R^2$ may independently be $R^8$-substituted or unsubstituted 5-6 membered heteroaryl. $R^2$ may independently be $R^8$-substituted 5-6 membered heteroaryl. $R^2$ may independently be substituted or unsubstituted 5 membered heteroaryl. $R^2$ may independently be substituted 5 membered heteroaryl. $R^2$ may independently be unsubstituted 5 membered heteroaryl. $R^2$ may independently be $R^8$-substituted or unsubstituted 5 membered heteroaryl. $R^2$ may independently be $R^8$-substituted 5 membered heteroaryl. $R^2$ may independently be substituted or unsubstituted 6 membered heteroaryl. $R^2$ may independently be substituted 6 membered heteroaryl. $R^2$ may independently be unsubstituted 6 membered heteroaryl. $R^2$ may independently be $R^8$-substituted or unsubstituted 6 membered heteroaryl. $R^2$ may independently be $R^8$-substituted 6 membered heteroaryl.

Two $R^2$ substituents attached to adjacent ring carbons may optionally be joined to form a substituted or unsubstituted aryl or substituted or unsubstituted heteroaryl when z2 is an integer of 2 to 5. z2 may be 2. The two $R^2$ substituents attached to adjacent ring carbons may optionally be joined to form a substituted or unsubstituted aryl. The two $R^2$ substituents attached to adjacent ring carbons may optionally be joined to form a substituted aryl. The two $R^2$ substituents attached to adjacent ring carbons may optionally be joined to form a unsubstituted aryl. The two $R^2$ substituents attached to adjacent ring carbons may optionally be joined to form a $R^8$-substituted or unsubstituted aryl. The two $R^2$ substituents attached to adjacent ring carbons may optionally be joined to form a $R^8$-substituted aryl.

The two $R^2$ substituents attached to adjacent ring carbons may optionally be joined to form a substituted or unsubstituted $C_5$-$C_8$ aryl. The two $R^2$ substituents attached to adjacent ring carbons may optionally be joined to form a substituted $C_5$-$C_8$ aryl. The two $R^2$ substituents attached to adjacent ring carbons may optionally be joined to form a unsubstituted $C_5$-$C_8$ aryl. The two $R^2$ substituents attached to adjacent ring carbons may optionally be joined to form a $R^8$-substituted or unsubstituted $C_5$-$C_8$ aryl. The two $R^2$ substituents attached to adjacent ring carbons may optionally be joined to form a $R^8$-substituted $C_5$-$C_8$ aryl. The two $R^2$ substituents attached to adjacent ring carbons may optionally be joined to form a substituted or unsubstituted $C_5$-$C_6$ aryl. The two $R^2$ substituents attached to adjacent ring carbons may optionally be joined to form a substituted $C_5$-$C_6$ aryl. The two $R^2$ substituents attached to adjacent ring carbons may optionally be joined to form a unsubstituted $C_5$-$C_6$ aryl. The two $R^2$ substituents attached to adjacent ring carbons may optionally be joined to form a $R^8$-substituted or unsubstituted $C_5$-$C_6$ aryl. The two $R^2$ substituents attached to adjacent ring carbons may optionally be joined to form a $R^8$-substituted $C_5$-$C_6$ aryl. The two $R^2$ substituents attached to adjacent ring carbons may optionally be joined to form a substituted or unsubstituted $C_6$ aryl (e.g. forming a napthyl). The two $R^2$ substituents attached to adjacent ring carbons may optionally be joined to form a substituted $C_6$ aryl (e.g. forming a napthyl). The two $R^2$ substituents attached to adjacent ring carbons may optionally be joined to form a unsubstituted $C_6$ aryl (e.g. forming a napthyl). The two $R^2$ substituents attached to adjacent ring carbons may optionally be joined to form a $R^8$-substituted or unsubstituted $C_6$ aryl (e.g. forming a napthyl). The two $R^2$ substituents attached to adjacent ring carbons may optionally be joined to form a $R^8$-substituted $C_6$ aryl (e.g. forming a napthyl). Thus, in embodiments, the two $R^2$ substituents attached to adjacent ring carbons are optionally joined to form a 5,5-, 5,6-, 6,5-, or 6,6-fused aryl.

The two $R^2$ substituents attached to adjacent ring carbons may optionally be joined to form a substituted or unsubstituted heteroaryl. The two $R^2$ substituents attached to adjacent ring carbons may optionally be joined to form a substituted heteroaryl. The two $R^2$ substituents attached to adjacent ring carbons may optionally be joined to form a unsubstituted heteroaryl. The two $R^2$ substituents attached to adjacent ring carbons may optionally be joined to form a $R^8$-substituted or unsubstituted heteroaryl. The two $R^2$ substituents attached to adjacent ring carbons may optionally be joined to form a $R^8$-substituted heteroaryl.

The two $R^2$ substituents attached to adjacent ring carbons may optionally be joined to form a substituted or unsubstituted 5 to 8 membered heteroaryl. The two $R^2$ substituents attached to adjacent ring carbons may optionally be joined to form a substituted 5 to 8 membered heteroaryl. The two $R^2$ substituents attached to adjacent ring carbons may optionally be joined to form a unsubstituted 5 to 8 membered heteroaryl. The two $R^2$ substituents attached to adjacent ring carbons may optionally be joined to form a $R^8$-substituted or unsubstituted 5 to 8 membered heteroaryl. The two $R^2$ substituents attached to adjacent ring carbons may optionally be joined to form a $R^8$-substituted 5 to 8 membered heteroaryl. The two $R^2$ substituents attached to adjacent ring carbons may optionally be joined to form a substituted or unsubstituted 5 or 6 membered heteroaryl. The two $R^2$ substituents attached to adjacent ring carbons may optionally be joined to form a substituted 5 or 6 membered heteroaryl. The two R² substituents attached to adjacent ring carbons may optionally be joined to form a unsubstituted 5 or 6 membered heteroaryl. The two R² substituents attached to adjacent ring carbons may optionally be joined to form a R⁸-substituted or unsubstituted 5 or 6 membered heteroaryl. The two R² substituents attached to adjacent ring carbons may optionally be joined to form a R⁸-substituted 5 or 6 membered heteroaryl. The two R² substituents attached to adjacent ring carbons may optionally be joined to form a substituted or unsubstituted 6 membered heteroaryl. The two R² substituents attached to adjacent ring carbons may optionally be joined to form a substituted 6 membered heteroaryl. The two R² substituents attached to adjacent ring carbons may optionally be joined to form a unsubstituted 6 membered heteroaryl. The two R² substituents attached to adjacent ring carbons may optionally be joined to form a R⁸-substituted or unsubstituted 6 membered heteroaryl. The two R² substituents attached to adjacent ring carbons may optionally be joined to form a R⁸-substituted 6 membered heteroaryl. Thus, in embodiments, the two R² substituents attached to adjacent ring carbons are optionally joined to form a 5,5-, 5,6-, 6,5-, or 6,6-fused heteroaryl.

The compound may therefore have the formula:

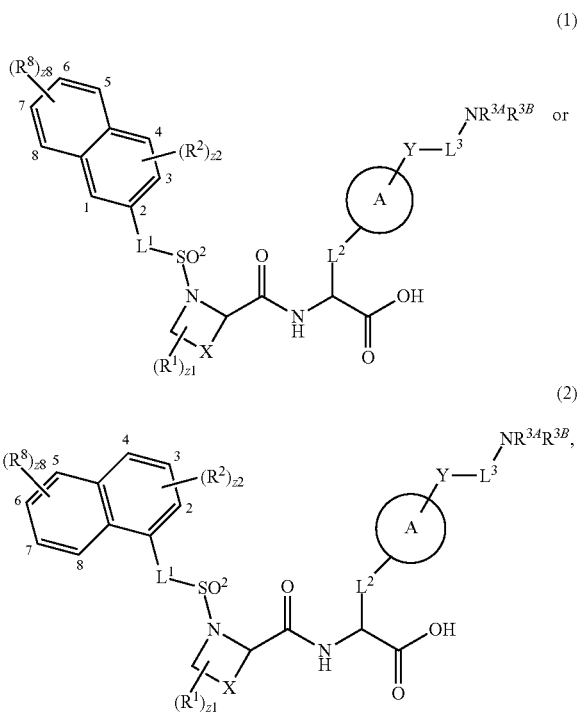

where the symbol z2 is 1, 2, or 3, the symbol z8 is an integer of 0, 1, 2, 3, or 4, and R⁸ is as described herein. R⁸ may be NH₂ or —N(CH₃)₂. R⁸ is attached to only 1 ring (e.g. the ring formed by the joining of two R² moieties—the ring identified by carbon numbers 5-8 in formula (1) and (2) above). R² is attached to only one ring (e.g. the ring identified by carbon numbers 1-4 in formula (1) and (2) above).

R⁸ is hydrogen, halogen, oxo, —N₃, —CF₃, —CCl₃, —CBr₃, —CI₃, —CN, —CHO, —OH, —NH₂, —N(CH₃)₂, —COOH, —CONH₂, —NO₂, —SH, —SO₂, —SO₂Cl, —SO₂CH₃ —SO₃H, —SO₄H, —SO₂NH₂, —NHNH₂, —ONH₂, —NHC(O)NHNH₂, R⁹-substituted or unsubstituted alkyl, R⁹-substituted or unsubstituted heteroalkyl, R⁹-substituted or unsubstituted cycloalkyl, R⁹-substituted or unsubstituted heterocycloalkyl, R⁹-substituted or unsubstituted aryl, or R⁹-substituted or unsubstituted heteroaryl.

R⁹ is hydrogen, halogen, oxo, —N₃, —CF₃, —CCl₃, —CBr₃, —CI₃, —CN, —CHO, —OH, —NH₂, —N(CH₃)₂, —COOH, —CONH₂, —NO₂, —SH, —SO₂, —SO₂Cl, —SO₂CH₃—SO₃H, —SO₄H, —SO₂NH₂, —NHNH₂, —ONH₂, —NHC(O)NHNH₂, unsubstituted alkyl, unsubstituted heteroalkyl, unsubstituted cycloalkyl, unsubstituted heterocycloalkyl, unsubstituted aryl, or unsubstituted heteroaryl.

R² may be independently hydrogen, halogen, —CF₃, —CCl₃, —CBr₃, —CI₃, —NH₂, —NO₂, —SO₂CH₃, substituted or unsubstituted C₁-C₅ alkyl, substituted or unsubstituted 2 to 5 membered heteroalkyl, substituted or unsubstituted 5 or 6 membered aryl, or a detectable moiety.

R³ᴬ and R³ᴮ may be independently hydrogen, —C(NH)NH₂, —C(NH)R³ᴰ, —C(NR³ᶜ)NH₂, —C(NR³ᶜ)R³ᴰ, —C(NCN)NH₂, NH, NH₂, substituted or unsubstituted heterocycloalkyl, substituted or unsubstituted aryl, or substituted or unsubstituted heteroaryl.

R³ᴬ and R³ᴮ may independently be —C(NH)NH₂, —C(NH)R³ᴰ, —C(NR³ᶜ)NH₂, —C(NR³ᶜ)R³ᴰ, —C(NCN) NH₂, NH, NH₂, or a detectable moiety.

R³ᴬ and R³ᴮ may independently be substituted or unsubstituted C₁-C₁₀ alkyl. R³ᴬ and R³ᴮ may independently be substituted C₁-C₁₀ alkyl. R³ᴬ and R³ᴮ may independently be unsubstituted C₁-C₁₀ alkyl. R³ᴬ and R³ᴮ may independently be R¹⁰-substituted or unsubstituted C₁-C₁₀ alkyl. R³ᴬ and R³ᴮ may independently be R¹⁰-substituted C₁-C₁₀ alkyl. R³ᴬ and R³ᴮ may independently be substituted or unsubstituted C₁-C₈ alkyl. R³ᴬ and R³ᴮ may independently be substituted C₁-C₈ alkyl. R³ᴬ and R³ᴮ may independently be unsubstituted C₁-C₈ alkyl. R³ᴬ and R³ᴮ may independently be R¹⁰-substituted or unsubstituted C₁-C₈ alkyl. R³ᴬ and R³ᴮ may independently be R¹⁰-substituted C₁-C₈ alkyl. R³ᴬ and R³ᴮ may independently be substituted or unsubstituted C₁-C₅ alkyl. R³ᴬ and R³ᴮ may independently be substituted C₁-C₅ alkyl. R³ᴬ and R³ᴮ may independently be unsubstituted C₁-C₅ alkyl. R³ᴬ and R³ᴮ may independently be R¹⁰-substituted or unsubstituted C₁-C₅ alkyl. R³ᴬ and R³ᴮ may independently be R¹⁰-substituted C₁-C₅ alkyl. R³ᴬ and R³ᴮ may independently be substituted or unsubstituted C₁-C₃ alkyl. R³ᴬ and R³ᴮ may independently be substituted C₁-C₃ alkyl. R³ᴬ and R³ᴮ may independently be unsubstituted C₁-C₃ alkyl. R³ᴬ and R³ᴮ may independently be R¹⁰-substituted or unsubstituted C₁-C₃ alkyl. R³ᴬ and R³ᴮ may independently be R¹⁰-substituted C₁-C₃ alkyl. In embodiments, one of R³ᴬ and R³ᴮ is hydrogen.

R³ᴬ and R³ᴮ may independently be substituted or unsubstituted 2 to 10 membered heteroalkyl. R³ᴬ and R³ᴮ may independently be substituted 2 to 10 membered heteroalkyl. R³ᴬ and R³ᴮ may independently be unsubstituted 2 to 10 membered heteroalkyl. R³ᴬ and R³ᴮ may independently be R¹⁰-substituted or unsubstituted 2 to 10 membered heteroalkyl. R³ᴬ and R³ᴮ may independently be R¹⁰-substituted 2 to 10 membered heteroalkyl. R³ᴬ and R³ᴮ may independently be substituted or unsubstituted 2 to 8 membered heteroalkyl. R³ᴬ and R³ᴮ may independently be substituted 2 to 8 membered heteroalkyl. R³ᴬ and R³ᴮ may independently be unsubstituted 2 to 8 membered heteroalkyl. R³ᴬ and R³ᴮ may independently be R¹⁰-substituted or unsubstituted 2 to 8 membered heteroalkyl. R³ᴬ and R³ᴮ may independently be R¹⁰-substituted 2 to 8 membered heteroalkyl. R³ᴬ and R³ᴮ may independently be substituted or unsubstituted 2 to 6 membered heteroalkyl. R³ᴬ and R³ᴮ may independently be substituted 2 to 6 membered heteroalkyl. $R^{3A}$ and $R^{3B}$ may independently be unsubstituted 2 to 6 membered heteroalkyl. $R^{3A}$ and $R^{3B}$ may independently be $R^{10}$-substituted or unsubstituted 2 to 6 membered heteroalkyl. $R^{3A}$ and $R^{3B}$ may independently be $R^{10}$-substituted 2 to 6 membered heteroalkyl. In embodiments, one of $R^{3A}$ and $R^{3B}$ is hydrogen.

$R^{3A}$ and $R^{3B}$ may independently be substituted or unsubstituted $C_3$-$C_8$ cycloalkyl. $R^{3A}$ and $R^{3B}$ may independently be unsubstituted $C_3$-$C_8$ cycloalkyl. $R^{3A}$ and $R^{3B}$ may independently be substituted $C_3$-$C_8$ cycloalkyl. $R^{3A}$ and $R^{3B}$ may independently be $R^{10}$-substituted or unsubstituted $C_3$-$C_8$ cycloalkyl. $R^{3A}$ and $R^{3B}$ may independently be $R^{10}$-substituted $C_3$-$C_8$ cycloalkyl. $R^{3A}$ and $R^{3B}$ may independently be substituted or unsubstituted $C_3$-$C_6$ cycloalkyl. $R^{3A}$ and $R^{3B}$ may independently be substituted $C_3$-$C_6$ cycloalkyl. $R^{3A}$ and $R^{3B}$ may independently be unsubstituted $C_3$-$C_6$ cycloalkyl. $R^{3A}$ and $R^{3B}$ may independently be $R^{10}$-substituted or unsubstituted $C_3$-$C_6$ cycloalkyl. $R^{3A}$ and $R^{3B}$ may independently be $R^{10}$-substituted $C_3$-$C_6$ cycloalkyl. $R^{3A}$ and $R^{3B}$ may independently be substituted or unsubstituted $C_4$-$C_6$ cycloalkyl. $R^{3A}$ and $R^{3B}$ may independently be substituted $C_4$-$C_6$ cycloalkyl. $R^{3A}$ and $R^{3B}$ may independently be unsubstituted $C_4$-$C_6$ cycloalkyl. $R^{3A}$ and $R^{3B}$ may independently be $R^{10}$-substituted or unsubstituted $C_4$-$C_6$ cycloalkyl. $R^{3A}$ and $R^{3B}$ may independently be $R^{10}$-substituted $C_4$-$C_6$ cycloalkyl. $R^{3A}$ and $R^{3B}$ may independently be substituted or unsubstituted $C_5$ cycloalkyl. $R^{3A}$ and $R^{3B}$ may independently be substituted $C_4$ cycloalkyl. $R^{3A}$ and $R^{3B}$ may independently be unsubstituted $C_4$ cycloalkyl. $R^{3A}$ and $R^{3B}$ may independently be $R^{10}$-substituted or unsubstituted $C_4$ cycloalkyl. $R^{3A}$ and $R^{3B}$ may independently be $R^{10}$-substituted $C_4$ cycloalkyl. $R^{3A}$ and $R^{3B}$ may independently be substituted or unsubstituted $C_5$ cycloalkyl. $R^{3A}$ and $R^{3B}$ may independently be substituted $C_5$ cycloalkyl. $R^{3A}$ and $R^{3B}$ may independently be unsubstituted $C_5$ cycloalkyl. $R^{3A}$ and $R^{3B}$ may independently be $R^{10}$-substituted or unsubstituted $C_5$ cycloalkyl. $R^{3A}$ and $R^{3B}$ may independently be $R^{10}$-substituted $C_5$ cycloalkyl. $R^{3A}$ and $R^{3B}$ may independently be substituted or unsubstituted $C_6$ cycloalkyl. $R^{3A}$ and $R^{3B}$ may independently be substituted $C_6$ cycloalkyl. $R^{3A}$ and $R^{3B}$ may independently be unsubstituted $C_6$ cycloalkyl. $R^{3A}$ and $R^{3B}$ may independently be $R^{10}$-substituted or unsubstituted $C_6$ cycloalkyl. $R^{3A}$ and $R^{3B}$ may independently be $R^{10}$-substituted $C_6$ cycloalkyl. In embodiments, one of $R^{3A}$ and $R^{3B}$ is hydrogen.

$R^{3A}$ and $R^{3B}$ may independently be substituted or unsubstituted 3 to 8 membered heterocycloalkyl. $R^{3A}$ and $R^{3B}$ may independently be unsubstituted 3 to 8 membered heterocycloalkyl. $R^{3A}$ and $R^{3B}$ may independently be substituted 3 to 8 membered heterocycloalkyl. $R^{3A}$ and $R^{3B}$ may independently be $R^{10}$-substituted or unsubstituted 3 to 8 membered heterocycloalkyl. $R^{3A}$ and $R^{3B}$ may independently be $R^{10}$-substituted 3 to 8 membered heterocycloalkyl. $R^{3A}$ and $R^{3B}$ may independently be substituted or unsubstituted 3 to 6 membered heterocycloalkyl. $R^{3A}$ and $R^{3B}$ may independently be substituted 3 to 6 membered heterocycloalkyl. $R^{3A}$ and $R^{3B}$ may independently be unsubstituted 3 to 6 membered heterocycloalkyl. $R^{3A}$ and $R^{3B}$ may independently be $R^{10}$-substituted or unsubstituted 3 to 6 membered heterocycloalkyl. $R^{3A}$ and $R^{3B}$ may independently be $R^{10}$-substituted 3 to 6 membered heterocycloalkyl. $R^{3A}$ and $R^{3B}$ may independently be substituted or unsubstituted 4 to 6 membered heterocycloalkyl. $R^{3A}$ and $R^{3B}$ may independently be substituted 4 to 6 membered heterocycloalkyl. $R^{3A}$ and $R^{3B}$ may independently be unsubstituted 4 to 6 membered heterocycloalkyl. $R^{3A}$ and $R^{3B}$ may independently be $R^{10}$-substituted or unsubstituted 4 to 6 membered heterocycloalkyl. $R^{3A}$ and $R^{3B}$ may independently be $R^{10}$-substituted 4 to 6 membered heterocycloalkyl. $R^{3A}$ and $R^{3B}$ may independently be substituted or unsubstituted 4 membered heterocycloalkyl. $R^{3A}$ and $R^{3B}$ may independently be substituted 4 membered heterocycloalkyl. $R^{3A}$ and $R^{3B}$ may independently be unsubstituted 4 membered heterocycloalkyl. $R^{3A}$ and $R^{3B}$ may independently be $R^{10}$-substituted or unsubstituted 4 membered heterocycloalkyl. $R^{3A}$ and $R^{3B}$ may independently be $R^{10}$-substituted 4 membered heterocycloalkyl. $R^{3A}$ and $R^{3B}$ may independently be substituted or unsubstituted 5 membered heterocycloalkyl. $R^{3A}$ and $R^{3B}$ may independently be substituted 5 membered heterocycloalkyl. $R^{3A}$ and $R^{3B}$ may independently be unsubstituted 5 membered heterocycloalkyl. $R^{3A}$ and $R^{3B}$ may independently be $R^{10}$-substituted or unsubstituted 5 membered heterocycloalkyl. $R^{3A}$ and $R^{3B}$ may independently be $R^{10}$-substituted 5 membered heterocycloalkyl. $R^{3A}$ and $R^{3B}$ may independently be substituted or unsubstituted 6 membered heterocycloalkyl. $R^{3A}$ and $R^{3B}$ may independently be substituted 6 membered heterocycloalkyl. $R^{3A}$ and $R^{3B}$ may independently be unsubstituted 6 membered heterocycloalkyl. $R^{3A}$ and $R^{3B}$ may independently be $R^{10}$-substituted or unsubstituted 6 membered heterocycloalkyl. $R^{3A}$ and $R^{3B}$ may independently be $R^{10}$-substituted 6 membered heterocycloalkyl. In embodiments, one of $R^{3A}$ and $R^{3B}$ is hydrogen.

$R^{3A}$ and $R^{3B}$ may independently be substituted or unsubstituted $C_5$-$C_8$ aryl. $R^{3A}$ and $R^{3B}$ may independently be substituted $C_5$-$C_8$ aryl. $R^{3A}$ and $R^{3B}$ may independently be unsubstituted $C_5$-$C_8$ aryl. $R^{3A}$ and $R^{3B}$ may independently be $R^{10}$-substituted or unsubstituted $C_5$-$C_8$ aryl. $R^{3A}$ and $R^{3B}$ may independently be $R^{10}$-substituted $C_5$-$C_8$ aryl. $R^{3A}$ and $R^{3B}$ may independently be substituted or unsubstituted $C_5$-$C_6$ aryl. $R^{3A}$ and $R^{3B}$ may independently be substituted $C_5$-$C_6$ aryl. $R^{3A}$ and $R^{3B}$ may independently be unsubstituted $C_5$-$C_6$ aryl. $R^{3A}$ and $R^{3B}$ may independently be $R^{10}$-substituted or unsubstituted $C_5$-$C_6$ aryl. $R^{3A}$ and $R^{3B}$ may independently be $R^{10}$-substituted $C_5$-$C_6$ aryl. $R^{3A}$ and $R^{3B}$ may independently be substituted or unsubstituted $C_5$ aryl. $R^{3A}$ and $R^{3B}$ may independently be substituted $C_5$ aryl. $R^{3A}$ and $R^{3B}$ may independently be unsubstituted $C_5$ aryl. $R^{3A}$ and $R^{3B}$ may independently be $R^{10}$-substituted or unsubstituted $C_5$ aryl. $R^{3A}$ and $R^{3B}$ may independently be $R^{10}$-substituted $C_5$ aryl. $R^{3A}$ and $R^{3B}$ may independently be substituted or unsubstituted $C_6$ aryl. $R^{3A}$ and $R^{3B}$ may independently be substituted $C_6$ aryl. $R^{3A}$ and $R^{3B}$ may independently be unsubstituted $C_6$ aryl. $R^{3A}$ and $R^{3B}$ may independently be $R^{10}$-substituted or unsubstituted $C_6$ aryl. $R^{3A}$ and $R^{3B}$ may independently be $R^{10}$-substituted $C_6$ aryl. In embodiments, one of $R^{3A}$ and $R^{3B}$ is hydrogen.

$R^{3A}$ and $R^{3B}$ may independently be substituted or unsubstituted 5-8 membered heteroaryl. $R^{3A}$ and $R^{3B}$ may independently be substituted 5-8 membered heteroaryl. $R^{3A}$ and $R^{3B}$ may independently be unsubstituted 5-8 membered heteroaryl. $R^{3A}$ and $R^{3B}$ may independently be $R^{10}$-substituted or unsubstituted 5-8 membered heteroaryl. $R^{3A}$ and $R^{3B}$ may independently be $R^{10}$-substituted 5-8 membered heteroaryl. $R^{3A}$ and $R^{3B}$ may independently be substituted or unsubstituted 5-6 membered heteroaryl. $R^{3A}$ and $R^{3B}$ may independently be substituted 5-6 membered heteroaryl. $R^{3A}$ and $R^{3B}$ may independently be unsubstituted 5-6 membered heteroaryl. $R^{3A}$ and $R^{3B}$ may independently be $R^{10}$-substituted or unsubstituted 5-6 membered heteroaryl. $R^{3A}$ and $R^{3B}$ may independently be $R^{10}$-substituted 5-6 membered heteroaryl. $R^{3A}$ and $R^{3B}$ may independently be substituted or unsubstituted 5 membered heteroaryl. $R^{3A}$ and $R^{3B}$ may independently be substituted 5 membered heteroaryl. $R^{3A}$ and $R^{3B}$ may independently be unsubstituted 5 membered heteroaryl. $R^{3A}$ and $R^{3B}$ may independently be $R^{10}$-substituted or unsubstituted 5 membered heteroaryl. $R^{3A}$ and $R^{3B}$ may independently be $R^{10}$-substituted 5 membered heteroaryl. $R^{3A}$ and $R^{3B}$ may independently be substituted or unsubstituted 6 membered heteroaryl. $R^{3A}$ and $R^{3B}$ may independently be substituted 6 membered heteroaryl. $R^{3A}$ and $R^{3B}$ may independently be 6 membered heteroaryl. $R^{3A}$ and $R^{3B}$ may independently be $R^{10}$-substituted or unsubstituted 6 membered heteroaryl. $R^{3A}$ and $R^{3B}$ may independently be $R^{10}$-substituted 6 membered heteroaryl. In embodiments, one of $R^{3A}$ and $R^{3B}$ is hydrogen.

$R^{3A}$ and $R^{3B}$ may be independently $R^{10}$-substituted or unsubstituted cycloalkyl, $R^{10}$-substituted or unsubstituted heterocycloalkyl, $R^{10}$-substituted or unsubstituted aryl, or $R^{10}$-substituted or unsubstituted heteroaryl. $R^{3A}$ and $R^{3B}$ may be independently substituted or unsubstituted 5 or 6 membered cycloalkyl, substituted or unsubstituted 5 or 6 membered heterocycloalkyl, substituted or unsubstituted 5 or 6 membered aryl or substituted or unsubstituted 5 or 6 membered heteroaryl. $R^{3A}$ and $R^{3B}$ may be independently hydrogen, —C(NH)NH$_2$, or —C(NCN)NH$_2$. $R^{3A}$ and $R^{3B}$ may be independently hydrogen or —C(NH)NH$_2$. $R^{3A}$ and $R^{3B}$ may be independently hydrogen or —C(NCN)NH$_2$. $R^{3A}$ and $R^{3B}$ may be independently —C(NH)NH$_2$, or —C(NCN)NH$_2$. $R^{3A}$ and $R^{3B}$ may be independently hydrogen or —C(NH)R$^{3C}$. $R^{3A}$ and $R^{3B}$ may be independently be hydrogen. $R^{3A}$ and $R^{3B}$ may independently be hydrogen and substituted or unsubstituted cycloalkyl as described herein. $R^{3A}$ and $R^{3B}$ may be independently hydrogen and substituted or unsubstituted heterocycloalkyl as described herein. $R^{3A}$ and $R^{3B}$ may be independently hydrogen and substituted or unsubstituted aryl as described herein. $R^{3A}$ and $R^{3B}$ may be independently hydrogen and substituted or unsubstituted heteroaryl as described herein. In embodiments, one of $R^{3A}$ and $R^{3B}$ is hydrogen.

$R^3$ is hydrogen, halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{3C}$ may be hydrogen, halogen, oxo, —N$_3$, —CF$_3$, —CCl$_3$, —CBr$_3$, —CI$_3$, —CN, —COR$^{3E}$, —OR$^{3E}$, —NR$^{3E}$R$^{3F}$, —COOR$^{3E}$, —CONR$^{3E}$R$^{3F}$, —NHC(O)R$^{3E}$, —NO$_2$, —SR$^{3E}$, —SO$_{n3}$R$^{3E}$, —NHNR$^{3E}$R$^{3F}$, —ONR$^{3E}$R$^{3F}$, —NHC(O)NHNR$^{3E}$R$^{3F}$, —C(NCN)R$^{3E}$, —C(NH)R$^{3E}$, substituted or unsubstituted alkyl, substituted or unsubstituted heteroalkyl, substituted or unsubstituted cycloalkyl, $R^{3G}$-substituted or unsubstituted heterocycloalkyl, substituted or unsubstituted aryl, or substituted or unsubstituted heteroaryl or a detectable moiety.

$R^{3C}$ may be hydrogen, halogen, oxo, —N$_3$, —CF$_3$, —CCl$_3$, —CBr$_3$, —CI$_3$, —CN, —COR$^{3E}$, —OR$^{3E}$, —NR$^{3E}$R$^{3F}$, —COOR$^{3E}$, —CONR$^{3E}$R$^{3F}$, —NHC(O)R$^{3E}$, —NO$_2$, —SR$^{3E}$, —SO$_{n3}$R$^{3E}$, —NHNR$^{3E}$R$^{3F}$, —ONR$^{3E}$R$^{3F}$, —NHC(O)NHNR$^{3E}$R$^{3F}$, —C(NCN)R$^{3E}$, —C(NH)R$^{3E}$, $R^{3G}$-substituted or unsubstituted alkyl, $R^{3G}$-substituted or unsubstituted heteroalkyl, $R^{3G}$-substituted or unsubstituted cycloalkyl, $R^{3G}$-substituted or unsubstituted heterocycloalkyl, $R^{3G}$-substituted or unsubstituted aryl, or $R^{3G}$-substituted or unsubstituted heteroaryl or a detectable moiety. The symbol n3 is 2, 3, or 4.

$R^{3E}$ and $R^{3F}$ are independently hydrogen, halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl or a detectable moiety.

$R^{3E}$ and $R^{3F}$ may independently be hydrogen, halogen, oxo, —N$_3$, —CF$_3$, —CCl$_3$, —CBr$_3$, —CI$_3$, —CN, —CHO, —OH, —NH$_2$, —COOH, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, $R^{3G}$-substituted or unsubstituted alkyl, $R^{3G}$-substituted or unsubstituted heteroalkyl, $R^{3G}$-substituted or unsubstituted cycloalkyl, $R^{3G}$-substituted or unsubstituted heterocycloalkyl, $R^{3G}$-substituted or unsubstituted aryl, or $R^{3G}$-substituted or unsubstituted heteroaryl or a detectable moiety.

$R^{3E}$ and $R^{3F}$ may independently be unsubstituted alkyl, unsubstituted heteroalkyl, unsubstituted cycloalkyl, unsubstituted heterocycloalkyl, unsubstituted aryl, unsubstituted heteroaryl, or a detectable moiety. $R^{3E}$ and $R^{3F}$ may independently be hydrogen, halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, unsubstituted alkyl, unsubstituted heteroalkyl, unsubstituted cycloalkyl, unsubstituted heterocycloalkyl, unsubstituted aryl, unsubstituted heteroaryl, or a detectable moiety.

$R^{3G}$ is halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, unsubstituted alkyl, unsubstituted heteroalkyl, unsubstituted cycloalkyl, unsubstituted heterocycloalkyl, unsubstituted aryl, unsubstituted heteroaryl, or a detectable moiety. $R^{3G}$ may be unsubstituted alkyl, unsubstituted heteroalkyl, unsubstituted cycloalkyl, unsubstituted heterocycloalkyl, unsubstituted aryl, unsubstituted heteroaryl, or a detectable moiety.

$R^{3D}$ is hydrogen, halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl or a detectable moiety.

$R^{3D}$ may be hydrogen, halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, $R^{3H}$-substituted or unsubstituted alkyl, $R^{3H}$-substituted or unsubstituted heteroalkyl, $R^{3H}$-substituted or unsubstituted cycloalkyl, $R^{3H}$-substituted or unsubstituted heterocycloalkyl, $R^{3H}$-substituted or unsubstituted aryl, or $R^{3H}$-substituted or unsubstituted heteroaryl or a detectable moiety.

$R^{3D}$ may be hydrogen, halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, unsubstituted alkyl, unsubstituted heteroalkyl, unsubstituted cycloalkyl, unsubstituted heterocycloalkyl, unsubstituted aryl, unsubstituted heteroaryl, or a detectable moiety.

$R^{3D}$ may be unsubstituted alkyl, unsubstituted heteroalkyl, unsubstituted cycloalkyl, unsubstituted heterocycloalkyl, unsubstituted aryl, unsubstituted heteroaryl, or a detectable moiety.

$R^{3H}$ is halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$— $SO_3H$, —$SO_4H$, —$SO_2NH_2$, —$NHNH_2$, —$ONH_2$, —NHC(O)$NHNH_2$, unsubstituted alkyl, unsubstituted heteroalkyl, unsubstituted cycloalkyl, unsubstituted heterocycloalkyl, unsubstituted aryl, unsubstituted heteroaryl, or a detectable moiety. $R^{3H}$ may be unsubstituted alkyl, unsubstituted heteroalkyl, unsubstituted cycloalkyl, unsubstituted heterocycloalkyl, unsubstituted aryl, unsubstituted heteroaryl, or a detectable moiety.

$R^{3A}$ and $R^{3B}$ may independently be substituted or unsubstituted 4,5-dihydro-imidazole or substituted or unsubstituted 1,4,5,6-tetrahydropyrimidine. $R^{3A}$ and $R^{3B}$ may independently be $R^{10}$-substituted or unsubstituted 4,5-dihydro-imidazole. $R^{3A}$ and $R^{3B}$ may independently be unsubstituted 4,5-dihydro-imidazole. $R^{3A}$ and $R^{3B}$ may independently be $R^{10}$-substituted or unsubstituted 1,4,5,6-tetrahydropyrimidine. $R^{3A}$ and $R^{3B}$ may independently be unsubstituted 1,4,5,6-tetrahydropyrimidine. $R^{3A}$ and $R^{3B}$ may independently be hydrogen, substituted or unsubstituted 4,5-dihydro-imidazole or substituted or unsubstituted 1,4,5,6-tetrahydropyrimidine. $R^{3A}$ and $R^{3B}$ may independently be hydrogen or $R^{10}$-substituted or unsubstituted 4,5-dihydro-imidazole. $R^{3A}$ and $R^{3B}$ may independently be hydrogen or unsubstituted 4,5-dihydro-imidazole. $R^{3A}$ and $R^{3B}$ may independently be hydrogen or $R^{10}$-substituted or unsubstituted 1,4,5,6-tetrahydropyrimidine. $R^{3A}$ and $R^{3B}$ may independently be hydrogen or unsubstituted 1,4,5,6-tetrahydropyrimidine. In embodiments, one of $R^{3A}$ and $R^{3B}$ is hydrogen.

$R^{3A}$ and $R^{3B}$ may be joined together to form substituted or unsubstituted 4,5-dihydro-imidazole, substituted or unsubstituted 1,4,5,6-tetrahydropyrimidine, $R^{10}$-substituted or unsubstituted 4,5-dihydro-imidazole, unsubstituted 4,5-dihydro-imidazole, $R^{10}$-substituted or unsubstituted 1,4,5,6-tetrahydropyrimidine, unsubstituted 1,4,5,6-tetrahydropyrimidine. In embodiments, one of $R^{3A}$ and $R^{3B}$ is hydrogen.

$R^{3A}$ and $R^{3B}$ may be joined together to form a substituted or unsubstituted heterocycloalkyl or substituted or unsubstituted heteroaryl. $R^{3A}$ and $R^{3B}$ may be joined together to form a $R^{10}$-substituted heterocycloalkyl. $R^{3A}$ and $R^{3B}$ may be joined together to form a $R^{10}$-substituted 3 to 8 membered heterocycloalkyl. $R^{3A}$ and $R^{3B}$ may be joined together to form a $R^{10}$-substituted 4 to 6 membered heterocycloalkyl. $R^{3A}$ and $R^{3B}$ may be joined together to form a $R^{10}$-substituted 5 membered heterocycloalkyl. $R^{3A}$ and $R^{3B}$ may be joined together to form a $R^{10}$-substituted 6 membered heterocycloalkyl. $R^{3A}$ and $R^{3B}$ may be joined together to form a $R^{10}$-substituted heteroaryl. $R^{3A}$ and $R^{3B}$ may be joined together to form a $R^{10}$-substituted 5 to 8 membered heteroaryl. $R^{3A}$ and $R^{3B}$ may be joined together to form a $R^{10}$-substituted 5 membered heteroaryl. $R^{3A}$ and $R^{3B}$ may be joined together to form a $R^{10}$-substituted 6 membered heteroaryl. In embodiments, one of $R^{3A}$ and $R^{3B}$ is hydrogen.

$R^{10}$ is hydrogen, halogen, oxo, —$N_3$, —$CF_3$, —$CCl_3$, —CN, —$COR^{10A}$, —$OR^{10A}$, —$NR^{10A}R^{10B}$, —$COOR^{10A}$, —$CONR^{10A}R^{10B}$, —$NHC(O)R^{10A}$, —$NO_2$, —$SR^{10A}$, $SO_{n3}R^{10A}$, —$NHNR^{10A}R^{10B}$, —$ONR^{10A}R^{10B}$, —$NHC(O)NHNR^{10A}R^{10B}$, —$C(NCN)R^{10A}$, —$C(NH)R^{10A}$, $R^{10C}$—substituted or unsubstituted alkyl, $R^{10C}$-substituted or unsubstituted heteroalkyl, $R^{10C}$-substituted or unsubstituted cycloalkyl, $R^{10C}$-substituted or unsubstituted heterocycloalkyl, $R^{10C}$-substituted or unsubstituted aryl, or $R^{10C}$-substituted or unsubstituted heteroaryl.

$R^{10}$ may be hydrogen, halogen, oxo, —$N_3$, —$CF_3$, —$CCl_3$, —CN, —CHO, —OH, —$NH_2$, —COOH, —$CONH_2$, —$NO_2$, —SH, —$SO_2$, —$SO_2Cl$, —$SO_2CH_3$— $SO_3H$, —$SO_4H$, —$SO_2NH_2$, —$NHNH_2$, —$ONH_2$, —NHC(O)$NHNH_2$, unsubstituted alkyl, unsubstituted heteroalkyl, unsubstituted cycloalkyl, unsubstituted heterocycloalkyl, unsubstituted aryl, or unsubstituted heteroaryl.

$R^{10A}$ and $R^{10B}$ are independently hydrogen, halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{10A}$ and $R^{10B}$ may independently be hydrogen, halogen, oxo, —$N_3$, —$CF_3$, —$CCl_3$, —$CBr_3$, —$CI_3$, —CN, —CHO, —OH, —$NH_2$, —COOH, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —$NHC(O)NHNH_2$, $R^{10D}$-substituted or unsubstituted alkyl, $R^{10D}$-substituted or unsubstituted heteroalkyl, $R^{10D}$-substituted or unsubstituted cycloalkyl, $R^{10D}$-substituted or unsubstituted heterocycloalkyl, $R^{10D}$-substituted or unsubstituted aryl, or $R^{10D}$-substituted or unsubstituted heteroaryl. $R^{10A}$ and $R^{10B}$ may independently be unsubstituted alkyl, unsubstituted heteroalkyl, unsubstituted cycloalkyl, unsubstituted heterocycloalkyl, unsubstituted aryl, unsubstituted heteroaryl, or a detectable moiety. $R^{10A}$ and $R^{10B}$ may independently be hydrogen, halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —$NHC(O)NHNH_2$, unsubstituted alkyl, unsubstituted heteroalkyl, unsubstituted cycloalkyl, unsubstituted heterocycloalkyl, unsubstituted aryl, unsubstituted heteroaryl, or a detectable moiety. $R^{10A}$ and $R^{10B}$ may independently be unsubstituted alkyl, unsubstituted heteroalkyl, unsubstituted cycloalkyl, unsubstituted heterocycloalkyl, unsubstituted aryl, unsubstituted heteroaryl, or a detectable moiety, or a detectable moiety.

$R^{10C}$ is hydrogen, halogen, oxo, —$N_3$, —$CF_3$, —$CCl_3$, —$CBr_3$, —$CI_3$, —CN, —$COR^{10E}$, —$OR^{10E}$, —$NR^{10E}R^{10F}$, —$COOR^{10E}$, —$CONR^{10E}R^{10F}$, —$NHC(O)R^{10E}$, —$NO_2$, —$SR^{10E}$, —$SO_{n3}R^{10E}$, $NHNR^{10E}R^{10F}$, $ONR^{10E}R^{10F}$, —$NHC(O)NHNR^{10E}R^{10F}$, $C(NCN)R^{10E}$, —$C(NH)R^{10E}$, $R^{10G}$-substituted or unsubstituted alkyl, $R^{10G}$-substituted or unsubstituted heteroalkyl, $R^{10G}$-substituted or unsubstituted cycloalkyl, $R^{10G}$-substituted or unsubstituted heterocycloalkyl, $R^{10G}$-substituted or unsubstituted aryl, or $R^{10G}$-substituted or unsubstituted heteroaryl, or a detectable moiety.

$R^{10C}$ may be oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, unsubstituted alkyl, unsubstituted heteroalkyl, unsubstituted cycloalkyl, unsubstituted heterocycloalkyl, unsubstituted aryl, or unsubstituted heteroaryl, or a detectable moiety.

$R^{10G}$ is hydrogen, halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$—

SO$_3$H, —SO$_4$H, —SO$_2$NH$_2$, —NHNH$_2$, —ONH$_2$, —NHC(O)NHNH$_2$—R$^{10M}$-substituted or unsubstituted heteroalkyl, R$^{10M}$-substituted or unsubstituted cycloalkyl, R$^{10M}$-substituted or unsubstituted heterocycloalkyl, R$^{10M}$-substituted or unsubstituted aryl, or R$^{10M}$-substituted or unsubstituted heteroaryl, or a detectable moiety.

R$^{10G}$ may be oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, unsubstituted alkyl, unsubstituted heteroalkyl, unsubstituted cycloalkyl, unsubstituted heterocycloalkyl, unsubstituted aryl, or unsubstituted heteroaryl, or a detectable moiety.

R$^{10D}$ is hydrogen, halogen, oxo, —N$_3$, —CF$_3$, —CCl$_3$, —CBr$_3$, —CI$_3$, —CN, —COR$^{10E}$, —OR$^{10E}$, —NR$^{10H}$R$^{10J}$, COOR$^{10H}$, —CONR$^{10H}$R$^{10J}$, —NHC(O)R$^{10H}$, —NO$_2$, —SR$^{10H}$, —SO$_{n3}$R$^{10H}$, —NHNR$^{10H}$R$^{10J}$, ONR$^{10H}$R$^{10J}$, NHC(O)NHNR$^{10H}$R$^{10J}$, —C(NCN)R$^{10H}$, —C(NH)R$^{10H}$, R$^{10K}$-substituted or unsubstituted alkyl, R$^{10K}$-substituted or unsubstituted heteroalkyl, substituted or unsubstituted cycloalkyl, R$^{10K}$-substituted or unsubstituted heterocycloalkyl, R$^{10K}$-substituted or unsubstituted aryl, or R$^{10K}$-substituted or unsubstituted heteroaryl, or a detectable moiety.

R$^{10K}$ is hydrogen, halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$—R$^{10L}$-substituted or unsubstituted heteroalkyl, R$^{10L}$-substituted or unsubstituted cycloalkyl, R$^{10L}$-substituted or unsubstituted heterocycloalkyl, R$^{10L}$-substituted or unsubstituted aryl, or R$^{10L}$-substituted or unsubstituted heteroaryl, or a detectable moiety.

R$^{10E}$, R$^{10F}$, R$^{10H}$, R$^{10J}$, R$^{10L}$, and R$^{10M}$ are independently be hydrogen, halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, unsubstituted alkyl, or unsubstituted heteroalkyl, unsubstituted cycloalkyl, unsubstituted heterocycloalkyl, unsubstituted aryl, or substituted or unsubstituted heteroaryl, or a detectable moiety.

R$^{3A}$ and R$^{3B}$ may independently be hydrogen, —C(NH)NH$_2$, unsubstituted 4,5-dihydro-imidazole, unsubstituted 1,4,5,6-tetrahydropyrimidine, unsubstituted 1,2,3,4-tetrahydro-1,8-naphthyridine, or unsubstituted pyridine.

Y may be —C(O)N(R$^4$)—. Y may be —O—. Y may be —C(O)O—Y may be —S—. Y may be —N(SO$_2$—R$^4$)—. Y may be —N(C(O)R$^4$)—. Y may be —N(C(O)OR$^4$)—. Y may be —(NR$^4$)C(O)—. Y may be —N(R$^4$)—. Y may be —NHC(O)—, —NCH$_3$—, —NC(O)CH$_3$—, —NC(O)OCH$_3$—, —N(SO$_2$CH$_3$)—, —S—, —O—, —C(O)O—, substituted or unsubstituted 3 to 6 membered heterocycloalkylene, or 5 to 6 membered unsubstituted heteroarylene, or unsubstituted 5 or 6 membered arylene. Y may be —NHC(O)—. Y may be —NCH$_3$—. Y may be —NC(O)CH$_3$—. Y may be —NC(O)OCH$_3$—. Y may be —N(SO$_2$CH$_3$)—. Y may be —S—. Y may be —O—. Y may be C(O)O. Y may be —S.

Y may be substituted or unsubstituted heterocycloalkylene. Y may be R$^{11}$-substituted or unsubstituted heterocycloalkylene. Y may be substituted or unsubstituted 3-8 membered heterocycloalkylene. Y may be R$^{11}$-substituted or unsubstituted 3-8 membered heterocycloalkylene. Y may be substituted or unsubstituted 3-6 membered heterocycloalkylene. Y may be R$^{11}$-substituted or unsubstituted 3-6 membered heterocycloalkylene. Y may be substituted or unsubstituted 3-5 membered heterocycloalkylene. Y may be R$^{11}$-substituted or unsubstituted 3-5 membered heterocycloalkylene. Y may be substituted or unsubstituted 4-6 membered heterocycloalkylene. Y may be R$^{11}$-substituted or unsubstituted 4-6 membered heterocycloalkylene. Y may be substituted or unsubstituted 5 membered heterocycloalkylene. Y may be R$^{11}$-substituted or unsubstituted 5 membered heterocycloalkylene. Y may be substituted or unsubstituted 6 membered heterocycloalkylene. Y may be R$^{11}$-substituted or unsubstituted 6 membered heterocycloalkylene. Y may be substituted or unsubstituted arylene. Y may be R$^{11}$-substituted or unsubstituted arylene. Y may be substituted or unsubstituted 5-8 membered arylene. Y may be R$^{11}$-substituted or unsubstituted 5-8 membered arylene. Y may be substituted or unsubstituted 5-6 membered arylene. Y may be R$^{11}$-substituted or unsubstituted 5-6 membered arylene. Y may be substituted or unsubstituted 5 membered arylene. Y may be R$^{11}$-substituted or unsubstituted 5 membered arylene. Y may be substituted or unsubstituted 6 membered arylene. Y may be R$^{11}$-substituted or unsubstituted 6 membered arylene. Y may be substituted or unsubstituted heteroarylene. Y may be R$^{11}$-substituted or unsubstituted heteroarylene. Y may be substituted or unsubstituted 5-8 membered heteroarylene. Y may be R$^{11}$-substituted or unsubstituted 5-8 membered heteroarylene. Y may be substituted or unsubstituted 5-6 membered heteroarylene. Y may be R$^{11}$-substituted or unsubstituted 5-6 membered heteroarylene. Y may be substituted or unsubstituted 5 membered heteroarylene. Y may be R$^{11}$-substituted or unsubstituted 5 membered heteroarylene. Y may be substituted or unsubstituted 6 membered heteroarylene. Y may be R$^{11}$-substituted or unsubstituted 6 membered heteroarylene.

R$^{11}$ is hydrogen, halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, unsubstituted alkyl, unsubstituted heteroalkyl, unsubstituted cycloalkyl, unsubstituted heterocycloalkyl, unsubstituted aryl, or unsubstituted heteroaryl.

R$^4$ may be hydrogen. R$^4$ may be methyl. R$^4$ may be ethyl. R$^4$ may be propyl.

The compound of formula (I) may have the formula:

(II)

$(R^2)_{z2}$

Y—L$^3$—NR$^{3A}$R$^{3B}$ or $(R^1)_{z1}$ (IIa)

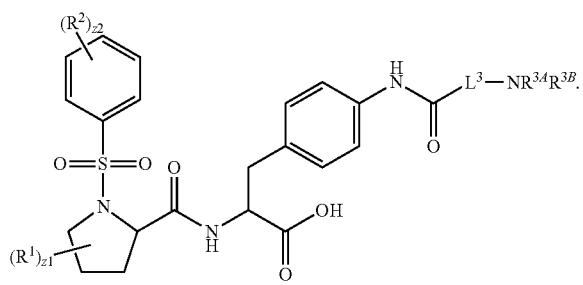

Y, $L^3$, $R^1$, $R^2$, $R^{3A}$, $R^{3B}$, z1, and z2 are as described herein, including embodiments thereof.

$L^3$ of formula (II) may be substituted or unsubstituted $C_1$-$C_6$ alkylene, substituted or unsubstituted 2 to 6 membered heteroalkylene, alkylarylene. $R^1$ of formula (II) may be hydrogen, substituted or unsubstituted methyl, or oxo. $R^2$ of formula (II) may be hydrogen, halogen, —$SO_2CH_3$, —$NO_2$, —$NH_2$, substituted or unsubstituted $C_1$-$C_3$ alkyl, or substituted or unsubstituted 2 to 5 membered heteroalkyl. $R^{3A}$ and $R^{3B}$ of formula (II) may independently be hydrogen, —C(NH)$NH_2$, —C(NCN)$NH_2$, or substituted or unsubstituted heterocycloalkyl, or substituted or unsubstituted heteroaryl.

The compound of formula (I) may have the formula:

(IIb)

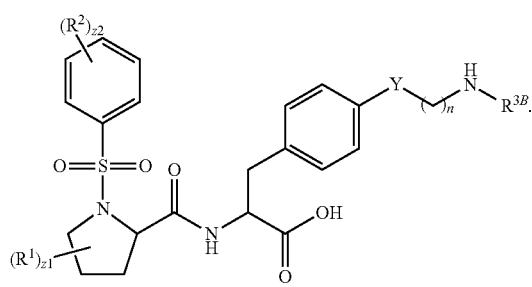

The symbol n is an integer from 1 to 8. The symbol n may be 1. The symbol n may be 2. The symbol n may be 3. The symbol n may be 4. The symbol n may be 5. The symbol n may be 6. The symbol n may be 7. The symbol n may be 8. Y, $R^1$, $R^2$, $R^{3B}$, z1, and z2 are as described herein, including embodiments thereof.

The compound of formula (I) may have the formula:

(IIc)

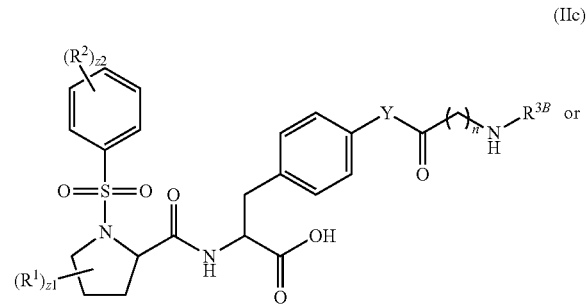

(IId)

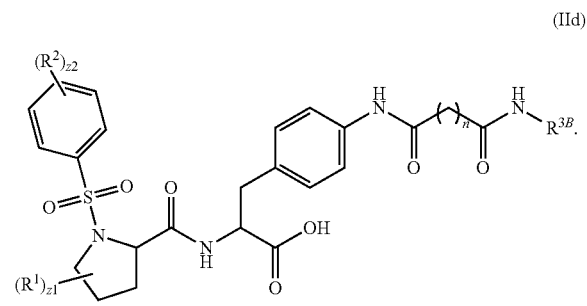

$R^1$, $R^2$, $R^{3B}$, z1, z2 and n are as described herein, including embodiments thereof.

The compound of formula (II) may have the formula:

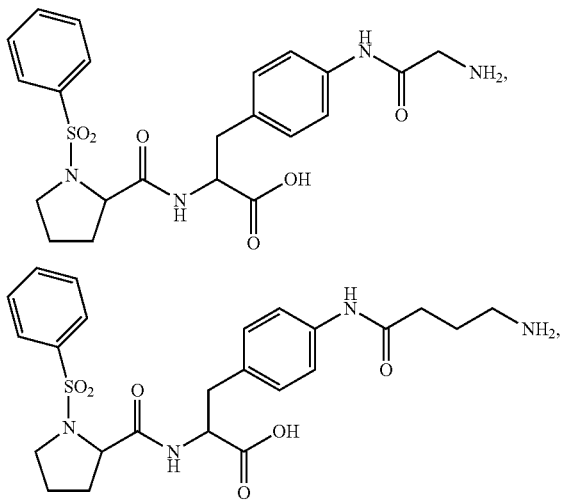

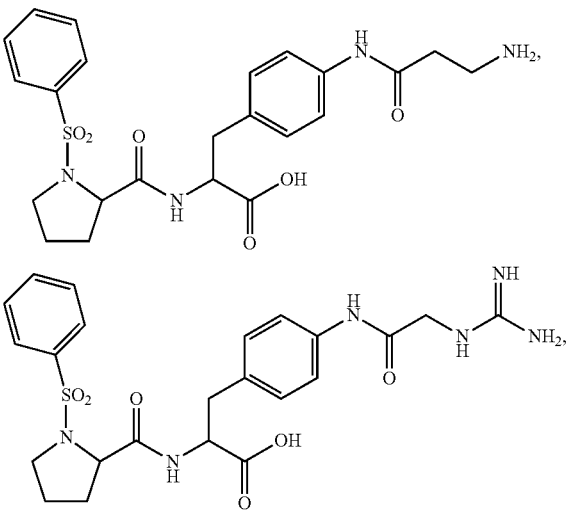

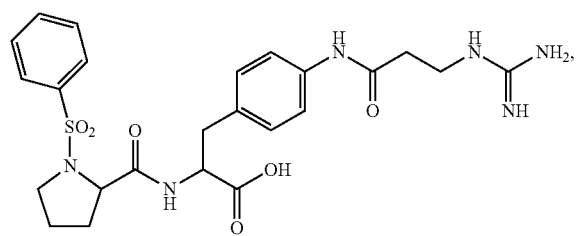
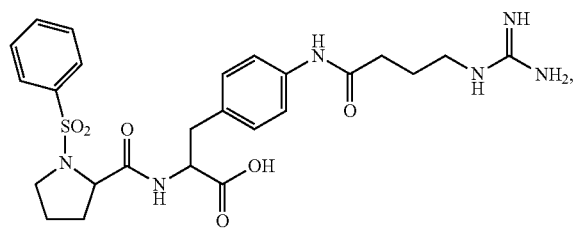
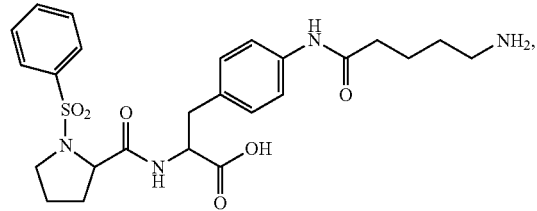
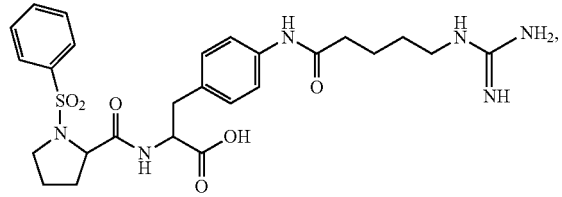
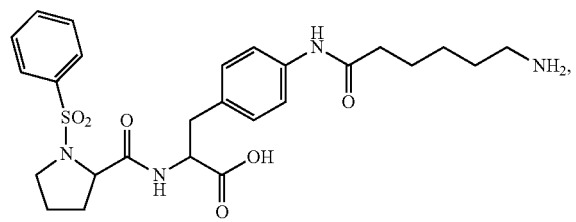
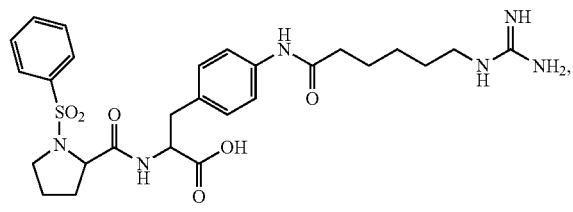
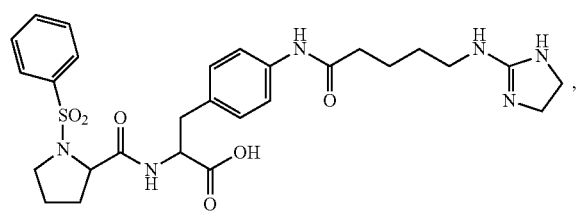
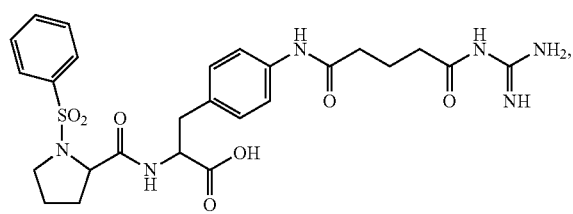
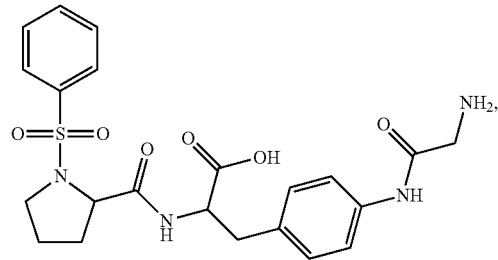
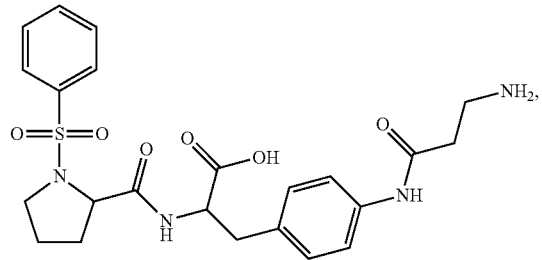
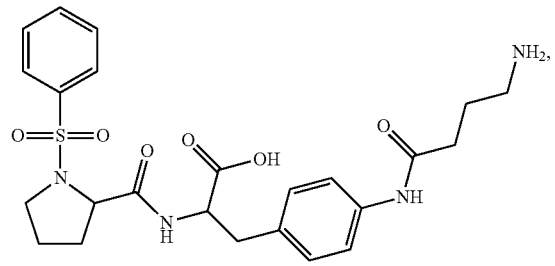
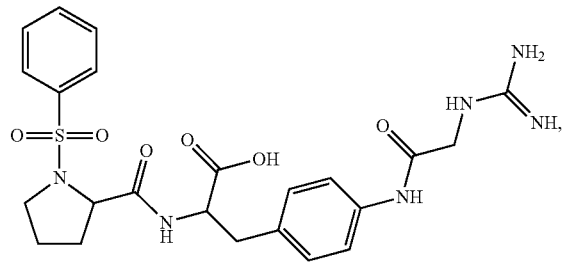
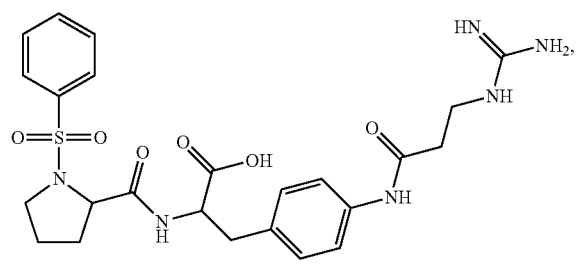
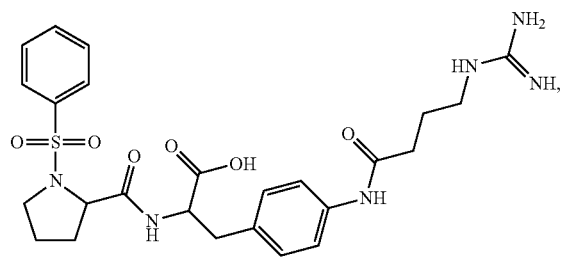

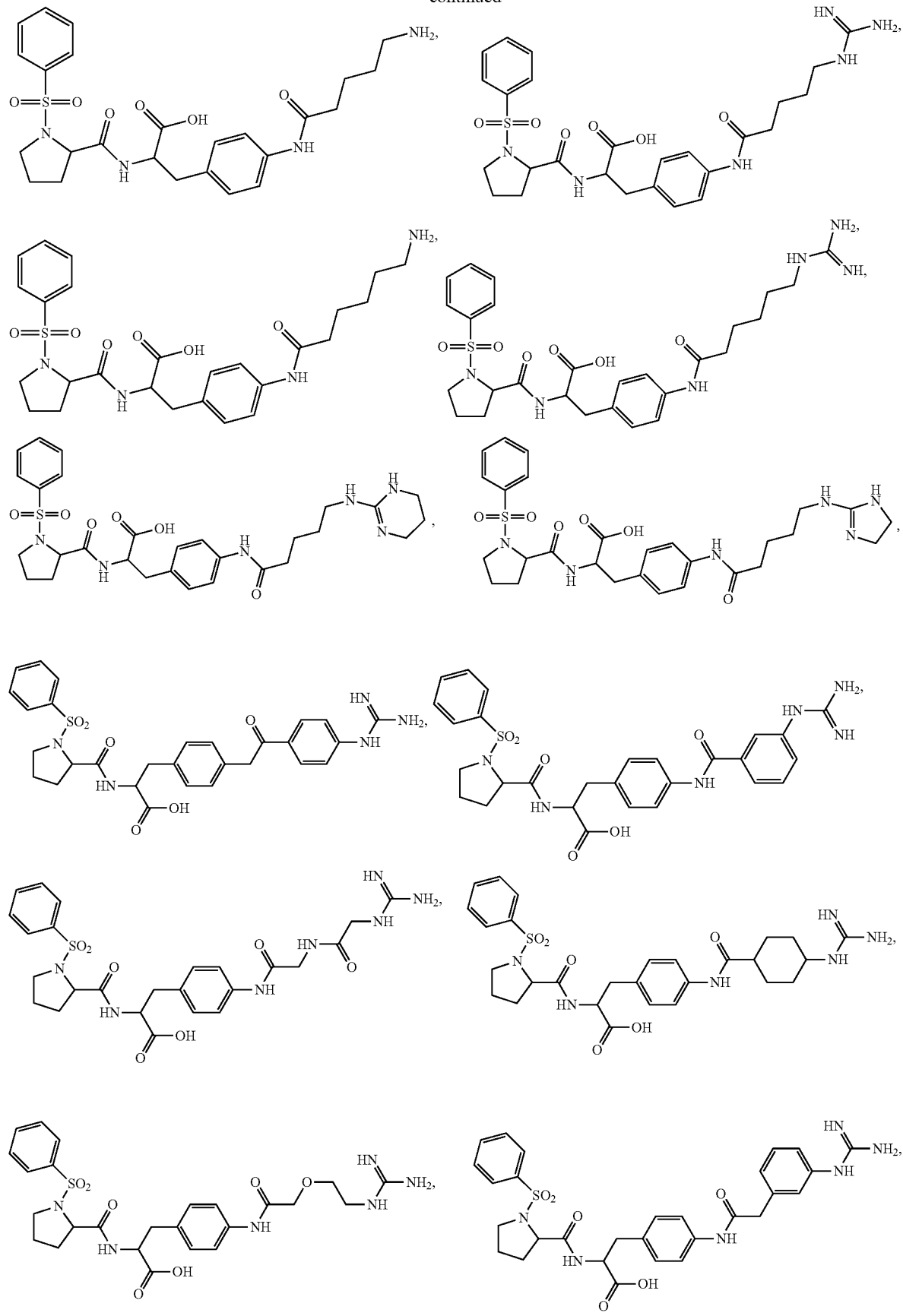

-continued
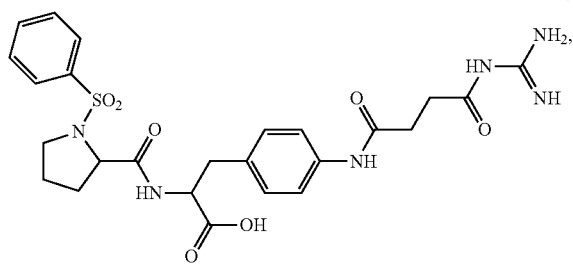
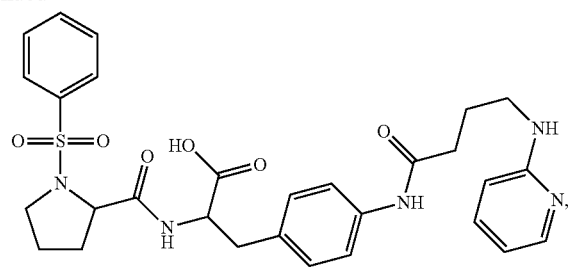
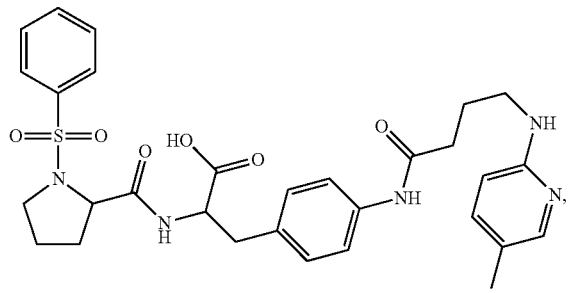
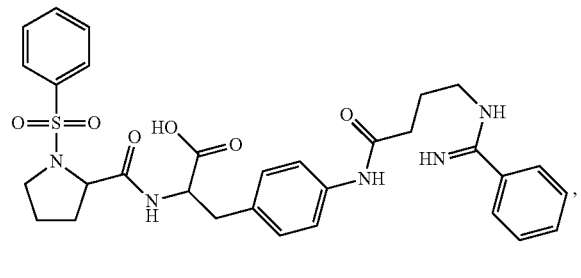
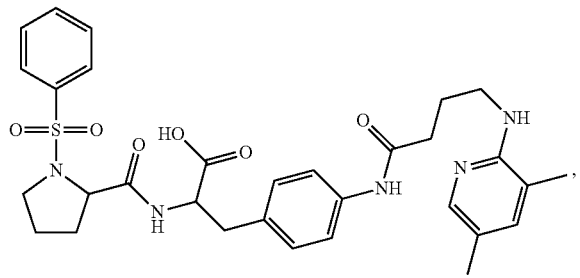
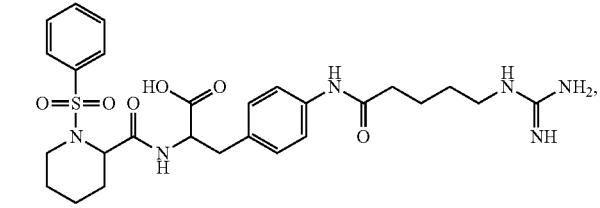
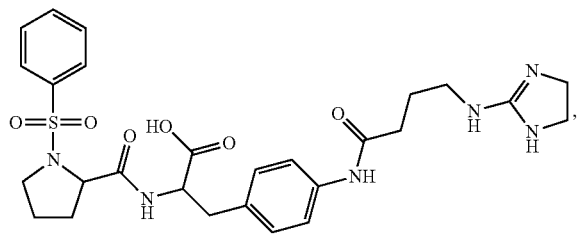
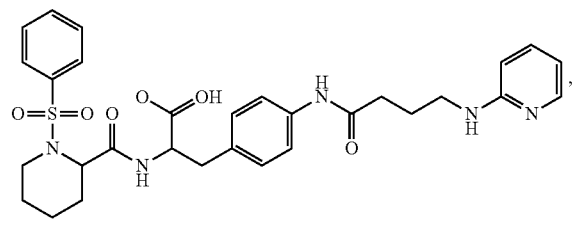
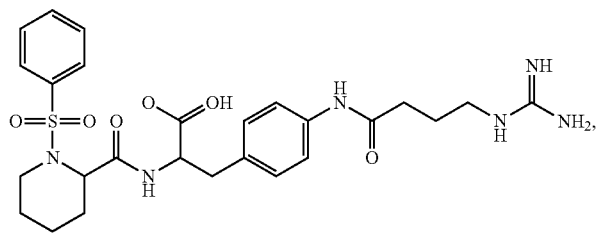
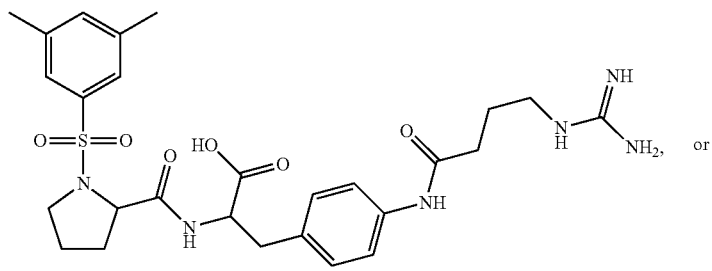

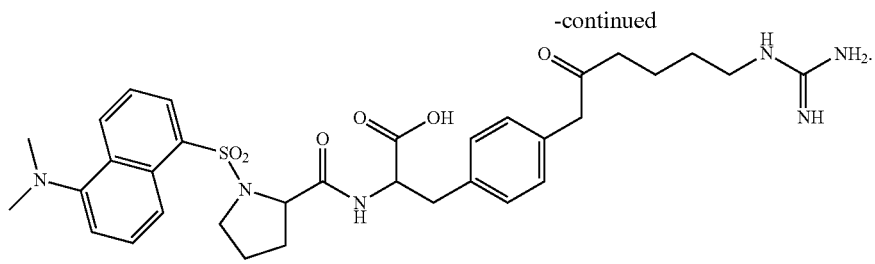
The compound of formula (I) may have the formula:
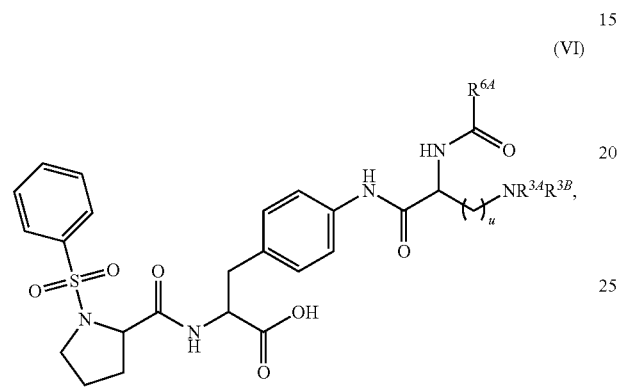
(VI)
where $R^{3A}$, $R^{3B}$, and $R^{6A}$ are as defined herein. The symbol u is an integer from 0 to 7. The symbol u may be an integer from 1 to 7.
The compound of formula (VI) may have the formula:
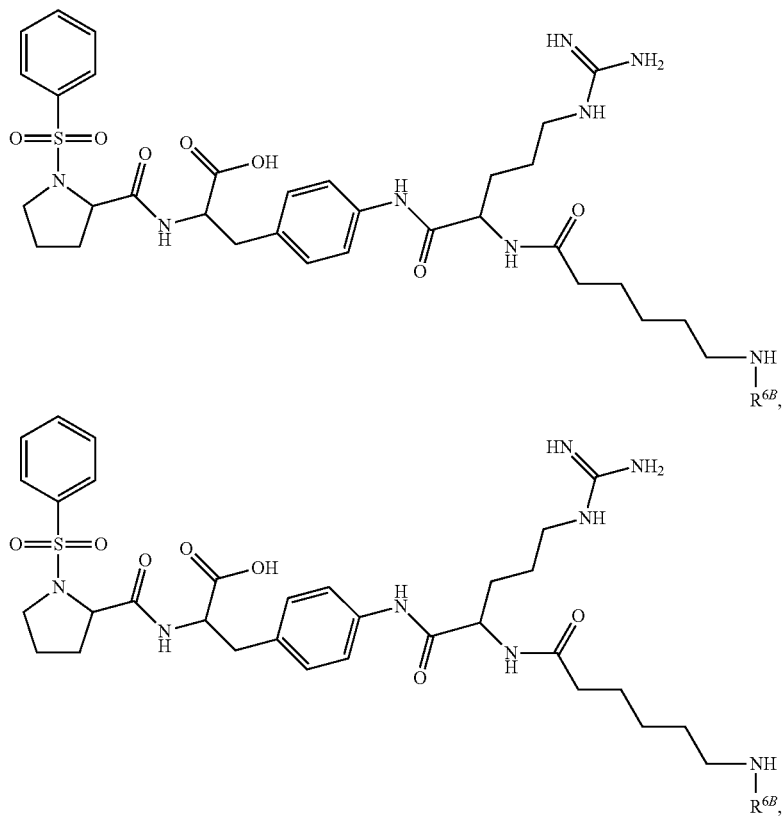

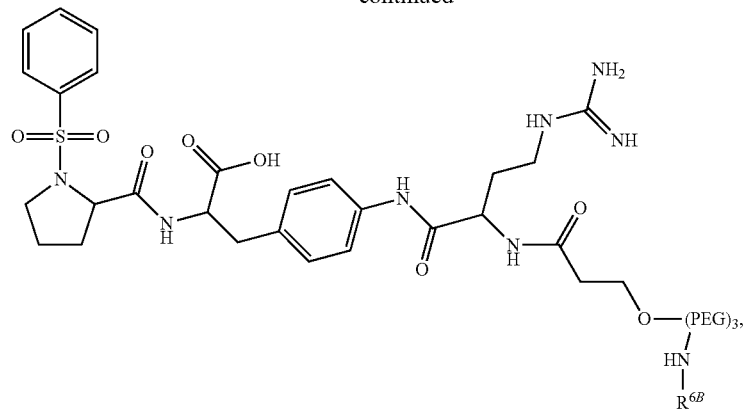

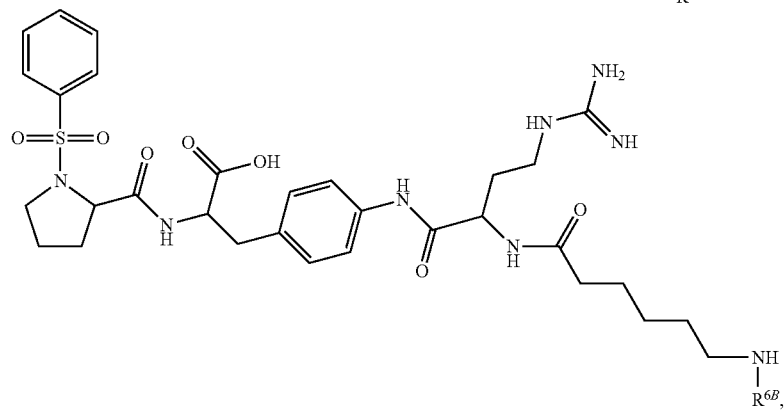

where $R^{6B}$ is a detectable moiety. The detectable moiety may be rhodamine, including analogues thereof, or fluorescein, including analogs thereof. The detectable moiety may be rhodamine, including analogues thereof. The rhodamine may be lissamine rhodamine sulfonyl or teramethylrhodamine isothiocyanate. The detectable moiety may be fluorescein, including analogs thereof. The fluorescein may be fluorescein isothiocyanate.

The compound may be a compound set forth in Table 1, Table 2, Table 3, Table 4 or Table 5. The compound may be a compound set forth in Table 1. The compound may be a compound set forth in Table 2. The compound may be a compound set forth in Table 3. The compound may be a compound set forth in Table 4. The compound may be a compound set forth in Table 5.

The compound of formula (I) may have the formula:

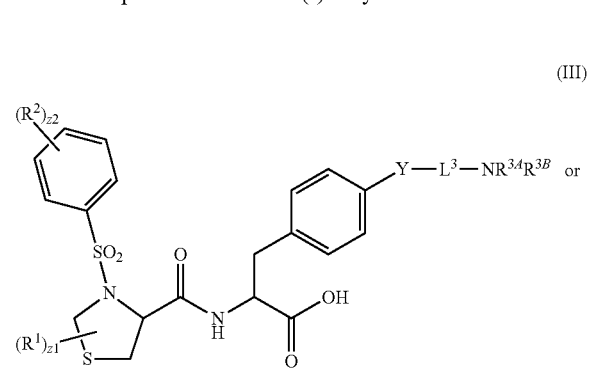

(III)

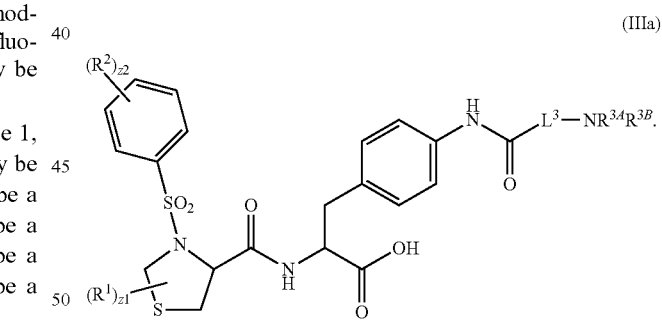

(IIIa)

Y, $L^3$, $R^1$, $R^2$, $R^{3A}$, $R^{3B}$, z1, and z2 are as described herein, including embodiments thereof.

$L^3$ may be substituted or unsubstituted $C_1$-$C_6$ alkylene, or substituted or unsubstituted 2 to 6 membered heteroalkylene. $R^1$ may be hydrogen or substituted or unsubstituted $C_1$-$C_3$ alkyl. $R^2$ may be hydrogen, halogen, —$SO_2CH_3$, —$NO_2$, —$NH_2$, substituted or unsubstituted $C_1$-$C_3$ alkyl, or substituted or unsubstituted 1 to 4 membered heteroalkyl. $R^{3A}$ and $R^{3B}$ may independently be hydrogen, —C(NH)NH_2, —C(NCN)NH_2, or substituted or unsubstituted heterocycloalkyl, or substituted or unsubstituted heteroaryl.

In embodiments, the compound of formula (III) has the formula:

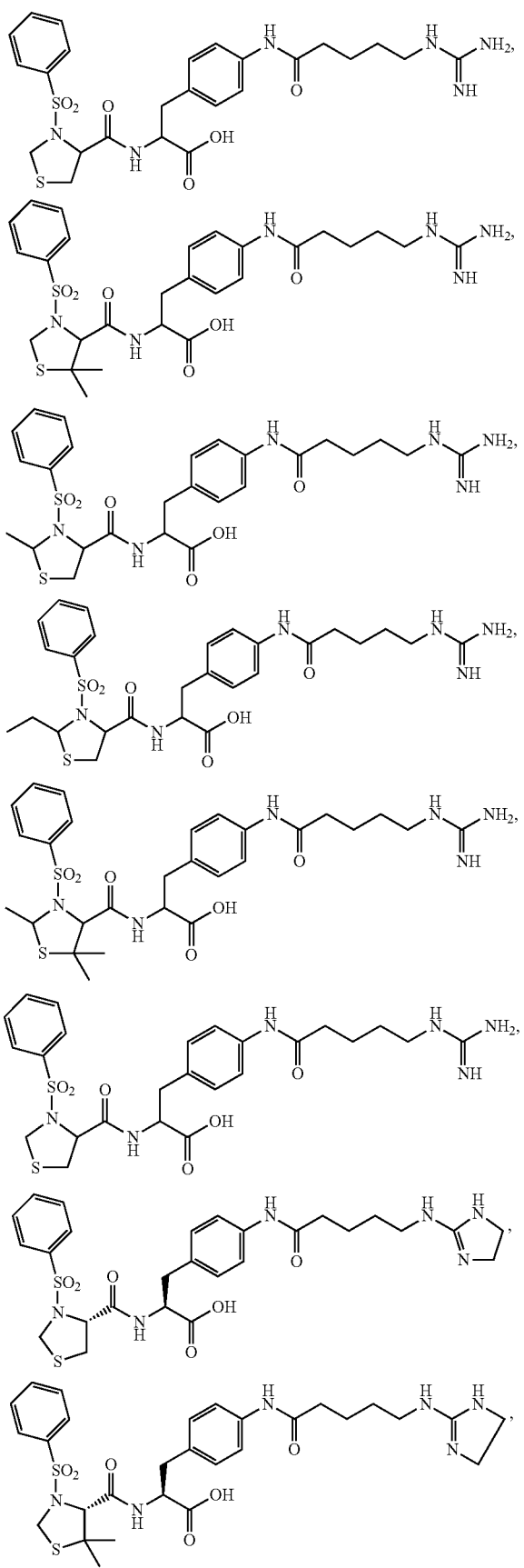
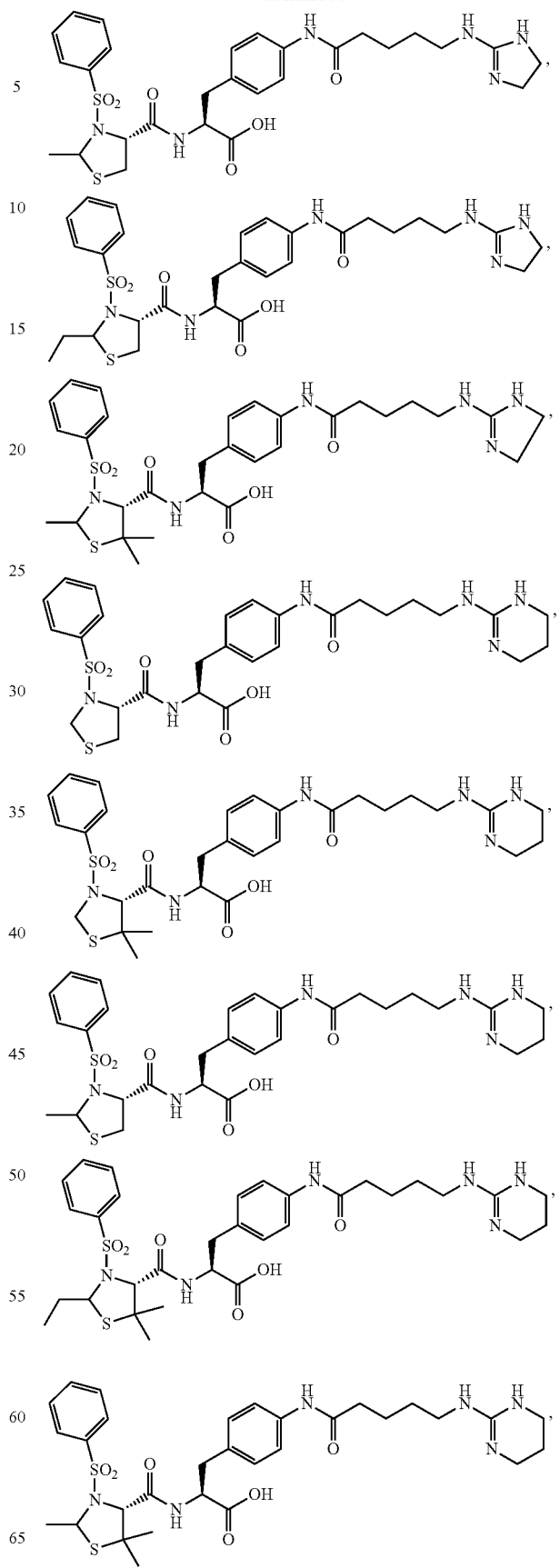

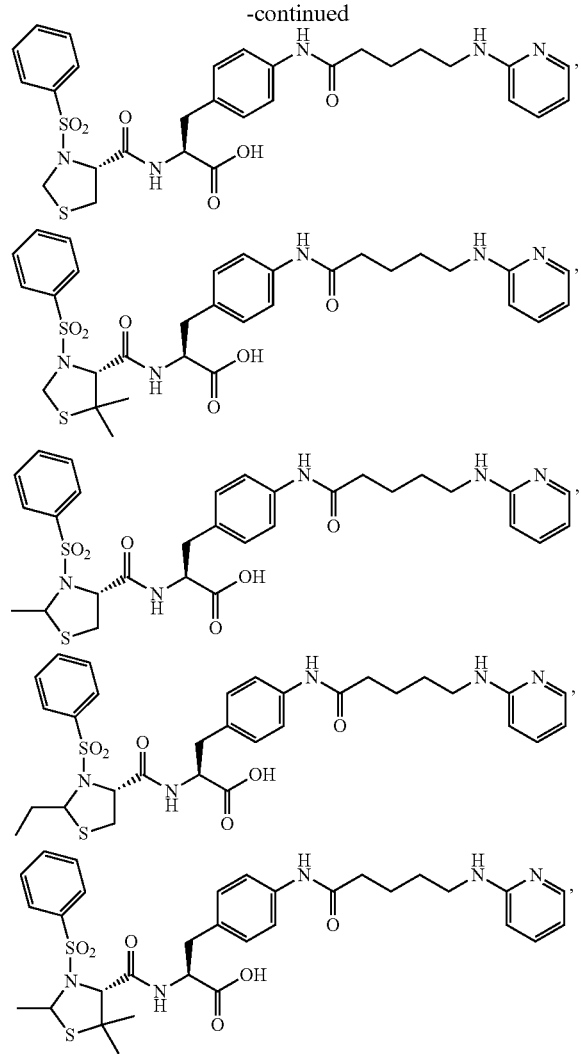
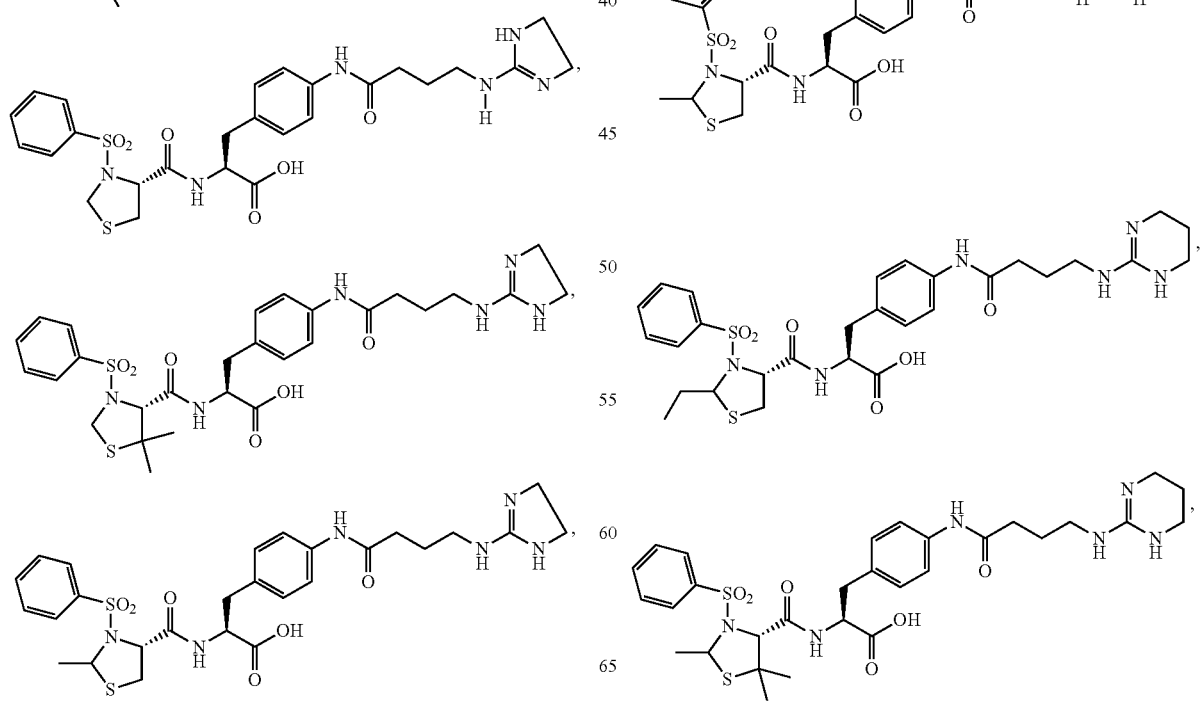

61
-continued
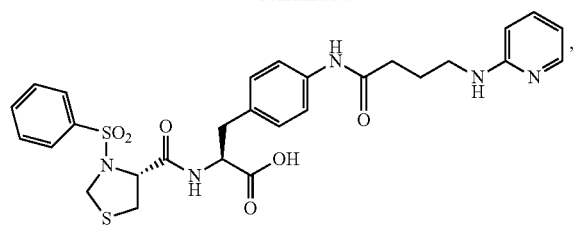
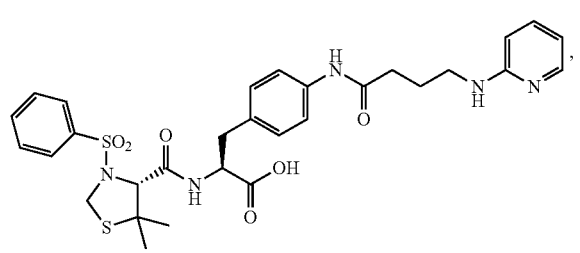
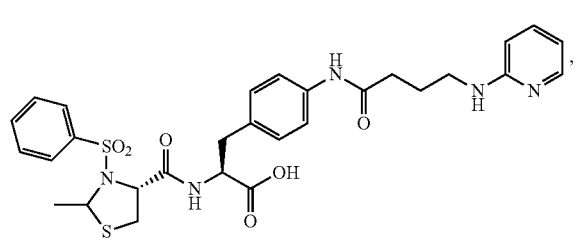
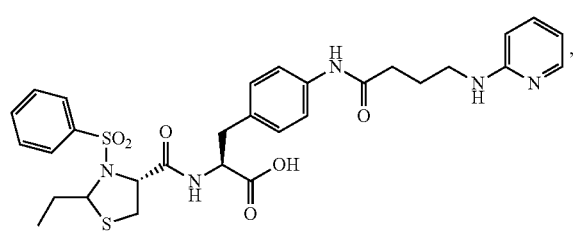
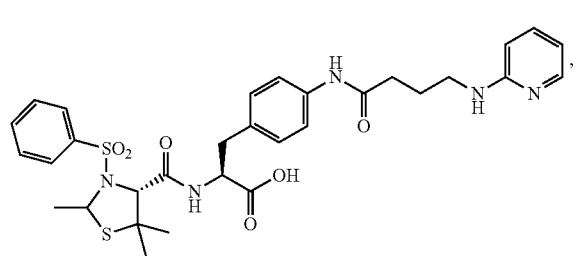
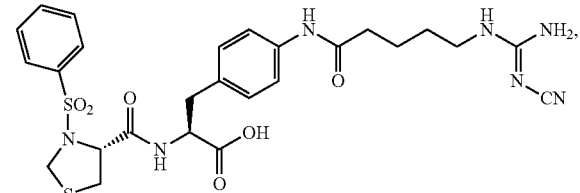
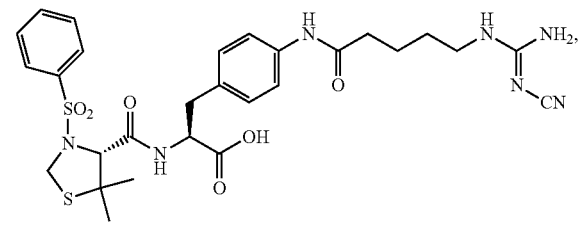
62
-continued
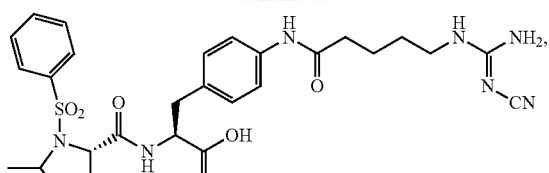
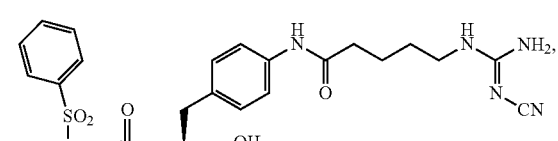
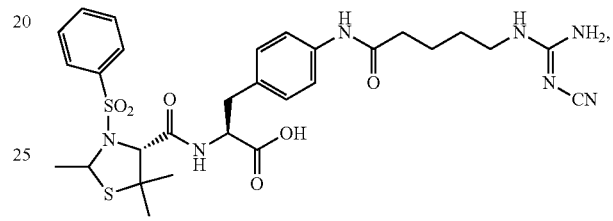
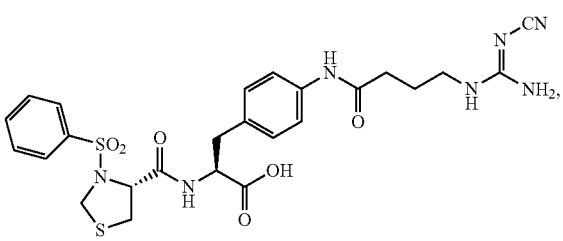
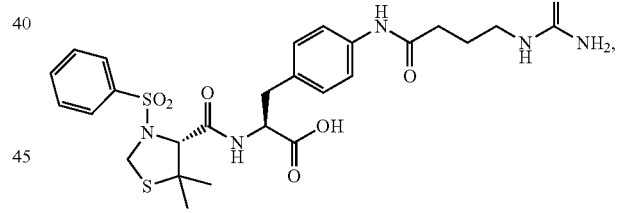
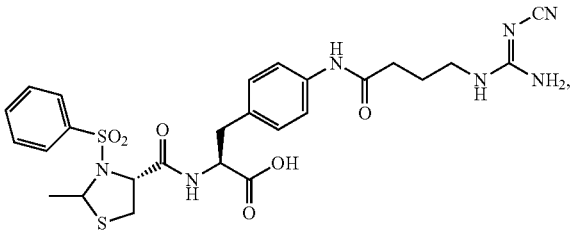
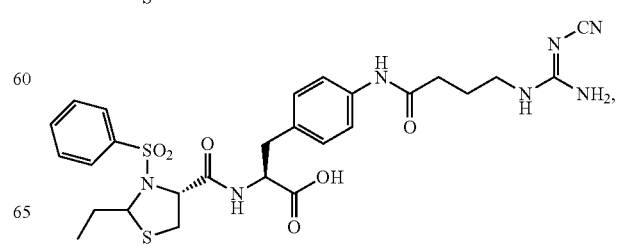

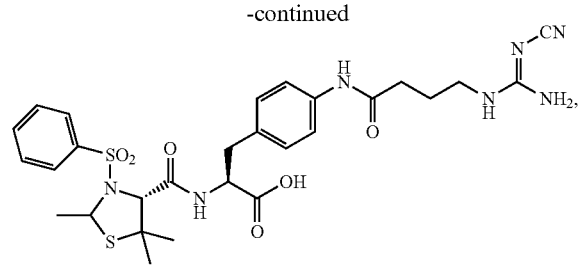
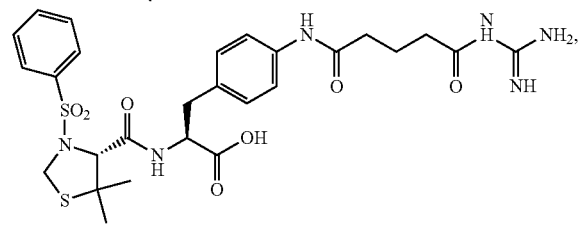
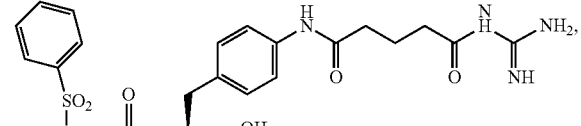
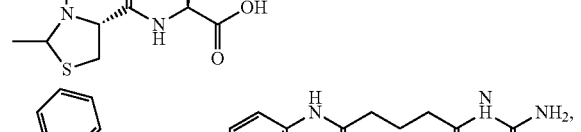
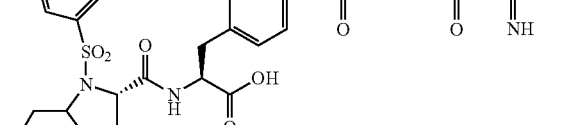
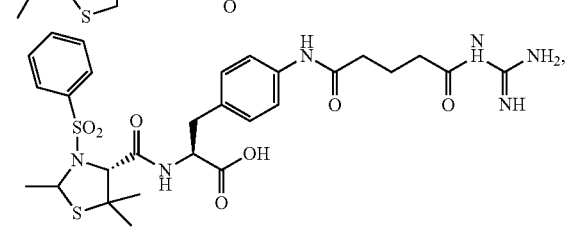

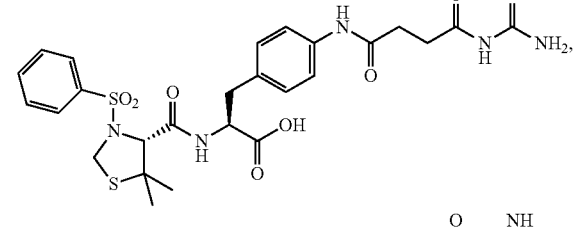
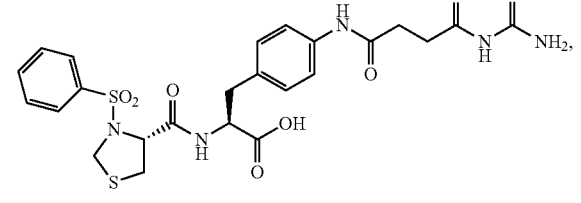
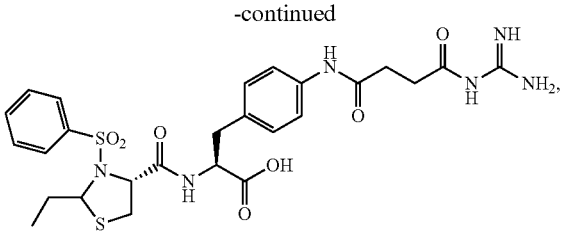
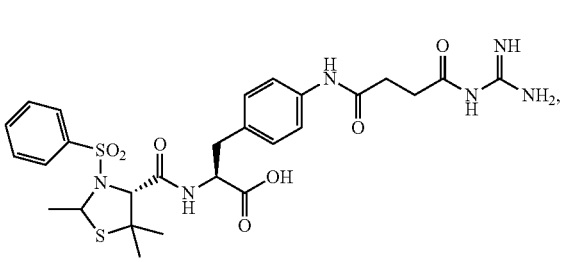
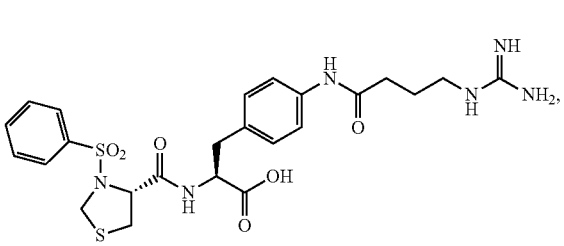 [SMILES: CC1OC(C)N(S(=O)(=O)c2ccccc2)[C@@H]1C(=O)N[C@@H](Cc1ccc(NC(=O)CCCNC(=N)N)cc1)C(=O)O]
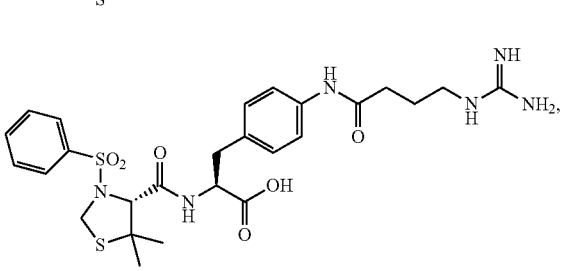
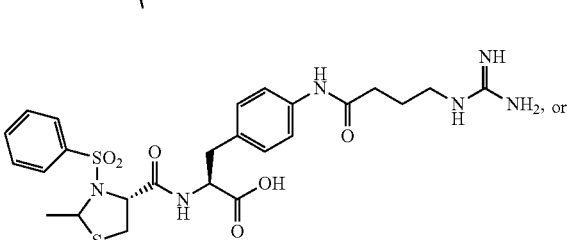
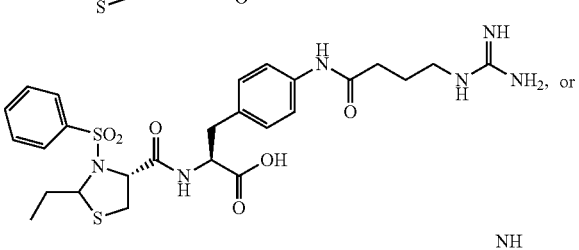
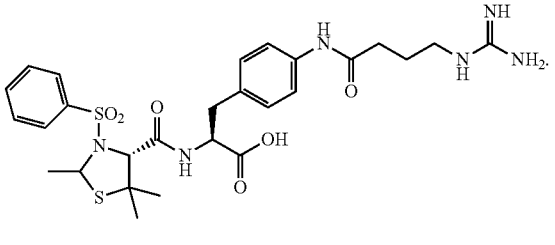
The compound of formula (III) may be a compound as set forth in Table 2.

The compound of formula (I) may have the formula:

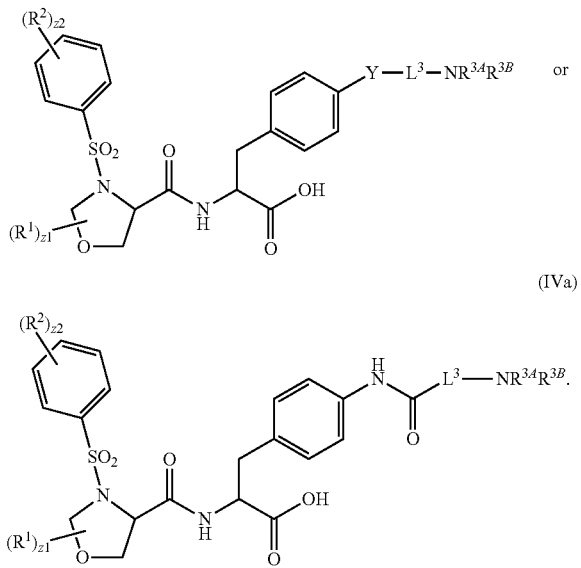

(IV)

(IVa)

Y, L³, R¹, R², R³ᴬ, R³ᴮ, z1, and z2 are as described herein, including embodiments thereof.

L³ may be substituted or unsubstituted $C_1$-$C_6$ alkylene, or substituted or unsubstituted 2 to 6 membered heteroalkylene. R¹ may be hydrogen or substituted or unsubstituted $C_1$-$C_3$ alkyl. R² is hydrogen. R³ᴬ and R³ᴮ may independently be hydrogen, —C(NH)NH$_2$, —C(NCN)NH$_2$, or substituted or unsubstituted heterocycloalkyl, or substituted or unsubstituted heteroaryl.

In embodiments, the compound of formula (IV) has the formula:

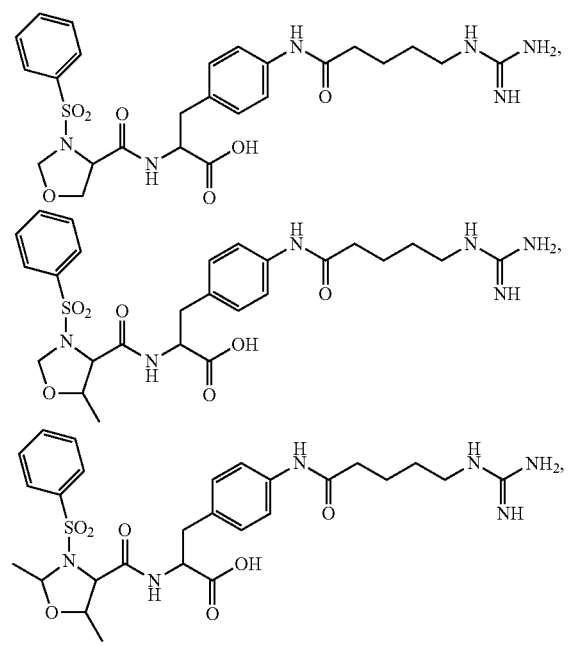

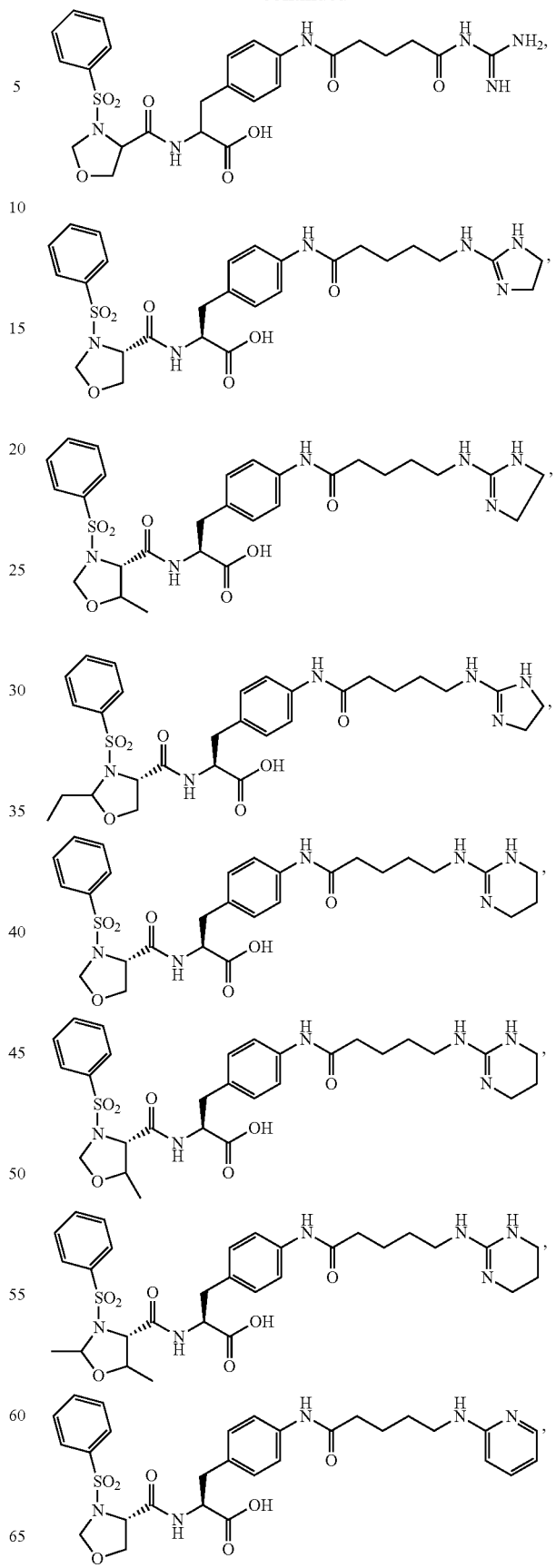

67
-continued
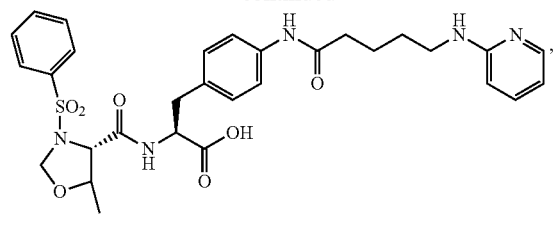
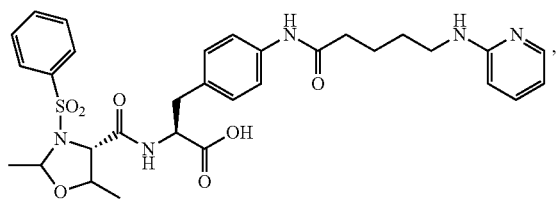
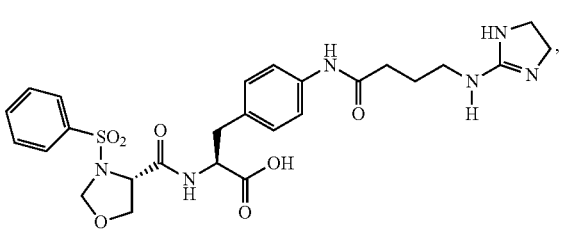
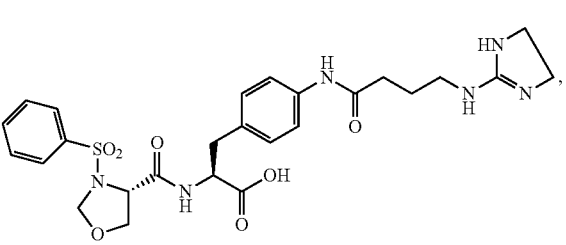
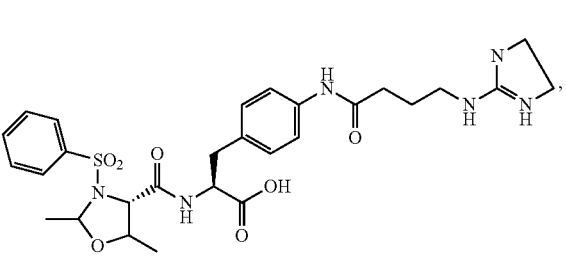
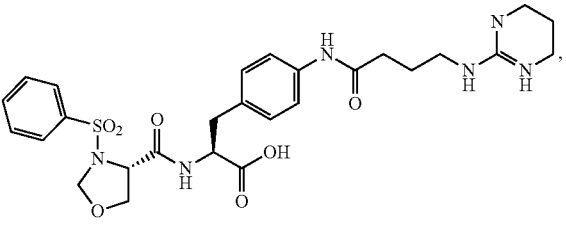
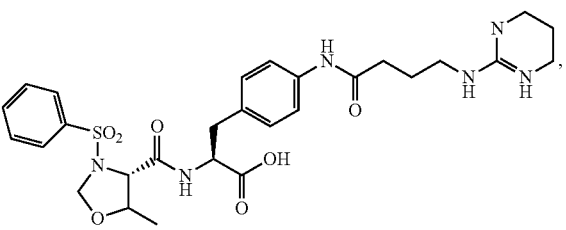
68
-continued
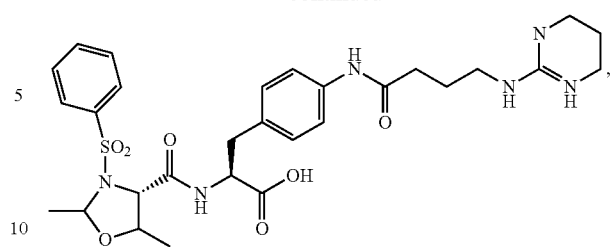
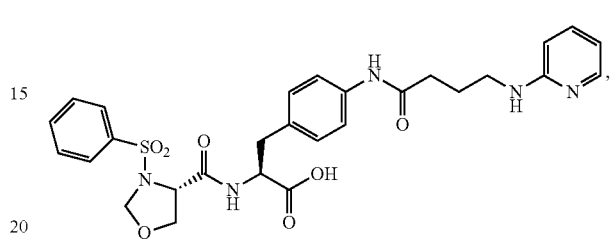
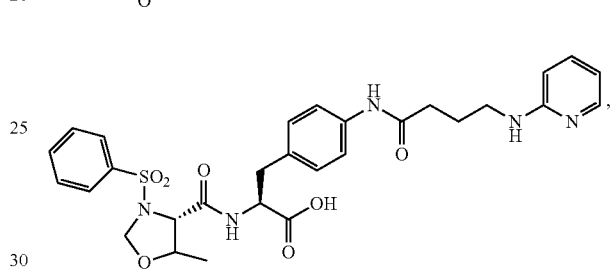
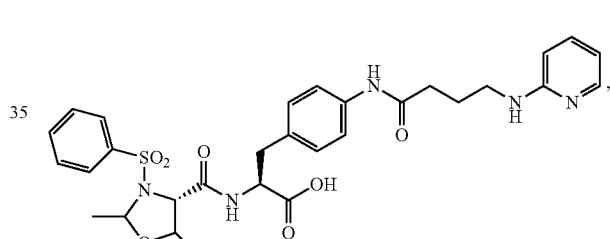
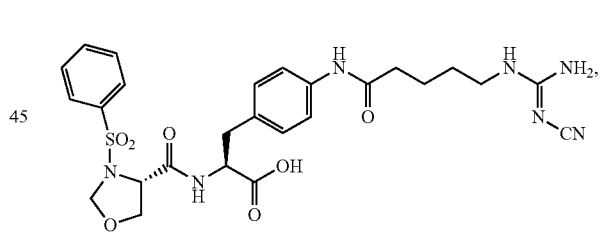
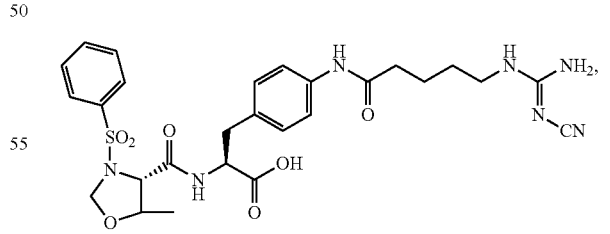
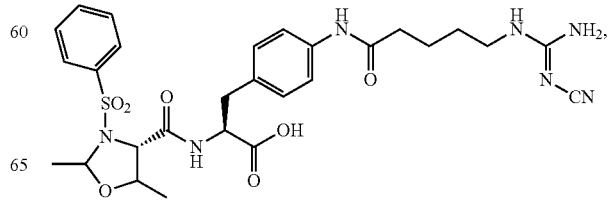

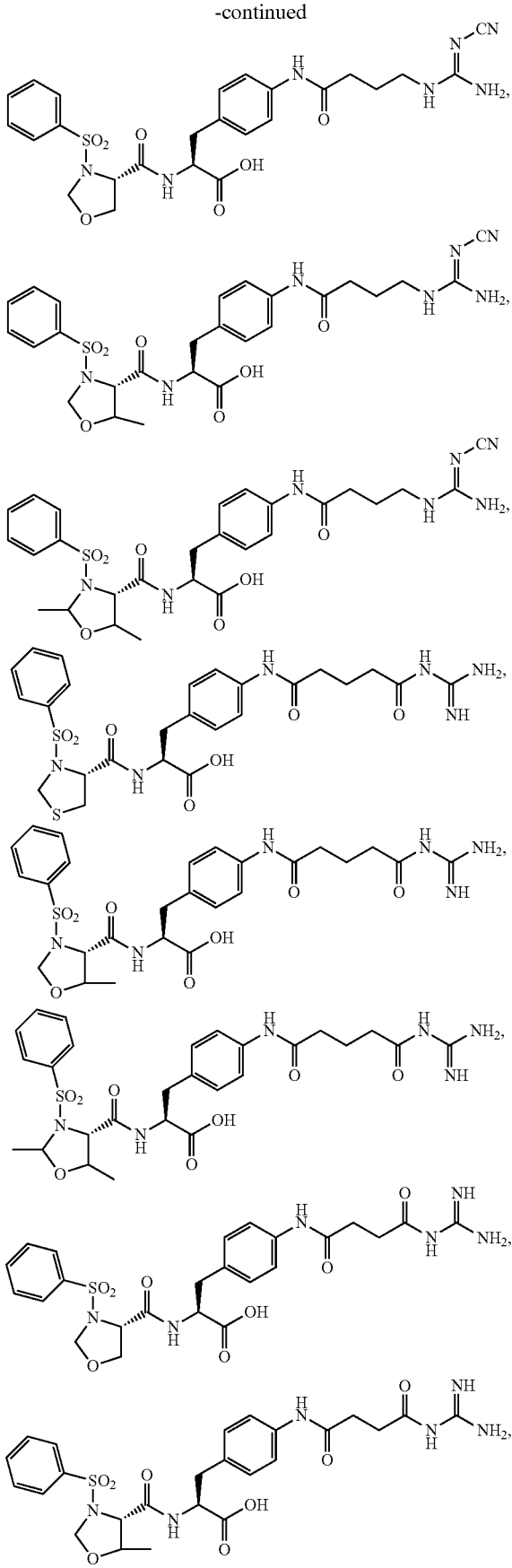
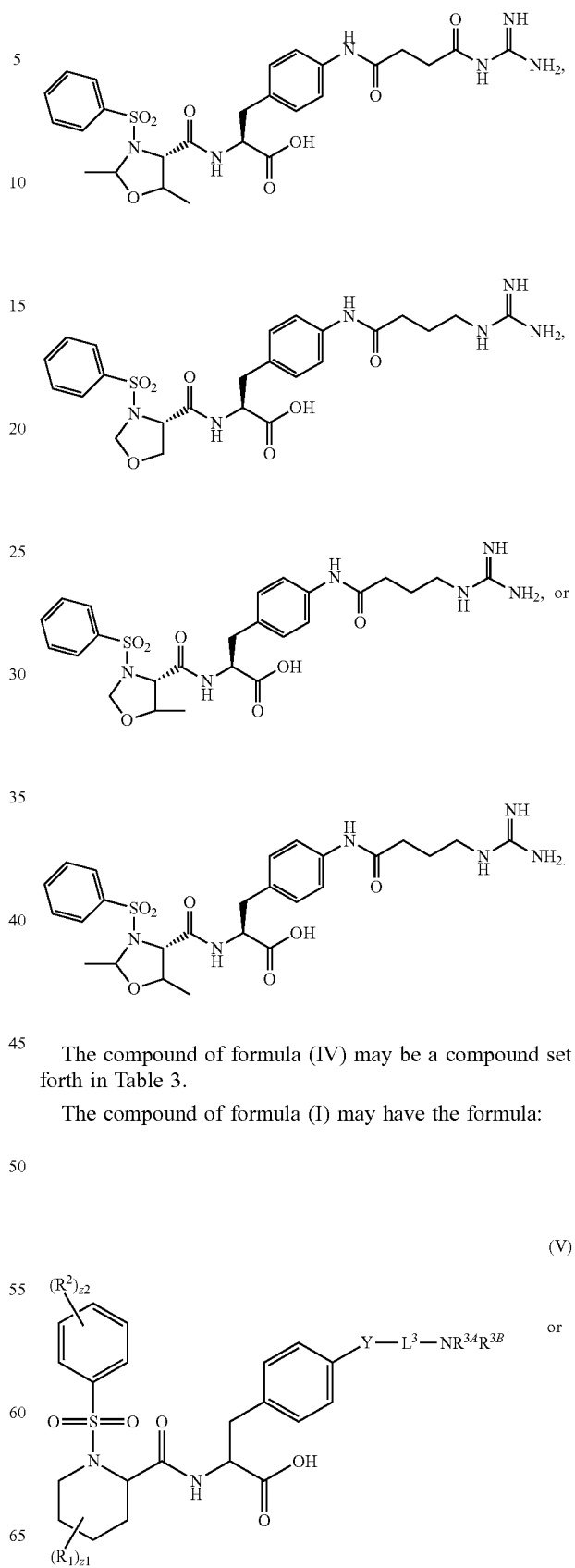
The compound of formula (IV) may be a compound set forth in Table 3.
The compound of formula (I) may have the formula:
(V)
or -continued (Va)

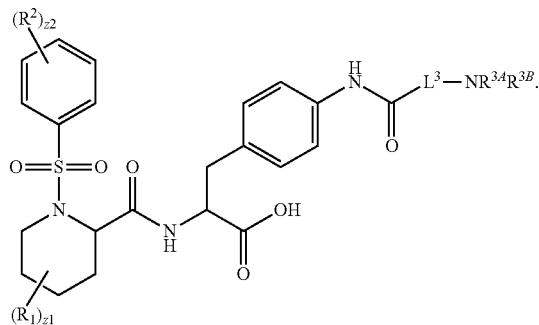

The compounds described herein may be prodrugs having formula:

(Ia)

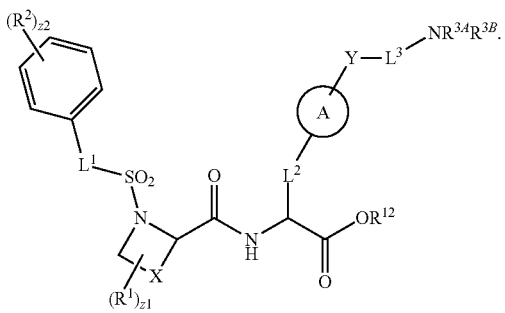

X, ring A, Y, $L^1$, $L^2$, $L^3$, $R^1$, $R^2$, $R^{3A}$, $R^{3B}$, z1 and z2 are as described herein, including embodiments thereof. $R^{12}$ is a pharmaceutically acceptable salt or substituted or unsubstituted $C_1$-$C_5$ alkyl. $R^{12}$ may be $R^{13}$-substituted or unsubstituted $C_1$-$C_5$ alkyl. $R^{12}$ may be $C_1$-$C_3$ unsubstituted alkyl. $R^{12}$ may be unsubstituted methyl, unsubstituted ethyl, or unsubstituted propyl.

$R^{13}$ is hydrogen, halogen, oxo, —$N_3$, —$CF_3$, —$CCl_3$, —$CI_3$, —CN, —CHO, —OH, —$NH_2$, —COOH, —$CONH_2$, —$NO_2$, —SH, —$SO_2$, —$SO_2Cl$, —$SO_2CH_3$—$SO_4H$, —$SO_2NH_2$, —$NHNH_2$, —$ONH_2$, —NHC(O)NHNH$_2$, unsubstituted alkyl, unsubstituted heteroalkyl, unsubstituted cycloalkyl, unsubstituted heterocycloalkyl, unsubstituted aryl, or unsubstituted heteroaryl.

In another aspect is a compound having formula:

(X)

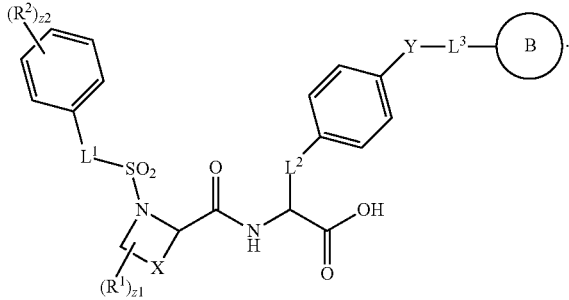

X, Y, $L^1$, $L^2$, $L^3$, $R^1$, $R^2$, z1 and z2 are as described herein for formula (I). Ring B is a substituted or unsubstituted cycloalkyl, substituted or unsubstituted heterocycloalkyl, substituted or unsubstituted aryl, substituted or unsubstituted heteroaryl, substituted or unsubstituted fused ring aryl or substituted or unsubstituted fused ring heteroaryl.

Ring B may be substituted or unsubstituted fused ring aryl or substituted or unsubstituted fused ring heteroaryl. Ring B may be substituted or unsubstituted fused ring aryl or substituted or unsubstituted fused ring heteroaryl where only one ring is aromatic. Ring B may substituted or unsubstituted fused ring aryl or substituted or unsubstituted fused ring heteroaryl where each ring has at least one heteroatom. The heteroatom may be N, O, or S. The heteroatom may be N. Ring B may be substituted or unsubstituted 5,5-, 5,6-, 6,5-, or 6,6-fused ring described herein (e.g. a substituted or unsubstituted 5,5-, 5,6-, 6,5-, or 6,6-fused ring aryl or substituted or unsubstituted 5,5-, 5,6-, 6,5-, or 6,6-fused ring heteroaryl). Ring B may be substituted or unsubstituted 6,6-fused ring aryl or substituted or unsubstituted 6,6-fused ring heteroaryl. Ring B may be substituted or unsubstituted 6,6-fused ring aryl or substituted or unsubstituted 6,6-fused ring heteroaryl where only one ring is aromatic.

Ring B may be $R^{10}$-substituted or unsubstituted fused ring aryl or $R^{15}$-substituted or unsubstituted fused ring heteroaryl. Ring B may be $R^{15}$-substituted or unsubstituted fused ring aryl or $R^{15}$-substituted or unsubstituted fused ring heteroaryl where only one ring is aromatic. Ring B may $R^{10}$-substituted or unsubstituted fused ring aryl or $R^{15}$-substituted or unsubstituted fused ring heteroaryl where each ring has at least one heteroatom. The heteroatom may be N, O, or S. The heteroatom may be N. Ring B may be $R^{15}$-substituted or unsubstituted 5,5-, 5,6-, 6,5-, or 6,6-fused ring described herein (e.g. a $R^{15}$-substituted or unsubstituted 5,5-, 5,6-, 6,5-, or 6,6-fused ring aryl or $R^{15}$-substituted or unsubstituted 5,5-, 5,6-, 6,5-, or 6,6-fused ring heteroaryl). Ring B may be $R^{10}$-substituted or unsubstituted 6,6-fused ring aryl or $R^{15}$-substituted or unsubstituted 6,6-fused ring heteroaryl. Ring B may be $R^{15}$-substituted or unsubstituted 6,6-fused ring aryl or $R^{15}$-substituted or unsubstituted 6,6-fused ring heteroaryl where only one ring is aromatic.

$R^{15}$ is hydrogen, halogen, oxo, —$N_3$, —$CF_3$, —$CCl_3$, —$CI_3$, —CN, —CHO, —OH, —$NH_2$, —N(CH$_3$)$_2$, —COOH, —$CONH_2$, —$NO_2$, —SH, —$SO_2$, —$SO_2Cl$, —$SO_2CH_3$—$SO_2NH_2$, —$NHNH_2$, —$ONH_2$, —NHC(O)NHNH$_2$, $R^{16}$-substituted or unsubstituted alkyl, $R^{16}$-substituted or unsubstituted heteroalkyl, $R^{16}$-substituted or unsubstituted cycloalkyl, substituted or unsubstituted heterocycloalkyl, $R^{16}$-substituted or unsubstituted aryl, or $R^{16}$-substituted or unsubstituted heteroaryl.

$R^{16}$ is hydrogen, halogen, oxo, —$N_3$, —$CF_3$, —$CCl_3$, —$CI_3$, —CN, —CHO, —OH, —$NH_2$, —N(CH$_3$)$_2$, —COOH, —$CONH_2$, —$NO_2$, —SH, —$SO_2$, —$SO_2Cl$, —$SO_2CH_3$—$SO_2NH_2$, —$NHNH_2$, —$ONH_2$, —NHC(O)NHNH$_2$, $R^{17}$-substituted or unsubstituted alkyl, $R^{17}$-substituted or unsubstituted heteroalkyl, $R^{17}$-substituted or unsubstituted cycloalkyl, substituted or unsubstituted heterocycloalkyl, $R^{17}$-substituted or unsubstituted aryl, or $R^{17}$-substituted or unsubstituted heteroaryl.

$R^{17}$ is hydrogen, halogen, oxo, —$N_3$, —$CF_3$, —$CCl_3$, —$CI_3$, —CN, —CHO, —OH, —$NH_2$, —COOH, —$CONH_2$, —$NO_2$, —SH, —$SO_2$, —$SO_2Cl$, —$SO_2CH_3$—$SO_2NH_2$, —$NHNH_2$, —$ONH_2$, —NHC(O)NHNH$_2$, unsubstituted alkyl, unsubstituted heteroalkyl, unsubstituted cycloalkyl, unsubstituted heterocycloalkyl, unsubstituted aryl, or unsubstituted heteroaryl. Ring B may be

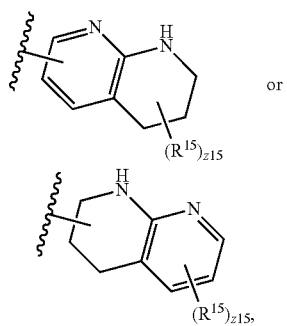

where $R^{15}$ is as described herein and z15 is an integer of 0 to 8. The symbol z15 may be 0, 1, or 2.

II. Pharmaceutical Compositions

In another aspect is a pharmaceutical composition including a compound described herein. The compound may have the formula (I), (II), (IIa), (IIb), (IIc), (IId), (III), (IIIa), (IV), (IVa), (V), or (Va), including embodiments and prodrugs thereof, and a pharmaceutically acceptable excipient. Also provided herein is a pharmaceutical composition that includes a compound having formula (X) and a pharmaceutically acceptable excipient.

III. Methods for Treating Fibrosis

Provided herein are methods for treating fibrosis. In one aspect, is a method for treating fibrosis by administering to a subject in need thereof a therapeutically effective amount of an αvβ1-inhibitor, where the αvβ1-inhibitor is an αvβ1-inhibitor antibody, an αvβ1-inhibitor RGD peptide, or an αvβ1-inhibitor compound having the formulae described herein, including embodiments thereof. The αvβ1-inhibitor compound is a compound having formula (I), (II), (IIa), (IIb), (IIc), (IId), (III), (IIIa), (IV), (IVa), (V), or (Va), including embodiments thereof. The αvβ1 inhibitor-compound may be a compound having formula (X), including embodiments thereof. The αvβ1-inhibitor compound may be a pharmaceutical composition as described herein, including embodiments thereof.

The fibrosis may be pulmonary fibrosis, liver fibrosis, lung fibrosis, skin fibrosis, cardiac fibrosis, peritoneal fibrosis or kidney fibrosis. The fibrosis may be pulmonary fibrosis. The fibrosis may be liver fibrosis. The fibrosis may be skin fibrosis. The fibrosis may be cardiac fibrosis. The fibrosis may be kidney fibrosis. The fibrosis may be peritoneal fibrosis.

The αvβ1-inhibitor may be an αvβ1-inhibitor antibody. The αvβ1-inhibitor antibody may be a humanized antibody. The αvβ1-inhibitor antibody may be a recombinant immunoglobulin. When an αvβ1-inhibitor antibody is a recombinant immunoglobulin, it may be formed using phage display.

The αvβ1-inhibitor may be an αvβ1-inhibitor RGD peptide. The αvβ1-inhibitor RGD peptide is as described herein, including embodiments thereof. The αvβ1-inhibitor RGD peptide may be Arg-Gly-Asp, Asp-Gly-Arg, cyclo-Gly-Arg-Gly-Asp-Ser-Pro, and KGD peptides include Cys-Asn-Thr-Leu-Lys-Gly-Asp-Cys or Asn-Thr-Leu-Lys-Gly-Asp.

The αvβ1-inhibitor may be an αvβ1-inhibitor compound. The αvβ1-inhibitor compound may have the formula (I), (II), (IIa), (IIb), (IIc), (IId), (III), (IIIa), (IV), (IVa), (V), or (Va), including embodiments thereof. The αvβ1-inhibitor compound may have formula (X), including embodiments thereof.

The αvβ1 inhibitor-compound may have the formula:

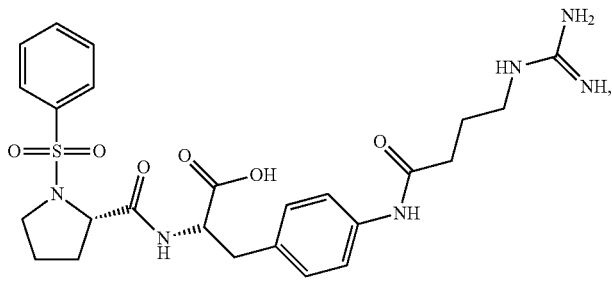

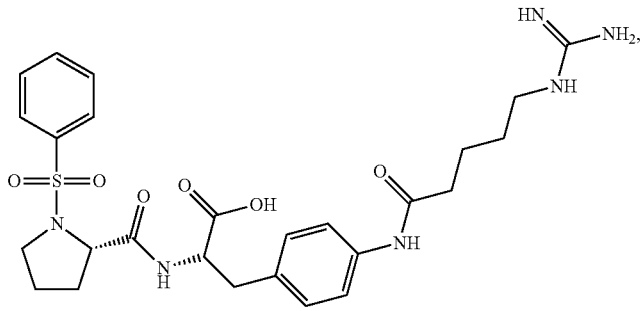

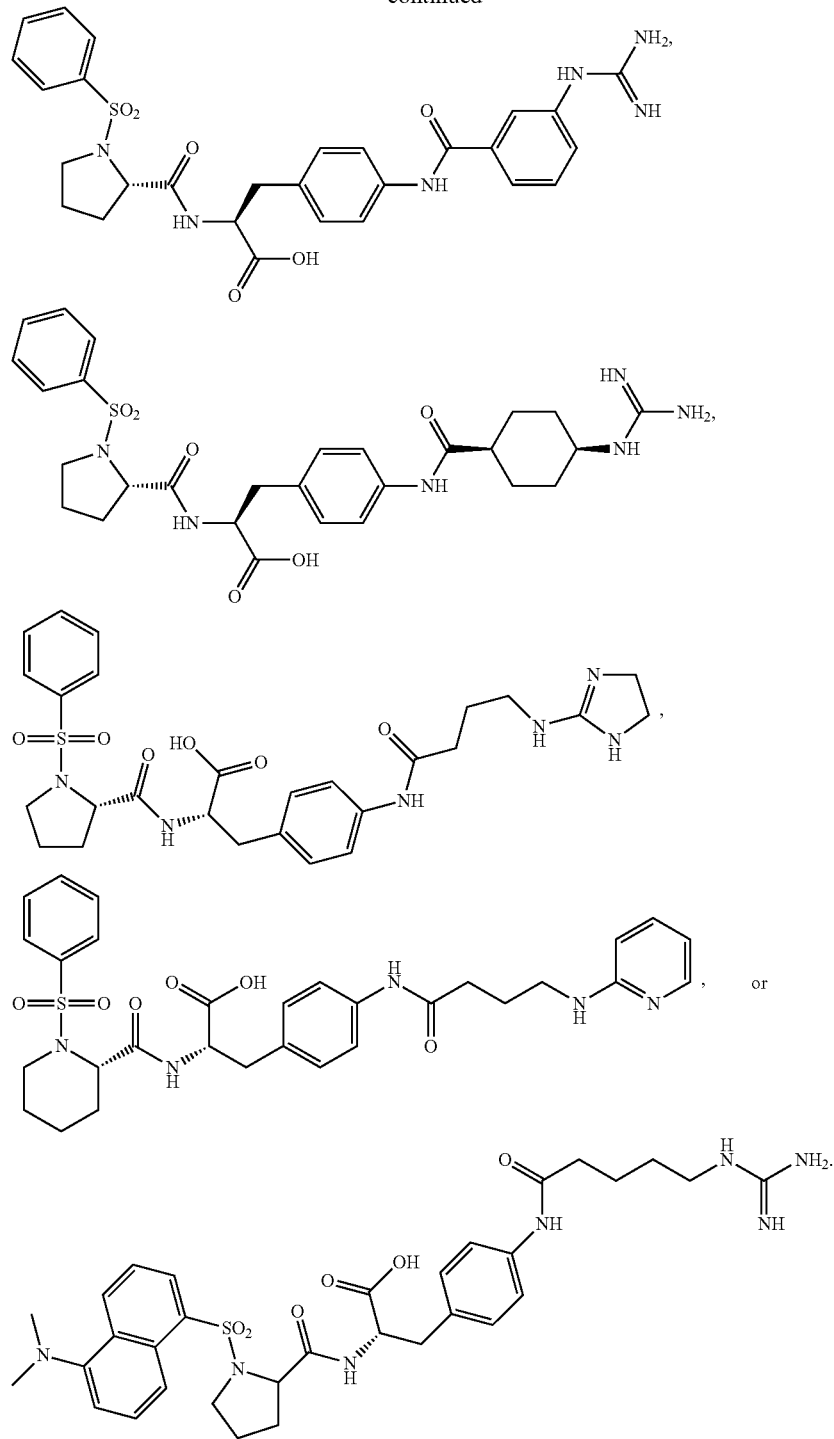

IV. Methods of Detecting αvβ1 Expression

Further provided herein are methods of detecting αvβ1 expression in a cell. In one aspect is a method of detecting αvβ1 expression in a cell by contacting a cell with an αvβ1-specific moiety and allowing the αvβ1-specific moiety to bind to the cell. The αvβ1-specific moiety is detected, thereby detecting αvβ1 expression in a cell. The detection may be performed using techniques known in the art (e.g. fluorescence detection or radiolabel detection). The cell may form part of an organism (e.g. a human). The cell may be a skin myofibroblast, a lung myofibroblast, or a hepatic myofibroblast. The cell may be a skin myofibroblast. The cell may be a lung myofibroblast. The cell may be a hepatic myofibroblast.

The detection may be performed by detecting a detectable moiety bound to the αvβ1-specific ligand. The detectable moiety may be covalently attached to the αvβ1-specific moiety. The detectable moiety may be non-covalently attached αvβ1-specific moiety. The αvβ1-specific moiety may be an αvβ1-specific antibody. The αvβ1-specific moiety may be an αvβ1-specific RGD peptide. The αvβ1-specific moiety may be an αvβ1-specific compound, where the compound is a compound described herein. The αvβ1-specific compound may be a compound having the formula (I), (II), (IIa), (IIb), (IIc), (IId), (III), (IIIa), (IV), (IVa), (V), or (Va) including embodiments thereof. The αvβ1-specific compound may be a compound having the formula (X), including embodiments thereof.

V. Methods of Inhibition

Further provided here are methods for determining inhibition of αvβ1 integrin binding. In one aspect is a method for determining whether a test compound inhibits αvβ1 integrin binding by combining an αvβ1 integrin-expressing cell and a test compound in a reaction vessel. The reaction vessel is covalently bonded to an αvβ1 ligand (e.g. a composition that binds to αvβ1). The method includes determining whether the αvβ1 integrin-expressing cell binds to the αvβ1 ligand in the presence of the test compound, thereby determining whether the test compound inhibits αvβ1 integrin binding. The reaction vessel may be a cell culture dish. The αvβ1 ligand may be fibronectin. The αvβ1 ligand may be latency associated peptide of TGFβ.

In another aspect is a method of inhibiting TGFβ activation by contacting a cell expressing αvβ1 integrin with an αvβ1-inhibitor and allowing the αvβ1-inhibitor to bind to αvβ1 in the presence of latent TGFβ. The method includes comparing a level of activated TGFβ to a control to thereby identify a level of TGFβ activation and identify inhibition of TGFβ activation. The control may be, for example, inactivated TGFβ, a level prior to administration of the αvβ1 inhibitor-compound, or a known level of TGFβ activation. The αvβ1-inhibitor may be an αvβ1 inhibitor-compound where the αvβ1 inhibitor-compound is as described herein (e.g. formula (I), (II), (IIa), (IIb), (IIc), (IId), (III), (IIIa), (IV), (IVa), (V), or (Va), including embodiments and prodrugs thereof). The αvβ1-inhibitor compound may be a compound having the formula (X), including embodiments and prodrugs thereof. The TGFβ may be latent TGFβ. The cell may form part of an organism (e.g. a human). The cell may be a skin myofibroblast, a lung myofibroblast, or a hepatic myofibroblast. The cell may be a skin myofibroblast. The cell may be a lung myofibroblast. The cell may be a hepatic myofibroblast. The method may further include adding an exogenous source of TGFβ and determining the activation of the exogenous TGFβ.

The binding of the αvβ1 inhibitor may be determined using the methods of detection described herein. The level of level of TGFβ activation may be determined using the methods of detection described herein.

TABLE 1

Exemplary compounds

| Compound Structure | Compound # |
|---|---|
| 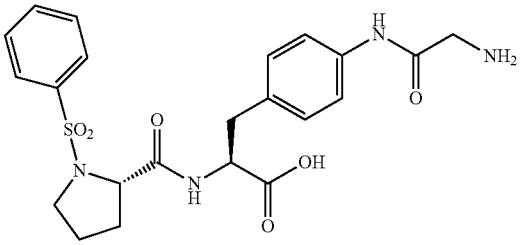 [SMILES: NCC(=O)Nc1ccc(C[C@H](NC(=O)[C@@H]2CCCN2S(=O)(=O)c2ccccc2)C(=O)O)cc1] | 1 |
| 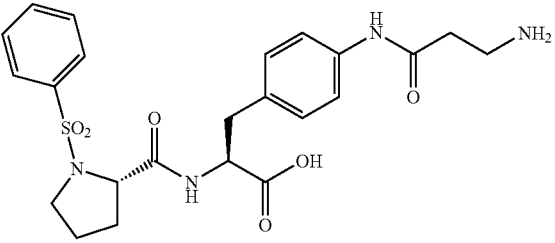 [SMILES: NCCC(=O)Nc1ccc(C[C@H](NC(=O)[C@@H]2CCCN2S(=O)(=O)c2ccccc2)C(=O)O)cc1] | 2 |
| 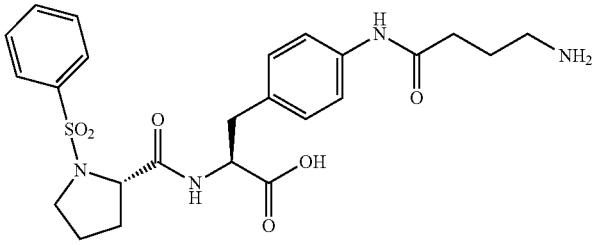 [SMILES: NCCCC(=O)Nc1ccc(C[C@H](NC(=O)[C@@H]2CCCN2S(=O)(=O)c2ccccc2)C(=O)O)cc1] | 3 |

TABLE 1-continued
Exemplary compounds
| Compound Structure | Compound # |
|---|---|
| 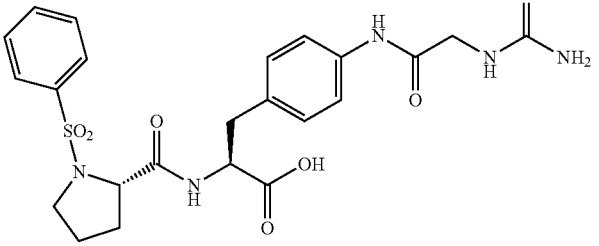 | 4 |
| 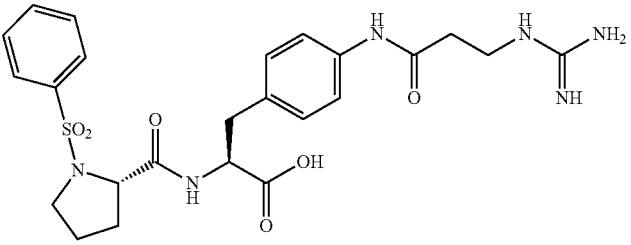 [SMILES: N=C(N)NCCC(=O)Nc1ccc(C[C@H](NC(=O)[C@@H]2CCCN2S(=O)(=O)c2ccccc2)C(=O)O)cc1] | 5 |
| 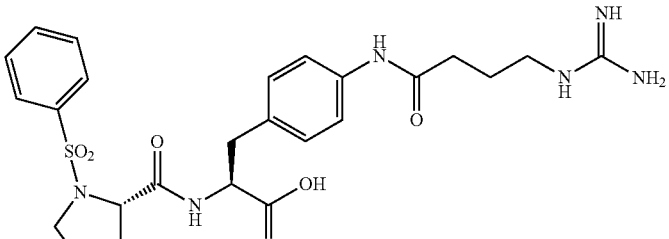 | 6 |
| 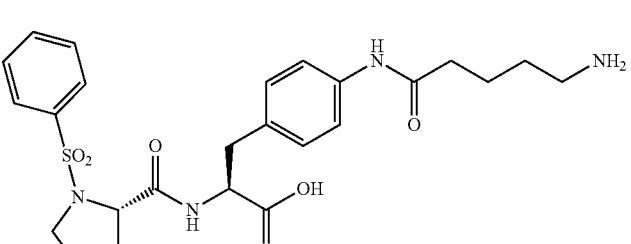 | 7 |
| 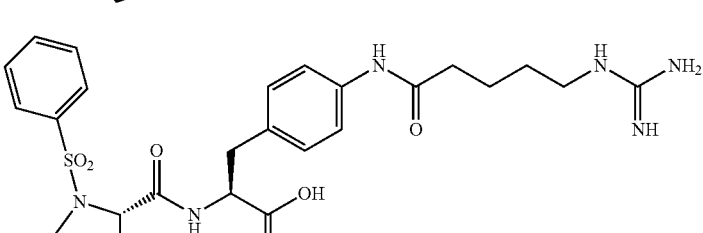 | 8 |
| 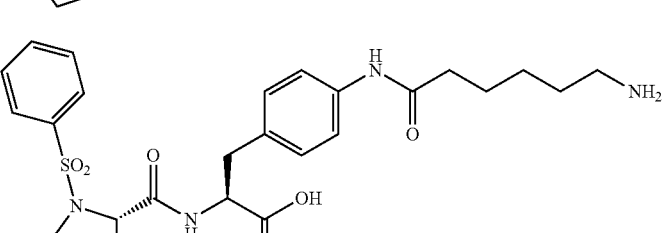 | 9 |

TABLE 1-continued

Exemplary compounds

| Compound Structure | Compound # |
| --- | --- |
| 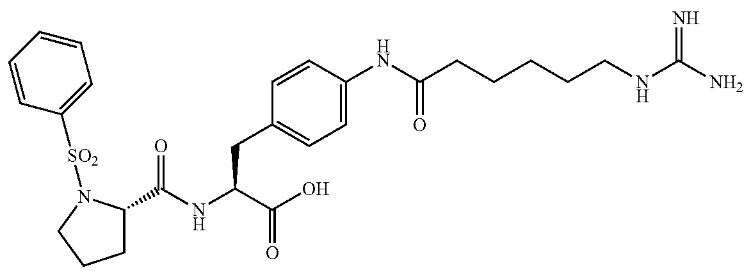 [SMILES: N=C(N)NCCCCCC(=O)Nc1ccc(C[C@H](NC(=O)[C@@H]2CCCN2S(=O)(=O)c2ccccc2)C(=O)O)cc1] | 10 |
| 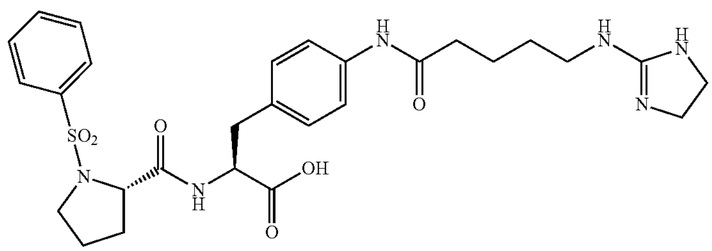 [SMILES: O=C(CCCCNC1=NCCN1)Nc1ccc(C[C@H](NC(=O)[C@@H]2CCCN2S(=O)(=O)c2ccccc2)C(=O)O)cc1] | 11 |
| 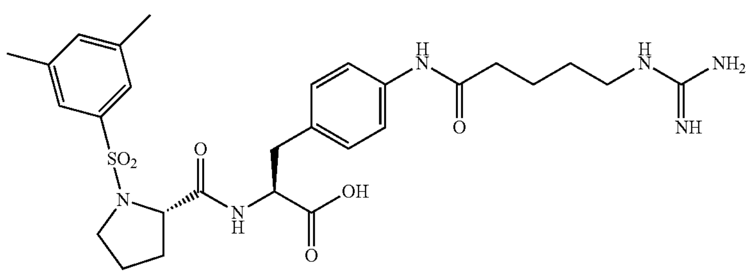 [SMILES: Cc1cc(C)cc(S(=O)(=O)N2CCC[C@H]2C(=O)N[C@@H](Cc2ccc(NC(=O)CCCCNC(=N)N)cc2)C(=O)O)c1] | 12 |
| 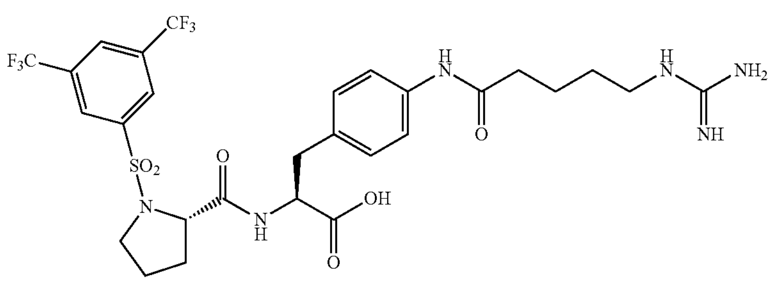 [SMILES: N=C(N)NCCCCC(=O)Nc1ccc(C[C@H](NC(=O)[C@@H]2CCCN2S(=O)(=O)c2cc(C(F)(F)F)cc(C(F)(F)F)c2)C(=O)O)cc1] | 13 |
| 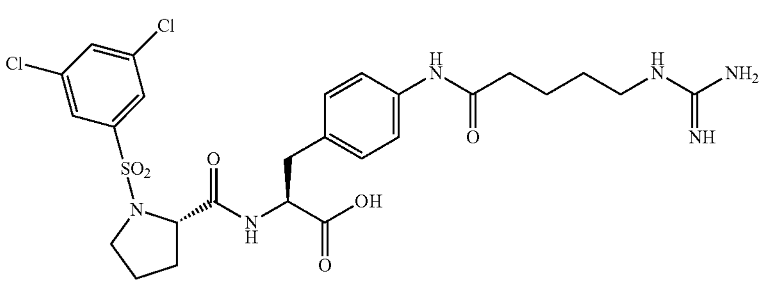 [SMILES: N=C(N)NCCCCC(=O)Nc1ccc(C[C@H](NC(=O)[C@@H]2CCCN2S(=O)(=O)c2cc(Cl)cc(Cl)c2)C(=O)O)cc1] | 14 |

TABLE 1-continued
Exemplary compounds
| Compound Structure | Compound # |
|---|---|
| 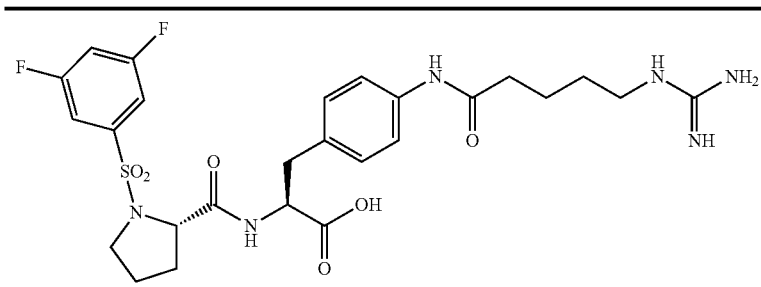 | 15 |
| 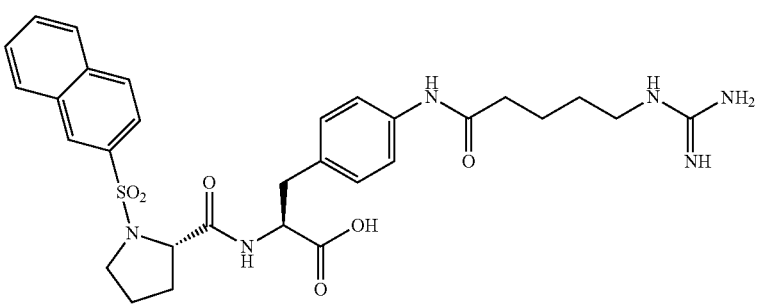 [SMILES: N=C(N)NCCCCC(=O)Nc1ccc(C[C@H](NC(=O)[C@@H]2CCCN2S(=O)(=O)c2ccc3ccccc3c2)C(=O)O)cc1] | 16 |
| 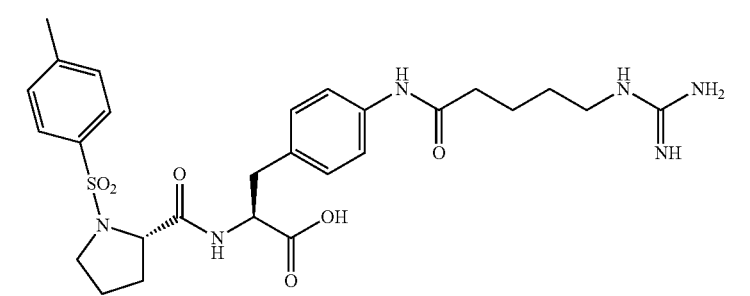 [SMILES: Cc1ccc(S(=O)(=O)N2CCC[C@H]2C(=O)N[C@@H](Cc2ccc(NC(=O)CCCCNC(=N)N)cc2)C(=O)O)cc1] | 17 |
| 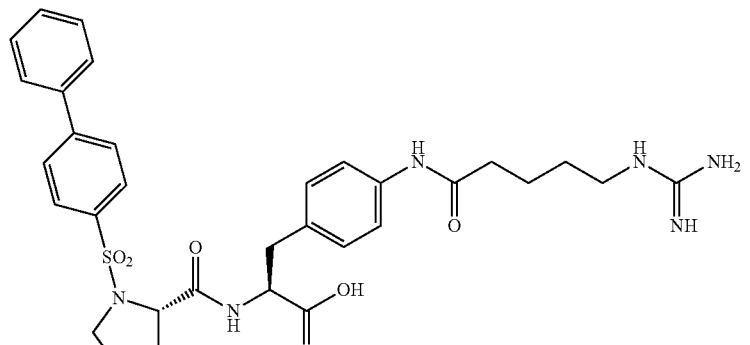 | 18 |
| 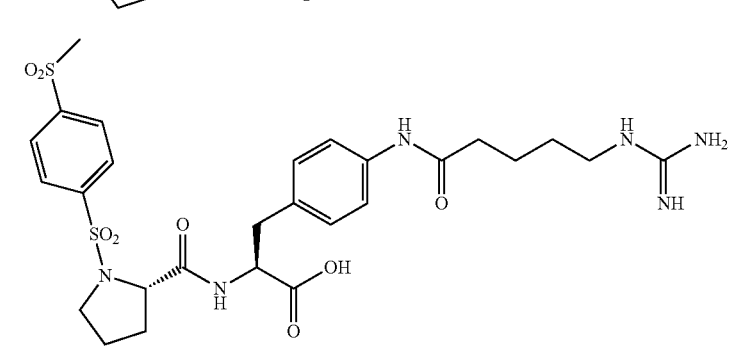 | 19 |

TABLE 1-continued

Exemplary compounds

| Compound Structure | Compound # |
|---|---|
| (structure) | 20 |
| (structure) | 21 |
| (structure) | 22 |
| (structure) | 23 |

TABLE 1-continued
Exemplary compounds
| Compound Structure | Compound # |
|---|---|
| 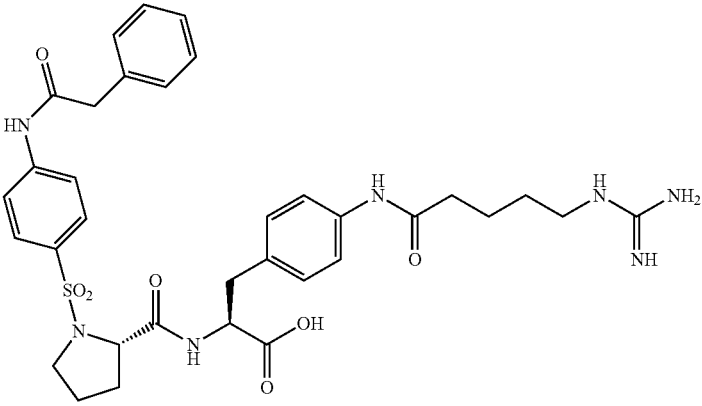 [SMILES: N=C(N)NCCCCC(=O)Nc1ccc(C[C@H](NC(=O)[C@@H]2CCCN2S(=O)(=O)c2ccc(NC(=O)Cc3ccccc3)cc2)C(=O)O)cc1] | 24 |
| 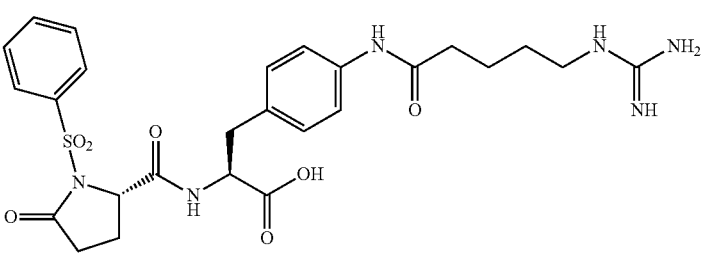 [SMILES: N=C(N)NCCCCC(=O)Nc1ccc(C[C@H](NC(=O)[C@@H]2CCC(=O)N2S(=O)(=O)c2ccccc2)C(=O)O)cc1] | 27 |
| 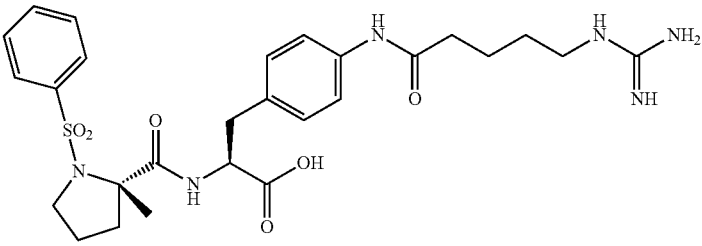 [SMILES: C[C@@]1(C(=O)N[C@@H](Cc2ccc(NC(=O)CCCCNC(=N)N)cc2)C(=O)O)CCCN1S(=O)(=O)c1ccccc1] | 28 |
| 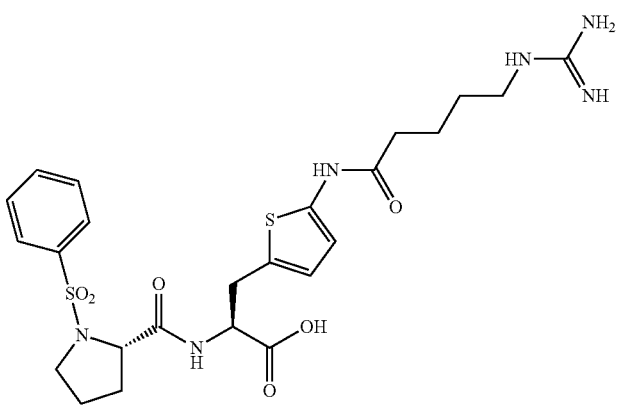 [SMILES: N=C(N)NCCCCC(=O)Nc1ccc(C[C@H](NC(=O)[C@@H]2CCCN2S(=O)(=O)c2ccccc2)C(=O)O)s1] | 29 |

TABLE 1-continued

Exemplary compounds

| Compound Structure | Compound # |
| --- | --- |
| 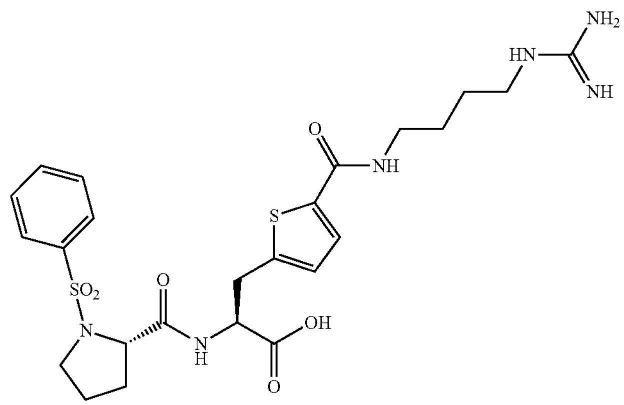 [SMILES: N=C(N)NCCCCNC(=O)c1ccc(C[C@H](NC(=O)[C@@H]2CCCN2S(=O)(=O)c2ccccc2)C(=O)O)s1] | 30 |
| 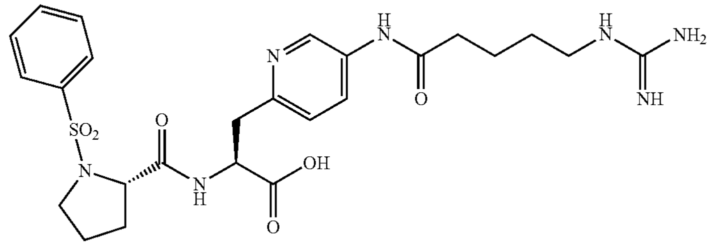 [SMILES: N=C(N)NCCCCC(=O)Nc1ccc(C[C@H](NC(=O)[C@@H]2CCCN2S(=O)(=O)c2ccccc2)C(=O)O)nc1] | 31 |
| 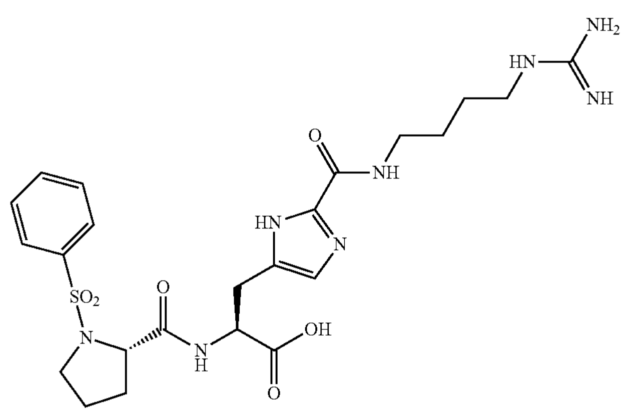 [SMILES: N=C(N)NCCCCNC(=O)c1ncc(C[C@H](NC(=O)[C@@H]2CCCN2S(=O)(=O)c2ccccc2)C(=O)O)[nH]1] | 32 |
| 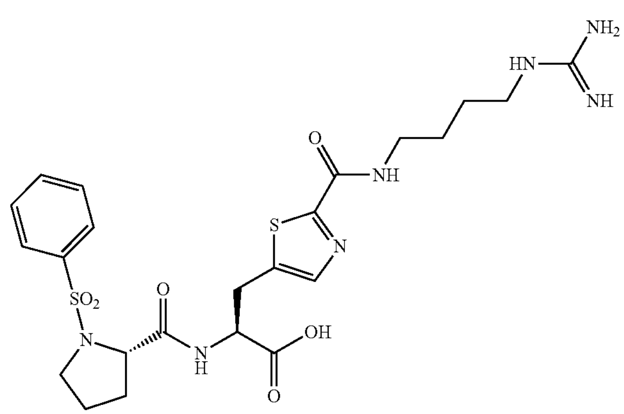 [SMILES: N=C(N)NCCCCNC(=O)c1ncc(C[C@H](NC(=O)[C@@H]2CCCN2S(=O)(=O)c2ccccc2)C(=O)O)s1] | 33 |

TABLE 1-continued
Exemplary compounds
| Compound Structure | Compound # |
|---|---|
| 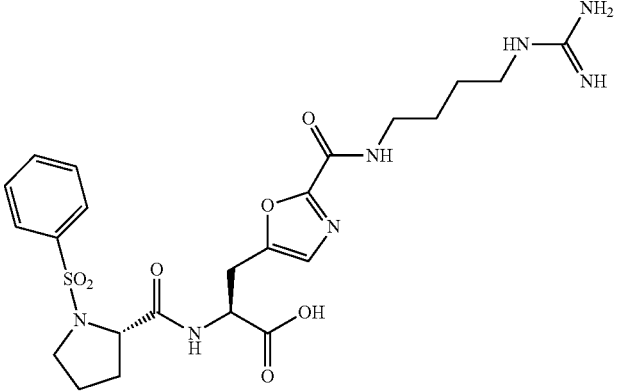 [SMILES: N=C(N)NCCCCNC(=O)c1ncc(C[C@H](NC(=O)[C@@H]2CCCN2S(=O)(=O)c2ccccc2)C(=O)O)o1] | 34 |
| 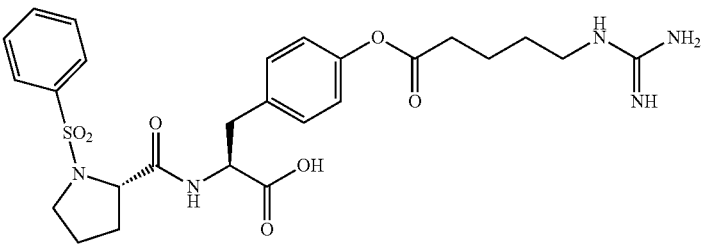 [SMILES: N=C(N)NCCCCC(=O)Oc1ccc(C[C@H](NC(=O)[C@@H]2CCCN2S(=O)(=O)c2ccccc2)C(=O)O)cc1] | 35 |
| 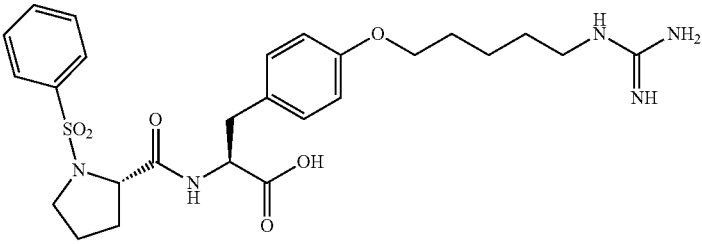 [SMILES: N=C(N)NCCCCCOc1ccc(C[C@H](NC(=O)[C@@H]2CCCN2S(=O)(=O)c2ccccc2)C(=O)O)cc1] | 36 |
| 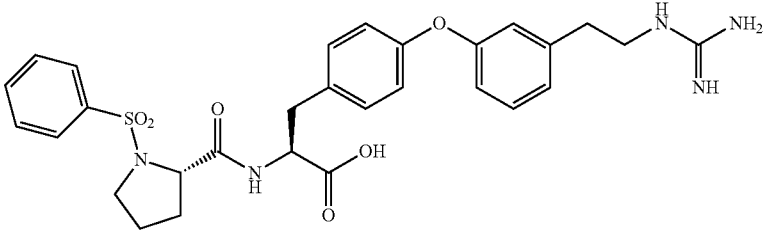 [SMILES: N=C(N)NCCc1cccc(Oc2ccc(C[C@H](NC(=O)[C@@H]3CCCN3S(=O)(=O)c3ccccc3)C(=O)O)cc2)c1] | 37 |
| 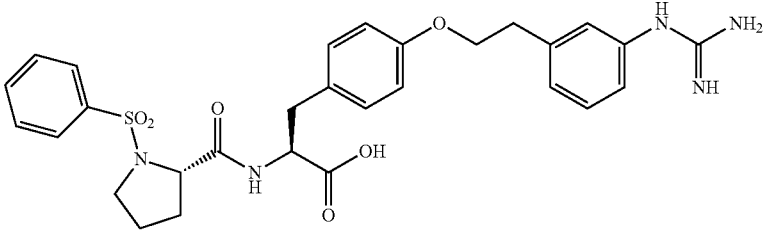 [SMILES: N=C(N)Nc1cccc(CCOc2ccc(C[C@H](NC(=O)[C@@H]3CCCN3S(=O)(=O)c3ccccc3)C(=O)O)cc2)c1] | 38 |

TABLE 1-continued

Exemplary compounds

| Compound Structure | Compound # |
|---|---|
| 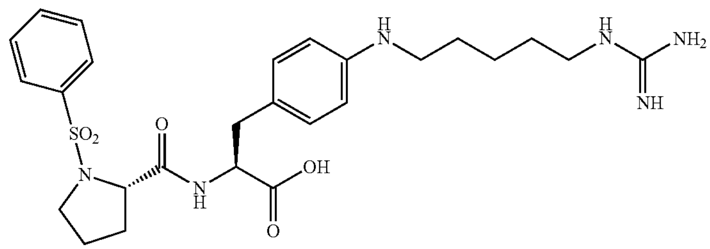 [SMILES: N=C(N)NCCCCCNc1ccc(C[C@H](NC(=O)[C@@H]2CCCN2S(=O)(=O)c2ccccc2)C(=O)O)cc1] | 39 |
| 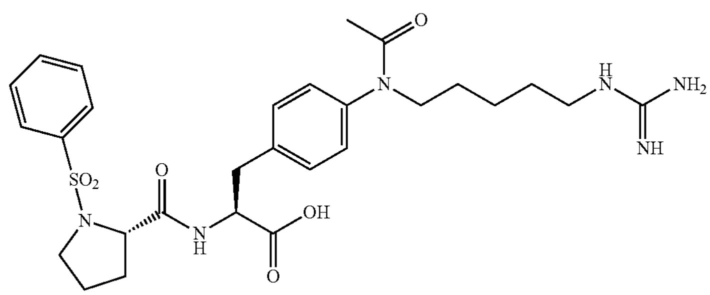 [SMILES: CC(=O)N(CCCCCNC(=N)N)c1ccc(C[C@H](NC(=O)[C@@H]2CCCN2S(=O)(=O)c2ccccc2)C(=O)O)cc1] | 40 |
| 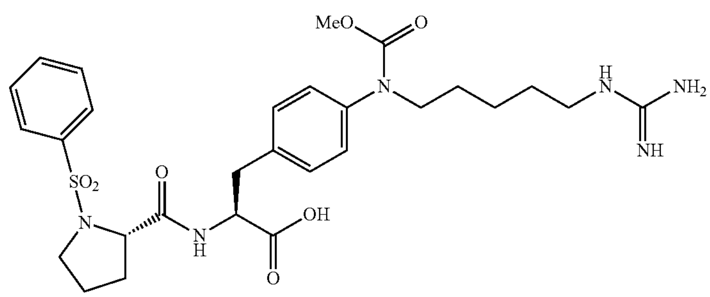 [SMILES: COC(=O)N(CCCCCNC(=N)N)c1ccc(C[C@H](NC(=O)[C@@H]2CCCN2S(=O)(=O)c2ccccc2)C(=O)O)cc1] | 41 |
| 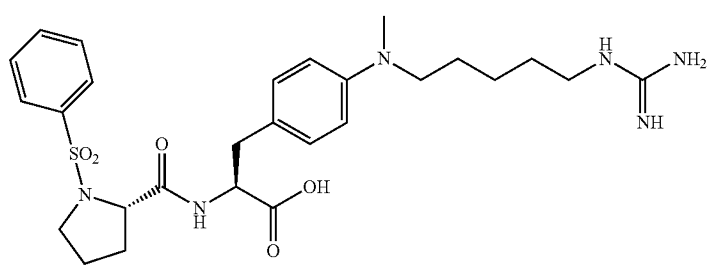 [SMILES: CN(CCCCCNC(=N)N)c1ccc(C[C@H](NC(=O)[C@@H]2CCCN2S(=O)(=O)c2ccccc2)C(=O)O)cc1] | 42 |
| 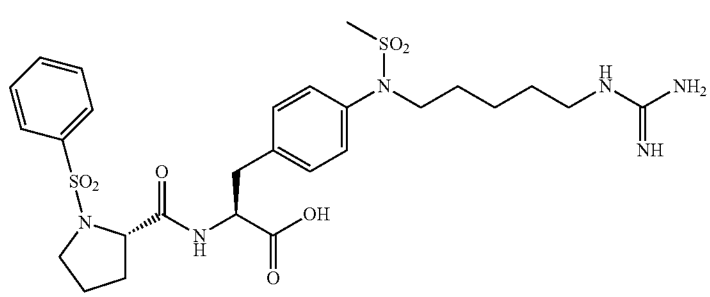 [SMILES: CS(=O)(=O)N(CCCCCNC(=N)N)c1ccc(C[C@H](NC(=O)[C@@H]2CCCN2S(=O)(=O)c2ccccc2)C(=O)O)cc1] | 43 |

TABLE 1-continued

Exemplary compounds

| Compound Structure | Compound # |
|---|---|
| 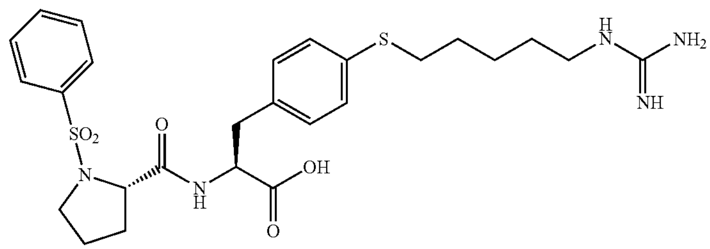 [SMILES: N=C(N)NCCCCCSc1ccc(C[C@H](NC(=O)[C@@H]2CCCN2S(=O)(=O)c2ccccc2)C(=O)O)cc1] | 44 |
| 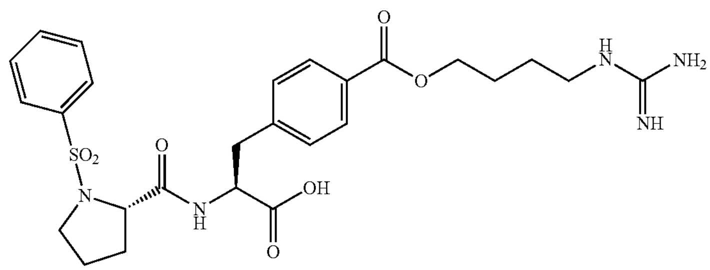 [SMILES: N=C(N)NCCCCOC(=O)c1ccc(C[C@H](NC(=O)[C@@H]2CCCN2S(=O)(=O)c2ccccc2)C(=O)O)cc1] | 45 |
| 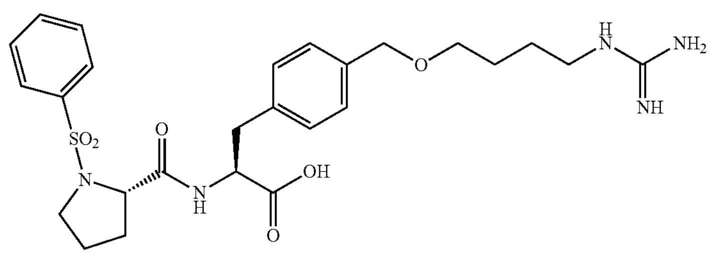 [SMILES: N=C(N)NCCCCOCc1ccc(C[C@H](NC(=O)[C@@H]2CCCN2S(=O)(=O)c2ccccc2)C(=O)O)cc1] | 46 |
| 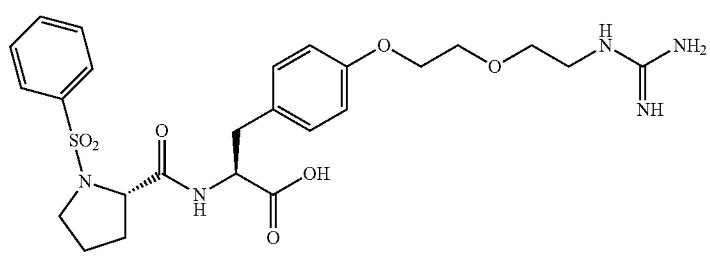 [SMILES: N=C(N)NCCSCCOc1ccc(C[C@H](NC(=O)[C@@H]2CCCN2S(=O)(=O)c2ccccc2)C(=O)O)cc1] | 47 |
| 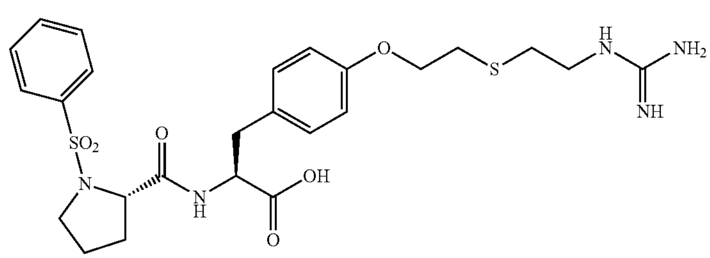 | 48 |
| 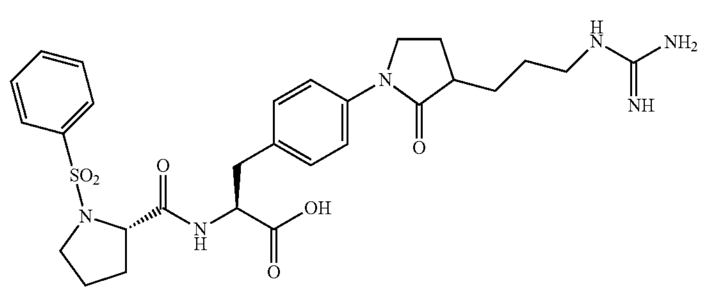 [SMILES: N=C(N)NCCCC1CCN(c2ccc(C[C@H](NC(=O)[C@@H]3CCCN3S(=O)(=O)c3ccccc3)C(=O)O)cc2)C1=O] | 49 |

TABLE 1-continued

Exemplary compounds

| Compound Structure | Compound # |
|---|---|
| 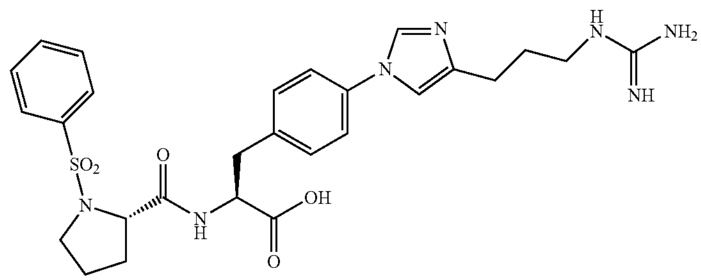 [SMILES: N=C(N)NCCCc1cn(-c2ccc(C[C@H](NC(=O)[C@@H]3CCCN3S(=O)(=O)c3ccccc3)C(=O)O)cc2)cn1] | 50 |
| 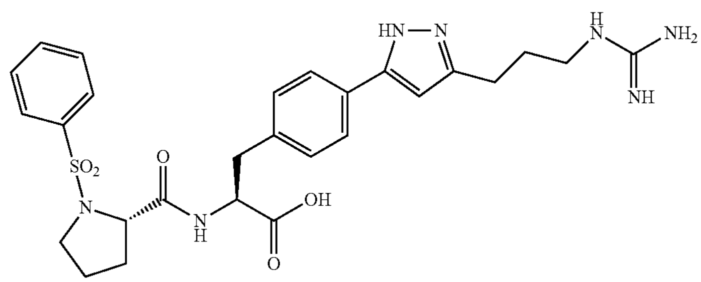 [SMILES: N=C(N)NCCCc1cc(-c2ccc(C[C@H](NC(=O)[C@@H]3CCCN3S(=O)(=O)c3ccccc3)C(=O)O)cc2)[nH]n1] | 51 |
| 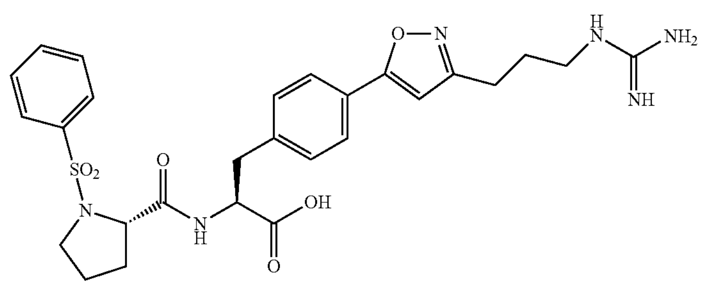 [SMILES: N=C(N)NCCCc1cc(-c2ccc(C[C@H](NC(=O)[C@@H]3CCCN3S(=O)(=O)c3ccccc3)C(=O)O)cc2)on1] | 52 |
| 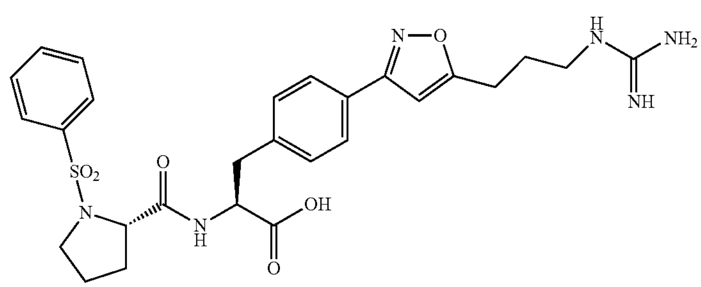 [SMILES: N=C(N)NCCCc1cc(-c2ccc(C[C@H](NC(=O)[C@@H]3CCCN3S(=O)(=O)c3ccccc3)C(=O)O)cc2)no1] | 53 |
| 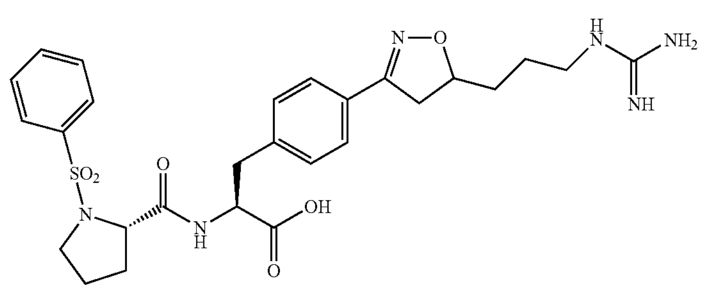 [SMILES: N=C(N)NCCCC1CC(c2ccc(C[C@H](NC(=O)[C@@H]3CCCN3S(=O)(=O)c3ccccc3)C(=O)O)cc2)=NO1] | 54 |

TABLE 1-continued

Exemplary compounds

| Compound Structure | Compound # |
|---|---|
| 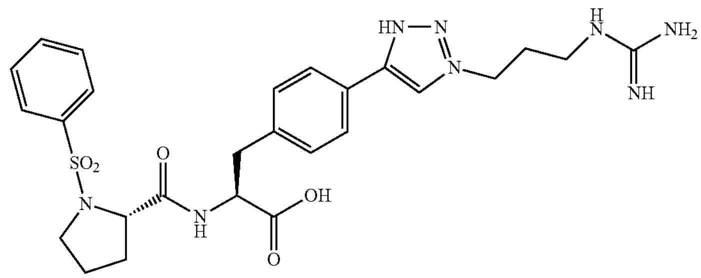 | 55 |
| 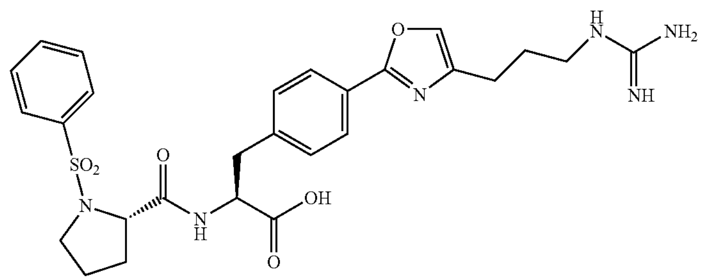 [SMILES: N=C(N)NCCCc1coc(-c2ccc(C[C@H](NC(=O)[C@@H]3CCCN3S(=O)(=O)c3ccccc3)C(=O)O)cc2)n1] | 56 |
| 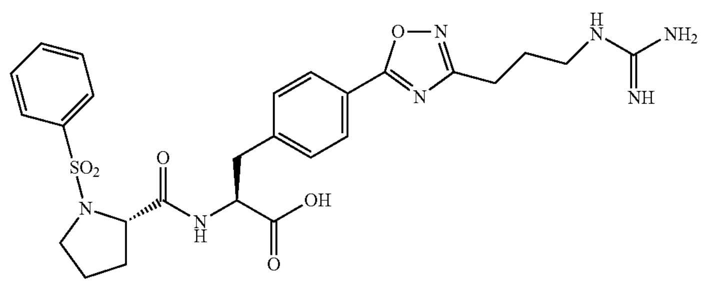 [SMILES: N=C(N)NCCCc1noc(-c2ccc(C[C@H](NC(=O)[C@@H]3CCCN3S(=O)(=O)c3ccccc3)C(=O)O)cc2)n1] | 57 |
| 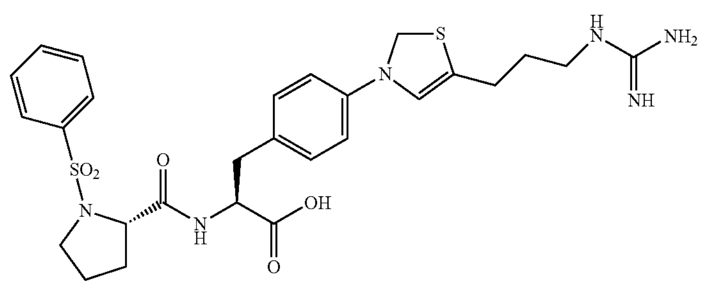 [SMILES: N=C(N)NCCCC1=CN(c2ccc(C[C@H](NC(=O)[C@@H]3CCCN3S(=O)(=O)c3ccccc3)C(=O)O)cc2)CS1] | 58 |
| 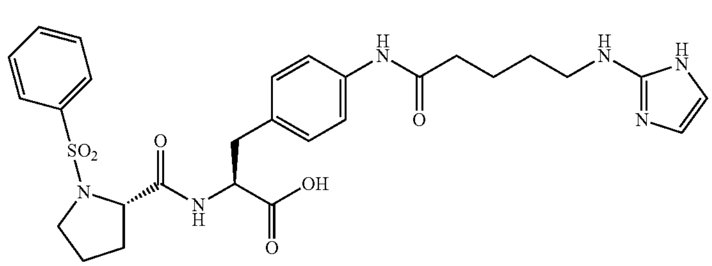 [SMILES: O=C(CCCCNc1ncc[nH]1)Nc1ccc(C[C@H](NC(=O)[C@@H]2CCCN2S(=O)(=O)c2ccccc2)C(=O)O)cc1] | 59 |

TABLE 1-continued

Exemplary compounds

| Compound Structure | Compound # |
|---|---|
| 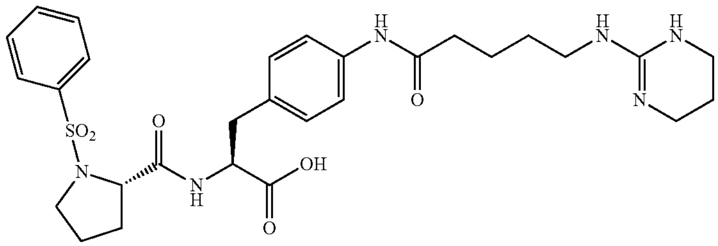 [SMILES: O=C(CCCCNC1=NCCCN1)Nc1ccc(C[C@H](NC(=O)[C@@H]2CCCN2S(=O)(=O)c2ccccc2)C(=O)O)cc1] | 60 |
| 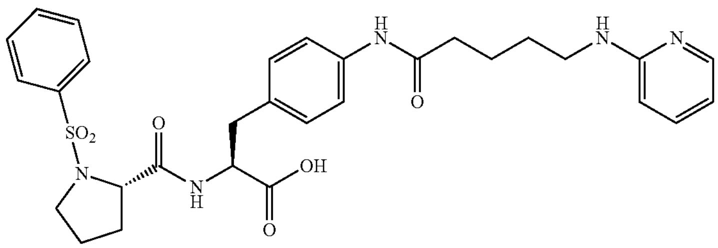 [SMILES: O=C(CCCCNc1ccccn1)Nc1ccc(C[C@H](NC(=O)[C@@H]2CCCN2S(=O)(=O)c2ccccc2)C(=O)O)cc1] | 61 |
| 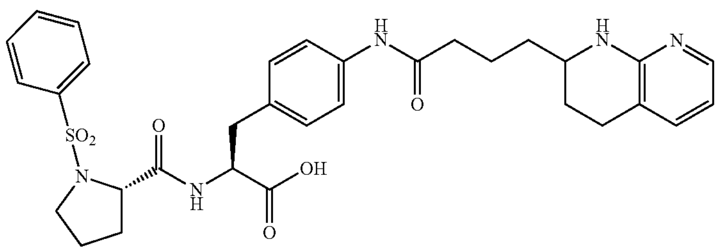 [SMILES: O=C(CCCC1CCc2cccnc2N1)Nc1ccc(C[C@H](NC(=O)[C@@H]2CCCN2S(=O)(=O)c2ccccc2)C(=O)O)cc1] | 62 |
| 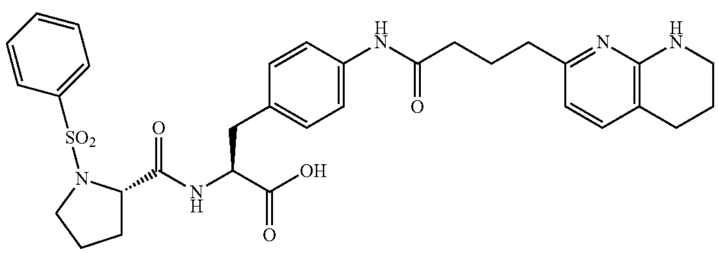 [SMILES: O=C(CCCc1ccc2c(n1)NCCC2)Nc1ccc(C[C@H](NC(=O)[C@@H]2CCCN2S(=O)(=O)c2ccccc2)C(=O)O)cc1] | 63 |
| 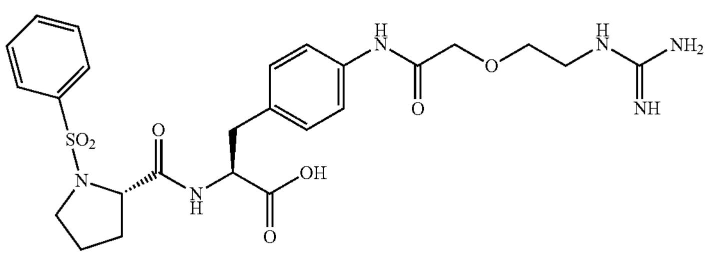 [SMILES: N=C(N)NCCSCC(=O)Nc1ccc(C[C@H](NC(=O)[C@@H]2CCCN2S(=O)(=O)c2ccccc2)C(=O)O)cc1] | 64 |
| 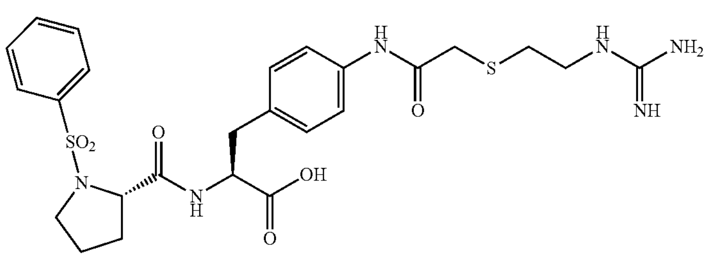 | 65 |

TABLE 1-continued
Exemplary compounds
| Compound Structure | Compound # |
|---|---|
| 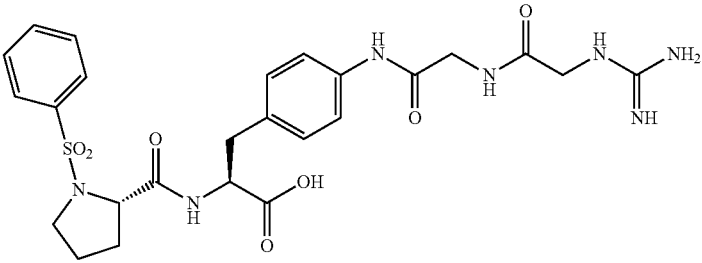 [SMILES: N=C(N)NCC(=O)NCC(=O)Nc1ccc(C[C@H](NC(=O)[C@@H]2CCCN2S(=O)(=O)c2ccccc2)C(=O)O)cc1] | 66 |
| 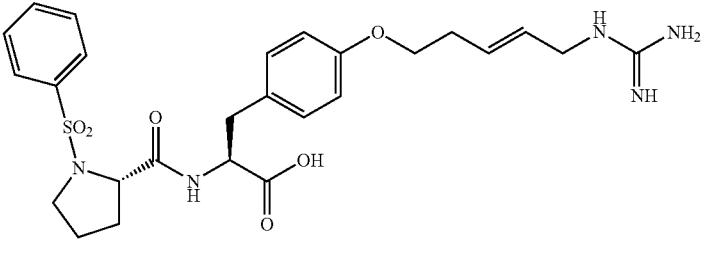 [SMILES: N=C(N)NC/C=C/CCOc1ccc(C[C@H](NC(=O)[C@@H]2CCCN2S(=O)(=O)c2ccccc2)C(=O)O)cc1] | 67 |
| 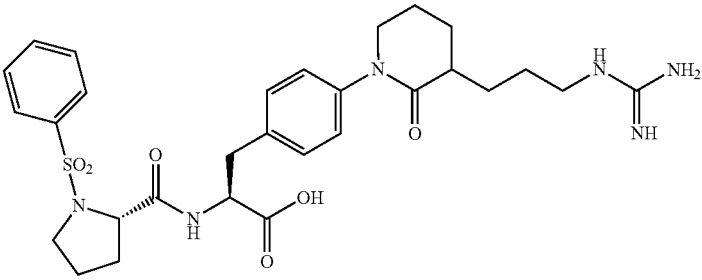 [SMILES: N=C(N)NCCCC1CCCN(c2ccc(C[C@H](NC(=O)[C@@H]3CCCN3S(=O)(=O)c3ccccc3)C(=O)O)cc2)C1=O] | 68 |
| 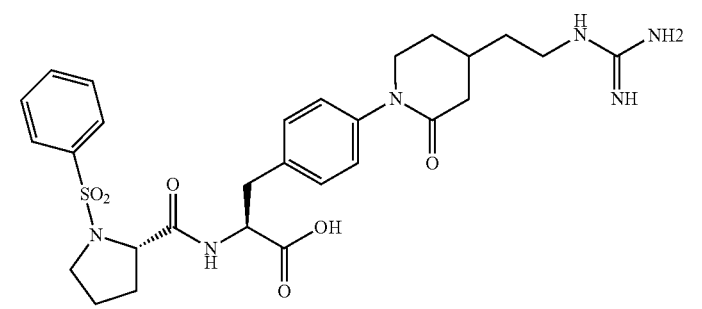 [SMILES: N=C(N)NCCC1CCN(c2ccc(C[C@H](NC(=O)[C@@H]3CCCN3S(=O)(=O)c3ccccc3)C(=O)O)cc2)C(=O)C1] | 69 |
| 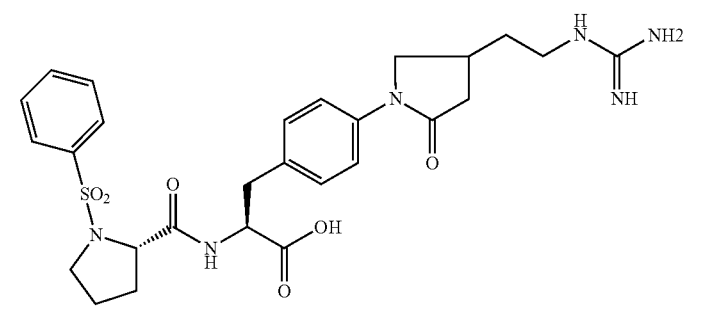 [SMILES: N=C(N)NCCC1CC(=O)N(c2ccc(C[C@H](NC(=O)[C@@H]3CCCN3S(=O)(=O)c3ccccc3)C(=O)O)cc2)C1] | 70 |

TABLE 1-continued

Exemplary compounds

| Compound Structure | Compound # |
|---|---|
| 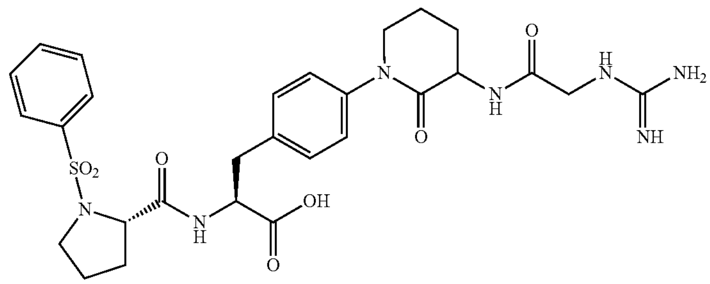 [SMILES: N=C(N)NCC(=O)NC1CCCN(c2ccc(C[C@H](NC(=O)[C@@H]3CCCN3S(=O)(=O)c3ccccc3)C(=O)O)cc2)C1=O] | 71 |
| 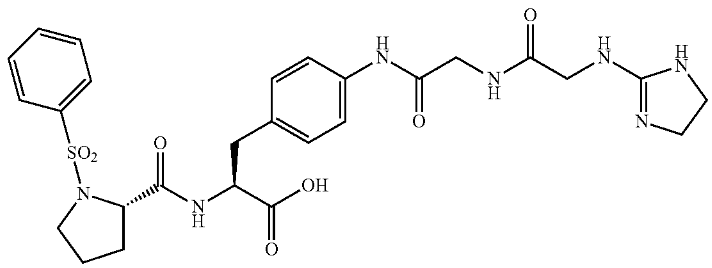 [SMILES: O=C(CNC1=NCCN1)NCC(=O)Nc1ccc(C[C@H](NC(=O)[C@@H]2CCCN2S(=O)(=O)c2ccccc2)C(=O)O)cc1] | 72 |
| 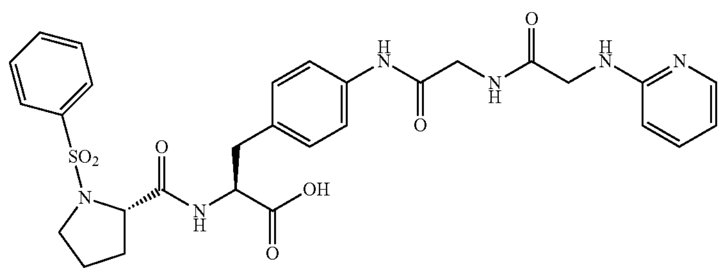 [SMILES: O=C(CNc1ccccn1)NCC(=O)Nc1ccc(C[C@H](NC(=O)[C@@H]2CCCN2S(=O)(=O)c2ccccc2)C(=O)O)cc1] | 73 |
| 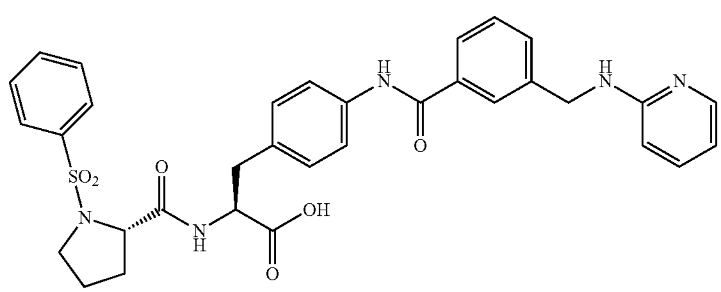 [SMILES: O=C(Nc1ccc(C[C@H](NC(=O)[C@@H]2CCCN2S(=O)(=O)c2ccccc2)C(=O)O)cc1)c1cccc(CNc2ccccn2)c1] | 74 |
| 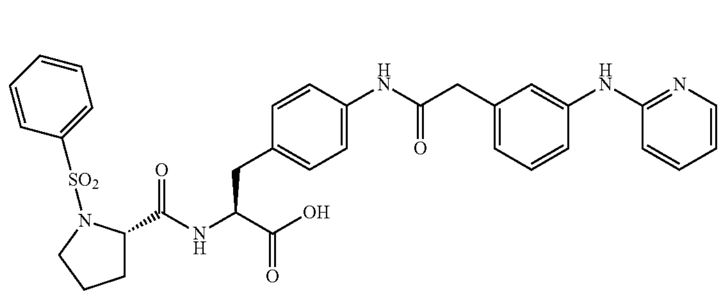 [SMILES: O=C(Cc1cccc(Nc2ccccn2)c1)Nc1ccc(C[C@H](NC(=O)[C@@H]2CCCN2S(=O)(=O)c2ccccc2)C(=O)O)cc1] | 75 |

TABLE 1-continued

Exemplary compounds

| Compound Structure | Compound # |
| --- | --- |
| 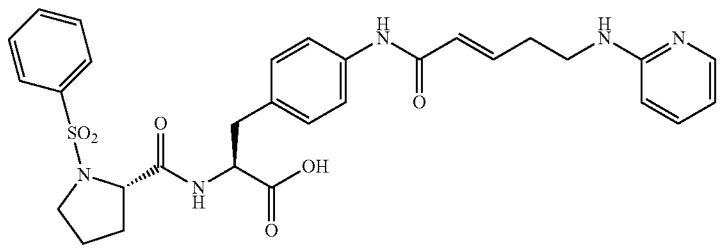 [SMILES: O=C(/C=C/CCNc1ccccn1)Nc1ccc(C[C@H](NC(=O)[C@@H]2CCCN2S(=O)(=O)c2ccccc2)C(=O)O)cc1] | 76 |
| 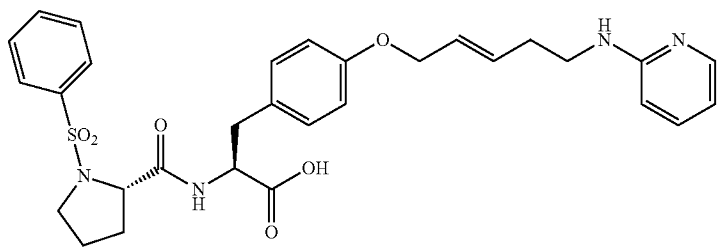 [SMILES: O=C(O)[C@H](Cc1ccc(OC/C=C/CCNc2ccccn2)cc1)NC(=O)[C@@H]1CCCN1S(=O)(=O)c1ccccc1] | 77 |
| 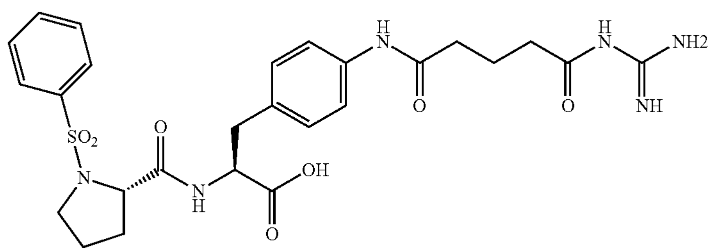 [SMILES: N=C(N)NC(=O)CCCC(=O)Nc1ccc(C[C@H](NC(=O)[C@@H]2CCCN2S(=O)(=O)c2ccccc2)C(=O)O)cc1] | 78 |
| 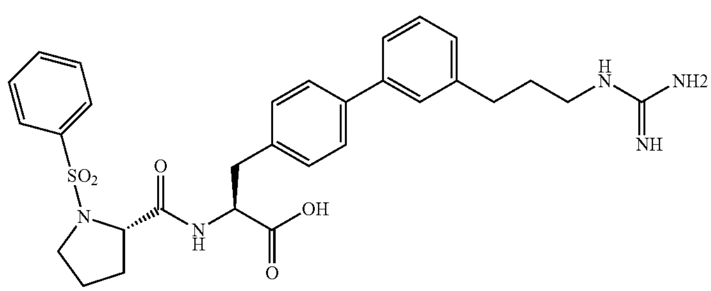 [SMILES: N=C(N)NCCCc1cccc(-c2ccc(C[C@H](NC(=O)[C@@H]3CCCN3S(=O)(=O)c3ccccc3)C(=O)O)cc2)c1] | 79 |
| 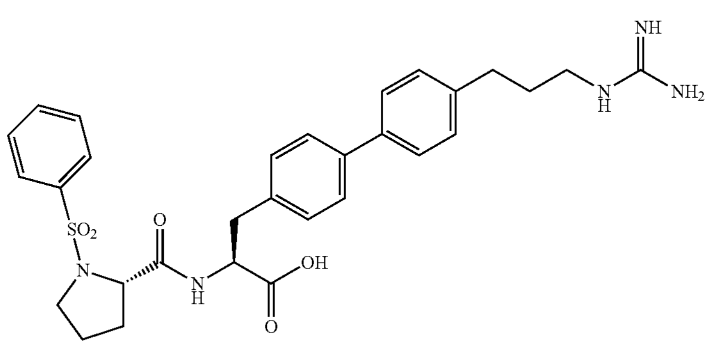 [SMILES: N=C(N)NCCCc1ccc(-c2ccc(C[C@H](NC(=O)[C@@H]3CCCN3S(=O)(=O)c3ccccc3)C(=O)O)cc2)cc1] | 80 |

TABLE 1-continued
Exemplary compounds
| Compound Structure | Compound # |
|---|---|
| 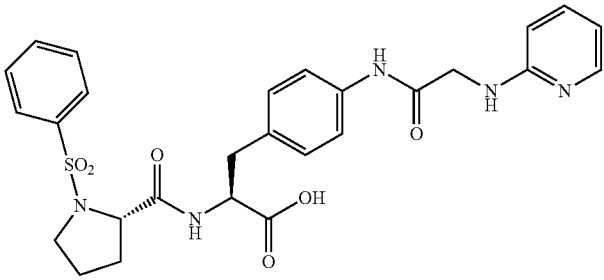 [SMILES: O=C(CNc1ccccn1)Nc1ccc(C[C@H](NC(=O)[C@@H]2CCCN2S(=O)(=O)c2ccccc2)C(=O)O)cc1] | 81 |
| 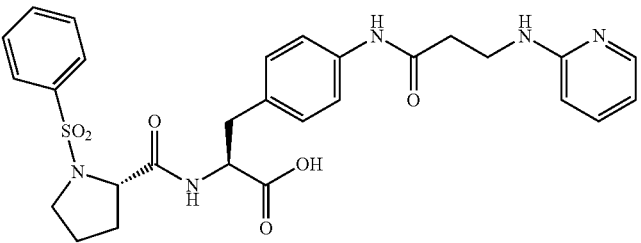 [SMILES: O=C(CCNc1ccccn1)Nc1ccc(C[C@H](NC(=O)[C@@H]2CCCN2S(=O)(=O)c2ccccc2)C(=O)O)cc1] | 82 |
| 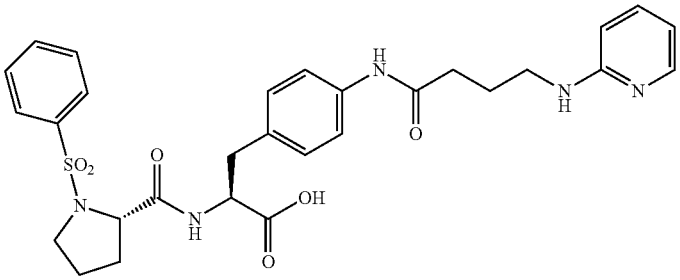 [SMILES: O=C(CCCNc1ccccn1)Nc1ccc(C[C@H](NC(=O)[C@@H]2CCCN2S(=O)(=O)c2ccccc2)C(=O)O)cc1] | 83 |
| 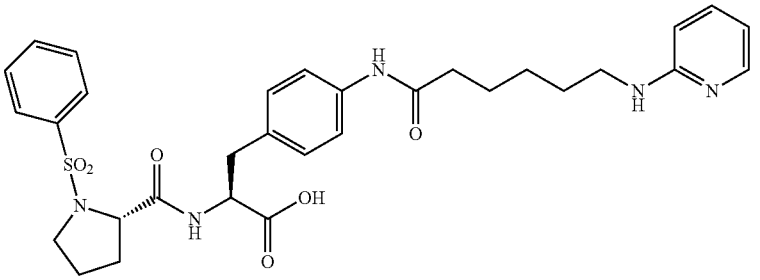 [SMILES: O=C(CCCCCNc1ccccn1)Nc1ccc(C[C@H](NC(=O)[C@@H]2CCCN2S(=O)(=O)c2ccccc2)C(=O)O)cc1] | 84 |
| 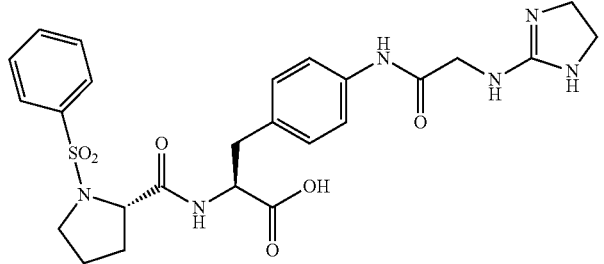 [SMILES: O=C(CNC1=NCCN1)Nc1ccc(C[C@H](NC(=O)[C@@H]2CCCN2S(=O)(=O)c2ccccc2)C(=O)O)cc1] | 85 |

TABLE 1-continued

Exemplary compounds

| Compound Structure | Compound # |
|---|---|
| 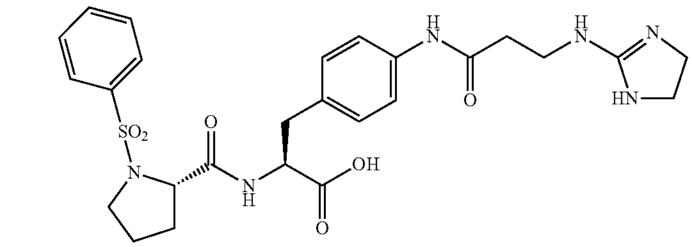 [SMILES: O=C(CCNC1=NCCN1)Nc1ccc(C[C@H](NC(=O)[C@@H]2CCCN2S(=O)(=O)c2ccccc2)C(=O)O)cc1] | 86 |
| 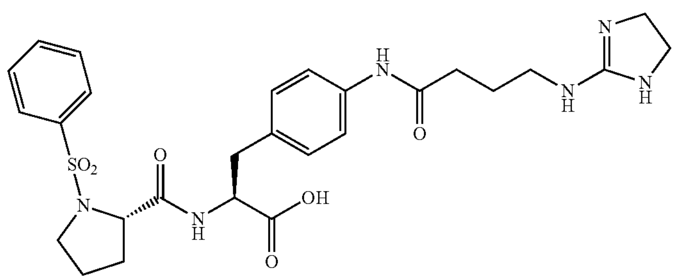 [SMILES: O=C(CCCNC1=NCCN1)Nc1ccc(C[C@H](NC(=O)[C@@H]2CCCN2S(=O)(=O)c2ccccc2)C(=O)O)cc1] | 87 |
| 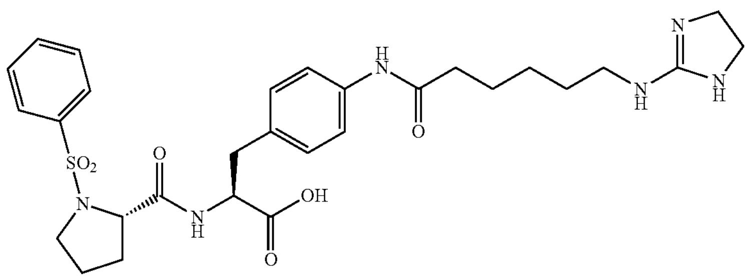 [SMILES: O=C(CCCCCNC1=NCCN1)Nc1ccc(C[C@H](NC(=O)[C@@H]2CCCN2S(=O)(=O)c2ccccc2)C(=O)O)cc1] | 88 |
| 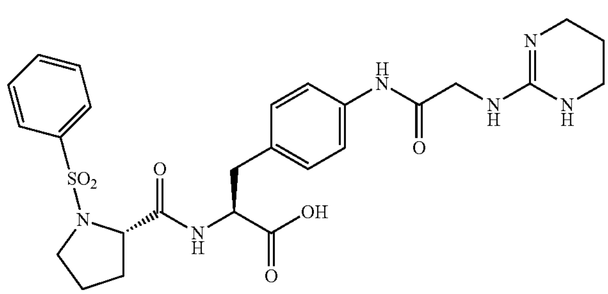 [SMILES: O=C(CNC1=NCCCN1)Nc1ccc(C[C@H](NC(=O)[C@@H]2CCCN2S(=O)(=O)c2ccccc2)C(=O)O)cc1] | 89 |
| 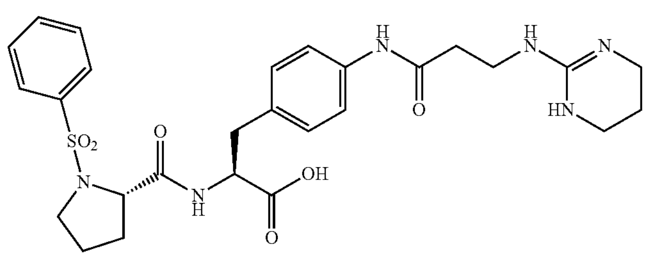 [SMILES: O=C(CCNC1=NCCCN1)Nc1ccc(C[C@H](NC(=O)[C@@H]2CCCN2S(=O)(=O)c2ccccc2)C(=O)O)cc1] | 90 |

TABLE 1-continued

Exemplary compounds

| Compound Structure | Compound # |
| --- | --- |
| 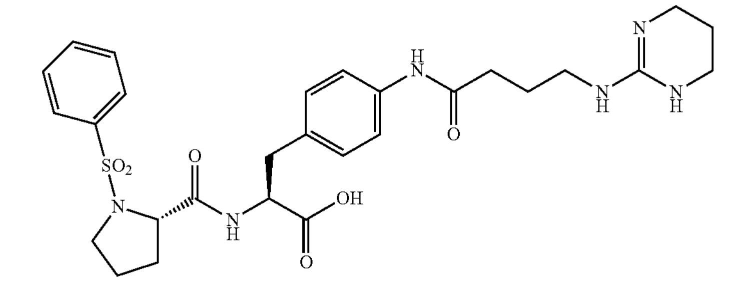 [SMILES: O=C(CCCNC1=NCCCN1)Nc1ccc(C[C@H](NC(=O)[C@@H]2CCCN2S(=O)(=O)c2ccccc2)C(=O)O)cc1] | 91 |
| 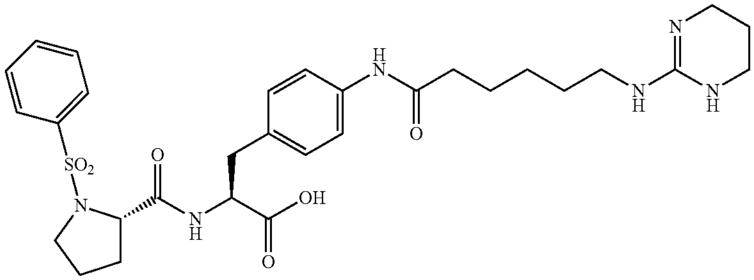 [SMILES: O=C(CCCCCNC1=NCCCN1)Nc1ccc(C[C@H](NC(=O)[C@@H]2CCCN2S(=O)(=O)c2ccccc2)C(=O)O)cc1] | 92 |
| 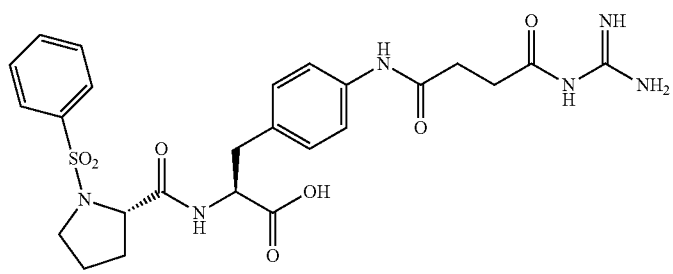 [SMILES: N=C(N)NC(=O)CCC(=O)Nc1ccc(C[C@H](NC(=O)[C@@H]2CCCN2S(=O)(=O)c2ccccc2)C(=O)O)cc1] | 93 |
| 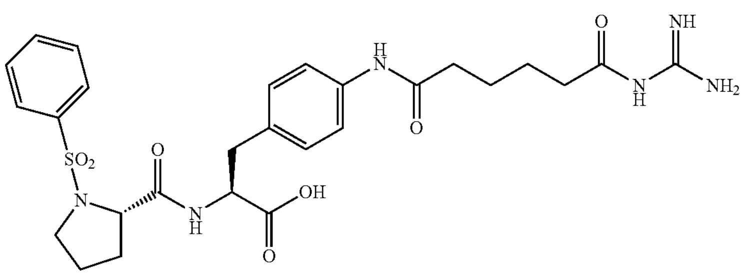 [SMILES: N=C(N)NC(=O)CCCCC(=O)Nc1ccc(C[C@H](NC(=O)[C@@H]2CCCN2S(=O)(=O)c2ccccc2)C(=O)O)cc1] | 94 |
| 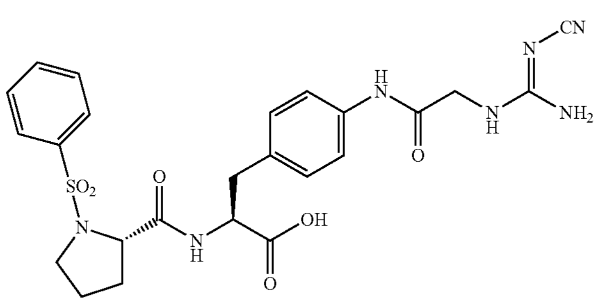 [SMILES: N#C/N=C(\N)NCC(=O)Nc1ccc(C[C@H](NC(=O)[C@@H]2CCCN2S(=O)(=O)c2ccccc2)C(=O)O)cc1] | 95 |

TABLE 1-continued
Exemplary compounds
| Compound Structure | Compound # |
|---|---|
| 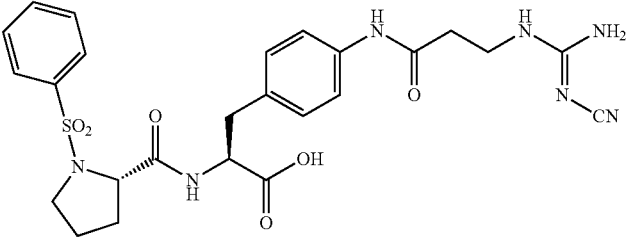 [SMILES: N#C/N=C(\N)NCCC(=O)Nc1ccc(C[C@H](NC(=O)[C@@H]2CCCN2S(=O)(=O)c2ccccc2)C(=O)O)cc1] | 96 |
| 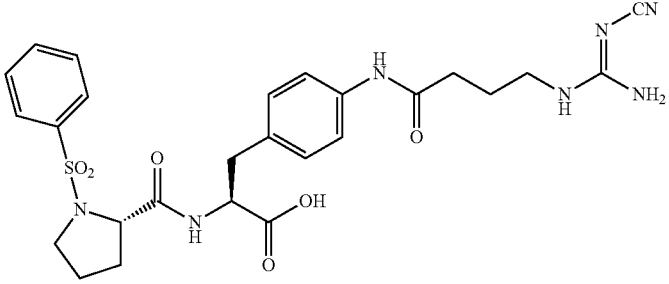 [SMILES: N#C/N=C(\N)NCCCC(=O)Nc1ccc(C[C@H](NC(=O)[C@@H]2CCCN2S(=O)(=O)c2ccccc2)C(=O)O)cc1] | 97 |
| 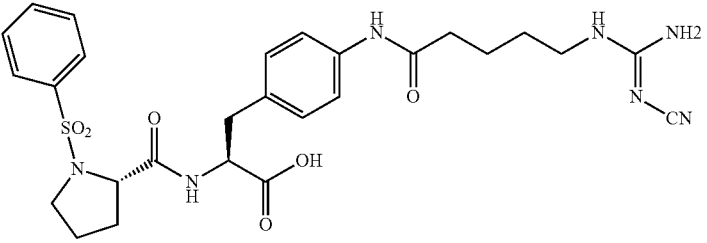 [SMILES: N#C/N=C(\N)NCCCCC(=O)Nc1ccc(C[C@H](NC(=O)[C@@H]2CCCN2S(=O)(=O)c2ccccc2)C(=O)O)cc1] | 98 |
| 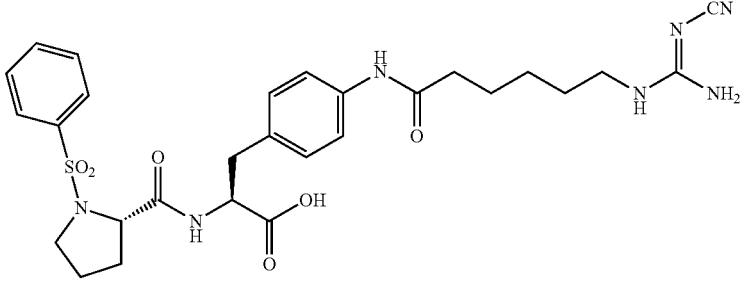 [SMILES: N#C/N=C(\N)NCCCCCC(=O)Nc1ccc(C[C@H](NC(=O)[C@@H]2CCCN2S(=O)(=O)c2ccccc2)C(=O)O)cc1] | 99 |
TABLE 2
Additional Exemplary compounds
| Compound Structure | Compound # |
|---|---|
| 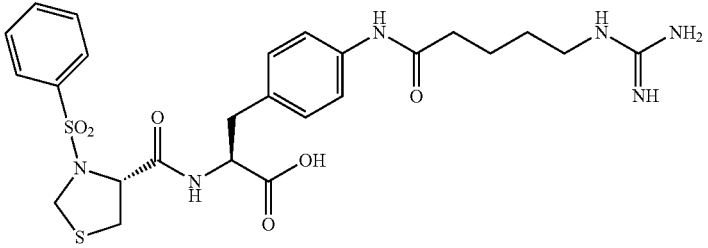 | 100 |

TABLE 2-continued

Additional Exemplary compounds

| Compound Structure | Compound # |
|---|---|
| 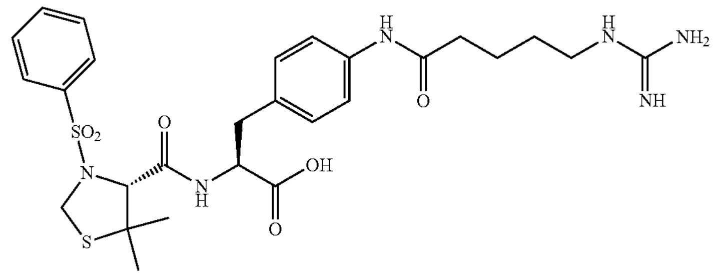 [SMILES: CC1(C)SCN(S(=O)(=O)c2ccccc2)[C@@H]1C(=O)N[C@@H](Cc1ccc(NC(=O)CCCCNC(=N)N)cc1)C(=O)O] | 101 |
| 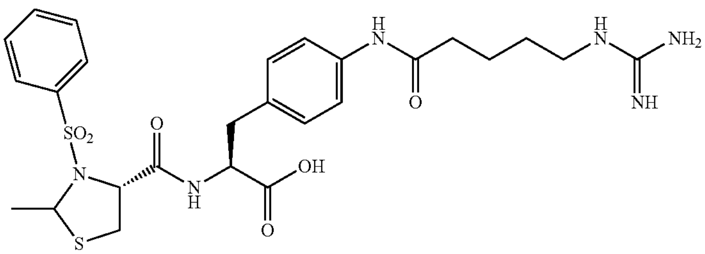 [SMILES: CC1SC[C@@H](C(=O)N[C@@H](Cc2ccc(NC(=O)CCCCNC(=N)N)cc2)C(=O)O)N1S(=O)(=O)c1ccccc1] | 102 |
| 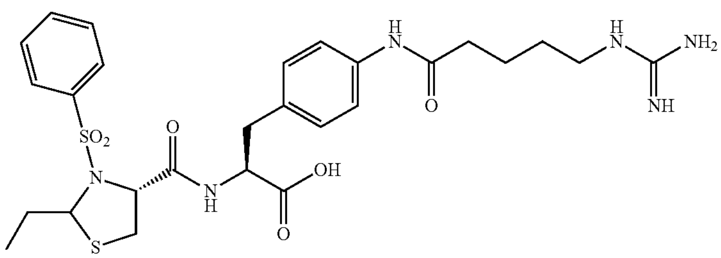 [SMILES: CCC1SC[C@@H](C(=O)N[C@@H](Cc2ccc(NC(=O)CCCCNC(=N)N)cc2)C(=O)O)N1S(=O)(=O)c1ccccc1] | 103 |
| 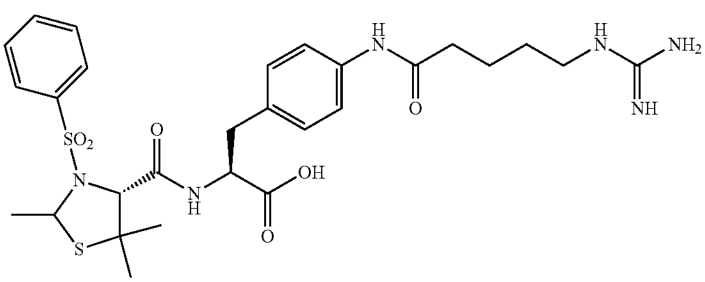 [SMILES: CC1SC(C)(C)[C@@H](C(=O)N[C@@H](Cc2ccc(NC(=O)CCCCNC(=N)N)cc2)C(=O)O)N1S(=O)(=O)c1ccccc1] | 104 |
| 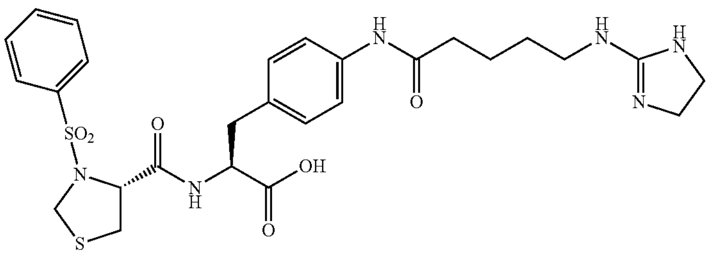 | 105 |

TABLE 2-continued

Additional Exemplary compounds

| Compound Structure | Compound # |
| --- | --- |
| 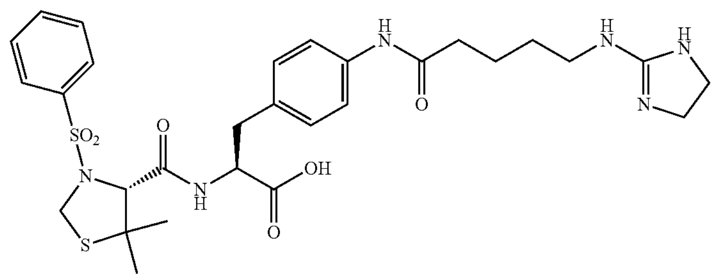 [SMILES: CC1(C)SCN(S(=O)(=O)c2ccccc2)[C@@H]1C(=O)N[C@@H](Cc1ccc(NC(=O)CCCCNC2=NCCN2)cc1)C(=O)O] | 106 |
| 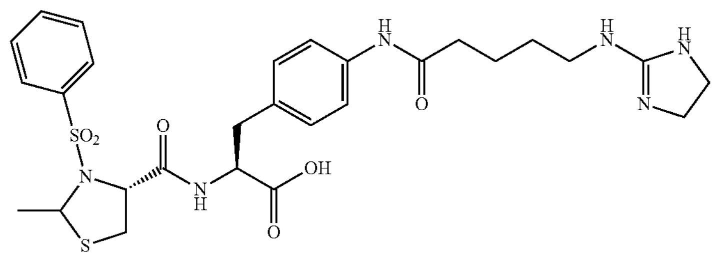 [SMILES: CC1SC[C@@H](C(=O)N[C@@H](Cc2ccc(NC(=O)CCCCNC3=NCCN3)cc2)C(=O)O)N1S(=O)(=O)c1ccccc1] | 107 |
| 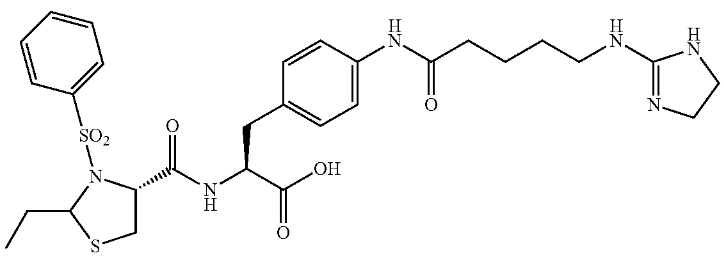 [SMILES: CCC1SC[C@@H](C(=O)N[C@@H](Cc2ccc(NC(=O)CCCCNC3=NCCN3)cc2)C(=O)O)N1S(=O)(=O)c1ccccc1] | 108 |
| 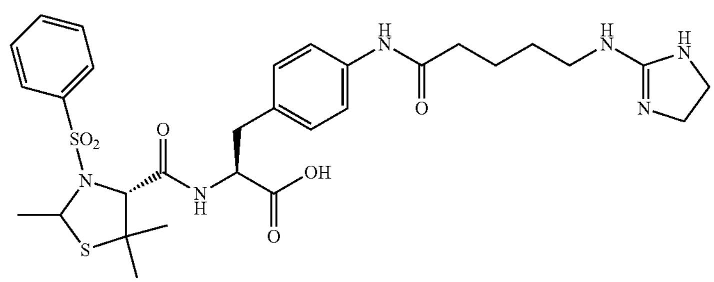 [SMILES: CC1SC(C)(C)[C@@H](C(=O)N[C@@H](Cc2ccc(NC(=O)CCCCNC3=NCCN3)cc2)C(=O)O)N1S(=O)(=O)c1ccccc1] | 109 |
| 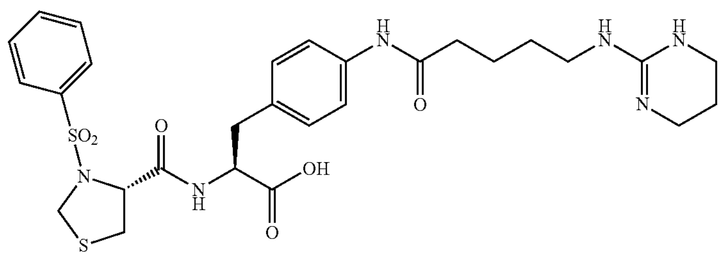 [SMILES: O=C(CCCCNC1=NCCCN1)Nc1ccc(C[C@H](NC(=O)[C@@H]2CSCN2S(=O)(=O)c2ccccc2)C(=O)O)cc1] | 110 |

TABLE 2-continued

Additional Exemplary compounds

| Compound Structure | Compound # |
|---|---|
| 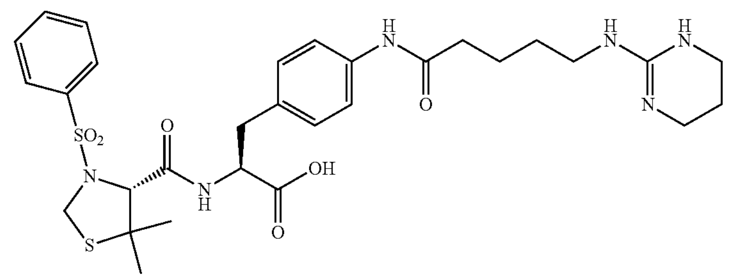 [SMILES: CC1(C)SCN(S(=O)(=O)c2ccccc2)[C@@H]1C(=O)N[C@@H](Cc1ccc(NC(=O)CCCCNC2=NCCCN2)cc1)C(=O)O] | 111 |
| 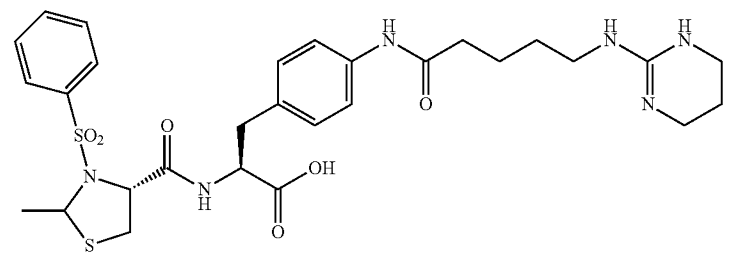 [SMILES: CC1SC[C@@H](C(=O)N[C@@H](Cc2ccc(NC(=O)CCCCNC3=NCCCN3)cc2)C(=O)O)N1S(=O)(=O)c1ccccc1] | 112 |
| 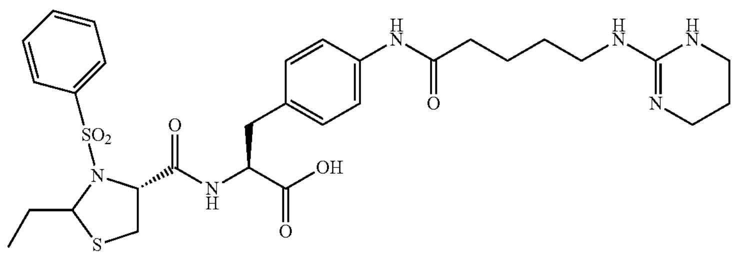 [SMILES: CCC1SC[C@@H](C(=O)N[C@@H](Cc2ccc(NC(=O)CCCCNC3=NCCCN3)cc2)C(=O)O)N1S(=O)(=O)c1ccccc1] | 113 |
| 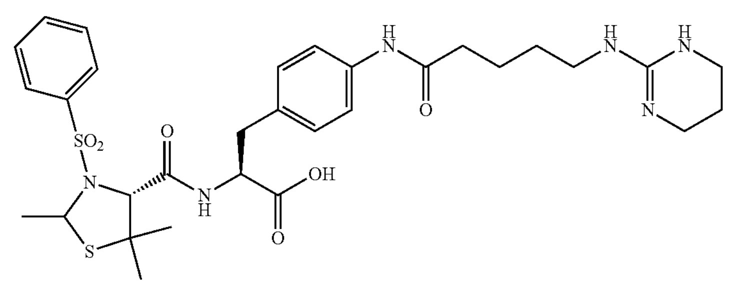 [SMILES: CC1SC(C)(C)[C@@H](C(=O)N[C@@H](Cc2ccc(NC(=O)CCCCNC3=NCCCN3)cc2)C(=O)O)N1S(=O)(=O)c1ccccc1] | 114 |
| 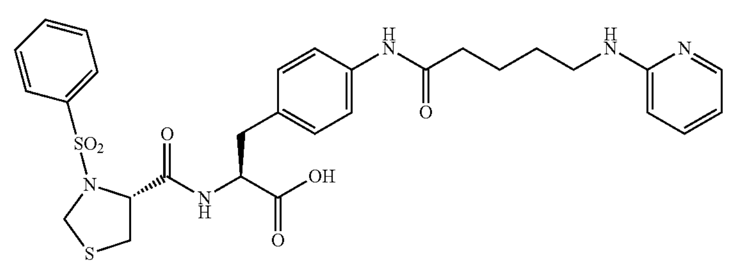 [SMILES: O=C(CCCCNc1ccccn1)Nc1ccc(C[C@H](NC(=O)[C@@H]2CSCN2S(=O)(=O)c2ccccc2)C(=O)O)cc1] | 115 |

TABLE 2-continued

Additional Exemplary compounds

| Compound Structure | Compound # |
|---|---|
| (structure) | 116 |
| (structure) | 117 |
| (structure) | 118 |
| (structure) | 119 |
| (structure) | 120 |

TABLE 2-continued

Additional Exemplary compounds

| Compound Structure | Compound # |
| --- | --- |
| (structure) | 121 |
| (structure) | 122 |
| (structure) | 123 |
| (structure) | 124 |
| (structure) | 125 |

TABLE 2-continued

Additional Exemplary compounds

| Compound Structure | Compound # |
|---|---|
| 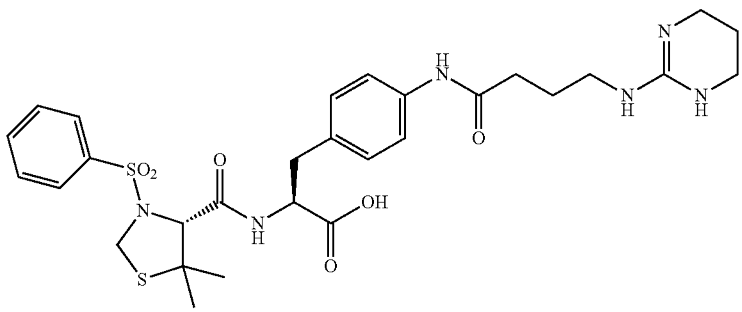 [SMILES: CC1(C)SCN(S(=O)(=O)c2ccccc2)[C@@H]1C(=O)N[C@@H](Cc1ccc(NC(=O)CCCNC2=NCCCN2)cc1)C(=O)O] | 126 |
| 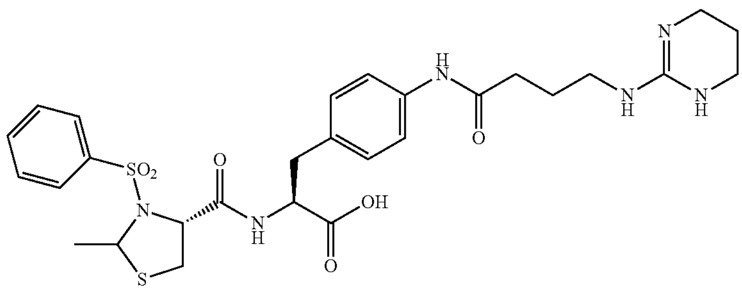 [SMILES: CC1SC[C@@H](C(=O)N[C@@H](Cc2ccc(NC(=O)CCCNC3=NCCCN3)cc2)C(=O)O)N1S(=O)(=O)c1ccccc1] | 127 |
| 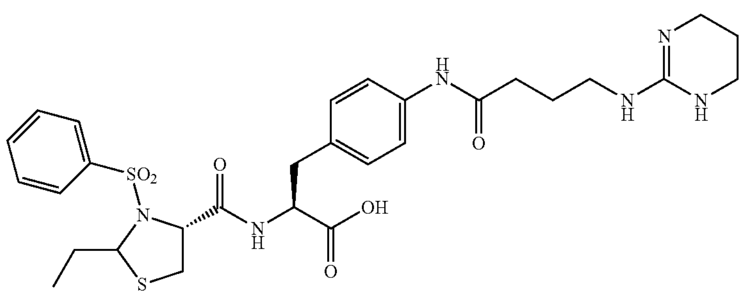 [SMILES: CCC1SC[C@@H](C(=O)N[C@@H](Cc2ccc(NC(=O)CCCNC3=NCCCN3)cc2)C(=O)O)N1S(=O)(=O)c1ccccc1] | 128 |
| 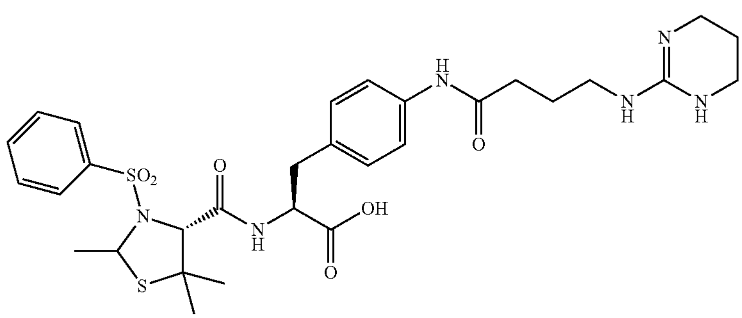 [SMILES: CC1SC(C)(C)[C@@H](C(=O)N[C@@H](Cc2ccc(NC(=O)CCCNC3=NCCCN3)cc2)C(=O)O)N1S(=O)(=O)c1ccccc1] | 129 |
| 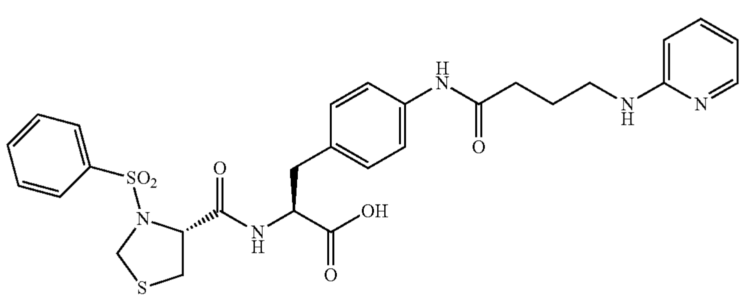 | 130 |

TABLE 2-continued

Additional Exemplary compounds

| Compound Structure | Compound # |
|---|---|
| *structure* | 131 |
| *structure* | 132 |
| *structure* | 133 |
| *structure* | 134 |
| *structure* | 135 |

TABLE 2-continued

Additional Exemplary compounds

| Compound Structure | Compound # |
| --- | --- |
| 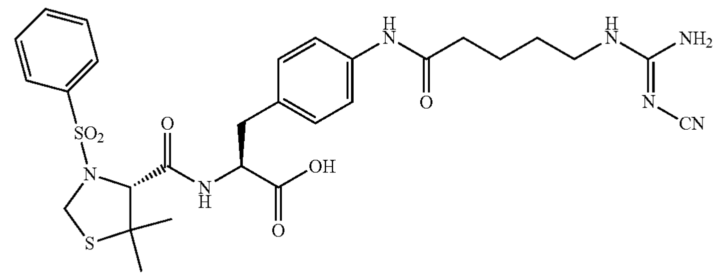 [SMILES: CC1(C)SCN(S(=O)(=O)c2ccccc2)[C@@H]1C(=O)N[C@@H](Cc1ccc(NC(=O)CCCCN/C(N)=N/C#N)cc1)C(=O)O] | 136 |
| 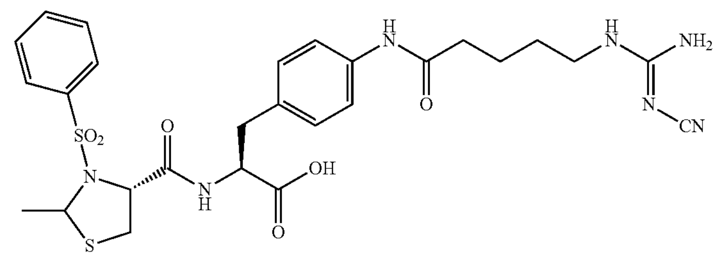 [SMILES: CC1SC[C@@H](C(=O)N[C@@H](Cc2ccc(NC(=O)CCCCN/C(N)=N/C#N)cc2)C(=O)O)N1S(=O)(=O)c1ccccc1] | 137 |
| 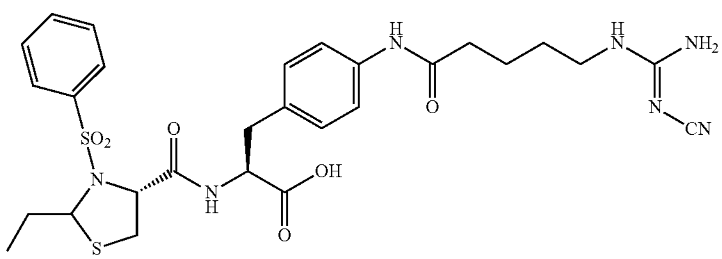 [SMILES: CCC1SC[C@@H](C(=O)N[C@@H](Cc2ccc(NC(=O)CCCCN/C(N)=N/C#N)cc2)C(=O)O)N1S(=O)(=O)c1ccccc1] | 138 |
| 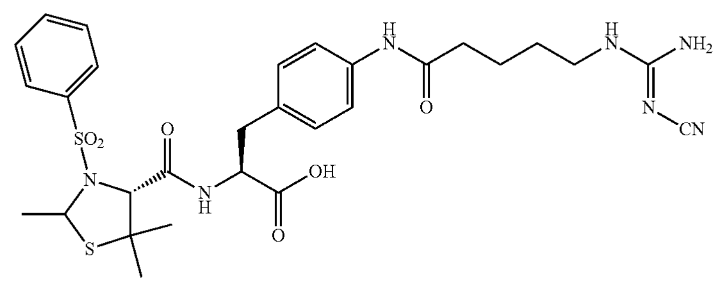 [SMILES: CC1SC(C)(C)[C@@H](C(=O)N[C@@H](Cc2ccc(NC(=O)CCCCN/C(N)=N/C#N)cc2)C(=O)O)N1S(=O)(=O)c1ccccc1] | 139 |
| 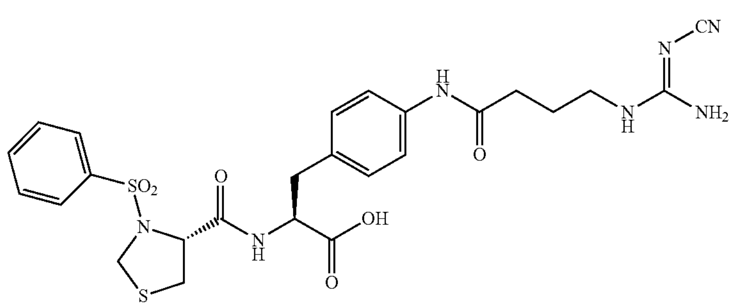 [SMILES: N#C/N=C(\N)NCCCC(=O)Nc1ccc(C[C@H](NC(=O)[C@@H]2CSCN2S(=O)(=O)c2ccccc2)C(=O)O)cc1] | 140 |

TABLE 2-continued

Additional Exemplary compounds

| Compound Structure | Compound # |
|---|---|
| 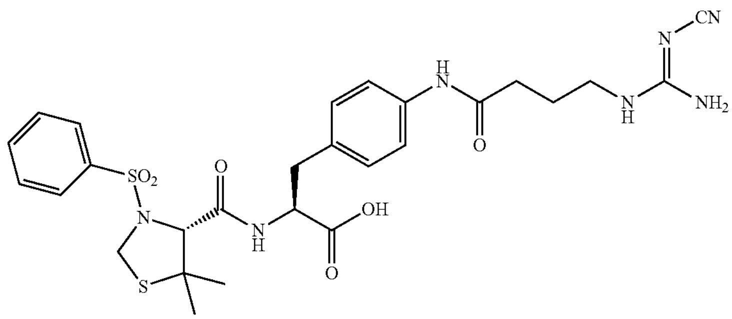 [SMILES: CC1(C)SCN(S(=O)(=O)c2ccccc2)[C@@H]1C(=O)N[C@@H](Cc1ccc(NC(=O)CCCN/C(N)=N/C#N)cc1)C(=O)O] | 141 |
| 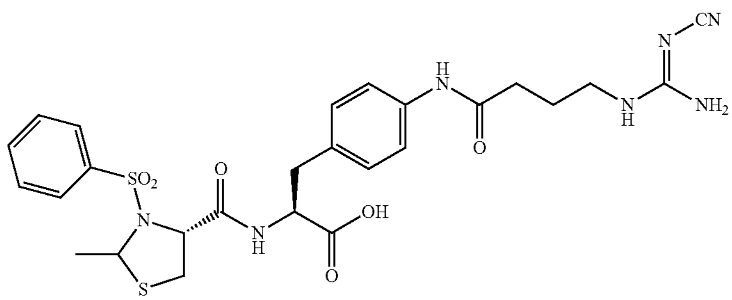 [SMILES: CC1SC[C@@H](C(=O)N[C@@H](Cc2ccc(NC(=O)CCCN/C(N)=N/C#N)cc2)C(=O)O)N1S(=O)(=O)c1ccccc1] | 142 |
| 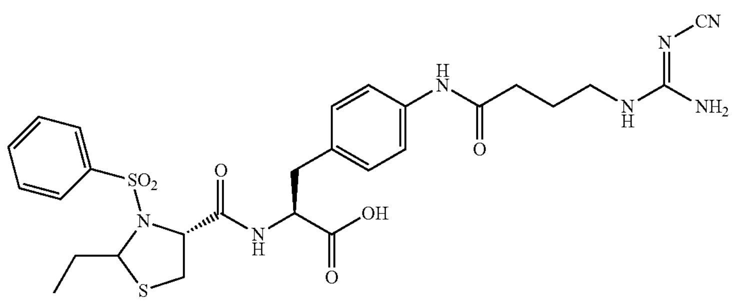 [SMILES: CCC1SC[C@@H](C(=O)N[C@@H](Cc2ccc(NC(=O)CCCN/C(N)=N/C#N)cc2)C(=O)O)N1S(=O)(=O)c1ccccc1] | 143 |
| 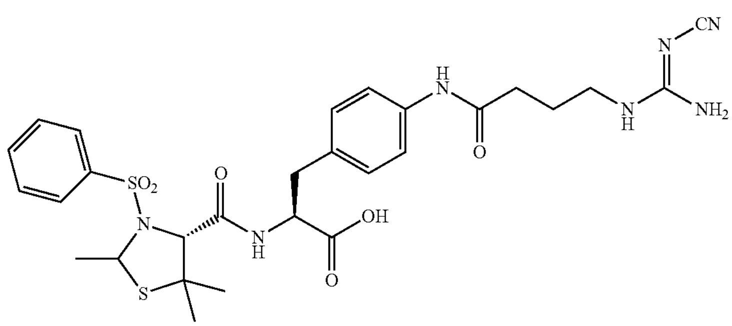 [SMILES: CC1SC(C)(C)[C@@H](C(=O)N[C@@H](Cc2ccc(NC(=O)CCCN/C(N)=N/C#N)cc2)C(=O)O)N1S(=O)(=O)c1ccccc1] | 144 |
| 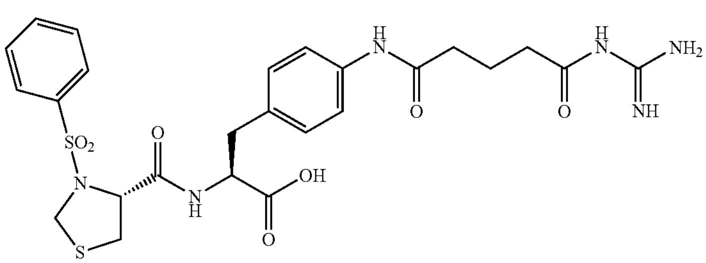 [SMILES: N=C(N)NC(=O)CCCC(=O)Nc1ccc(C[C@H](NC(=O)[C@@H]2CSCN2S(=O)(=O)c2ccccc2)C(=O)O)cc1] | 145 |

TABLE 2-continued
Additional Exemplary compounds
| Compound Structure | Compound # |
|---|---|
| 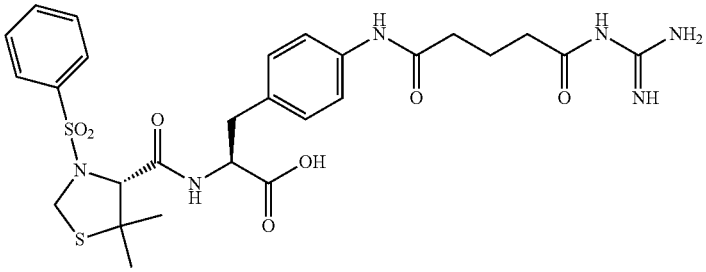 [SMILES: CC1(C)SCN(S(=O)(=O)c2ccccc2)[C@@H]1C(=O)N[C@@H](Cc1ccc(NC(=O)CCCC(=O)NC(=N)N)cc1)C(=O)O] | 146 |
| 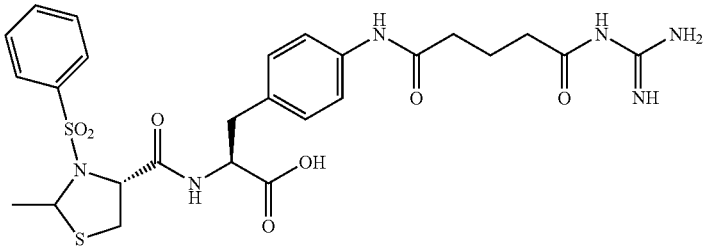 [SMILES: CC1SC[C@@H](C(=O)N[C@@H](Cc2ccc(NC(=O)CCCC(=O)NC(=N)N)cc2)C(=O)O)N1S(=O)(=O)c1ccccc1] | 147 |
| 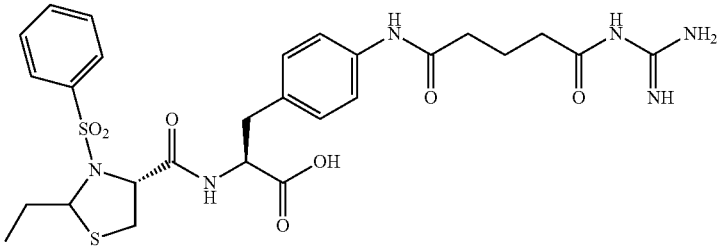 [SMILES: CCC1SC[C@@H](C(=O)N[C@@H](Cc2ccc(NC(=O)CCCC(=O)NC(=N)N)cc2)C(=O)O)N1S(=O)(=O)c1ccccc1] | 148 |
| 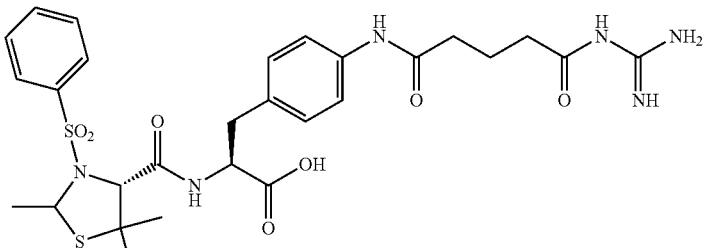 | 149 |
| 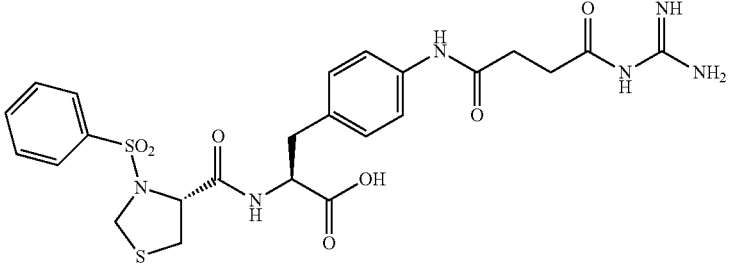 [SMILES: N=C(N)NC(=O)CCC(=O)Nc1ccc(C[C@H](NC(=O)[C@@H]2CSCN2S(=O)(=O)c2ccccc2)C(=O)O)cc1] | 150 |

TABLE 2-continued

Additional Exemplary compounds

| Compound Structure | Compound # |
|---|---|
| 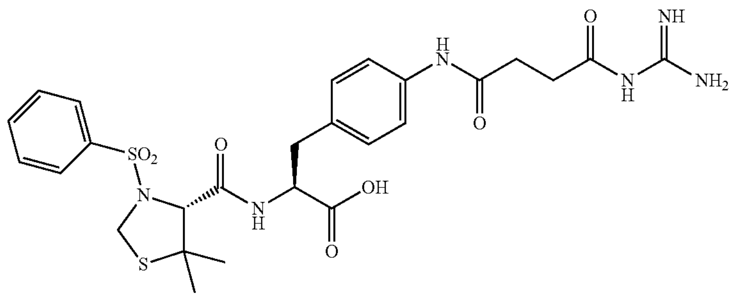 [SMILES: CC1(C)SCN(S(=O)(=O)c2ccccc2)[C@@H]1C(=O)N[C@@H](Cc1ccc(NC(=O)CCC(=O)NC(=N)N)cc1)C(=O)O] | 151 |
| 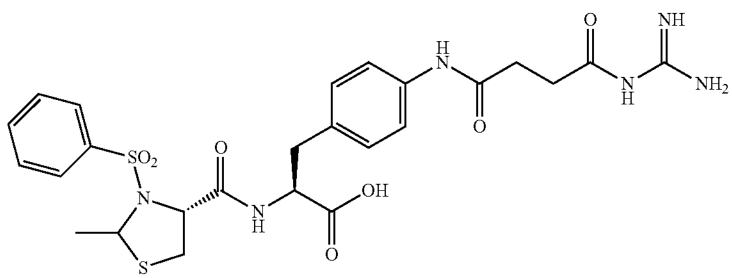 [SMILES: CC1SC[C@@H](C(=O)N[C@@H](Cc2ccc(NC(=O)CCC(=O)NC(=N)N)cc2)C(=O)O)N1S(=O)(=O)c1ccccc1] | 152 |
| 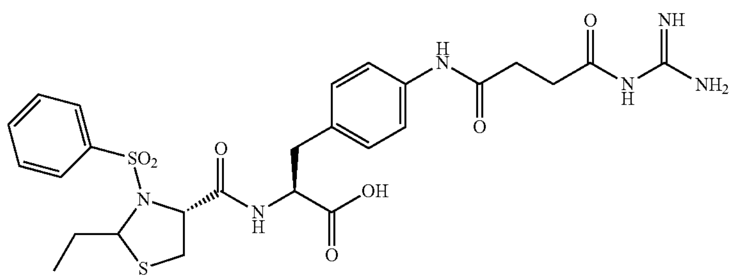 [SMILES: CCC1SC[C@@H](C(=O)N[C@@H](Cc2ccc(NC(=O)CCC(=O)NC(=N)N)cc2)C(=O)O)N1S(=O)(=O)c1ccccc1] | 153 |
| 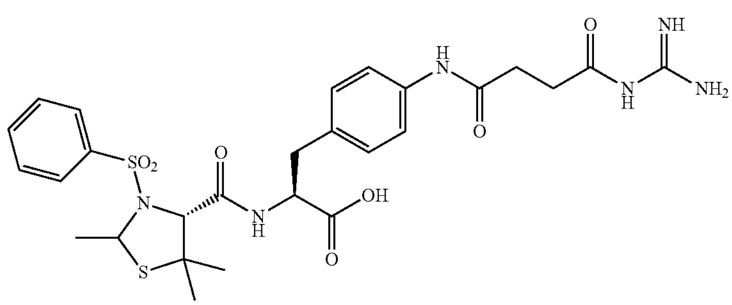 [SMILES: CC1SC(C)(C)[C@@H](C(=O)N[C@@H](Cc2ccc(NC(=O)CCC(=O)NC(=N)N)cc2)C(=O)O)N1S(=O)(=O)c1ccccc1] | 154 |
| 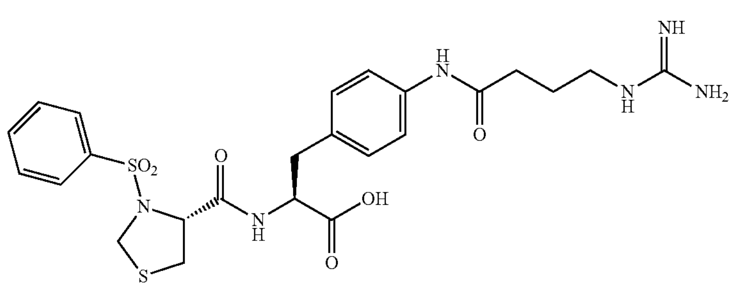 [SMILES: N=C(N)NCCCC(=O)Nc1ccc(C[C@H](NC(=O)[C@@H]2CSCN2S(=O)(=O)c2ccccc2)C(=O)O)cc1] | 155 |

TABLE 2-continued

Additional Exemplary compounds

| Compound Structure | Compound # |
|---|---|
| 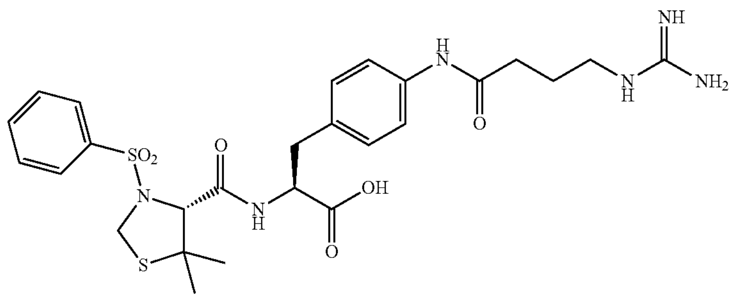 [SMILES: CC1(C)SCN(S(=O)(=O)c2ccccc2)[C@@H]1C(=O)N[C@@H](Cc1ccc(NC(=O)CCCNC(=N)N)cc1)C(=O)O] | 156 |
| 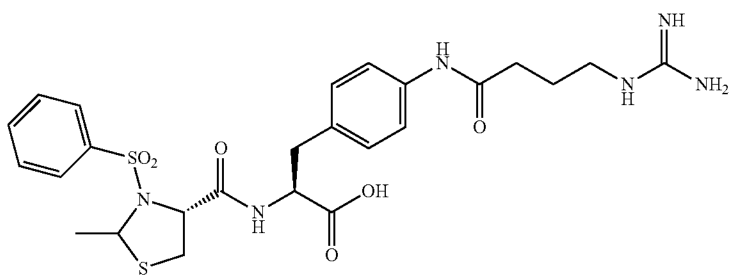 [SMILES: CC1SC[C@@H](C(=O)N[C@@H](Cc2ccc(NC(=O)CCCNC(=N)N)cc2)C(=O)O)N1S(=O)(=O)c1ccccc1] | 157 |
| 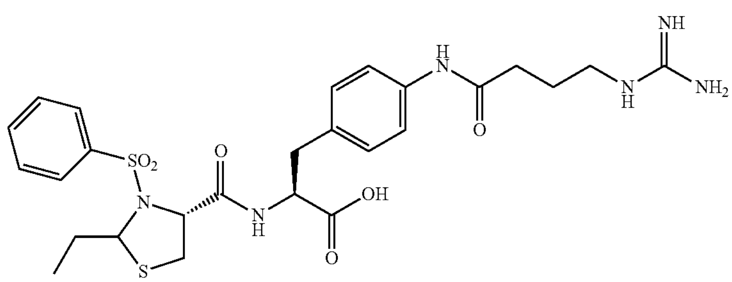 [SMILES: CCC1SC[C@@H](C(=O)N[C@@H](Cc2ccc(NC(=O)CCCNC(=N)N)cc2)C(=O)O)N1S(=O)(=O)c1ccccc1] | 158 |
| 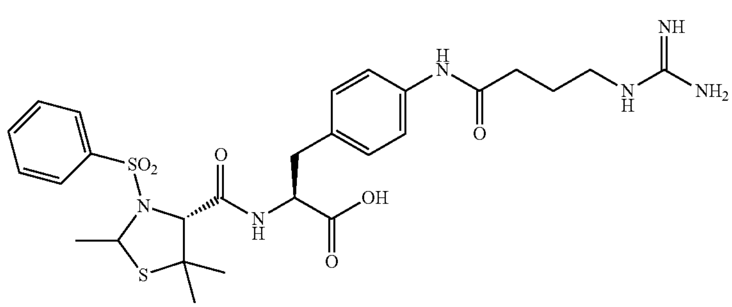 [SMILES: CC1SC(C)(C)[C@@H](C(=O)N[C@@H](Cc2ccc(NC(=O)CCCNC(=N)N)cc2)C(=O)O)N1S(=O)(=O)c1ccccc1] | 159 |

142
TABLE 3
Additional Exemplary Compounds
| Compound Structure | Compound # |
|---|---|
| 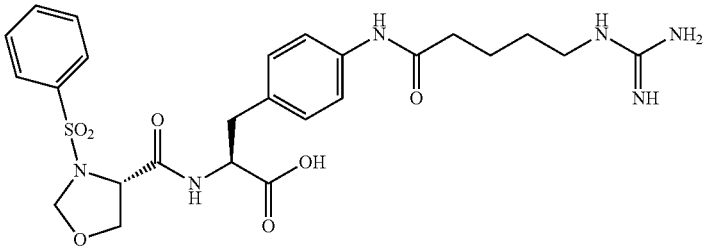 [SMILES: N=C(N)NCCCCC(=O)Nc1ccc(C[C@H](NC(=O)[C@@H]2COCN2S(=O)(=O)c2ccccc2)C(=O)O)cc1] | 160 |
| 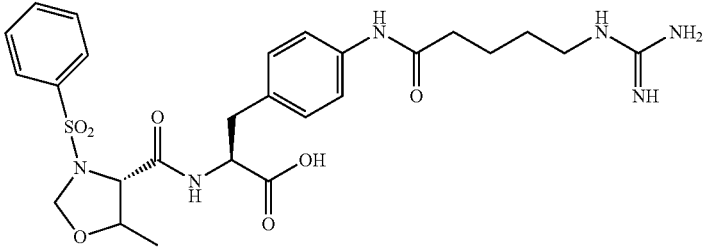 [SMILES: CC1OCN(S(=O)(=O)c2ccccc2)[C@@H]1C(=O)N[C@@H](Cc1ccc(NC(=O)CCCCNC(=N)N)cc1)C(=O)O] | 161 |
| 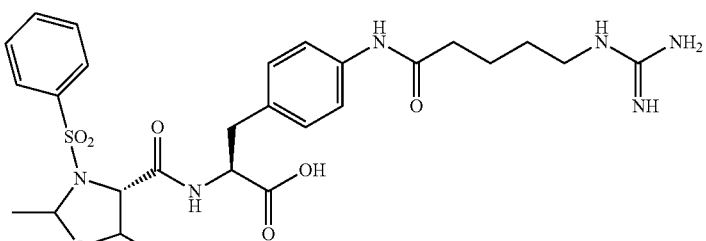 | 162 |
| 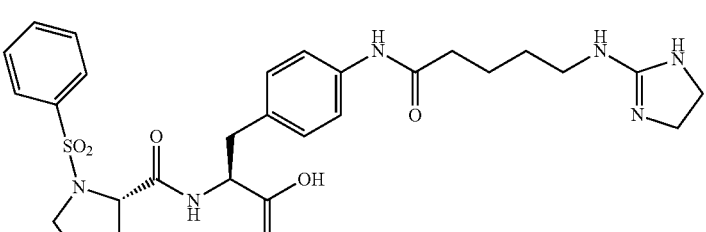 | 163 |
| 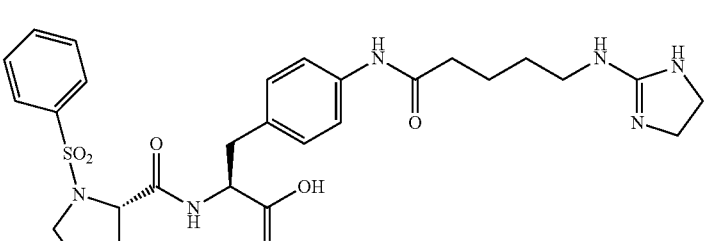 | 164 |
| 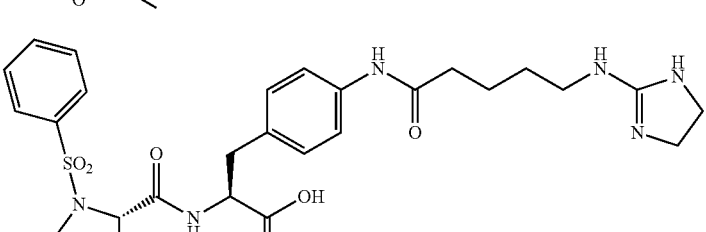 | 165 |

TABLE 3-continued

Additional Exemplary Compounds

| Compound Structure | Compound # |
| --- | --- |
| 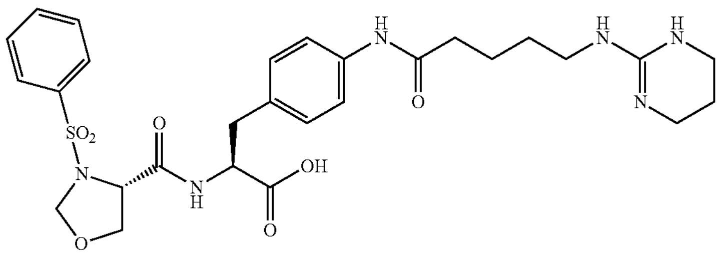 | 166 |
| 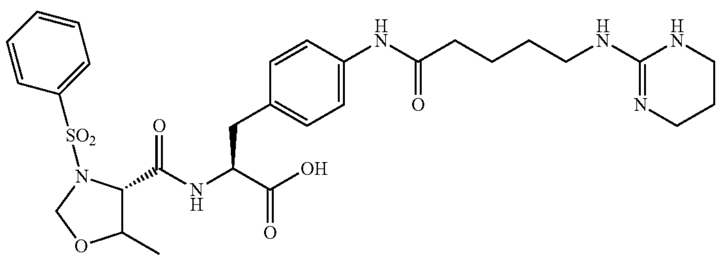 [SMILES: CC1OCN(S(=O)(=O)c2ccccc2)[C@@H]1C(=O)N[C@@H](Cc1ccc(NC(=O)CCCCNC2=NCCCN2)cc1)C(=O)O] | 167 |
| 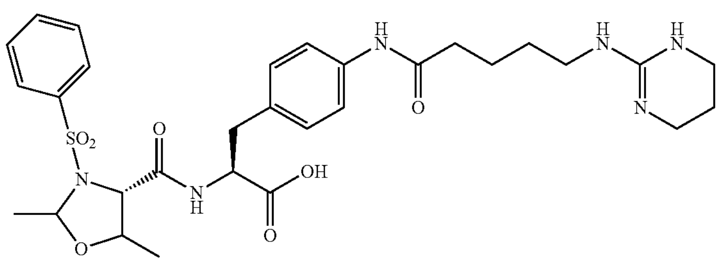 [SMILES: CC1OC(C)N(S(=O)(=O)c2ccccc2)[C@@H]1C(=O)N[C@@H](Cc1ccc(NC(=O)CCCCNC2=NCCCN2)cc1)C(=O)O] | 168 |
| 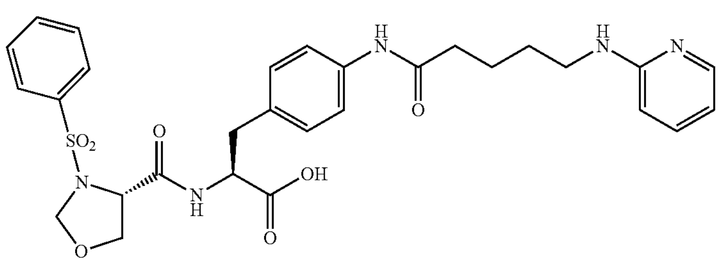 [SMILES: O=C(CCCCNc1ccccn1)Nc1ccc(C[C@H](NC(=O)[C@@H]2COCN2S(=O)(=O)c2ccccc2)C(=O)O)cc1] | 169 |
| 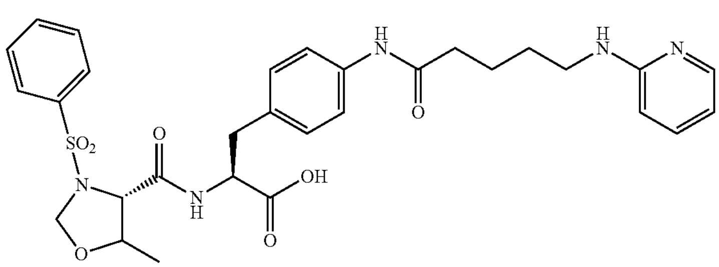 [SMILES: CC1OCN(S(=O)(=O)c2ccccc2)[C@@H]1C(=O)N[C@@H](Cc1ccc(NC(=O)CCCCNc2ccccn2)cc1)C(=O)O] | 170 |

TABLE 3-continued

Additional Exemplary Compounds

| Compound Structure | Compound # |
|---|---|
| 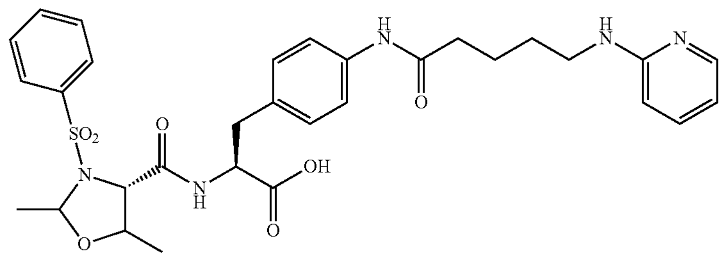 [SMILES: CC1OC(C)N(S(=O)(=O)c2ccccc2)[C@@H]1C(=O)N[C@@H](Cc1ccc(NC(=O)CCCCNc2ccccn2)cc1)C(=O)O] | 171 |
| 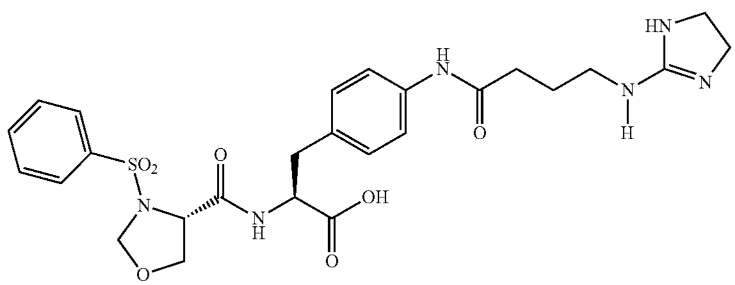 [SMILES: O=C(CCCNC1=NCCN1)Nc1ccc(C[C@H](NC(=O)[C@@H]2COCN2S(=O)(=O)c2ccccc2)C(=O)O)cc1] | 172 |
| 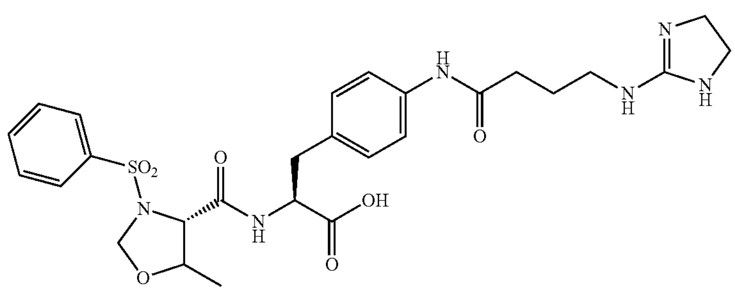 [SMILES: CC1OCN(S(=O)(=O)c2ccccc2)[C@@H]1C(=O)N[C@@H](Cc1ccc(NC(=O)CCCNC2=NCCN2)cc1)C(=O)O] | 173 |
| 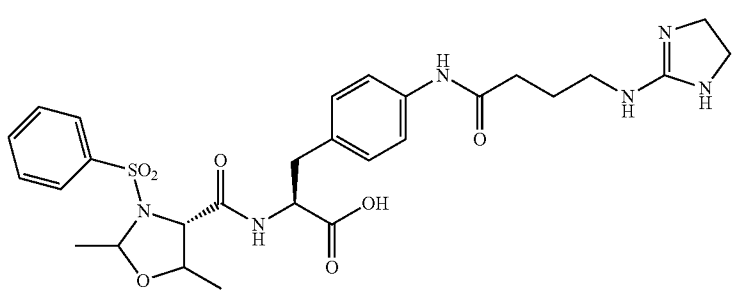 [SMILES: CC1OC(C)N(S(=O)(=O)c2ccccc2)[C@@H]1C(=O)N[C@@H](Cc1ccc(NC(=O)CCCNC2=NCCN2)cc1)C(=O)O] | 174 |
| 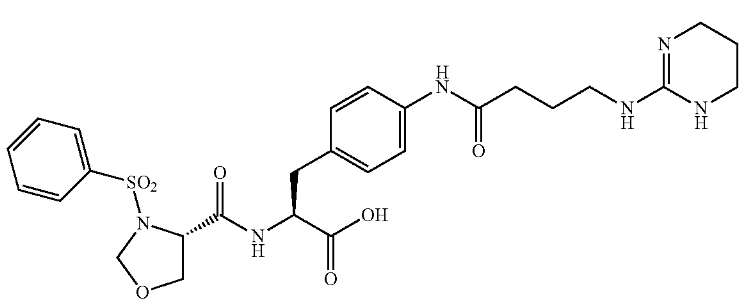 [SMILES: O=C(CCCNC1=NCCCN1)Nc1ccc(C[C@H](NC(=O)[C@@H]2COCN2S(=O)(=O)c2ccccc2)C(=O)O)cc1] | 175 |

TABLE 3-continued

Additional Exemplary Compounds

| Compound Structure | Compound # |
|---|---|
| 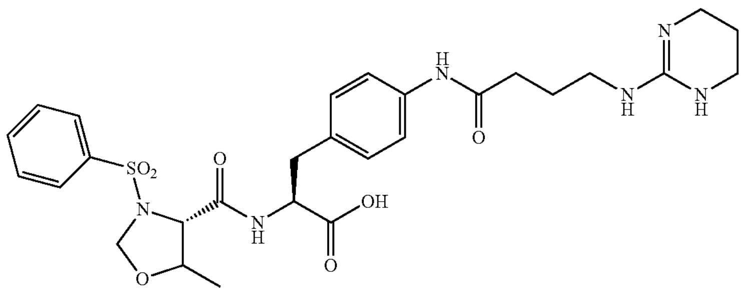 [SMILES: CC1OCN(S(=O)(=O)c2ccccc2)[C@@H]1C(=O)N[C@@H](Cc1ccc(NC(=O)CCCNC2=NCCCN2)cc1)C(=O)O] | 176 |
| 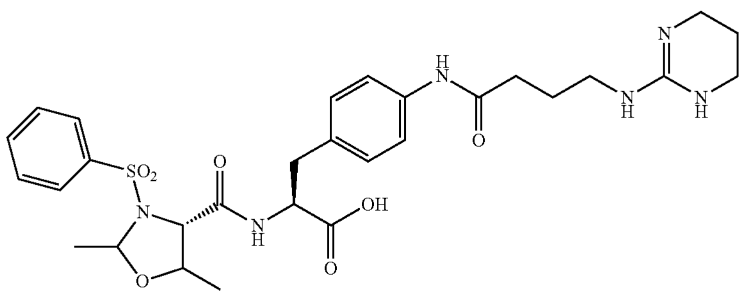 [SMILES: CC1OC(C)N(S(=O)(=O)c2ccccc2)[C@@H]1C(=O)N[C@@H](Cc1ccc(NC(=O)CCCNC2=NCCCN2)cc1)C(=O)O] | 177 |
| 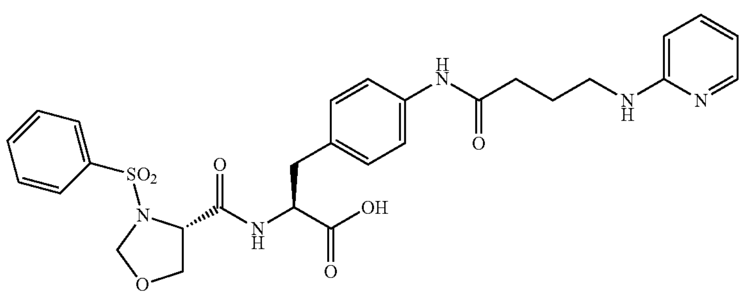 [SMILES: O=C(CCCNc1ccccn1)Nc1ccc(C[C@H](NC(=O)[C@@H]2COCN2S(=O)(=O)c2ccccc2)C(=O)O)cc1] | 178 |
| 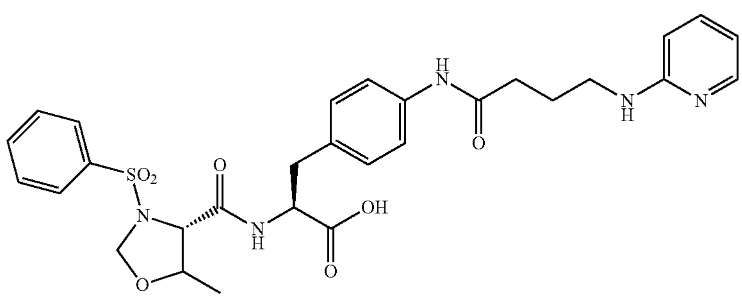 [SMILES: CC1OCN(S(=O)(=O)c2ccccc2)[C@@H]1C(=O)N[C@@H](Cc1ccc(NC(=O)CCCNc2ccccn2)cc1)C(=O)O] | 179 |
| 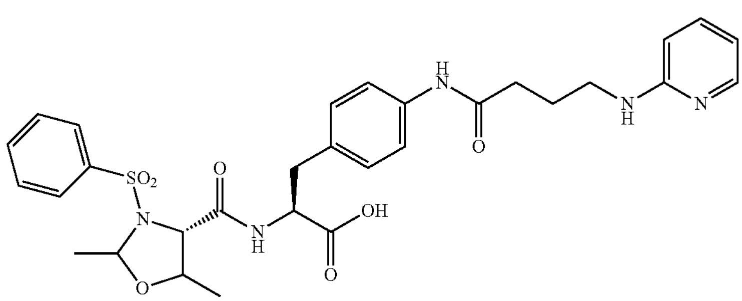 [SMILES: CC1OC(C)N(S(=O)(=O)c2ccccc2)[C@@H]1C(=O)N[C@@H](Cc1ccc(NC(=O)CCCNc2ccccn2)cc1)C(=O)O] | 180 |

TABLE 3-continued
Additional Exemplary Compounds
| Compound Structure | Compound # |
|---|---|
| 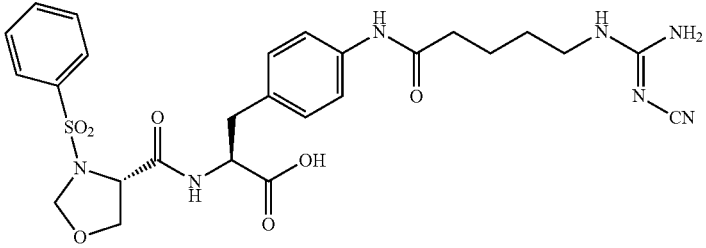 [SMILES: N#C/N=C(\N)NCCCCC(=O)Nc1ccc(C[C@H](NC(=O)[C@@H]2COCN2S(=O)(=O)c2ccccc2)C(=O)O)cc1] | 181 |
| 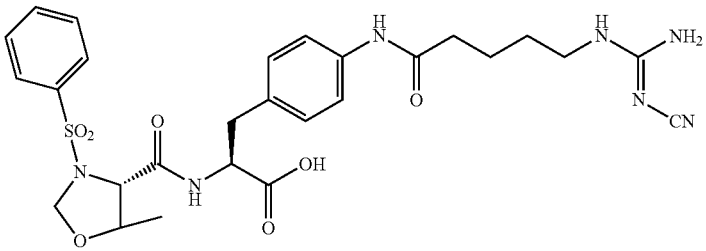 [SMILES: CC1OCN(S(=O)(=O)c2ccccc2)[C@@H]1C(=O)N[C@@H](Cc1ccc(NC(=O)CCCCN/C(N)=N/C#N)cc1)C(=O)O] | 182 |
| 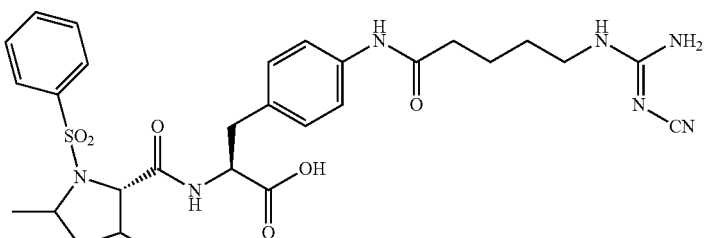 | 183 |
| 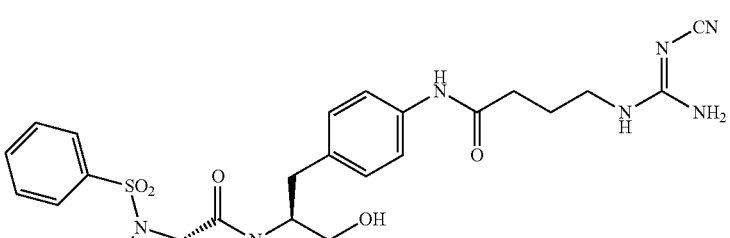 | 184 |
| 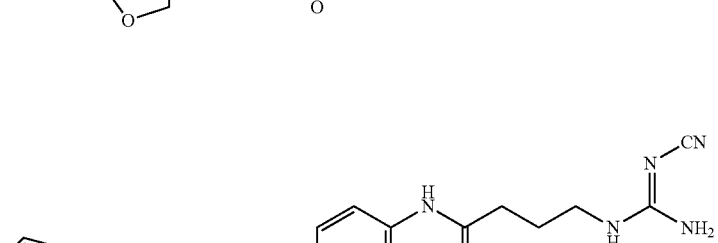 | 185 |

TABLE 3-continued
Additional Exemplary Compounds
| Compound Structure | Compound # |
|---|---|
| 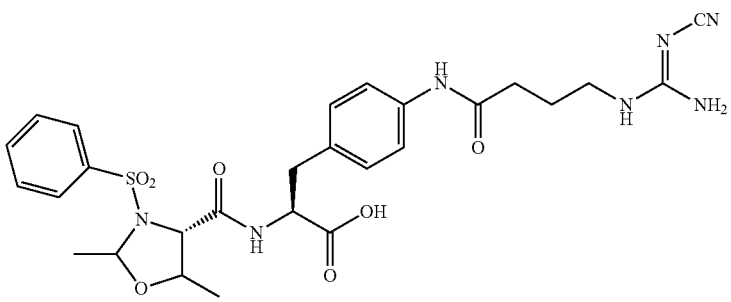 [SMILES: CC1OC(C)N(S(=O)(=O)c2ccccc2)[C@@H]1C(=O)N[C@@H](Cc1ccc(NC(=O)CCCN/C(N)=N/C#N)cc1)C(=O)O] | 186 |
| 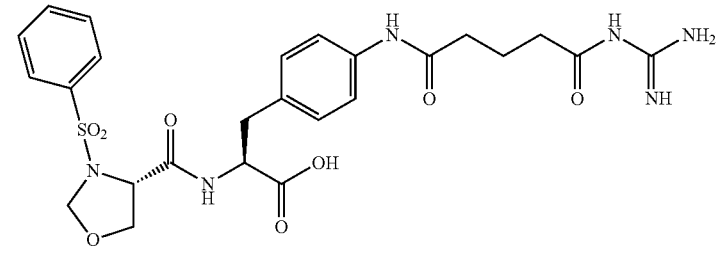 [SMILES: N=C(N)NC(=O)CCCC(=O)Nc1ccc(C[C@H](NC(=O)[C@@H]2COCN2S(=O)(=O)c2ccccc2)C(=O)O)cc1] | 187 |
| 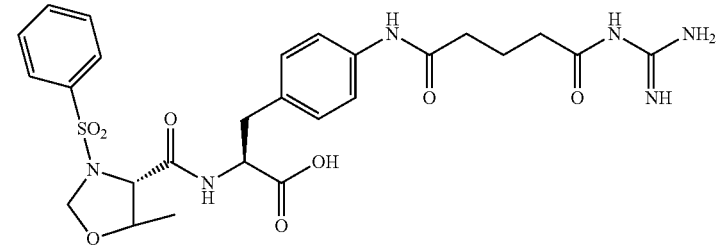 [SMILES: CC1OCN(S(=O)(=O)c2ccccc2)[C@@H]1C(=O)N[C@@H](Cc1ccc(NC(=O)CCCC(=O)NC(=N)N)cc1)C(=O)O] | 188 |
| 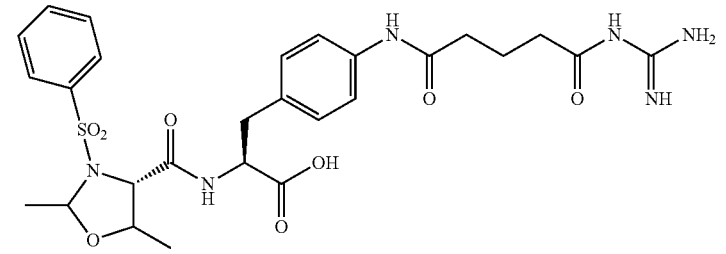 [SMILES: CC1OC(C)N(S(=O)(=O)c2ccccc2)[C@@H]1C(=O)N[C@@H](Cc1ccc(NC(=O)CCCC(=O)NC(=N)N)cc1)C(=O)O] | 189 |
| 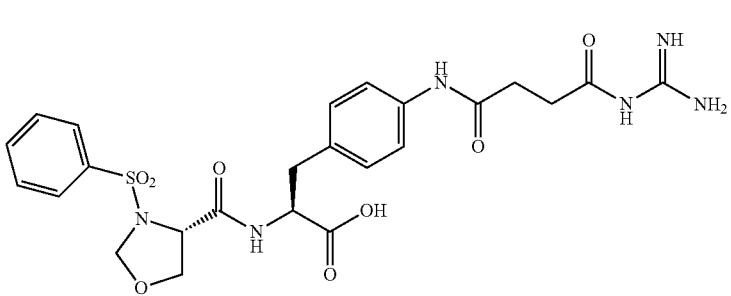 [SMILES: N=C(N)NC(=O)CCC(=O)Nc1ccc(C[C@H](NC(=O)[C@@H]2COCN2S(=O)(=O)c2ccccc2)C(=O)O)cc1] | 190 |

TABLE 3-continued

Additional Exemplary Compounds

| Compound Structure | Compound # |
|---|---|
| 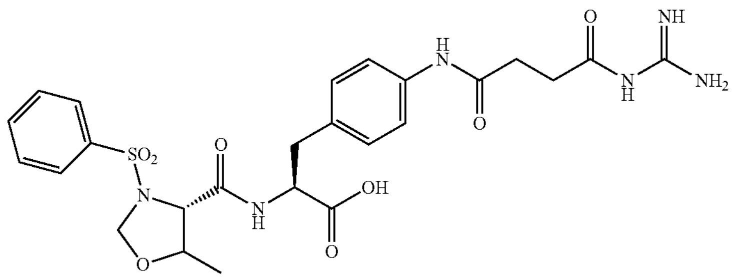 [SMILES: CC1OCN(S(=O)(=O)c2ccccc2)[C@@H]1C(=O)N[C@@H](Cc1ccc(NC(=O)CCC(=O)NC(=N)N)cc1)C(=O)O] | 191 |
| 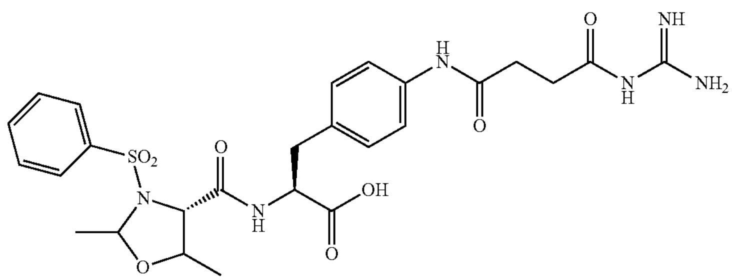 [SMILES: CC1OC(C)N(S(=O)(=O)c2ccccc2)[C@@H]1C(=O)N[C@@H](Cc1ccc(NC(=O)CCC(=O)NC(=N)N)cc1)C(=O)O] | 192 |
| 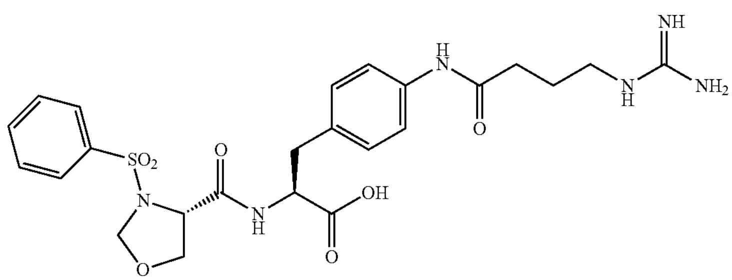 | 193 |
| 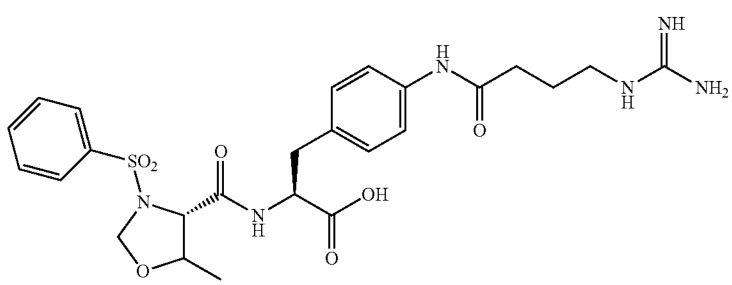 [SMILES: CC1OCN(S(=O)(=O)c2ccccc2)[C@@H]1C(=O)N[C@@H](Cc1ccc(NC(=O)CCCNC(=N)N)cc1)C(=O)O] | 194 |
| 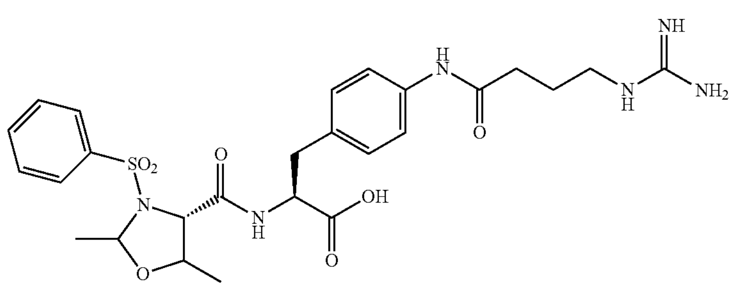 [SMILES: CC1OC(C)N(S(=O)(=O)c2ccccc2)[C@@H]1C(=O)N[C@@H](Cc1ccc(NC(=O)CCCNC(=N)N)cc1)C(=O)O] | 195 |

TABLE 4

Additional Exemplary Compounds

| Compound Structure | Compound # |
|---|---|
| (structure with phenylsulfonyl-pyrrolidine, tyrosine-like residue, arginine, and hexanoyl linker to Lissamine Rhodamine sulfonyl label) | 196 |
| (structure with phenylsulfonyl-pyrrolidine, tyrosine-like residue, arginine, and –CH₂CH₂–O–(PEG)₃–NH– linker to Lissamine Rhodamine Sulfonyl label) | 197 |
| (structure with phenylsulfonyl-pyrrolidine, tyrosine-like residue, arginine, and hexanoyl linker to Fluorescein isothiocyanate label) | 198 |

TABLE 4-continued

Additional Exemplary Compounds

| Compound Structure | Compound # |
| --- | --- |
| 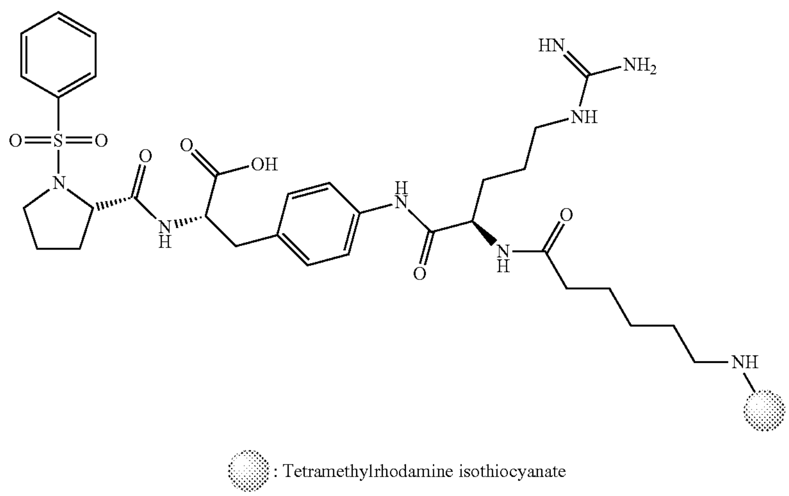 | 199 |
| 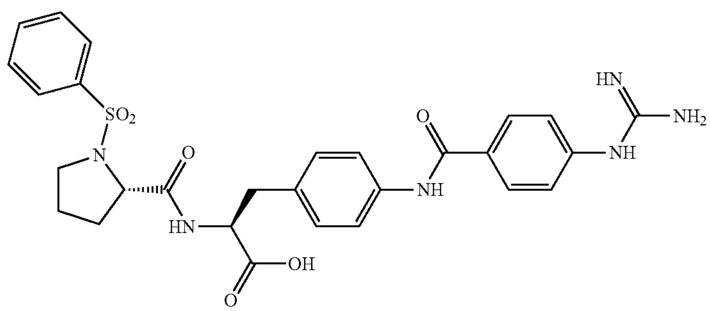 [SMILES: N=C(N)Nc1ccc(C(=O)Nc2ccc(C[C@H](NC(=O)[C@@H]3CCCN3S(=O)(=O)c3ccccc3)C(=O)O)cc2)cc1] | 200 |
| 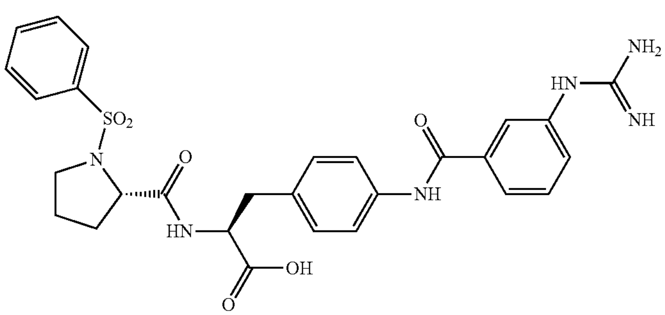 [SMILES: N=C(N)Nc1cccc(C(=O)Nc2ccc(C[C@H](NC(=O)[C@@H]3CCCN3S(=O)(=O)c3ccccc3)C(=O)O)cc2)c1] | 201 |
| 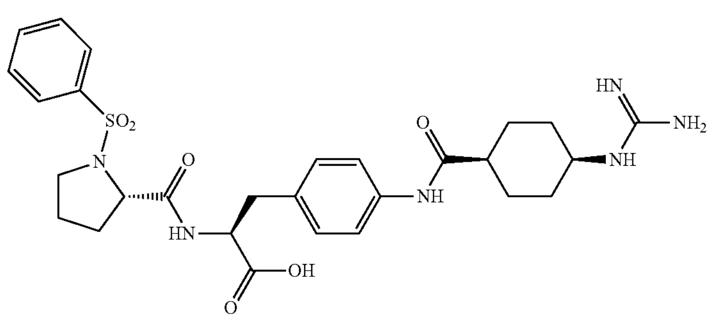 [SMILES: N=C(N)N[C@H]1CC[C@@H](C(=O)Nc2ccc(C[C@H](NC(=O)[C@@H]3CCCN3S(=O)(=O)c3ccccc3)C(=O)O)cc2)CC1] | 202 |

: Tetramethylrhodamine isothiocyanate

TABLE 4-continued
Additional Exemplary Compounds
| Compound Structure | Compound # |
|---|---|
| 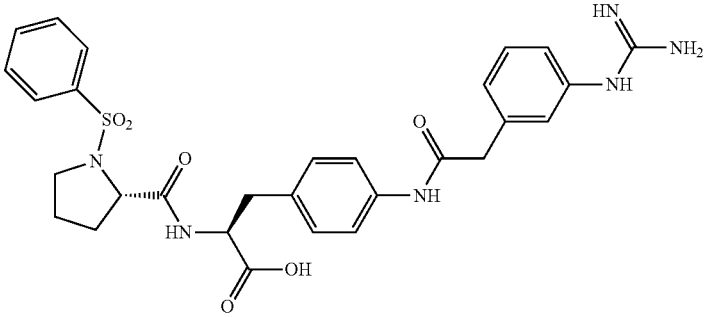 [SMILES: N=C(N)Nc1cccc(CC(=O)Nc2ccc(C[C@H](NC(=O)[C@@H]3CCCN3S(=O)(=O)c3ccccc3)C(=O)O)cc2)c1] | 203 |
| 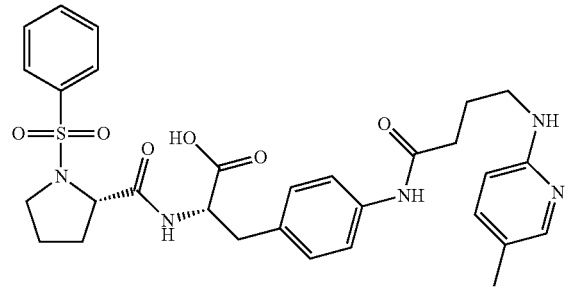 [SMILES: Cc1ccc(NCCCC(=O)Nc2ccc(C[C@H](NC(=O)[C@@H]3CCCN3S(=O)(=O)c3ccccc3)C(=O)O)cc2)nc1] | 204 |
| 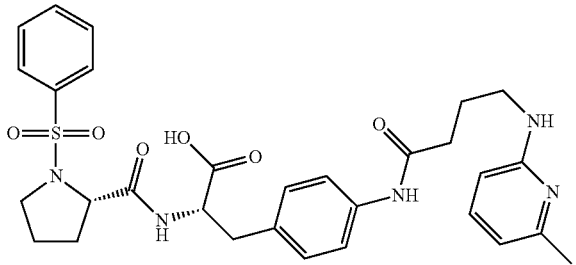 [SMILES: Cc1cccc(NCCCC(=O)Nc2ccc(C[C@H](NC(=O)[C@@H]3CCCN3S(=O)(=O)c3ccccc3)C(=O)O)cc2)n1] | 205 |
| 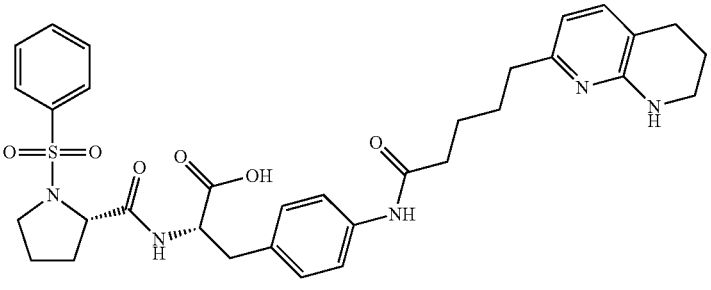 [SMILES: O=C(CCCCc1ccc2c(n1)NCCC2)Nc1ccc(C[C@H](NC(=O)[C@@H]2CCCN2S(=O)(=O)c2ccccc2)C(=O)O)cc1] | 206 |
| 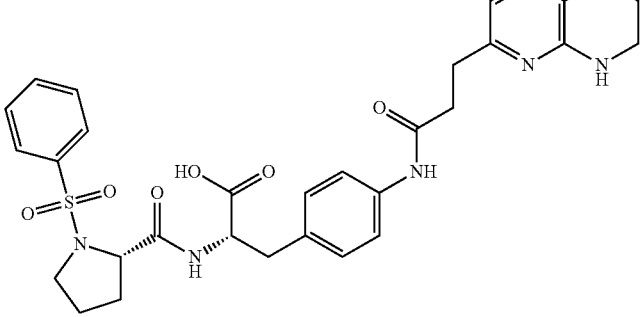 | 207 |

TABLE 4-continued

Additional Exemplary Compounds

| Compound Structure | Compound # |
|---|---|
| 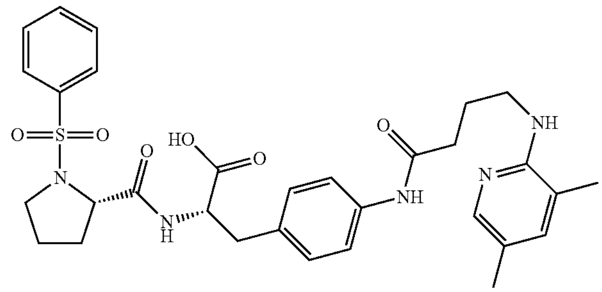 [SMILES: Cc1cnc(NCCCC(=O)Nc2ccc(C[C@H](NC(=O)[C@@H]3CCCN3S(=O)(=O)c3ccccc3)C(=O)O)cc2)c(C)c1] | 208 |
| 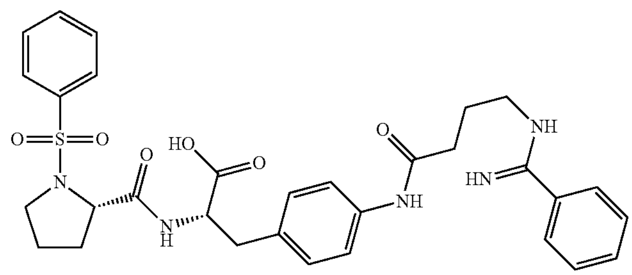 [SMILES: N=C(NCCCC(=O)Nc1ccc(C[C@H](NC(=O)[C@@H]2CCCN2S(=O)(=O)c2ccccc2)C(=O)O)cc1)c1ccccc1] | 209 |
| 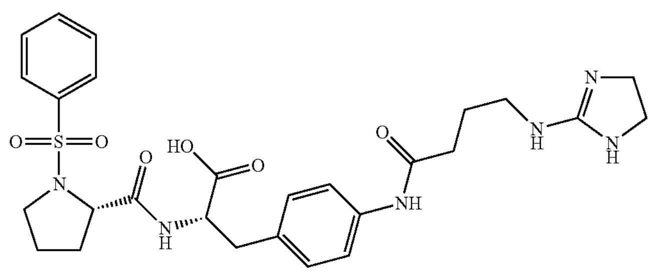 [SMILES: O=C(CCCNC1=NCCN1)Nc1ccc(C[C@H](NC(=O)[C@@H]2CCCN2S(=O)(=O)c2ccccc2)C(=O)O)cc1] | 210 |
| 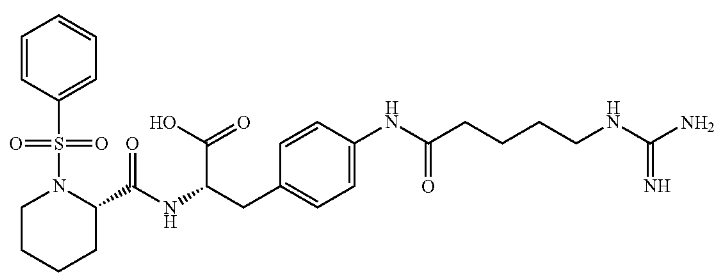 [SMILES: N=C(N)NCCCCC(=O)Nc1ccc(C[C@H](NC(=O)[C@@H]2CCCCN2S(=O)(=O)c2ccccc2)C(=O)O)cc1] | 211 |
| 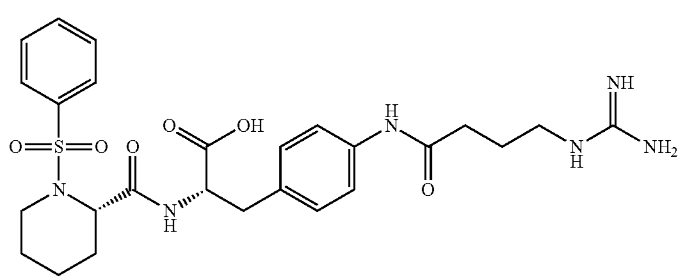 [SMILES: N=C(N)NCCCC(=O)Nc1ccc(C[C@H](NC(=O)[C@@H]2CCCCN2S(=O)(=O)c2ccccc2)C(=O)O)cc1] | 212 |

TABLE 4-continued
Additional Exemplary Compounds
| Compound Structure | Compound # |
|---|---|
| 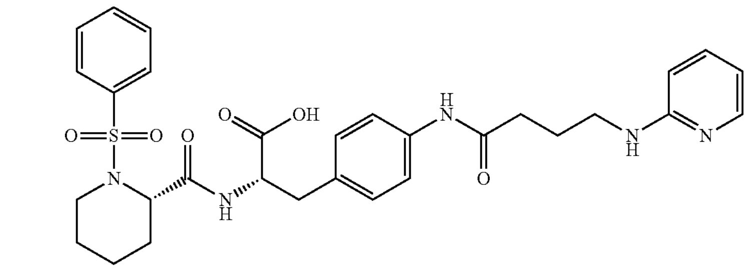 [SMILES: O=C(CCCNc1ccccn1)Nc1ccc(C[C@H](NC(=O)[C@@H]2CCCCN2S(=O)(=O)c2ccccc2)C(=O)O)cc1] | 213 |
| 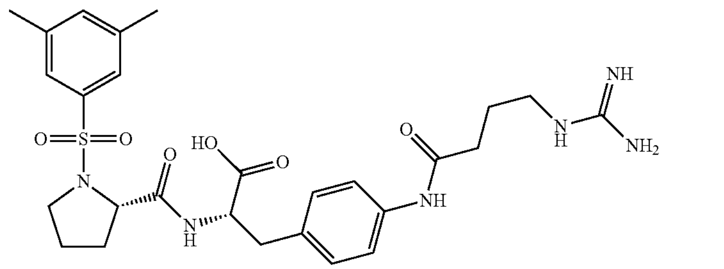 [SMILES: Cc1cc(C)cc(S(=O)(=O)N2CCC[C@H]2C(=O)N[C@@H](Cc2ccc(NC(=O)CCCNC(=N)N)cc2)C(=O)O)c1] | 214 |
| 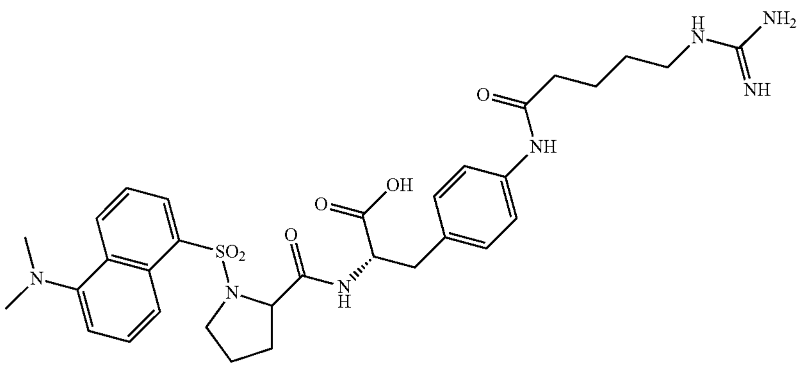 [SMILES: CN(C)c1cccc2c(S(=O)(=O)N3CCCC3C(=O)N[C@@H](Cc3ccc(NC(=O)CCCCNC(=N)N)cc3)C(=O)O)cccc12] | 215 |
VI. Examples
Example 1
Solid phase synthesis schematic for synthesis of compounds described herein.
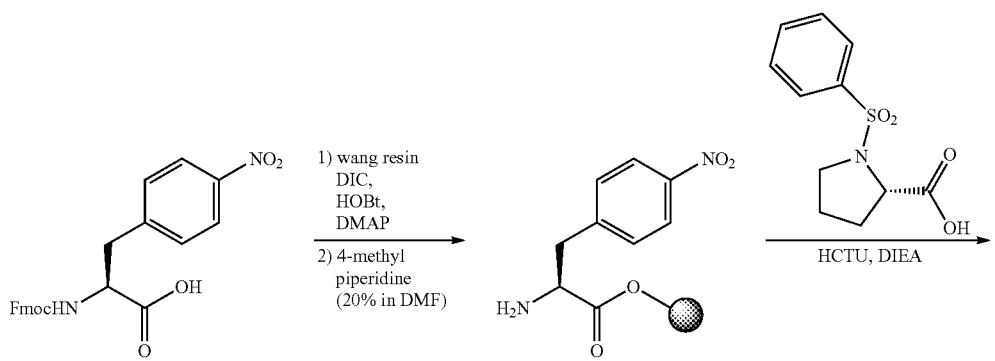

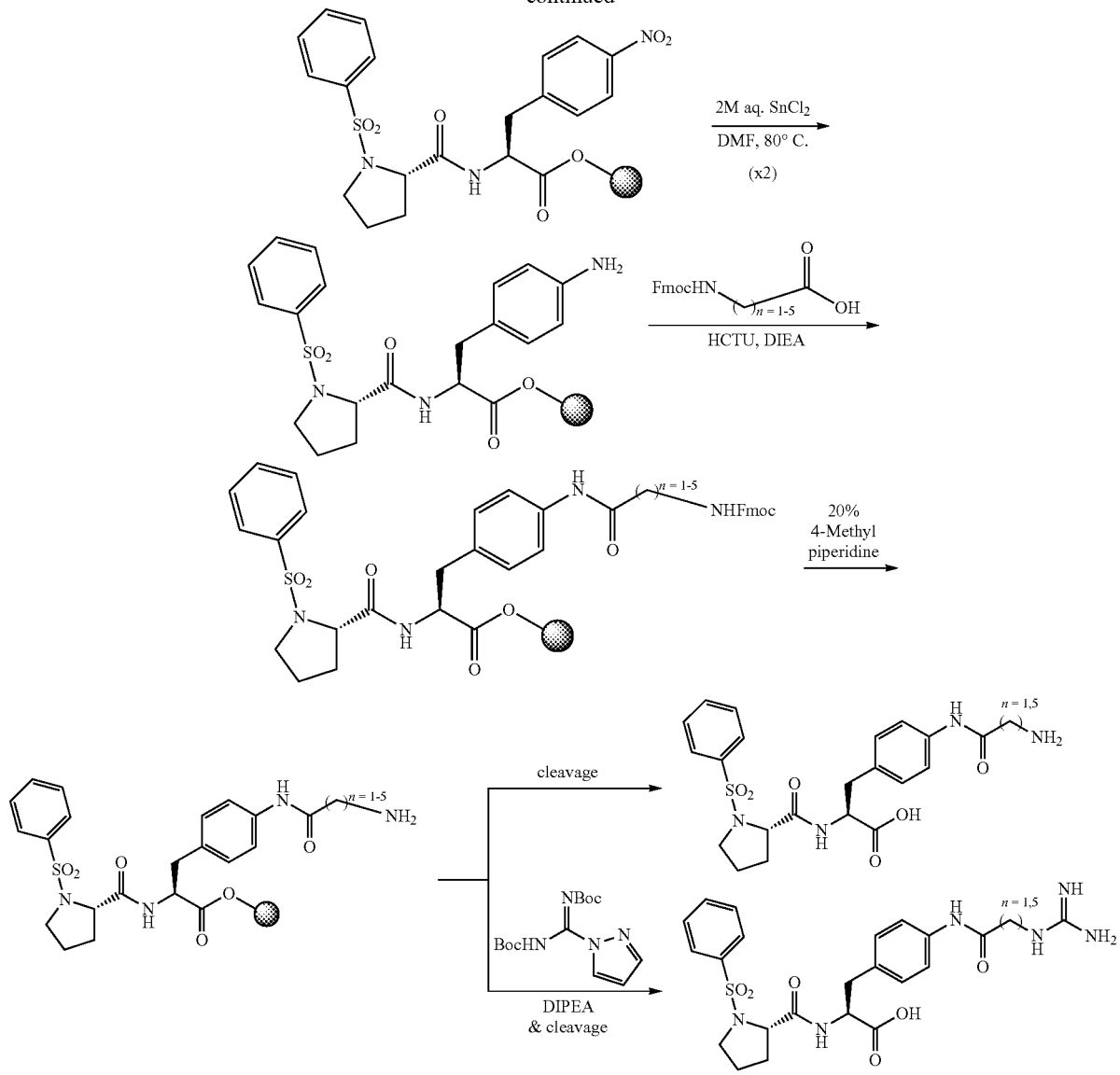

[General Method A]

Fmoc-(p-NO2)-Phe-Wang resin (6 mmol) was treated with 4-methyl piperidine (25 mL, 20% in DMF) for 5 min to remove Fmoc protecting group. The deprotection step was repeated once and filtered, washed with DMF thoroughly. Then, a mixture of benzenesulfonylproline (3 eq) (1), HCTU (3 eq) and DIEA (6 eq) in DMF (25 mL) was added and stirred for 1 h at rt. Then the resin was filtered and washed with DMF thoroughly. To a suspension of resin (2.3 mmol) in DMF (40 mL) was added aqueous 2M $SnCl_2$ solution (20eq, 23 mL) and stirred at 80° C. for 5 h, then was kept stirring 16 h at rt. The mixture was filtered and washed with water, DMF, DCM, and iPrOH successively. Then a portion of resin (0.3 mmol) was taken and stirred for 5 min with a mixture of Fmoc-aminocarboxylic acid (5eq), HCTU (5eq), and DIEA (10eq). The resin was filtered, and washed with DMF thoroughly. Then the resin was treated with 4-methyl piperidine (9 mL, 20% in DMF) for 5 min to remove Fmoc protecting group. Then the resin was washed with DMF thoroughly and washed with DCM and MeOH. The product was cleaved from the resin by 3-hr treatement with a mixture of TFA:TIPS:$H_2O$ (95:2.5:2.5) and was purified by RP-HPLC. LC-MS profile (solvent A (0.5% formic acid in $H_2O$), solvent B (0.5% formic acid in 90% acetonitrile), solvent B' (0.1% trifluoroacetic acid in a mixture of isopropanol/acetonitrile/water (60/30/10)) (condition 1: 2.1×50 mm XTerra MS C18, 125 Å, solvent A, solvent B, flow rate: 0.3 ml/min, gradient: 5% to 100% solvent B for 5 min, detection: 220 nm and 254 nm), condition 2: 2.1×50 mm Vydac 214MSC4, 300 Å, solvent, solvent B (0.5% formic acid in 90% acetonitrile), flow rate: 0.3 ml/min, gradient: 5% to 100% solvent B for 5 min, detection: 220 nm and 254 nm).

[Compound 1] (n=1) Prepared from Fmoc-glycine as Fmoc-amino acid by General Method A ((S)-3-(4-(2-aminoacetamido)phenyl)-2-((S)-1-(phenylsulfonyl)pyrrolidine-2-carboxamido)propanoic acid); retention time (condition 1) 3.64 min, m/z=475 (MH+).

[Compound 2] (n=2) Prepared from Fmoc-beta-alanine by General Method A ((S)-3-(4-(3-aminopropanamido)phenyl)-2-((S)-1-(phenylsulfonyl)pyrrolidine-2-carboxamido) propanoic acid); retention time (condition 1) 3.79 min, m/z=489 (MH+).

[Compound 3] (n=3) Prepared from 4-Fmoc-amino butanoic acid by General Method A ((S)-3-(4-(4-aminobutanamido)phenyl)-2-((S)-1-(phenylsulfonyl)pyrrolidine-2-carboxamido)propanoic acid); retention time (condition 1) 3.68 min, m/z=503 (MH+).

[Compound 7] (n=4) Prepared from 5-Fmoc-amino pentanoic acid by General Method A ((S)-3-(4-(5-aminopentanamido)phenyl)-2-((S)-1-(phenylsulfonyl)pyrrolidine-2-carboxamido)propanoic acid); retention time (condition 1) 4.04 min, m/z=517 (MH+).

[Compound 9] (n=5) Prepared from 6-Fmoc-amino hexanoic acid by General Method A ((S)-3-(4-(6-aminohexanamido)phenyl)-2-((S)-1-(phenylsulfonyl)pyrrolidine-2-carboxamido)propanoic acid); retention time (condition 2) 3.65 min, m/z=531 (MH+)

[General Method B]

Fmoc-(p-NO2)-Phe-Wang resin (6 mmol) was treated with 4-methyl piperidine (25 mL, 20% in DMF) for 5 min to remove Fmoc protecting group. The deprotection step was repeated once and filtered, washed with DMF thoroughly. Then, a mixture of benzenesulfonylproline (3 eq)(1), HCTU (3 eq) and DIEA (6 eq) in DMF(25 mL) was added and stirred for 1 h at rt. Then the resin was filtered and washed with DMF thoroughly. To a suspension of resin (2.3 mmol) in DMF (40 mL) was added aqueous 2M $SnCl_2$ solution (20eq, 23 mL) and stirred at 80° C. for 5 h, then was kept stirring 16 h at rt. The mixture was filtered and washed with water, DMF, DCM, and iPrOH successively. Then a portion of resin (0.3 mmol) was taken and stirred for 5 min with a mixture of Fmoc-aminocarboxylic acid (5eq), HCTU (5eq), and DIEA (10eq). The resin was filtered, and washed with DMF thoroughly. Then the resin was treated with 4-methyl piperidine (9 mL, 20% in DMF) for 5 min to remove Fmoc protecting group. After washing with DMF, N,N-bis-Boc-guanylpyrazole (2eq) and DIPEA (5eq) was added and agitated overnight. Then the resin was washed with DMF thoroughly and washed with DCM and MeOH. The product was cleaved from the resin by 3-hr treatement with a mixture of TFA:TIPS:$H_2O$ (95:2.5:2.5) and was purified by RP-HPLC. LC-MS profile (solvent A (0.5% formic acid in $H_2O$), solvent B (0.5% formic acid in 90% acetonitrile), solvent B' (0.1% trifluoroacetic acid in a mixture of isopropanol/acetonitrile/water (60/30/10)) (condition 1: 2.1×50 mm XTerra MS C18, 125 Å, solvent A, solvent B, flow rate: 0.3 ml/min, gradient: 5% to 100% solvent B for 5 min, detection: 220 nm and 254 nm), condition 2: 2.1×50 mm Vydac 214MSC4, 300 Å, solvent, solvent B (0.5% formic acid in 90% acetonitrile), flow rate: 0.3 ml/min, gradient: 5% to 100% solvent B for 5 min, detection: 220 nm and 254 nm).

[Compound 4] (n=1) Prepared from Fmoc-glycine as Fmoc-amino acid by General Method B ((S)-3-(4-(2-guanidinoacetamido)phenyl)-2-((S)-1-(phenylsulfonyl)pyrrolidine-2-carboxamido)propanoic acid); retention time (condition 1) 3.80 min, m/z=517.

[Compound 5] (n=2) Prepared from Fmoc-beta-alanine by General Method B ((S)-3-(4-(3-guanidinopropanamido)phenyl)-2-((S)-1-(phenylsulfonyl)pyrrolidine-2-carboxamido)propanoic acid); retention time (condition 1) 4.00 min, m/z=531 (MH+).

[Compound 6] (n=3) Prepared from 4-Fmoc-amino butanoic acid ((S)-3-(4-(4-aminobutanamido)phenyl)-2-((S)-1-(phenylsulfonyl)pyrrolidine-2-carboxamido)propanoic acid); retention time (condition 1) 3.68 min, m/z=503 (MH+).

[Compound 8] (n=4) Prepared from 5-Fmoc-amino pentanoic acid by General Method B ((S)-3-(4-(5-guanidinopentanamido)phenyl)-2-((S)-1-(phenylsulfonyl)pyrrolidine-2-carboxamido)propanoic acid); retention time (condition 1) 4.09 min, m/z=559 (MH+).

[Compound 10] (n=5) Prepared from 6-Fmoc-amino hexanoic acid by General Method B ((S)-3-(4-(6-guanidinohexanamido)phenyl)-2-((S)-1-(phenylsulfonyl)pyrrolidine-2-carboxamido)propanoic acid); retention time (condition 2) 3.77 min, m/z=573 (MH+).

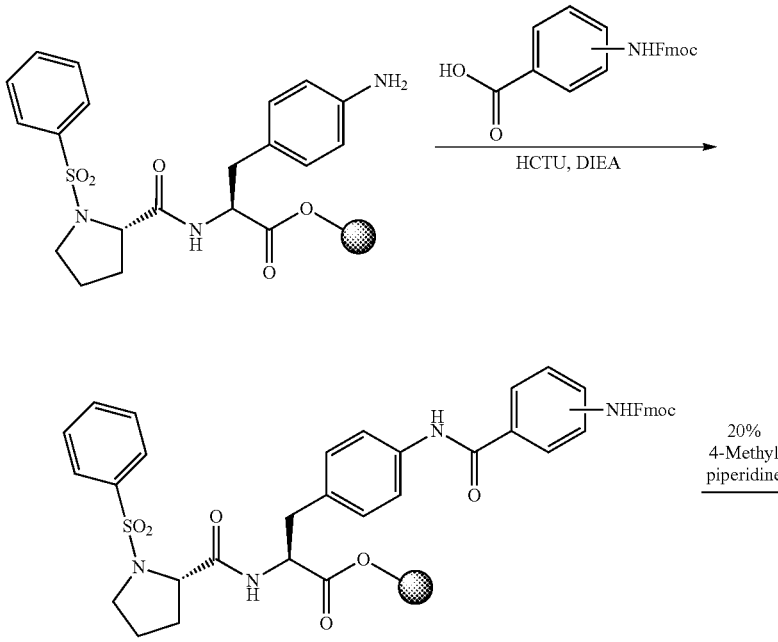

-continued

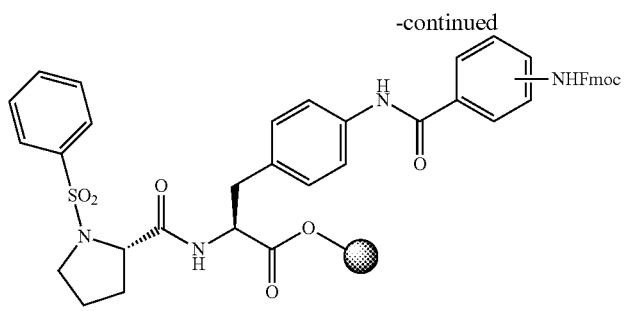
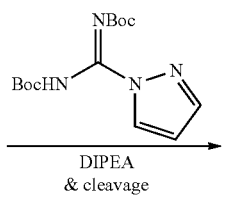

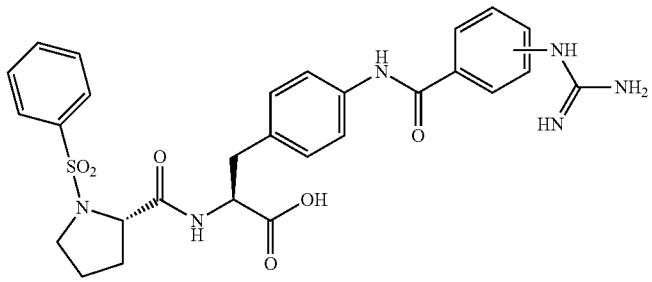

[General Method C]

(Benzenesulfonyl)Pro-(4-amino)Phe-Wang resin (0.25 mmol) agitated for 5 min with a mixture of Fmoc-aminobenzoic acid (5eq), HCTU (5eq), and DIEA (10eq) at 75° C. The resin was filtered, and washed with DMF thoroughly. Then the resin was treated with 4-methyl piperidine (9 mL, 20% in DMF) for 5 min to remove Fmoc protecting group. After washing with DMF, N,N-bis-Boc-guanylpyrazole (2eq) and DIPEA (5eq) was added and agitated overnight. Then the resin was washed with DMF thoroughly and washed with DCM and MeOH. The product was cleaved from the resin by 3-hr treatement with a mixture of TFA:TIPS:H₂O (95:2.5:2.5) and was purified by RP-HPLC. HPLC profile (condition 4: 19×100 mm Atlantis T3 OBD, solvent A, solvent B', flow rate: 15 ml/min, gradient: 5% to 100% solvent B' for 37 min, detection: 254 nm), (condition 5: 19×100 mm Atlantis T3 OBD, solvent A, solvent B', flow rate: 15 ml/min, gradient: 5% to 100% solvent B' for 35 min, detection: 254 nm).

[Compound No. 200] Prepared from 4-Fmoc-amino benzoic acid by general method C ((S)-3-(4-(4-guanidinobenzamido)phenyl)-2-((S)-1-(phenylsulfonyl)pyrrolidine-2-carboxamido)propanoic acid) retention time (condition 4) 14.68 min, m/z=579 (MH+).

[Compound No. 201] Prepared from 3-Fmoc-amino benzoic acid by general method C ((S)-3-(4-(3-guanidinobenzamido)phenyl)-2-((S)-1-(phenylsulfonyl)pyrrolidine-2-carboxamido)propanoic acid) retention time (condition 4) 15.95 min, m/z=579 (MH+).

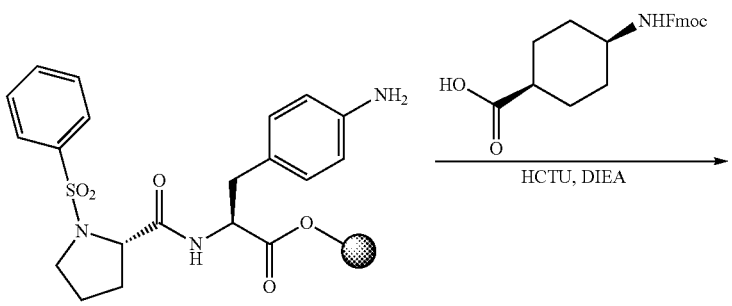

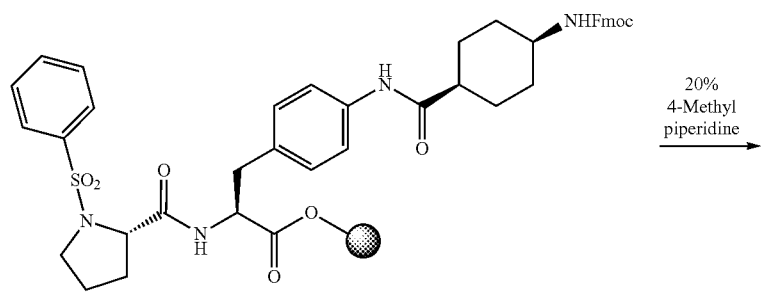

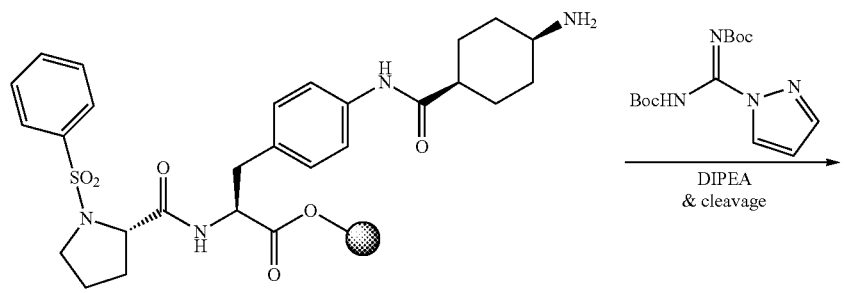

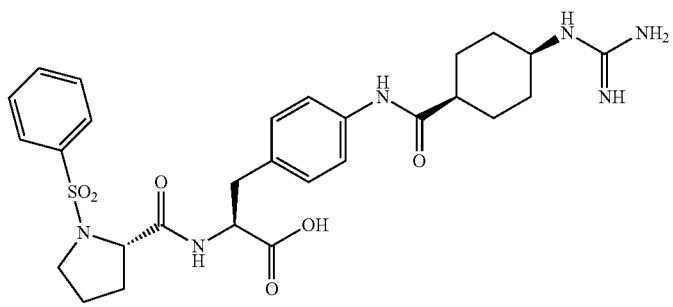

[Compound No. 203] (Benzenesulfonyl)Pro-(4-amino) Phe-Wang resin (0.25 mmol) agitated for 5 min with a mixture of 4-Fmoc-amino cis-cyclohexane carboxylic acid (5eq), HCTU (5eq), and DIEA (10eq) at 75° C. The resin was filtered, and washed with DMF thoroughly. Then the resin was treated with 4-methyl piperidine (9 mL, 20% in DMF) for 5 min to remove Fmoc protecting group. After washing with DMF, N,N-bis-Boc-guanylpyrazole (2eq) and DIPEA (5eq) was added and agitated overnight. Then the resin was washed with DMF thoroughly and washed with DCM and MeOH. The product was cleaved from the resin by 3-hr treatement with a mixture of TFA:TIPS:H$_2$O (95:2.5:2.5) and was purified by RP-HPLC. ((S)-3-(4-((1s,4R)-4-guanidinocyclohexane-1-carboxamido)phenyl)-2-((S)-1-(phenylsulfonyl)pyrrolidine-2-carboxamido)propanoic acid) retention time (condition 5) 11.8 min, m/z=586 (MH+).

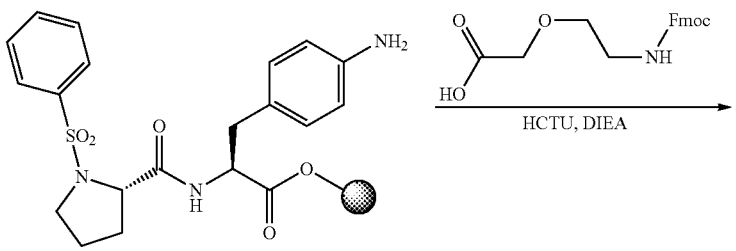

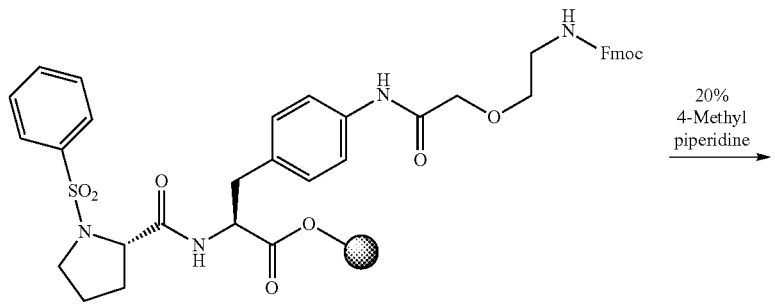

-continued

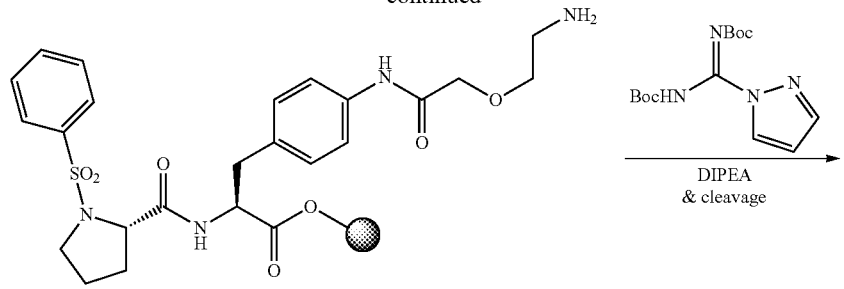

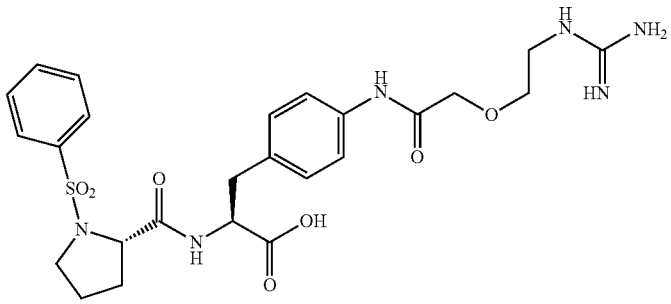

[Compound No. 204] (Benzenesulfonyl)Pro-(4-amino) Phe-Wang resin (0.25 mmol) agitated for 5 min with a mixture of 2-Fmoc-amino ethoxy acetic acid (5eq), HCTU (5eq), and DIEA (10eq) at 75° C. The resin was filtered, and washed with DMF thoroughly. Then the resin was treated with 4-methyl piperidine (9 mL, 20% in DMF) for 5 min to remove Fmoc protecting group. After washing with DMF, N,N-bis-Boc-guanylpyrazole (2eq) and DIPEA (5eq) was added and agitated overnight. Then the resin was washed with DMF thoroughly and washed with DCM and MeOH. The product was cleaved from the resin by 3-hr treateent with a mixture of TFA:TIPS:$H_2O$ (95:2.5:2.5) and was purified by RP-HPLC. ((S)-3-(4-(2-(2-guanidinoethoxy)ac- etamido)phenyl)-2-((S)-1-(phenylsulfonyl)pyrrolidine-2-carboxamido)propanoic acid) retention time (condition 5) 14.54 min, m/z=562.0 (MH+).

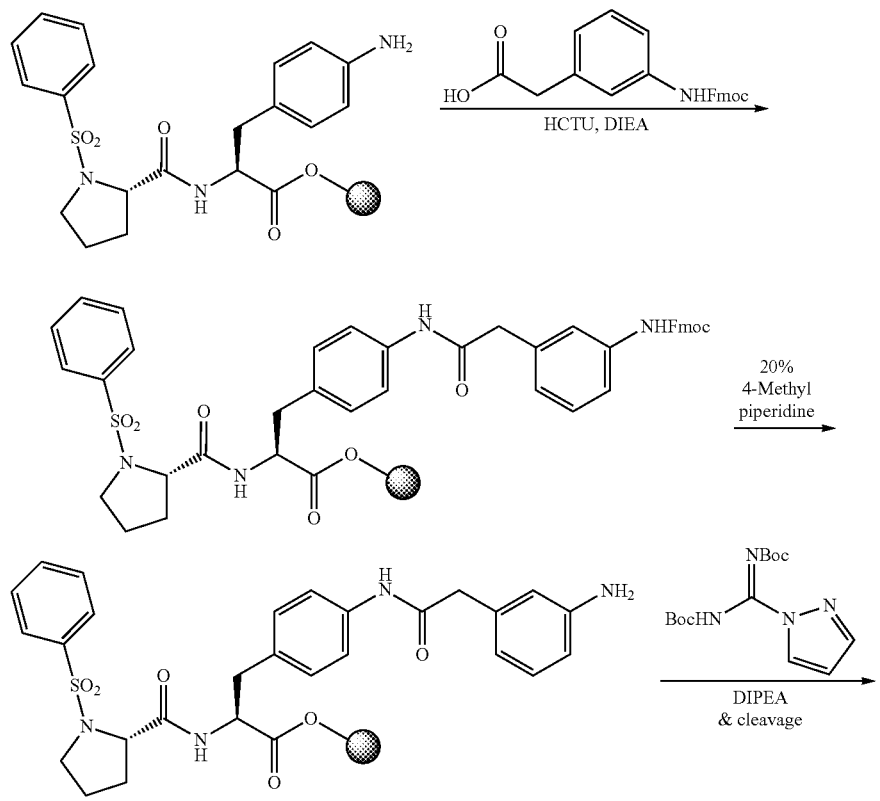

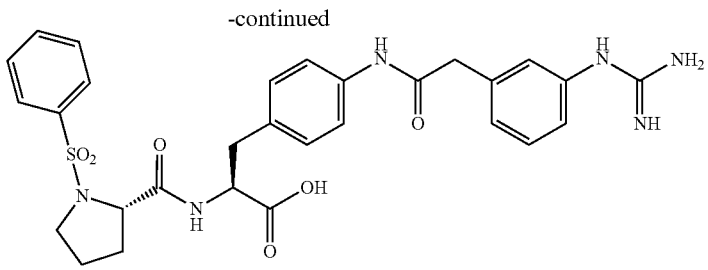

[Compound No. 205] (Benzenesulfonyl)Pro-(4-amino) Phe-Wang resin (0.25 mmol) agitated for 5 min with a mixture of 3-Fmoc-amino phenyl acetic acid (5eq), HCTU (5eq), and DIEA (10eq) at 75° C. The resin was filtered, and washed with DMF thoroughly. Then the resin was treated with 4-methyl piperidine (9 mL, 20% in DMF) for 5 min to remove Fmoc protecting group. After washing with DMF, N,N-bis-Boc-guanylpyrazole (2eq) and DIPEA (5eq) was added and agitated overnight. Then the resin was washed with DMF thoroughly and washed with DCM and MeOH. The product was cleaved from the resin by 3-hr treatement with a mixture of TFA:TIPS:$H_2O$ (95:2.5:2.5) and was purified by RP-HPLC. ((S)-3-(4-(2-(3-guanidinophenyl)acetamido)phenyl)-2-((S)-1-(phenylsulfonyl)pyrrolidine-2-carboxamido)propanoic acid) retention time (condition 5) 15.9 min, m/z=593 (MH+).

(5-((4,5-dihydro-1H-imidazol-2-yl)amino)pentanamido) phenyl)-2-((S)-1-(phenylsulfonyl)pyrrolidine-2-carboxamido)propanoic acid) retention time (condition 2) 3.77 min, m/z=585.9 (MH+)

[Compound No. 87] (n=3) Prepared by general method D 2-methylthio imidazoline hydriodide (m=1) ((S)-3-(4-(4-((4,5-dihydro-1H-imidazol-2-yl)amino)butanamido)phenyl)-2-((S)-1-(phenylsulfonyl)pyrrolidine-2-carboxamido)propanoic acid) retention time (condition 6) retention time (condition 6) 21.5 min, m/z=639.9 (MH+)

[Compound No. 60] (n=4) Prepared by general method D using 1,4,5,6-tetrahydro-2-(methylthio)-pyrimidine hydriodide (m=2) (5 eq) and DIPEA (15 eq) HPLC (condition: 19×100 mm Atlantis T3 OBD, solvent A, solvent B', flow rate: 13 ml/min, gradient: 8% solvent B' for 5 min, 8% to 18% solvent B' for 1 min, 18% to 24% solvent B' for 24 min, detection: 254 nm) retention time 18.57 min, m/z=598 (MH+)

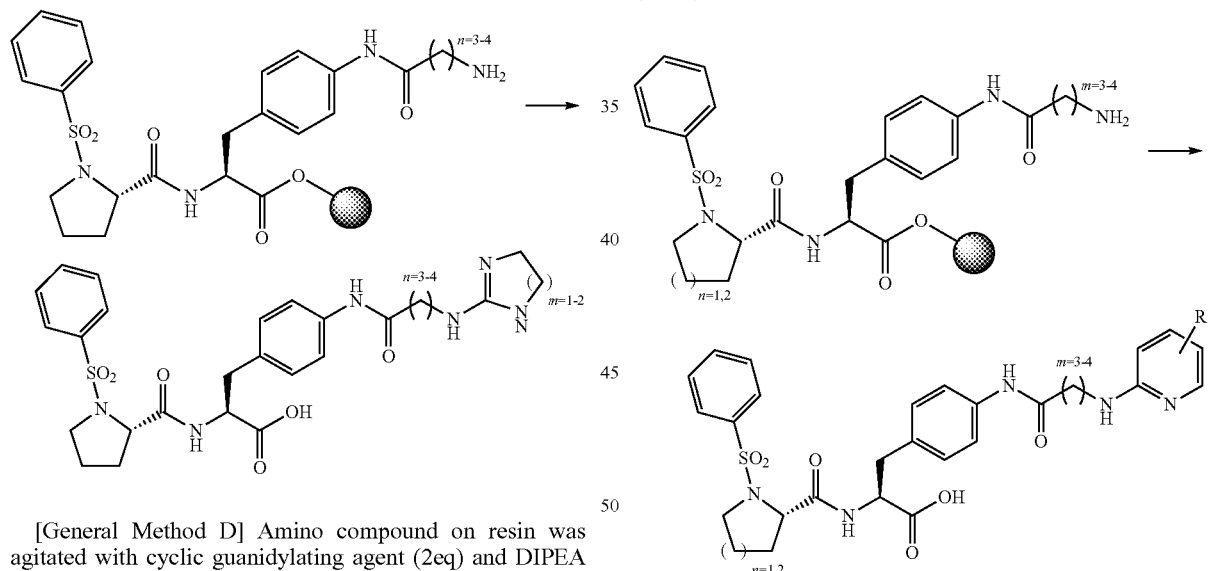

[General Method D] Amino compound on resin was agitated with cyclic guanidylating agent (2eq) and DIPEA (3eq) at 75° C. for 20 min. The resin was washed with DMF, DCM and MeOH. The product was cleaved from the resin by 3-hr treatement with a mixture of TFA:TIPS:$H_2O$ (95: 2.5:2.5) and was purified by RP-HPLC. HPLC profile (solvent A (0.5% formic acid in $H_2O$), solvent B (0.5% formic acid in 90% acetonitrile), solvent B' (0.1% trifluoroacetic acid in a mixture of isopropanol/acetonitrile/water (60/30/10)) (condition 2: 2.1×50 mm Vydac 214MSC4, 300 Å, solvent A, solvent B, flow rate: 0.3 ml/min, gradient: 5% to 100% solvent B for 5 min, detection: 220 nm and 254 nm) (condition 6: 19×100 mm Atlantis T3 OBD, solvent A, solvent B', flow rate: 10 ml/min, gradient: 5% to 70% solvent B' for 43 min, detection: 254 nm)

[Compound No. 11] (n=4) Prepared by general method D using 2-methylthio imidazoline hydriodide (m=1) ((S)-3-(4-

[General Method E] Amino compound on resin was agitated with a premixed solution of pyridine N-oxide (1eq), PyBroP (1.3eq), DIPEA (3.75 eq) in DCM at rt for 1 h. The resin was washed with DMF, DCM and MeOH. The product was cleaved from the resin by 3-hr treatement with a mixture of TFA:TIPS:$H_2O$ (95:2.5:2.5) and was purified by RP-HPLC. HPLC profile (solvent A (0.5% formic acid in $H_2O$), solvent B (0.5% formic acid in 90% acetonitrile), solvent B' (0.1% trifluoroacetic acid in a mixture of isopropanol/acetonitrile/water (60/30/10) (condition 6: 19×100 mm Atlantis T3 OBD, solvent A, solvent B', flow rate: 10 ml/min, gradient: 5% to 70% solvent B' for 43 min, detection: 254 nm) (condition 7: 19×100 mm Atlantis T3 OBD, solvent A, solvent B', flow rate: 10 ml/min, gradient: 5% to 60% solvent B' for 30 min, detection: 254 nm))

[Compound No. 212] (n=2, m=3) Prepared from pyridine N-oxide by general method E. retention time (condition: 19×100 mm Altantis T3 OBD, solvent A, solvent B', flow rate: 15 ml/min, gradient: 8% solvent B' for 5 min, 8% to 18% solvent B' for 1 min, 18% to 24% solvent B' for 24 min, detection: 254 nm) 23.91 min, m/z=594.8 (MH+)

[Compound No. 206] (n=1, m=3) Prepared from 3-methyl pyridine N-oxide by general method E. ((S)-3-(4-(4-((5-methylpyridin-2-yl)amino)butanamido)phenyl)-2-((S)-1-(phenylsulfonyl)pyrrolidine-2-carboxamido)propanoic acid) retention time (condition 7) 23.6 min, m/z=595.0 (MH+)

[Compound No. 207] (n=1, m=3) Prepared from 2-methyl pyridine N-oxide by general method E. ((S)-3-(4-(4-((6-methylpyridin-2-yl)amino)butanamido)phenyl)-2-((S)-1-(phenylsulfonyl)pyrrolidine-2-carboxamido)propanoic acid, retention time (condition 6) 26.2 min, m/z=594.9 (MH+)

[Compound No. 210] (n=1, m=3) Prepared from 3,5-dimethyl pyridine N-oxide by general method E. (S)-3-(4-(4-((3,5-dimethylpyridin-2-yl)amino)butanamido)phenyl)-2-((S)-1-(phenylsulfonyl)pyrrolidine-2-carboxamido) propanoic acid, retention time (condition 6) 27.3 min, m/z=608.8 (MH+)

[Compound No. 61] (n=1, m=4) Prepared from pyridine N-oxide by general method E. HPLC (condition1: 19×100 mm Altantis T3 OBD, solvent A, solvent B', flow rate: 13 ml/min, gradient: 8% solvent B' for 5 min, 8% to 20% solvent B' for 1 min, 20% to 26% solvent B' for 24 min, detection: 254 nm) 15.52 min, m/z=593 (MH+).

[Compound No. 83] (n=1, m=3) Prepared from pyridine N-oxide by general method E. HPLC (condition: 19×100 mm Altantis T3 OBD, solvent A, solvent B', flow rate: 15 ml/min, gradient: 8% solvent B' for 3 min, 8% to 15% solvent B' for 1 min, 15% to 24% solvent B' for 30 min, detection: 254 nm) retention time 19.17 min, m/z=580 (MH+)

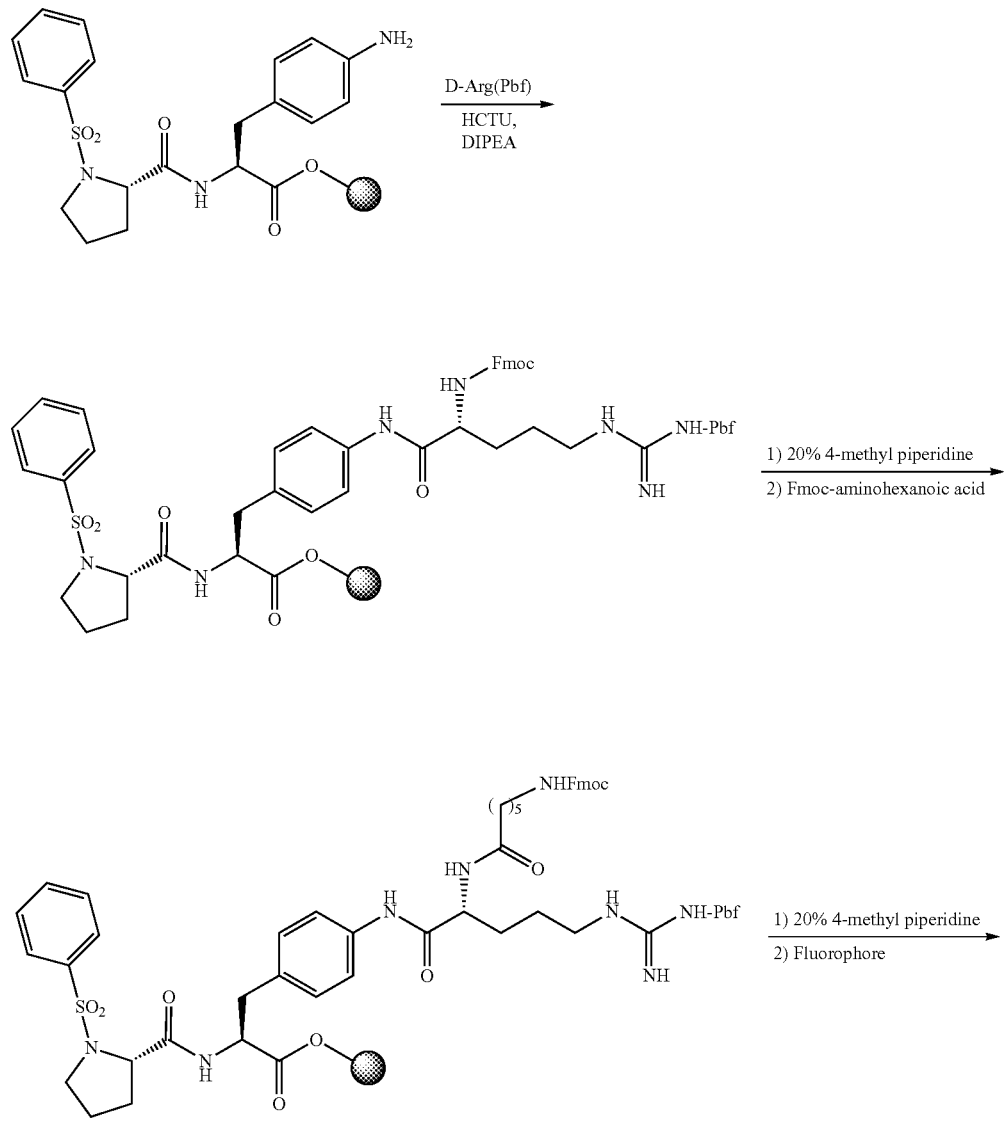

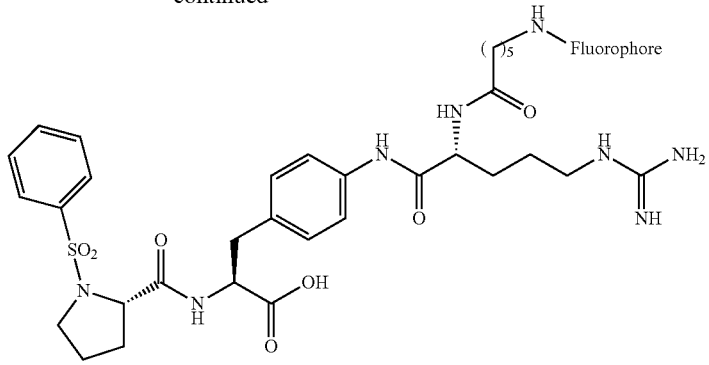

[General Method F]

Amino compound on resin was agitated for 5 min with a mixture of Fmoc-D-Arg (Pbf) (5eq), HCTU (5eq), and DIEA (10eq) at 75° C. The resin was filtered, and washed with DMF thoroughly. Then the resin was treated with 4-methyl piperidine (9 mL, 20% in DMF) for 5 min to remove Fmoc protecting group. After washing with DMF, Fmoc-amino hexanoic acid linker (5eq), HCTU (5eq), and DIEA (10eq) were added and agitated for 5 min at 75° C. Then the resin was washed with DMF thoroughly. Final Fmoc deprotection was performed with 4-methyl piperidine (9 mL, 20% in DMF) for 5 min. After washing with DMF, fluorophore (1.5eq) and DIPEA (3eq) was added at rt and stirred for 1 h. The resin was washed with DMF, DCM and MeOH, successively. The product was cleaved from the resin by 3-hr treatement with a mixture of TFA:TIPS:H$_2$O (95:2.5:2.5) and was purified by RP-HPLC. HPLC condition (solvent A (0.5% formic acid in H$_2$O), solvent B (0.5% formic acid in 90% acetonitrile), solvent B' (0.1% trifluoroacetic acid in a mixture of isopropanol/acetonitrile/water (60/30/10) (condition 3: 19×100 mm Atlantis T3 OBD, solvent A, solvent B', flow rate: 15 ml/min, gradient: 5% to 100% solvent B for 17 min, detection: 254 nm) (condition 6: 19×100 mm Atlantis T3 OBD, solvent A, solvent B', flow rate: 10 ml/min, gradient: 5% to 70% solvent B' for 43 min, detection: 254 nm) (condition 7: 19×100 mm Atlantis T3 OBD, solvent A, solvent B', flow rate: 10 ml/min, gradient: 5% to 60% solvent B' for 30 min, detection: 254 nm)

[Compound No. 198] Prepared by general method F with FITC. Retention time (condition 6) 32.94 min, m/z=1077.2 (MH+)

[Compound No. 199] Prepared by general method F with TMRITC. Retention time (condition 7) 25.6 min, m/z=1131.4 (MH+)

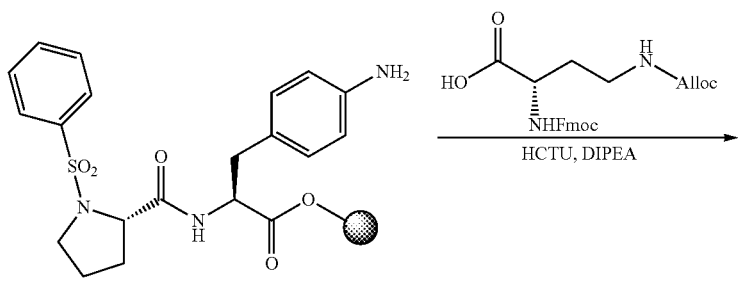

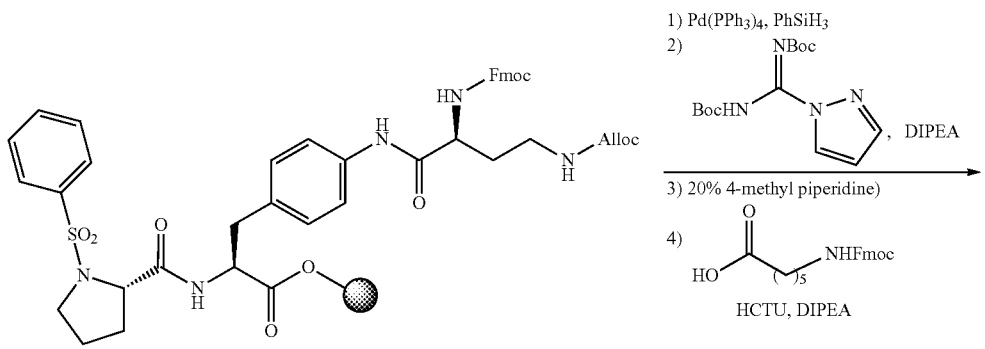

-continued

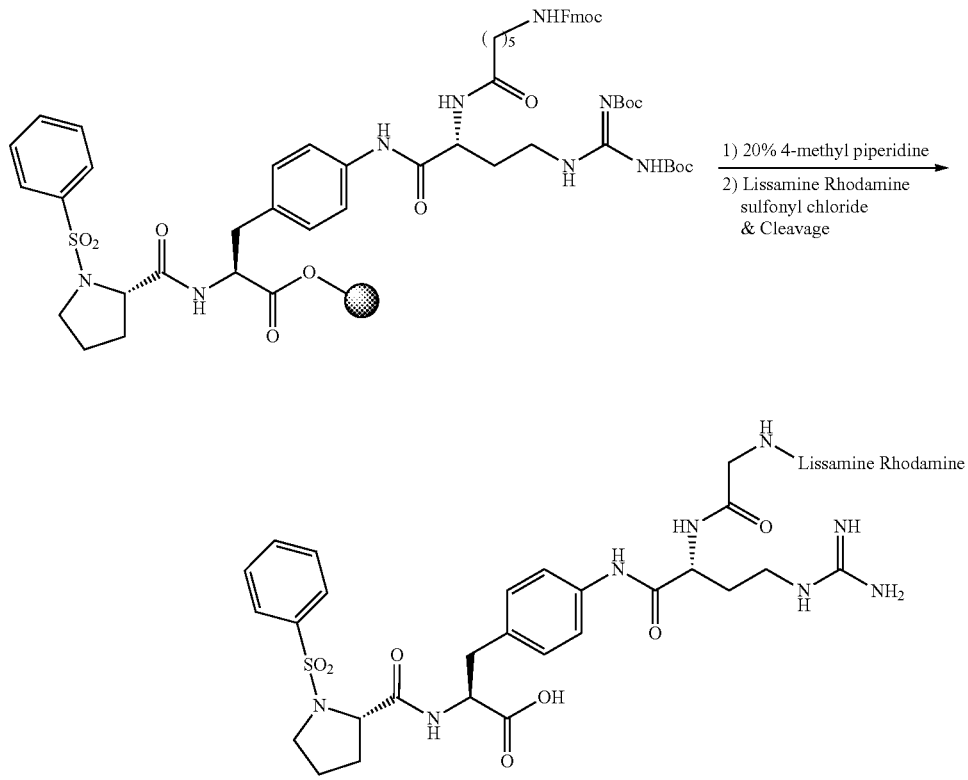

[Compound No. 196] Amino compound on resin was agitated for 5 min with a mixture of Nα-Fmoc-γ-N-Alloc diaminobutanoic acid (5eq), HCTU (5eq), and DIEA (10eq) at 75° C. The resin was filtered, and washed with DMF thoroughly. Then the resin was washed with DCM under $N_2$ and $PhSiH_3$ (24eq) in DCM followed by $Pd(PPh_3)_4$ in DCM were added and agitate for 10 min to remove Alloc protecting group. Deprotection step was once repeated and washed with DCM and DMF. Then N,N-bis-Boc guanyl pyrazole (5eq) and DIPEA (10eq) were added to the resin and agitated for overnight. The resin was washed with DMF and treated with 4-methyl piperidine (9 mL, 20% in DMF) for 5 min to remove Fmoc protecting group. After washing with DMF, 6-Fmoc amino hexanoic acid (5eq), HCTU (5eq), and DIEA (10eq) were added and agitated for 5 min at 75° C. Then the resin was washed with DMF thoroughly. Final Fmoc deprotection was performed with 4-methyl piperidine (9 mL, 20% in DMF) for 5 min. After washing with DMF, Lissamine rhodamine sulfonyl chloride (1.5eq) and DIPEA (3eq) was added at rt and stirred for 1 h. The resin was washed with DMF, DCM and MeOH, successively. The product was cleaved from the resin by 3-hr treatement with a mixture of TFA:TIPS:$H_2O$ (95:2.5:2.5) and was purified by RP-HPLC. HPLC condition (solvent A (0.5% formic acid in $H_2O$), solvent B (0.5% formic acid in 90% acetonitrile), solvent B' (0.1% trifluoroacetic acid in a mixture of isopropanol/acetonitrile/water (60/30/10) (condition 3: 19×100 mm Atlantis T3 OBD, solvent A, solvent B', flow rate: 15 ml/min, gradient: 5% to 100% solvent B for 17 min, detection: 254 nm) Retention time (condition 3) 14.68 min, m/z=1214.5

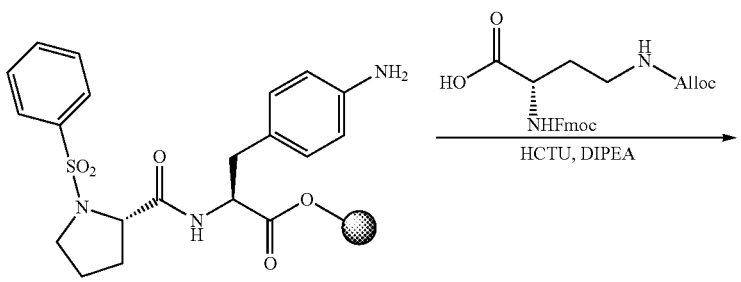

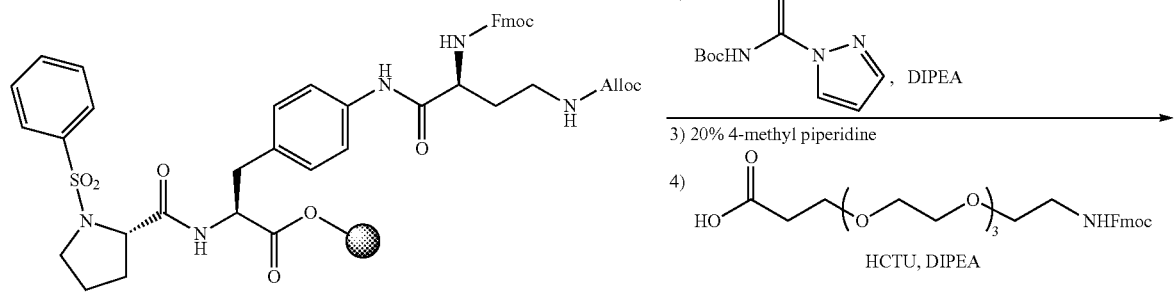

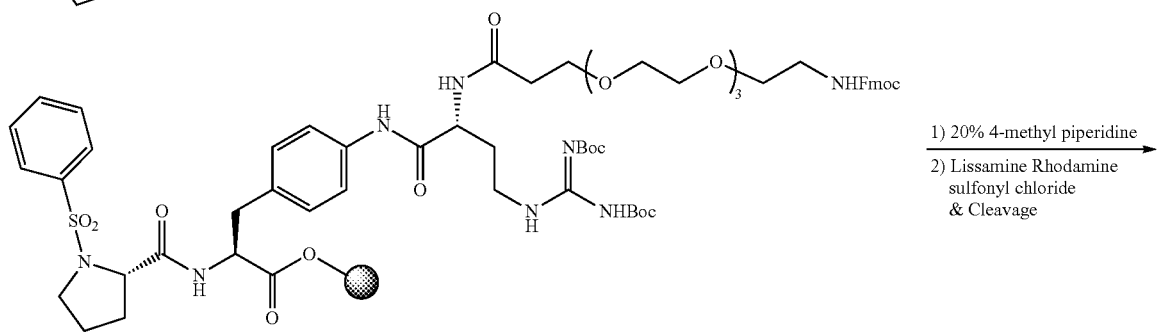

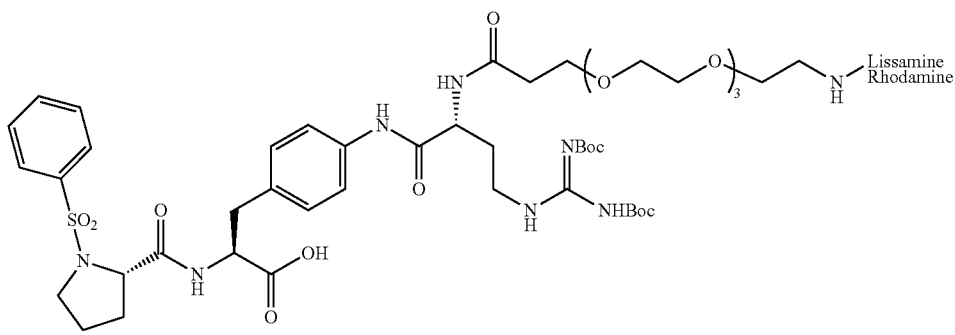

[Compound No. 197] Amino compound on resin was agitated for 5 min with a mixture of Nα-Fmoc-γ-N-Alloc diaminobutanoic acid (5eq), HCTU (5eq), and DIEA (10eq) at 75° C. The resin was filtered, and washed with DMF thoroughly. Then the resin was washed with DCM under N2 and PhSiH$_3$ (24eq) in DCM followed by Pd(PPh$_3$)$_4$ in DCM were added and agitate for 10 min to remove Alloc protecting group. Deprotection step was once repeated and washed with DCM and DMF. Then N,N-bis-Boc guanyl pyrazole (5eq) and DIPEA (10eq) were added to the resin and agitated for overnight. The resin was washed with DMF and treated with 4-methyl piperidine (9 mL, 20% in DMF) for 5 min to remove Fmoc protecting group. After washing with DMF, Fmoc amino-(PEG)$_3$-carboxylic acid (5eq), HCTU (5eq), and DIEA (10eq) were added and agitated for 5 min at 75° C. Then the resin was washed with DMF thoroughly. Final Fmoc deprotection was performed with 4-methyl piperidine (9 mL, 20% in DMF) for 5 min. After washing with DMF, Lissamine rhodamine sulfonyl chloride (1.5eq) and DIPEA (3eq) was added at rt and stirred for 1 h. The resin was washed with DMF, DCM and MeOH, successively. The product was cleaved from the resin by 3-hr treatement with a mixture of TFA:TIPS:H$_2$O (95:2.5:2.5) and was purified by RP-HPLC. Retention time (condition 3) 14.2 min, m/z=1304.5

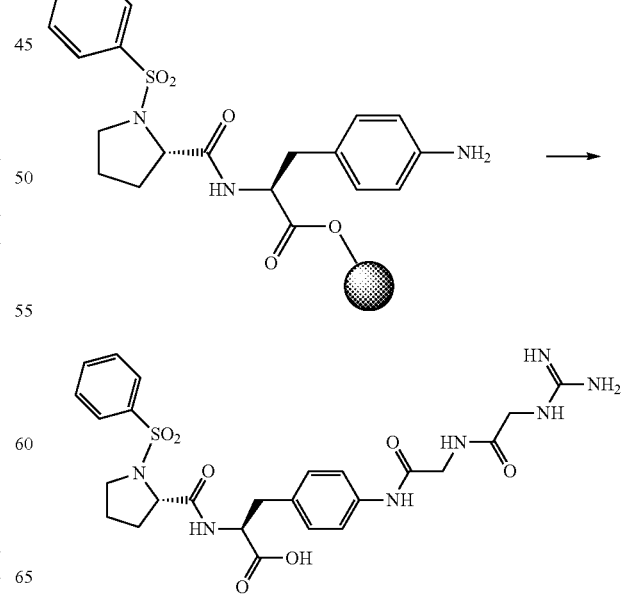

[Compound No. 202] Amino compound on resin was agitated for 5 min with a mixture of Fmoc-Gly (5eq), HCTU (5eq), and DIEA (10eq) at 75° C. The resin was filtered, and washed with DMF thoroughly. Then the resin was treated with 4-methyl piperidine (9 mL, 20% in DMF) for 5 min to remove Fmoc protecting group. This process was repeated once and after washing with DMF, N,N-bis-Boc-guanylpyrazole (2eq) and DIPEA (5eq) was added and agitated overnight. Then the resin was washed with DMF thoroughly and washed with DCM and MeOH. The product was cleaved from the resin by 3-hr treatement with a mixture of TFA:TIPS:H$_2$O (95:2.5:2.5) and was purified by RP-HPLC. HPLC profile (condition 4: 19×100 mm Atlantis T3 OBD, solvent A, solvent B', flow rate: 15 ml/min, gradient: 5% to 100% solvent B' for 37 min, detection: 254 nm), retention time 13.8 min, m/z=575.0 (MH+)

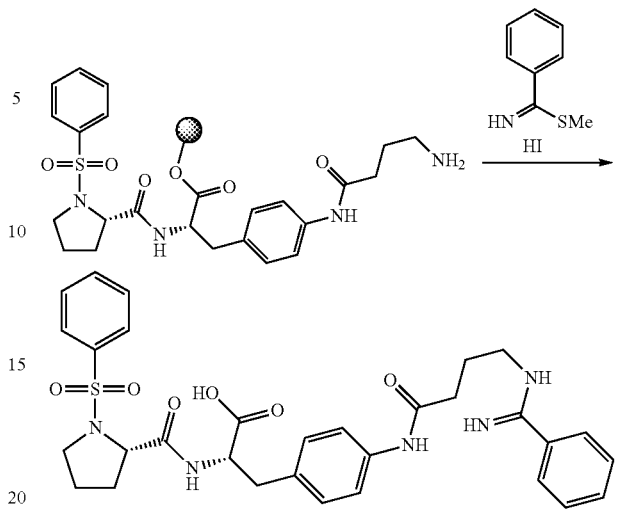

[Compound No. 211] Amino compound on resin was agitated for 1.5 h with a mixture of phenyliminothioester (5eq), DIEA (15eq) at 75° C. The resin was filtered, and washed with DMF thoroughly. Then the resin was washed with DCM and MeOH. The product was cleaved from the resin by 3-hr treatement with a mixture of TFA:TIPS:H$_2$O (95:2.5:2.5) and was purified by RP-HPLC. HPLC profile (condition 6: 19×100 mm Atlantis T3 OBD, solvent A, solvent B', flow rate: 10 ml/min, gradient: 5% to 70% solvent B' for 43 min, detection: 254 nm), retention time 26.18 min, m/z=607 (MH+)

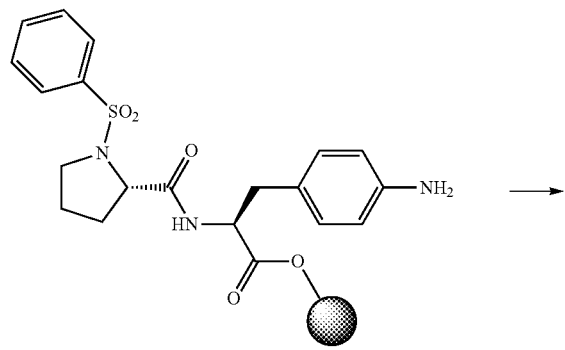

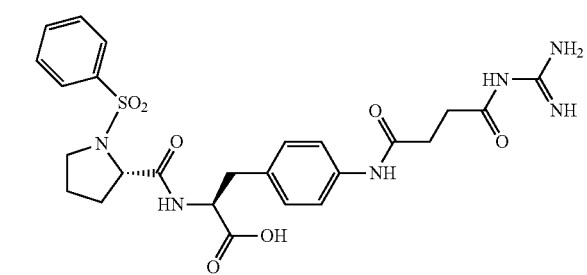

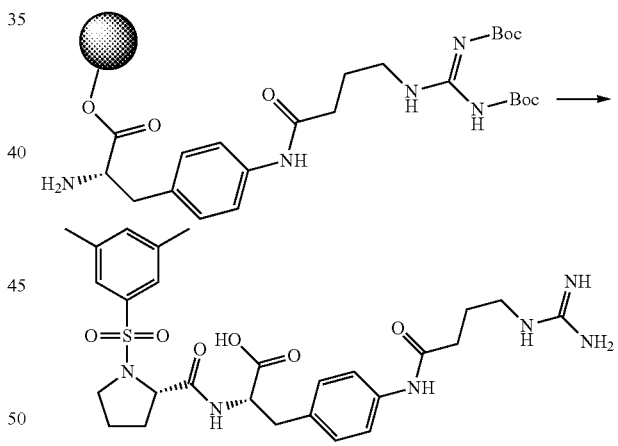

[Compound No. 93] Succinic anhydride (5 mmol) and N-Boc guanidine (1eq) was mixed in DCM in presence of DIPEA (2eq) and stirred for 1 h. The volatiles were removed under reduced pressure. Et$_2$O was added and the solidified monoacid was filtered and dried. Amino compound on resin was agitated for 5 min with a mixture of the monoacid (5eq), HCTU (5eq), and DIEA (10eq) at 75° C. The resin was filtered, and washed with DMF thoroughly. Then the resin was washed with DCM and MeOH. The product was cleaved from the resin by 3-hr treatement with a mixture of TFA:TIPS:H$_2$O (95:2.5:2.5) and was purified by RP-HPLC. HPLC profile (condition 8: 19×100 mm Atlantis T3 OBD, solvent A, solvent B', flow rate: 15 ml/min, gradient: 5% to 46% solvent B' for 30 min, detection: 254 nm), retention time 19.45 min, m/z=559.9 (MH+)

[Compound No. 214] Amino compound on resin was agitated for 5 min with a mixture of Fmoc-Pro (5eq), HCTU (5 eq), DIEA (10eq) at 75° C. The resin was filtered, and washed with DMF thoroughly. Then the resin was treated with 20% 4-methyl piperidine for 5 min and washed with DMF thoroughly. 3,5-dimethylbenzenesulfonyl chloride (2eq) and DIPEA (4 eq) in DMF was added and agitaed for 1 h at rt. The resin was washed with DMF, DCM, and MeOH successively. The product was cleaved from the resin by 3-hr treatement with a mixture of TFA:TIPS:H$_2$O (95:2.5:2.5) and was purified by RP-HPLC. HPLC profile (condition 7: 19×100 mm Atlantis T3 OBD, solvent A, solvent B', flow rate: 10 ml/min, gradient: 5% to 60% solvent B' for 30 min, detection: 254 nm), retention time 27.5 min, m/z=573.9 (MH+)

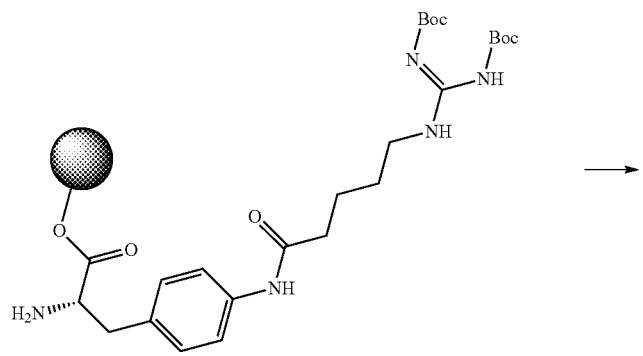

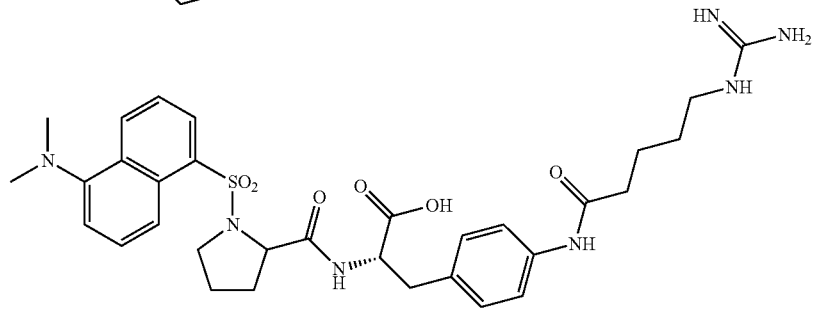

[Compound No. 215] Amino compound on resin was agitated for 5 min with a mixture of Fmoc-Pro (5eq), HCTU (5 eq), DIEA (10eq) at 75° C. The resin was filtered, and washed with DMF thoroughly. Then the resin was treated with 20% 4-methyl piperidine in DMF for 5 min and washed with DMF thoroughly. Dansyl chloride (2eq) and DIPEA (4 eq) in DMF was added and agitated for 1 h at rt. The resin was washed with DMF, DCM, and MeOH successively. The product was cleaved from the resin by 3-hr treatement with a mixture of TFA:TIPS:H$_2$O (95:2.5:2.5) and was purified by RP-HPLC. HPLC profile. HPLC profile (condition 7: 19×100 mm Atlantis T3 OBD, solvent A, solvent B', flow rate: 20 ml/min, gradient: 5% to 100% solvent B' for 15 min, detection: 254 nm), retention time 9.2 min, m/z=652.8 (MH+)

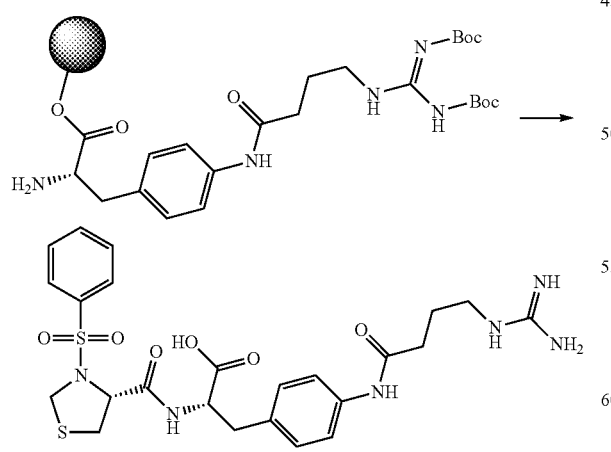

Amino compound on resin was agitated for 5 min with a mixture of Fmoc-Thz (5eq), HCTU (5 eq), DIEA (10eq) at 75° C. The resin was filtered, and washed with DMF thoroughly. Then the resin was treated with 20% 4-methyl piperidine for 5 min and washed with DMF thoroughly. Benzenesulfonyl chloride (2eq) and DIPEA (4 eq) in DMF was added and agitaed for 1 h at rt. The resin was washed with DMF, DCM, and MeOH successively. The product was cleaved from the resin by 3-hr treatement with a mixture of TFA:TIPS:H$_2$O (95:2.5:2.5) and was purified by RP-HPLC. HPLC profile (condition 7: 19×100 mm Atlantis T3 OBD, solvent A, solvent B', flow rate: 10 ml/min, gradient: 5% to 60% solvent B' for 30 min, detection: 254 nm) retention time 24.5 min, m/z=563.9 (MH+)

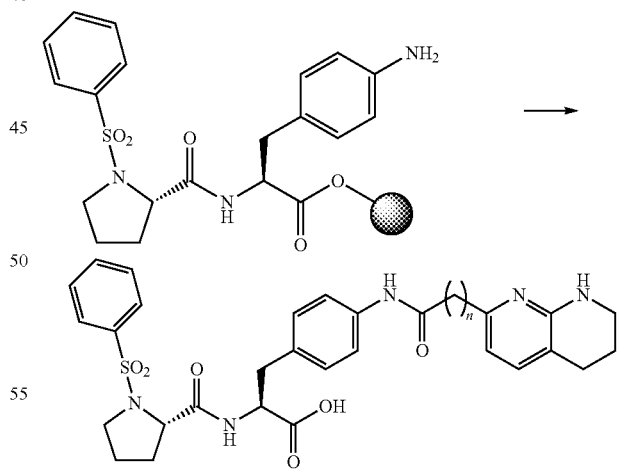

[General Method G]

Amino compound on resin was agitated for 3 h with a mixture of tetrahydronaphthypyridine acid (1.5eq), HCTU (1.5 eq), DIEA (3eq) at rt. The resin was filtered, and washed with DMF thoroughly. Then the resin was treated with 20% 4-methyl piperidine for 5 min and washed with DMF thoroughly. Benzenesulfonyl chloride (2eq) and DIPEA (4 eq) in DMF was added and agitaed for 1 h at rt. The resin was washed with DMF, DCM, and MeOH successively. The product was washed from the resin by 3-hr treatement with a mixture of TFA:TIPS:H$_2$O (95:2.5:2.5) and was purified by RP-HPLC.

[Compound No. 63] (n=3) prepared by general method G using tetrahydronaphthyridine acid. retention time (condition: 19×100 mm Altantis T3 OBD, solvent A, solvent B', flow rate: 15 ml/min, gradient: 8% solvent B' for 3 min, 8% to 18% solvent B' for 1 min, 18% to 24% solvent B' for 32 min, detection: 254 nm) 20.73 min, m/z=602 (MH+)

(n=4) prepared by general method G using tetrahydronaphthyridine acid. retention time (condition: 19×100 mm Altantis T3 OBD, solvent A, solvent B', flow rate: 15 ml/min, gradient: 8% solvent B' for 5 min, 8% to 18% solvent B' for 1 min, 18% to 22% solvent B' for 24 min, detection: 254 nm) 17.02 min, m/z=630.8 (MH+)

[Compound No. 209] (n=2) prepared by general method G using naphthyridine acid retention time 120 retention time (condition6: 19×100 mm Altantis T3 OBD, solvent A, solvent B', flow rate: 15 ml/min, gradient: 8% solvent B' for 5 min, 8% to 18% solvent B' for 1 min, 18% to 24% solvent B' for 24 min, detection: 254 nm) 18.12 min, m/z=607 (MH+)

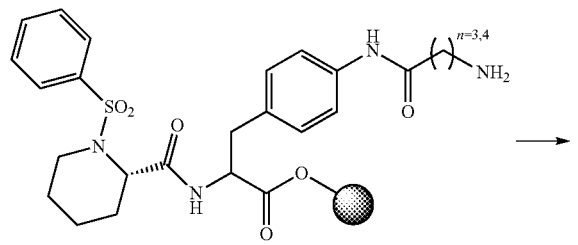

-continued

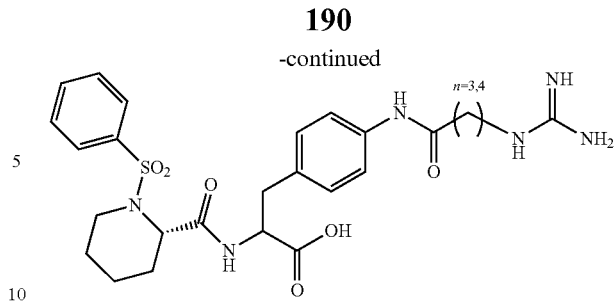

[General Method H]

Amino compound on resin was mixed with N,N-bis-Boc-guanylpyrazole (2eq) and DIPEA (5eq) was added and agitated overnight. Then the resin was washed with DMF thoroughly and washed with DCM and MeOH. The product was cleaved from the resin by 3-hr treatement with a mixture of TFA:TIPS:H$_2$O (95:2.5:2.5) and was purified by RP-HPLC.

[Compound No. 213] (n=3) Prepared by general method H. retention time (condition: 19×100 mm Altantis T3 OBD, solvent A, solvent B', flow rate: 15 ml/min, gradient: 8% solvent B' for 5 min, 8% to 18% solvent B' for 1 min, 18% to 24% solvent B' for 24 min, detection: 254 nm) 20.63 min, m/z=560 (MH+)

[Compound No. 212] (n=4) Prepared by general method H. retention time (condition: 19×100 mm Altantis T3 OBD, solvent A, solvent B', flow rate: 15 ml/min, gradient: 8% solvent B' for 5 min, 8% to 18% solvent B' for 1 min, 18% to 24% solvent B' for 24 min, detection: 254 nm) 22.08 min, m/z=573.9 (MH+)

Solution phase synthesis of compounds described herein.

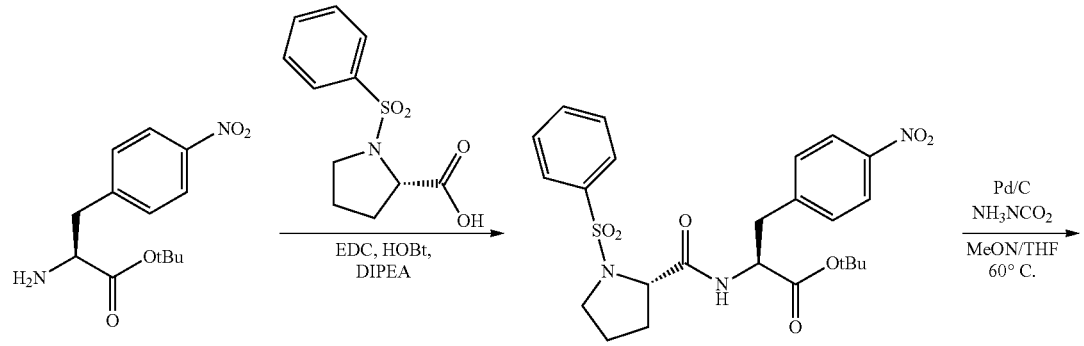

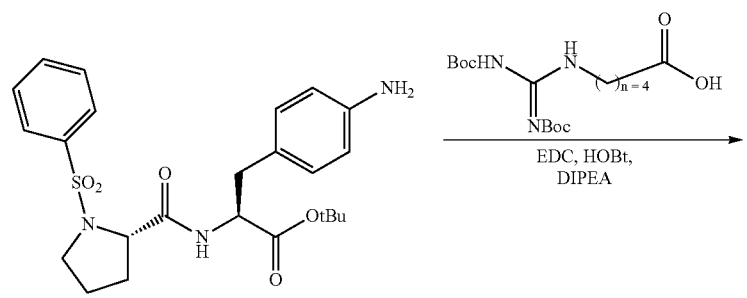

-continued

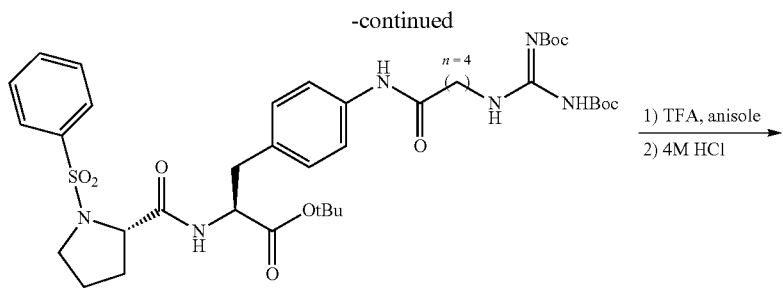

1) TFA, anisole
2) 4M HCl

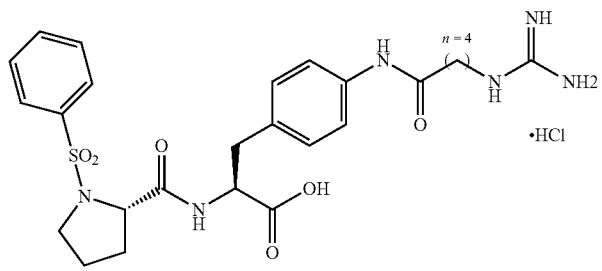

·HCl

Preparation of (PhSO₂)Pro-(pNO₂)Phe-OtBu: To benzenesulfonylproline (40 mmol) in anhydrous DCM (100 mL) was added DIPEA (1eq), HOBt (1eq), EDCI (1eq) at 0° C. and stirred 1 min. Then nitrophenylalanine t-butylester in DCM (300 mL) was added at the same temperature and warmed to rt and stirred overnight. The reaction mixture was washed with 1N HCl, 10% NaHCO3, brine successively. The volatiles were removed under reduced pressure and the crude product was used without further purification. 1H NMR (DMSO-d₆, 300 MHz) δ ppm 8.4 (1H, s), 8.25 (2H, br s), 7.81-7.57 (7H, m), 4.49 (1H, s), 4.09 (1H, s), 3.34-3.12 (5H, m), 1.58 (3H, br s), 1.38 (9H, s); LRMS (ESI+) 526.4 (MNa+).

Preparation of (PhSO₂)Pro-(pNH₂)Phe-OtBu: To a solution of nitrobenzene (27.8 mmol) in MeOH:THF (1:1 v/v, 300 mL) was added a slurry of Pd/C (0.1 eq based upon weight) in MeOH:H₂O (1:1, 10 mL) and ammonium formate (9 eq) at rt. The mixture was heated at 60° C. for 3 h and cooled to rt. The mixture was filtered through a pad of Celite and concentrated. The crude residue was dissolved in Ethyl acetate and washed with sat. NaHCO₃ solution, dried over Na₂SO₄ and concentrated under reduced pressure. The crude product was used without further purification. ¹H NMR (CDCl₃, 300 MHz) δ ppm 7.82 (1H, d, J=9.6 Hz), 7.62-7.53 (3H, m), 7.26-7.22 (1H, m), 6.92 (1H, d, J=10.7 Hz), 6.57 (1H, d, J=10.8 Hz), 4.65-4.54 (1H, m), 4.2-4.05 (1H, m), 3.7-3.3 (m, 2H), 3.2-3.0 (2H, m), 2.95-2.85 (1H, m), 2.05 (1H, br s), 1.6-1.3 (11H, br s); LRMS (ESI+) 496.2 (MNa+), 474.5 (MH+).

Preparation of (PhSO₂)Pro-(pNHCOCH₂CH₂CH₂CH₂NHNBocNHBoc)Phe-OtBu: To the Bis-Boc-protected aminopentanoic acid (11.2 mmol) in anhydrous DCM (80 mL) was added DIPEA (1eq), HOBt (1eq), EDCI (1eq) at 0° C. and then the amine 3 (1 eq) in DCM (20 mL) was added at the same temperature and warmed to rt and stirred overnight. The reaction mixture was washed with 1N HCl, 10% NaHCO₃, brine successively. The solvent was removed under reduced pressure and purified by silica gel column chromatography (DCM/MeOH 2% to 5%) to give off-white foam.

Preparation of compound 8: The Bis-Boc-protected compound 4 (8.3 mmol) was treated with 5% anisole in TFA (30 mL) for 3 h at rt. The volatiles were removed under reduced pressure and the crude product was washed with diethyl ether several times. The TFA-salt was replaced by Cl— using 4M HCl in dioxane and evaporation under reduced pressure (3 times). The final salt was passed through a short pad of silica and dried under reduced pressure. ¹H NMR (TFA salt) (300 MHz, DMSO-d₆) ppm δ 9.86 (s, 1H), 8.12 (d, J=7.8 Hz, 1H), 7.81 (d, J=6.9 Hz, 2H), 7.70 (d, J=7.2 Hz, 1H), 7.62-7.15 (m, 7H), 4.41 (s, 1H), 4.15 (s, 1H), 3.33 (s, 1H), 3.1-2.92 (m, 5H), 2.3 (s, 2H), 1.59-1.48 (m, 8H) LRMS: m/z=559 (MH+).

TABLE 5

IC₅₀ data of the compounds

| Cmpd No. | Compound Structure | IC₅₀ |
|---|---|---|
| 1 | 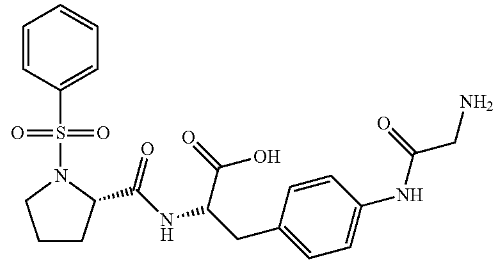 | C |

TABLE 5-continued
IC$_{50}$ data of the compounds
| Cmpd No. | Compound Structure | IC$_{50}$ |
|---|---|---|
| 2 | 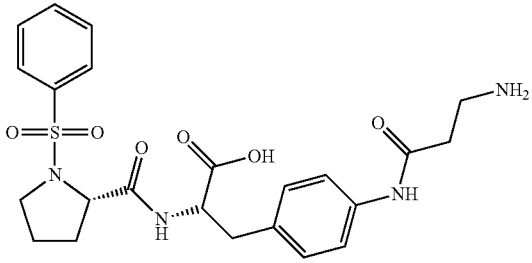 | B |
| 3 | 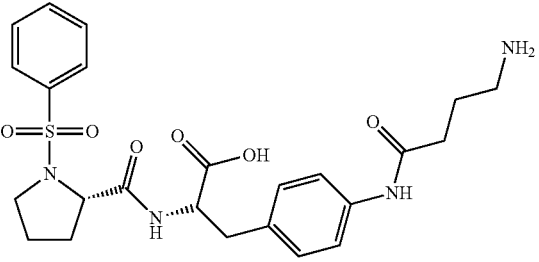 | B |
| 4 | 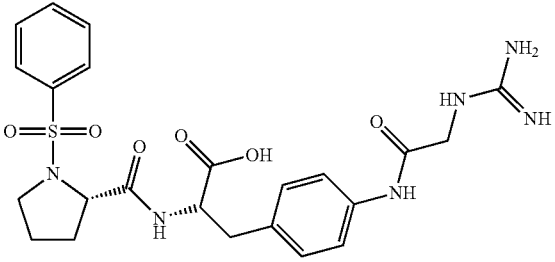 | B |
| 5 | 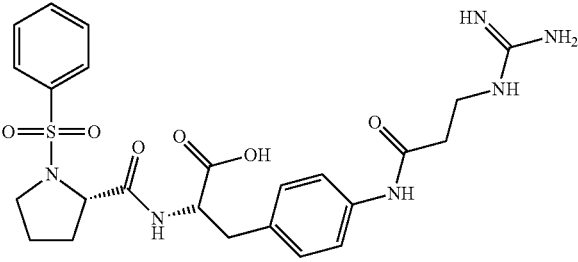 | A |
| 6 | 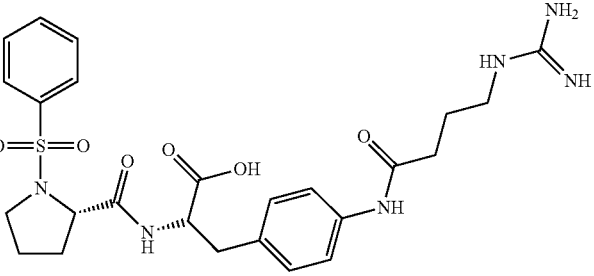 | A |

TABLE 5-continued

IC$_{50}$ data of the compounds

| Cmpd No. | Compound Structure | IC$_{50}$ |
|---|---|---|
| 7 | 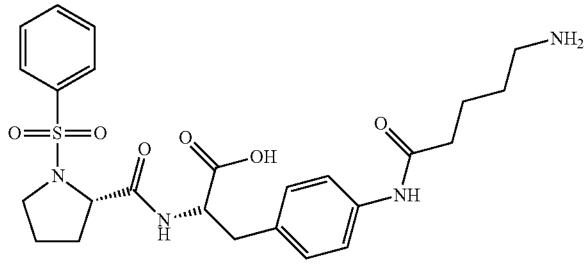 | C |
| 8 | 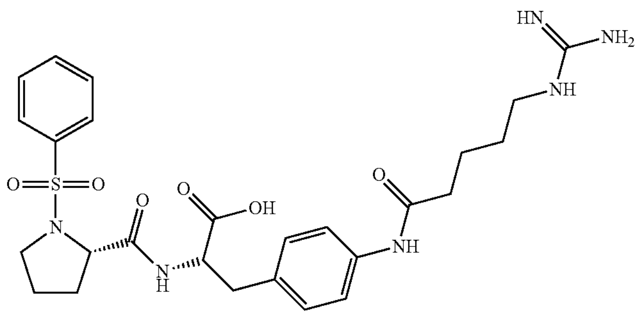 | A |
| 9 | 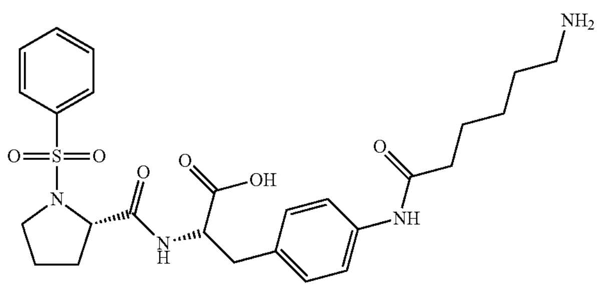 | C |
| 10 | 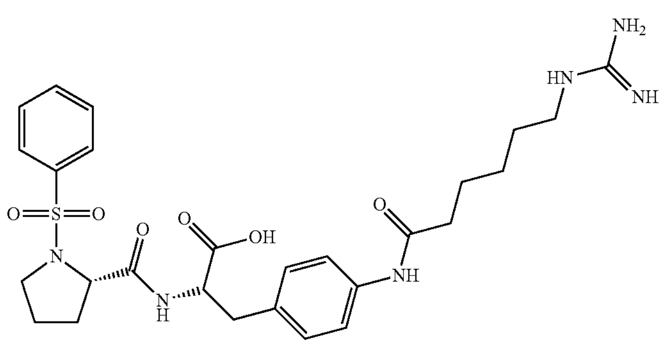 | B |
| 60 | 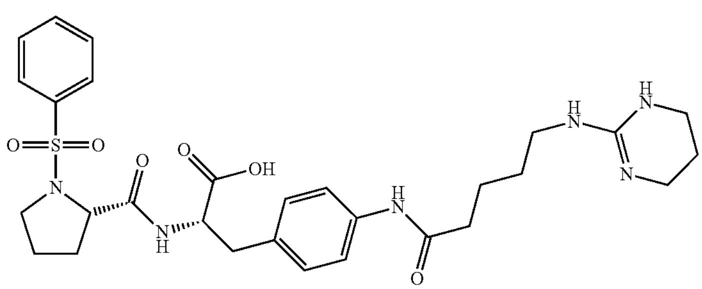 | B |

TABLE 5-continued
IC$_{50}$ data of the compounds
| Cmpd No. | Compound Structure | IC$_{50}$ |
|---|---|---|
| 11 | 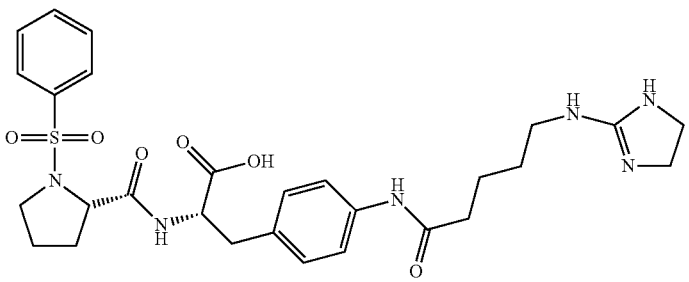 | B |
| 196 | 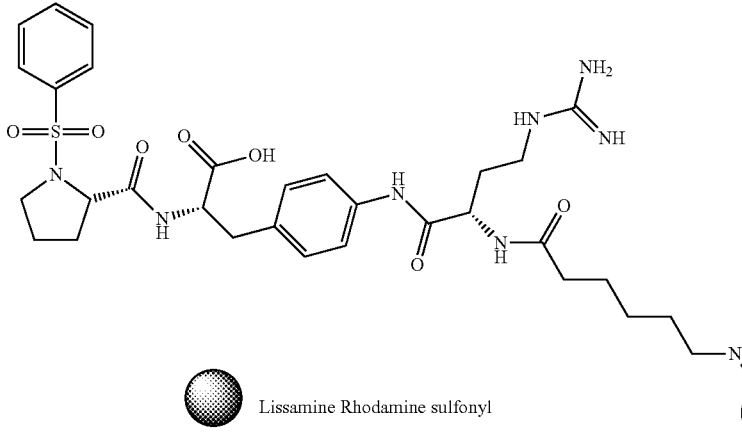 Lissamine Rhodamine sulfonyl | B |
| 197 | 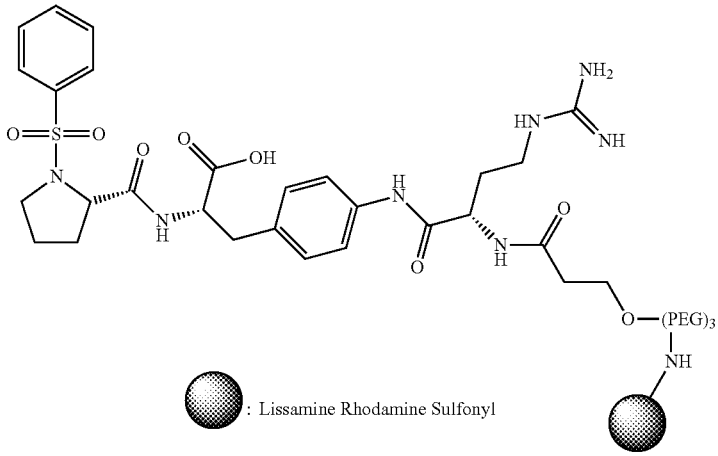 : Lissamine Rhodamine Sulfonyl | B |
| 63 | 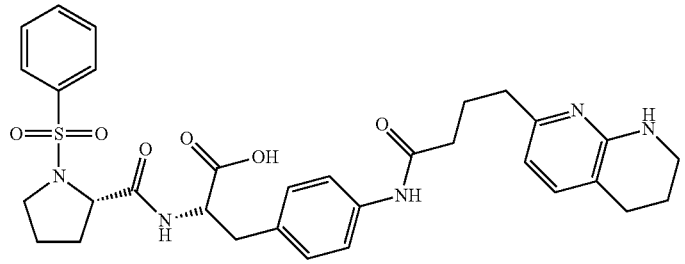 | B |

TABLE 5-continued

IC$_{50}$ data of the compounds

| Cmpd No. | Compound Structure | IC$_{50}$ |
|---|---|---|
| 200 | 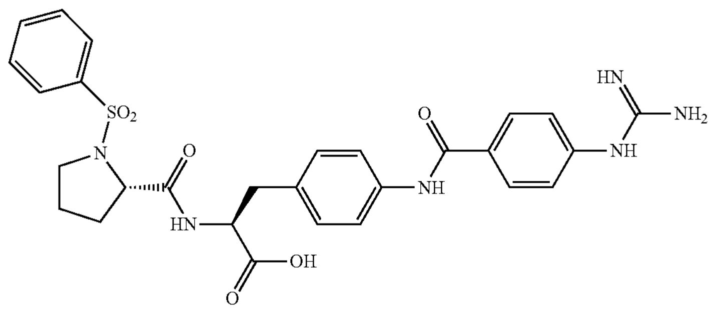 [SMILES: N=C(N)Nc1ccc(C(=O)Nc2ccc(C[C@H](NC(=O)[C@@H]3CCCN3S(=O)(=O)c3ccccc3)C(=O)O)cc2)cc1] | B |
| 201 | 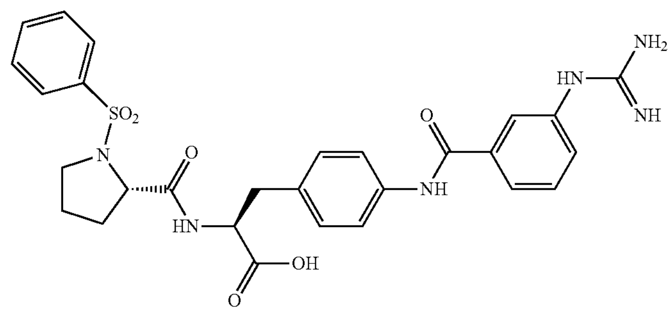 [SMILES: N=C(N)Nc1cccc(C(=O)Nc2ccc(C[C@H](NC(=O)[C@@H]3CCCN3S(=O)(=O)c3ccccc3)C(=O)O)cc2)c1] | A |
| 202 | 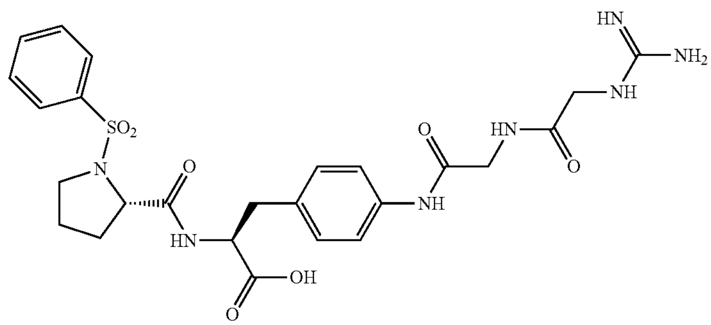 [SMILES: N=C(N)NCC(=O)NCC(=O)Nc1ccc(C[C@H](NC(=O)[C@@H]2CCCN2S(=O)(=O)c2ccccc2)C(=O)O)cc1] | B |
| 203 | 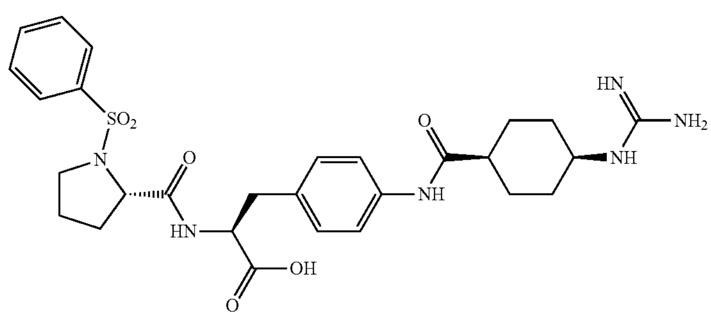 [SMILES: N=C(N)N[C@H]1CC[C@@H](C(=O)Nc2ccc(C[C@H](NC(=O)[C@@H]3CCCN3S(=O)(=O)c3ccccc3)C(=O)O)cc2)CC1] | A |
| 204 | 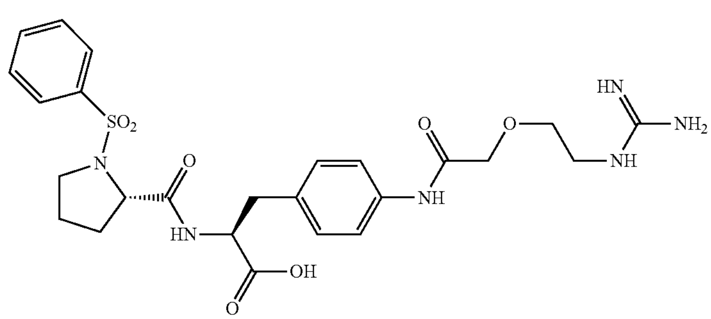 [SMILES: N=C(N)NCCOCC(=O)Nc1ccc(C[C@H](NC(=O)[C@@H]2CCCN2S(=O)(=O)c2ccccc2)C(=O)O)cc1] | B |

TABLE 5-continued
IC$_{50}$ data of the compounds
| Cmpd No. | Compound Structure | IC$_{50}$ |
|---|---|---|
| 205 | 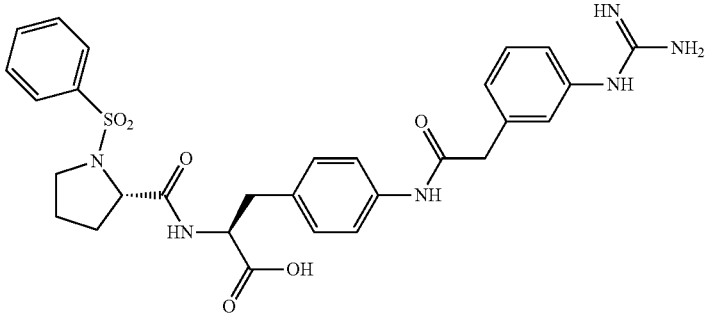 [SMILES: N=C(N)Nc1cccc(CC(=O)Nc2ccc(C[C@H](NC(=O)[C@@H]3CCCN3S(=O)(=O)c3ccccc3)C(=O)O)cc2)c1] | B |
| 93 | 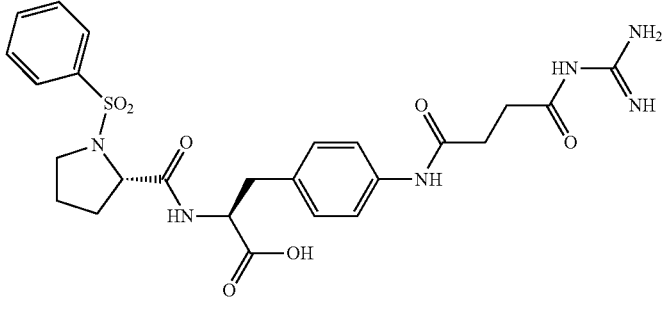 [SMILES: N=C(N)NC(=O)CCC(=O)Nc1ccc(C[C@H](NC(=O)[C@@H]2CCCN2S(=O)(=O)c2ccccc2)C(=O)O)cc1] | B |
| 61 | 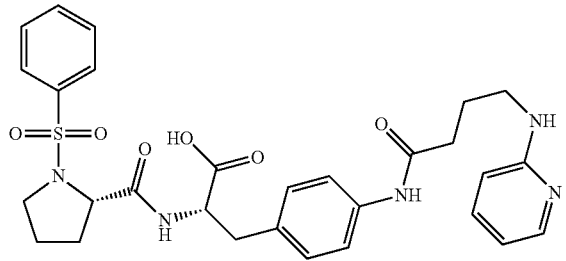 [SMILES: O=C(CCCNc1ccccn1)Nc1ccc(C[C@H](NC(=O)[C@@H]2CCCN2S(=O)(=O)c2ccccc2)C(=O)O)cc1] | B |
| 206 | 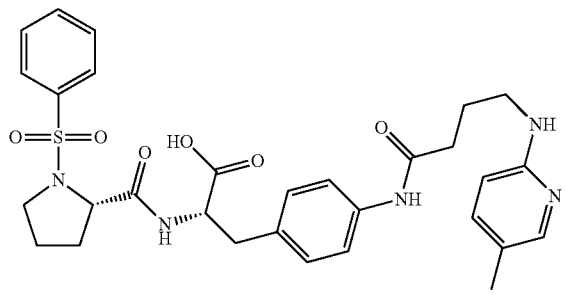 [SMILES: Cc1ccc(NCCCC(=O)Nc2ccc(C[C@H](NC(=O)[C@@H]3CCCN3S(=O)(=O)c3ccccc3)C(=O)O)cc2)nc1] | B |
| 207 | 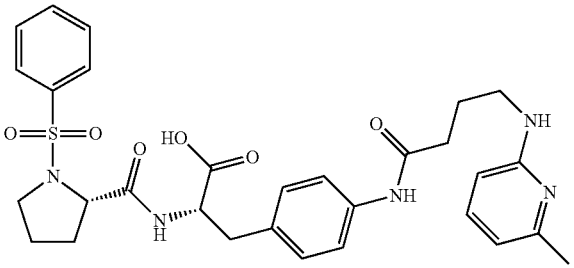 [SMILES: Cc1cccc(NCCCC(=O)Nc2ccc(C[C@H](NC(=O)[C@@H]3CCCN3S(=O)(=O)c3ccccc3)C(=O)O)cc2)n1] | B |

TABLE 5-continued

IC$_{50}$ data of the compounds

| Cmpd No. | Compound Structure | IC$_{50}$ |
|---|---|---|
| 198 | 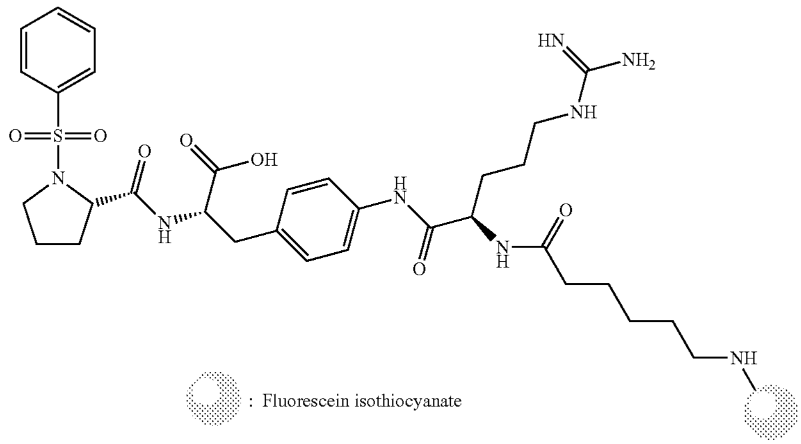 | B |
| 208 | 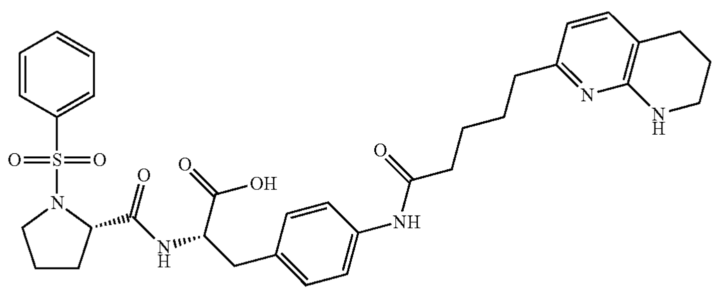 [SMILES: O=C(CCCCc1ccc2c(n1)NCCC2)Nc1ccc(C[C@H](NC(=O)[C@@H]2CCCN2S(=O)(=O)c2ccccc2)C(=O)O)cc1] | B |
| 209 | 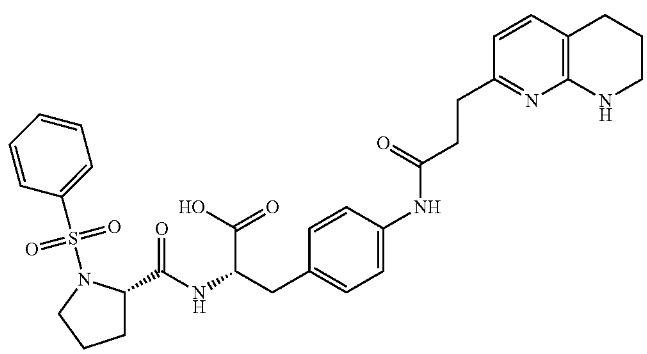 [SMILES: O=C(CCc1ccc2c(n1)NCCC2)Nc1ccc(C[C@H](NC(=O)[C@@H]2CCCN2S(=O)(=O)c2ccccc2)C(=O)O)cc1] | B |
| 210 | 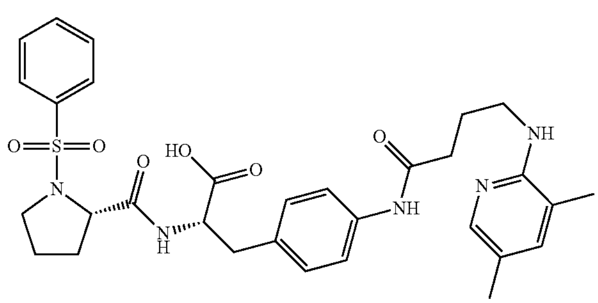 [SMILES: Cc1cnc(NCCCC(=O)Nc2ccc(C[C@H](NC(=O)[C@@H]3CCCN3S(=O)(=O)c3ccccc3)C(=O)O)cc2)c(C)c1] | B |

TABLE 5-continued
IC$_{50}$ data of the compounds
| Cmpd No. | Compound Structure | IC$_{50}$ |
|---|---|---|
| 211 | 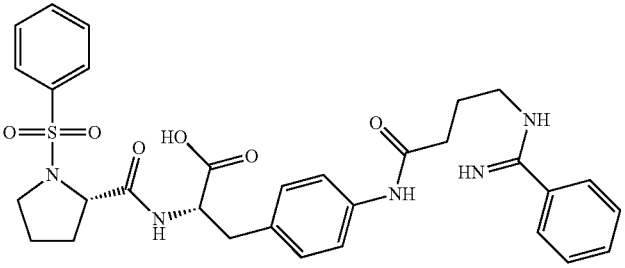 [SMILES: N=C(NCCCC(=O)Nc1ccc(C[C@H](NC(=O)[C@@H]2CCCN2S(=O)(=O)c2ccccc2)C(=O)O)cc1)c1ccccc1] | B |
| 87 | 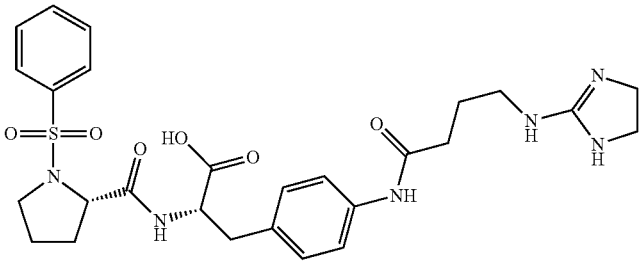 [SMILES: O=C(CCCNC1=NCCN1)Nc1ccc(C[C@H](NC(=O)[C@@H]2CCCN2S(=O)(=O)c2ccccc2)C(=O)O)cc1] | A |
| 211 | 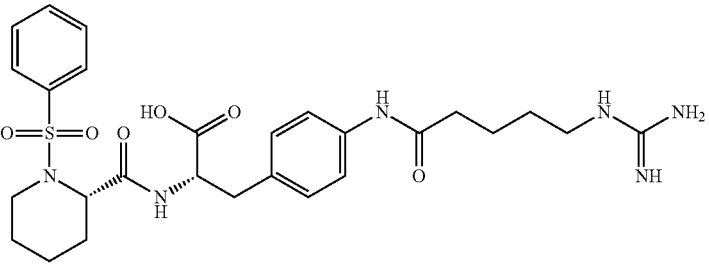 [SMILES: N=C(N)NCCCCC(=O)Nc1ccc(C[C@H](NC(=O)[C@@H]2CCCCN2S(=O)(=O)c2ccccc2)C(=O)O)cc1] | B |
| 212 | 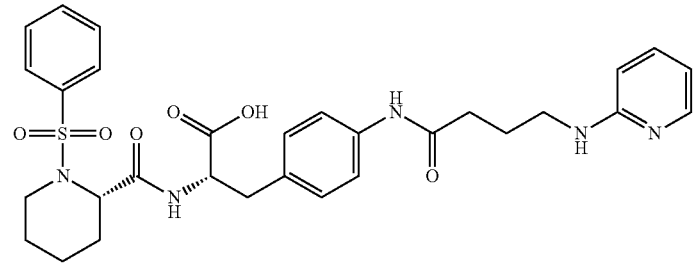 | B |
| 213 | 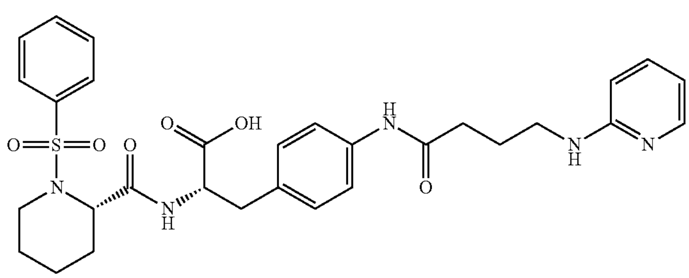 [SMILES: O=C(CCCNc1ccccn1)Nc1ccc(C[C@H](NC(=O)[C@@H]2CCCCN2S(=O)(=O)c2ccccc2)C(=O)O)cc1] | A |

TABLE 5-continued

IC$_{50}$ data of the compounds

| Cmpd No. | Compound Structure | IC$_{50}$ |
|---|---|---|
| 214 | 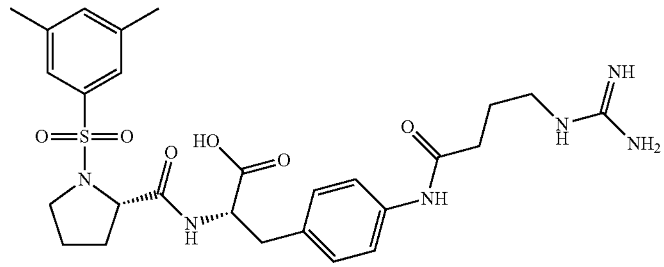 [SMILES: Cc1cc(C)cc(S(=O)(=O)N2CCC[C@H]2C(=O)N[C@@H](Cc2ccc(NC(=O)CCCNC(=N)N)cc2)C(=O)O)c1] | B |
| 199 | (: Tetramethylrhodamine isothiocyanate) | A |
| 215 | 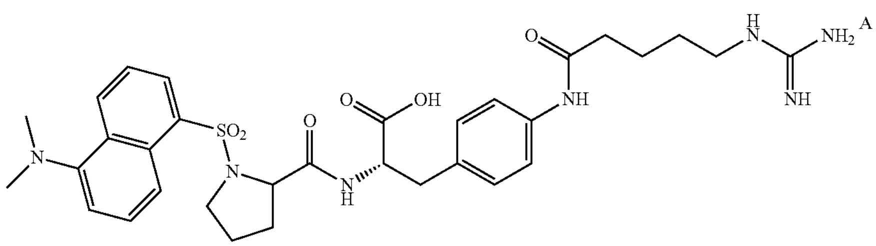 | A |

"A" indicates an IC$_{50}$ value in the Cell Adhesion Assay less than about 10 nM.
"B" indicates an IC$_{50}$ value in the Cell Adhesion Assay between about 10 nM and about 1 μM.
"C" indicates an IC$_{50}$ value in the Cell Adhesion Assay between about 1 μM and about 10 μM.

Example 2

Fibrosis Models

Lung and liver fibrosis were induced as described previously [1, 2]. For CCl$_4$—Induced liver fibrosis, mice were injected intraperitoneally (i.p.) with 1 ul/g body weight sterile CCl$_4$ in a 1:3 ratio with olive oil or olive oil (control), twice weekly for six weeks. ALZET osmotic pumps (Durect, Cupertino, Calif.) were inserted after three weeks of treatment to deliver either c8 or the inactive control small molecule, C16, each dissolved in 50% DMSO (in sterile water) and administered at a dose of 70 mg/kg/day. Livers were harvested 24 hours after the last CCl$_4$ injection. For bleomycin-induced lung fibrosis, 3 U/kg bleomycin (bleo) or water (control) was administered by direct airway intubation with a microsprayer (PennCentury, city). ALZET osmotic pumps were inserted 14 days after treatment, as above and lungs were harvested at 28 days [1].

Primary Cell Isolation

Primary mouse lung fibroblasts were isolated from 4-12 day old mice using a previously reported method, with minor modifications [3]. Mice lungs were removed, pooled together and digested in enzyme solution for total 1 h with removal of dispersed cells every 10 minutes. The enzyme solution consisted of Hanks buffered salt solution (HBSS, without Ca or Mg) with 0.3 mg/ml of type I collagenase (Sigma), and 0.5 mg/ml of trypsin (Sigma) in a shaking water bath maintained at 37° C. After each digestion interval, dispersed cells was passed through a sterile filter (70 μm) into DMEM-Ham's F-12 media (Sigma), 10% fetal bovine serum, and undigested lung tissue placed in fresh enzyme solution. Once digestion was complete, erythrocytes were lysed at room temperature 10 min using red blood cell lysing buffer (Sigma). Then, the cells were pelleted by centrifugation, and cultured in DMEM medium with 10% fetal bovine serum, 1% penicillin/streptomycin in 100 mm tissue culture dishes. The nonadherent cells were aspirated, and the adherent fibroblast were grown in culture. Primary murine hepatic stellate cells were isolated and passaged as described previously [1]. Mouse liver was perfused through the inferior vena cava sequentially with liver perfusion media (Invitrogen). 0.3% pronase (Roche) and 0.02% collagenase (Sigma). The liver was excised and minced with scissors and further digested in 0.044% pronase and 0.008% DNAse (Roche). The cell suspension was shaken (200-250 rpm) at 37° C. for 10 minutes and strained through a sterile filter (70 μm). To remove hepatocytes the cell suspension was centrifuged at 90×g for 2 minutes, the supernatant collected, DNAse added and this procedure was repeated twice. The supernatant was centrifuged at 700×g for 7 minutes to collect the non-parenchymal cell fraction. Collected cells were re-suspended in 10 ml of complete DMEM (10% fetal bovine serum, 1% penicillin/streptomycin) and allowed to differentiate in culture into myofibroblasts before use.

Hydroxyproline Assay

Mouse lung, liver, and kidney tissue was homogenized with trichloroacetic acid and incubated overnight at 110° C. in HCl. Samples were reconstituted in water, and hydroxyproline content was measured using the chloramine T assay [4].

Immunoprecipitation and Western Blotting

Cells were lysed in RIPA buffer (50 mM Tris-HCL, ph 7.4, 10 mM MgCl2, 125 mM NaCl, 2% NP-40), cell lysates were centrifuged at 14,000 rpm for ten minutes at 4° C. and the supernatant collected. 10 μg of anti-αv antibody (for human fibroblast L230, and for murine fibroblast RMV-7, a kind gift from Dr. H Yagita, Juntendo University, Japan) was added to the supernatant and this was rotated at 4° C. for two hours, followed by the addition of 30 μl of prewashed protein G sepharose slurry (GE Healthcare) for one hour at 4° C. The beads were washed three times with PBS/protease inhibitor mixture, and once with PBS only. Laemmli sample buffer was added and the samples were boiled for five minutes followed by SDS-PAGE and western blotting using the following antibodies: αv integrin 611012, 1:500 (BD Biosciences), β1 integrin 04-11-09, 1:500 (Millipore).

TGFB Activation Assay

Test cells were plated at 50K cells/well in 96-well plates together with mink lung epithelial cells expressing firefly luciferase downstream of the TGFβ sensitive portion of the plasminogen activator inhibitor 1 promoter (15K cells/well) [1]. Cells were co-cultured for 16 hours and TGFβ activity was calculated by measurement of luminescencein the presence and absence of TGFβ-blocking antibody, 1D11.

Integrin-Specific Adhesion Assays

The effects of c8 and c16 on cell adhesion mediated by α5β1, α8β1, αvβ1, αvβ3, αvβ5, αvβ6, and αvβ8 were measured using pairs of cell lines and ligands selected to isolate the effect of each individual integrin. For α5β1 we utilized the colon carcinoma cell line, SW480, plated on 0.3 μg/ml fibronectin, for α8β1, we utilized SW480 cells transfected with human α8 adhering to 1 μg/ml recombinant TGFβ1 LAP [5], for αvβ1 we used Chinese Hamster Ovary Cells (CHO cells) transfected with human αv adhering to 0.3 μg/ml fibronectin [6], for αvβ3 we used SW480 cells transfected with human β3, for αvβ5 we used wild type SW480 cells adhering to 0.1 μg/ml vitronectin. For αvβ6 we used SW480 cells transfected with human (36 adhering to 0.01 μg/ml recombinant human TGFβ1 LAP. For αvβ8 we used glioma cell line (SNB19) expressing β8 adhering to 1 μg/ml recombinant human TGFβ1 LAP. In every case, we confirmed that adhesion could be inhibited by blocking antibodies to the relevant integrin (complex-specific blocking antibodies in all cases except αvβ1 for which we showed equivalent effects of blocking αv and β1). Cells were resuspended in DMEM for 30 min at 4° C. with 10-fold dilutions of c8 with a starting concentration of 10 μM. Each sample was then added to triplicate wells of a 96-well plate which had been coated overnight at 4° C. with the relevant ligand, washed, blocked by 1 hr incubation with 1% BSA, and washed again. Cells were allowed to attach for 30-60 min at 37° C. After incubation, non-adherent cells were removed by discarding the media and spinning the plate top-side down at 500 rpm for 5 minutes. Cells were then fixed and stained with 40 ul of 0.5% Crystal violet, 1% Formaldehyde, 20% Methanol for 30 minutes and lysed with 2% Triton-X. Absorbance was measured at 595 nm in a Microplate reader. For all assays, concentration-response curves were constructed by non-linear regression analysis and $IC_{50}$ values were calculated using GraphPad Prism software.

Tissue Staining

Paraffin-embedded sections were processed as described previously [1]. 5 μM sections were stained Hematoxylin and Eosin or with picrosirius red. Pictures were taken from random fields from each section, at a final magnification of 10×. Staining area was calculated by pixel counting with NIH image J. For florescence microscopy, fixed livers and lungs were transferred to 30% sucrose in PBS overnight, embedded in OCT, then cryosectioned at 5 μm. Cryosections were permeabilized and blocked with 0.3% Triton X-100 and 3% BSA in PBS. Sections were incubated with primary antibodies (rabbit anti-phospho-Smad3 Epitomics, 1880-1, 1:100; rat anti-PDGFRb eBiosciences 14-1402, 1:100) overnight at 4° C., then with fluorophore-conjugated secondary antibodies (Invitrogen). Confocal imaging was performed on a Zeiss LSMS Pascal microscope. Phospho-Smad immunofluorescent staining was quantified as described [7].

Statistics

All data are presented as mean±S.E.M unless otherwise noted. Statistical significance was calculated using a one way analysis of variance and Tukey test to determine post-hoc significance between individual groups. p-values were defined using Student's t test for paired comparisons. Differences with a P value of less than 0.05 were considered statistically significant.

Example 3

Fibrosis is a pathologic process, characterized by overproduction of extracellular matrix (ECM) as a response to tissue injury. Nearly 45% of all deaths in the developed world can be attributed to some type of chronic fibroproliferative disease (1, 2). Despite their high prevalence, current therapeutic options for fibrotic diseases are quite limited to elimination of triggering stimuli and organ transplantation. No effective agent exists that can directly halt the disease progression at the cellular level, which represents a major unmet medical need. However, our understanding of fibrogenesis has rapidly grown for the last two decades to shed light on new therapeutic targets in the vast complexity of fibrogenesis pathways (3-10). Cellular damage triggers the recruitment of inflammatory cells, which in turn secrete cytokines that induce the accumulation of activated fibroblasts. These so-called myofibroblasts are key executors of fibrosis as they are the main producers of collagen and other ECM. The origin of myofibroblasts is still under debate (11) but it is generally agreed that transforming growth factor beta (TGFβ) plays a role as a central pro-fibrotic factor in fibroblast activation and differentiation to myofibroblasts. TGFβ is secreted as a latent form and requires integrin binding to be fully active, which suggests that inhibition of integrin binding to the latent TGFβ complex is a promising therapeutic target.

Integrins are a family of transmembrane receptors consisting of two non-covalently bound a and 13 subunits (12, 13). In the process of fibroblast activation, there is a positive feedback loop between TGFβ and αv integrins (14, 15). In fact, epithelium-derived αvβ6 integrin is known to directly activate TGFβ in pulmonary fibrosis, and an αvβ6 blocking antibody is currently in phase II clinical trials for pulmonary fibrosis (16-18). In contrast to αvβ6 which is restricted to the epithelium, other αv integrins (αvβ1, αvβ3, αvβ5 and αvβ8) are expressed in myofibroblasts in many organs. Despite the fact that myofibroblasts are responsible for the majority of ECM production, little is known concerning the role of these av integrins in fibrosis. We produced mice lacking all αv integrins on myofibroblasts (αv f/f PDGFRβ Cre+) and found they are protected from CC14-induced liver fibrosis. These mice are also protected from renal fibrosis induced by unilateral ureteral obstruction and pulmonary fibrosis induced by bleomycin. However, global deletion of αvβ3 or αvβ5 or fibroblast-specific deletion of αvβ8 (mice with global β8 deletion die in utero) did not protect against hepatic fibrosis. These results strongly suggest that hepatic protection is mostly due to the loss of αvβ1 integrin. However, experimental validation to identify the critical role of αvβ1 integrin in fibrosis poses a very challenging problem: it is not possible to study the in vivo role of αvβ1 using knockout mice since mice lacking β1 on myofibroblasts do not survive. Effective blocking monoclonal antibodies against αvβ1 integrin are not available, either. Thus pharmacological modulation of αvβ1 integrin by small molecules is a very attractive route to test the role of αvβ1 integrin in tissue fibrosis.

Given that 16 of 24 integrins contain either an αv chain or β1 chain, it is important to develop potent, selective αvβ1 integrin inhibitors. These molecules can be used to probe the role of αvβ1 integrin in tissue fibrosis as well as other diseases. In preliminary studies we prepared a small series of αvβ1 antagonists by combining fragments known to target the av and β1 subunits based on our earlier published studies (19, 20). So far, we have identified one compound 8 that inhibits cell adhesion by αvβ1 integrin in a highly selective manner at <100 pM concentration.

We have found that compound 8 inhibits TGFβ activation by cultured liver myofibroblasts, whereas antibodies that block αvβ3, αvβ5 and αvβ8 do not. Encouraged by these data, we will conduct more in-depth studies of cell adhesion inhibition mediate by all RGD-binding integrins. We will also inititate more extensive structure-activity relationships (SAR) to obtain a panel of small molecules with the greatest potency and selectivity against αvβ1. The best compound thus identified will be tested in cell-based assays as well as a mouse liver fibrosis model as described below. In addition, large-scale preparation will be pursued to ensure a sufficient supply for animal studies.

αvβ1 integrin inhibition is effective in cell adhesion assay/mouse liver fibrosis model: Inhibitors were tested in cell adhesion assay to test their potency/selectivity. A panel of cell lines and integrin ligands were developed to allow rapid examination of potency and specificity of inhibitors against all 8 integrins that recognize RGD sequences in ligands. A subset of these was used to generate the very encouraging data about 8 shown above. These cell lines were used to calculate $IC_{50}$ concentrations for each inhibitor synthesized to rapidly generate structure activity information to drive subsequent modification and synthesis. Inhibitors were evaluated for showing better potency/selectivity in $CCl_4$-induced liver fibrosis. A general inhibitor of αv integrins can reverse fibrosis in this model when administered as a continuous subcutaneous infusion (from Alzet pumps) beginning 3 weeks after $CCl_4$ initiation. However, global inhibition of all αv integrins is likely to cause unacceptable side effects. We will therefore take a similar approach for each of the most promising αvβ1 inhibitors identified in aim 1, using Alzet pumps to administer the inhibitor, or an inactive relative, to groups of 10 mice treated with either vehicle or $CCl_4$ 3× weekly for 6 weeks. As above, pumps will be inserted after 3 weeks of CCl4 treatment. Once we find small molecules that are effective, each will be further tested in the UUO model of renal fibrosis and the bleomycin model of pulmonary fibrosis. Again we will examine therapeutic rather than prophylactic efficacy by beginning treatment in each model after the onset of fibrosis.

References

Miller M W, Basra S, Kulp D W, Billings P C, Choi S, Beavers M P, et al. Proceedings of the National Academy of Sciences of the United States of America. 2009; 106(3):719-24. Epub 2009 Jan. 15. doi: 10.1073/pnas.0811622106. PubMed PMID: 19141632; PubMed Central PMCID: PMC2625282.

Wick G, Grundtman C, Mayerl C, Wimpissinger T F, Feichtinger J, Zelger B, et al. Annual review of immunology. 2013; 31:107-35. Epub 2013 Mar. 23. doi: 10.1146/annurev-immunol-032712-095937. PubMed PMID: 23516981.

Gerber, E. E., et al., Nature, 2013. 503(7474): p. 126-30.

Henderson, N.C., et al., Nat Med, 2013. 19(12): p. 1617-24.

Bruce, M. C. and C. E. Honaker, Am J Physiol, 1998. 274(6 Pt 1): p. L940-50.

Reddy, G. K. and C. S. Enwemeka, A simplified method for the analysis of hydroxyproline in biological tissues. Clin Biochem, 1996. 29(3): p. 225-9.

Lu, M., et al., Integrin alpha8beta1 mediates adhesion to LAP-TGFbeta1. J Cell Sci, 2002. 115(Pt 23): p. 4641-8.

Zhang, Z. H., et al., Journal of Cell Biology, 1993. 122(1): p. 235-242.

Arnold, T. D., et al., J Neurosci, 2012. 32(4): p. 1197-206.

Wynn T A. Fibrotic disease and the T(H)1/T(H)2 paradigm. Nature reviews Immunology. 2004; 4(8):583-94. Epub 2004 Aug. 3. doi: 10.1038/nri1412. PubMed PMID: 15286725; PubMed Central PMCID:PMC2702150.

Klingberg F, Hinz B, White E S. The Journal of pathology. 2013; 229(2):298-309. Epub 2012 Sep. 22. doi: 10.1002/path.4104. PubMed PMID:22996908.

MacDonald E M, Cohn R D. TGCurrent opinion in rheumatology. 2012; 24(6):628-34. Epub 2012 Aug. 25. doi: 10.1097/BOR.0b013e328358df34. PubMed PMID: 22918531.

Phan S H. Proceedings of the American Thoracic Society. 2012; 9(3):148-52. Epub 2012 Jul. 18. doi: 10.1513/pats.201201-011AW. PubMed PMID:22802289.

Wynn T A, Ramalingam T R. Nature medicine. 2012; 18(7):1028-40. Epub 2012 Jul. 10. doi: 10.1038/nm.2807. PubMed PMID: 22772564; PubMed Central PMCID: PMC3405917.

Margaritopoulos G A, Romagnoli M, Poletti V, Siafakas N M, Wells A U, Antoniou K M. European respiratory review: an official journal of the European Respiratory Society. 2012; 21(123):48-56. Epub 2012 Mar. 2. doi: 10.1183/09059180.00007611. PubMed PMID: 22379174.

Ghosh A K, Vaughan D E. Front Biosci (Elite Ed). 2012; 4:1556-70. Epub 2011 Dec. 29. PubMed PMID: 22201975.

Xu R, Zhang Z, Wang F S. Cellular & molecular immunology. 2012; 9(4):296-301. Epub 2011 Dec. 14. doi: 10.1038/cmi.2011.53. PubMed PMID:22157623.

Cernaro V, Lacquaniti A, Donato V, Fazio M R, Buemi A, Buemi M. Nephrology, dialysis, transplantation: official publication of the European Dialysis and Transplant Association—European Renal Association. 2012; 27(1): 21-7. Epub 2011 Nov. 22. doi:10.1093/ndt/gfr567. PubMed PMID: 22102616.

Iwaisako K, Brenner D A, Kisseleva T. Journal of gastroenterology and hepatology. 2012; 27 Suppl 2:65-8. Epub 2012 Feb. 15. doi:10.1111/j.1440-1746.2011.07002.x. PubMed PMID: 22320919.

Hu P, Luo B H. Journal of cellular physiology. 2013; 228(2):306-12. Epub 2012 Jul. 7. doi: 10.1002/jcp.24154. PubMed PMID: 22767296.

Hynes R O. Cell. 2002; 110(6):673-87. Epub 2002 Sep. 26. PubMed PMID: 12297042.

Munger J S, Sheppard D. Cold Spring Harbor perspectives in biology. 2011; 3(11):a005017. doi: 10.1101/cshperspect.a005017. PubMed PMID: 21900405.

Margadant C, Sonnenberg A. EMBO reports. 2010; 11(2): 97-105. doi: 10.1038/embor.2009.276. PubMed PMID: 20075988; PubMed Central PMCID: PMC2828749.

Hahm K, Lukashev M E, Luo Y, Yang W J, Dolinski B M, Weinreb P H, et al. The American journal of pathology. 2007; 170(1):110-25. doi: 10.2353/ajpath.2007.060158. PubMed PMID: 17200187; PubMed Central PMCID: PMC1762706.

Ma L J, Yang H, Gaspert A, Carlesso G, Barry M M, Davidson J M, et al. The American journal of pathology. 2003; 163(4):1261-73. PubMed PMID: 14507636; PubMed Central PMCID:PMC1868298.

Munger J S, Huang X, Kawakatsu H, Griffiths M J, Dalton S L, Wu J, et al. Cell. 1999; 96(3):319-28. PubMed PMID: 10025398.

Choi S, Vilaire G, Marcinkiewicz C, Winkler J D, Bennett J S, DeGrado W F. J Med Chem. 2007; 50(22):5457-62. PubMed PMID: 17915848.

Xue C B, Roderick J, Jackson S, Rafalski M, Rockwell A, Mousa S, et al. Bioorganic & medicinal chemistry. 1997; 5(4):693-705. Epub 1997 Apr. 1. PubMed PMID: 9158868.

Miller M W, Basra S, Kulp D W, Billings P C, Choi S, Beavers M P, et al. Proc Natl Acad Sci USA. 2009; 106(3):719-24. Epub 2009 Jan. 15. doi: 0811622106 [pii] 10.1073/pnas.0811622106. PubMed PMID: 19141632; PubMed Central PMCID: PMC2625282.

Yin H, Gerlach L O, Miller M W, Moore D T, Liu D, Vilaire G, et al. Bioorg Med Chem Lett. 2006; 16(13):3380-2. PubMed PMID: 16678410.

Rockwell A L, Rafalski M, Pitts W J, Batt D G, Petraitis J J, DeGrado W F, et al. Bioorg Med Chem Lett. 1999; 9(7):937-42.

Xue C B, Roderick J, Mousa S, Olson R E, DeGrado W F. Bioorg Med Chem Lett. 1998; 8(24):3499-504. PubMed PMID: 9934460.

Mousa S A, Forsythe M, Lorelli W, Bozarth J, Xue C B, Wityak J, et al. Coron Artery Dis. 1996; 7(10):767-74. PubMed PMID: 8970768.

Mousa S A, DeGrado W F, Mu D X, Kapil R P, Lucchesi B R, Reilly T M. Circulation. 1996; 93(3):537-43. Epub 1996 Feb. 1. PubMed PMID: 8565173.

Corbett J W, Graciani N R, Mousa S A, DeGrado W F. Bioorganic & Medicinal Chemistry Letters. 1997; 7(11): 1371-6. doi: Doi 10.1016/S0960-894x(97)00200-X. PubMed PMID: ISI:A1997XE59800002.

De Corte B L, Kinney W A, Liu L, Ghosh S, Brunner L, Hoekstra W J, et al. Bioorganic & Medicinal Chemistry Letters. 2004; 14(20):5227-32. doi: DOI 10.1016/j.bmcl.2004.06.061. PubMed PMID: ISI: 000224165900041.

VII. Embodiments

Embodiment P1

A method for treating fibrosis, said method comprising administering to a subject in need thereof a therapeutically effective amount of an αvβ1 inhibitor, wherein said αvβ1 inhibitor is an αvβ1 inhibitor-antibody, an αvβ1 inhibitor-RGD peptide, or an αvβ1 inhibitor-compound having the formula:

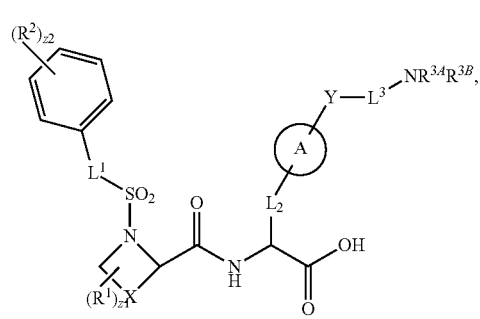

(I)

wherein, Ring A is heterocycloalkyl, aryl, or heteroaryl; $L^1$ and $L^2$ are independently a bond or substituted or unsubstituted $C_1$-$C_{10}$ alkylene. $L^3$ is a bond, substituted or unsubstituted $C_1$-$C_{10}$ alkylene, substituted or unsubstituted 2 to 10 membered heteroalkylene, or substituted or unsubstituted alkylarylene. X is a bond, —C—, —C—C—, —C=C—, —C—C—C—, —C=C—C—, —C—C=C—, —O—C—, —C—O—, —C—O—C, —S—C—, —C—S—, —C—S—C—. Y is a bond, —C(O)N($R^4$)—, —O—, —C(O)O—, —S—, —N($SO_2$—$R^4$)—, —N(C(O)$R^4$)—, —N(C(O)O$R^4$)—, —($NR^4$)C(O)—, —N($R^4$)—, substituted or unsubstituted heterocycloalkylene, substituted or unsubstituted arylene, or substituted or unsubstituted heteroarylene. $R^1$ is independently halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$OSO_3H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety. $R^2$ is independently halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$OSO_3H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety. $R^{3A}$ and $R^{3B}$ are independently hydrogen, —C(NH)$NH_2$, —C(NCN)$NH_2$, substituted or unsubstituted cycloalkyl, substituted or unsubstituted heterocycloalkyl, substituted or unsubstituted aryl or substituted or unsubstituted heteroaryl, or $R^{3A}$ and $R^{3B}$ are optionally joined to form a substituted or unsubstituted heterocycloalkyl or substituted or unsubstituted heteroaryl. $R^4$ is independently hydrogen or unsubstituted $C_1$-$C_5$ alkyl. z1 is an integer from 1 to 9. z2 is an integer from 1 to 5.

Embodiment P2

The method of embodiment 1, wherein the fibrosis is pulmonary fibrosis, liver fibrosis, skin fibrosis, cardiac fibrosis, or kidney fibrosis.

Embodiment P3

The method of embodiment 1, wherein the αvβ1 inhibitor-antibody is a humanized antibody.

Embodiment P4

The method of embodiment 3, wherein the αvβ1 inhibitor-antibody is a recombinant immunoglobulin.

Embodiment P5

The method of embodiment 4, wherein the recombinant immunoglobulin is formed using phage display.

Embodiment P6

The method of embodiment 1, wherein the αvβ1 inhibitor is an αvβ1 inhibitor-RGD peptide.

Embodiment P7

The method of embodiment 1, wherein the αvβ1 inhibitor is an αvβ1 inhibitor-compound.

Embodiment P8

The method of embodiment 7, wherein the αvβ1 inhibitor-compound has the formula:

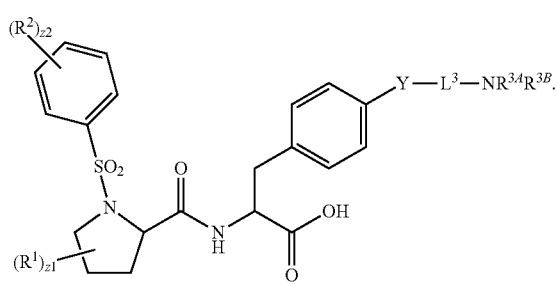

(II)

Embodiment P9

The method of embodiment 7, wherein the αvβ1 inhibitor-compound has the formula:

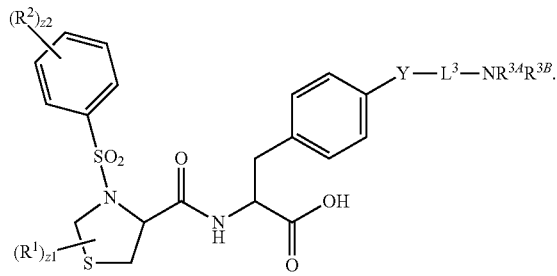

(III)

Embodiment P10

The method of embodiment 7, wherein the αvβ1 inhibitor-compound has the formula:

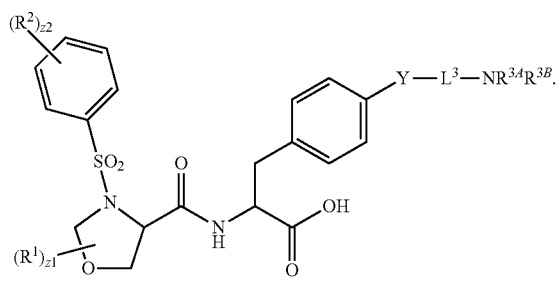

(IV)

Embodiment P11

The method of any one of embodiments 8 to 10, wherein Y is —NH(CO)—.

Embodiment P12

The method of embodiment 11, wherein $L^3$ is unsubstituted $C_1$-$C_5$ alkylene.

Embodiment P13

The method of embodiment 11, wherein $L^3$ is unsubstituted 2 to 6 membered heteroalkylene.

Embodiment P14

The method of embodiment 11, wherein $L^3$ is unsubstituted alkylarylene.

Embodiment P15
The method of embodiment 8, wherein the αvβ1 inhibitor-compound has the formula:
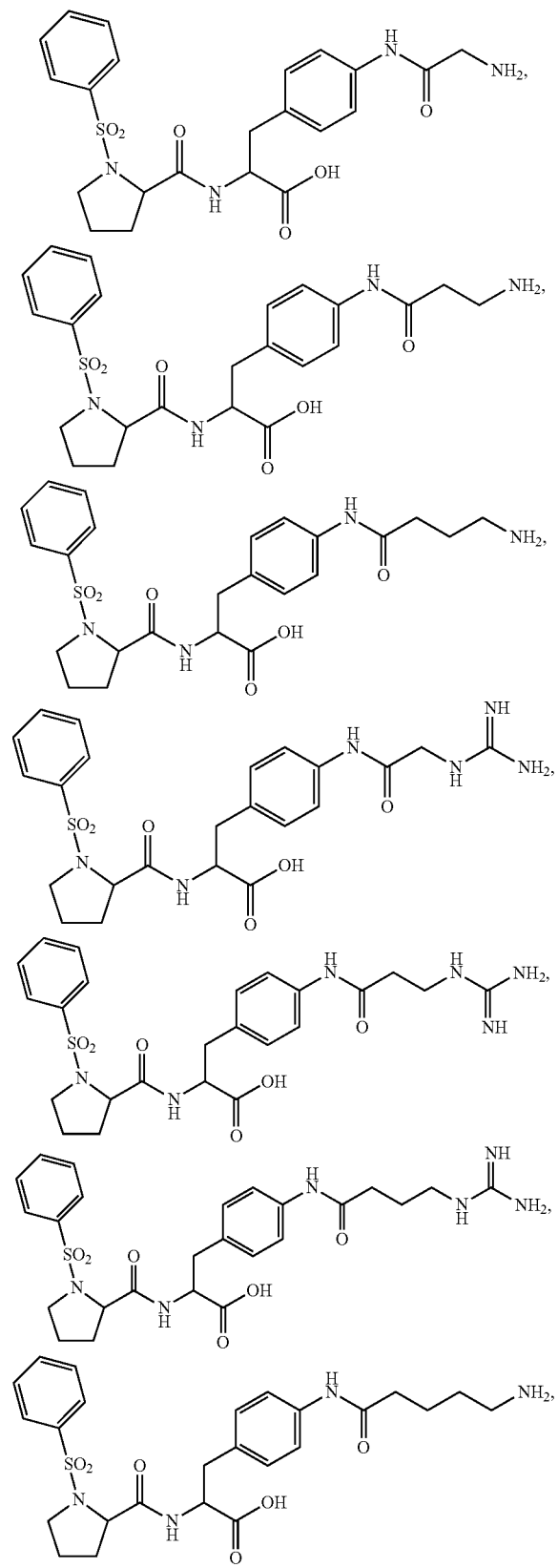
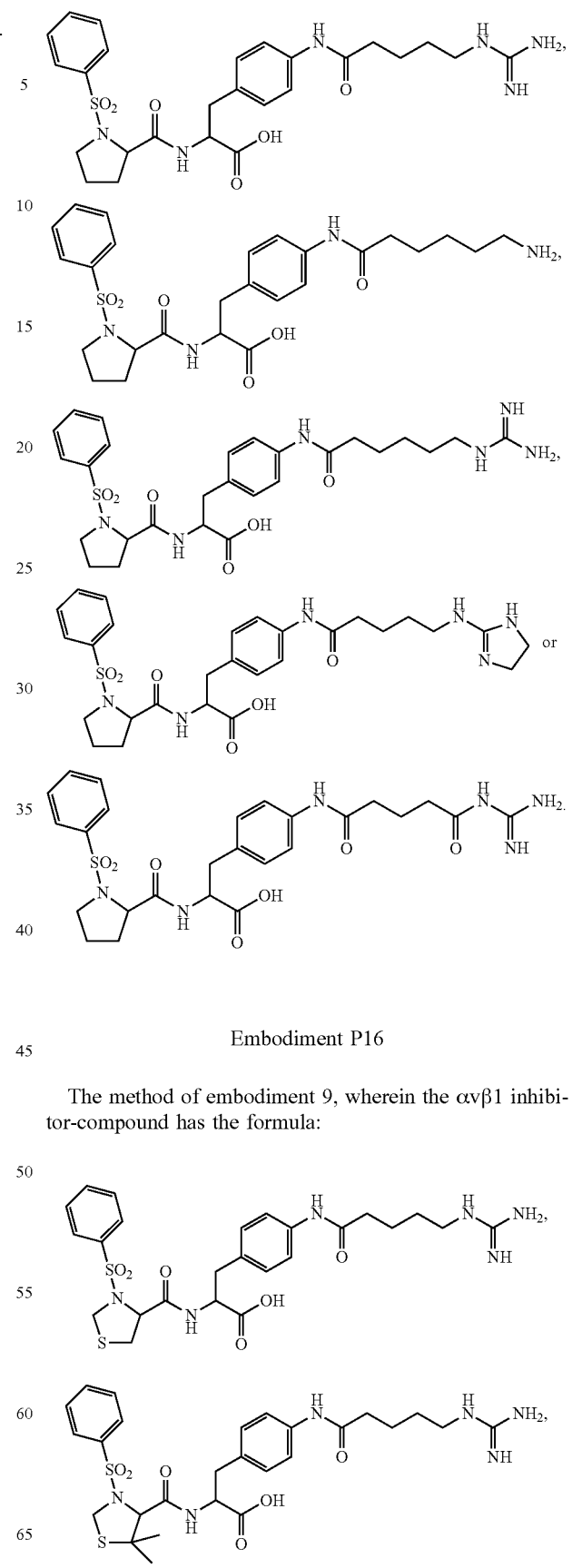
Embodiment P16
The method of embodiment 9, wherein the αvβ1 inhibitor-compound has the formula:

219
-continued

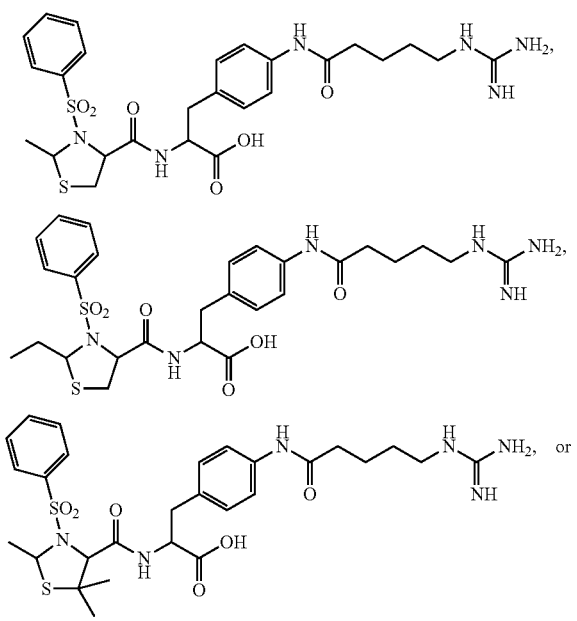

Embodiment P17

The method of embodiment 10, wherein the αvβ1 inhibitor-compound has the formula:

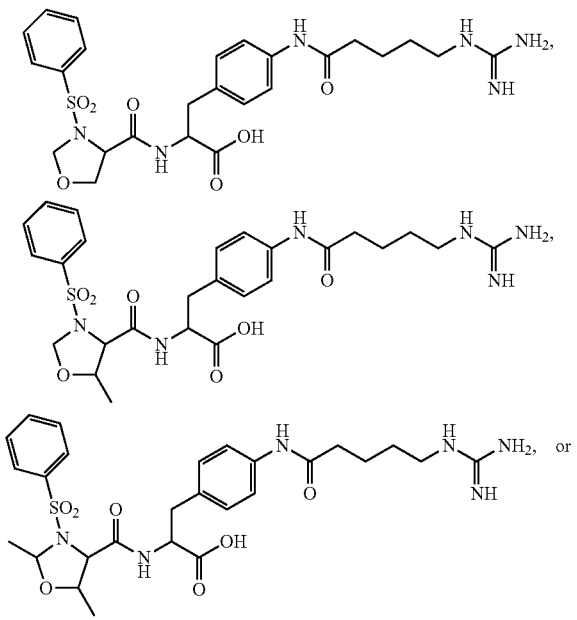

220
-continued

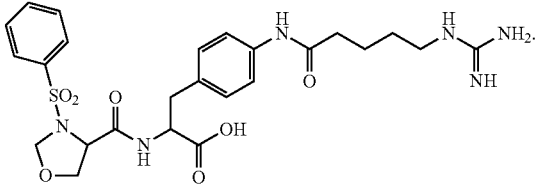

Embodiment P18

A method for determining whether a test compound inhibits αvβ1 integrin binding, the method comprising: (i) combining an αvβ1 integrin-expressing cell and a test compound in a reaction vessel comprising an integrin ligand covalently bonded to the reaction vessel; (ii) determining whether the αvβ1 integrin-expressing cell binds to the integrin ligand in the presence of the test compound, thereby determining whether the test compound inhibits αvβ1 integrin binding.

Embodiment P19

A compound having the formula:

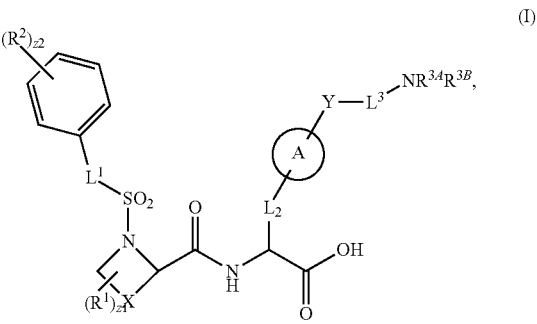

(I)

wherein, Ring A is heterocycloalkyl, aryl, or heteroaryl. $L^1$ and $L^2$ are independently a bond or substituted or unsubstituted $C_1$-$C_{10}$ alkylene. $L^3$ is a bond, substituted or unsubstituted $C_1$-$C_{10}$ alkylene or substituted, unsubstituted 2 to 10 membered heteroalkylene, or substituted or unsubstituted alkylarylene. X is a bond, —C—, —C—C—, —C=C—, —C—C—C—, —C=C—C—, —C—C=C—, —O—C—, —C—O—, —C—O—C, —S—C—, —C—S—, —C—S—C—. Y is a bond, —C(O)N($R^4$)—, —O—, —C(O)O—, —S—, —N($SO_2$—$R^4$)—, —N(C(O)$R^4$)—, —N(C(O)O$R^4$)—, —(N$R^4$)C(O)—, —N($R^4$)—, substituted or unsubstituted heterocycloalkylene, substituted or unsubstituted arylene, or substituted or unsubstituted heteroarylene. $R^1$ is independently halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$OSO_3H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety. $R^2$ is independently halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$OSO_3H$, —$SO_2NH_2$, —$NHNH_2$, —$ONH_2$, —NHC(O)

NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety. R$^{3A}$ and R$^{3B}$ are independently hydrogen, —C(NH)NH$_2$, —C(NCN)NH$_2$, substituted or unsubstituted cycloalkyl, substituted or unsubstituted heterocycloalkyl, substituted or unsubstituted aryl, substituted or unsubstituted heteroaryl, or R$^{3A}$ and R$^{3B}$ are optionally joined to form a substituted or unsubstituted heterocycloalkyl or substituted or unsubstituted heteroaryl. R$^4$ is independently hydrogen or unsubstituted C$_1$-C$_5$ alkyl. z1 is an integer from 1 to 9 and z2 is an integer from 1 to 5.

Embodiment P20

The compound of embodiment 19, wherein L$^1$ is a bond.

Embodiment P21

The compound of embodiment 20, wherein L$^2$ is unsubstituted methylene.

Embodiment P22

The compound of embodiment 21, wherein L$^3$ is substituted or unsubstituted C$_1$-C$_5$ alkylene, substituted, unsubstituted 2 to 6 membered heteroalkylene, or substituted or unsubstituted alkylarylene.

Embodiment P23

The compound of embodiment 22, wherein X is —C—C—, —C≡C—, —O—C—, —C—O—, —C—O—C—, —C—S—, —S—C, or —C—S—C—.

Embodiment P24

The compound of embodiment 23, wherein Y is —NHC(O)—, —NCH$_3$—, —NC(O)CH$_3$—, —NC(O)OCH$_3$—, —N(SO$_2$CH$_3$)—, —S—, —O—, C(O)O—, substituted or unsubstituted 3 to 6 membered heterocycloalkylene, or 4 to 6 membered unsubstituted heteroarylene, or unsubstituted arylene.

Embodiment P25

The compound of embodiment 24, wherein R$^1$ is independently hydrogen, oxo, substituted or unsubstituted C$_1$-C$_5$ alkyl, or a detectable moiety.

Embodiment P26

The compound of embodiment 25, wherein R$^2$ is independently hydrogen, halogen, —CF$_3$, —CCl$_3$, —CBr$_3$, —CI$_3$, —NH$_2$, —NO$_2$, —SO$_2$CH$_3$, substituted or unsubstituted C$_1$-C$_5$ alkyl, substituted or unsubstituted 2 to 5 membered heteroalkyl, substituted or unsubstituted 5 or 6 membered aryl, or a detectable moiety.

Embodiment P27

The compound of embodiment 26, wherein R$^{3A}$ and R$^{3B}$ are independently hydrogen, —C(NH)NH$_2$, —C(NCN)NH$_2$, substituted or unsubstituted heterocycloalkyl, substituted or unsubstituted heteroaryl, or joined to form a substituted or unsubstituted 5 or 6 membered heterocycloalkyl or substituted or unsubstituted 5 or 6 membered heteroaryl.

Embodiment P28

The compound of embodiment 19 having the formula:

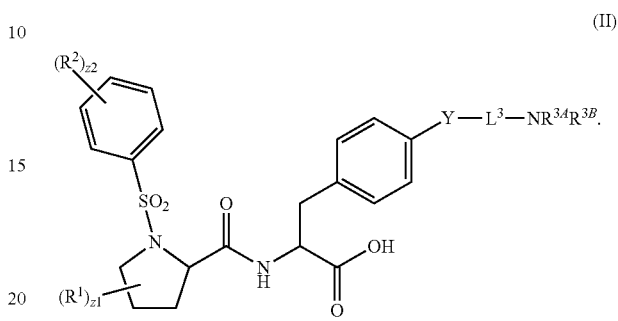

(II)

Embodiment P29

The compound of embodiment 28 having the formula:

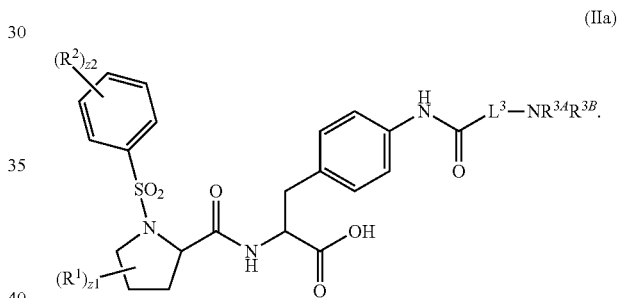

(IIa)

Embodiment P30

The compound of embodiment 29, wherein L$^3$ is substituted or unsubstituted C$_1$-C$_6$ alkylene, substituted or unsubstituted 2 to 6 membered heteroalkylene, alkylarylene.

Embodiment P31

The compound of embodiment 30, wherein R$^1$ is hydrogen, substituted or unsubstituted methyl, or oxo.

Embodiment P32

The compound of embodiment 31, wherein R$^2$ is hydrogen, halogen, —SO$_2$CH$_3$, —NO$_2$, —NH$_2$, substituted or unsubstituted C$_1$-C$_3$ alkyl, or substituted or unsubstituted 2 to 5 membered heteroalkyl.

Embodiment P33

The compound of embodiment 32, wherein R$^{3A}$ and R$^{3B}$ are independently hydrogen, —C(NH)NH$_2$, —C(NCN)

NH₂, or substituted or unsubstituted heterocycloalkyl, or substituted or unsubstituted heteroaryl.
Embodiment P34
The compound of embodiment 29 having the formula:
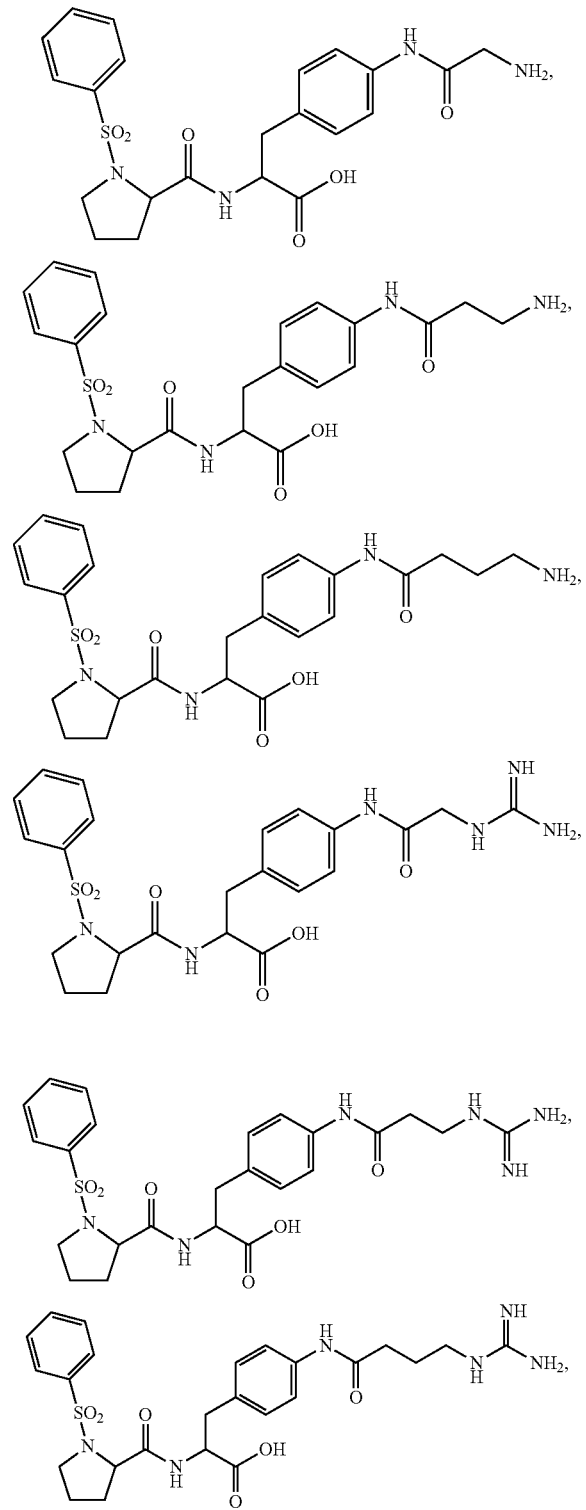
-continued
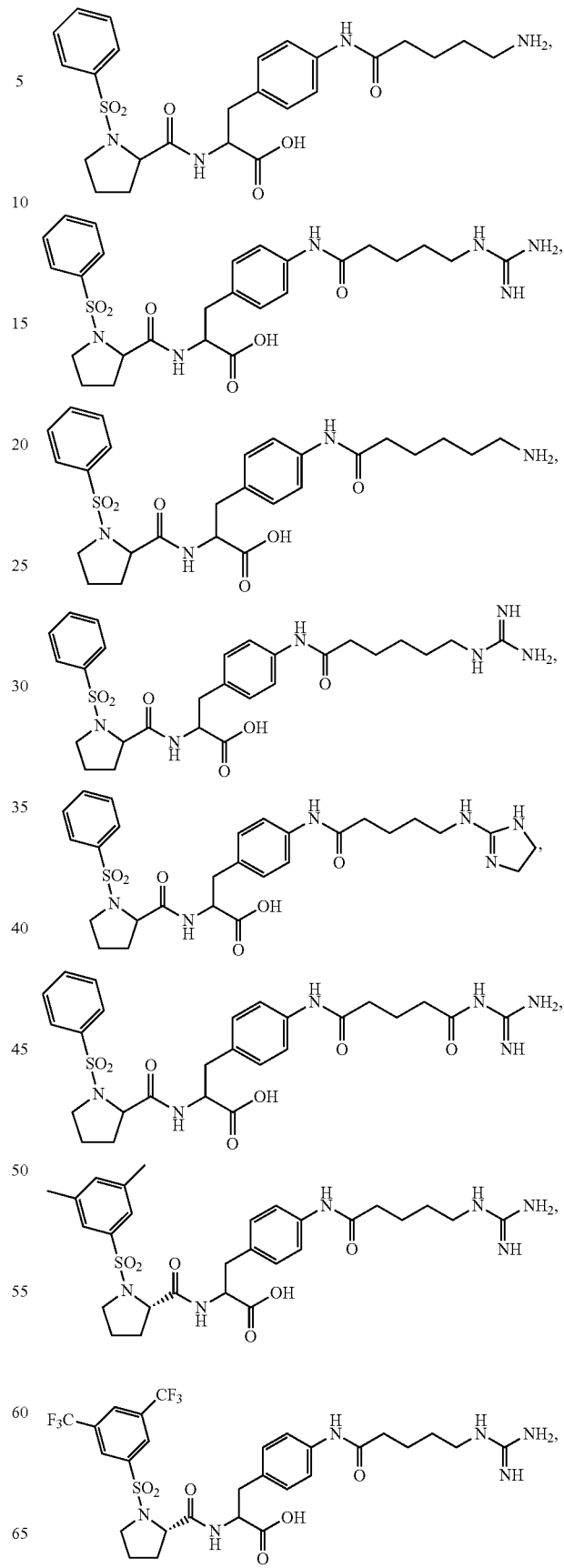

225
-continued
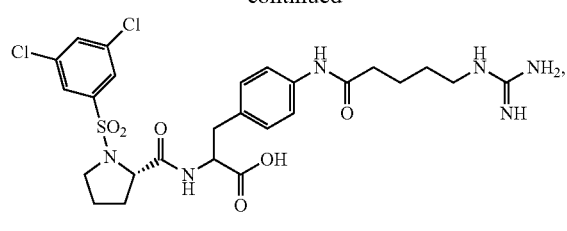
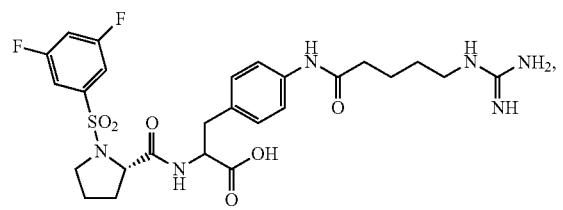
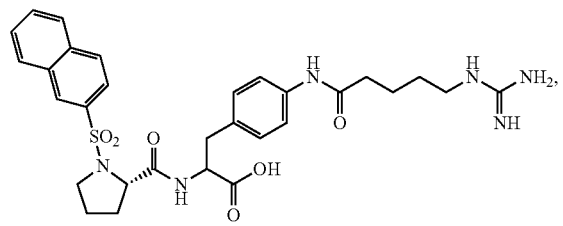
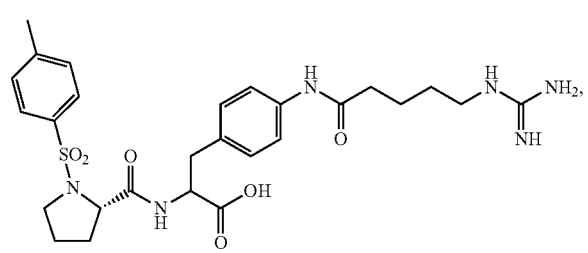
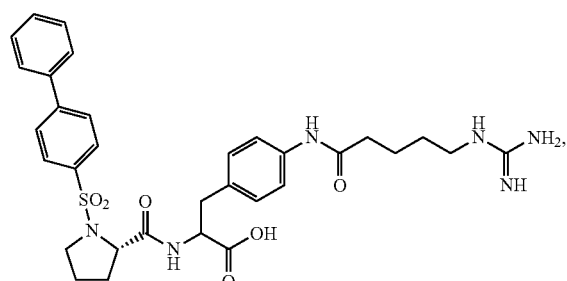
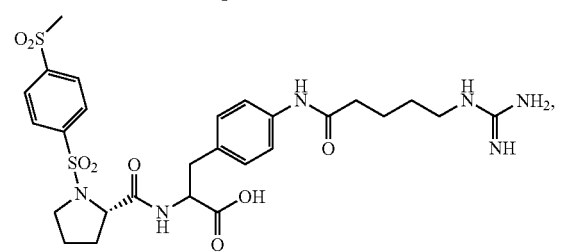
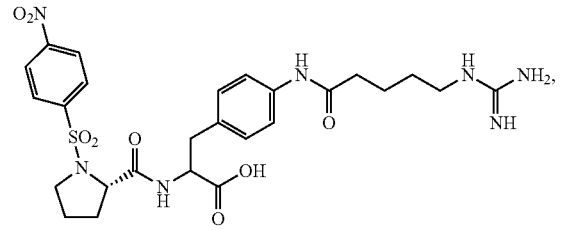
226
-continued
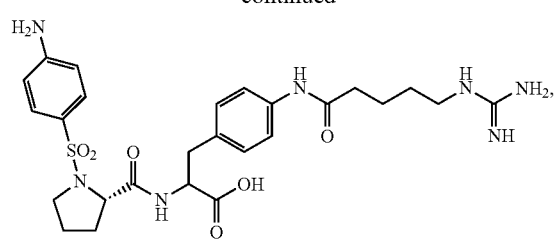
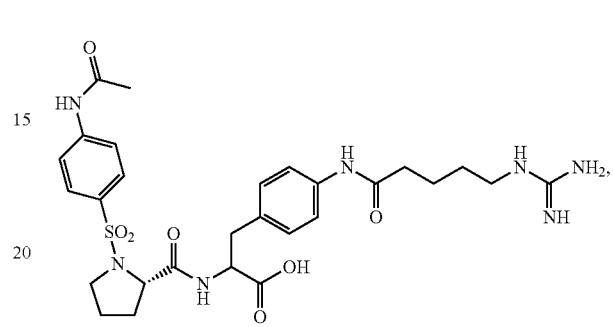
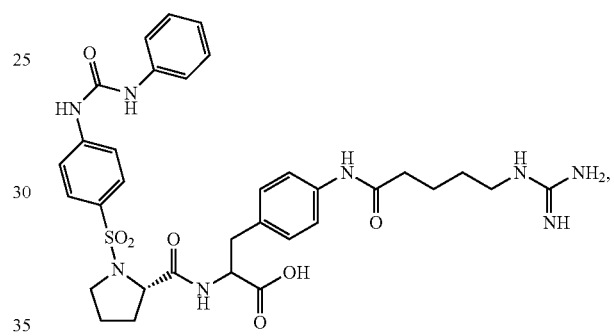
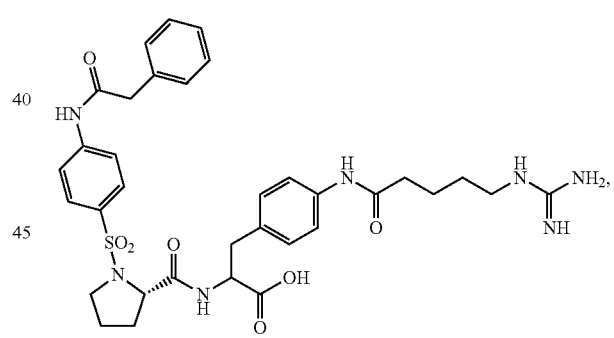
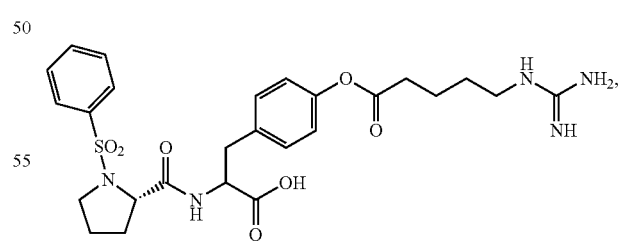
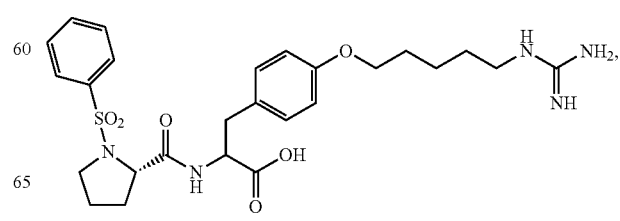

227
-continued
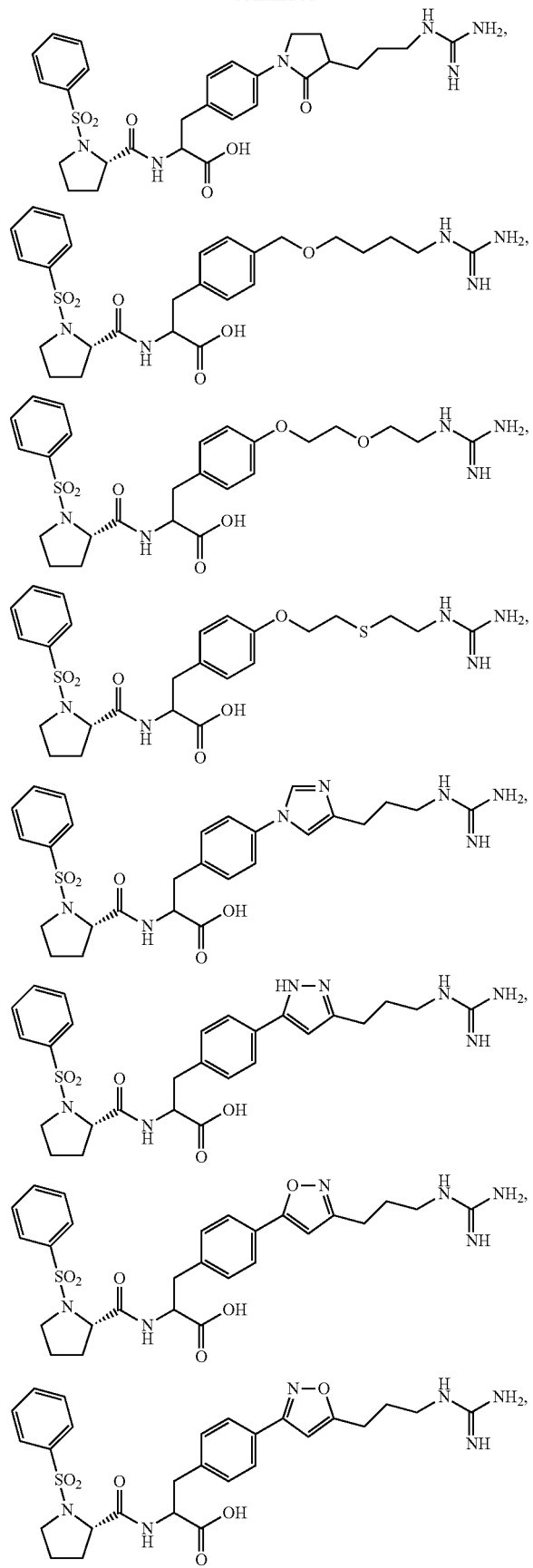
228
-continued
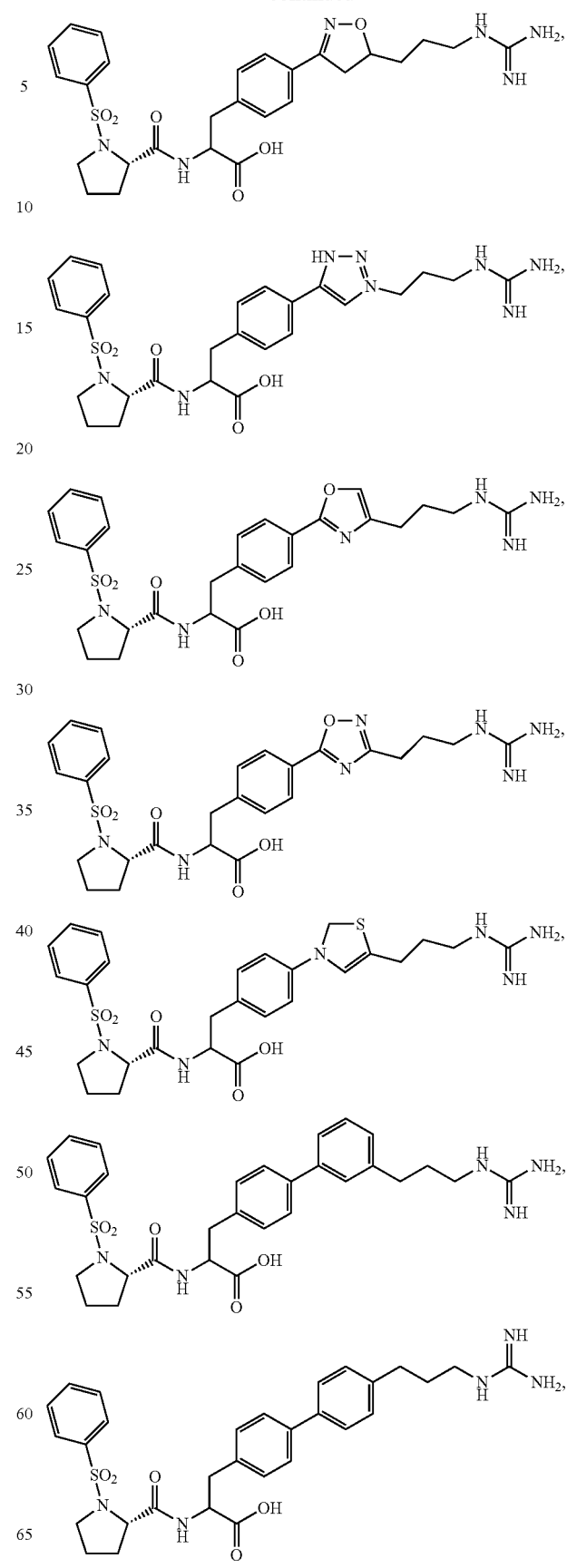

229
-continued
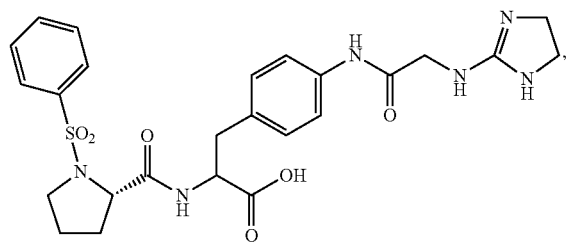
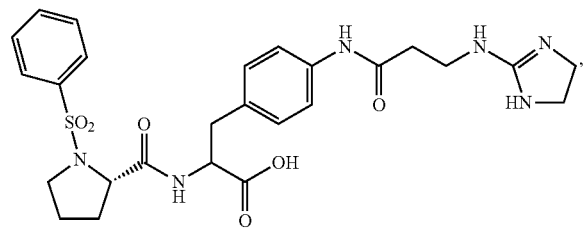
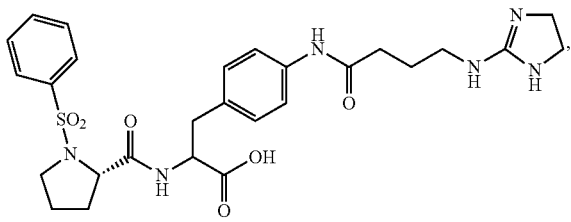
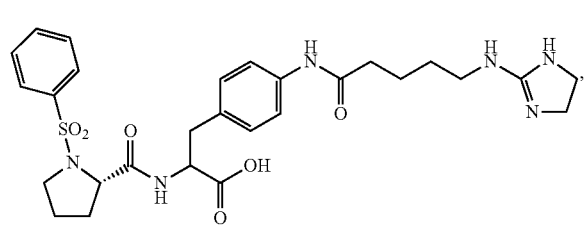
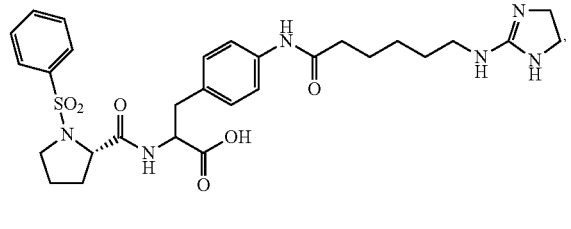
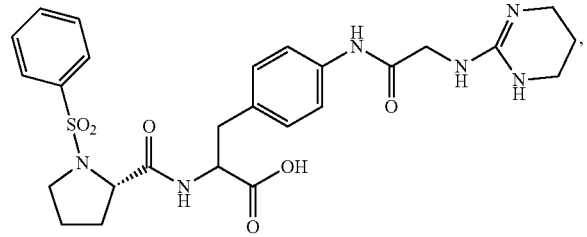
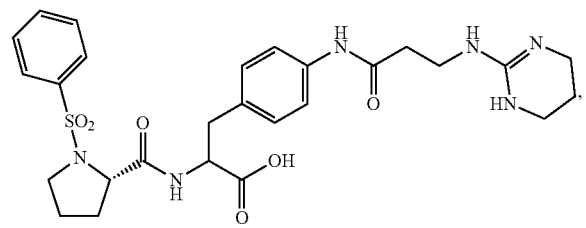
230
-continued
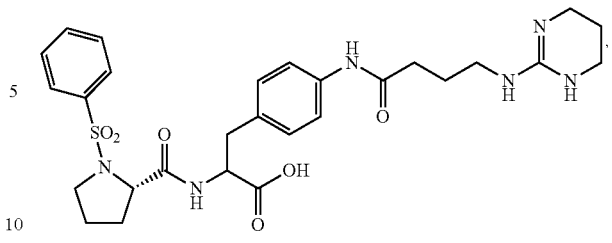
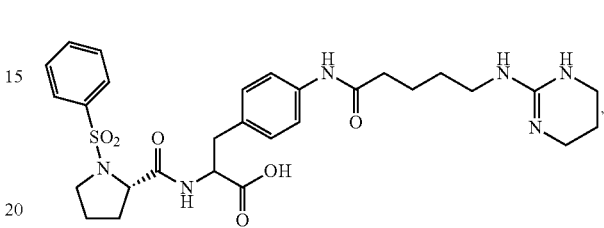
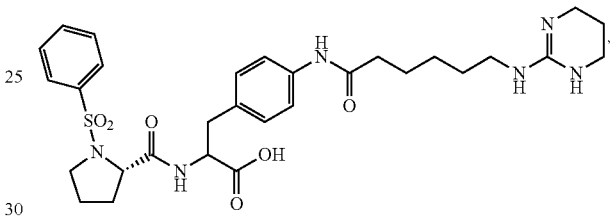
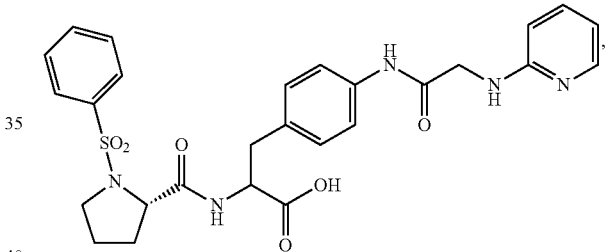
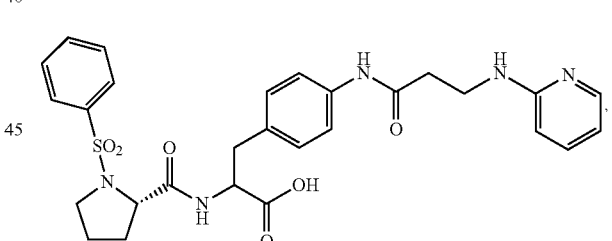
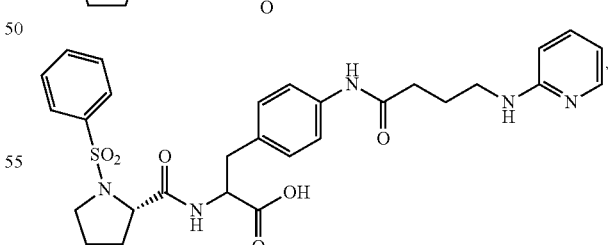
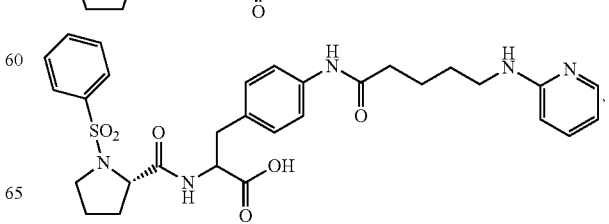

231
-continued
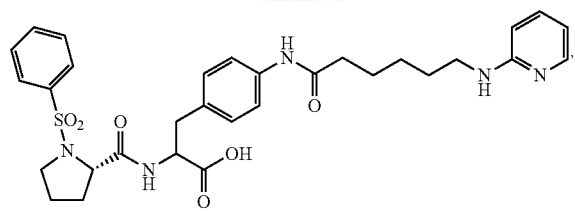
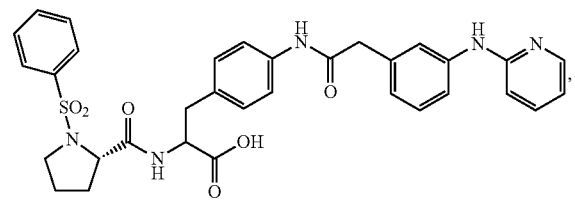
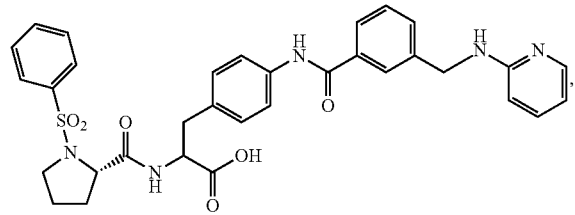
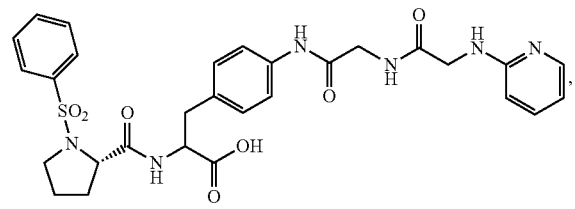
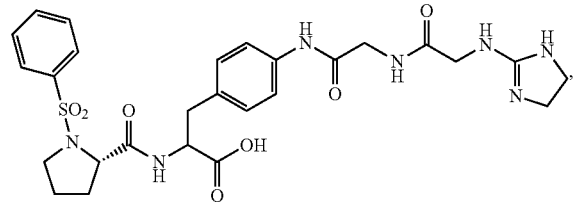
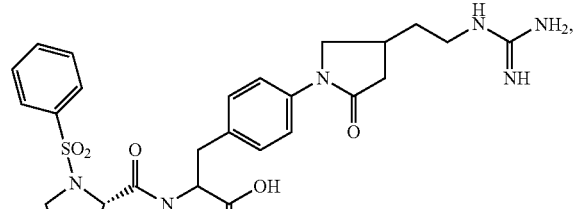
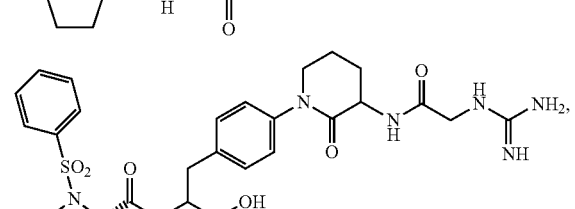
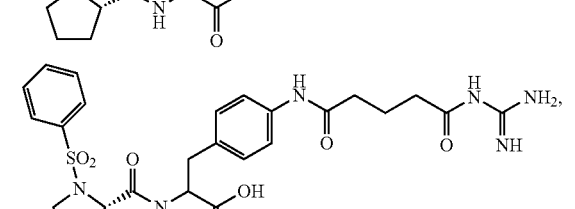
232
-continued
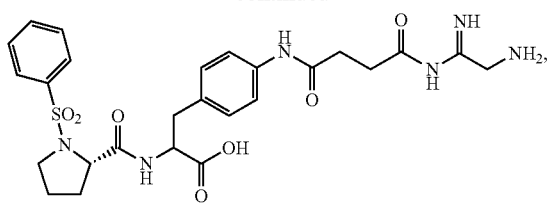
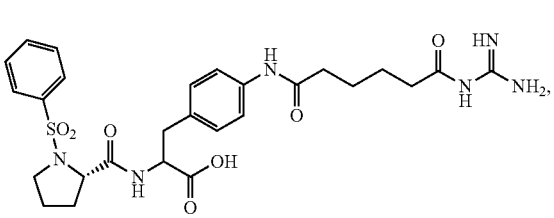
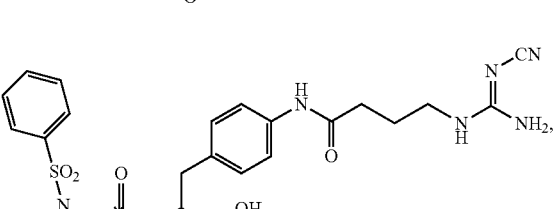
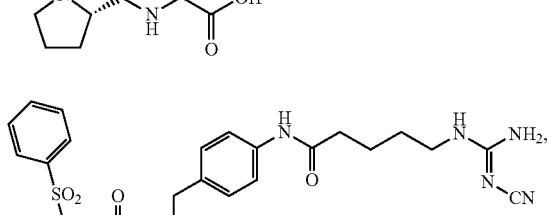
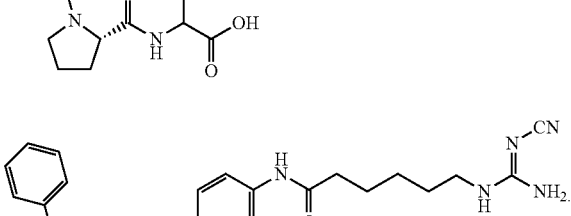
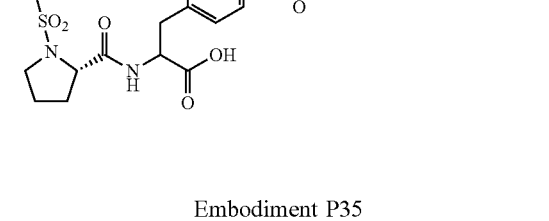
Embodiment P35
The compound of embodiment 19 having the formula:
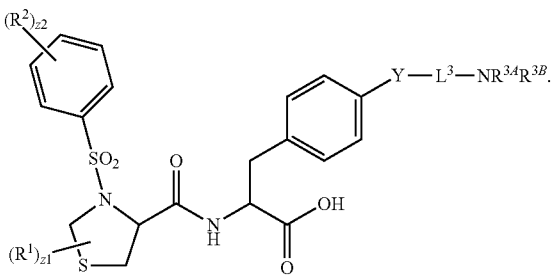

Embodiment P36

The compound of embodiment 35 having the formula:

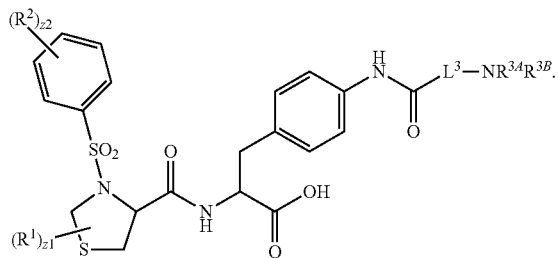

(IIIa)

Embodiment P37

The compound of embodiment 36, wherein $L^3$ is substituted or unsubstituted $C_1$-$C_6$ alkylene, or substituted or unsubstituted 2 to 6 membered heteroalkylene.

Embodiment P38

The compound of embodiment 37, wherein $R^1$ is hydrogen or substituted or unsubstituted $C_1$-$C_3$ alkyl.

Embodiment P39

The compound of embodiment 38, wherein $R^2$ is hydrogen, halogen, —$SO_2CH_3$, —$NO_2$, —$NH_2$, substituted or unsubstituted $C_1$-$C_3$ alkyl, or substituted or unsubstituted 1 to 4 membered heteroalkyl.

Embodiment P40

The compound of embodiment 39, wherein $R^{3A}$ and $R^{3B}$ are independently hydrogen, —C(NH)$NH_2$, —C(NCN)$NH_2$, or substituted or unsubstituted heterocycloalkyl, or substituted or unsubstituted heteroaryl.

Embodiment P41

The compound of embodiment 36 having formula:

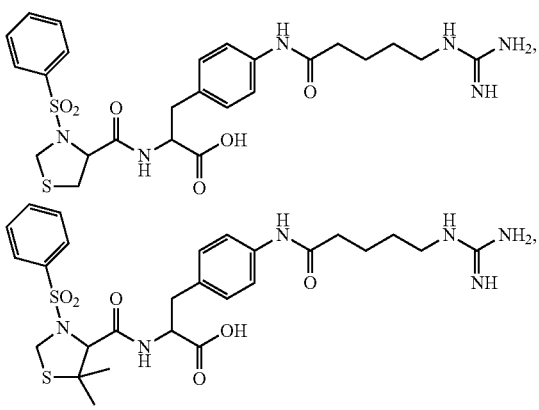

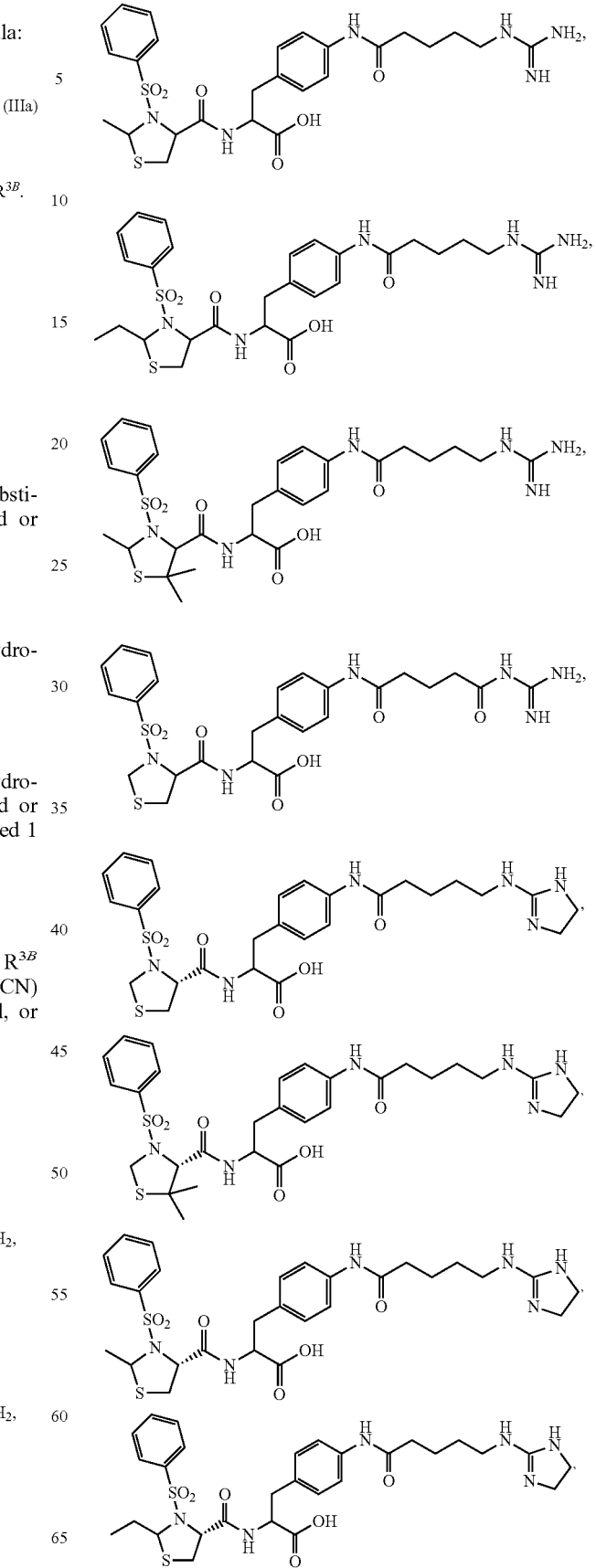

235
-continued
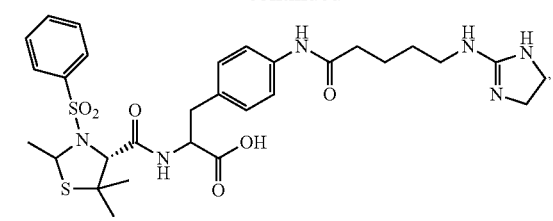
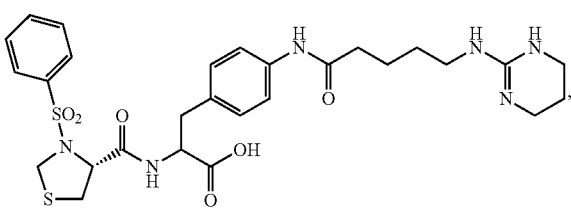
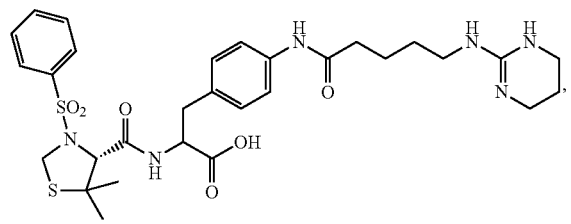
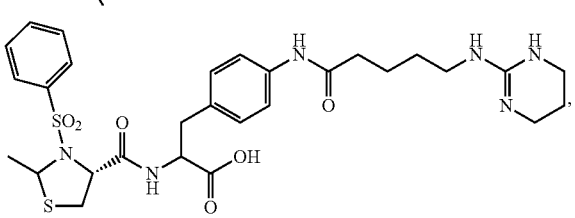
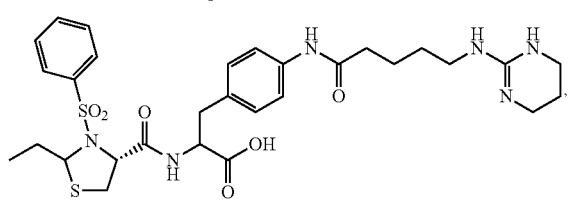
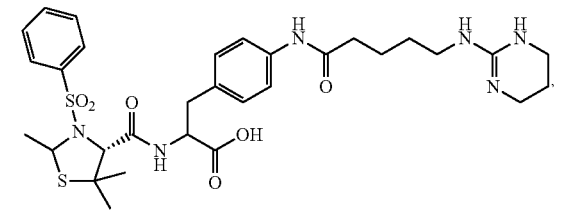
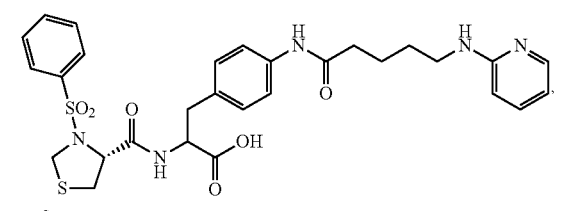
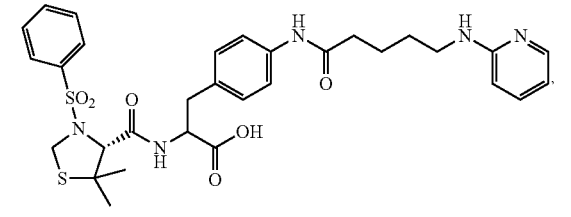
236
-continued
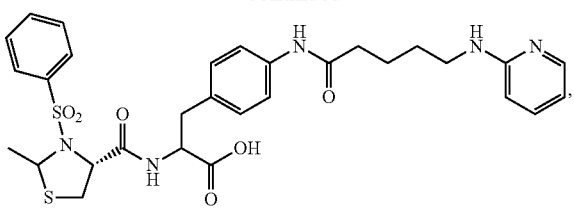
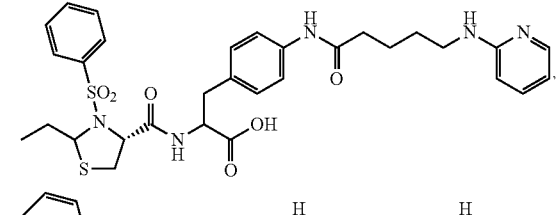
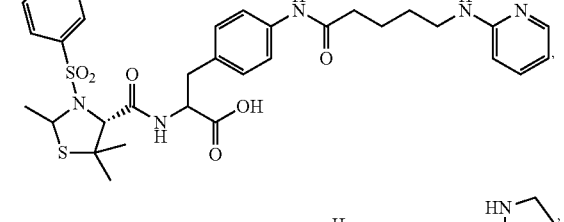
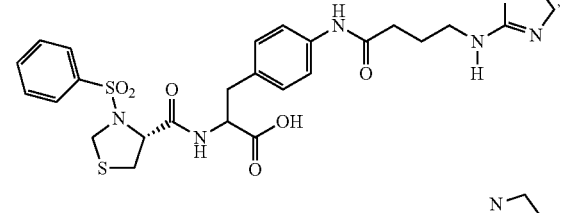
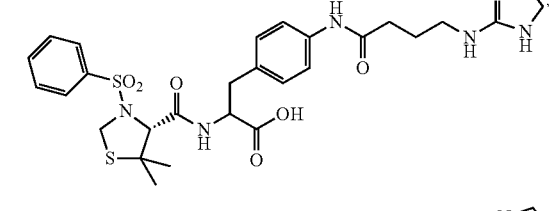
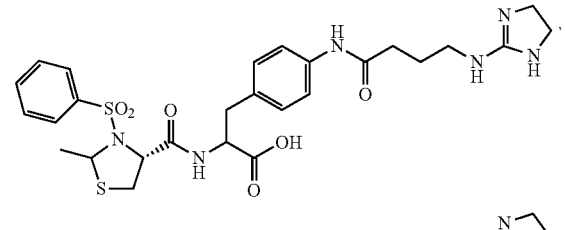
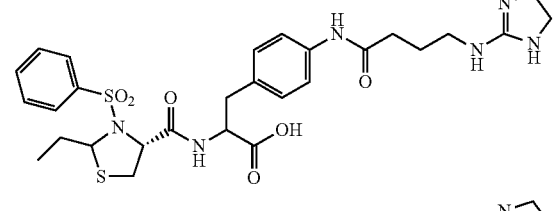
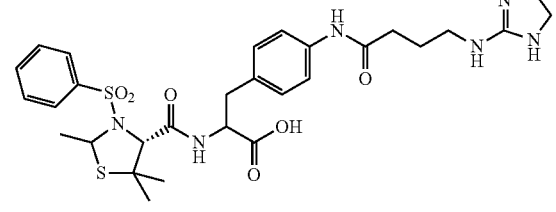

-continued
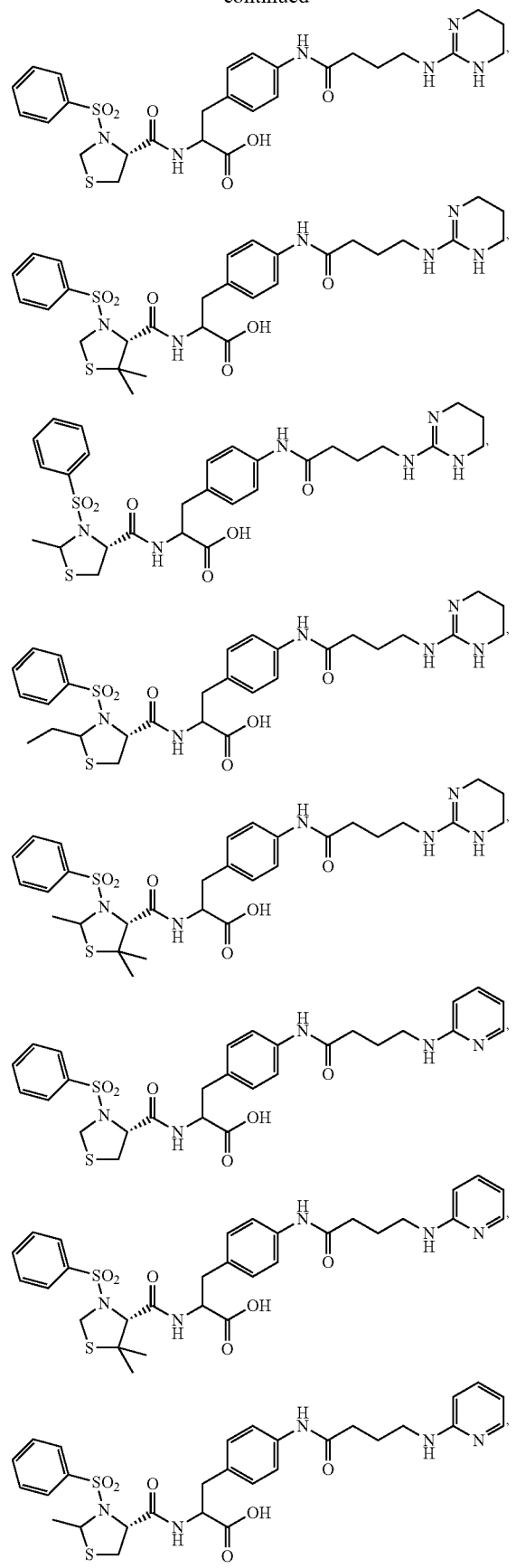
-continued
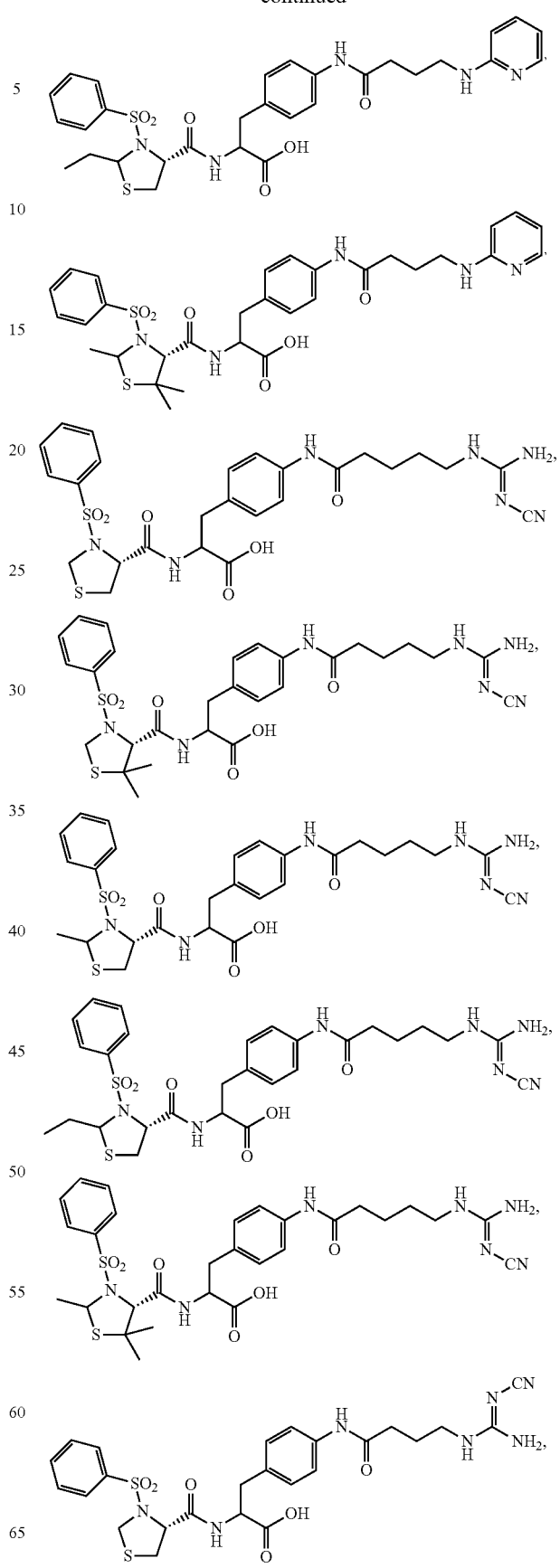

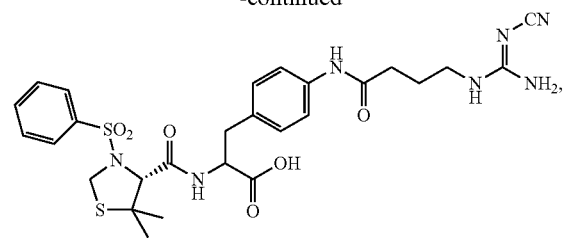
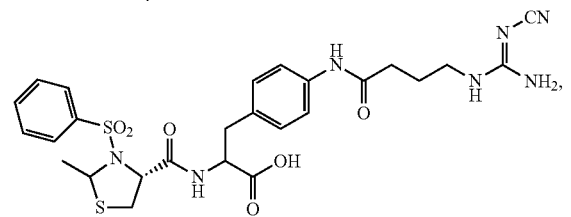
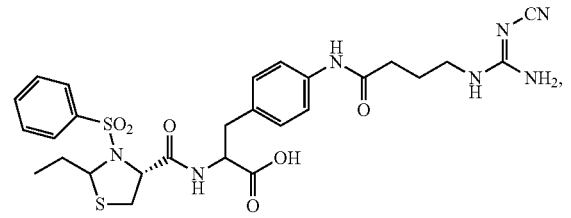
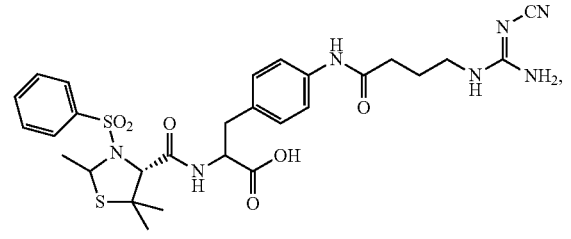
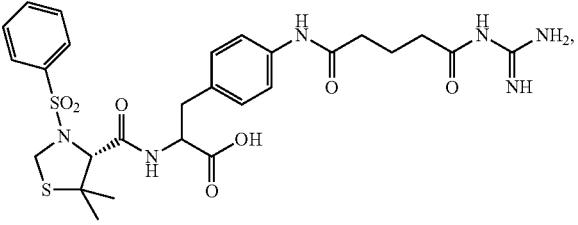
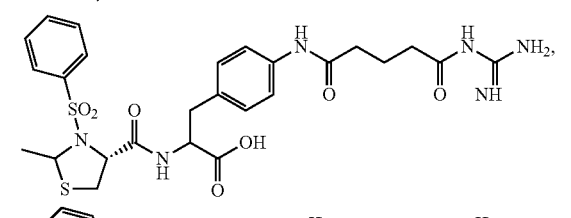
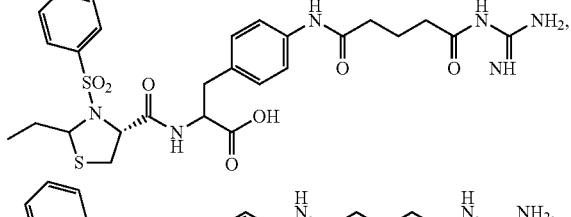
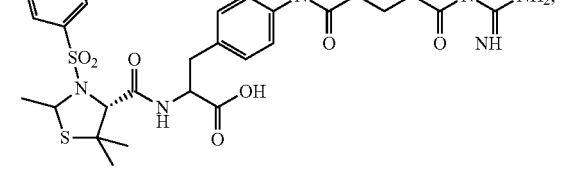
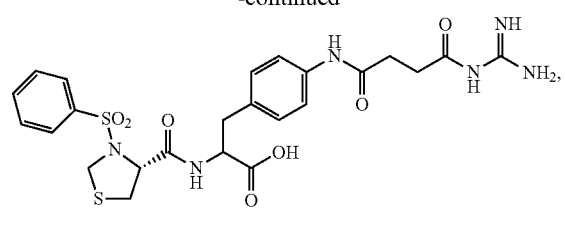
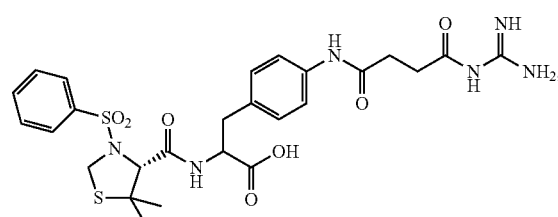
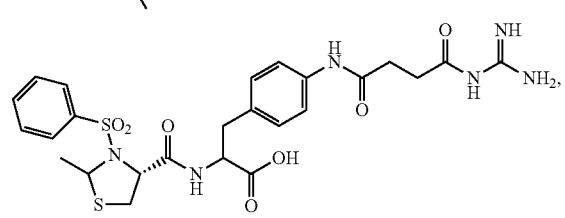
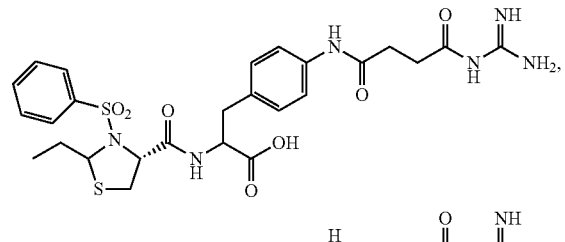
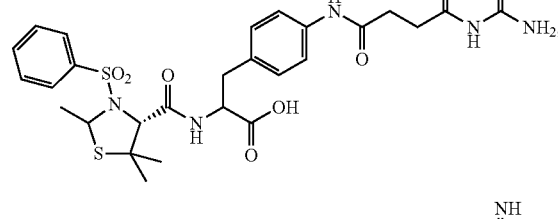
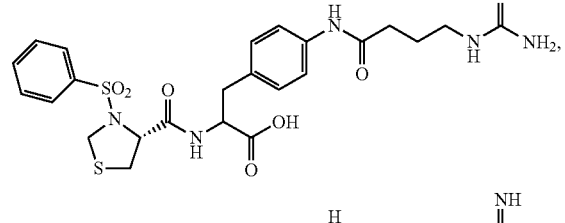
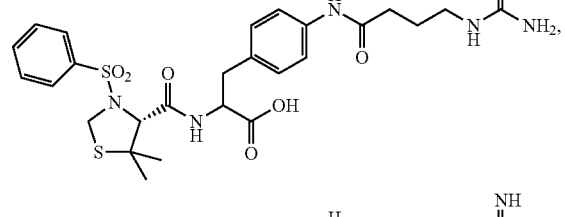
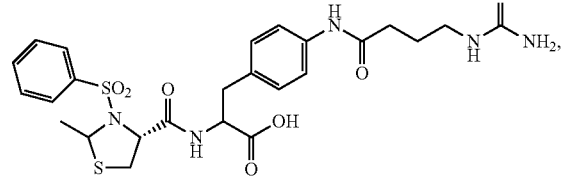

-continued

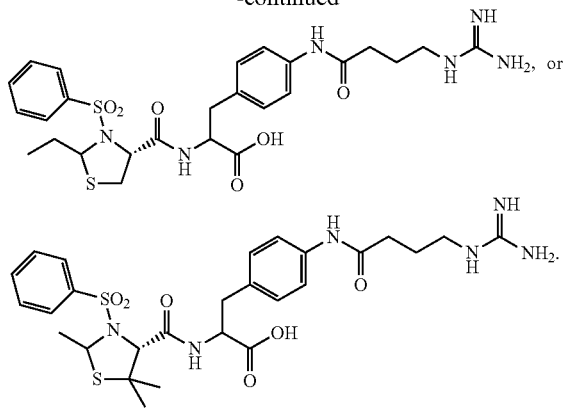

Embodiment P42

The compound of embodiment 19 having the formula:

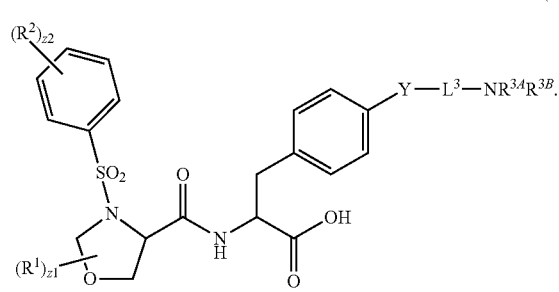
(IV)

Embodiment P43

The compound of embodiment 42 having the formula:

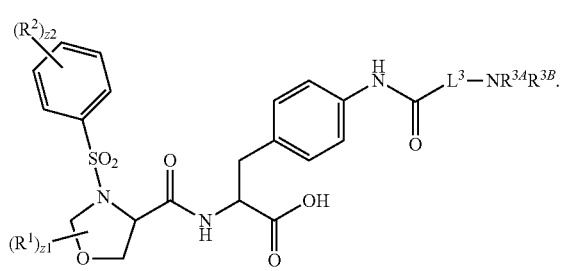
(IVa)

Embodiment P44

The compound of embodiment 43, wherein $L^3$ is substituted or unsubstituted $C_1$-$C_6$ alkylene, or substituted or unsubstituted 2 to 6 membered heteroalkylene.

Embodiment P45

The compound of embodiment 44, wherein $R^1$ is hydrogen or substituted or unsubstituted $C_1$-$C_3$ alkyl.

Embodiment P46

The compound of embodiment 45, wherein $R^2$ is hydrogen.

Embodiment P47

The compound of embodiment 46, wherein $R^{3A}$ and $R^{3B}$ are independently hydrogen, —C(NH)NH$_2$, —C(NCN)NH$_2$, or substituted or unsubstituted heterocycloalkyl, or substituted or unsubstituted heteroaryl.

Embodiment P48

The compound of embodiment 43 having formula:

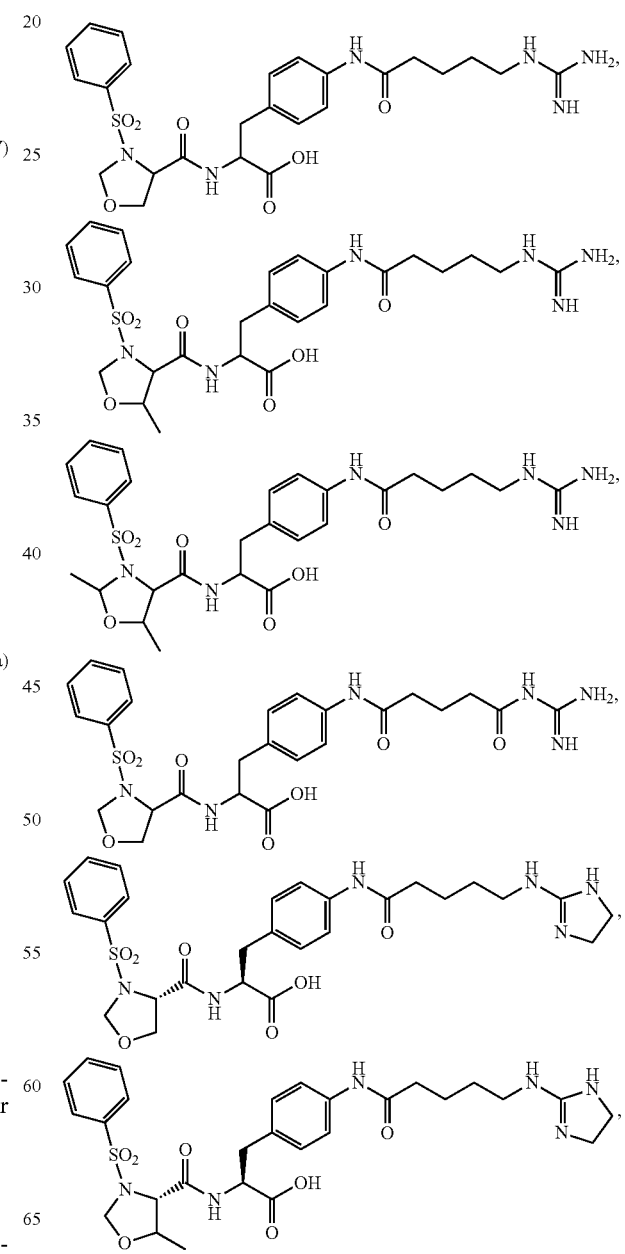

243
-continued
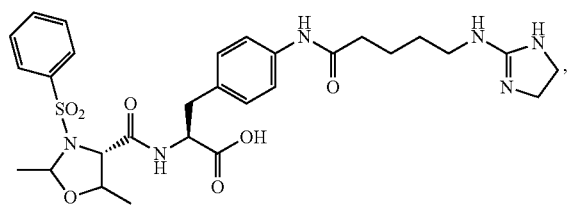
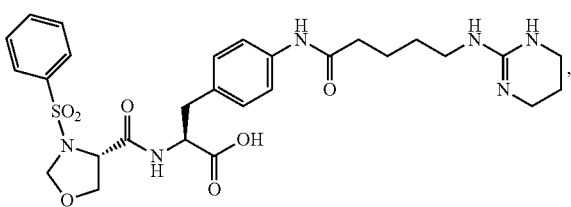
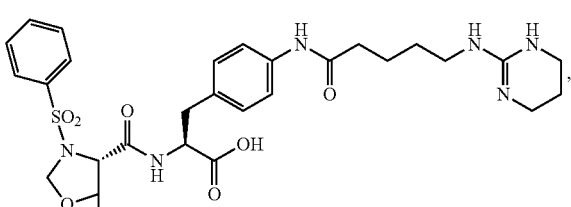
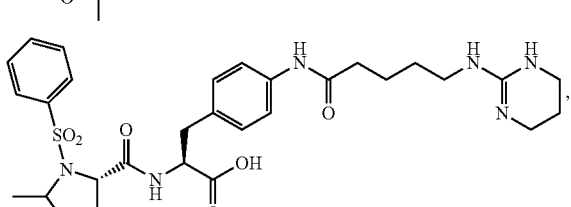
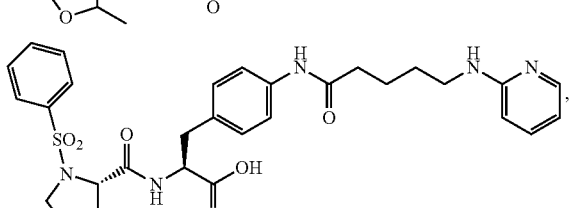
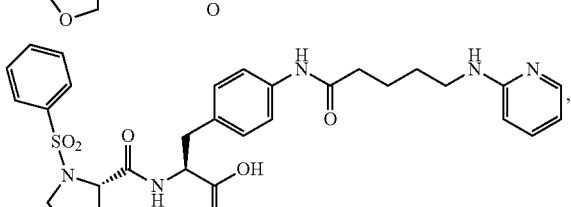
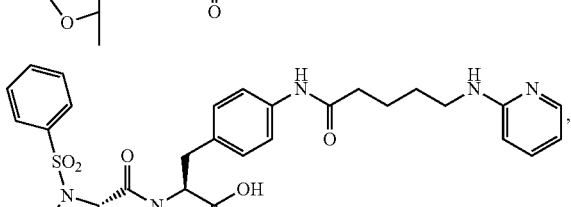
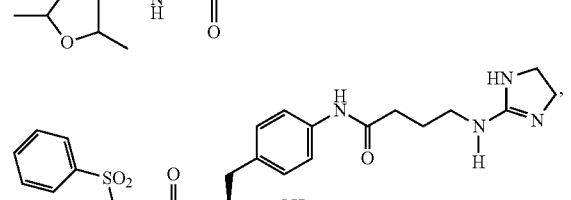
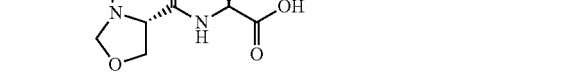
244
-continued
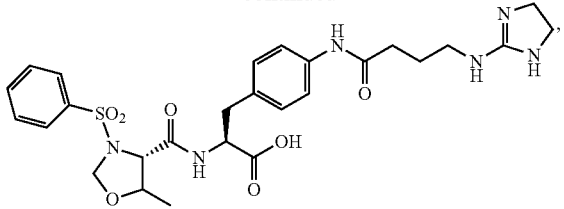
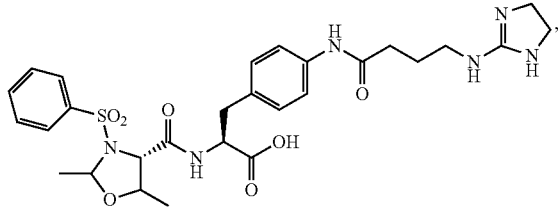
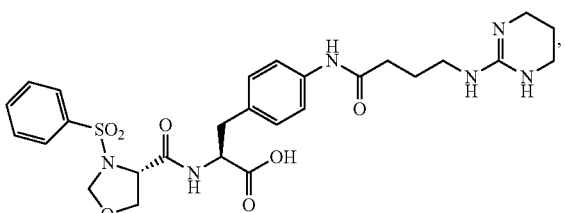
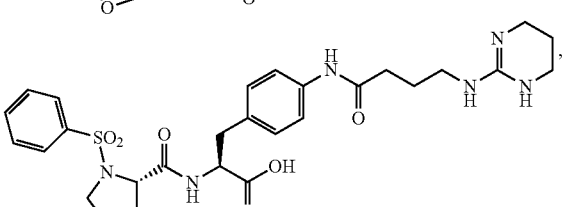
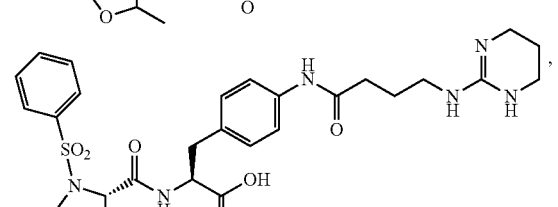
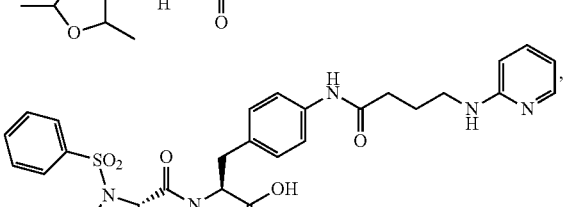
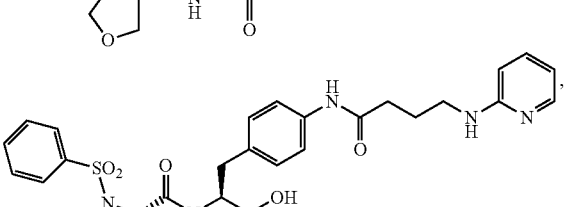
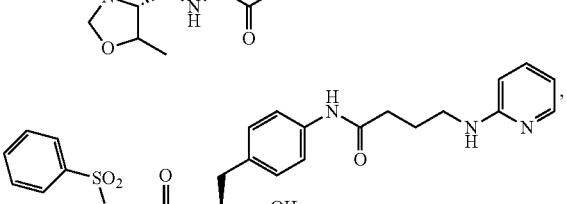
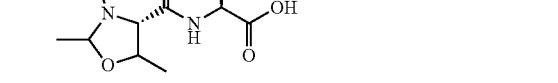

-continued
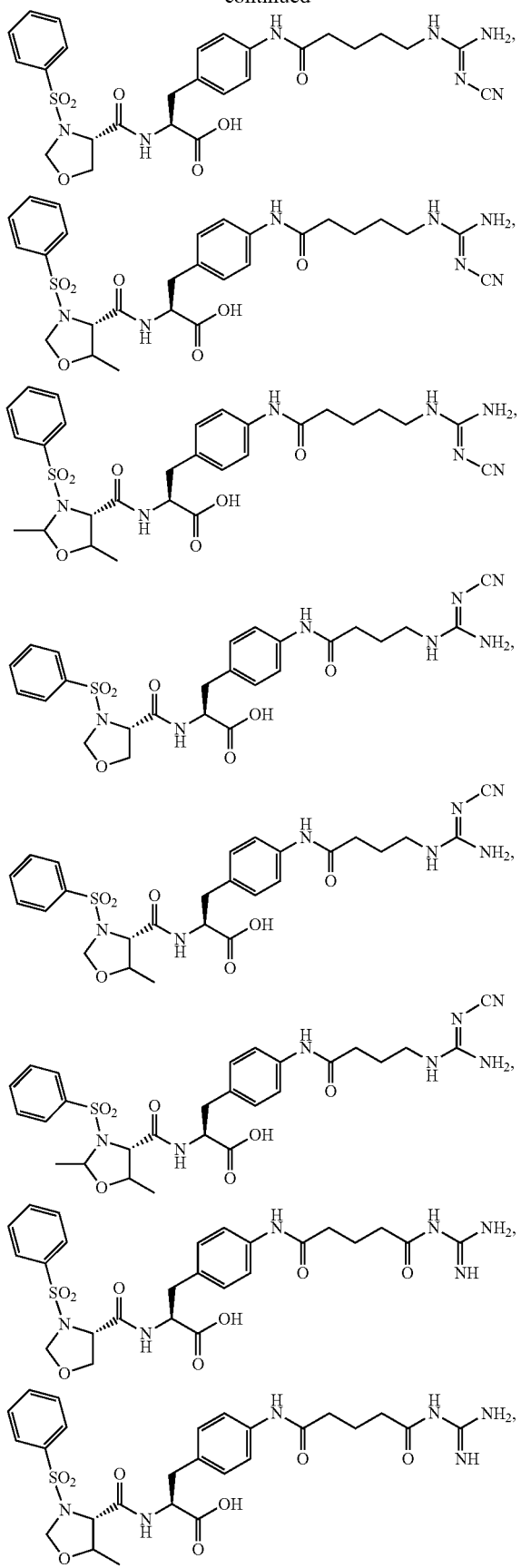
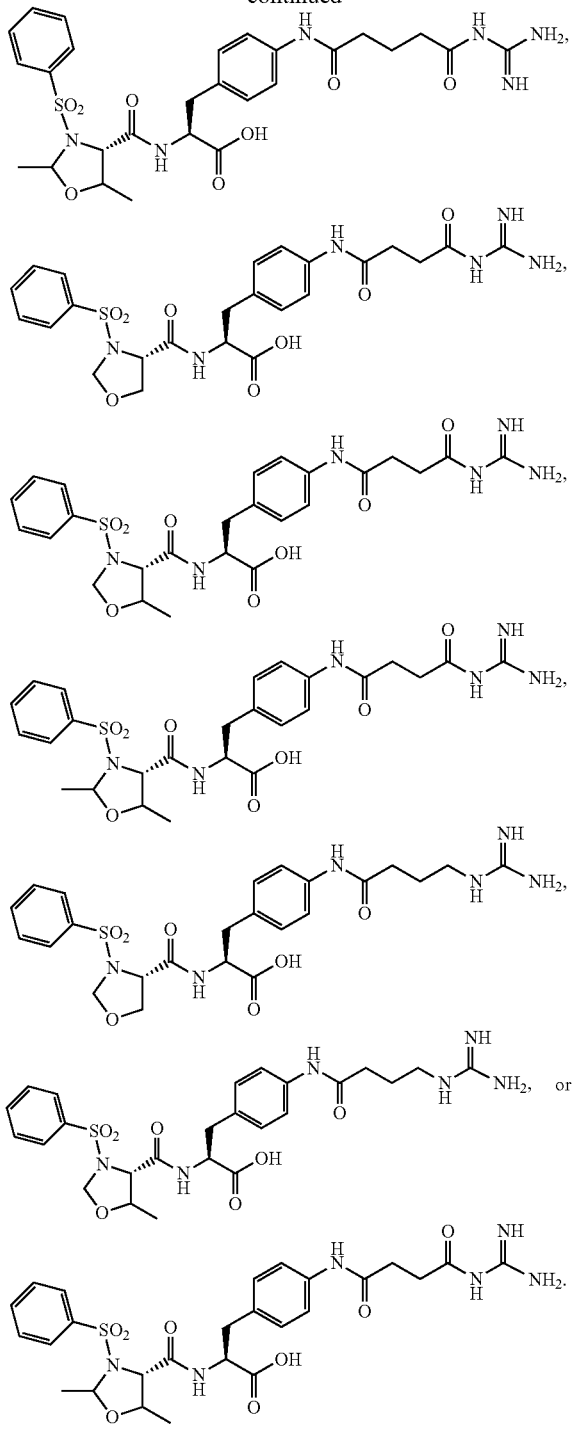
Embodiment P49
A pharmaceutical composition comprising the compound of any one of embodiments 19 to 48 and a pharmaceutically acceptable excipient.
Embodiment P50
A method of detecting αvβ1 expression in a cell, the method comprising; (i) contacting a cell with an αvβ1- specific compound; (ii) allowing the αvβ1-specific compound to bind to the cell; and (iii) detecting the αvβ1-specific compound, thereby detecting αvβ1 expression in a cell.

Embodiment P51

The method of embodiment 50, wherein the αvβ1-specific compound is a compound having the formula of a compound of embodiment 19.

Embodiment P52

A method of inhibiting TGFβ activation, the method comprising: (i) contacting a cell expressing αvβ1 integrin with an αvβ1 inhibitor-compound; and (ii) allowing the compound to bind to αvβ1 in the presence of TGFβ; (iii) comparing a level of activated TGFβ to a control to thereby identify a lower level of TGFB activation and inhibition of TGFβ activation.

Embodiment P52

The method of embodiment 52, wherein the αvβ1 inhibitor-compound is a compound having the formula of a compound of embodiment Error! Reference source not found.

Embodiment P52

The method of embodiment 52, wherein the cell is a skin myofibroblast, a lung myofibroblast, or a hepatic myofibroblast.

Embodiment 1

A compound having the formula:

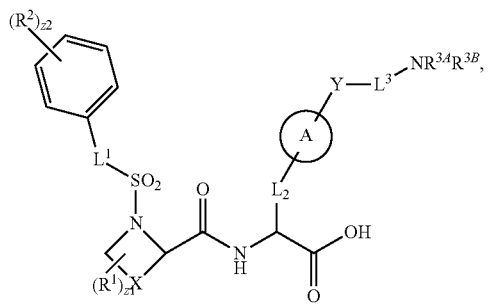

(I)

Ring A is cycloalkyl, heterocycloalkyl, aryl, or heteroaryl. $L^1$ and $L^2$ are independently a bond or substituted or unsubstituted $C_1$-$C_{10}$ alkylene. $L^3$ is a bond, substituted or unsubstituted $C_1$-$C_{10}$ alkylene, substituted or unsubstituted 2 to 10 membered heteroalkylene, substituted or unsubstituted cycloalkylene, substituted or unsubstituted heterocycloalkylene, or substituted or unsubstituted alkylarylene. X is a bond, —C—, —C—C—, —C=C—, —C—C—C—, —C=C—C—, —C—C=C—, —O—C—, —C—O—, —C—O—C, —S—C—, —C—S—, —C—S—C—. Y is a bond, —C(O)N($R^4$)—, —O—, —C(O)O—, —S—, —N($SO_2$—$R^4$)—, —N(C(O)$R^4$)—, —N(C(O)O$R^4$)—, —(N$R^4$)C(O)—, —N($R^4$)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^1$ is independently halogen, oxo, —$N_3$, —$CF_3$, —$CCl_3$, —$CBr_3$, —$CI_3$, —CN, —CHO, —OH, —$NH_2$, —COOH, —CON$H_2$, —$NO_2$, —SH, —$SO_2$, —$SO_2$Cl, —$SO_2CH_3$— $SO_3$H, —O$SO_3$H, —$SO_2NH_2$, —NHN$H_2$, —ON$H_2$, —NHC(O)NHN$H_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety. $R^2$ is independently halogen, —$N_3$, —$CF_3$, —$CCl_3$, —$CBr_3$, —$CI_3$, —CN, —CHO, —OH, —$NH_2$, —COOH, —CON$H_2$, —$NO_2$, —SH, —$SO_2$, —$SO_2$Cl, —$SO_2CH_3$—$SO_3$H, —O$SO_3$H, —$SO_2NH_2$, —NHN$H_2$, —ON$H_2$, —NHC(O)NHN$H_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety, or wherein if z2 an integer of 2 to 5, two $R^2$ substituents attached to adjacent ring carbons are optionally joined to form a substituted or unsubstituted aryl or substituted or unsubstituted heteroaryl. $R^{3A}$ and $R^{3B}$ are independently hydrogen, —C(NH)N$H_2$, —C(NH)$R^{3D}$, —C(N$R^{3C}$)N$H_2$, —C(N$R^{3C}$)$R^{3D}$, —C(NCN)N$H_2$, NH, N$H_2$, —C(NH)NH$R^{3D}$, —C(N$R^{3C}$)NH$R^{3D}$, —C(NCN)NH$R^{3D}$, substituted or unsubstituted cycloalkyl, substituted or unsubstituted heterocycloalkyl, substituted or unsubstituted aryl, substituted or unsubstituted heteroaryl, or $R^{3A}$ and $R^{3B}$ are optionally joined to form a substituted or unsubstituted heterocycloalkyl or substituted or unsubstituted heteroaryl. $R^{3C}$ and $R^{3D}$ are independently hydrogen, halogen, oxo, —$N_3$, —$CF_3$, —$CCl_3$, —$CBr_3$, —$CI_3$, —CN, —CHO, —OH, —$NH_2$, —COOH, —CON$H_2$, —$NO_2$, —SH, —$SO_2$, —$SO_2$Cl, —$SO_2CH_3$—$SO_3$H, —$SO_4$H, —$SO_2NH_2$, —NHN$H_2$, —ON$H_2$, —NHC(O)NHN$H_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^4$ is independently hydrogen or unsubstituted $C_1$-$C_5$ alkyl. z1 is an integer from 1 to 9. z2 is an integer from 1 to 5.

Embodiment 1a

A compound having the formula:

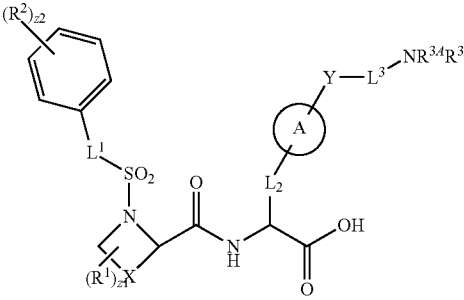

(I)

wherein, Ring A is cycloalkyl, heterocycloalkyl, aryl, or heteroaryl. $L^1$ and $L^2$ are independently a bond or substituted or unsubstituted $C_1$-$C_{10}$ alkylene. $L^3$ is a bond, substituted or unsubstituted $C_1$-$C_{10}$ alkylene, substituted or unsubstituted 2 to 10 membered heteroalkylene, substituted or unsubstituted cycloalkylene, substituted or unsubstituted heterocycloalkylene, or substituted or unsubstituted alkylarylene. X is a bond, —C—, —C—C—, —C═C—, —C—C—C—, —C═C—C—, —C—C═C—, —O—C—, —C—O—, —C—O—C, —S—C—, —C—S—, —C—S—C—. Y is a bond, —C(O)N(R$^4$)—, —O—, —C(O)O—, —S—, —N(SO$_2$—R$^4$)—, —N(C(O)R$^4$)—, —N(C(O)OR$^4$)—, —(NR$^4$)C(O)—, —N(R$^4$)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. R$^1$ and R$^2$ are independently halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_2$CH$_3$— SO$_3$H, —OSO$_3$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety. R$^{3A}$ and R$^{3B}$ are independently hydrogen, —C(NH)NH$_2$, —C(NCN)NH$_2$, substituted or unsubstituted cycloalkyl, substituted or unsubstituted heterocycloalkyl, substituted or unsubstituted aryl, substituted or unsubstituted heteroaryl, or R$^{3A}$ and R$^{3B}$ are optionally joined to form a substituted or unsubstituted heterocycloalkyl or substituted or unsubstituted heteroaryl. R$^4$ is independently hydrogen or unsubstituted C$_1$-C$_5$ alkyl. z1 is an integer from 1 to 9. z2 is an integer from 1 to 5.

Embodiment 2

The compound of embodiment 1, wherein L$^1$ is a bond.

Embodiment 3

The compound of embodiment 1 or embodiment 2, wherein L$^2$ is unsubstituted methylene.

Embodiment 4

The compound of any one of embodiments 1 to 3, wherein L$^3$ is substituted or unsubstituted C$_1$-C$_5$ alkylene, substituted, unsubstituted 2 to 6 membered heteroalkylene, or substituted or unsubstituted alkylarylene.

Embodiment 5

The compound of any one of embodiments 1 to 4, wherein L$^3$ is R$^6$-substituted C$_1$-C$_3$ alkylene. R$^6$ is —NHC(O)R$^{6A}$. R$^{6A}$ is —C(NCN)R$^{6C}$, —C(NH)R$^{6C}$, R$^{3C}$-substituted or unsubstituted alkyl, or R$^{3C}$-substituted or unsubstituted heteroalkyl. R$^{3C}$ hydrogen, halogen, oxo, —N$_3$, —CF$_3$, —CCl$_3$, —CBr$_3$, —CI$_3$, —CN, —COR$^{6D}$, —OR$^{6D}$, —NR$^{6D}$R$^{6E}$, —COOR$^{6E}$, —CONR$^{6D}$R$^{6E}$, —NHC(O)R$^{6D}$, —NO$_2$, —SR$^{6D}$, —SO$_{n6}$R$^{6D}$, —NHNR$^{6D}$R$^{6E}$, —ONR$^{6D}$R$^{6E}$, —NHC(O)NHNR$^{6D}$R$^{6E}$, —C(NCN)R$^{6D}$, —SR$^{6D}$, —C(NH)R$^{6D}$, R$^{6F}$-substituted or unsubstituted alkyl, R$^{6F}$-substituted or unsubstituted heteroalkyl, R$^{6F}$-substituted or unsubstituted cycloalkyl, R$^{6F}$-substituted or unsubstituted heterocycloalkyl, R$^{6F}$-substituted or unsubstituted aryl, or R$^{6F}$-substituted or unsubstituted heteroaryl. n6 is 2, 3, or 4. R$^{6D}$, R$^{6E}$ and R$^{6F}$ are independently hydrogen, halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety.

Embodiment 6

The compound of any one of embodiments 1 to 5, wherein R$^{6C}$ or R$^{6D}$ is a detectable moiety.

Embodiment 7

The compound of any one of embodiments 1 to 6, wherein X is —C—C—, —C═C—, —O—C—, —C—O—, —C—O—C—, —C—S—, —S—C, or —C—S—C—.

Embodiment 8

The compound of any one of embodiments 1 to 7, wherein Y is —NHC(O)—, —NCH$_3$—, —NC(O)CH$_3$—, —NC(O)OCH$_3$—, —N(SO$_2$CH$_3$)—, —S—, —O—, C(O)O—, substituted or unsubstituted 3 to 6 membered heterocycloalkylene, 4 to 6 membered unsubstituted heteroarylene, or unsubstituted 5 or 6 membered arylene.

Embodiment 9

The compound of any one of embodiments 1 to 8, wherein R$^1$ is independently hydrogen, oxo, substituted or unsubstituted C$_1$-C$_5$ alkyl, or a detectable moiety.

Embodiment 10

The compound of any one of embodiments 1 to 9, wherein R$^2$ is independently hydrogen, halogen, —CF$_3$, —CCl$_3$, —CBr$_3$, —CI$_3$, —NH$_2$, —NO$_2$, —SO$_2$CH$_3$, substituted or unsubstituted C$_1$-C$_5$ alkyl, substituted or unsubstituted 2 to 5 membered heteroalkyl, substituted or unsubstituted 5 or 6 membered aryl, or a detectable moiety.

Embodiment 11

The compound of any one of embodiments 1 to 10, wherein R$^{3A}$ and R$^{3B}$ are independently hydrogen, —C(NH)NH$_2$, —C(NCN)NH$_2$, substituted or unsubstituted heterocycloalkyl, substituted or unsubstituted heteroaryl, or joined to form a substituted or unsubstituted 5 or 6 membered heterocycloalkyl or substituted or unsubstituted 5 or 6 membered heteroaryl.

Embodiment 12

The compound of any one of embodiments 1 to 11 having the formula:

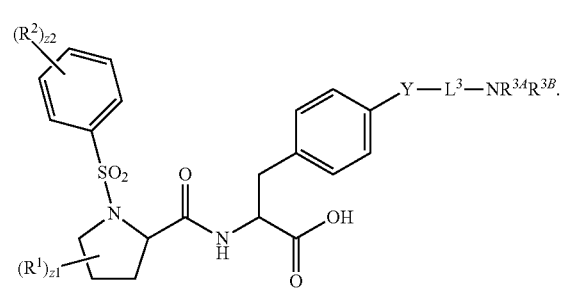

Embodiment 13

The compound of embodiment 12 having the formula:

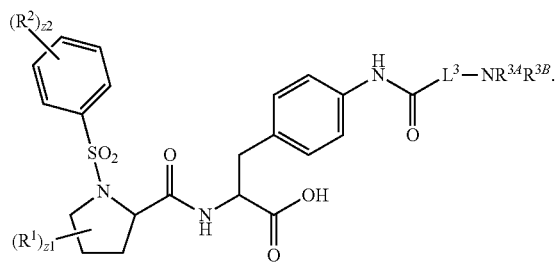

Embodiment 14

The compound of embodiment 12 or embodiment 13, wherein $L^3$ is substituted or unsubstituted $C_1$-$C_6$ alkylene, substituted or unsubstituted 2 to 6 membered heteroalkylene, alkylarylene.

Embodiment 15

The compound of any one of embodiments 12 to 14, wherein $R^1$ is hydrogen, substituted or unsubstituted methyl, or oxo.

Embodiment 16

The compound of any one of embodiments 12 to 15, wherein $R^2$ is hydrogen, halogen, —$SO_2CH_3$, —$NO_2$, —$NH_2$, substituted or unsubstituted $C_1$-$C_3$ alkyl, or substituted or unsubstituted 2 to 5 membered heteroalkyl.

Embodiment 17

The compound of any one of embodiments 12 to 16, wherein $R^{3A}$ and $R^{3B}$ are independently hydrogen, —C(NH)NH_2, —C(NCN)NH_2, or substituted or unsubstituted heterocycloalkyl, or substituted or unsubstituted heteroaryl.

Embodiment 18

The compound of any one of embodiments 12 to 17 having the formula:

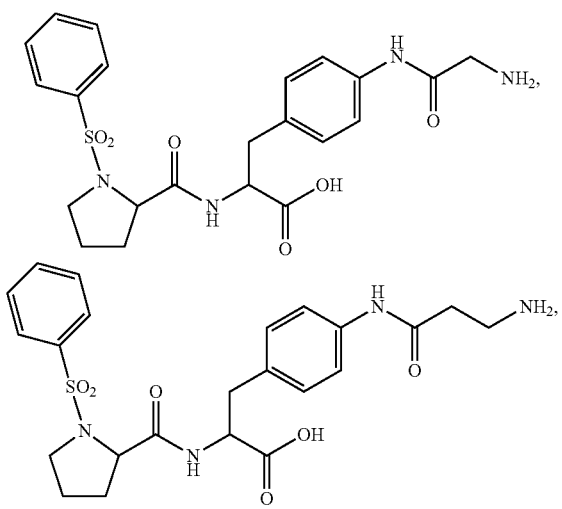

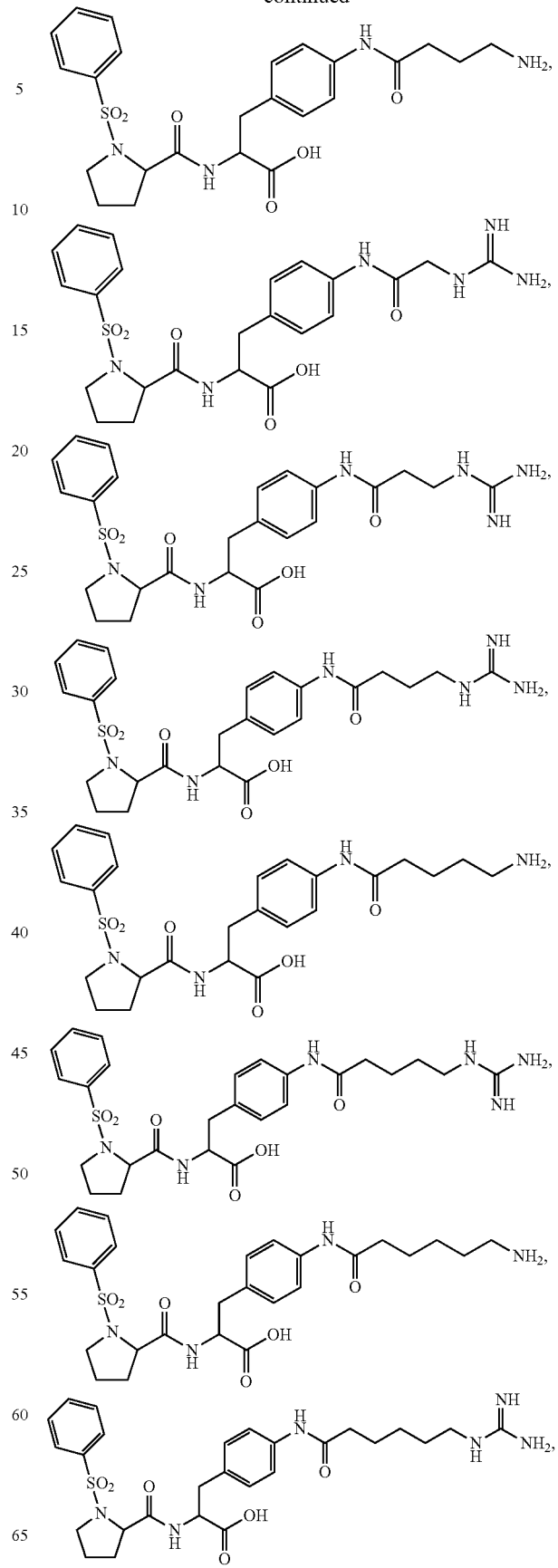

253
-continued
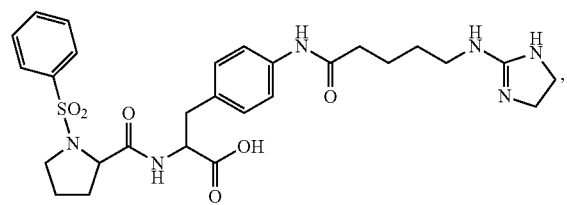
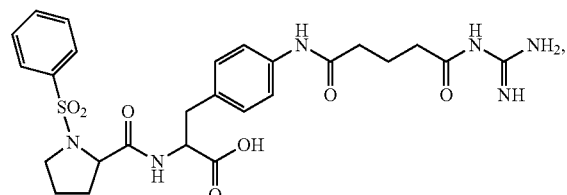
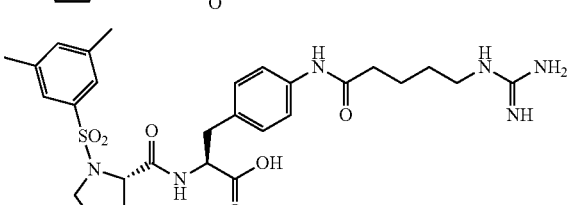
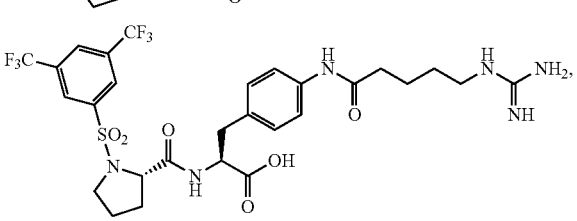
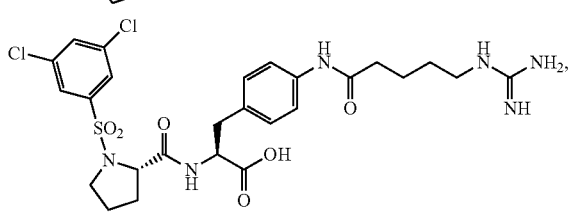
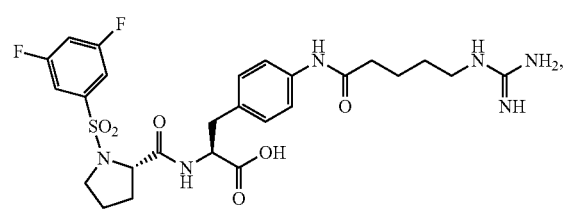
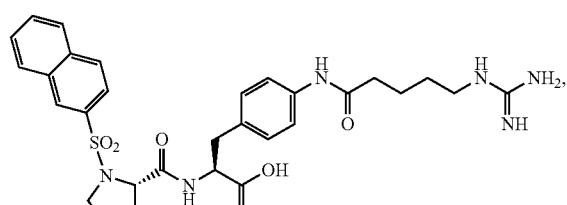
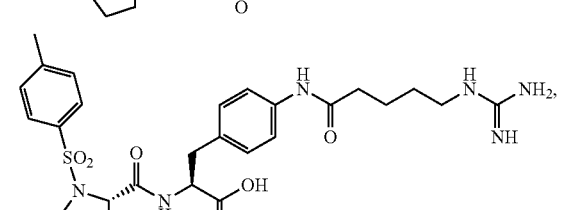
254
-continued
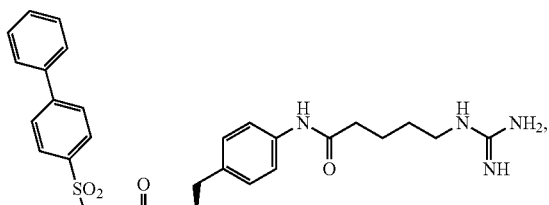
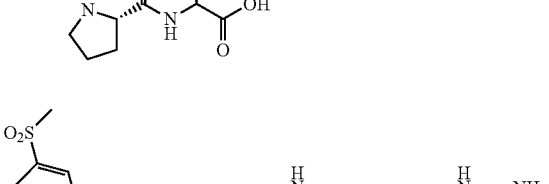
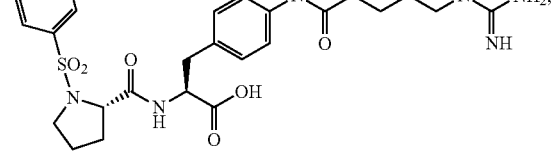
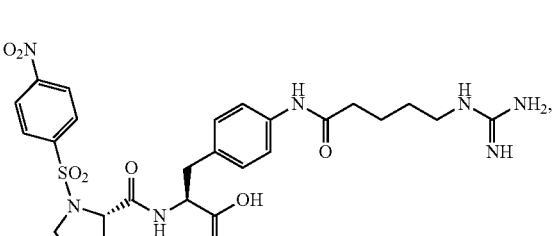
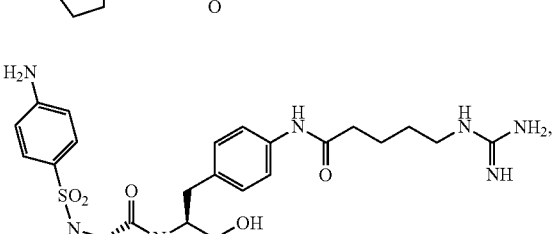
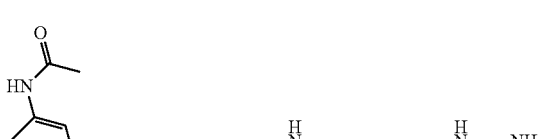
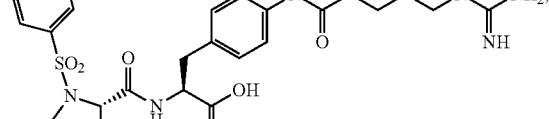
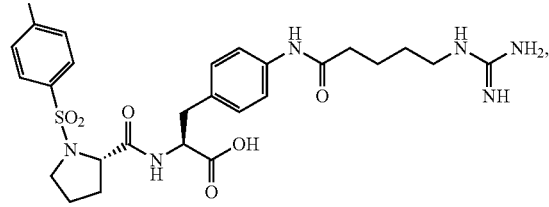

255
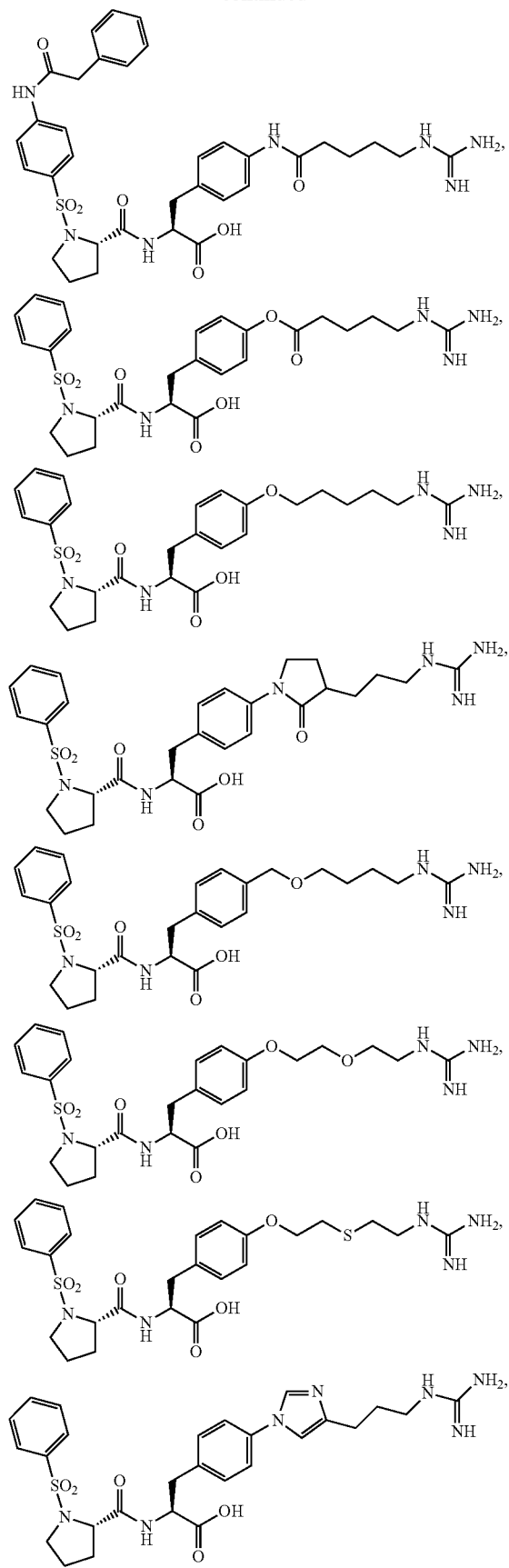
256
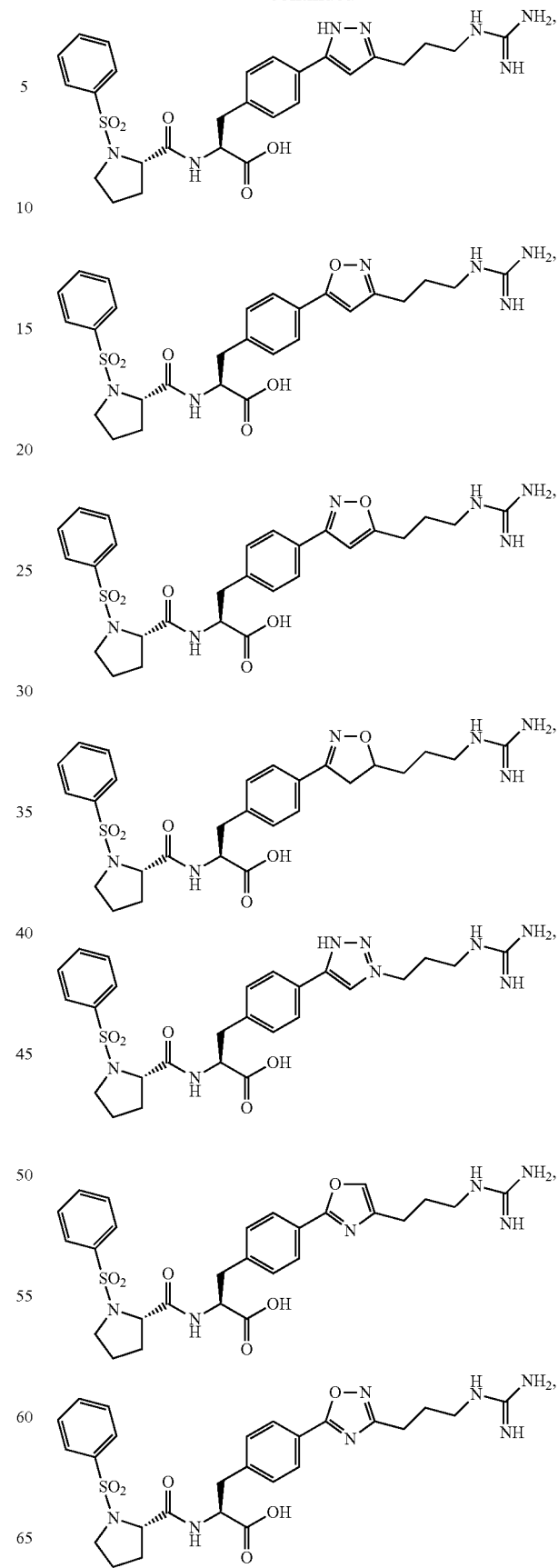

257
-continued
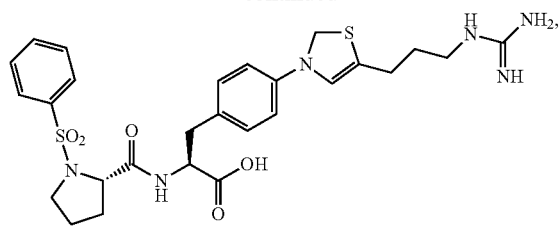
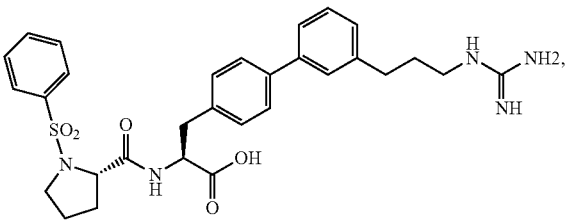
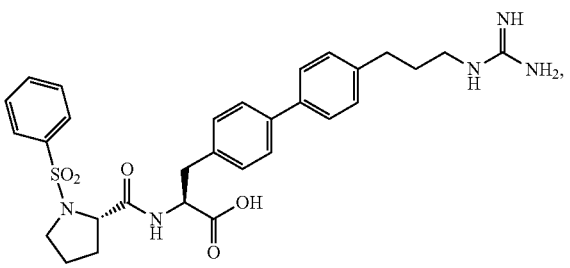
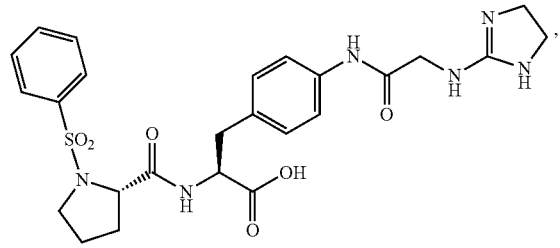
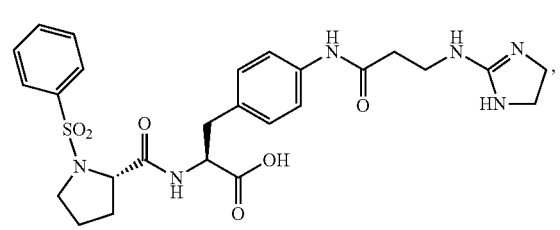
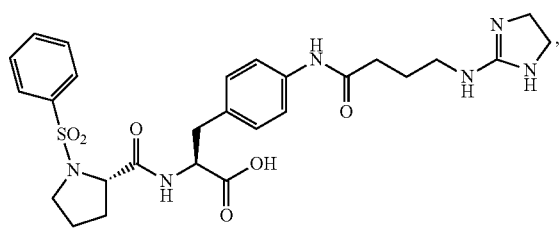
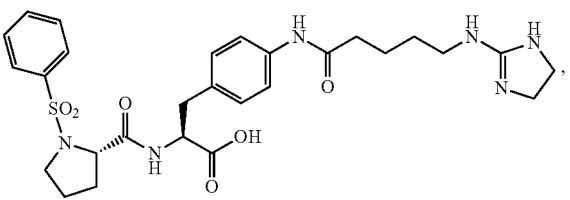
258
-continued
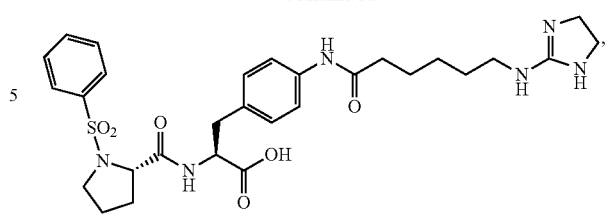
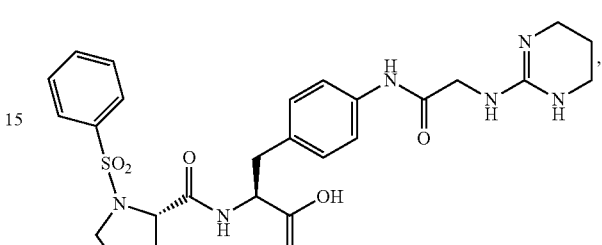
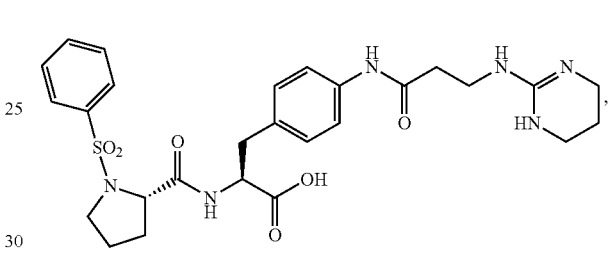
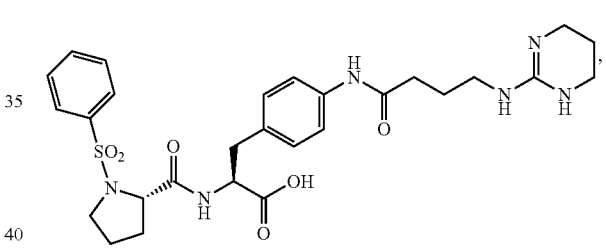
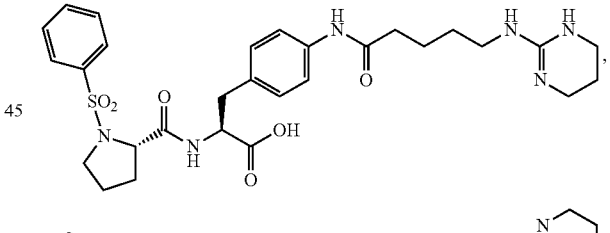
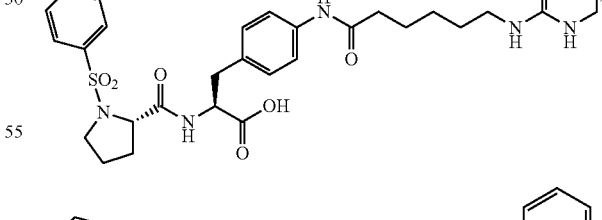

259
-continued
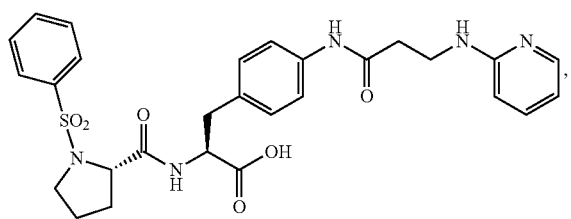,
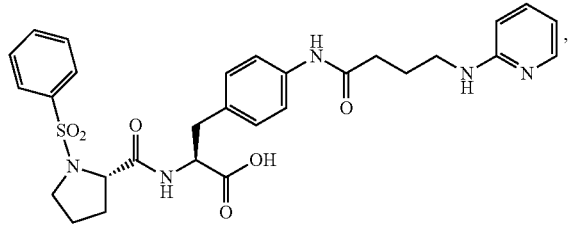,
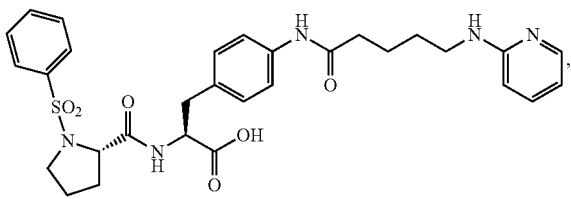,
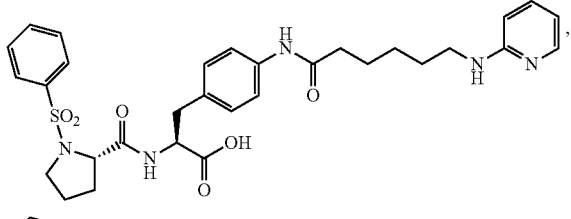,
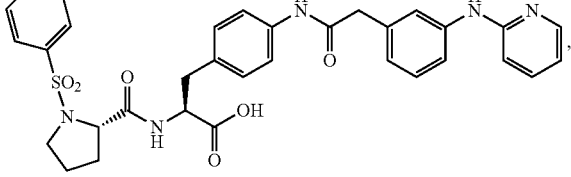,
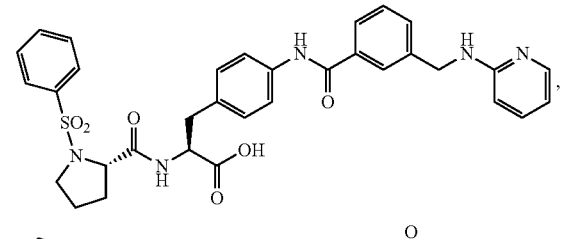,
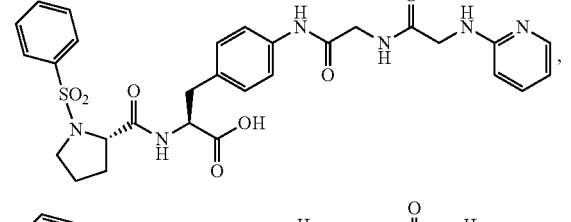,
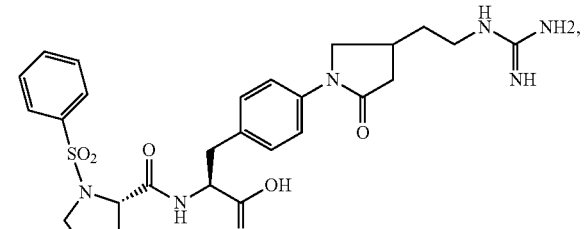,
260
-continued
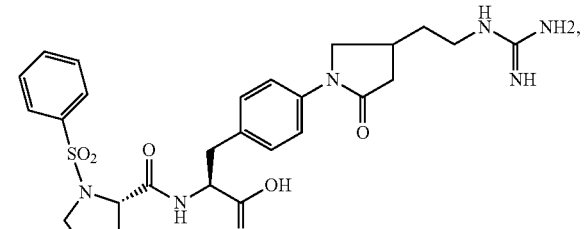,
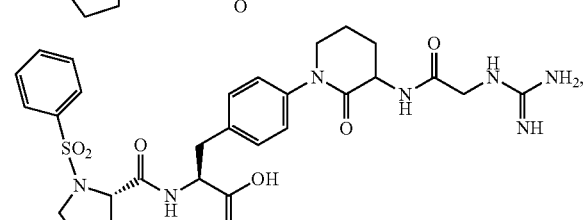,
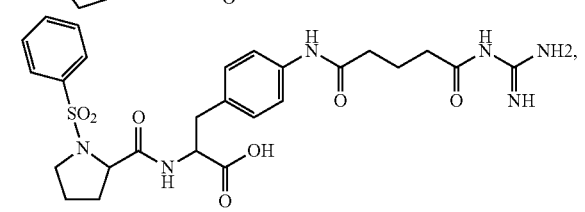,
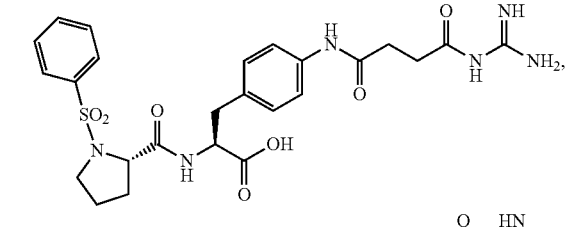,
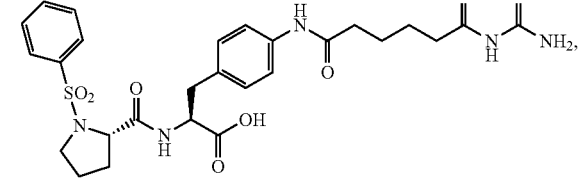,
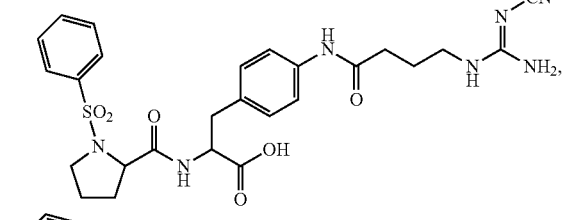,
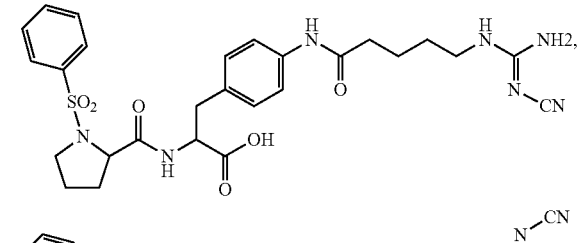, 261
-continued
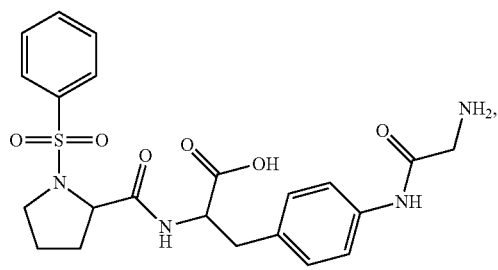
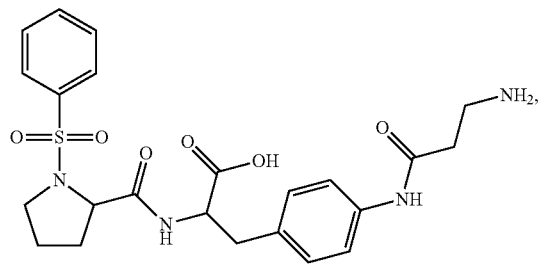
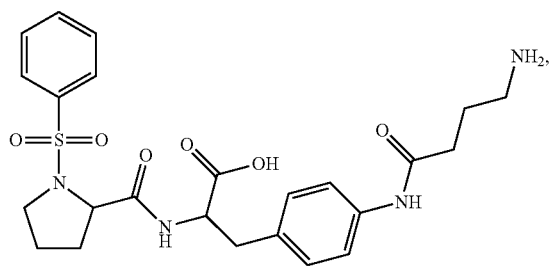
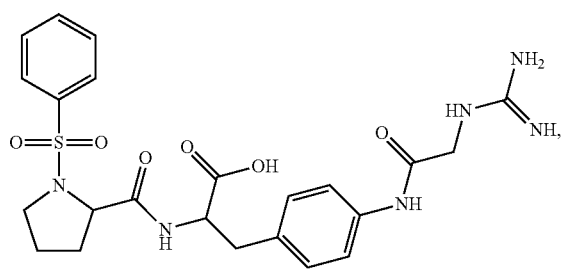
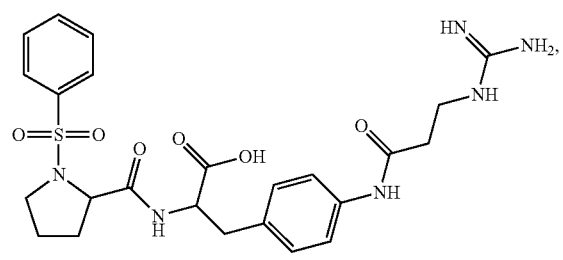
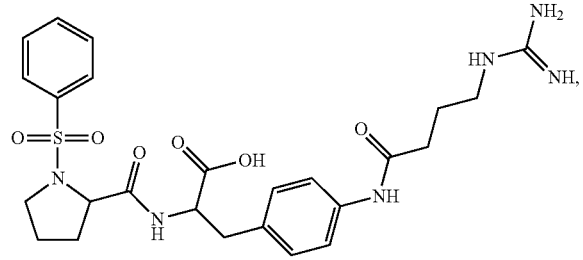
262
-continued
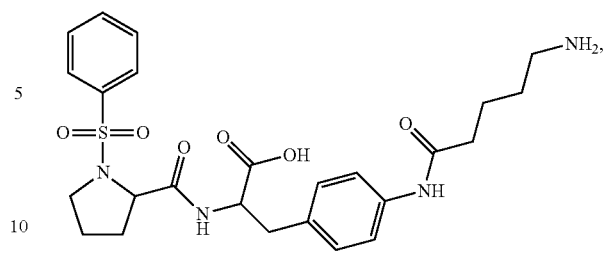
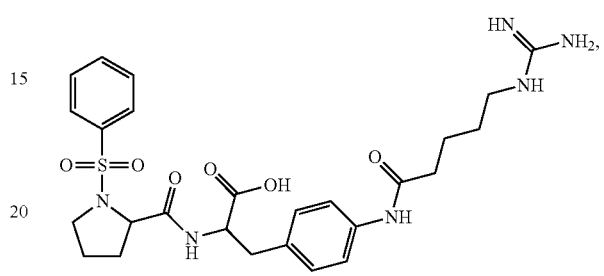
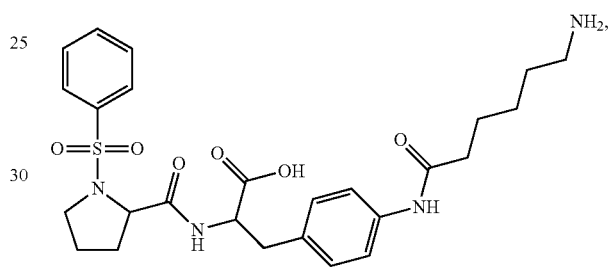
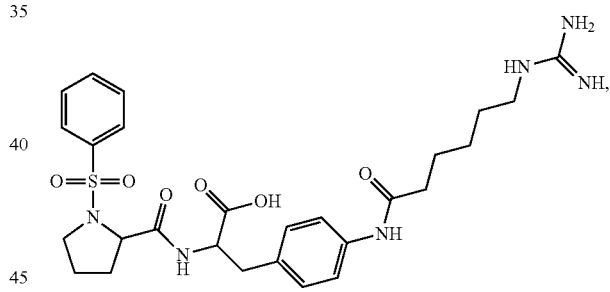
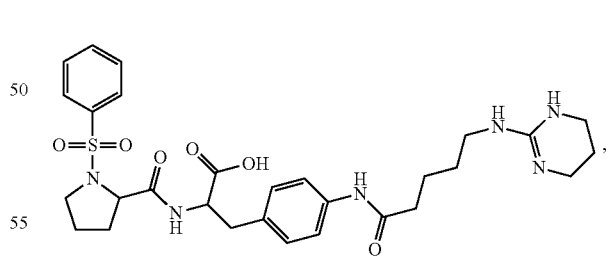
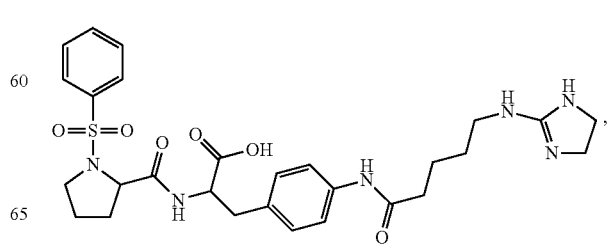

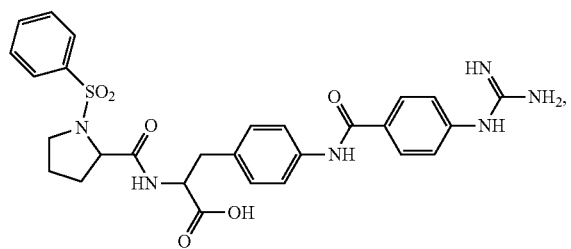
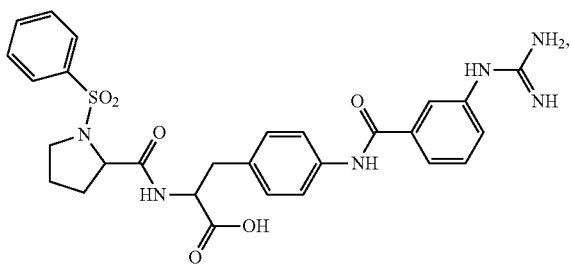
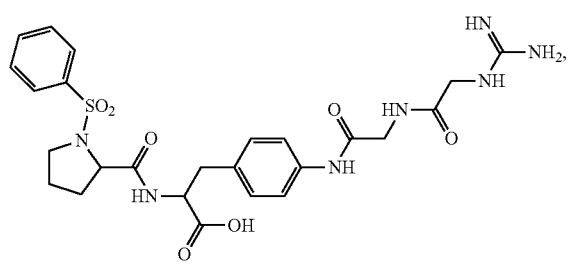
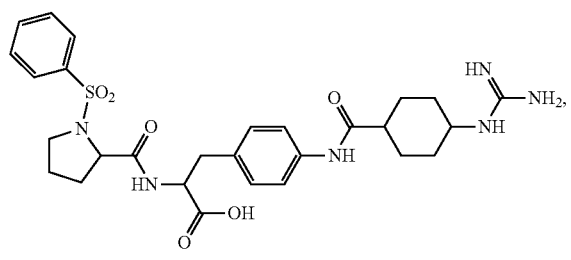
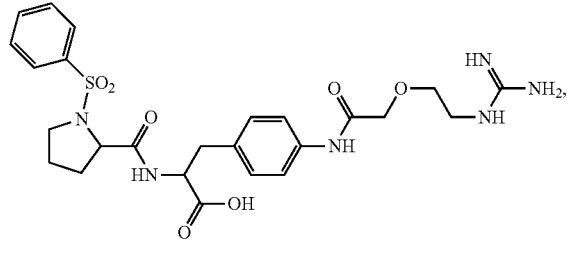
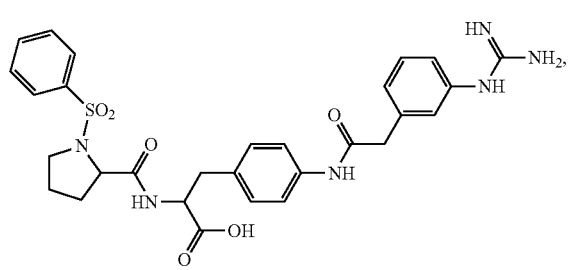
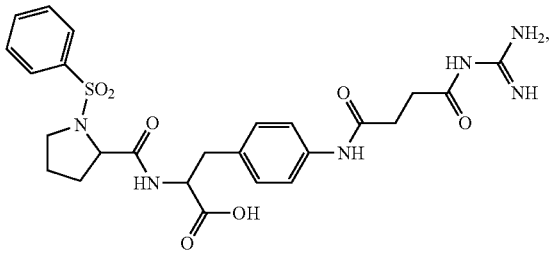
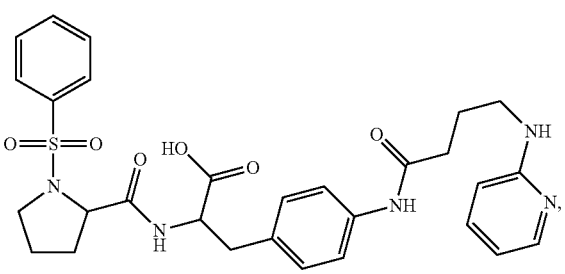
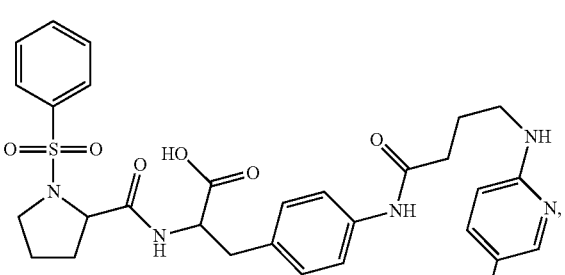
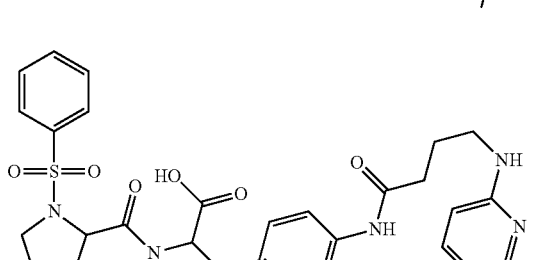
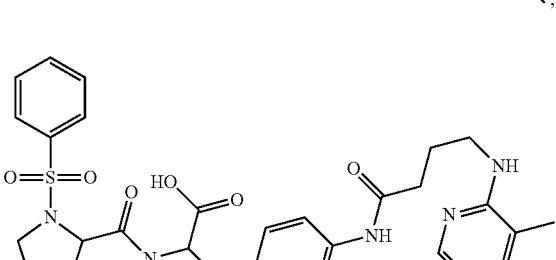
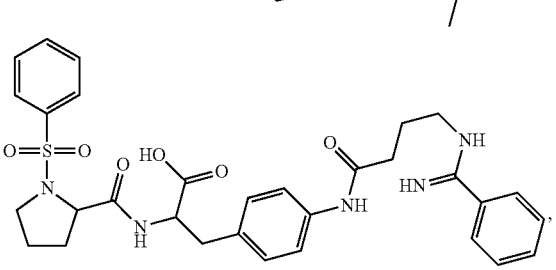

-continued

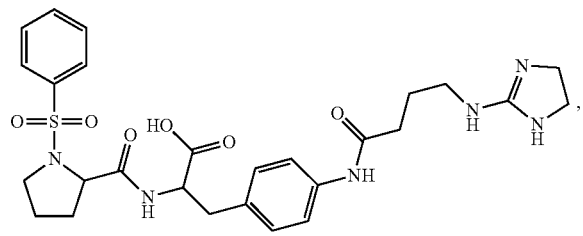

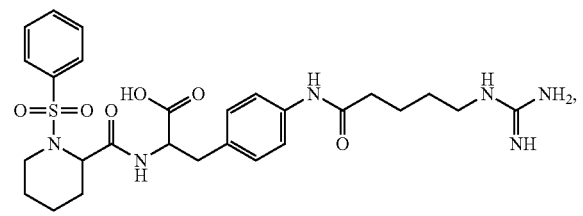

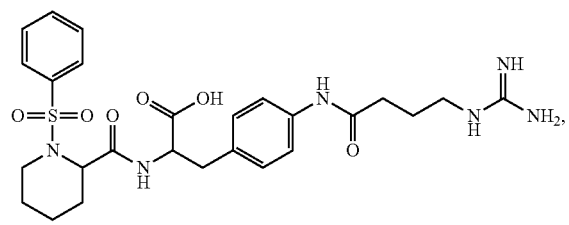

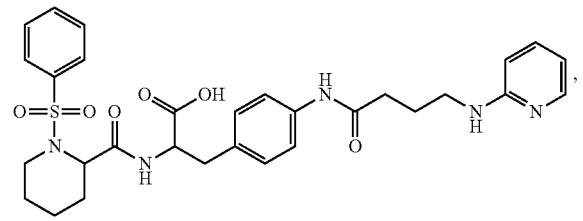

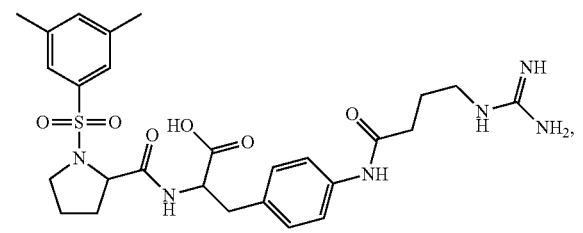

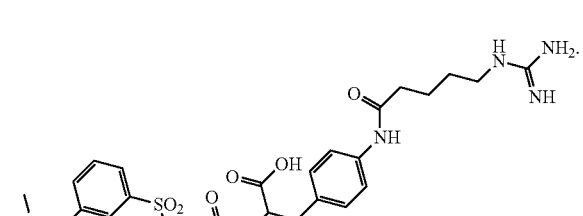

Embodiment 19

The compound of any one of embodiments 1 to 11 having the formula:

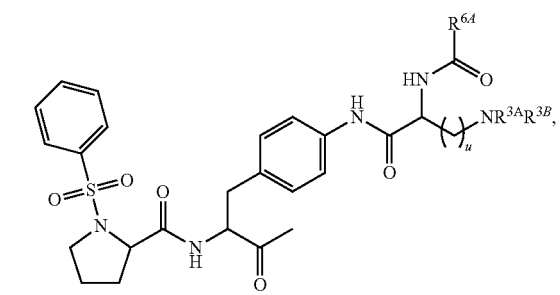

$R^{6A}$ is $R^{6C}$ substituted or unsubstituted alkyl or $R^{3C}$-substituted or unsubstituted heteroalkyl. $R^{6C}$ is —NR$^{6D}$R$^{6E}$, —NHC(O)R$^{6D}$, —C(NCN)R$^{6D}$, —C(NH)R$^{6D}$, $R^{6F}$-substituted or unsubstituted alkyl, $R^{6F}$-substituted or unsubstituted heteroalkyl, $R^{6F}$-substituted or unsubstituted cycloalkyl, $R^{6F}$-substituted or unsubstituted heterocycloalkyl, $R^{6F}$-substituted or unsubstituted aryl, or $R^{6F}$-substituted. $R^{6D}$ is a detectable moiety. $R^{6E}$ and $R^{6F}$ are independently hydrogen, halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —OSO$_3$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety. u is an integer of 1 to 7.

Embodiment 20

The compound of any one of embodiments 1 to 11 having the formula:

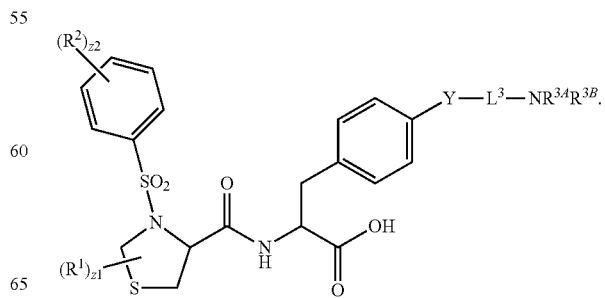

Embodiment 21

The compound of embodiment 20 having the formula:

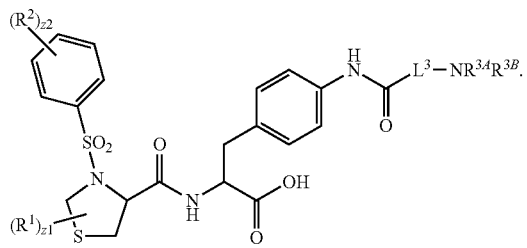

Embodiment 22

The compound of embodiment 20 or embodiment 21, wherein $L^3$ is substituted or unsubstituted $C_1$-$C_6$ alkylene, or substituted or unsubstituted 2 to 6 membered heteroalkylene.

Embodiment 23

The compound of any one of embodiments 20 to 22, wherein $R^1$ is hydrogen or substituted or unsubstituted $C_1$-$C_3$ alkyl.

Embodiment 24

The compound of any one of embodiments 20 to 23, wherein $R^2$ is hydrogen, halogen, —$SO_2CH_3$, —$NO_2$, —$NH_2$, substituted or unsubstituted $C_1$-$C_3$ alkyl, or substituted or unsubstituted 1 to 4 membered heteroalkyl.

Embodiment 25

The compound of any one of embodiments 20 to 24, wherein $R^{3A}$ and $R^{3B}$ are independently hydrogen, —C(NH)NH$_2$, —C(NCN)NH$_2$, or substituted or unsubstituted heterocycloalkyl, or substituted or unsubstituted heteroaryl.

Embodiment 26

The compound of any one of embodiments 20 to 25 having formula:

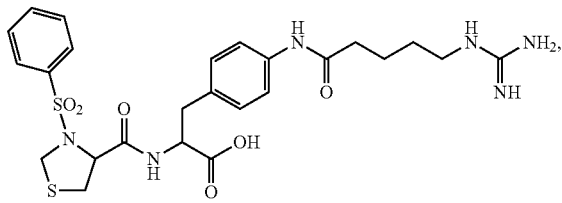

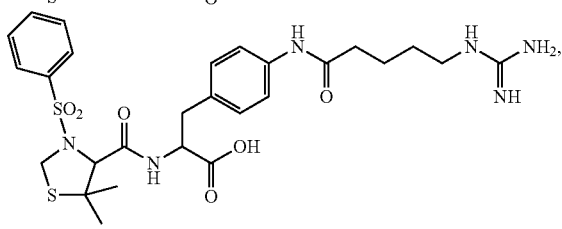

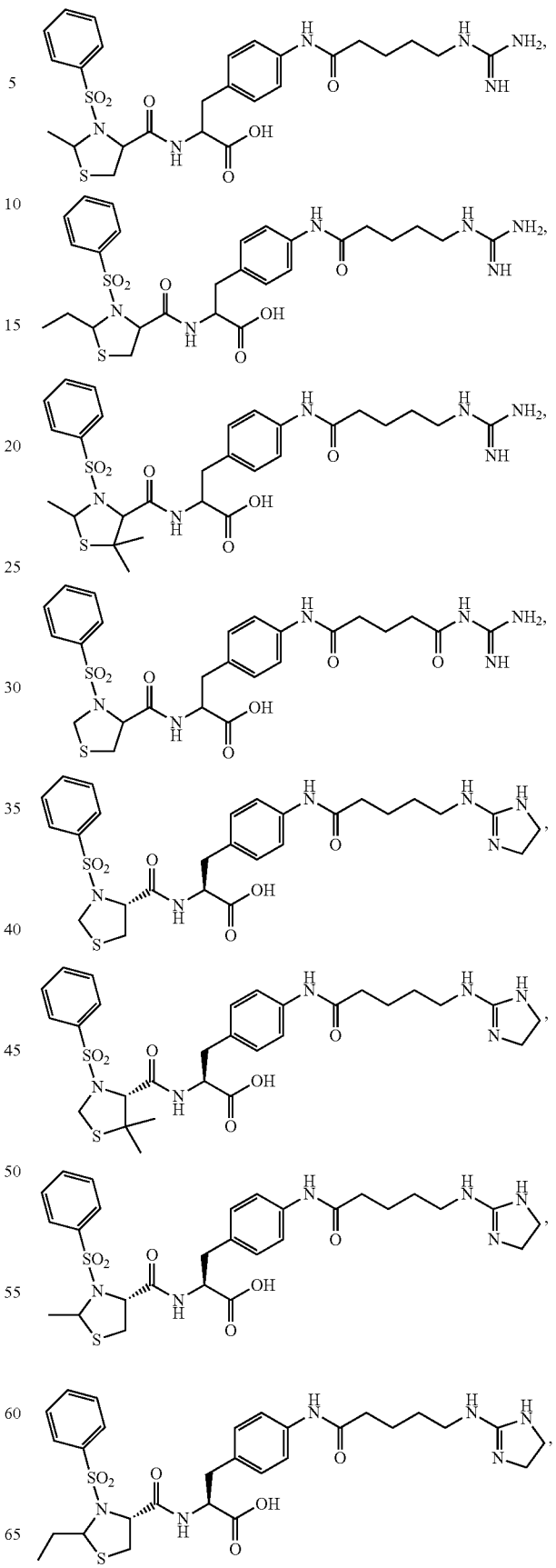

269
-continued
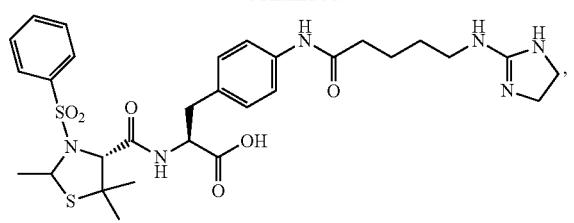
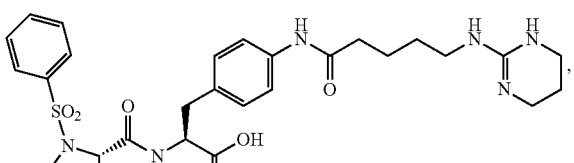
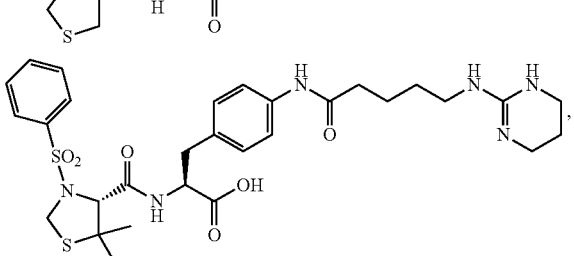
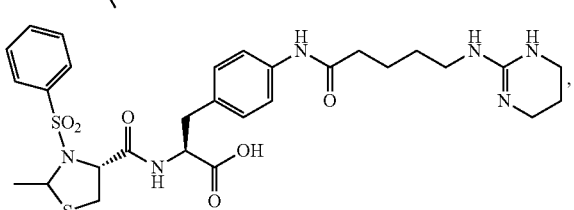
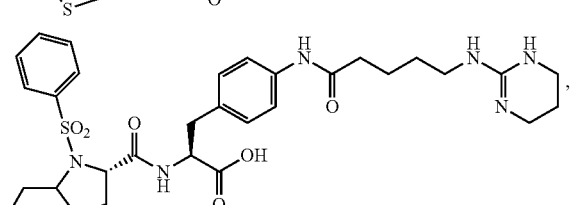
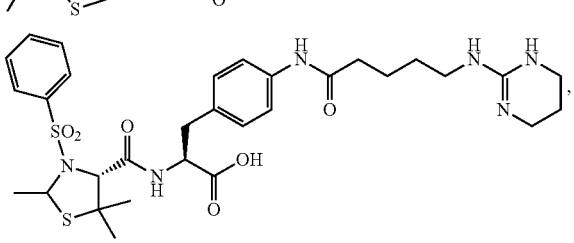
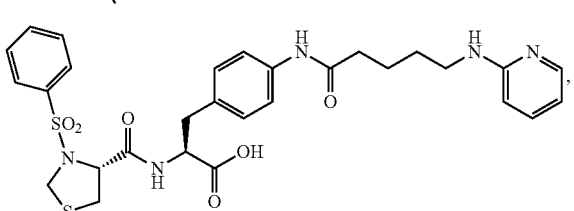
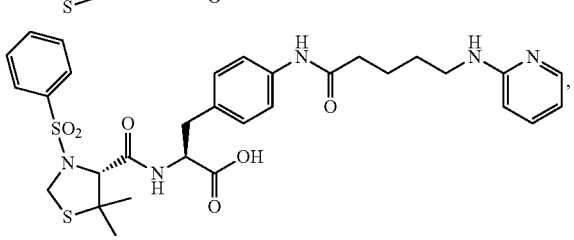
270
-continued
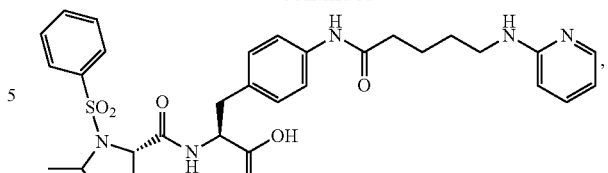
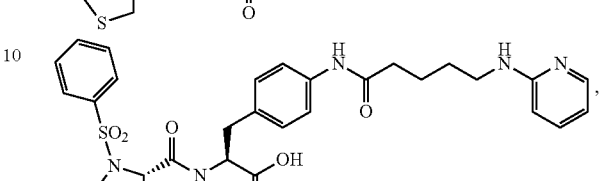
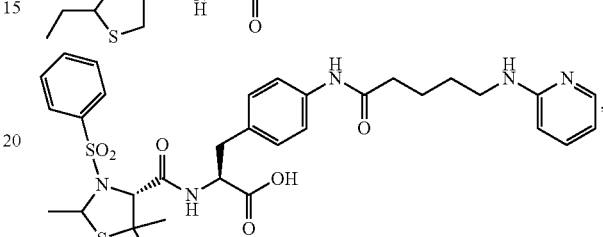
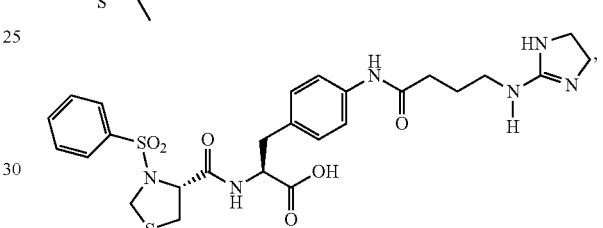
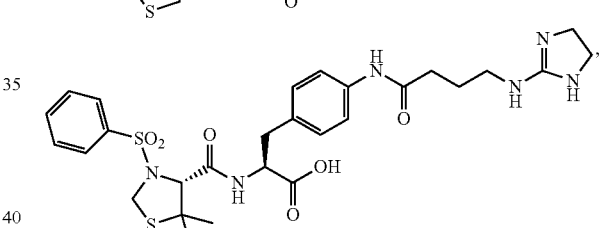
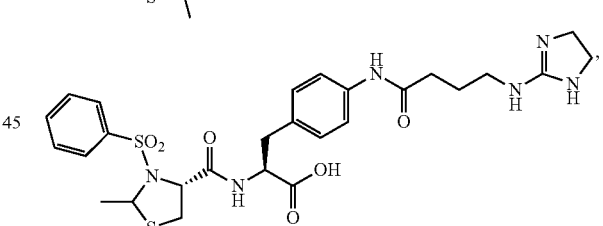
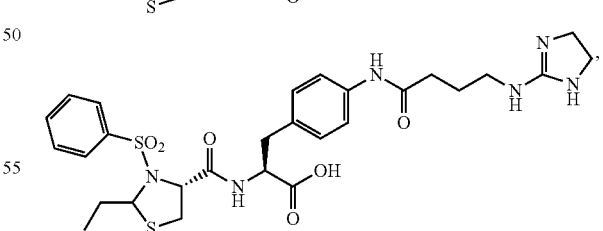
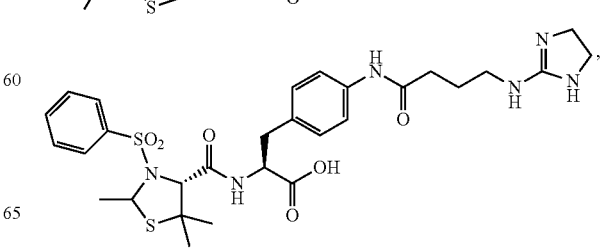

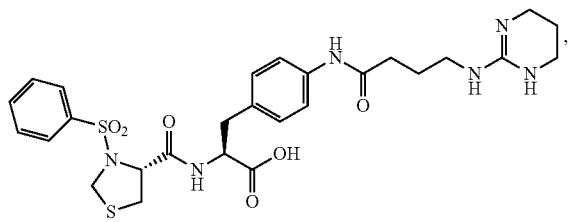
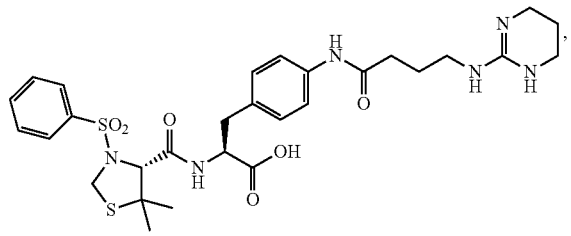
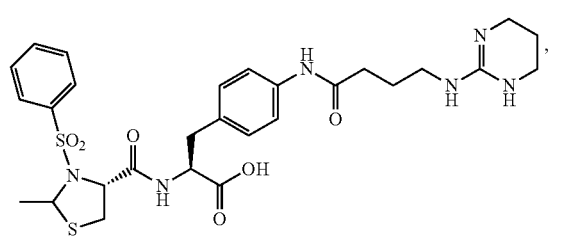
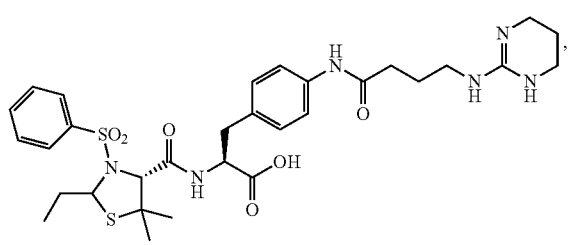
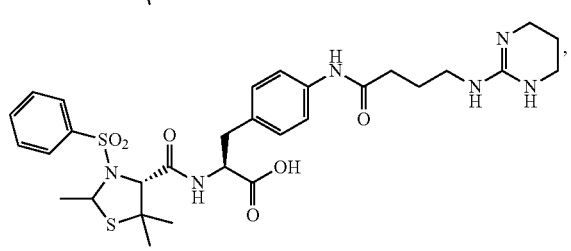
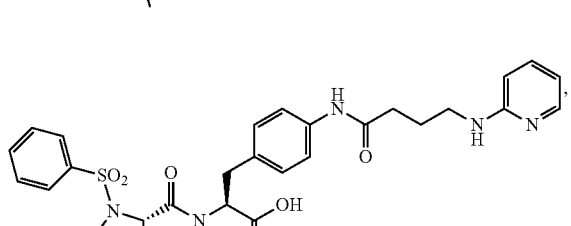
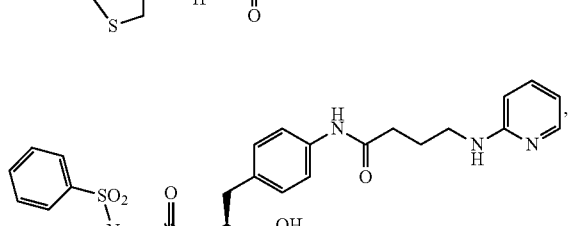
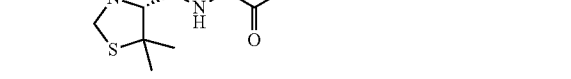
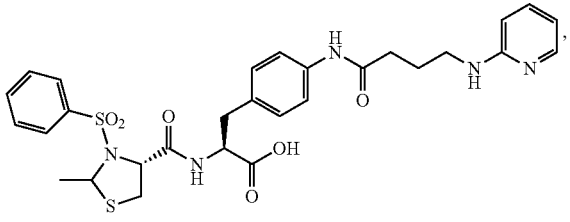
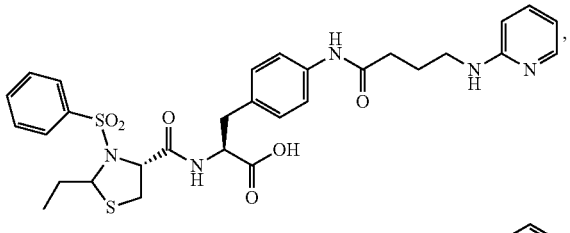
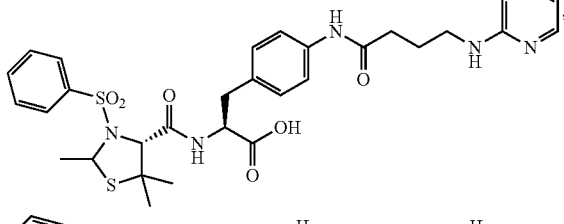
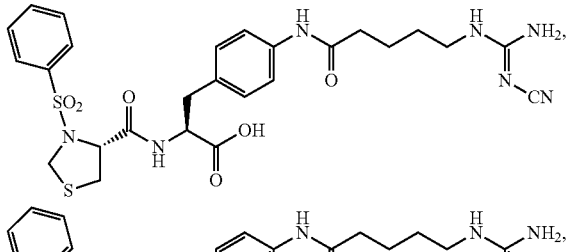
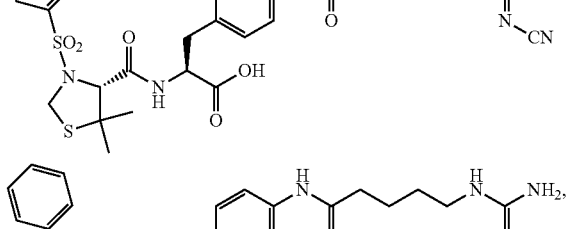
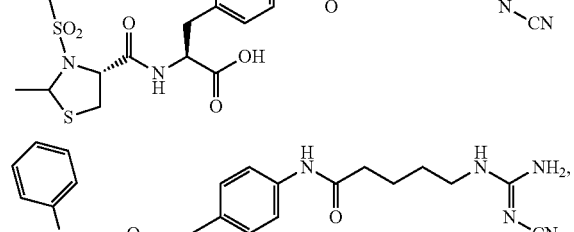
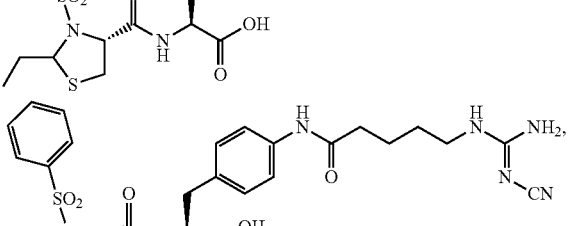

-continued
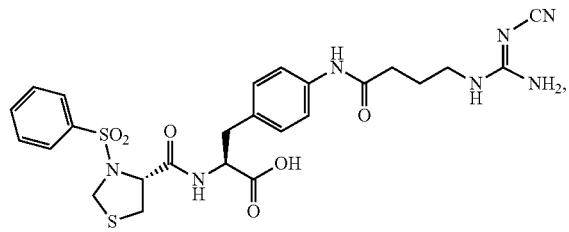
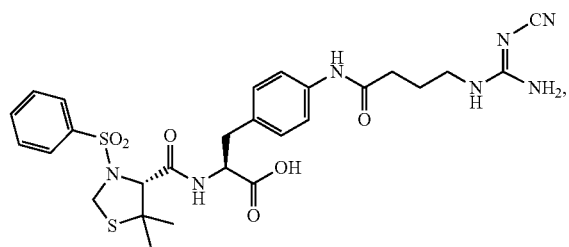
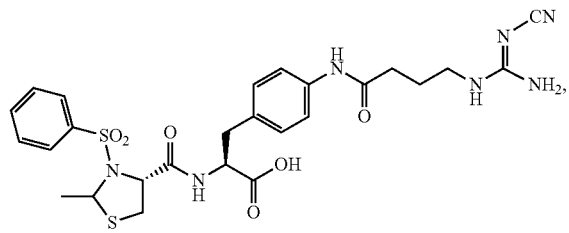
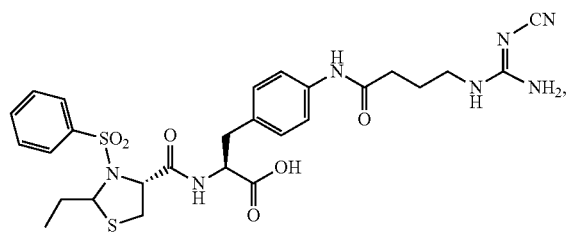
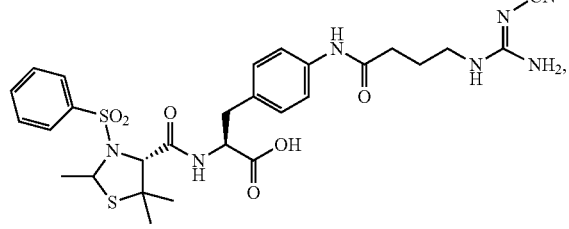
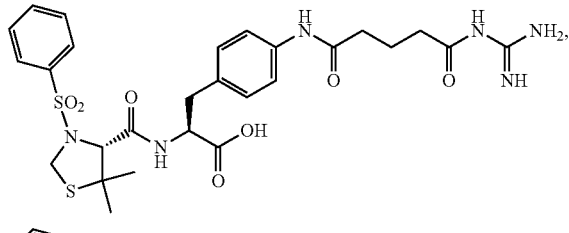
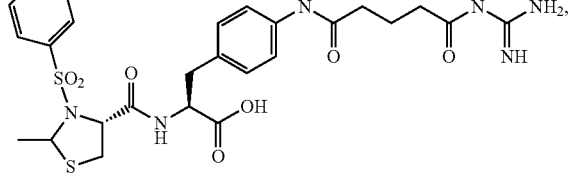
-continued
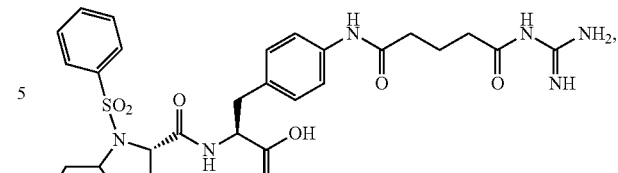
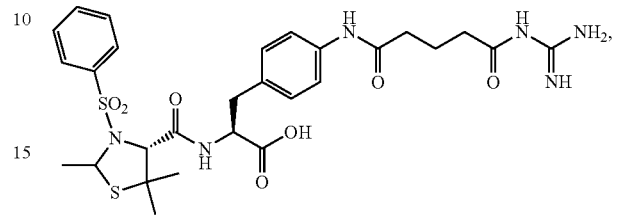
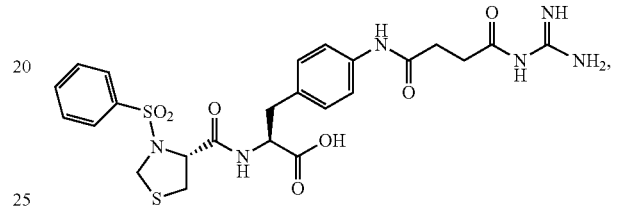
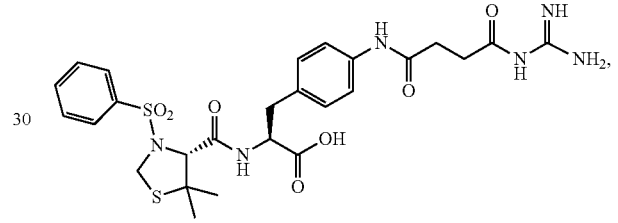
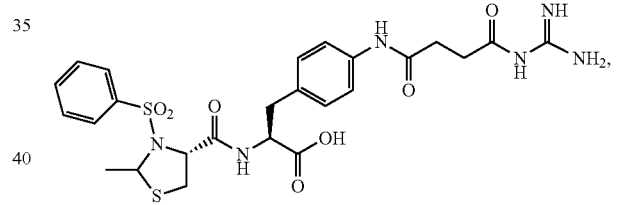
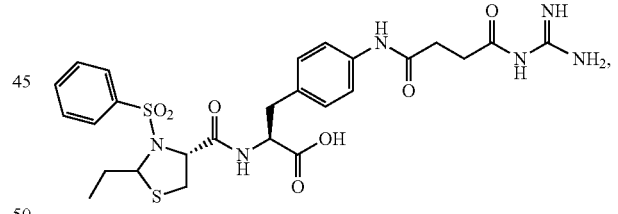
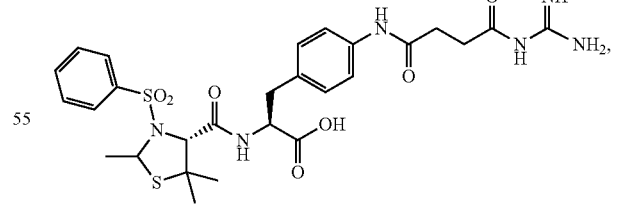
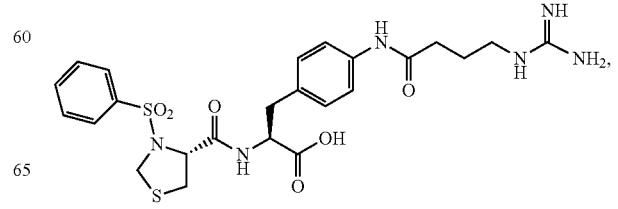

275
-continued

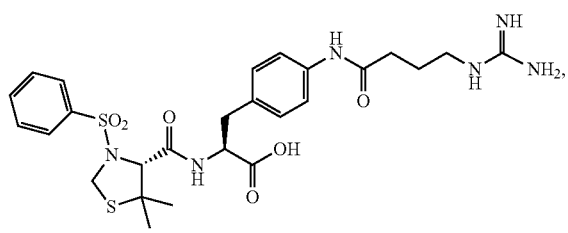

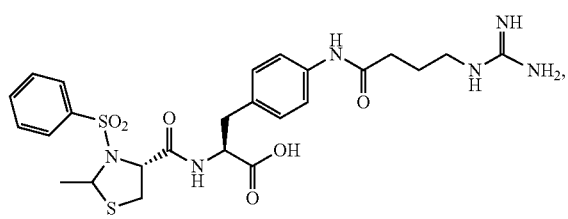

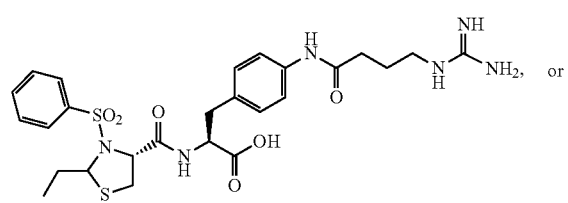

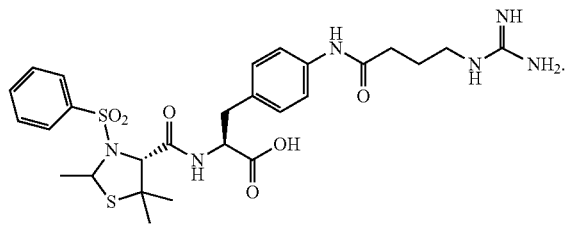

Embodiment 27

The compound of any one of embodiments 1 to 11 having the formula:

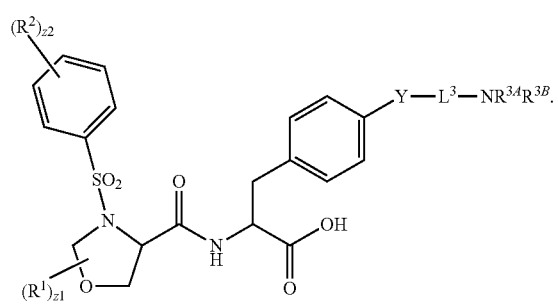

276

Embodiment 28

The compound of embodiment 27 having the formula:

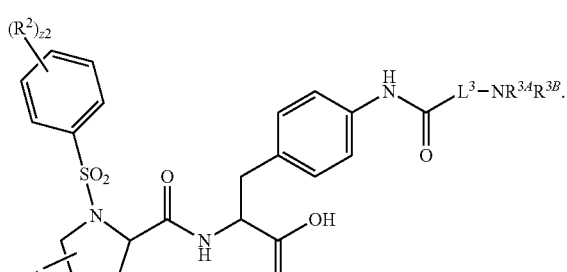

Embodiment 29

The compound of embodiment 27 or embodiment 28, wherein $L^3$ is substituted or unsubstituted $C_1$-$C_6$ alkylene, or substituted or unsubstituted 2 to 6 membered heteroalkylene.

Embodiment 30

The compound of any one of embodiments 27 to 29, wherein $R^1$ is hydrogen or substituted or unsubstituted $C_1$-$C_3$ alkyl.

Embodiment 31

The compound of any one of embodiments 27 to 30, wherein $R^2$ is hydrogen.

Embodiment 32

The compound of any one of embodiments 27 to 31, wherein $R^{3A}$ and $R^{3B}$ are independently hydrogen, —C(NH)NH$_2$, —C(NCN)NH$_2$, or substituted or unsubstituted heterocycloalkyl, or substituted or unsubstituted heteroaryl.

Embodiment 33

The compound of any one of embodiments 27 to 32 having formula:

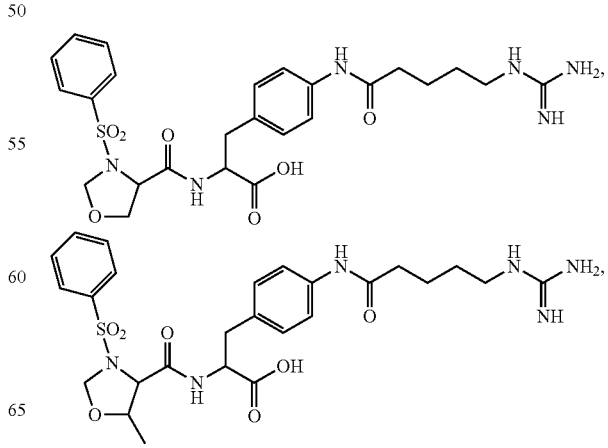

277
-continued
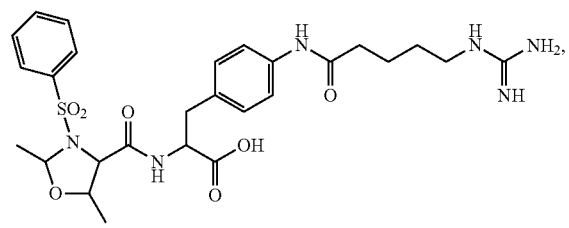
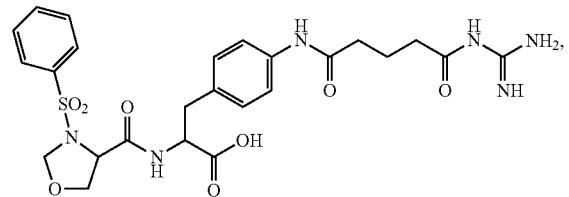
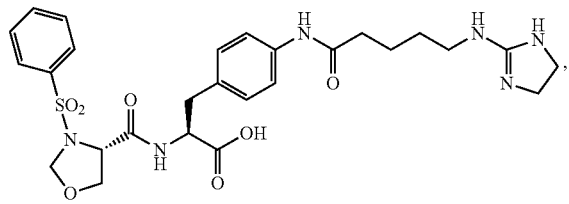
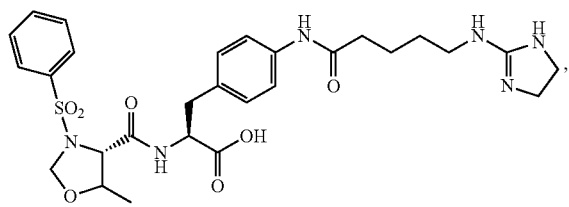
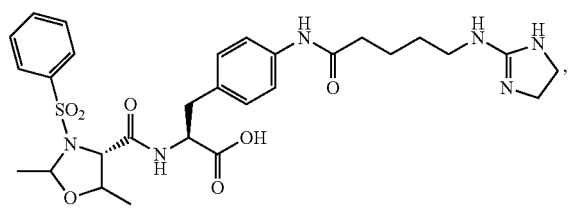
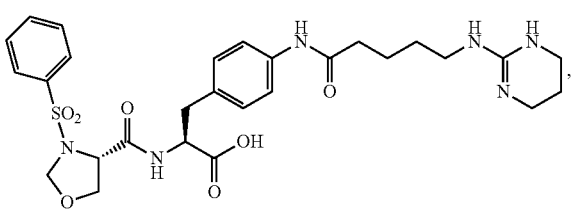
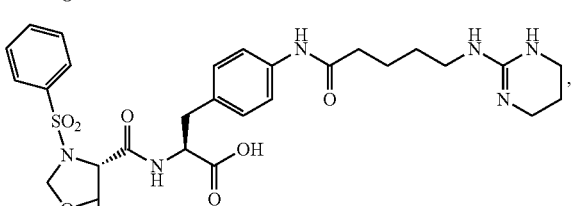
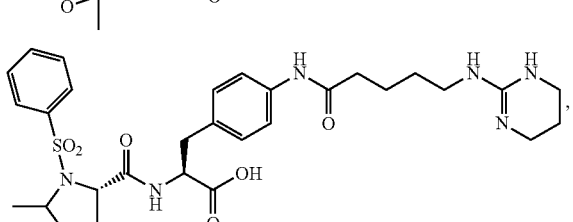
278
-continued
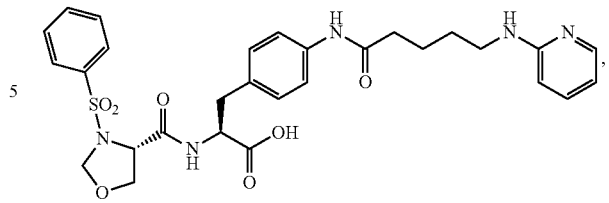
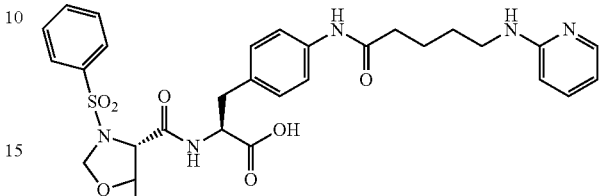
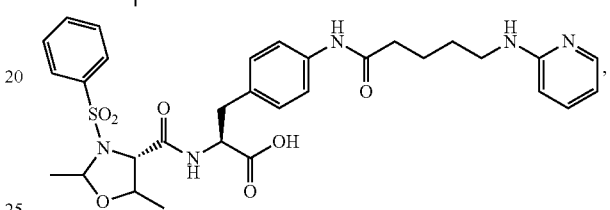
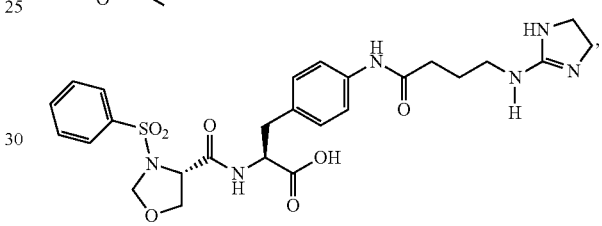
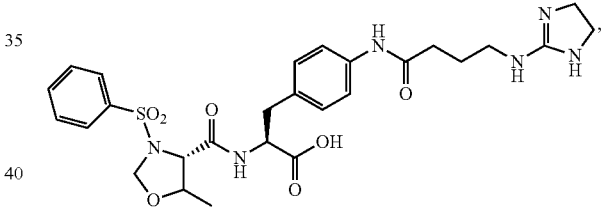
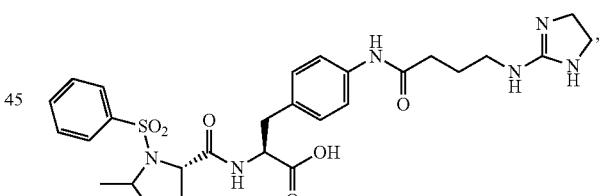
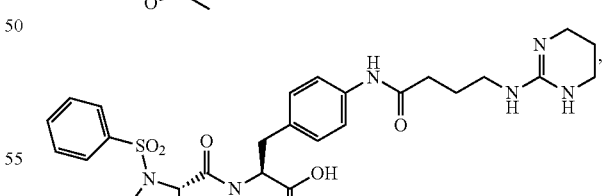
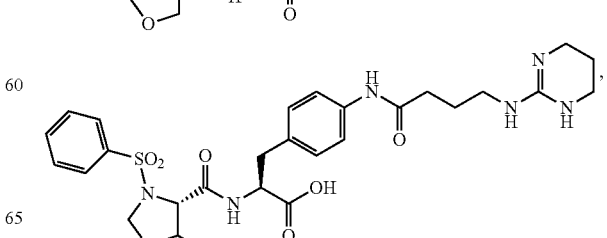

279
-continued
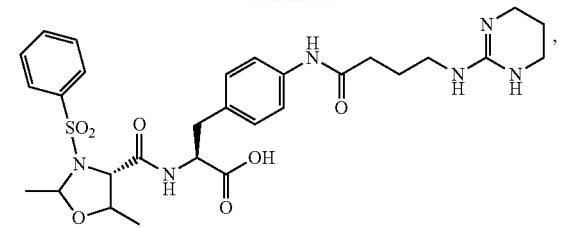
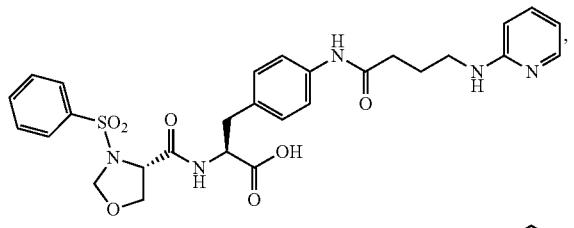
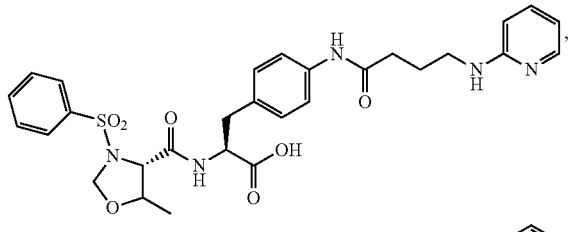
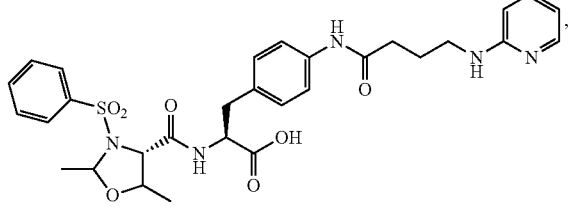
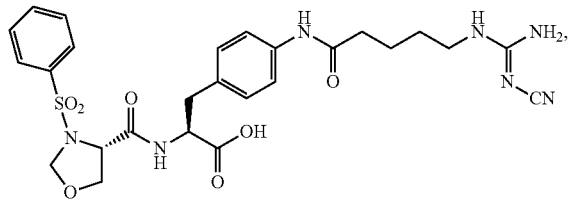
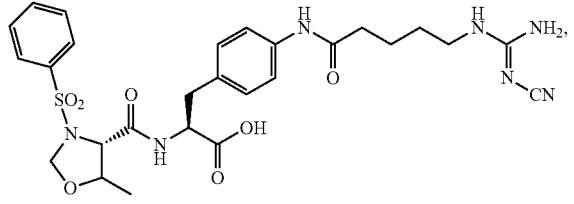
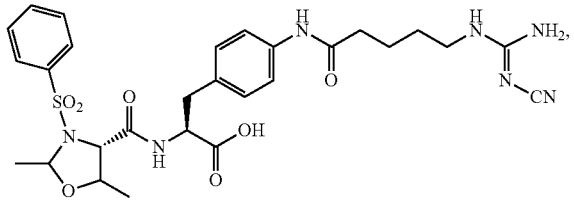
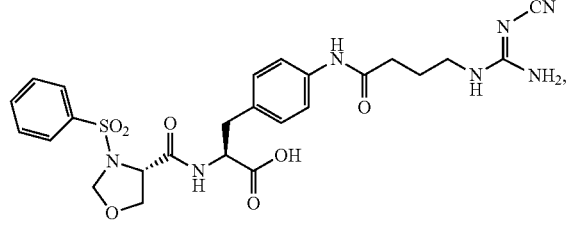
280
-continued
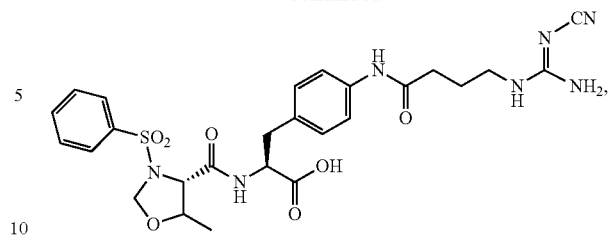
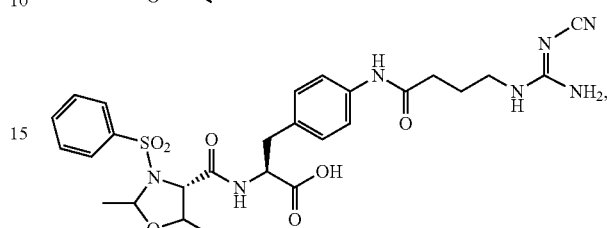
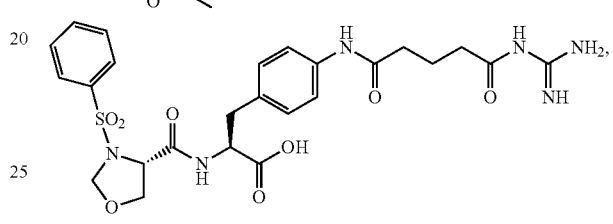
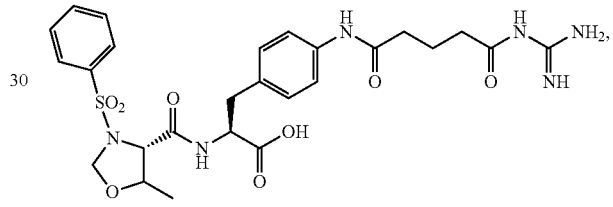
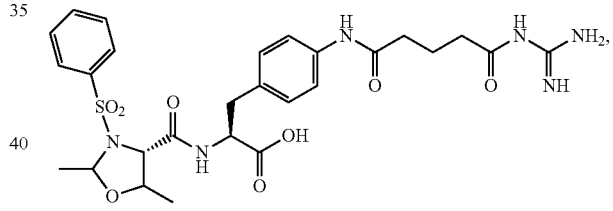
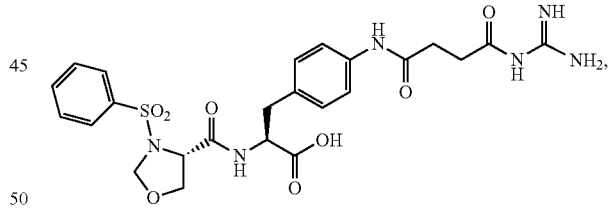
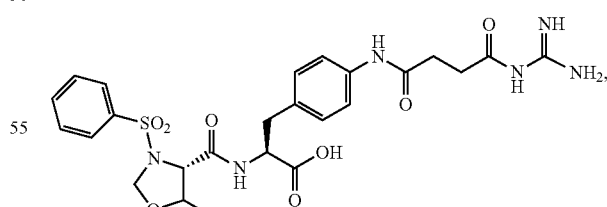
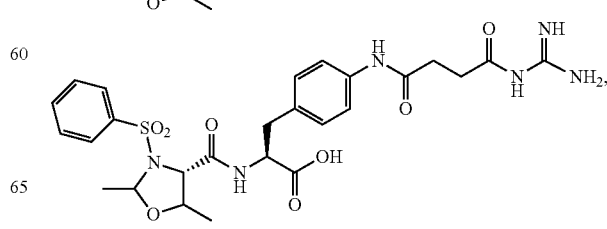

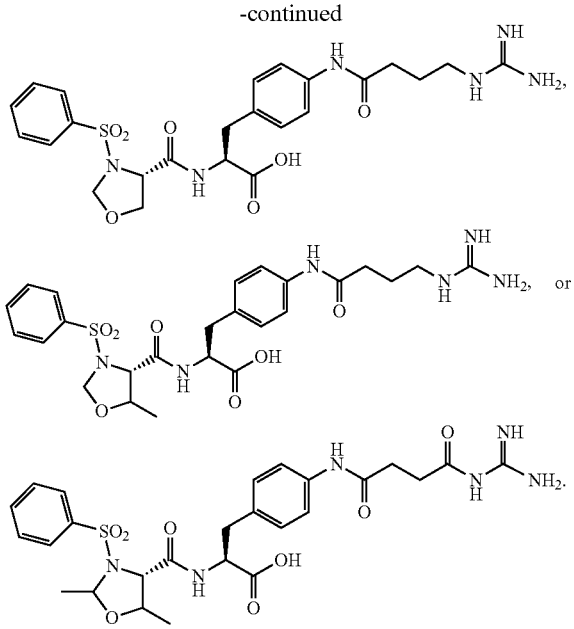

Embodiment 34

A pharmaceutical composition comprising the compound of any one of embodiments 1 to 33 and a pharmaceutically acceptable excipient.

Embodiment 35

A method of detecting αvβ1 expression in a cell, the method comprising: (i) contacting a cell with an αvβ1-specific moiety; (ii) allowing the αvβ1-specific moiety to bind to the cell; and (iii) detecting the αvβ1-specific moiety, thereby detecting αvβ1 expression in a cell.

Embodiment 36

The method of embodiment 35, wherein the αvβ1-specific moiety is an αvβ1-specific compound having the formula of a compound of any one of embodiments 1 to 34.

Embodiment 37

A method of inhibiting TGFβ activation, the method comprising: (i) contacting a cell expressing αvβ1 integrin with an αvβ1-inhibitor; (ii) allowing the αvβ1-inhibitor to bind to αvβ1 in the presence of TGFβ; and (iii) comparing a level of activated TGFβ to a control to thereby identify a lower level of TGFβ activation and inhibition of TGFβ activation.

Embodiment 38

The method of embodiment 37, wherein the αvβ1-inhibitor is an αvβ1-inhibitor compound having the formula of a compound of any one of embodiments 1 to 34.

Embodiment 39

The method of embodiment 37, wherein the cell is a skin myofibroblast, a lung myofibroblast, or a hepatic myofibroblast.

Embodiment 40

A method for treating fibrosis, the method comprising administering to a subject in need thereof a therapeutically effective amount of an αvβ1-inhibitor, wherein the αvβ1-inhibitor is an αvβ1-inhibitor antibody, an αvβ1-inhibitor RGD peptide, or an αvβ1-inhibitor compound, wherein the αvβ1-inhibitor compound has the formula of any one of embodiments 1 to 34.

Embodiment 41

The method of embodiment 40, wherein the fibrosis is pulmonary fibrosis, liver fibrosis, skin fibrosis, cardiac fibrosis, or kidney fibrosis.

Embodiment 42

The method of embodiment 40, wherein the αvβ1-inhibitor antibody is a humanized antibody.

Embodiment 43

The method of embodiment 42, wherein the αvβ1-inhibitor antibody is a recombinant immunoglobulin.

Embodiment 44

The method of embodiment 43, wherein the recombinant immunoglobulin is formed using phage display.

Embodiment 45

The method of embodiment 40, wherein the αvβ1-inhibitor is an αvβ1-inhibitor RGD peptide.

Embodiment 46

The method of embodiment 40, wherein the αvβ1-inhibitor compound has the formula:

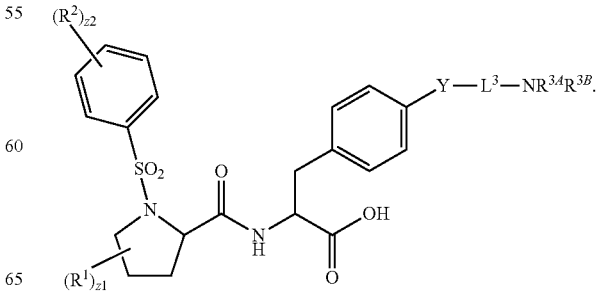

Embodiment 47

The method of embodiment 46, wherein the αvβ1-inhibitor compound has the formula:

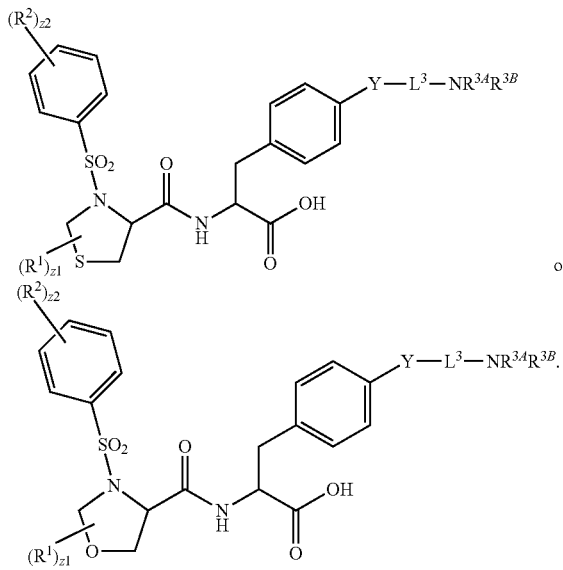

or

Embodiment 48

The method of any one of embodiments 46 to 47, wherein Y is —NH(CO)—.

Embodiment 49

The method of any one of embodiments 46 to 48, wherein $L^3$ is unsubstituted $C_1$-$C_5$ alkylene.

Embodiment 50

The method of any one of embodiments 46 to 48, wherein $L^3$ is unsubstituted 2 to 6 membered heteroalkylene.

Embodiment 51

The method of any one of embodiments 46 to 48, wherein $L^3$ is unsubstituted alkylarylene.

Embodiment 52

The method of any one of embodiments 46 or 48 to 51, wherein the αvβ1-inhibitor compound has the formula:

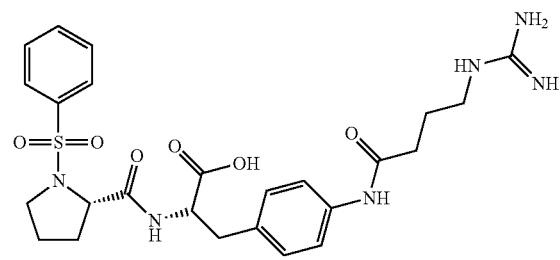

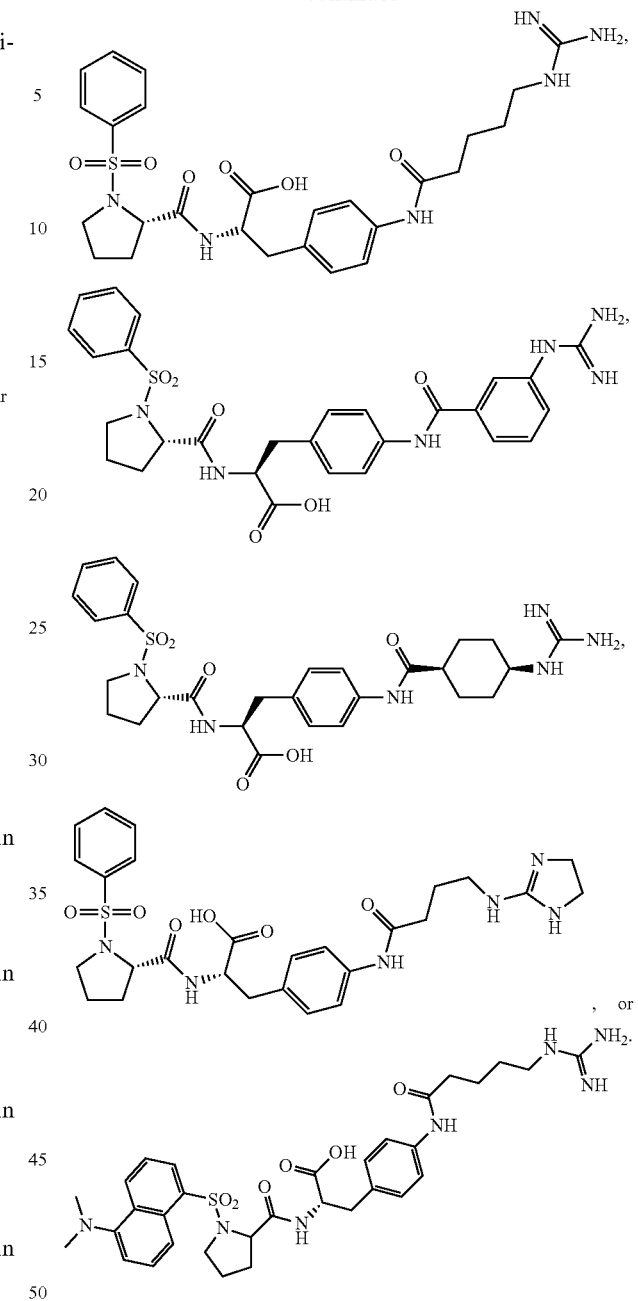

Embodiment 53

The method of embodiment 47, wherein the αvβ1-inhibitor compound has the formula:

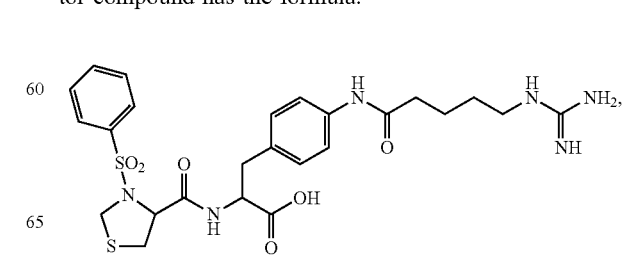

285
-continued

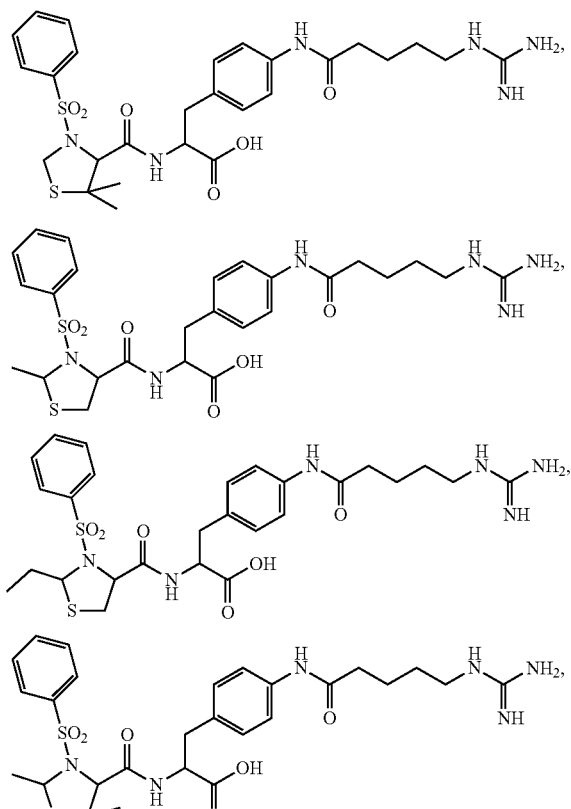

Embodiment 54

The method of embodiment 47, wherein the αvβ1-inhibitor compound has the formula:

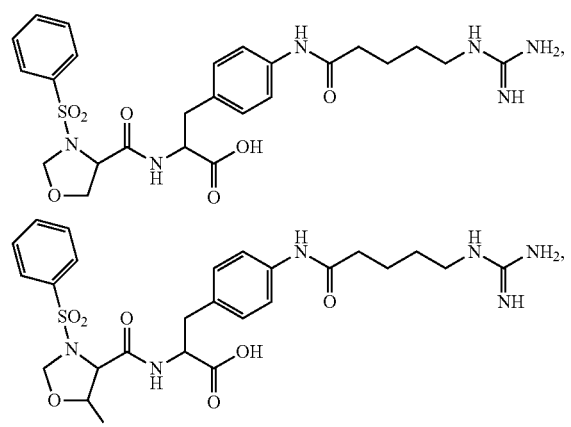

286
-continued

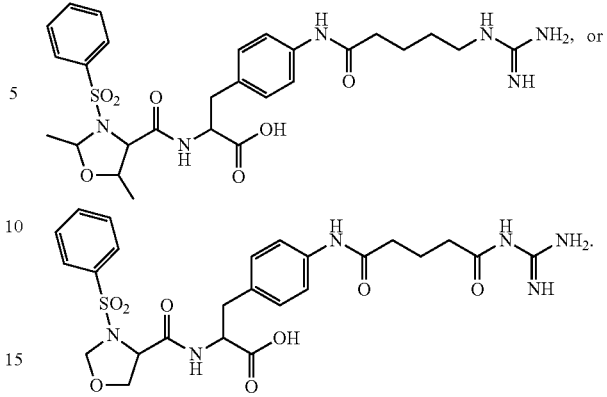

Embodiment 55

A method for determining whether a test compound inhibits αvβ1 integrin binding, the method comprising: (i) combining an αvβ1 integrin-expressing cell and a test compound in a reaction vessel comprising an integrin ligand covalently bonded to the reaction vessel; and (ii) determining whether the αvβ1 integrin-expressing cell binds to the integrin ligand in the presence of the test compound, thereby determining whether the test compound inhibits αvβ1 integrin binding.

What is claimed is:

1. A compound, or a salt thereof, having the formula: wherein,

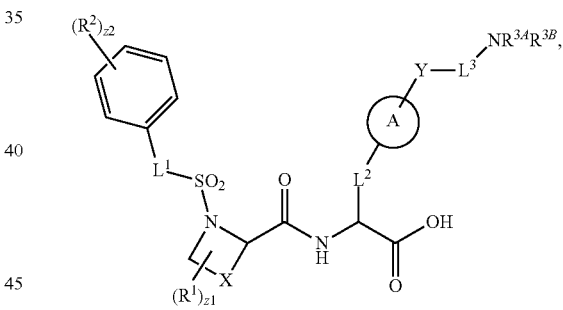

Ring A is cycloalkyl, heterocycloalkyl, aryl, or heteroaryl;
$L^1$ is a bond;
$L^2$ is unsubstituted methylene;
$L^3$ is substituted or unsubstituted $C_1$-$C_{10}$ alkylene, substituted or unsubstituted 2 to 10 membered heteroalkylene, substituted or unsubstituted $C_3$-$C_6$ cycloalkylene, or substituted or unsubstituted alkylarylene;
X is a bond, —C—, —C—C—, —C=C—, —C—C—C—, —C=C—C—, —C—C=C—, —O—C—, —C—O—, —C—O—C, —S—C—, —C—S—, —C—S—C—;
Y is a —C(O)N($R^4$)—, substituted or unsubstituted arylene, or substituted or unsubstituted heteroarylene;
$R^1$ is independently hydrogen, halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$OSO_3H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety;

$R^2$ is independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$OSO_3H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety, or wherein if z2 an integer of 2 to 5, two $R^2$ substituents attached to adjacent ring carbons are optionally joined to form a substituted or unsubstituted aryl or substituted or unsubstituted heteroaryl;

$R^{3A}$ is hydrogen, —$C(NH)NH_2$, —$C(NH)R^{3D}$, —$C(NR^{3C})NH_2$, —$C(NR^{3C})R^{3D}$, —$C(NCN)NH_2$, NH, $NH_2$, —$C(NH)NHR^{3D}$, —$C(NR^{3C})NHR^{3D}$, —$C(NCN)NHR^{3D}$, substituted or unsubstituted cycloalkyl, substituted or unsubstituted heterocycloalkyl, substituted or unsubstituted aryl, substituted or unsubstituted heteroaryl;

$R^{3B}$ is —$C(NH)NH_2$, —$C(NH)R^{3D}$, —$C(NR^{3C})NH_2$, —$C(NR^{3C})R^{3D}$, —$C(NCN)NH_2$, NH, $NH_2$, —$C(NH)NHR^{3D}$, —$C(NR^{3C})NHR^{3D}$, —$C(NCN)NHR^{3D}$, substituted or unsubstituted cycloalkyl, substituted or unsubstituted heterocycloalkyl, substituted or unsubstituted aryl, substituted or unsubstituted heteroaryl;

$R^{3A}$ and $R^{3B}$ are optionally joined to form a substituted or unsubstituted heterocycloalkyl or substituted or unsubstituted heteroaryl;

$R^{3C}$ and $R^{3D}$ are independently hydrogen, halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is independently hydrogen or unsubstituted $C_1$-$C_5$ alkyl;

z1 is an integer from 1 to 9; and z2 is an integer from 1 to 5.

2. The compound of claim 1, wherein $L^3$ is substituted or unsubstituted $C_1$-$C_5$ alkylene, substituted or unsubstituted 2 to 6 membered heteroalkylene, or substituted or unsubstituted alkylarylene.

3. The compound of claim 1, wherein
$L^3$ is $R^6$-substituted $C_1$-$C_3$ alkylene;
$R^6$ is —$NHC(O)R^{6A}$;
$R^{6A}$ is —$C(NCN)R^{6c}$, —$C(NH)R^{6C}$, $R^{6C}$-substituted or unsubstituted alkyl, or $R^{6C}$-substituted or unsubstituted heteroalkyl;
$R^{6C}$ is hydrogen, halogen, oxo, —$N_3$, —$CF_3$, —$CCl_3$, —$CBr_3$, —$CI_3$, —CN, —$COR^{6D}$, —$OR^{6D}$, —$NR^{6D}R^{6E}$, —$COOR^{6E}$, —$CONR^{6D}R^{6E}$, —$NHC(O)R^{6D}$, —$NO_2$, —$SR^{6D}$, —$SO_{n6}R^{6D}$, —$NHNR^{6D}R^{6E}$, —$ONR^{6D}R^{6E}$, —$NHC(O)NHNR^{6D}R^{6E}$, —$C(NCN)R^{6D}$, —$C(NH)R^{6D}$, $R^{6F}$-substituted or unsubstituted alkyl, $R^{6F}$-substituted or unsubstituted heteroalkyl, $R^{6F}$-substituted or unsubstituted cycloalkyl, $R^{6F}$-substituted or unsubstituted heterocycloalkyl, $R^{6F}$-substituted or unsubstituted aryl, or $R^{6F}$-substituted or unsubstituted heteroaryl;

n6 is 2, 3, or 4; and $R^{6D}$, $R^{6E}$ and $R^{6F}$ are independently hydrogen, halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety.

4. The compound of claim 1, wherein Y is —NHC(O)—, —$NCH_3$—, —$NC(O)CH_3$—, —$NC(O)OCH_3$—, 4 to 6 membered unsubstituted heteroarylene, or unsubstituted 5 or 6 membered arylene.

5. The compound of claim 1, wherein $R^2$ is independently hydrogen, halogen, —$CF_3$, —$CCl_3$, —$CBr_3$, —$CI_3$, —$NH_2$, —$NO_2$, —$SO_2CH_3$, substituted or unsubstituted $C_1$-$C_5$ alkyl, substituted or unsubstituted 2 to 5 membered heteroalkyl, substituted or unsubstituted 5 or 6 membered aryl, or a detectable moiety.

6. The compound of claim 1, wherein $R^{3A}$ is hydrogen, —$C(NH)NH_2$, —$C(NCN)NH_2$, substituted or unsubstituted heterocycloalkyl, or substituted or unsubstituted heteroaryl.

7. The compound of claim 1 having the formula:

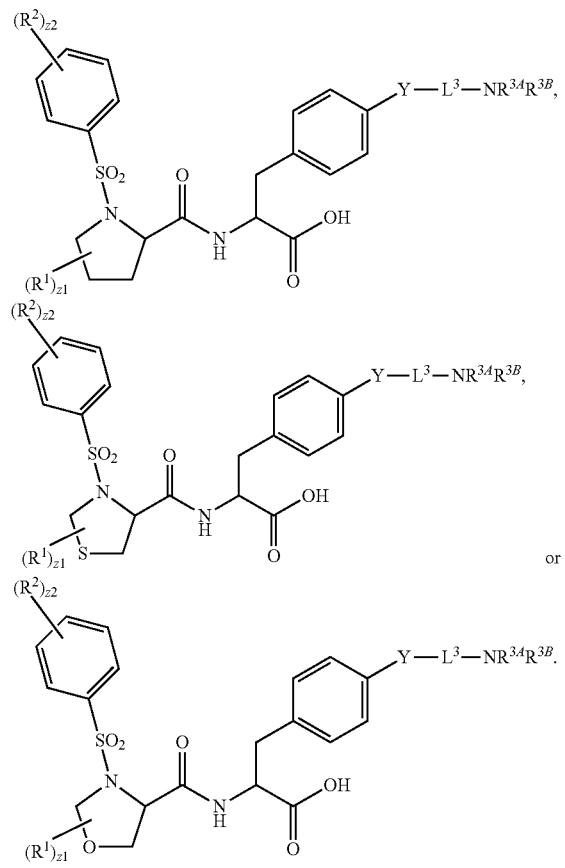

8. The compound of claim 7 having the formula:

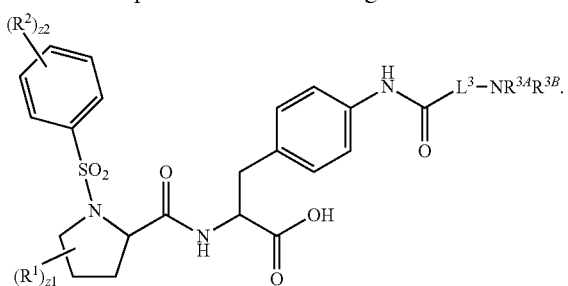

9. The compound of claim 7, wherein $R^2$ is hydrogen, halogen, —$SO_2CH_3$, —$NO_2$, —$NH_2$, substituted or unsubstituted $C_1$-$C_3$ alkyl, or substituted or unsubstituted 2 to 5 membered heteroalkyl.

10. The compound of claim 7, wherein $R^{3A}$ is independently hydrogen, —$C(NH)NH_2$, —$C(NCN)NH_2$, or substituted or unsubstituted heterocycloalkyl, or substituted or unsubstituted heteroaryl.

11. The compound of claim 1 having the formula:

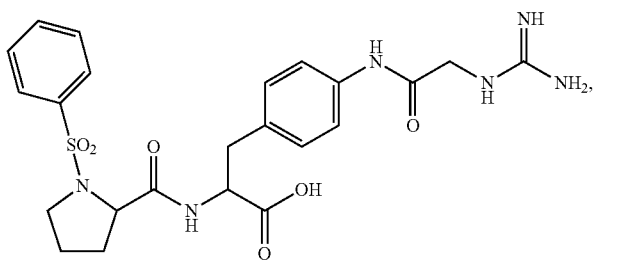

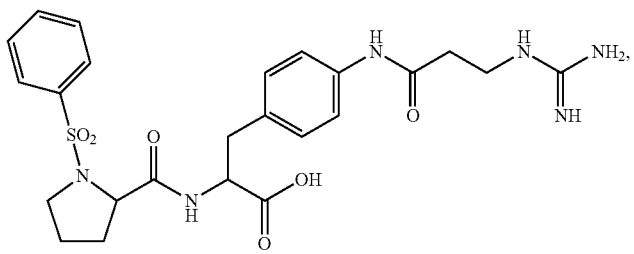

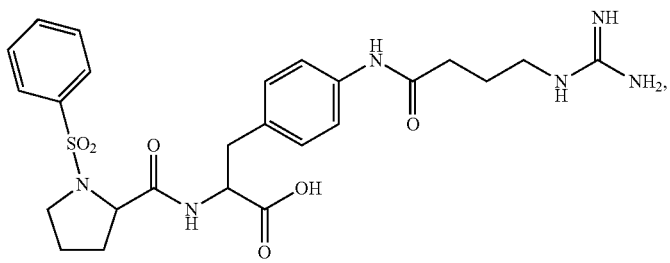

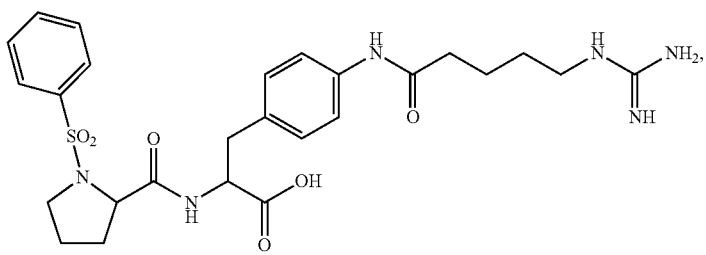

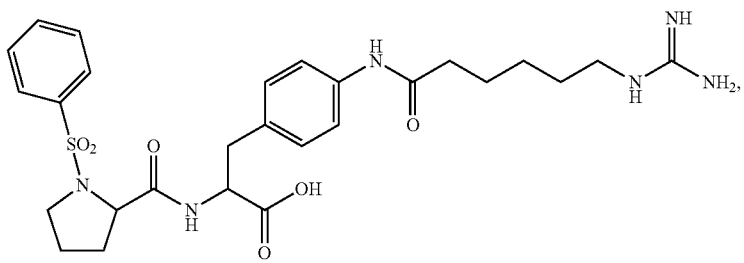

-continued
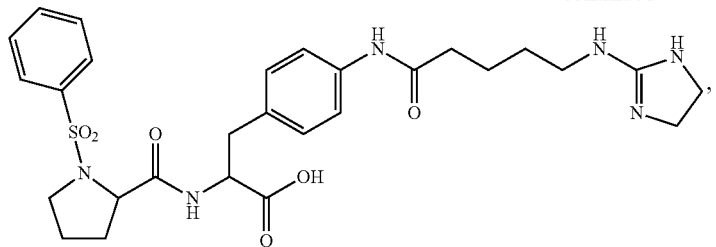
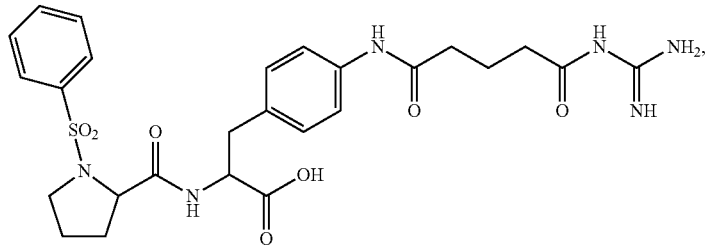
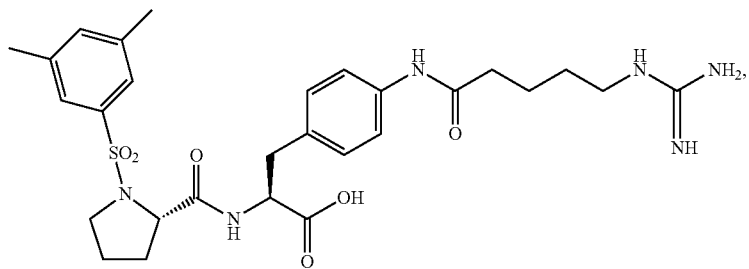
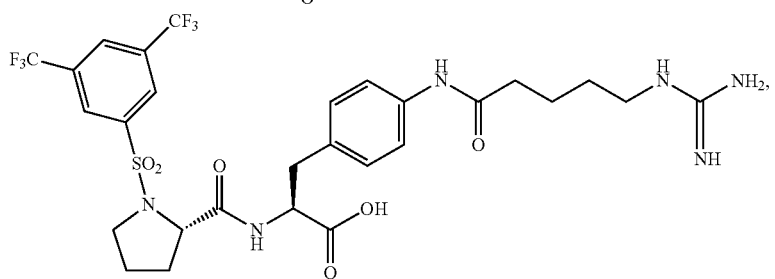
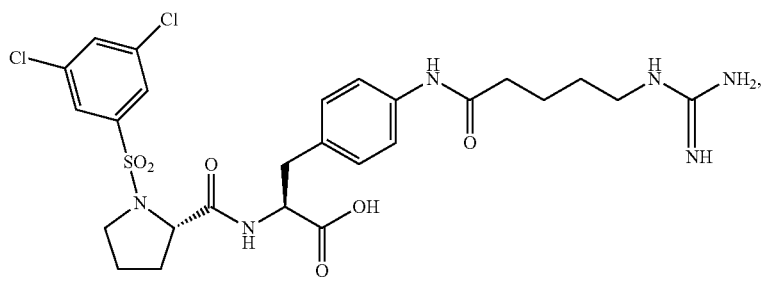
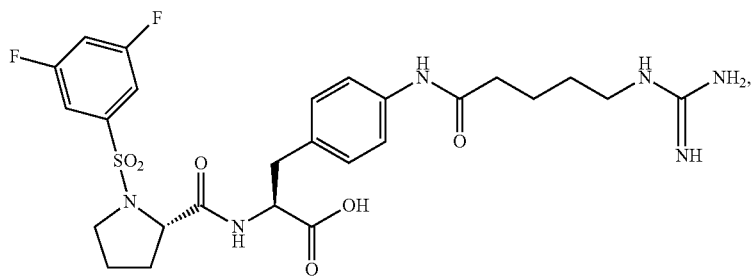

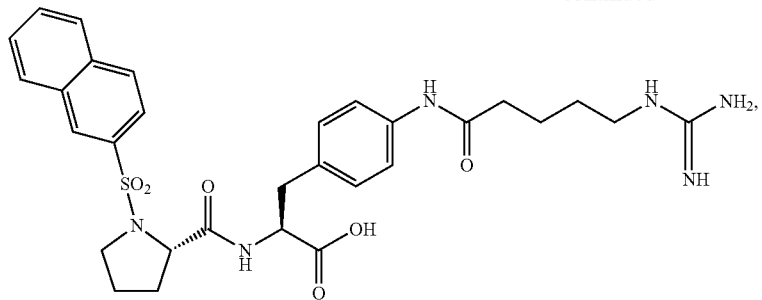
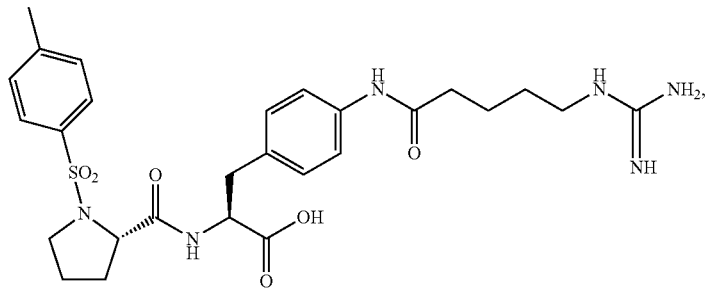
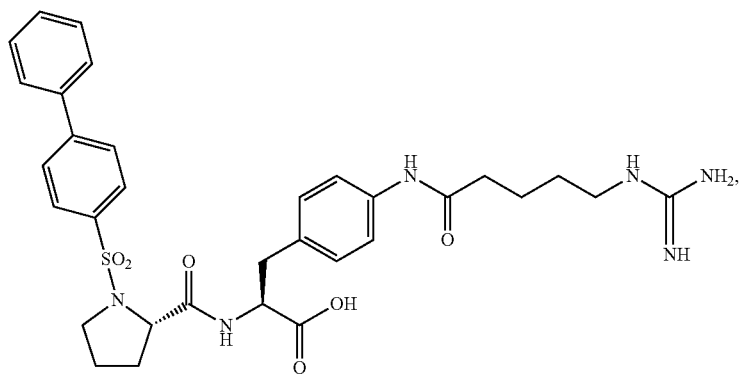
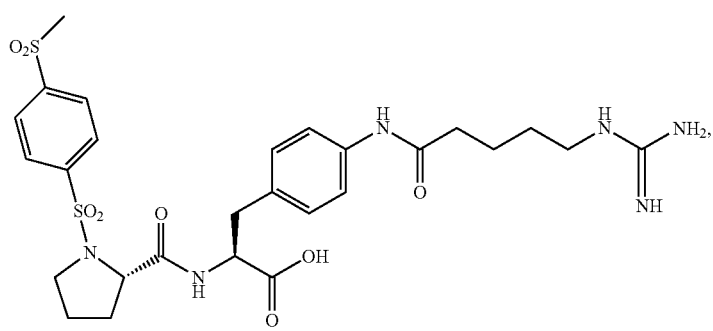
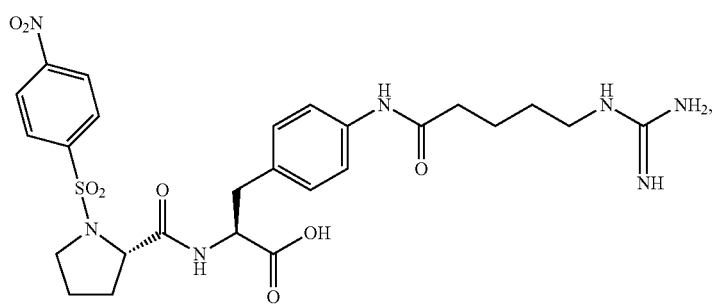

-continued
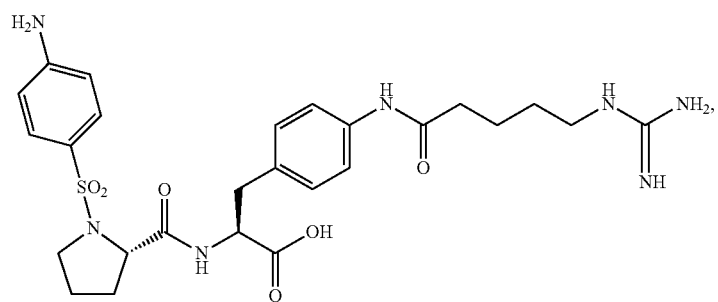
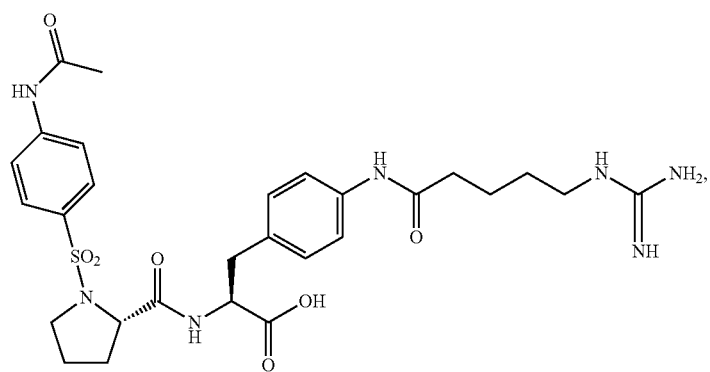
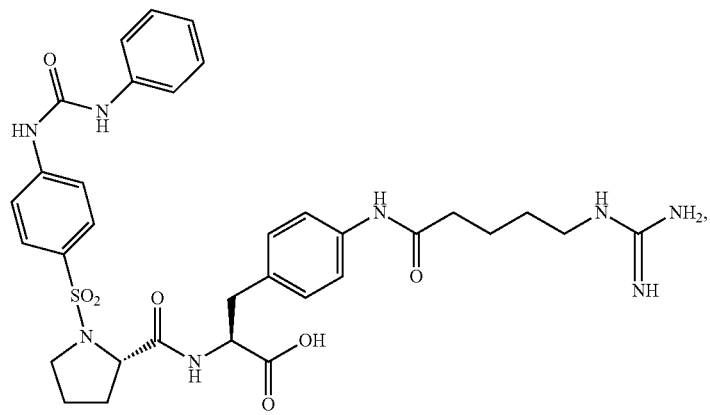
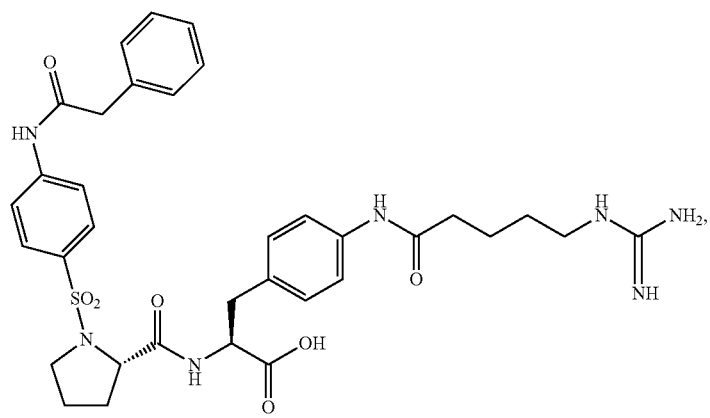

-continued
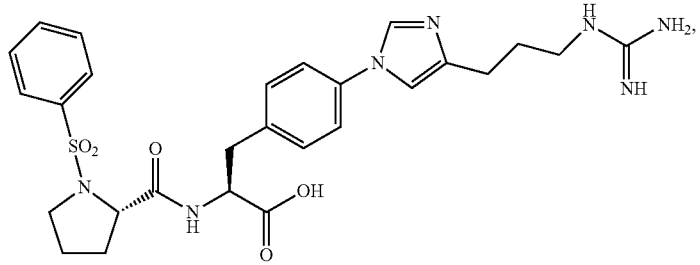
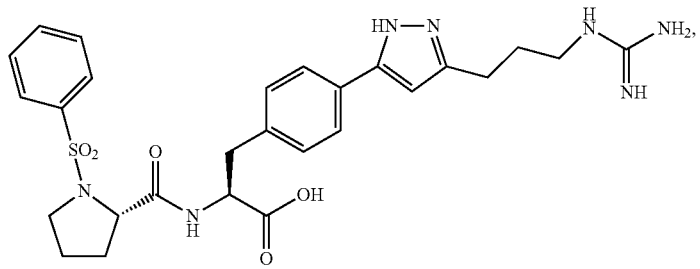
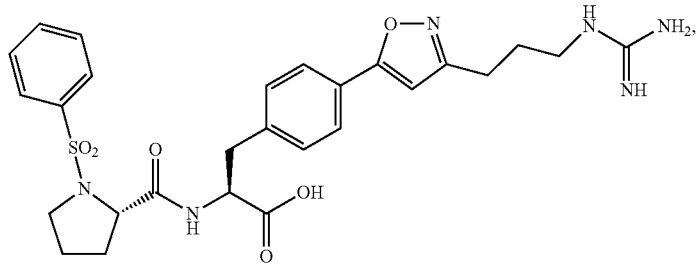
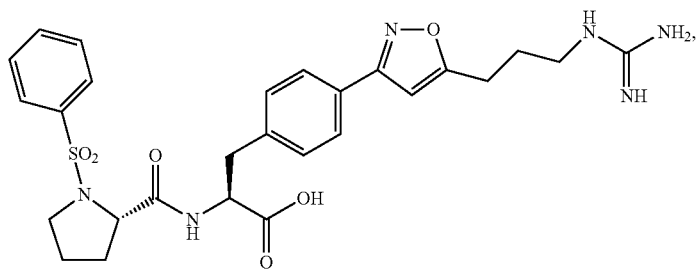
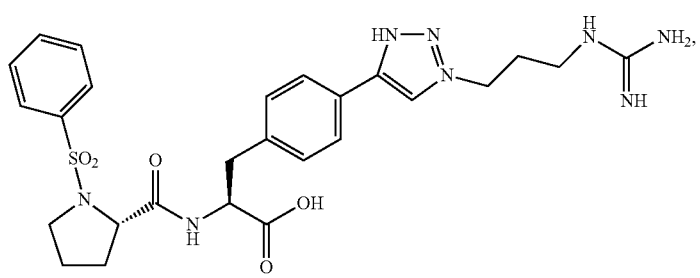
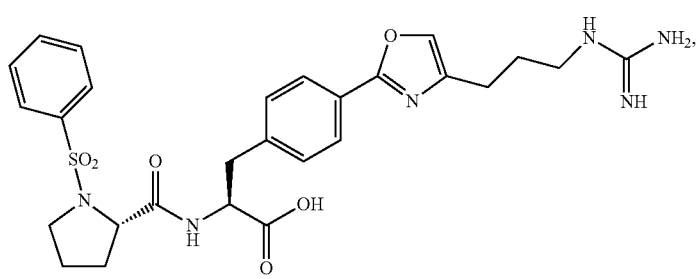

-continued
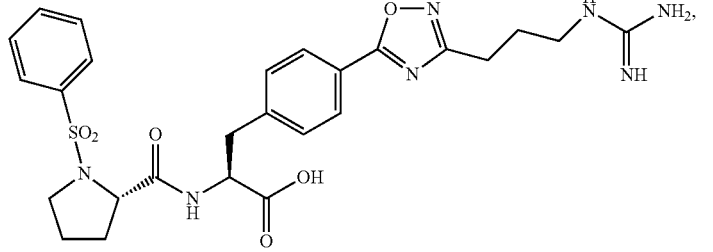
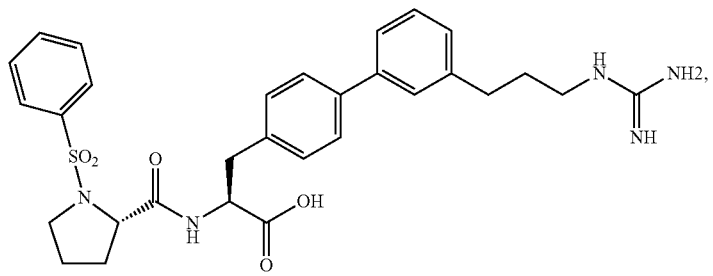
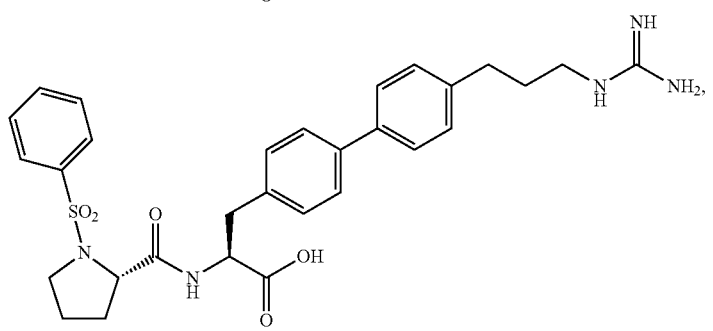
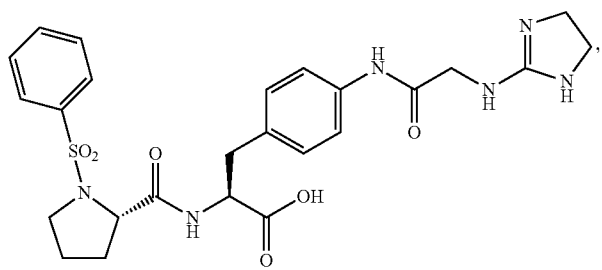
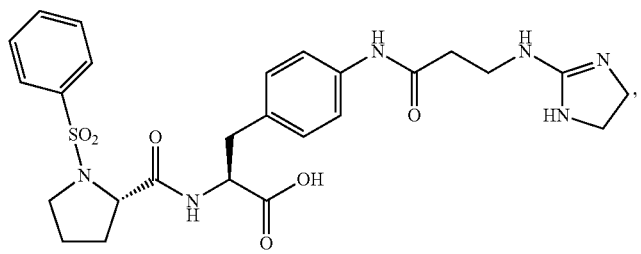
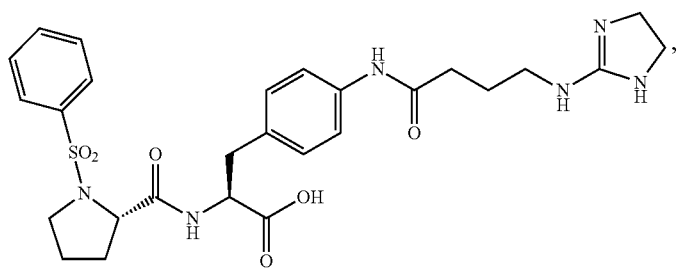

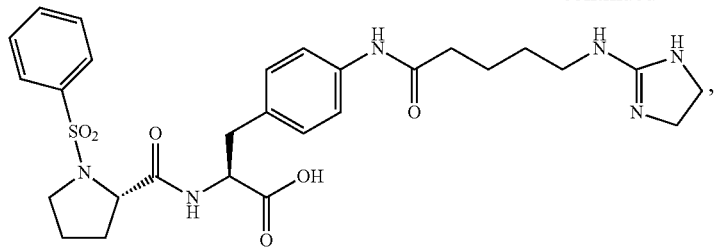
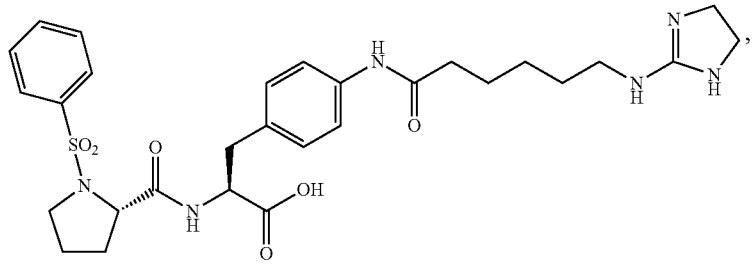
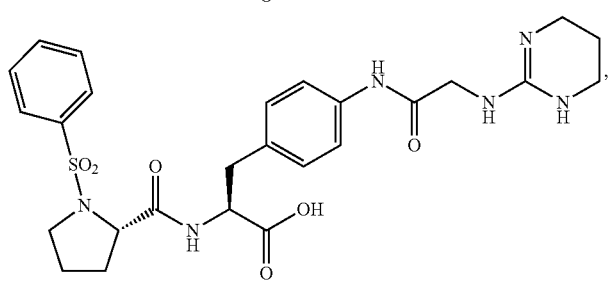
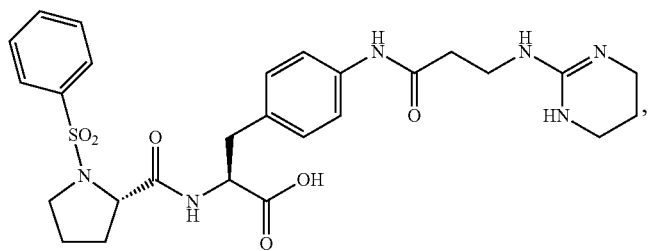
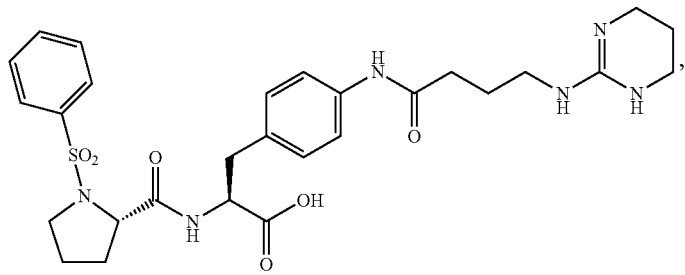
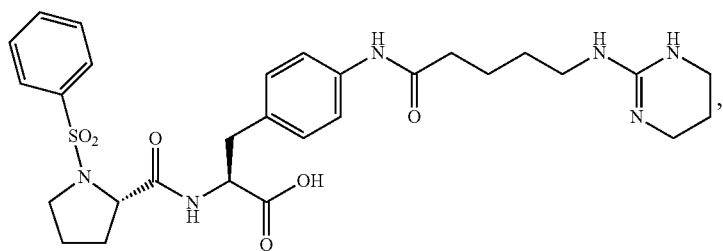

-continued
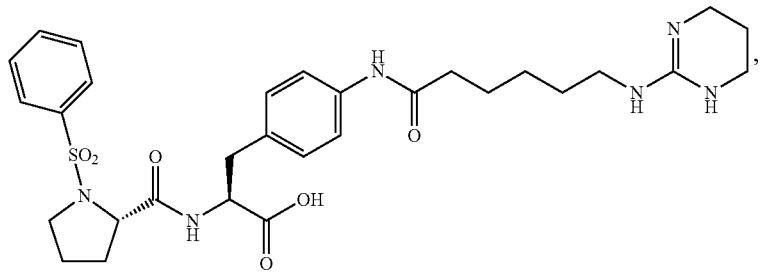
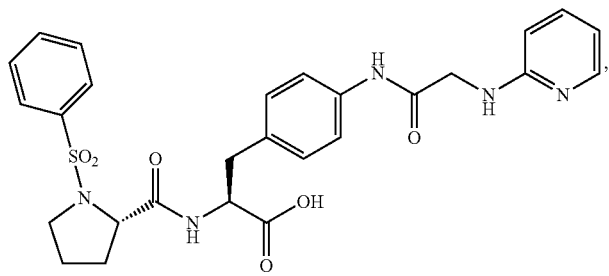
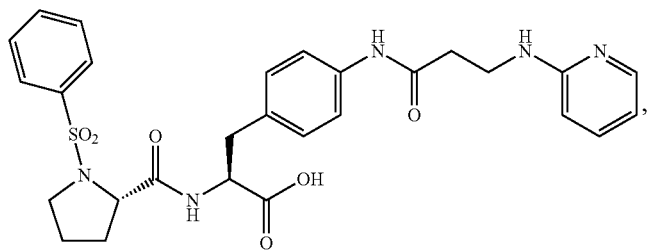
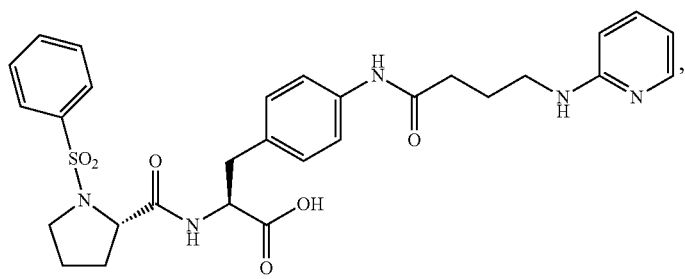
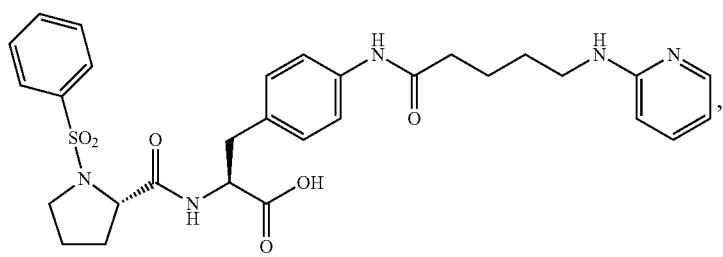
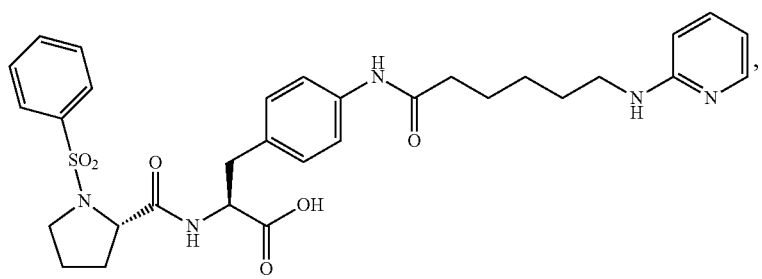

-continued
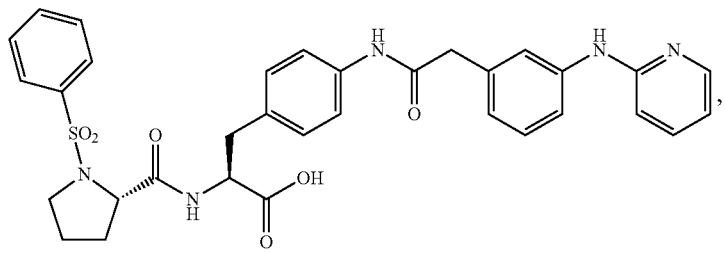
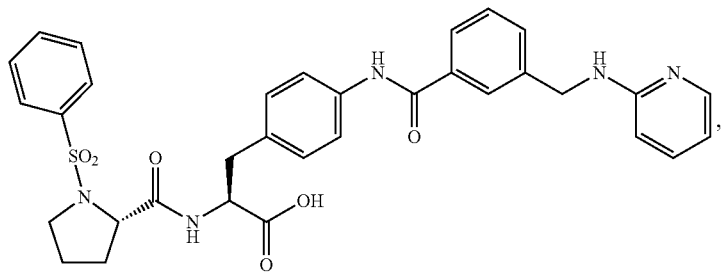
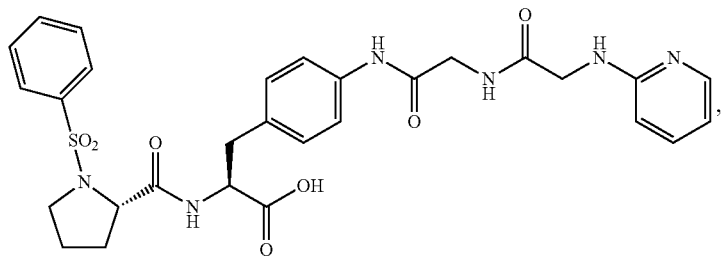
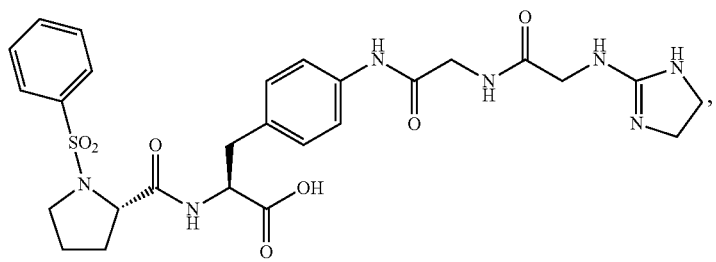
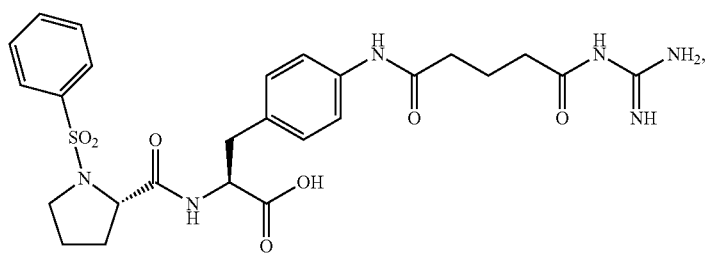
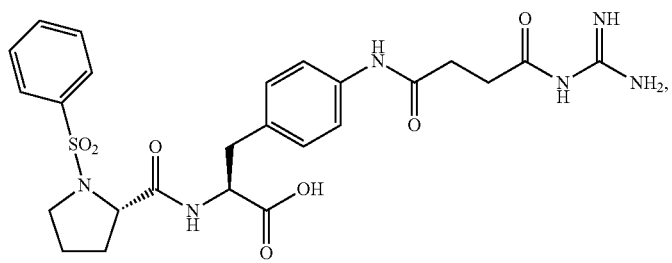

-continued
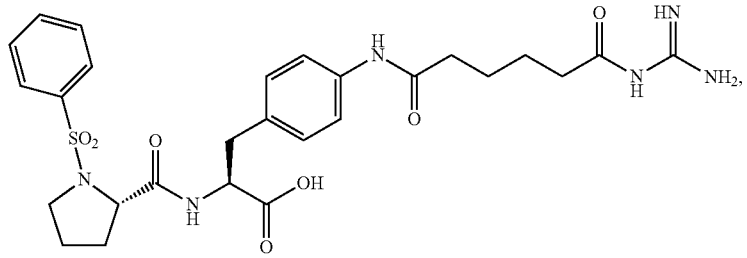
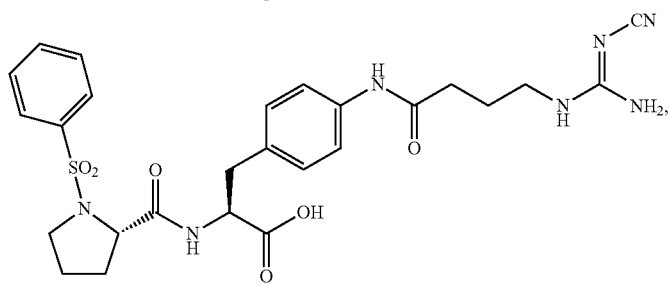
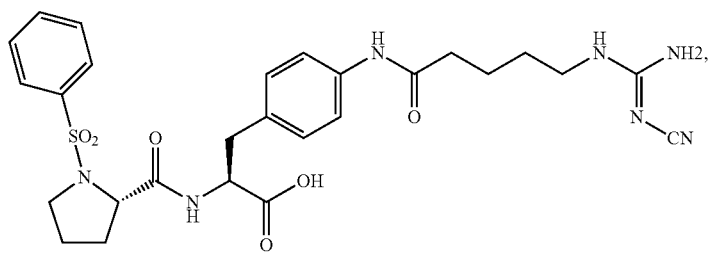
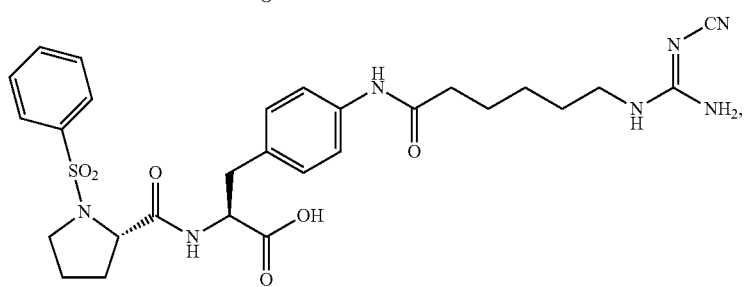
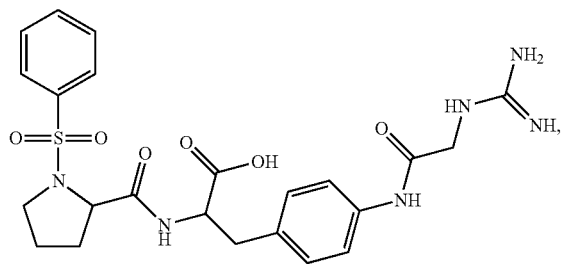
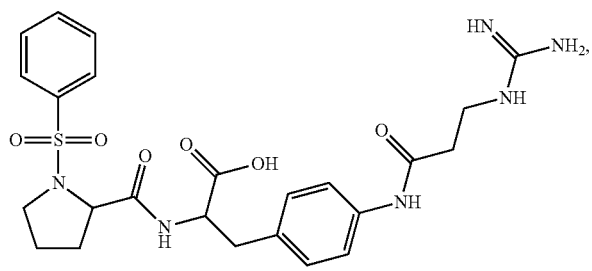

-continued
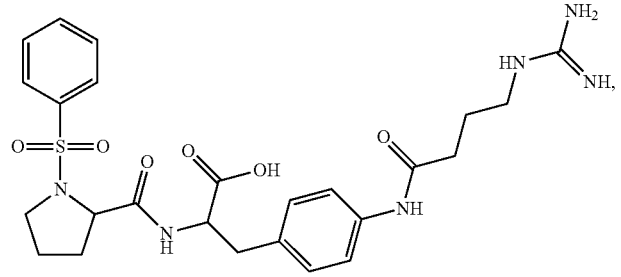
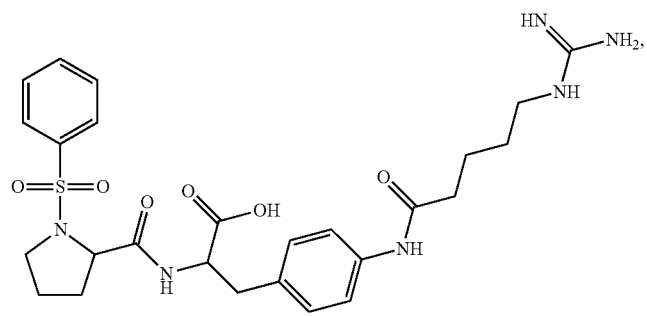
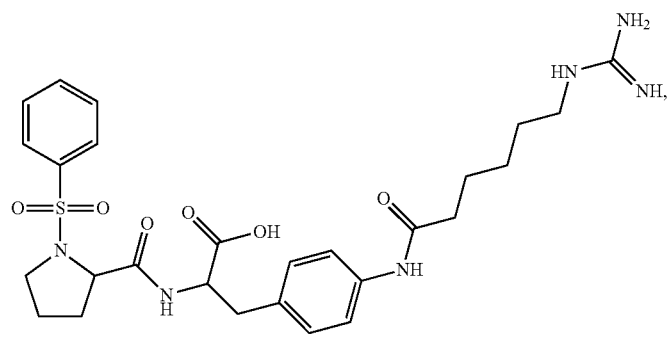
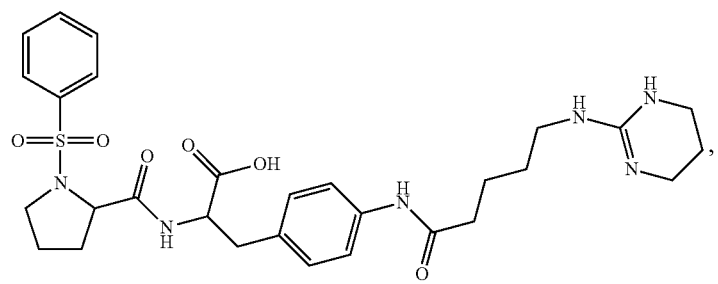
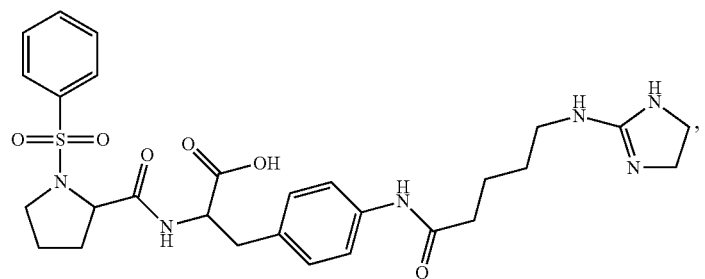

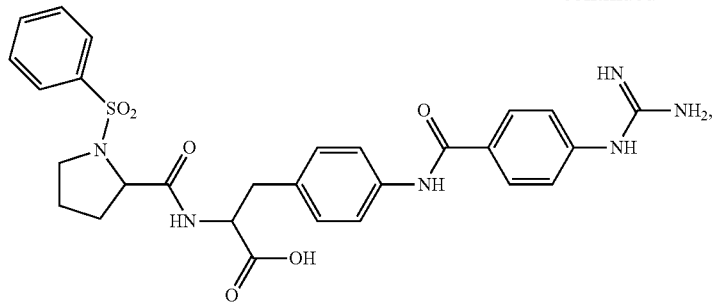
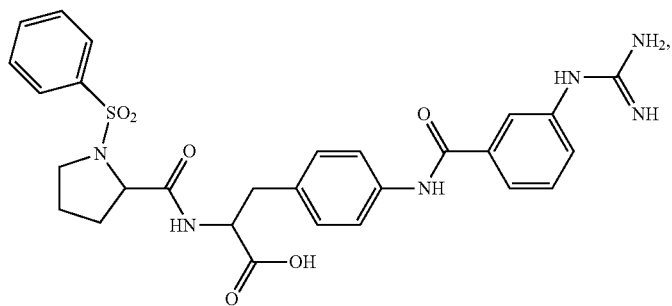
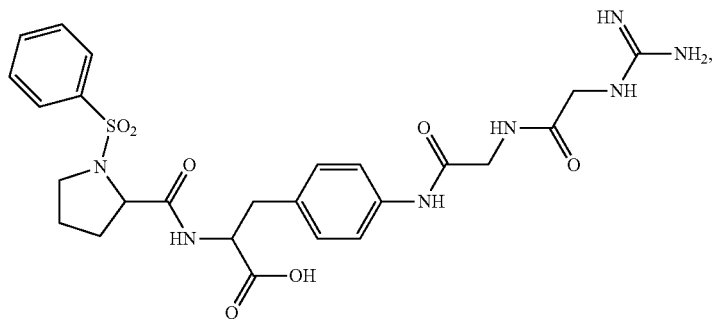
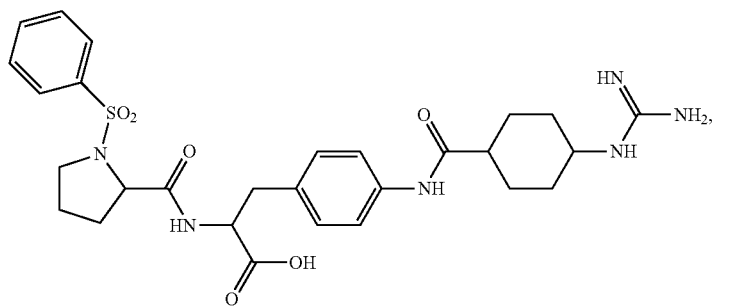
1p;2p
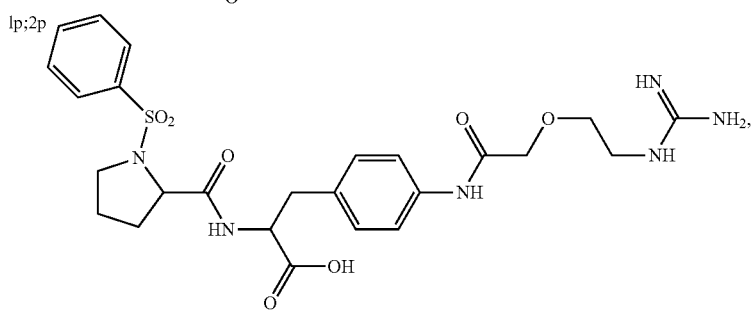

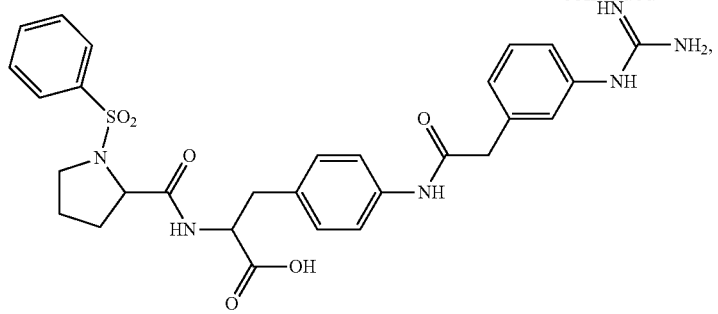
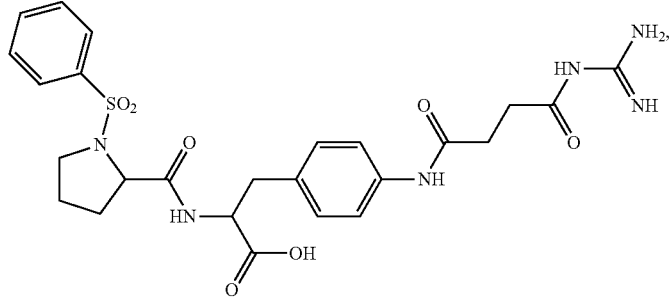
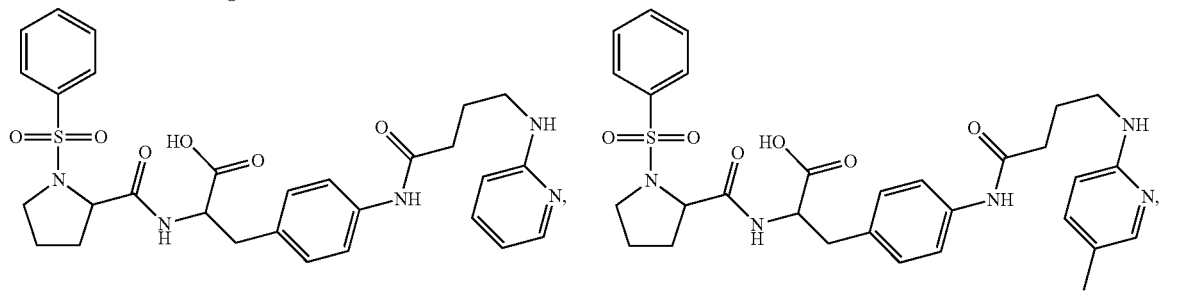
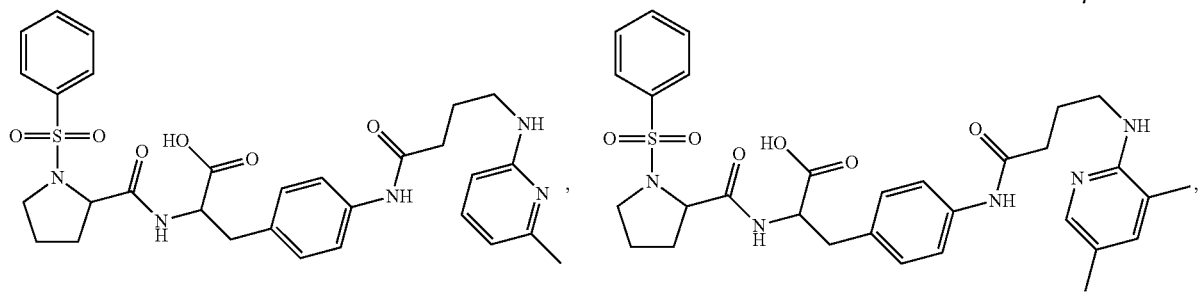
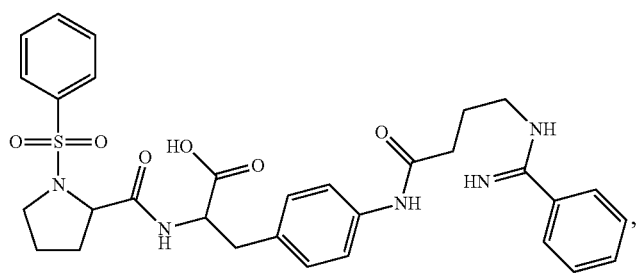
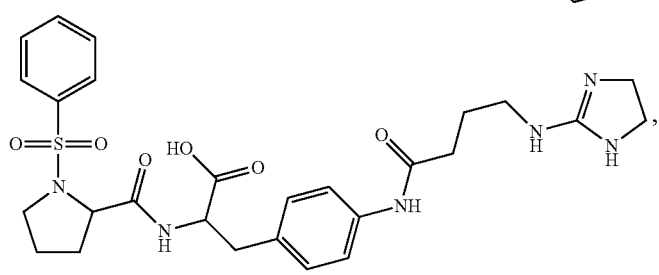

-continued
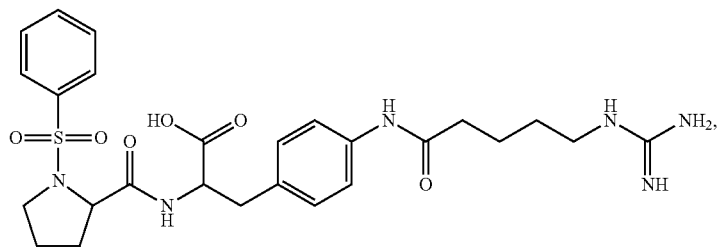
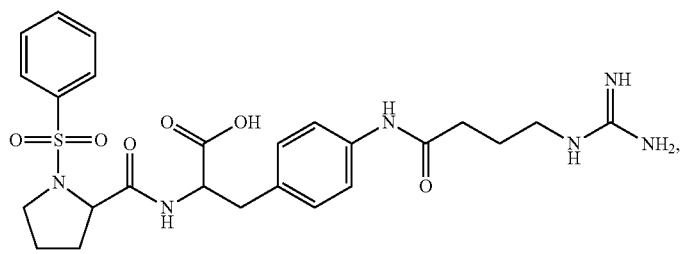
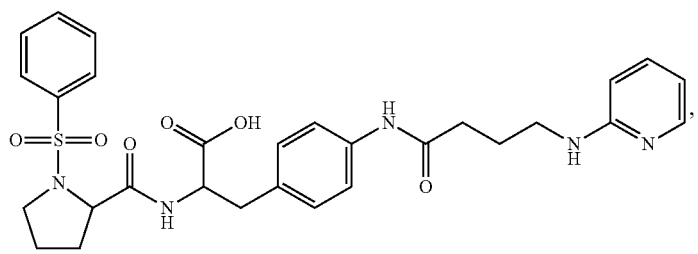
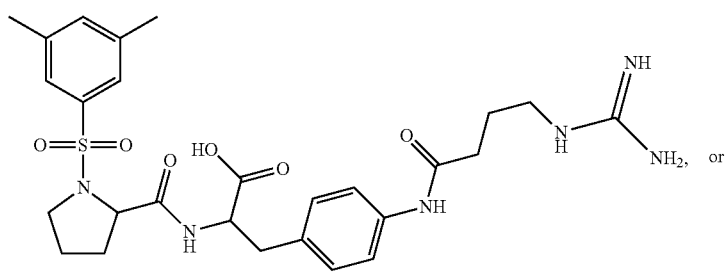 or
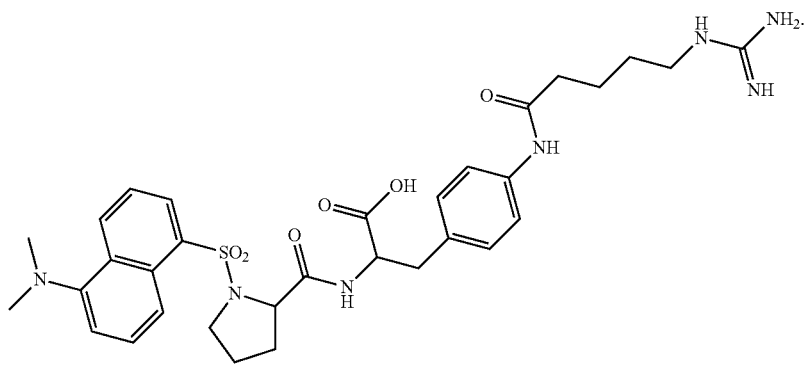

12. The compound of claim 1 having the formula:

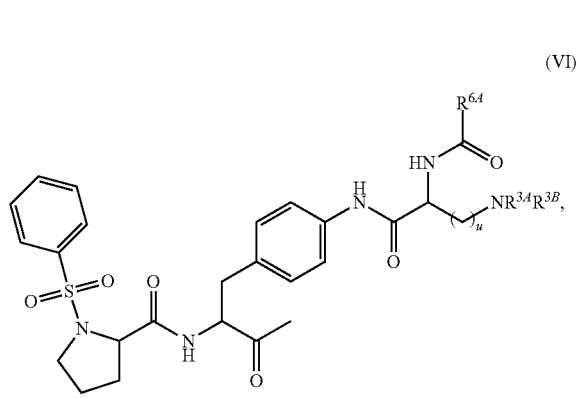
(VI)

wherein $R^{6A}$ is $R^{6C}$-substituted or unsubstituted alkyl or $R^{6C}$-substituted or unsubstituted heteroalkyl;

$R^{6C}$ is —NR$^{6D}$R$^{6E}$, —NHC(O)R$^{6D}$, —C(NCN)R$^{6D}$, —C(NH)R$^{6D}$, R$^{6F}$-substituted or unsubstituted alkyl, R$^{6F}$-substituted or unsubstituted heteroalkyl, R$^{6F}$-substituted or unsubstituted cycloalkyl, R$^{6F}$-substituted or unsubstituted heterocycloalkyl, R$^{6F}$-substituted or unsubstituted aryl, or R$^{6F}$-substituted;

$R^{6D}$ is a detectable moiety;

$R^{6E}$ and $R^{6F}$ are independently hydrogen, halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —OSO$_3$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety.

13. The compound of claim 7 having the formula:

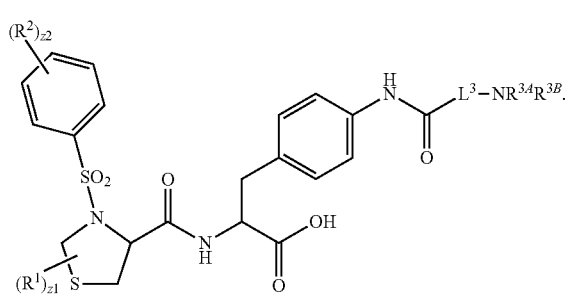

14. The compound of claim 7 having formula:

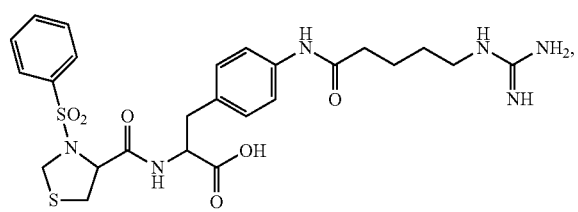

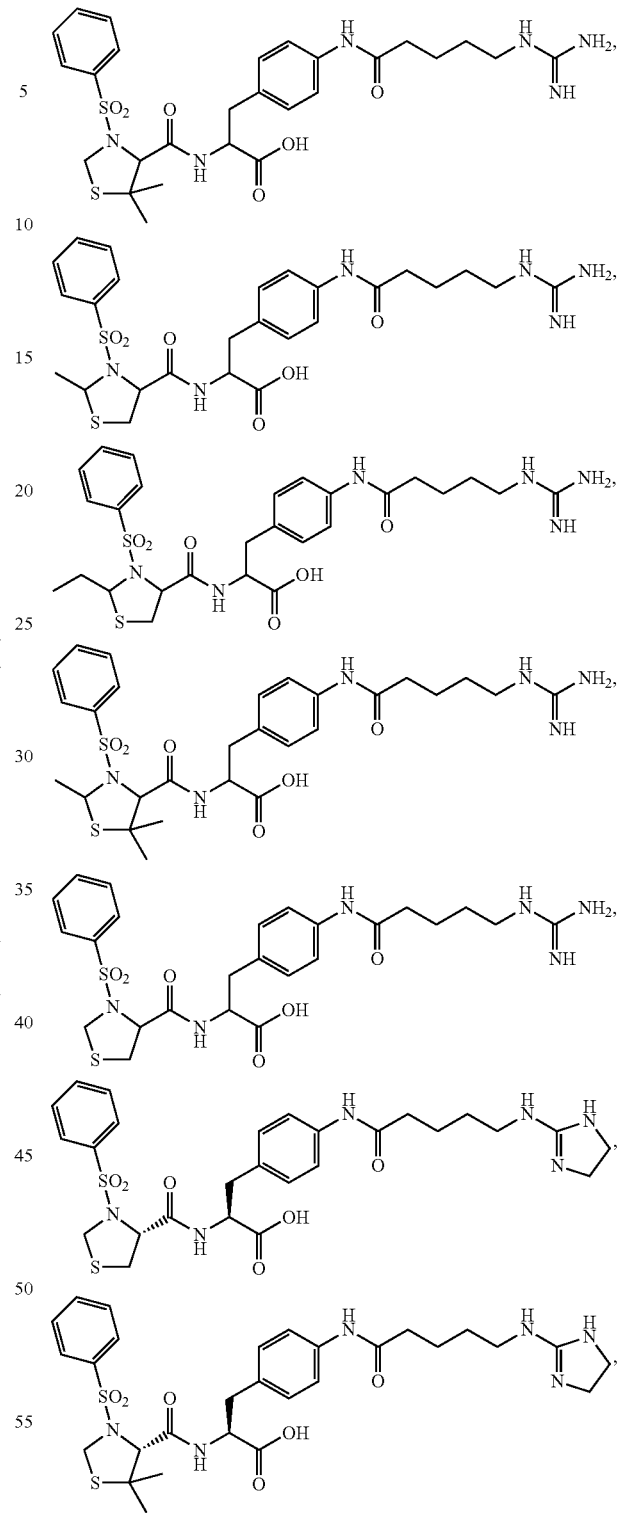

-continued

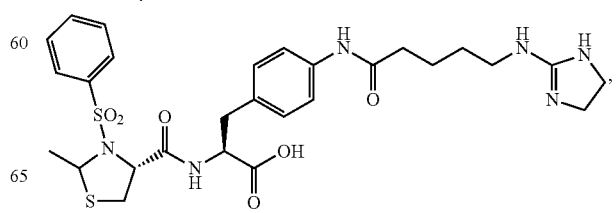

319
-continued
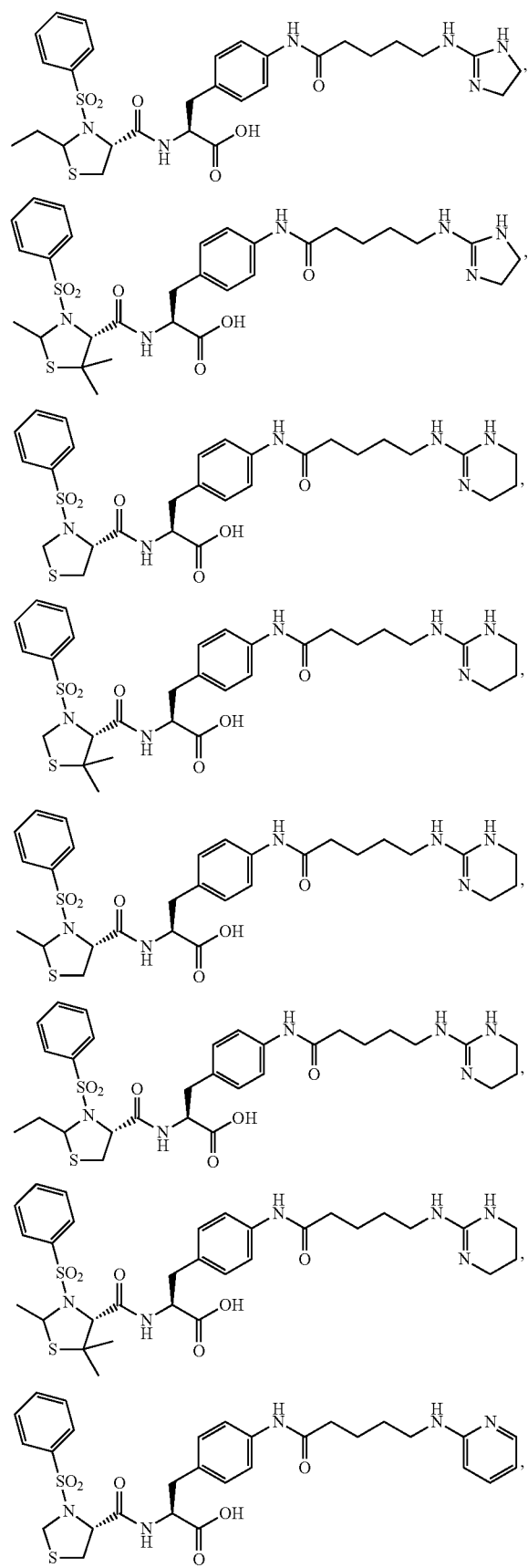
320
-continued
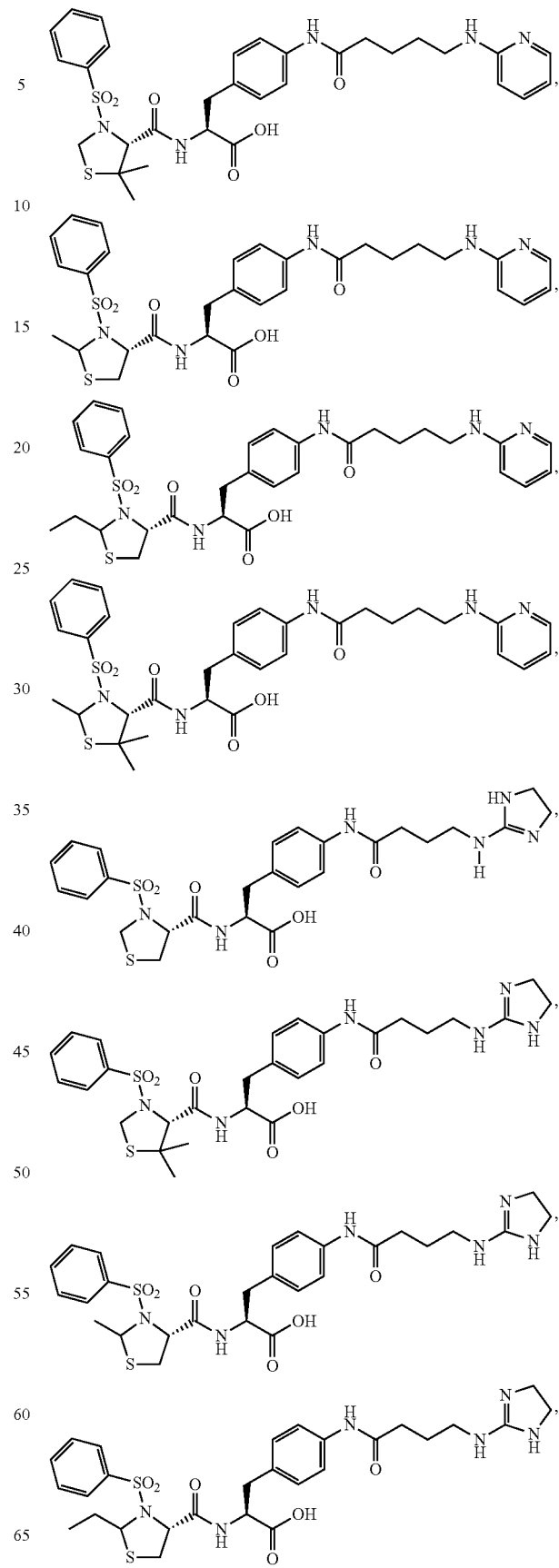

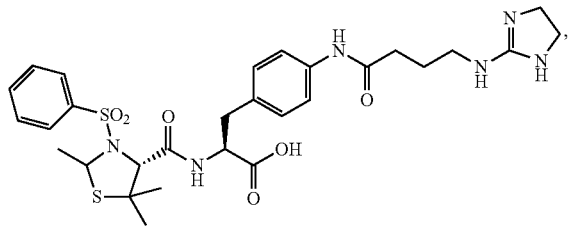
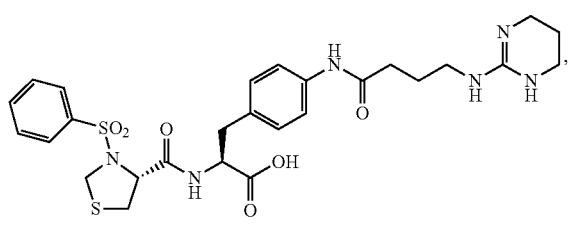
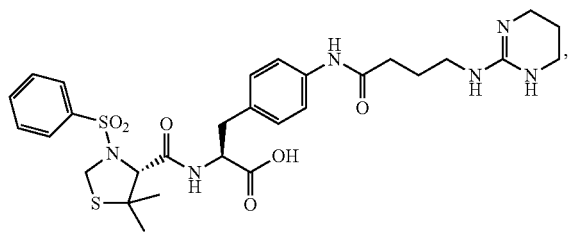
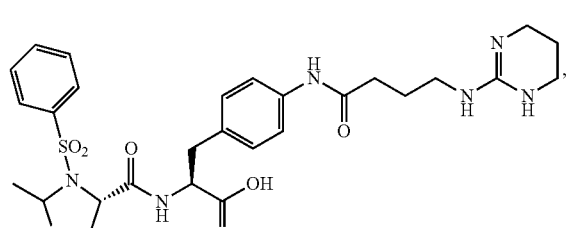
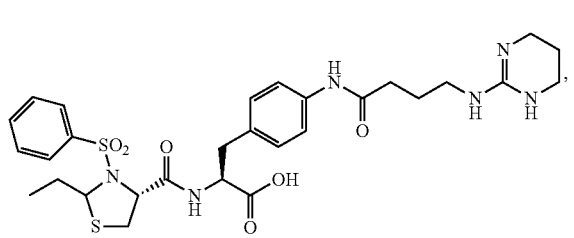
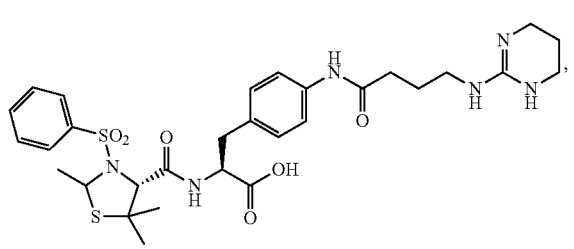
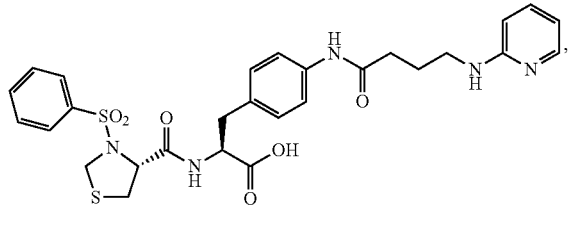
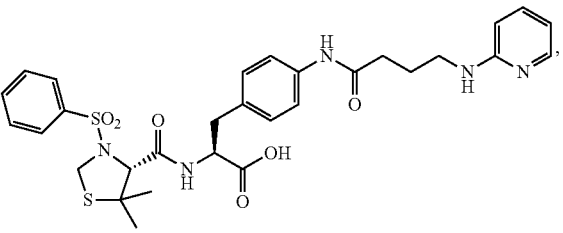
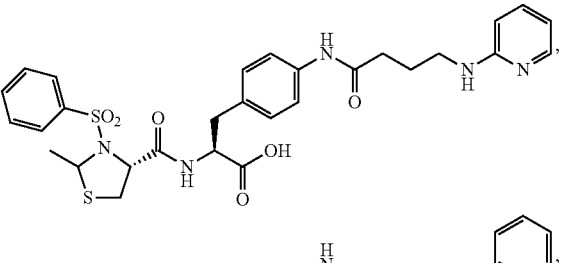
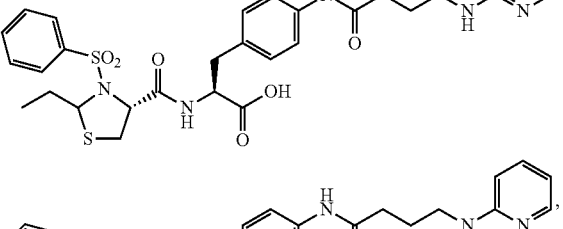
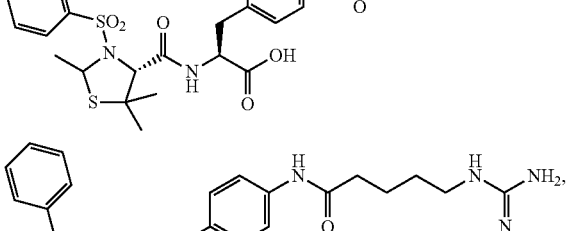
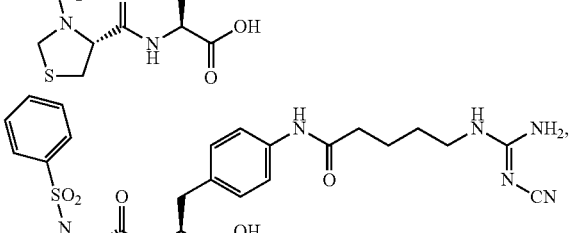
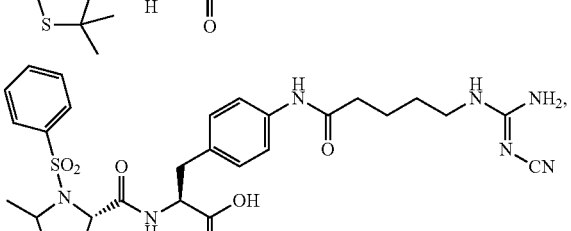
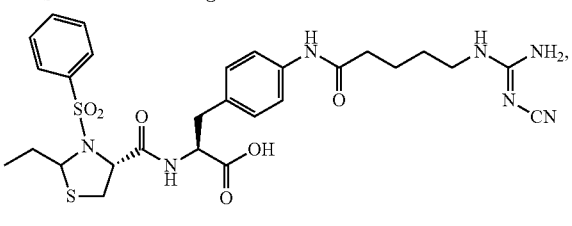

323
-continued
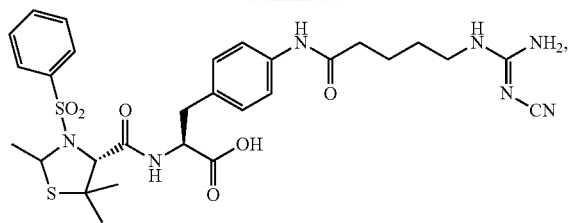
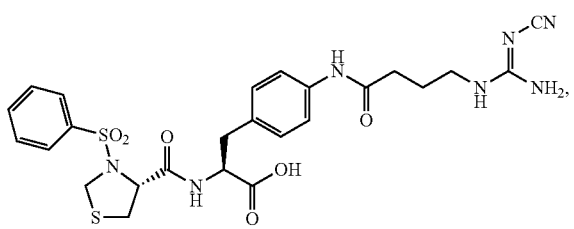
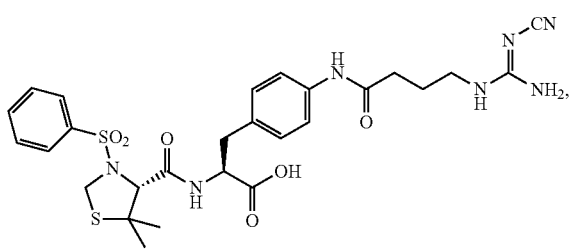
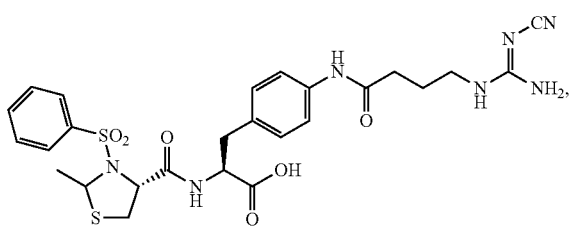
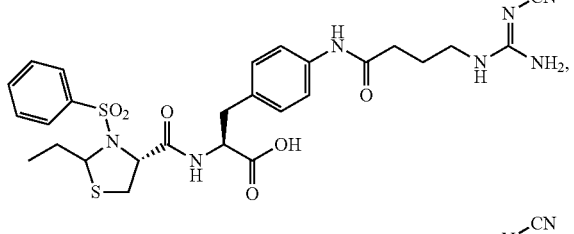
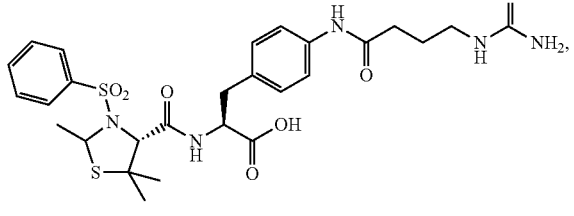
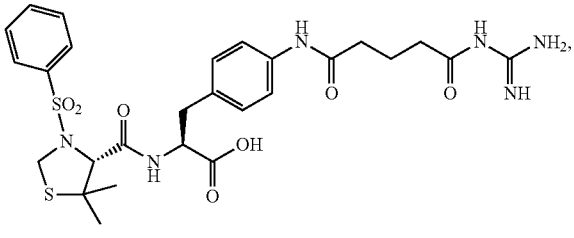
324
-continued
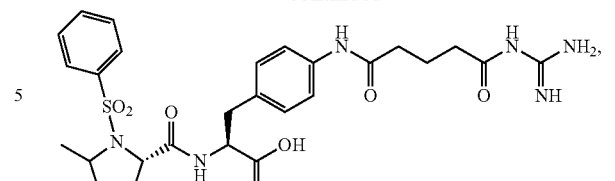
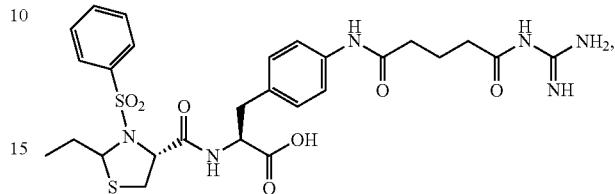
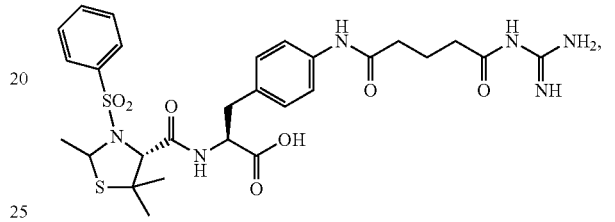
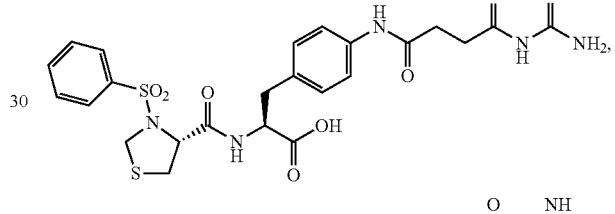
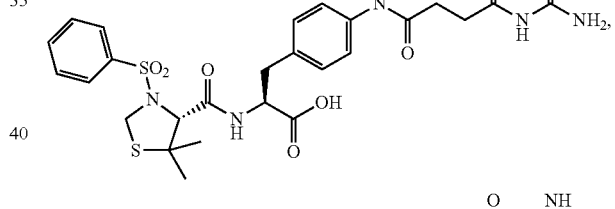
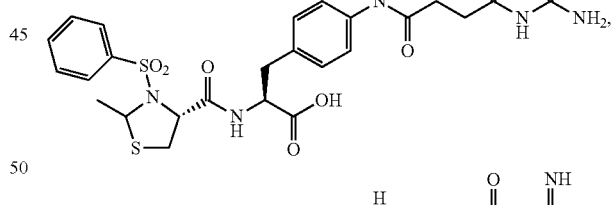
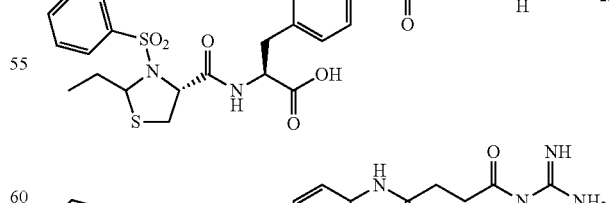
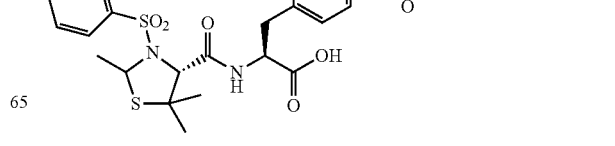

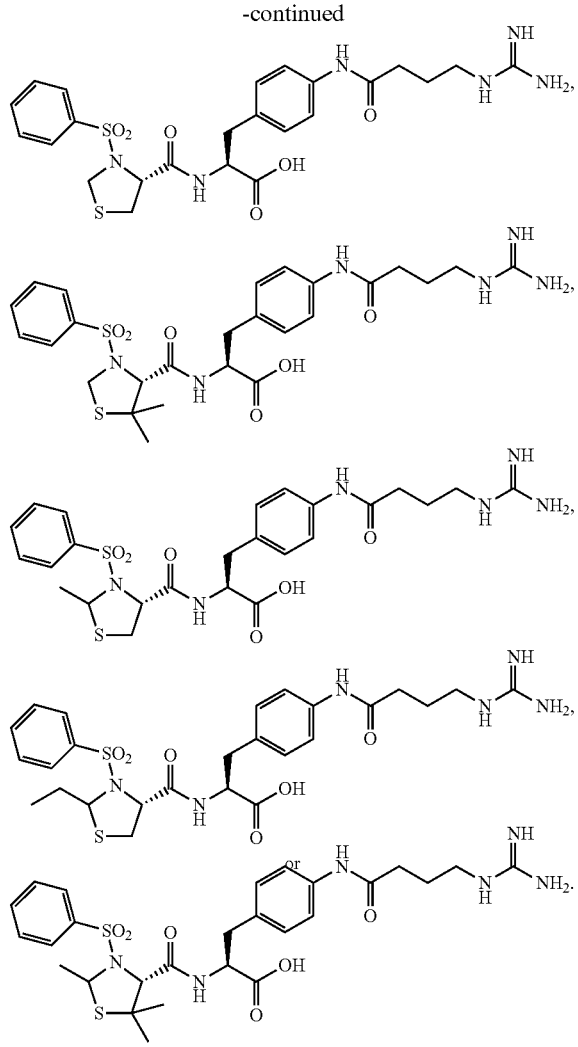
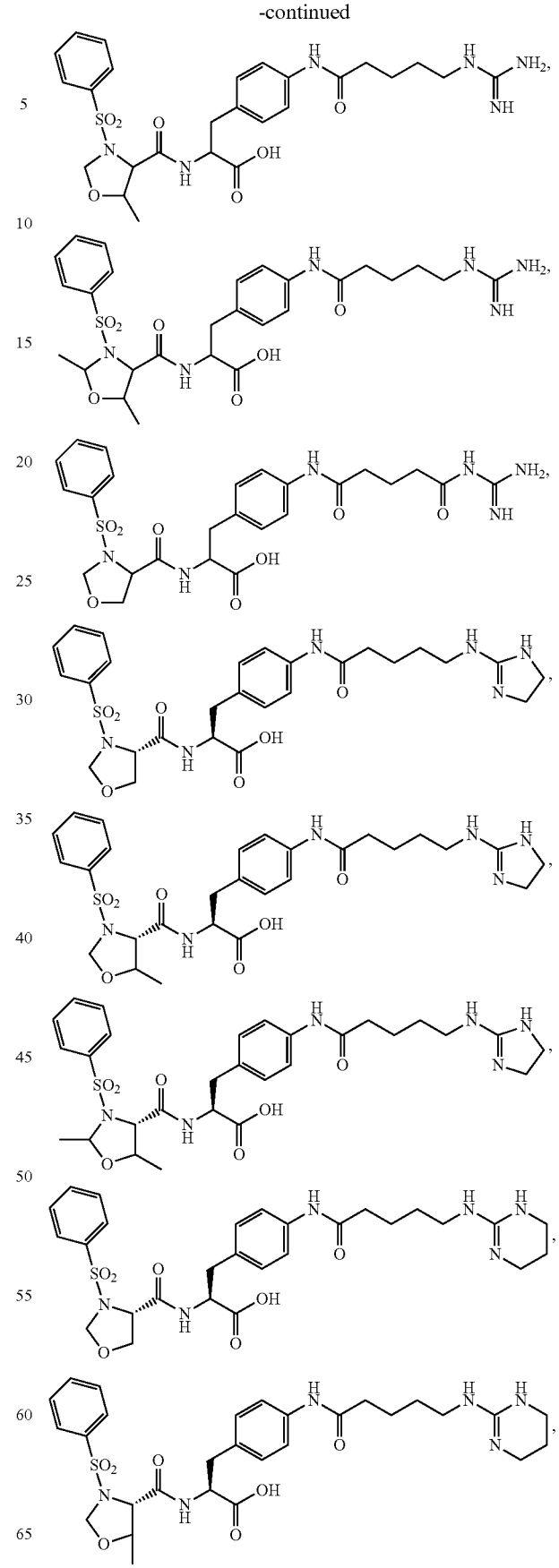
15. The compound of claim 7 having the formula:
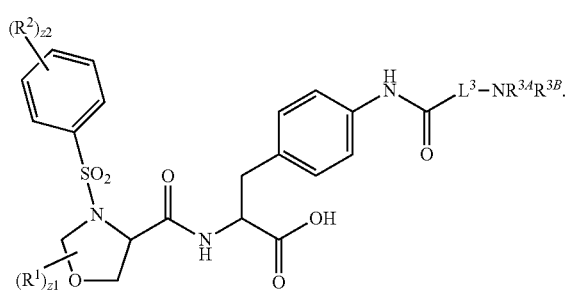
16. The compound of claim 7 having formula:
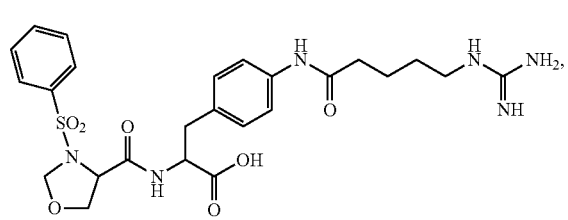

327
-continued
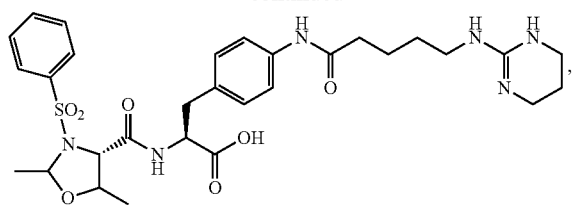
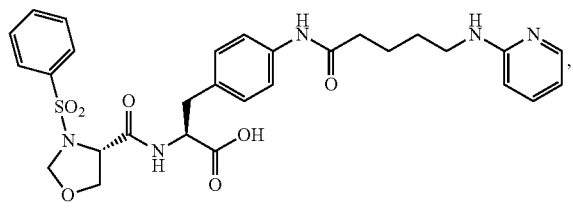
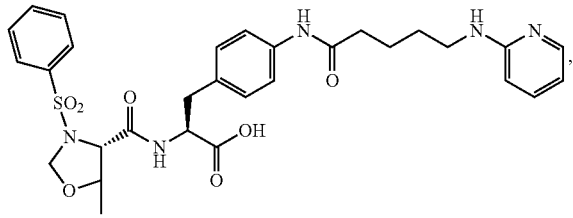
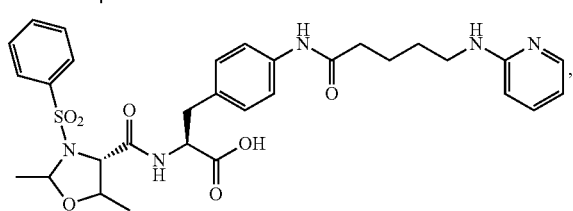
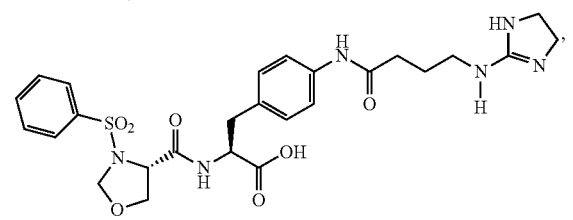
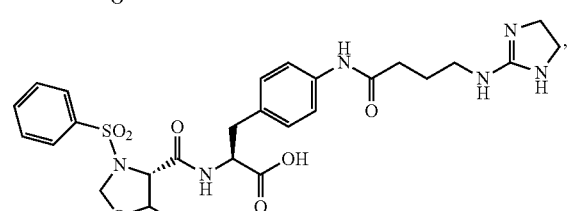
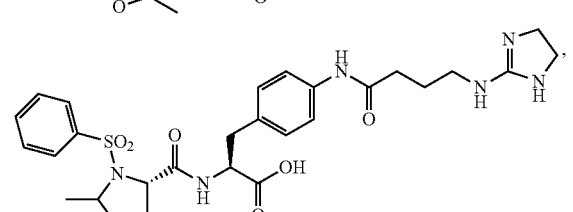
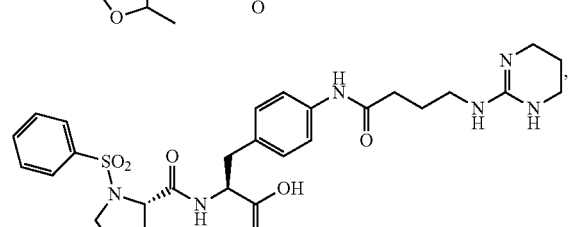
328
-continued
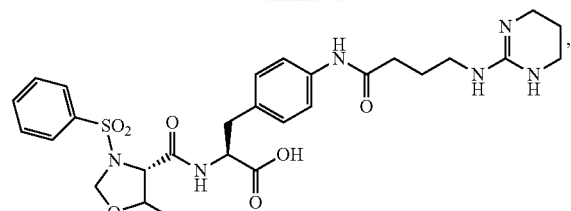
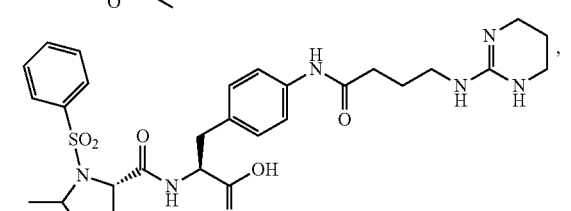
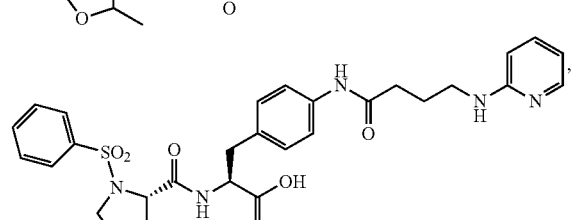
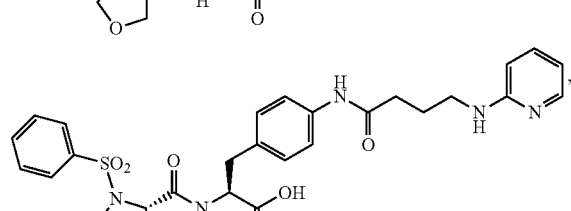
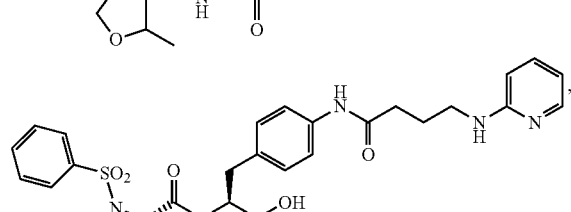
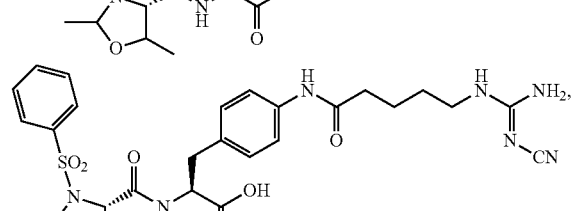
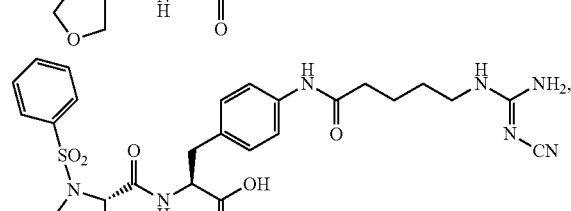
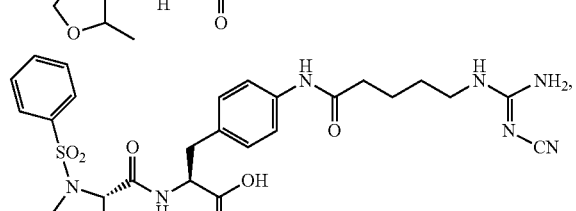

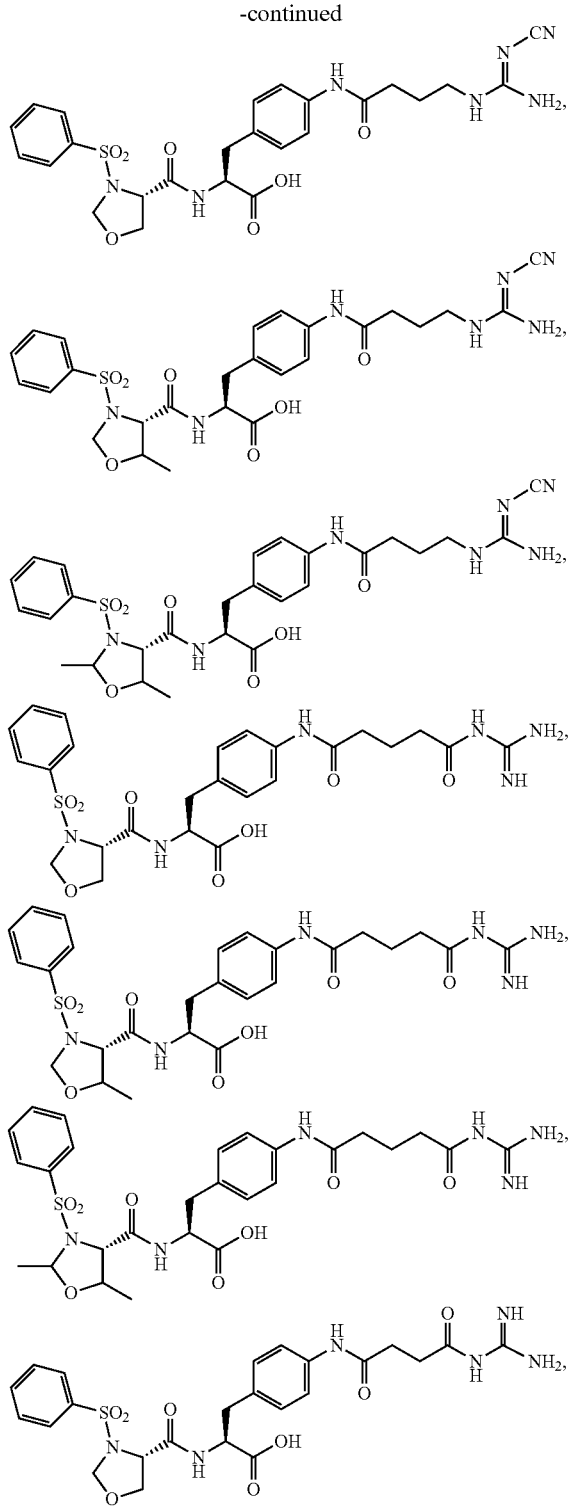
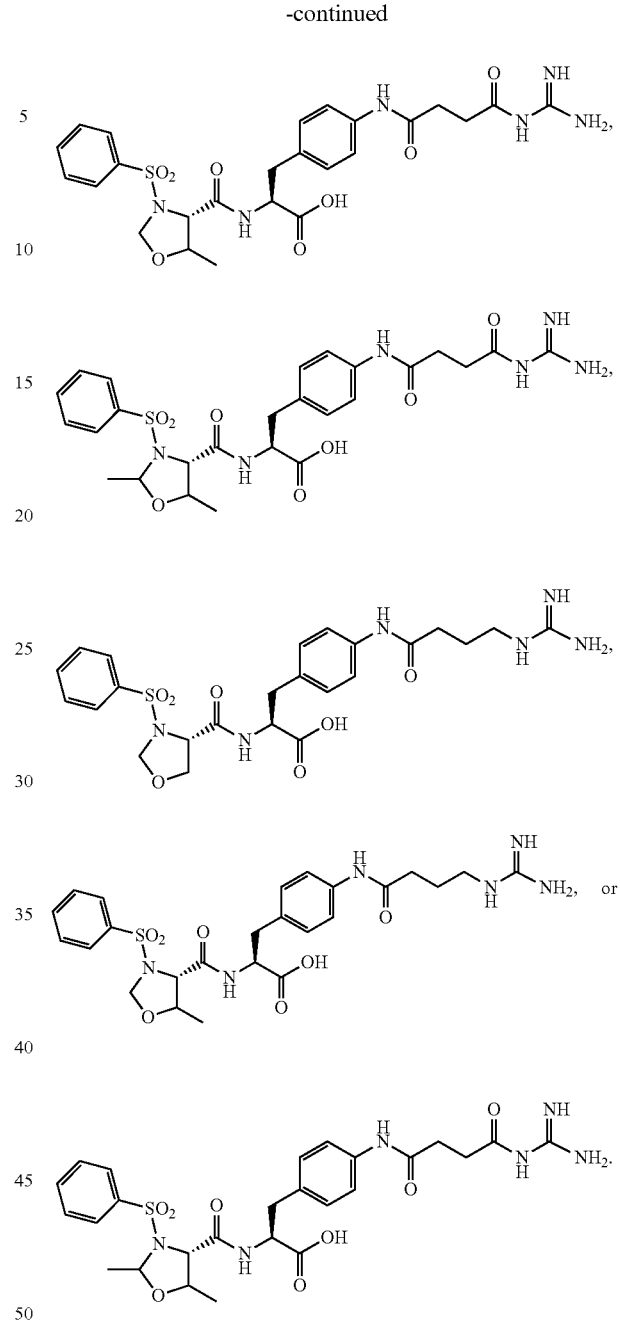
17. A pharmaceutical composition comprising the compound of claim 1, or a salt thereof.
18. A method for treating fibrosis, said method comprising administering to a subject in need thereof a therapeutically effective amount of the compound of claim 1.
* * * * *

UNITED STATES PATENT AND TRADEMARK OFFICE
CERTIFICATE OF CORRECTION

Page 1 of 1

PATENT NO. : 10,131,658 B2
APPLICATION NO. : 15/083836
DATED : November 20, 2018
INVENTOR(S) : William F. DeGrado et al.

It is certified that error appears in the above-identified patent and that said Letters Patent is hereby corrected as shown below:

On the Title Page

Item (60) should read:
*Related U.S. Application Priority Data
(60) Provisional application No. 61/884,583, filed on Sep. 30, 2013.

Signed and Sealed this
Ninth Day of July, 2019

Andrei Iancu
*Director of the United States Patent and Trademark Office*